(12) United States Patent
Oakes et al.

(10) Patent No.: US 11,613,742 B2
(45) Date of Patent: *Mar. 28, 2023

(54) COMPOSITIONS AND METHODS FOR THE TARGETING OF SOD1

(71) Applicant: Scribe Therapeutics Inc., Alameda, CA (US)

(72) Inventors: Benjamin Oakes, El Cerrito, CA (US); Sean Higgins, Alameda, CA (US); Hannah Spinner, Boston, MA (US); Sarah Denny, San Francisco, CA (US); Brett T. Staahl, Tiburon, CA (US); Kian Taylor, Atlanta, GA (US); Katherine Baney, Berkeley, CA (US); Isabel Colin, Oakland, CA (US); Maroof Adil, Davis, CA (US); Cole Urnes, Los Angeles, CA (US)

(73) Assignee: SCRIBE THERAPEUTICS INC., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/483,692

(22) Filed: Sep. 23, 2021

(65) Prior Publication Data

US 2022/0090036 A1 Mar. 24, 2022

Related U.S. Application Data

(63) Continuation of application No. PCT/US2020/050000, filed on Sep. 9, 2020.

(60) Provisional application No. 63/074,375, filed on Sep. 3, 2020, provisional application No. 62/945,138, filed on Dec. 7, 2019, provisional application No. 62/897,941, filed on Sep. 9, 2019.

(51) Int. Cl.
| | | |
|---|---|---|
| *C12N 9/22* | (2006.01) | |
| *C12N 15/11* | (2006.01) | |
| *C12N 15/86* | (2006.01) | |
| *C12N 15/90* | (2006.01) | |
| *A61P 25/28* | (2006.01) | |
| *C12N 9/06* | (2006.01) | |
| *C12N 15/10* | (2006.01) | |
| *C12N 15/113* | (2010.01) | |

(52) U.S. Cl.
CPC .............. *C12N 9/22* (2013.01); *A61P 25/28* (2018.01); *C12N 9/003* (2013.01); *C12N 15/101* (2013.01); *C12N 15/1051* (2013.01); *C12N 15/11* (2013.01); *C12N 15/1133* (2013.01); *C12N 15/86* (2013.01); *C12N 15/907* (2013.01); *C12N 2310/20* (2017.05); *C12N 2750/14143* (2013.01)

(58) Field of Classification Search
CPC .... C12N 15/11; C12N 15/907; C12N 15/102; C12N 15/1137; C12N 15/111; C12N 2310/20

See application file for complete search history.

(56) References Cited

U.S. PATENT DOCUMENTS

| | | |
|---|---|---|
| 5,173,414 A | 12/1992 | Lebkowski et al. |
| 5,405,733 A | 4/1995 | Pirrung et al. |
| 5,412,087 A | 5/1995 | Mcgall et al. |
| 5,445,934 A | 8/1995 | Fodor et al. |
| 5,695,937 A | 12/1997 | Kinzler et al. |
| 10,369,232 B2 | 8/2019 | Chivukula et al. |
| 11,174,469 B2 | 11/2021 | Lundberg et al. |
| 2015/0301028 A1* | 10/2015 | Eggan ................ G01N 33/6872 435/29 |
| 2017/0369870 A1 | 12/2017 | Gill et al. |
| 2018/0148711 A1 | 5/2018 | Finer et al. |
| 2018/0258424 A1 | 9/2018 | Greenberg et al. |
| 2019/0330603 A1 | 10/2019 | Ahlfors et al. |
| 2022/0081681 A1 | 3/2022 | Oakes et al. |
| 2022/0220508 A1 | 7/2022 | Oakes et al. |

FOREIGN PATENT DOCUMENTS

| | | | |
|---|---|---|---|
| WO | WO-2010/075303 A1 | 7/2010 | |
| WO | WO-2012/068627 A1 | 5/2012 | |
| WO | WO-2017/068077 A1 | 4/2017 | |
| WO | WO-2017216771 A2 * | 12/2017 | .............. A61P 35/00 |
| WO | WO-2018/002762 A1 | 1/2018 | |
| WO | WO-2018/027078 A1 | 2/2018 | |
| WO | WO-2018/064371 A1 | 4/2018 | |
| WO | WO-2018/195555 A1 | 10/2018 | |
| WO | WO-2018/220211 A1 | 12/2018 | |
| WO | WO-2019/051278 A1 | 3/2019 | |

(Continued)

OTHER PUBLICATIONS

Yin et al. Partial DNA-guided Cas9 enables genome editing with reduced off-target activity. Nature Chemical Biology, vol. 14, pp. 311-316, p. 1/1 of Online Methods, and pp. 1/14-14/14 of Supplementary Information, Jan. 29, 2018. (Year: 2018).*

(Continued)

*Primary Examiner* — Jennifer Dunston
(74) *Attorney, Agent, or Firm* — Cooley LLP

(57) ABSTRACT

Provided herein are CasX:gNA systems comprising CasX polypeptides, guide nucleic acids (gNA), and optionally donor template nucleic acids useful in the modification of a SOD1 gene. The systems are also useful for introduction into cells, for example eukaryotic cells having mutations in the SOD1 protein or the SOD1 regulatory element. Also provided are methods of using such CasX:gNA systems to modify cells having such mutations and utility in methods of treatment of a subject with a SOD1-related disease.

25 Claims, 102 Drawing Sheets

Specification includes a Sequence Listing.

(56) References Cited

FOREIGN PATENT DOCUMENTS

| WO | WO-2020/023529 A1 | 1/2020 |
|---|---|---|
| WO | WO-2020/041456 A1 | 2/2020 |
| WO | WO-2020/168075 A1 | 8/2020 |
| WO | WO-2020/247882 A1 | 12/2020 |

OTHER PUBLICATIONS

Moon et al. Improving CRISPR genome editing by engineering guide RNAs. Trends in Biotechnology, vol. 37, No. 8, pp. 870-881, Mar. 4, 2019. (Year: 2019).*
Fowler et al. Measuring the activity of protein variants on a large scale using deep mutational scanning. Nature Protocols, vol. 9, No. 9, pp. 2267-2284, 2014. (Year: 2014).*
Kiskinis et al. Pathways disrupted in human ALS motor neurons identified through genetic correction of mutant SOD1. Cell Stem Cell, vol. 14, pp. 781-795, Jun. 5, 2014. (Year: 2014).*
Deng et al. Amytrophic Lateral Sclerosis and structural defects in Cu, Zn superoxide dismutase. Science, vol. 261, pp. 1047-1051, Aug. 20, 1993. (Year: 1993).*
Aguilera, T.A. et al. (Jun. 2009). "Systemic in vivo distribution of activatable cell penetrating peptides is superior to that of cell penetrating peptides," Inegr. Bio. (Camb) 1(5-6):371-381. Published online May 11, 2009.
Aitschul, S.F. et al. (1990). "Basic local alignment search tool," J. Mol. Biol. 215:403-410.
Andersen, P.M. et al. (1995). "Amyotrophic lateral sclerosis associated with homozygosity for an ASp90Ala mutation in CuZn-superoxide dismutase," Nat. Genet. 10:61-66.
Baskoylu, S.N. et al. (2018). "Single copy/knock-n models of ALS SOD1 in *C. elegans* suggest loss and gain of function have different contributions to cholinergic and glutamatergic neurodegeneration," PLoS Genet. 14:e1007682.
Bhinge, A. et al. (2017). "Genetic Correction of SOD1 Mutant iPSCs Reveals ERK and JNK Activated API as a Driver of Neurodegeneration in Amyotrophic Lateral Sclerosis," Stem Cell Reports 8:856-869.
Bunton-Stasyshyn et al. (2015). "SODI Function and Its Implications for Amyotrophic Lateral Sclerosis Pathology: New and Renascent Themes," Neuroscientist 21:519-529.
Burstein, D. et al. (Feb. 2017), "New CRISPR-Cas systems from uncultivated microbes," Nature 542:237-241. Published online Dec. 22, 2016, with Supplemental Materials, 28 total pages.
Chen, B. et al. (2003). "Influence of histidine on the stability and physical properties of a fully human antibody in aqueous and solid forms," Pharm. Res. 20:1952-1960.
Dirren, E. et al. (2015). "SOD1 silencing in motoneurons or glia rescues neuromuscular function in ALS mice," Ann. Clin. Transl. Neurol. 2:167-184.
Forsberg et al. (2011). "Glial nuclear aggregates of superoxide dismutase-1 are regularly present in patients with amyotrophic lateral sclerosis," Acta Neuropathol. 121:623-634.
Foust, K.D. et al. (2013). "Therapeutic AAV9-mediated Suppression of Mutant SOD1 Slows Disease Progression and Extends Survival in Models of inherited ALS," Mol. Ther. 21:2148-2159.
Fox, L.M. et al. (2015). "Chapter 7: Macroautophagy of aggregating-prone proteins of neurodegenerative disease," Autophagy: Cancer, Other Pathologies, Inflammation, Immunity, Infection, and Aging, Academic Press, M. A. Hayat, Editor, pp. 117-137.
Gaj et al. (2017). "in vivo genome editing improves motor function and extends survival in a mouse model of ALS," Science 3:3952, 10 pages.
Ghirlando, R. et al. (1999). "Glycosylation of human IgG-Fc: influences on structure revealed by differential scanning microcalorimetry," Immunol Letters 68:47-52.
Gurey, M.E. et al. (1994). "Motor neuron degeneration in mice that express a human Cu,Zn 38 superoxide dismutase mutation," Science 264:1772-1775.

Hermonat, P.L. et al. (1984). "Use of adeno-associated virus as a mammalian DNA cloning vector: Transduction of neomycin resistance into mammalian tissue culture cells," PNAS 81:6466-6470.
Imamura, K. et al. (2017). "The Src/c-Abl pathway is a potential therapeutic target 40 in amyotrophic lateral sclerosis," Sci. Transl. Med. 9:eaaf3962, 10 pages.
International Search Report dated Feb. 17. 2021. for PCT Application No. PCT/US2020/050000, filed on Sep. 9, 2020, 8 pages.
Kiernan, M. et al. (2011). "Amyotrophic lateral sclerosis," Lancet 377:942-955.
Kotin, R.M. (1994). "Prospects for the use of adeno-associated virus as a vector for human gene therapy," Human Gene Therapy 5:793-801.
Kruminis-Kaszkiel, E. et al. (2018). "CRISPR/Cas9 Technology as an Emerging Tool for Targeting Amyotrophic Lateral Sclerosis (ALS)," Int. J. Mol. Sci. 19:906, 13 pages.
Kunkel, G.R. et al. (1986). "U6 small nuclear RNA is transcribed by RNA polymerase III," PNAS 83:8575-8579.
Lee, H. et al. (2017). "Assay development for high content qualification of SOD1 mutant protein aggregate formation in living cells," J. Vis. Exp. 128:56425, 13 total pages.
Liu, J.J. et al. "CasX enzymes comprise a distinct family of RNA-guided genome editors," Nature 566:218-223. Published online Feb. 4, 2019, 38 pages.
Liu, J.J. et al. "CasX enzymes comprise a distinct family of RNA-guided genome editors," Nature 48 568:E8-E10. (Author correction: published online Apr. 3, 2019).
Murray, A. et al. (2002). "Epitope Affinity Chromatography and Biophysical Studies of Monoclonal 49 Antibodies and Recombinant Antibody Fragments," J. Chromatogr Sci 40:343-349.
Niwa, J-I. et al. (2007). "Disulfide bond mediates aggregation, toxicity, and ubiquitylation of familial 50 amyotrophic lateral sclerosis-linked mutant SOD1," Biol. Chem. 282:28087-28095.
Noguchi, H. et. al. (Jul. 2003), "PDX-1 protein containing its own antennapedia-like protein transduction domain can transduce pancreatic duct and islet cells," Diabetes 52:1732-1737.
Pardo, C.A. et al. (1995). "Superoxide dismutase is an abundant, component in cell bodies, dendrites, and axons of motor neurons and in a subset of other neurons," PNAS 92:954-958.
Petrov D. et al. (2017). "ALS Clinical Trials Review: 20 Years of Failure. Are We Any Closer to Registering a New Treatment?" Front Aging Neurosci. 9:68, 11 pages.
Philips, T. et al. (2015). "Rodent models of amyotrophic lateral sclerosis," Curr. Protoc. Pharmacol. 54, 69:5.67.1-5.67.21.
Pochet, R. (2017). "Genetics and ALS: Cause for Optimism," Cerebrum 2017:cer-05-17, 13 pages.
Qi, L.S. et al. (Feb. 2013). "Repurposing CRISPR as an RNA-guided platform for sequence-specific control of gene expression," Cell 152:1173-1183, 22 pages.
Sakeilariou, G.K, et al. (2018). "Comparison of Whole Body SOD1 Knockout with Muscle-Specific SOD1 Knockout Mice Reveals a Role for Nerve Redox Signaling in Regulation of Degenerative Pathways in Skeletal Muscle," Antioxid Redox Signal 28:275-295.
Samulski, R.J. et al. (1989). "Helper-Free Stocks of Recombinant Adeno-Associated Viruses: Normal Integration Does Not Require Viral Gene Expression," J. Virol. 63:3822-3828.
Sharma, A. et al. (2016). "ALS-associated mutant FUS induces selective motor neuron gegeneration through toxic gain of function," Nat. Commun. 7:10465, 14 pages.
Sherman et al. (1983). "Nucleotide sequence and expression of human chromosome 21-encoded superoxide dismutase mRNA," PNAS 80:5465-5469.
Smith, T.F. et al. (1981). "Comparison of biosequences," Adv. Appl. Math. 2:482-489. Published online Sep. 3, 2004.
Stevens, J.C. et al. (2010). "Modification of superoxide Dismutase 1 (SOD1) Properties by a GFP Tag-Implications for Research into amyotrophic lateral sclerosis (ALS)," PLoS One 5:e9541. 10 pages.
Stolca, L. et al. (2016). "AAV delivered artificial microRNA extends survival and delays paralysis in an Amyotrophic Lateral Sclerosis mouse model," Ann. Neurol. 79:687-700, 24 pages.
Tratschin, J-D. et al., (1985). "Adeno-Associated Virus Vector for High-Frequency Integration, Expression, and Rescue of Genes in Mammalian Ceils," Mol. Cell. Biol. 5:3251-3260.

(56) References Cited

OTHER PUBLICATIONS

Tratschin, J-D. et al. (1984). "A Human Parvovirus, Adeno-Associated Virus, as a Eucaryotic Vector: Transient Expression and Encapsidation of the Procaryotic Gene for Chloramphenicol Acetyltransferase," Mol. Cell. Biol. 4:2072-2081.

Tréhin, R. et al. (Jul. 2004). "Cellular uptake but low permeation of human calcitonin-derived cell penetrating peptides and Tat(47-57) through well-differentiated epithelial models," Pharm. Res. 21:1248-1256.

Wang, L. et al. (2017). "CRISPR/Casg-mediated targeted gene correction in amyotrophic lateral sclerosis palter iPSCs," Protein Cell. 8:365-378.

Wender, P.A. et al. (Nov. 2000). "The design, synthesis, arsd evaluation of molecules that enable or enhance cellular uptake: peptoid molecular transporters," PNAS 97:13003-13008.

Written Opinion of the International Searching Authority dated Feb. 17, 2021, for PCT Application No. PCT/US2020/050000, filed on Sep. 9, 2020, 12 pages.

Yang, H. et al. (May 2019). "CasX: a new and small CRISPR gene-editing protein," Cell Res. 29:345-346. Published online Apr. 16, 2019.

Zender, L. et al, (Jun. 2002). "VP22-mediated intercellular transport of p53 in hepatoma ceils in vitro and in vivo," Cancer Gene Ther. 9:489-496.

Zhang, J. et al. (Jun. 1997). "PowerBLAST: a new network BLAST application for interactive or automated sequence analysis and annotation," Genome Res. 7:649-656.

\* cited by examiner

Endogenous Reporter line generation

FIG. 33: Table 3 - gNA Targeting Sequences for the SOD1 Gene

| Construct | SEQ ID NO | Construct | SEQ ID NO | Construct | SEQ ID NO | Construct | SEQ ID NO |
|---|---|---|---|---|---|---|---|
| TTCN_0 | 372 | CTCN_1940 | 6525 | CTCN_17 | 412 | TTCN_1783 | 6565 |
| TTCN_1 | 373 | TTCN_1766 | 6526 | ATCN_5 | 413 | ATCN_1235 | 6566 |
| GTCN_0 | 374 | TTCN_1767 | 6527 | GTCN_3 | 414 | ATCN_1236 | 6567 |
| ATCN_1 | 375 | TTCN_1768 | 6528 | ATCN_6 | 415 | TTCN_1784 | 6568 |
| TTCN_2 | 376 | GTCN_1041 | 6529 | CTCN_18 | 416 | TTCN_1785 | 6569 |
| CTCN_0 | 377 | GTCN_1042 | 6530 | TTCN_16 | 417 | CTCN_1947 | 6570 |
| ATCN_2 | 378 | ATCN_1227 | 6531 | CTCN_19 | 418 | GTCN_1049 | 6571 |
| TTCN_3 | 379 | TTCN_1769 | 6532 | TTCN_17 | 419 | TTCN_1786 | 6572 |
| GTCN_1 | 380 | TTCN_1770 | 6533 | TTCN_18 | 420 | TTCN_1787 | 6573 |
| ATCN_3 | 381 | TTCN_1771 | 6534 | ATCN_7 | 421 | CTCN_1948 | 6574 |
| TTCN_4 | 382 | TTCN_1772 | 6535 | TTCN_19 | 422 | TTCN_1788 | 6575 |
| TTCN_5 | 383 | GTCN_1043 | 6536 | GTCN_4 | 423 | GTCN_1050 | 6576 |
| ATCN_4 | 384 | TTCN_1773 | 6537 | GTCN_5 | 424 | CTCN_1949 | 6577 |
| CTCN_1 | 385 | GTCN_1044 | 6538 | ATCN_8 | 425 | GTCN_1051 | 6578 |
| CTCN_2 | 386 | ATCN_1228 | 6539 | CTCN_20 | 426 | CTCN_1950 | 6579 |
| TTCN_6 | 387 | ATCN_1229 | 6540 | GTCN_6 | 427 | TTCN_1789 | 6580 |
| TTCN_7 | 388 | ATCN_1230 | 6541 | TTCN_20 | 428 | ATCN_1237 | 6581 |
| CTCN_3 | 389 | TTCN_1774 | 6542 | TTCN_21 | 429 | ATCN_1238 | 6582 |
| CTCN_4 | 390 | TTCN_1775 | 6543 | ATCN_9 | 430 | ATCN_1239 | 6583 |
| CTCN_5 | 391 | TTCN_1776 | 6544 | ATCN_10 | 431 | ATCN_1240 | 6584 |
| CTCN_6 | 392 | ATCN_1231 | 6545 | TTCN_22 | 432 | ATCN_1241 | 6585 |
| CTCN_7 | 393 | ATCN_1232 | 6546 | GTCN_7 | 433 | TTCN_1790 | 6586 |
| TTCN_8 | 394 | TTCN_1777 | 6547 | ATCN_11 | 434 | CTCN_1951 | 6587 |
| CTCN_8 | 395 | GTCN_1045 | 6548 | ATCN_12 | 435 | GTCN_1052 | 6588 |
| CTCN_9 | 396 | CTCN_1941 | 6549 | CTCN_21 | 436 | GTCN_1053 | 6589 |
| CTCN_10 | 397 | GTCN_1046 | 6550 | ATCN_13 | 437 | GTCN_1054 | 6590 |
| CTCN_11 | 398 | CTCN_1942 | 6551 | CTCN_22 | 438 | ATCN_1242 | 6591 |
| CTCN_12 | 399 | TTCN_1778 | 6552 | GTCN_8 | 439 | ATCN_1243 | 6592 |
| CTCN_13 | 400 | TTCN_1779 | 6553 | CTCN_23 | 440 | GTCN_1055 | 6593 |
| CTCN_14 | 401 | TTCN_1780 | 6554 | TTCN_23 | 441 | TTCN_1791 | 6594 |
| CTCN_15 | 402 | TTCN_1781 | 6555 | TTCN_24 | 442 | ATCN_1244 | 6595 |
| CTCN_16 | 403 | GTCN_1047 | 6556 | ATCN_14 | 443 | TTCN_1792 | 6596 |
| TTCN_9 | 404 | ATCN_1233 | 6557 | GTCN_9 | 444 | ATCN_1245 | 6597 |
| TTCN_10 | 405 | ATCN_1234 | 6558 | GTCN_10 | 445 | ATCN_1246 | 6598 |
| TTCN_11 | 406 | CTCN_1943 | 6559 | ATCN_15 | 446 | CTCN_1952 | 6599 |
| TTCN_12 | 407 | GTCN_1048 | 6560 | GTCN_11 | 447 | CTCN_1953 | 6600 |
| TTCN_13 | 408 | CTCN_1944 | 6561 | ATCN_16 | 448 | CTCN_1954 | 6601 |
| TTCN_14 | 409 | CTCN_1945 | 6562 | CTCN_24 | 449 | CTCN_1955 | 6602 |
| TTCN_15 | 410 | CTCN_1946 | 6563 | TTCN_25 | 450 | GTCN_1056 | 6603 |
| GTCN_2 | 411 | TTCN_1782 | 6564 | GTCN_12 | 451 | ATCN_1247 | 6604 |
|  |  |  |  | TTCN_26 | 452 | TTCN_1793 | 6605 |
|  |  |  |  | GTCN_13 | 453 | ATCN_1248 | 6606 |

FIG. 33 (continued)

| | | | | | | | |
|---|---|---|---|---|---|---|---|
| CTCN_25 | 454 | TTCN_1794 | 6607 | GTCN_24 | 497 | GTCN_1065 | 6650 |
| GTCN_14 | 455 | TTCN_1795 | 6608 | CTCN_38 | 498 | TTCN_1814 | 6651 |
| CTCN_26 | 456 | GTCN_1057 | 6609 | TTCN_40 | 499 | GTCN_1066 | 6652 |
| ATCN_17 | 457 | ATCN_1249 | 6610 | CTCN_39 | 500 | ATCN_1262 | 6653 |
| GTCN_15 | 458 | TTCN_1796 | 6611 | CTCN_40 | 501 | TTCN_1815 | 6654 |
| CTCN_27 | 459 | ATCN_1250 | 6612 | CTCN_41 | 502 | ATCN_1263 | 6655 |
| GTCN_16 | 460 | GTCN_1058 | 6613 | TTCN_41 | 503 | TTCN_1816 | 6656 |
| ATCN_18 | 461 | TTCN_1797 | 6614 | TTCN_42 | 504 | GTCN_1067 | 6657 |
| CTCN_28 | 462 | ATCN_1251 | 6615 | GTCN_25 | 505 | CTCN_1958 | 6658 |
| GTCN_17 | 463 | ATCN_1252 | 6616 | TTCN_43 | 506 | CTCN_1959 | 6659 |
| TTCN_27 | 464 | ATCN_1253 | 6617 | ATCN_24 | 507 | CTCN_1960 | 6660 |
| CTCN_29 | 465 | TTCN_1798 | 6618 | CTCN_42 | 508 | CTCN_1961 | 6661 |
| TTCN_28 | 466 | TTCN_1799 | 6619 | TTCN_44 | 509 | TTCN_1817 | 6662 |
| ATCN_19 | 467 | GTCN_1059 | 6620 | TTCN_45 | 510 | GTCN_1068 | 6663 |
| TTCN_29 | 468 | TTCN_1800 | 6621 | ATCN_25 | 511 | TTCN_1818 | 6664 |
| GTCN_18 | 469 | TTCN_1801 | 6622 | TTCN_46 | 512 | TTCN_1819 | 6665 |
| TTCN_30 | 470 | ATCN_1254 | 6623 | CTCN_43 | 513 | TTCN_1820 | 6666 |
| CTCN_30 | 471 | GTCN_1060 | 6624 | GTCN_26 | 514 | CTCN_1962 | 6667 |
| TTCN_31 | 472 | TTCN_1802 | 6625 | GTCN_27 | 515 | TTCN_1821 | 6668 |
| ATCN_20 | 473 | TTCN_1803 | 6626 | GTCN_28 | 516 | ATCN_1264 | 6669 |
| TTCN_32 | 474 | ATCN_1255 | 6627 | CTCN_44 | 517 | TTCN_1822 | 6670 |
| CTCN_31 | 475 | GTCN_1061 | 6628 | TTCN_47 | 518 | TTCN_1823 | 6671 |
| TTCN_33 | 476 | ATCN_1256 | 6629 | ATCN_26 | 519 | ATCN_1265 | 6672 |
| CTCN_32 | 477 | ATCN_1257 | 6630 | GTCN_29 | 520 | ATCN_1266 | 6673 |
| GTCN_19 | 478 | CTCN_1956 | 6631 | GTCN_30 | 521 | GTCN_1069 | 6674 |
| GTCN_20 | 479 | TTCN_1804 | 6632 | CTCN_45 | 522 | TTCN_1824 | 6675 |
| TTCN_34 | 480 | TTCN_1805 | 6633 | ATCN_27 | 523 | TTCN_1825 | 6676 |
| TTCN_35 | 481 | GTCN_1062 | 6634 | ATCN_28 | 524 | CTCN_1963 | 6677 |
| TTCN_36 | 482 | ATCN_1258 | 6635 | ATCN_29 | 525 | TTCN_1826 | 6678 |
| ATCN_21 | 483 | TTCN_1806 | 6636 | GTCN_31 | 526 | TTCN_1827 | 6679 |
| CTCN_33 | 484 | ATCN_1259 | 6637 | CTCN_46 | 527 | TTCN_1828 | 6680 |
| CTCN_34 | 485 | TTCN_1807 | 6638 | CTCN_47 | 528 | TTCN_1829 | 6681 |
| ATCN_22 | 486 | CTCN_1957 | 6639 | TTCN_48 | 529 | CTCN_1964 | 6682 |
| CTCN_35 | 487 | TTCN_1808 | 6640 | CTCN_48 | 530 | GTCN_1070 | 6683 |
| TTCN_37 | 488 | ATCN_1260 | 6641 | TTCN_49 | 531 | TTCN_1830 | 6684 |
| ATCN_23 | 489 | GTCN_1063 | 6642 | TTCN_50 | 532 | CTCN_1965 | 6685 |
| GTCN_21 | 490 | TTCN_1809 | 6643 | TTCN_51 | 533 | ATCN_1267 | 6686 |
| TTCN_38 | 491 | TTCN_1810 | 6644 | CTCN_49 | 534 | GTCN_1071 | 6687 |
| CTCN_36 | 492 | TTCN_1811 | 6645 | TTCN_52 | 535 | TTCN_1831 | 6688 |
| TTCN_39 | 493 | TTCN_1812 | 6646 | TTCN_53 | 536 | GTCN_1072 | 6689 |
| CTCN_37 | 494 | TTCN_1813 | 6647 | TTCN_54 | 537 | GTCN_1073 | 6690 |
| GTCN_22 | 495 | GTCN_1064 | 6648 | CTCN_50 | 538 | TTCN_1832 | 6691 |
| GTCN_23 | 496 | ATCN_1261 | 6649 | TTCN_55 | 539 | CTCN_1966 | 6692 |

FIG. 33 (continued)

| | | | | | | | |
|---|---|---|---|---|---|---|---|
| CTCN_51 | 540 | TTCN_1833 | 6693 | ATCN_39 | 583 | TTCN_1846 | 6736 |
| CTCN_52 | 541 | ATCN_1268 | 6694 | ATCN_40 | 584 | ATCN_1282 | 6737 |
| CTCN_53 | 542 | CTCN_1967 | 6695 | ATCN_41 | 585 | ATCN_1283 | 6738 |
| CTCN_54 | 543 | CTCN_1968 | 6696 | CTCN_72 | 586 | ATCN_1284 | 6739 |
| TTCN_56 | 544 | ATCN_1269 | 6697 | CTCN_73 | 587 | TTCN_1847 | 6740 |
| CTCN_55 | 545 | TTCN_1834 | 6698 | TTCN_63 | 588 | ATCN_1285 | 6741 |
| GTCN_32 | 546 | CTCN_1969 | 6699 | CTCN_74 | 589 | CTCN_1976 | 6742 |
| CTCN_56 | 547 | TTCN_1835 | 6700 | ATCN_42 | 590 | GTCN_1081 | 6743 |
| ATCN_30 | 548 | ATCN_1270 | 6701 | ATCN_43 | 591 | TTCN_1848 | 6744 |
| ATCN_31 | 549 | CTCN_1970 | 6702 | CTCN_75 | 592 | GTCN_1082 | 6745 |
| CTCN_57 | 550 | CTCN_1971 | 6703 | TTCN_64 | 593 | GTCN_1083 | 6746 |
| CTCN_58 | 551 | ATCN_1271 | 6704 | CTCN_76 | 594 | ATCN_1286 | 6747 |
| CTCN_59 | 552 | GTCN_1074 | 6705 | GTCN_38 | 595 | ATCN_1287 | 6748 |
| TTCN_57 | 553 | ATCN_1272 | 6706 | CTCN_77 | 596 | GTCN_1084 | 6749 |
| TTCN_58 | 554 | TTCN_1836 | 6707 | GTCN_39 | 597 | TTCN_1849 | 6750 |
| CTCN_60 | 555 | GTCN_1075 | 6708 | GTCN_40 | 598 | TTCN_1850 | 6751 |
| CTCN_61 | 556 | TTCN_1837 | 6709 | CTCN_78 | 599 | GTCN_1085 | 6752 |
| CTCN_62 | 557 | ATCN_1273 | 6710 | GTCN_41 | 600 | TTCN_1851 | 6753 |
| CTCN_63 | 558 | GTCN_1076 | 6711 | CTCN_79 | 601 | TTCN_1852 | 6754 |
| ATCN_32 | 559 | TTCN_1838 | 6712 | CTCN_80 | 602 | CTCN_1977 | 6755 |
| CTCN_64 | 560 | TTCN_1839 | 6713 | CTCN_81 | 603 | TTCN_1853 | 6756 |
| CTCN_65 | 561 | TTCN_1840 | 6714 | CTCN_82 | 604 | ATCN_1288 | 6757 |
| GTCN_33 | 562 | GTCN_1077 | 6715 | ATCN_44 | 605 | TTCN_1854 | 6758 |
| TTCN_59 | 563 | TTCN_1841 | 6716 | CTCN_83 | 606 | CTCN_1978 | 6759 |
| GTCN_34 | 564 | TTCN_1842 | 6717 | CTCN_84 | 607 | ATCN_1289 | 6760 |
| TTCN_60 | 565 | GTCN_1078 | 6718 | CTCN_85 | 608 | TTCN_1855 | 6761 |
| CTCN_66 | 566 | ATCN_1274 | 6719 | ATCN_45 | 609 | TTCN_1856 | 6762 |
| GTCN_35 | 567 | ATCN_1275 | 6720 | CTCN_86 | 610 | ATCN_1290 | 6763 |
| TTCN_61 | 568 | TTCN_1843 | 6721 | TTCN_65 | 611 | ATCN_1291 | 6764 |
| ATCN_33 | 569 | ATCN_1276 | 6722 | CTCN_87 | 612 | TTCN_1857 | 6765 |
| ATCN_34 | 570 | GTCN_1079 | 6723 | ATCN_46 | 613 | CTCN_1979 | 6766 |
| CTCN_67 | 571 | CTCN_1972 | 6724 | CTCN_88 | 614 | GTCN_1086 | 6767 |
| CTCN_68 | 572 | CTCN_1973 | 6725 | CTCN_89 | 615 | ATCN_1292 | 6768 |
| ATCN_35 | 573 | ATCN_1277 | 6726 | TTCN_66 | 616 | GTCN_1087 | 6769 |
| CTCN_69 | 574 | ATCN_1278 | 6727 | GTCN_42 | 617 | CTCN_1980 | 6770 |
| ATCN_36 | 575 | TTCN_1844 | 6728 | TTCN_67 | 618 | GTCN_1088 | 6771 |
| TTCN_62 | 576 | ATCN_1279 | 6729 | TTCN_68 | 619 | GTCN_1089 | 6772 |
| CTCN_70 | 577 | ATCN_1280 | 6730 | GTCN_43 | 620 | TTCN_1858 | 6773 |
| ATCN_37 | 578 | ATCN_1281 | 6731 | ATCN_47 | 621 | TTCN_1859 | 6774 |
| GTCN_36 | 579 | GTCN_1080 | 6732 | TTCN_69 | 622 | TTCN_1860 | 6775 |
| GTCN_37 | 580 | TTCN_1845 | 6733 | TTCN_70 | 623 | GTCN_1090 | 6776 |
| CTCN_71 | 581 | CTCN_1974 | 6734 | CTCN_90 | 624 | ATCN_1293 | 6777 |
| ATCN_38 | 582 | CTCN_1975 | 6735 | CTCN_91 | 625 | TTCN_1861 | 6778 |

FIG. 33 (continued)

| | | | | | | | |
|---|---|---|---|---|---|---|---|
| CTCN_92 | 626 | CTCN_1981 | 6779 | CTCN_109 | 669 | TTCN_1880 | 6822 |
| CTCN_93 | 627 | CTCN_1982 | 6780 | GTCN_53 | 670 | TTCN_1881 | 6823 |
| TTCN_71 | 628 | GTCN_1091 | 6781 | TTCN_81 | 671 | TTCN_1882 | 6824 |
| TTCN_72 | 629 | ATCN_1294 | 6782 | CTCN_110 | 672 | ATCN_1302 | 6825 |
| TTCN_73 | 630 | CTCN_1983 | 6783 | CTCN_111 | 673 | CTCN_1993 | 6826 |
| TTCN_74 | 631 | CTCN_1984 | 6784 | TTCN_82 | 674 | CTCN_1994 | 6827 |
| GTCN_44 | 632 | ATCN_1295 | 6785 | ATCN_55 | 675 | ATCN_1303 | 6828 |
| GTCN_45 | 633 | CTCN_1985 | 6786 | ATCN_56 | 676 | ATCN_1304 | 6829 |
| TTCN_75 | 634 | TTCN_1862 | 6787 | TTCN_83 | 677 | CTCN_1995 | 6830 |
| ATCN_48 | 635 | CTCN_1986 | 6788 | CTCN_112 | 678 | CTCN_1996 | 6831 |
| TTCN_76 | 636 | ATCN_1296 | 6789 | ATCN_57 | 679 | TTCN_1883 | 6832 |
| CTCN_94 | 637 | ATCN_1297 | 6790 | TTCN_84 | 680 | TTCN_1884 | 6833 |
| GTCN_46 | 638 | TTCN_1863 | 6791 | CTCN_113 | 681 | GTCN_1096 | 6834 |
| CTCN_95 | 639 | TTCN_1864 | 6792 | CTCN_114 | 682 | ATCN_1305 | 6835 |
| GTCN_47 | 640 | TTCN_1865 | 6793 | ATCN_58 | 683 | TTCN_1885 | 6836 |
| CTCN_96 | 641 | GTCN_1092 | 6794 | ATCN_59 | 684 | TTCN_1886 | 6837 |
| CTCN_97 | 642 | ATCN_1298 | 6795 | CTCN_115 | 685 | TTCN_1887 | 6838 |
| ATCN_49 | 643 | ATCN_1299 | 6796 | CTCN_116 | 686 | ATCN_1306 | 6839 |
| CTCN_98 | 644 | TTCN_1866 | 6797 | CTCN_117 | 687 | CTCN_1997 | 6840 |
| GTCN_48 | 645 | ATCN_1300 | 6798 | CTCN_118 | 688 | CTCN_1998 | 6841 |
| CTCN_99 | 646 | TTCN_1867 | 6799 | GTCN_54 | 689 | TTCN_1888 | 6842 |
| CTCN_100 | 647 | TTCN_1868 | 6800 | TTCN_85 | 690 | TTCN_1889 | 6843 |
| CTCN_101 | 648 | GTCN_1093 | 6801 | GTCN_55 | 691 | TTCN_1890 | 6844 |
| ATCN_50 | 649 | TTCN_1869 | 6802 | CTCN_119 | 692 | CTCN_1999 | 6845 |
| ATCN_51 | 650 | CTCN_1987 | 6803 | TTCN_86 | 693 | CTCN_2000 | 6846 |
| GTCN_49 | 651 | TTCN_1870 | 6804 | GTCN_56 | 694 | GTCN_1097 | 6847 |
| CTCN_102 | 652 | TTCN_1871 | 6805 | TTCN_87 | 695 | CTCN_2001 | 6848 |
| ATCN_52 | 653 | TTCN_1872 | 6806 | ATCN_60 | 696 | TTCN_1891 | 6849 |
| TTCN_77 | 654 | CTCN_1988 | 6807 | CTCN_120 | 697 | TTCN_1892 | 6850 |
| CTCN_103 | 655 | GTCN_1094 | 6808 | ATCN_61 | 698 | ATCN_1307 | 6851 |
| CTCN_104 | 656 | TTCN_1873 | 6809 | TTCN_88 | 699 | GTCN_1098 | 6852 |
| TTCN_78 | 657 | CTCN_1989 | 6810 | GTCN_57 | 700 | TTCN_1893 | 6853 |
| ATCN_53 | 658 | CTCN_1990 | 6811 | CTCN_121 | 701 | GTCN_1099 | 6854 |
| ATCN_54 | 659 | CTCN_1991 | 6812 | TTCN_89 | 702 | TTCN_1894 | 6855 |
| TTCN_79 | 660 | TTCN_1874 | 6813 | ATCN_62 | 703 | GTCN_1100 | 6856 |
| CTCN_105 | 661 | TTCN_1875 | 6814 | TTCN_90 | 704 | ATCN_1308 | 6857 |
| TTCN_80 | 662 | CTCN_1992 | 6815 | CTCN_122 | 705 | ATCN_1309 | 6858 |
| CTCN_106 | 663 | GTCN_1095 | 6816 | TTCN_91 | 706 | TTCN_1895 | 6859 |
| GTCN_50 | 664 | TTCN_1876 | 6817 | ATCN_63 | 707 | TTCN_1896 | 6860 |
| GTCN_51 | 665 | TTCN_1877 | 6818 | GTCN_58 | 708 | TTCN_1897 | 6861 |
| GTCN_52 | 666 | TTCN_1878 | 6819 | ATCN_64 | 709 | GTCN_1101 | 6862 |
| CTCN_107 | 667 | TTCN_1879 | 6820 | CTCN_123 | 710 | TTCN_1898 | 6863 |
| CTCN_108 | 668 | ATCN_1301 | 6821 | TTCN_92 | 711 | CTCN_2002 | 6864 |

FIG. 33 (continued)

| | | | | | | | |
|---|---|---|---|---|---|---|---|
| GTCN_59 | 712 | GTCN_1102 | 6865 | CTCN_133 | 755 | TTCN_1915 | 6908 |
| ATCN_65 | 713 | ATCN_1310 | 6866 | TTCN_104 | 756 | TTCN_1916 | 6909 |
| ATCN_66 | 714 | TTCN_1899 | 6867 | CTCN_134 | 757 | TTCN_1917 | 6910 |
| CTCN_124 | 715 | CTCN_2003 | 6868 | CTCN_135 | 758 | TTCN_1918 | 6911 |
| CTCN_125 | 716 | CTCN_2004 | 6869 | TTCN_105 | 759 | CTCN_2011 | 6912 |
| GTCN_60 | 717 | TTCN_1900 | 6870 | CTCN_136 | 760 | TTCN_1919 | 6913 |
| ATCN_67 | 718 | TTCN_1901 | 6871 | TTCN_106 | 761 | TTCN_1920 | 6914 |
| CTCN_126 | 719 | GTCN_1103 | 6872 | TTCN_107 | 762 | TTCN_1921 | 6915 |
| TTCN_93 | 720 | ATCN_1311 | 6873 | GTCN_69 | 763 | TTCN_1922 | 6916 |
| TTCN_94 | 721 | TTCN_1902 | 6874 | TTCN_108 | 764 | TTCN_1923 | 6917 |
| TTCN_95 | 722 | CTCN_2005 | 6875 | TTCN_109 | 765 | GTCN_1109 | 6918 |
| GTCN_61 | 723 | ATCN_1312 | 6876 | TTCN_110 | 766 | CTCN_2012 | 6919 |
| ATCN_68 | 724 | GTCN_1104 | 6877 | GTCN_70 | 767 | CTCN_2013 | 6920 |
| ATCN_69 | 725 | CTCN_2006 | 6878 | CTCN_137 | 768 | ATCN_1322 | 6921 |
| ATCN_70 | 726 | CTCN_2007 | 6879 | GTCN_71 | 769 | TTCN_1924 | 6922 |
| GTCN_62 | 727 | TTCN_1903 | 6880 | TTCN_111 | 770 | TTCN_1925 | 6923 |
| TTCN_96 | 728 | CTCN_2008 | 6881 | TTCN_112 | 771 | TTCN_1926 | 6924 |
| ATCN_71 | 729 | ATCN_1313 | 6882 | CTCN_138 | 772 | ATCN_1323 | 6925 |
| GTCN_63 | 730 | TTCN_1904 | 6883 | ATCN_78 | 773 | TTCN_1927 | 6926 |
| GTCN_64 | 731 | GTCN_1105 | 6884 | CTCN_139 | 774 | GTCN_1110 | 6927 |
| CTCN_127 | 732 | CTCN_2009 | 6885 | GTCN_72 | 775 | TTCN_1928 | 6928 |
| CTCN_128 | 733 | TTCN_1905 | 6886 | GTCN_73 | 776 | GTCN_1111 | 6929 |
| ATCN_72 | 734 | CTCN_2010 | 6887 | ATCN_79 | 777 | ATCN_1324 | 6930 |
| ATCN_73 | 735 | TTCN_1906 | 6888 | GTCN_74 | 778 | ATCN_1325 | 6931 |
| CTCN_129 | 736 | TTCN_1907 | 6889 | TTCN_113 | 779 | ATCN_1326 | 6932 |
| ATCN_74 | 737 | TTCN_1908 | 6890 | TTCN_114 | 780 | TTCN_1929 | 6933 |
| GTCN_65 | 738 | ATCN_1314 | 6891 | GTCN_75 | 781 | ATCN_1327 | 6934 |
| ATCN_75 | 739 | GTCN_1106 | 6892 | GTCN_76 | 782 | CTCN_2014 | 6935 |
| TTCN_97 | 740 | ATCN_1315 | 6893 | ATCN_80 | 783 | TTCN_1930 | 6936 |
| ATCN_76 | 741 | GTCN_1107 | 6894 | CTCN_140 | 784 | TTCN_1931 | 6937 |
| TTCN_98 | 742 | ATCN_1316 | 6895 | TTCN_115 | 785 | CTCN_2015 | 6938 |
| CTCN_130 | 743 | TTCN_1909 | 6896 | CTCN_141 | 786 | ATCN_1328 | 6939 |
| GTCN_66 | 744 | TTCN_1910 | 6897 | ATCN_81 | 787 | TTCN_1932 | 6940 |
| ATCN_77 | 745 | ATCN_1317 | 6898 | CTCN_142 | 788 | TTCN_1933 | 6941 |
| CTCN_131 | 746 | TTCN_1911 | 6899 | ATCN_82 | 789 | GTCN_1112 | 6942 |
| GTCN_67 | 747 | GTCN_1108 | 6900 | ATCN_83 | 790 | GTCN_1113 | 6943 |
| TTCN_99 | 748 | ATCN_1318 | 6901 | CTCN_143 | 791 | CTCN_2016 | 6944 |
| GTCN_68 | 749 | TTCN_1912 | 6902 | TTCN_116 | 792 | ATCN_1329 | 6945 |
| TTCN_100 | 750 | ATCN_1319 | 6903 | TTCN_117 | 793 | TTCN_1934 | 6946 |
| CTCN_132 | 751 | TTCN_1913 | 6904 | TTCN_118 | 794 | CTCN_2017 | 6947 |
| TTCN_101 | 752 | ATCN_1320 | 6905 | GTCN_77 | 795 | TTCN_1935 | 6948 |
| TTCN_102 | 753 | ATCN_1321 | 6906 | TTCN_119 | 796 | GTCN_1114 | 6949 |
| TTCN_103 | 754 | TTCN_1914 | 6907 | ATCN_84 | 797 | TTCN_1936 | 6950 |

FIG. 33 (continued)

| | | | | | | | |
|---|---|---|---|---|---|---|---|
| CTCN_144 | 798 | ATCN_1330 | 6951 | TTCN_139 | 841 | CTCN_2031 | 6994 |
| TTCN_120 | 799 | GTCN_1115 | 6952 | CTCN_155 | 842 | CTCN_2032 | 6995 |
| TTCN_121 | 800 | GTCN_1116 | 6953 | CTCN_156 | 843 | CTCN_2033 | 6996 |
| ATCN_85 | 801 | CTCN_2018 | 6954 | TTCN_140 | 844 | TTCN_1952 | 6997 |
| CTCN_145 | 802 | CTCN_2019 | 6955 | ATCN_92 | 845 | ATCN_1337 | 6998 |
| CTCN_146 | 803 | GTCN_1117 | 6956 | ATCN_93 | 846 | TTCN_1953 | 6999 |
| TTCN_122 | 804 | TTCN_1937 | 6957 | TTCN_141 | 847 | TTCN_1954 | 7000 |
| TTCN_123 | 805 | ATCN_1331 | 6958 | TTCN_142 | 848 | ATCN_1338 | 7001 |
| ATCN_86 | 806 | TTCN_1938 | 6959 | GTCN_84 | 849 | CTCN_2034 | 7002 |
| TTCN_124 | 807 | TTCN_1939 | 6960 | GTCN_85 | 850 | CTCN_2035 | 7003 |
| TTCN_125 | 808 | TTCN_1940 | 6961 | CTCN_157 | 851 | CTCN_2036 | 7004 |
| TTCN_126 | 809 | TTCN_1941 | 6962 | ATCN_94 | 852 | TTCN_1955 | 7005 |
| GTCN_78 | 810 | CTCN_2020 | 6963 | TTCN_143 | 853 | TTCN_1956 | 7006 |
| TTCN_127 | 811 | ATCN_1332 | 6964 | ATCN_95 | 854 | GTCN_1123 | 7007 |
| TTCN_128 | 812 | CTCN_2021 | 6965 | CTCN_158 | 855 | CTCN_2037 | 7008 |
| TTCN_129 | 813 | CTCN_2022 | 6966 | GTCN_86 | 856 | GTCN_1124 | 7009 |
| GTCN_79 | 814 | TTCN_1942 | 6967 | TTCN_144 | 857 | TTCN_1957 | 7010 |
| ATCN_87 | 815 | GTCN_1118 | 6968 | TTCN_145 | 858 | CTCN_2038 | 7011 |
| CTCN_147 | 816 | CTCN_2023 | 6969 | GTCN_87 | 859 | TTCN_1958 | 7012 |
| CTCN_148 | 817 | CTCN_2024 | 6970 | ATCN_96 | 860 | TTCN_1959 | 7013 |
| CTCN_149 | 818 | TTCN_1943 | 6971 | CTCN_159 | 861 | GTCN_1125 | 7014 |
| TTCN_130 | 819 | ATCN_1333 | 6972 | CTCN_160 | 862 | TTCN_1960 | 7015 |
| TTCN_131 | 820 | GTCN_1119 | 6973 | CTCN_161 | 863 | CTCN_2039 | 7016 |
| GTCN_80 | 821 | TTCN_1944 | 6974 | ATCN_97 | 864 | TTCN_1961 | 7017 |
| TTCN_132 | 822 | TTCN_1945 | 6975 | TTCN_146 | 865 | GTCN_1126 | 7018 |
| TTCN_133 | 823 | TTCN_1946 | 6976 | ATCN_98 | 866 | GTCN_1127 | 7019 |
| TTCN_134 | 824 | TTCN_1947 | 6977 | CTCN_162 | 867 | CTCN_2040 | 7020 |
| ATCN_88 | 825 | ATCN_1334 | 6978 | CTCN_163 | 868 | TTCN_1962 | 7021 |
| CTCN_150 | 826 | TTCN_1948 | 6979 | CTCN_164 | 869 | TTCN_1963 | 7022 |
| TTCN_135 | 827 | CTCN_2025 | 6980 | CTCN_165 | 870 | CTCN_2041 | 7023 |
| TTCN_136 | 828 | ATCN_1335 | 6981 | TTCN_147 | 871 | TTCN_1964 | 7024 |
| CTCN_151 | 829 | ATCN_1336 | 6982 | CTCN_166 | 872 | TTCN_1965 | 7025 |
| CTCN_152 | 830 | CTCN_2026 | 6983 | ATCN_99 | 873 | TTCN_1966 | 7026 |
| GTCN_81 | 831 | CTCN_2027 | 6984 | TTCN_148 | 874 | CTCN_2042 | 7027 |
| ATCN_89 | 832 | CTCN_2028 | 6985 | TTCN_149 | 875 | CTCN_2043 | 7028 |
| GTCN_82 | 833 | TTCN_1949 | 6986 | TTCN_150 | 876 | CTCN_2044 | 7029 |
| GTCN_83 | 834 | GTCN_1120 | 6987 | TTCN_151 | 877 | GTCN_1128 | 7030 |
| ATCN_90 | 835 | GTCN_1121 | 6988 | ATCN_100 | 878 | CTCN_2045 | 7031 |
| CTCN_153 | 836 | TTCN_1950 | 6989 | TTCN_152 | 879 | CTCN_2046 | 7032 |
| CTCN_154 | 837 | TTCN_1951 | 6990 | TTCN_153 | 880 | ATCN_1339 | 7033 |
| ATCN_91 | 838 | GTCN_1122 | 6991 | CTCN_167 | 881 | CTCN_2047 | 7034 |
| TTCN_137 | 839 | CTCN_2029 | 6992 | CTCN_168 | 882 | TTCN_1967 | 7035 |
| TTCN_138 | 840 | CTCN_2030 | 6993 | ATCN_101 | 883 | ATCN_1340 | 7036 |

FIG. 33 (continued)

| | | | | | | | |
|---|---|---|---|---|---|---|---|
| GTCN_88 | 884 | CTCN_2048 | 7037 | ATCN_109 | 927 | TTCN_1980 | 7080 |
| ATCN_102 | 885 | CTCN_2049 | 7038 | ATCN_110 | 928 | CTCN_2064 | 7081 |
| GTCN_89 | 886 | CTCN_2050 | 7039 | CTCN_186 | 929 | ATCN_1348 | 7082 |
| ATCN_103 | 887 | CTCN_2051 | 7040 | CTCN_187 | 930 | TTCN_1981 | 7083 |
| CTCN_169 | 888 | GTCN_1129 | 7041 | ATCN_111 | 931 | GTCN_1137 | 7084 |
| TTCN_154 | 889 | CTCN_2052 | 7042 | CTCN_188 | 932 | CTCN_2065 | 7085 |
| TTCN_155 | 890 | ATCN_1341 | 7043 | GTCN_93 | 933 | GTCN_1138 | 7086 |
| CTCN_170 | 891 | CTCN_2053 | 7044 | GTCN_94 | 934 | TTCN_1982 | 7087 |
| CTCN_171 | 892 | GTCN_1130 | 7045 | CTCN_189 | 935 | GTCN_1139 | 7088 |
| CTCN_172 | 893 | TTCN_1968 | 7046 | CTCN_190 | 936 | CTCN_2066 | 7089 |
| CTCN_173 | 894 | CTCN_2054 | 7047 | CTCN_191 | 937 | TTCN_1983 | 7090 |
| TTCN_156 | 895 | CTCN_2055 | 7048 | TTCN_168 | 938 | TTCN_1984 | 7091 |
| TTCN_157 | 896 | TTCN_1969 | 7049 | CTCN_192 | 939 | GTCN_1140 | 7092 |
| CTCN_174 | 897 | GTCN_1131 | 7050 | TTCN_169 | 940 | TTCN_1985 | 7093 |
| CTCN_175 | 898 | CTCN_2056 | 7051 | TTCN_170 | 941 | TTCN_1986 | 7094 |
| ATCN_104 | 899 | GTCN_1132 | 7052 | CTCN_193 | 942 | CTCN_2067 | 7095 |
| CTCN_176 | 900 | GTCN_1133 | 7053 | TTCN_171 | 943 | CTCN_2068 | 7096 |
| TTCN_158 | 901 | CTCN_2057 | 7054 | CTCN_194 | 944 | ATCN_1349 | 7097 |
| TTCN_159 | 902 | CTCN_2058 | 7055 | CTCN_195 | 945 | GTCN_1141 | 7098 |
| TTCN_160 | 903 | TTCN_1970 | 7056 | CTCN_196 | 946 | CTCN_2069 | 7099 |
| CTCN_177 | 904 | CTCN_2059 | 7057 | TTCN_172 | 947 | ATCN_1350 | 7100 |
| CTCN_178 | 905 | CTCN_2060 | 7058 | CTCN_197 | 948 | GTCN_1142 | 7101 |
| CTCN_179 | 906 | CTCN_2061 | 7059 | CTCN_198 | 949 | ATCN_1351 | 7102 |
| TTCN_161 | 907 | GTCN_1134 | 7060 | TTCN_173 | 950 | TTCN_1987 | 7103 |
| TTCN_162 | 908 | ATCN_1342 | 7061 | GTCN_95 | 951 | CTCN_2070 | 7104 |
| TTCN_163 | 909 | CTCN_2062 | 7062 | CTCN_199 | 952 | TTCN_1988 | 7105 |
| TTCN_164 | 910 | ATCN_1343 | 7063 | TTCN_174 | 953 | CTCN_2071 | 7106 |
| ATCN_105 | 911 | ATCN_1344 | 7064 | CTCN_200 | 954 | CTCN_2072 | 7107 |
| TTCN_165 | 912 | TTCN_1971 | 7065 | TTCN_175 | 955 | ATCN_1352 | 7108 |
| ATCN_106 | 913 | TTCN_1972 | 7066 | GTCN_96 | 956 | CTCN_2073 | 7109 |
| CTCN_180 | 914 | GTCN_1135 | 7067 | ATCN_112 | 957 | GTCN_1143 | 7110 |
| CTCN_181 | 915 | TTCN_1973 | 7068 | GTCN_97 | 958 | TTCN_1989 | 7111 |
| TTCN_166 | 916 | TTCN_1974 | 7069 | CTCN_201 | 959 | GTCN_1144 | 7112 |
| GTCN_90 | 917 | ATCN_1345 | 7070 | GTCN_98 | 960 | ATCN_1353 | 7113 |
| ATCN_107 | 918 | ATCN_1346 | 7071 | CTCN_202 | 961 | TTCN_1990 | 7114 |
| CTCN_182 | 919 | TTCN_1975 | 7072 | CTCN_203 | 962 | GTCN_1145 | 7115 |
| ATCN_108 | 920 | TTCN_1976 | 7073 | ATCN_113 | 963 | GTCN_1146 | 7116 |
| CTCN_183 | 921 | TTCN_1977 | 7074 | CTCN_204 | 964 | CTCN_2074 | 7117 |
| GTCN_91 | 922 | GTCN_1136 | 7075 | TTCN_176 | 965 | CTCN_2075 | 7118 |
| CTCN_184 | 923 | CTCN_2063 | 7076 | ATCN_114 | 966 | GTCN_1147 | 7119 |
| TTCN_167 | 924 | TTCN_1978 | 7077 | ATCN_115 | 967 | GTCN_1148 | 7120 |
| CTCN_185 | 925 | TTCN_1979 | 7078 | GTCN_99 | 968 | TTCN_1991 | 7121 |
| GTCN_92 | 926 | ATCN_1347 | 7079 | GTCN_100 | 969 | ATCN_1354 | 7122 |

FIG. 33 (continued)

| | | | | | | | | |
|---|---|---|---|---|---|---|---|---|
| CTCN_205 | 970 | CTCN_2076 | 7123 | ATCN_128 | 1013 | ATCN_1360 | 7166 |
| TTCN_177 | 971 | TTCN_1992 | 7124 | ATCN_129 | 1014 | ATCN_1361 | 7167 |
| TTCN_178 | 972 | TTCN_1993 | 7125 | ATCN_130 | 1015 | CTCN_2087 | 7168 |
| ATCN_116 | 973 | TTCN_1994 | 7126 | GTCN_105 | 1016 | GTCN_1157 | 7169 |
| ATCN_117 | 974 | ATCN_1355 | 7127 | CTCN_218 | 1017 | CTCN_2088 | 7170 |
| CTCN_206 | 975 | TTCN_1995 | 7128 | CTCN_219 | 1018 | GTCN_1158 | 7171 |
| ATCN_118 | 976 | TTCN_1996 | 7129 | CTCN_220 | 1019 | CTCN_2089 | 7172 |
| GTCN_101 | 977 | CTCN_2077 | 7130 | CTCN_221 | 1020 | ATCN_1362 | 7173 |
| TTCN_179 | 978 | GTCN_1149 | 7131 | ATCN_131 | 1021 | GTCN_1159 | 7174 |
| TTCN_180 | 979 | CTCN_2078 | 7132 | GTCN_106 | 1022 | ATCN_1363 | 7175 |
| CTCN_207 | 980 | GTCN_1150 | 7133 | GTCN_107 | 1023 | ATCN_1364 | 7176 |
| ATCN_119 | 981 | ATCN_1356 | 7134 | TTCN_191 | 1024 | TTCN_2011 | 7177 |
| CTCN_208 | 982 | CTCN_2079 | 7135 | GTCN_108 | 1025 | TTCN_2012 | 7178 |
| ATCN_120 | 983 | TTCN_1997 | 7136 | GTCN_109 | 1026 | TTCN_2013 | 7179 |
| ATCN_121 | 984 | TTCN_1998 | 7137 | GTCN_110 | 1027 | ATCN_1365 | 7180 |
| TTCN_181 | 985 | TTCN_1999 | 7138 | CTCN_222 | 1028 | CTCN_2090 | 7181 |
| TTCN_182 | 986 | CTCN_2080 | 7139 | ATCN_132 | 1029 | ATCN_1366 | 7182 |
| ATCN_122 | 987 | GTCN_1151 | 7140 | GTCN_111 | 1030 | GTCN_1160 | 7183 |
| ATCN_123 | 988 | ATCN_1357 | 7141 | TTCN_192 | 1031 | TTCN_2014 | 7184 |
| CTCN_209 | 989 | CTCN_2081 | 7142 | CTCN_223 | 1032 | CTCN_2091 | 7185 |
| CTCN_210 | 990 | TTCN_2000 | 7143 | CTCN_224 | 1033 | TTCN_2015 | 7186 |
| TTCN_183 | 991 | TTCN_2001 | 7144 | TTCN_193 | 1034 | TTCN_2016 | 7187 |
| CTCN_211 | 992 | GTCN_1152 | 7145 | CTCN_225 | 1035 | TTCN_2017 | 7188 |
| ATCN_124 | 993 | TTCN_2002 | 7146 | CTCN_226 | 1036 | TTCN_2018 | 7189 |
| TTCN_184 | 994 | CTCN_2082 | 7147 | CTCN_227 | 1037 | TTCN_2019 | 7190 |
| CTCN_212 | 995 | CTCN_2083 | 7148 | TTCN_194 | 1038 | TTCN_2020 | 7191 |
| CTCN_213 | 996 | TTCN_2003 | 7149 | ATCN_133 | 1039 | TTCN_2021 | 7192 |
| GTCN_102 | 997 | GTCN_1153 | 7150 | GTCN_112 | 1040 | TTCN_2022 | 7193 |
| CTCN_214 | 998 | CTCN_2084 | 7151 | TTCN_195 | 1041 | GTCN_1161 | 7194 |
| CTCN_215 | 999 | ATCN_1358 | 7152 | ATCN_134 | 1042 | TTCN_2023 | 7195 |
| GTCN_103 | 1000 | TTCN_2004 | 7153 | GTCN_113 | 1043 | GTCN_1162 | 7196 |
| TTCN_185 | 1001 | ATCN_1359 | 7154 | ATCN_135 | 1044 | TTCN_2024 | 7197 |
| TTCN_186 | 1002 | TTCN_2005 | 7155 | ATCN_136 | 1045 | TTCN_2025 | 7198 |
| CTCN_216 | 1003 | TTCN_2006 | 7156 | ATCN_137 | 1046 | ATCN_1367 | 7199 |
| ATCN_125 | 1004 | GTCN_1154 | 7157 | CTCN_228 | 1047 | CTCN_2092 | 7200 |
| TTCN_187 | 1005 | TTCN_2007 | 7158 | ATCN_138 | 1048 | CTCN_2093 | 7201 |
| CTCN_217 | 1006 | CTCN_2085 | 7159 | ATCN_139 | 1049 | ATCN_1368 | 7202 |
| TTCN_188 | 1007 | GTCN_1155 | 7160 | GTCN_114 | 1050 | CTCN_2094 | 7203 |
| ATCN_126 | 1008 | GTCN_1156 | 7161 | CTCN_229 | 1051 | GTCN_1163 | 7204 |
| TTCN_189 | 1009 | TTCN_2008 | 7162 | CTCN_230 | 1052 | TTCN_2026 | 7205 |
| ATCN_127 | 1010 | TTCN_2009 | 7163 | GTCN_115 | 1053 | GTCN_1164 | 7206 |
| GTCN_104 | 1011 | CTCN_2086 | 7164 | GTCN_116 | 1054 | TTCN_2027 | 7207 |
| TTCN_190 | 1012 | TTCN_2010 | 7165 | GTCN_117 | 1055 | TTCN_2028 | 7208 |

FIG. 33 (continued)

| | | | | | | | |
|---|---|---|---|---|---|---|---|
| CTCN_231 | 1056 | TTCN_2029 | 7209 | TTCN_210 | 1099 | CTCN_2102 | 7252 |
| CTCN_232 | 1057 | TTCN_2030 | 7210 | ATCN_145 | 1100 | ATCN_1380 | 7253 |
| CTCN_233 | 1058 | ATCN_1369 | 7211 | TTCN_211 | 1101 | TTCN_2046 | 7254 |
| CTCN_234 | 1059 | CTCN_2095 | 7212 | TTCN_212 | 1102 | CTCN_2103 | 7255 |
| GTCN_118 | 1060 | CTCN_2096 | 7213 | TTCN_213 | 1103 | TTCN_2047 | 7256 |
| TTCN_196 | 1061 | ATCN_1370 | 7214 | TTCN_214 | 1104 | ATCN_1381 | 7257 |
| GTCN_119 | 1062 | GTCN_1165 | 7215 | TTCN_215 | 1105 | TTCN_2048 | 7258 |
| GTCN_120 | 1063 | ATCN_1371 | 7216 | GTCN_124 | 1106 | CTCN_2104 | 7259 |
| TTCN_197 | 1064 | TTCN_2031 | 7217 | ATCN_146 | 1107 | TTCN_2049 | 7260 |
| CTCN_235 | 1065 | CTCN_2097 | 7218 | TTCN_216 | 1108 | GTCN_1173 | 7261 |
| CTCN_236 | 1066 | TTCN_2032 | 7219 | TTCN_217 | 1109 | TTCN_2050 | 7262 |
| CTCN_237 | 1067 | ATCN_1372 | 7220 | TTCN_218 | 1110 | TTCN_2051 | 7263 |
| ATCN_140 | 1068 | TTCN_2033 | 7221 | CTCN_249 | 1111 | TTCN_2052 | 7264 |
| ATCN_141 | 1069 | TTCN_2034 | 7222 | CTCN_250 | 1112 | GTCN_1174 | 7265 |
| CTCN_238 | 1070 | TTCN_2035 | 7223 | GTCN_125 | 1113 | ATCN_1382 | 7266 |
| TTCN_198 | 1071 | TTCN_2036 | 7224 | CTCN_251 | 1114 | GTCN_1175 | 7267 |
| ATCN_142 | 1072 | GTCN_1166 | 7225 | GTCN_126 | 1115 | CTCN_2105 | 7268 |
| CTCN_239 | 1073 | CTCN_2098 | 7226 | TTCN_219 | 1116 | CTCN_2106 | 7269 |
| TTCN_199 | 1074 | ATCN_1373 | 7227 | GTCN_127 | 1117 | ATCN_1383 | 7270 |
| CTCN_240 | 1075 | ATCN_1374 | 7228 | TTCN_220 | 1118 | ATCN_1384 | 7271 |
| TTCN_200 | 1076 | TTCN_2037 | 7229 | CTCN_252 | 1119 | TTCN_2053 | 7272 |
| TTCN_201 | 1077 | GTCN_1167 | 7230 | GTCN_128 | 1120 | TTCN_2054 | 7273 |
| ATCN_143 | 1078 | GTCN_1168 | 7231 | CTCN_253 | 1121 | TTCN_2055 | 7274 |
| TTCN_202 | 1079 | TTCN_2038 | 7232 | CTCN_254 | 1122 | TTCN_2056 | 7275 |
| TTCN_203 | 1080 | GTCN_1169 | 7233 | ATCN_147 | 1123 | ATCN_1385 | 7276 |
| TTCN_204 | 1081 | TTCN_2039 | 7234 | ATCN_148 | 1124 | ATCN_1386 | 7277 |
| GTCN_121 | 1082 | ATCN_1375 | 7235 | CTCN_255 | 1125 | TTCN_2057 | 7278 |
| GTCN_122 | 1083 | TTCN_2040 | 7236 | TTCN_221 | 1126 | GTCN_1176 | 7279 |
| CTCN_241 | 1084 | TTCN_2041 | 7237 | GTCN_129 | 1127 | GTCN_1177 | 7280 |
| CTCN_242 | 1085 | ATCN_1376 | 7238 | CTCN_256 | 1128 | CTCN_2107 | 7281 |
| CTCN_243 | 1086 | CTCN_2099 | 7239 | TTCN_222 | 1129 | GTCN_1178 | 7282 |
| CTCN_244 | 1087 | ATCN_1377 | 7240 | ATCN_149 | 1130 | TTCN_2058 | 7283 |
| TTCN_205 | 1088 | CTCN_2100 | 7241 | TTCN_223 | 1131 | TTCN_2059 | 7284 |
| ATCN_144 | 1089 | GTCN_1170 | 7242 | CTCN_257 | 1132 | ATCN_1387 | 7285 |
| TTCN_206 | 1090 | TTCN_2042 | 7243 | CTCN_258 | 1133 | TTCN_2060 | 7286 |
| CTCN_245 | 1091 | CTCN_2101 | 7244 | TTCN_224 | 1134 | TTCN_2061 | 7287 |
| CTCN_246 | 1092 | TTCN_2043 | 7245 | ATCN_150 | 1135 | TTCN_2062 | 7288 |
| CTCN_247 | 1093 | GTCN_1171 | 7246 | TTCN_225 | 1136 | TTCN_2063 | 7289 |
| TTCN_207 | 1094 | TTCN_2044 | 7247 | TTCN_226 | 1137 | ATCN_1388 | 7290 |
| CTCN_248 | 1095 | ATCN_1378 | 7248 | TTCN_227 | 1138 | CTCN_2108 | 7291 |
| GTCN_123 | 1096 | TTCN_2045 | 7249 | TTCN_228 | 1139 | TTCN_2064 | 7292 |
| TTCN_208 | 1097 | GTCN_1172 | 7250 | TTCN_229 | 1140 | CTCN_2109 | 7293 |
| TTCN_209 | 1098 | ATCN_1379 | 7251 | TTCN_230 | 1141 | ATCN_1389 | 7294 |

FIG. 33 (continued)

| | | | | | | | |
|---|---|---|---|---|---|---|---|
| ATCN_151 | 1142 | CTCN_2110 | 7295 | TTCN_242 | 1185 | CTCN_2119 | 7338 |
| CTCN_259 | 1143 | GTCN_1179 | 7296 | TTCN_243 | 1186 | CTCN_2120 | 7339 |
| GTCN_130 | 1144 | TTCN_2065 | 7297 | CTCN_269 | 1187 | ATCN_1403 | 7340 |
| CTCN_260 | 1145 | TTCN_2066 | 7298 | CTCN_270 | 1188 | TTCN_2080 | 7341 |
| GTCN_131 | 1146 | ATCN_1390 | 7299 | CTCN_271 | 1189 | ATCN_1404 | 7342 |
| TTCN_231 | 1147 | TTCN_2067 | 7300 | CTCN_272 | 1190 | TTCN_2081 | 7343 |
| GTCN_132 | 1148 | TTCN_2068 | 7301 | ATCN_166 | 1191 | ATCN_1405 | 7344 |
| TTCN_232 | 1149 | TTCN_2069 | 7302 | TTCN_244 | 1192 | TTCN_2082 | 7345 |
| ATCN_152 | 1150 | GTCN_1180 | 7303 | GTCN_137 | 1193 | GTCN_1185 | 7346 |
| GTCN_133 | 1151 | CTCN_2111 | 7304 | ATCN_167 | 1194 | ATCN_1406 | 7347 |
| CTCN_261 | 1152 | ATCN_1391 | 7305 | CTCN_273 | 1195 | TTCN_2083 | 7348 |
| CTCN_262 | 1153 | GTCN_1181 | 7306 | CTCN_274 | 1196 | TTCN_2084 | 7349 |
| ATCN_153 | 1154 | TTCN_2070 | 7307 | ATCN_168 | 1197 | TTCN_2085 | 7350 |
| ATCN_154 | 1155 | CTCN_2112 | 7308 | ATCN_169 | 1198 | TTCN_2086 | 7351 |
| ATCN_155 | 1156 | ATCN_1392 | 7309 | CTCN_275 | 1199 | GTCN_1186 | 7352 |
| CTCN_263 | 1157 | GTCN_1182 | 7310 | CTCN_276 | 1200 | TTCN_2087 | 7353 |
| CTCN_264 | 1158 | ATCN_1393 | 7311 | CTCN_277 | 1201 | GTCN_1187 | 7354 |
| ATCN_156 | 1159 | CTCN_2113 | 7312 | TTCN_245 | 1202 | TTCN_2088 | 7355 |
| TTCN_233 | 1160 | TTCN_2071 | 7313 | GTCN_138 | 1203 | ATCN_1407 | 7356 |
| ATCN_157 | 1161 | CTCN_2114 | 7314 | ATCN_170 | 1204 | CTCN_2121 | 7357 |
| TTCN_234 | 1162 | CTCN_2115 | 7315 | CTCN_278 | 1205 | TTCN_2089 | 7358 |
| ATCN_158 | 1163 | TTCN_2072 | 7316 | CTCN_279 | 1206 | TTCN_2090 | 7359 |
| TTCN_235 | 1164 | ATCN_1394 | 7317 | TTCN_246 | 1207 | TTCN_2091 | 7360 |
| ATCN_159 | 1165 | ATCN_1395 | 7318 | TTCN_247 | 1208 | TTCN_2092 | 7361 |
| TTCN_236 | 1166 | GTCN_1183 | 7319 | TTCN_248 | 1209 | TTCN_2093 | 7362 |
| ATCN_160 | 1167 | TTCN_2073 | 7320 | ATCN_171 | 1210 | GTCN_1188 | 7363 |
| TTCN_237 | 1168 | GTCN_1184 | 7321 | TTCN_249 | 1211 | ATCN_1408 | 7364 |
| ATCN_161 | 1169 | ATCN_1396 | 7322 | CTCN_280 | 1212 | ATCN_1409 | 7365 |
| TTCN_238 | 1170 | CTCN_2116 | 7323 | TTCN_250 | 1213 | ATCN_1410 | 7366 |
| TTCN_239 | 1171 | TTCN_2074 | 7324 | CTCN_281 | 1214 | CTCN_2122 | 7367 |
| ATCN_162 | 1172 | CTCN_2117 | 7325 | TTCN_251 | 1215 | TTCN_2094 | 7368 |
| ATCN_163 | 1173 | ATCN_1397 | 7326 | TTCN_252 | 1216 | TTCN_2095 | 7369 |
| TTCN_240 | 1174 | TTCN_2075 | 7327 | TTCN_253 | 1217 | TTCN_2096 | 7370 |
| GTCN_134 | 1175 | ATCN_1398 | 7328 | CTCN_282 | 1218 | ATCN_1411 | 7371 |
| TTCN_241 | 1176 | ATCN_1399 | 7329 | ATCN_172 | 1219 | TTCN_2097 | 7372 |
| ATCN_164 | 1177 | ATCN_1400 | 7330 | ATCN_173 | 1220 | TTCN_2098 | 7373 |
| GTCN_135 | 1178 | CTCN_2118 | 7331 | GTCN_139 | 1221 | CTCN_2123 | 7374 |
| GTCN_136 | 1179 | ATCN_1401 | 7332 | TTCN_254 | 1222 | GTCN_1189 | 7375 |
| ATCN_165 | 1180 | TTCN_2076 | 7333 | TTCN_255 | 1223 | TTCN_2099 | 7376 |
| CTCN_265 | 1181 | TTCN_2077 | 7334 | CTCN_283 | 1224 | TTCN_2100 | 7377 |
| CTCN_266 | 1182 | TTCN_2078 | 7335 | TTCN_256 | 1225 | GTCN_1190 | 7378 |
| CTCN_267 | 1183 | ATCN_1402 | 7336 | TTCN_257 | 1226 | TTCN_2101 | 7379 |
| CTCN_268 | 1184 | TTCN_2079 | 7337 | ATCN_174 | 1227 | GTCN_1191 | 7380 |

FIG. 33 (continued)

| | | | | | | | |
|---|---|---|---|---|---|---|---|
| ATCN_175 | 1228 | TTCN_2102 | 7381 | TTCN_275 | 1271 | GTCN_1200 | 7424 |
| TTCN_258 | 1229 | CTCN_2124 | 7382 | CTCN_295 | 1272 | CTCN_2135 | 7425 |
| ATCN_176 | 1230 | ATCN_1412 | 7383 | TTCN_276 | 1273 | TTCN_2117 | 7426 |
| ATCN_177 | 1231 | CTCN_2125 | 7384 | TTCN_277 | 1274 | ATCN_1421 | 7427 |
| ATCN_178 | 1232 | GTCN_1192 | 7385 | CTCN_296 | 1275 | ATCN_1422 | 7428 |
| TTCN_259 | 1233 | CTCN_2126 | 7386 | CTCN_297 | 1276 | TTCN_2118 | 7429 |
| TTCN_260 | 1234 | TTCN_2103 | 7387 | ATCN_187 | 1277 | ATCN_1423 | 7430 |
| ATCN_179 | 1235 | ATCN_1413 | 7388 | TTCN_278 | 1278 | ATCN_1424 | 7431 |
| TTCN_261 | 1236 | CTCN_2127 | 7389 | ATCN_188 | 1279 | ATCN_1425 | 7432 |
| TTCN_262 | 1237 | GTCN_1193 | 7390 | TTCN_279 | 1280 | ATCN_1426 | 7433 |
| TTCN_263 | 1238 | ATCN_1414 | 7391 | CTCN_298 | 1281 | TTCN_2119 | 7434 |
| TTCN_264 | 1239 | GTCN_1194 | 7392 | ATCN_189 | 1282 | ATCN_1427 | 7435 |
| CTCN_284 | 1240 | TTCN_2104 | 7393 | GTCN_143 | 1283 | CTCN_2136 | 7436 |
| TTCN_265 | 1241 | ATCN_1415 | 7394 | ATCN_190 | 1284 | TTCN_2120 | 7437 |
| CTCN_285 | 1242 | ATCN_1416 | 7395 | ATCN_191 | 1285 | CTCN_2137 | 7438 |
| CTCN_286 | 1243 | CTCN_2128 | 7396 | TTCN_280 | 1286 | CTCN_2138 | 7439 |
| CTCN_287 | 1244 | TTCN_2105 | 7397 | GTCN_144 | 1287 | CTCN_2139 | 7440 |
| GTCN_140 | 1245 | CTCN_2129 | 7398 | CTCN_299 | 1288 | TTCN_2121 | 7441 |
| ATCN_180 | 1246 | TTCN_2106 | 7399 | CTCN_300 | 1289 | CTCN_2140 | 7442 |
| ATCN_181 | 1247 | GTCN_1195 | 7400 | CTCN_301 | 1290 | TTCN_2122 | 7443 |
| TTCN_266 | 1248 | ATCN_1417 | 7401 | CTCN_302 | 1291 | ATCN_1428 | 7444 |
| TTCN_267 | 1249 | GTCN_1196 | 7402 | CTCN_303 | 1292 | GTCN_1201 | 7445 |
| CTCN_288 | 1250 | TTCN_2107 | 7403 | ATCN_192 | 1293 | ATCN_1429 | 7446 |
| CTCN_289 | 1251 | TTCN_2108 | 7404 | CTCN_304 | 1294 | GTCN_1202 | 7447 |
| GTCN_141 | 1252 | CTCN_2130 | 7405 | GTCN_145 | 1295 | CTCN_2141 | 7448 |
| CTCN_290 | 1253 | TTCN_2109 | 7406 | CTCN_305 | 1296 | GTCN_1203 | 7449 |
| CTCN_291 | 1254 | GTCN_1197 | 7407 | ATCN_193 | 1297 | TTCN_2123 | 7450 |
| TTCN_268 | 1255 | ATCN_1418 | 7408 | ATCN_194 | 1298 | CTCN_2142 | 7451 |
| ATCN_182 | 1256 | TTCN_2110 | 7409 | CTCN_306 | 1299 | CTCN_2143 | 7452 |
| GTCN_142 | 1257 | TTCN_2111 | 7410 | ATCN_195 | 1300 | CTCN_2144 | 7453 |
| TTCN_269 | 1258 | TTCN_2112 | 7411 | TTCN_281 | 1301 | ATCN_1430 | 7454 |
| TTCN_270 | 1259 | CTCN_2131 | 7412 | GTCN_146 | 1302 | CTCN_2145 | 7455 |
| ATCN_183 | 1260 | TTCN_2113 | 7413 | CTCN_307 | 1303 | GTCN_1204 | 7456 |
| CTCN_292 | 1261 | ATCN_1419 | 7414 | GTCN_147 | 1304 | TTCN_2124 | 7457 |
| TTCN_271 | 1262 | CTCN_2132 | 7415 | TTCN_282 | 1305 | GTCN_1205 | 7458 |
| CTCN_293 | 1263 | TTCN_2114 | 7416 | CTCN_308 | 1306 | GTCN_1206 | 7459 |
| TTCN_272 | 1264 | CTCN_2133 | 7417 | ATCN_196 | 1307 | TTCN_2125 | 7460 |
| TTCN_273 | 1265 | ATCN_1420 | 7418 | CTCN_309 | 1308 | GTCN_1207 | 7461 |
| ATCN_184 | 1266 | GTCN_1198 | 7419 | TTCN_283 | 1309 | ATCN_1431 | 7462 |
| ATCN_185 | 1267 | TTCN_2115 | 7420 | ATCN_197 | 1310 | TTCN_2126 | 7463 |
| CTCN_294 | 1268 | CTCN_2134 | 7421 | ATCN_198 | 1311 | CTCN_2146 | 7464 |
| TTCN_274 | 1269 | TTCN_2116 | 7422 | TTCN_284 | 1312 | CTCN_2147 | 7465 |
| ATCN_186 | 1270 | GTCN_1199 | 7423 | CTCN_310 | 1313 | CTCN_2148 | 7466 |

FIG. 33 (continued)

| | | | | | | | |
|---|---|---|---|---|---|---|---|
| CTCN_311 | 1314 | ATCN_1432 | 7467 | GTCN_152 | 1357 | GTCN_1213 | 7510 |
| TTCN_285 | 1315 | GTCN_1208 | 7468 | ATCN_207 | 1358 | GTCN_1214 | 7511 |
| TTCN_286 | 1316 | ATCN_1433 | 7469 | ATCN_208 | 1359 | TTCN_2143 | 7512 |
| ATCN_199 | 1317 | ATCN_1434 | 7470 | GTCN_153 | 1360 | ATCN_1444 | 7513 |
| ATCN_200 | 1318 | TTCN_2127 | 7471 | TTCN_300 | 1361 | CTCN_2159 | 7514 |
| TTCN_287 | 1319 | CTCN_2149 | 7472 | TTCN_301 | 1362 | CTCN_2160 | 7515 |
| ATCN_201 | 1320 | ATCN_1435 | 7473 | CTCN_327 | 1363 | TTCN_2144 | 7516 |
| CTCN_312 | 1321 | CTCN_2150 | 7474 | GTCN_154 | 1364 | ATCN_1445 | 7517 |
| CTCN_313 | 1322 | TTCN_2128 | 7475 | TTCN_302 | 1365 | TTCN_2145 | 7518 |
| CTCN_314 | 1323 | TTCN_2129 | 7476 | GTCN_155 | 1366 | TTCN_2146 | 7519 |
| TTCN_288 | 1324 | CTCN_2151 | 7477 | CTCN_328 | 1367 | GTCN_1215 | 7520 |
| TTCN_289 | 1325 | GTCN_1209 | 7478 | GTCN_156 | 1368 | GTCN_1216 | 7521 |
| CTCN_315 | 1326 | TTCN_2130 | 7479 | ATCN_209 | 1369 | CTCN_2161 | 7522 |
| TTCN_290 | 1327 | CTCN_2152 | 7480 | TTCN_303 | 1370 | GTCN_1217 | 7523 |
| CTCN_316 | 1328 | GTCN_1210 | 7481 | ATCN_210 | 1371 | CTCN_2162 | 7524 |
| GTCN_148 | 1329 | ATCN_1436 | 7482 | CTCN_329 | 1372 | GTCN_1218 | 7525 |
| ATCN_202 | 1330 | CTCN_2153 | 7483 | TTCN_304 | 1373 | ATCN_1446 | 7526 |
| CTCN_317 | 1331 | TTCN_2131 | 7484 | CTCN_330 | 1374 | GTCN_1219 | 7527 |
| CTCN_318 | 1332 | TTCN_2132 | 7485 | GTCN_157 | 1375 | ATCN_1447 | 7528 |
| ATCN_203 | 1333 | TTCN_2133 | 7486 | TTCN_305 | 1376 | CTCN_2163 | 7529 |
| TTCN_291 | 1334 | TTCN_2134 | 7487 | TTCN_306 | 1377 | GTCN_1220 | 7530 |
| CTCN_319 | 1335 | CTCN_2154 | 7488 | TTCN_307 | 1378 | ATCN_1448 | 7531 |
| GTCN_149 | 1336 | TTCN_2135 | 7489 | GTCN_158 | 1379 | CTCN_2164 | 7532 |
| ATCN_204 | 1337 | ATCN_1437 | 7490 | ATCN_211 | 1380 | ATCN_1449 | 7533 |
| CTCN_320 | 1338 | TTCN_2136 | 7491 | ATCN_212 | 1381 | CTCN_2165 | 7534 |
| TTCN_292 | 1339 | GTCN_1211 | 7492 | CTCN_331 | 1382 | ATCN_1450 | 7535 |
| TTCN_293 | 1340 | ATCN_1438 | 7493 | CTCN_332 | 1383 | TTCN_2147 | 7536 |
| TTCN_294 | 1341 | ATCN_1439 | 7494 | TTCN_308 | 1384 | CTCN_2166 | 7537 |
| GTCN_150 | 1342 | ATCN_1440 | 7495 | ATCN_213 | 1385 | ATCN_1451 | 7538 |
| TTCN_295 | 1343 | CTCN_2155 | 7496 | ATCN_214 | 1386 | ATCN_1452 | 7539 |
| CTCN_321 | 1344 | GTCN_1212 | 7497 | ATCN_215 | 1387 | TTCN_2148 | 7540 |
| CTCN_322 | 1345 | ATCN_1441 | 7498 | GTCN_159 | 1388 | CTCN_2167 | 7541 |
| CTCN_323 | 1346 | ATCN_1442 | 7499 | GTCN_160 | 1389 | TTCN_2149 | 7542 |
| GTCN_151 | 1347 | TTCN_2137 | 7500 | CTCN_333 | 1390 | GTCN_1221 | 7543 |
| TTCN_296 | 1348 | TTCN_2138 | 7501 | GTCN_161 | 1391 | CTCN_2168 | 7544 |
| ATCN_205 | 1349 | TTCN_2139 | 7502 | ATCN_216 | 1392 | TTCN_2150 | 7545 |
| TTCN_297 | 1350 | CTCN_2156 | 7503 | GTCN_162 | 1393 | CTCN_2169 | 7546 |
| CTCN_324 | 1351 | CTCN_2157 | 7504 | TTCN_309 | 1394 | GTCN_1222 | 7547 |
| TTCN_298 | 1352 | TTCN_2140 | 7505 | TTCN_310 | 1395 | ATCN_1453 | 7548 |
| ATCN_206 | 1353 | TTCN_2141 | 7506 | CTCN_334 | 1396 | TTCN_2151 | 7549 |
| CTCN_325 | 1354 | ATCN_1443 | 7507 | ATCN_217 | 1397 | TTCN_2152 | 7550 |
| CTCN_326 | 1355 | TTCN_2142 | 7508 | ATCN_218 | 1398 | CTCN_2170 | 7551 |
| TTCN_299 | 1356 | CTCN_2158 | 7509 | ATCN_219 | 1399 | ATCN_1454 | 7552 |

FIG. 33 (continued)

| | | | | | | | |
|---|---|---|---|---|---|---|---|
| CTCN_335 | 1400 | CTCN_2171 | 7553 | GTCN_169 | 1443 | GTCN_1225 | 7596 |
| TTCN_311 | 1401 | CTCN_2172 | 7554 | TTCN_325 | 1444 | CTCN_2189 | 7597 |
| GTCN_163 | 1402 | CTCN_2173 | 7555 | ATCN_230 | 1445 | GTCN_1226 | 7598 |
| CTCN_336 | 1403 | ATCN_1455 | 7556 | ATCN_231 | 1446 | CTCN_2190 | 7599 |
| TTCN_312 | 1404 | ATCN_1456 | 7557 | ATCN_232 | 1447 | CTCN_2191 | 7600 |
| GTCN_164 | 1405 | ATCN_1457 | 7558 | TTCN_326 | 1448 | TTCN_2164 | 7601 |
| GTCN_165 | 1406 | GTCN_1223 | 7559 | ATCN_233 | 1449 | TTCN_2165 | 7602 |
| ATCN_220 | 1407 | TTCN_2153 | 7560 | ATCN_234 | 1450 | GTCN_1227 | 7603 |
| ATCN_221 | 1408 | TTCN_2154 | 7561 | CTCN_348 | 1451 | TTCN_2166 | 7604 |
| CTCN_337 | 1409 | TTCN_2155 | 7562 | GTCN_170 | 1452 | TTCN_2167 | 7605 |
| ATCN_222 | 1410 | CTCN_2174 | 7563 | CTCN_349 | 1453 | ATCN_1467 | 7606 |
| ATCN_223 | 1411 | TTCN_2156 | 7564 | GTCN_171 | 1454 | TTCN_2168 | 7607 |
| CTCN_338 | 1412 | CTCN_2175 | 7565 | TTCN_327 | 1455 | GTCN_1228 | 7608 |
| TTCN_313 | 1413 | CTCN_2176 | 7566 | GTCN_172 | 1456 | ATCN_1468 | 7609 |
| CTCN_339 | 1414 | TTCN_2157 | 7567 | GTCN_173 | 1457 | TTCN_2169 | 7610 |
| CTCN_340 | 1415 | TTCN_2158 | 7568 | TTCN_328 | 1458 | CTCN_2192 | 7611 |
| CTCN_341 | 1416 | CTCN_2177 | 7569 | CTCN_350 | 1459 | GTCN_1229 | 7612 |
| CTCN_342 | 1417 | CTCN_2178 | 7570 | GTCN_174 | 1460 | ATCN_1469 | 7613 |
| TTCN_314 | 1418 | ATCN_1458 | 7571 | TTCN_329 | 1461 | CTCN_2193 | 7614 |
| CTCN_343 | 1419 | ATCN_1459 | 7572 | GTCN_175 | 1462 | GTCN_1230 | 7615 |
| TTCN_315 | 1420 | CTCN_2179 | 7573 | ATCN_235 | 1463 | TTCN_2170 | 7616 |
| TTCN_316 | 1421 | TTCN_2159 | 7574 | ATCN_236 | 1464 | GTCN_1231 | 7617 |
| TTCN_317 | 1422 | ATCN_1460 | 7575 | CTCN_351 | 1465 | CTCN_2194 | 7618 |
| TTCN_318 | 1423 | TTCN_2160 | 7576 | ATCN_237 | 1466 | TTCN_2171 | 7619 |
| TTCN_319 | 1424 | ATCN_1461 | 7577 | TTCN_330 | 1467 | ATCN_1470 | 7620 |
| TTCN_320 | 1425 | CTCN_2180 | 7578 | GTCN_176 | 1468 | GTCN_1232 | 7621 |
| CTCN_344 | 1426 | CTCN_2181 | 7579 | ATCN_238 | 1469 | CTCN_2195 | 7622 |
| GTCN_166 | 1427 | TTCN_2161 | 7580 | CTCN_352 | 1470 | TTCN_2172 | 7623 |
| ATCN_224 | 1428 | ATCN_1462 | 7581 | ATCN_239 | 1471 | TTCN_2173 | 7624 |
| ATCN_225 | 1429 | ATCN_1463 | 7582 | CTCN_353 | 1472 | ATCN_1471 | 7625 |
| CTCN_345 | 1430 | CTCN_2182 | 7583 | TTCN_331 | 1473 | TTCN_2174 | 7626 |
| ATCN_226 | 1431 | CTCN_2183 | 7584 | ATCN_240 | 1474 | TTCN_2175 | 7627 |
| CTCN_346 | 1432 | GTCN_1224 | 7585 | TTCN_332 | 1475 | TTCN_2176 | 7628 |
| ATCN_227 | 1433 | CTCN_2184 | 7586 | ATCN_241 | 1476 | ATCN_1472 | 7629 |
| ATCN_228 | 1434 | CTCN_2185 | 7587 | GTCN_177 | 1477 | ATCN_1473 | 7630 |
| CTCN_347 | 1435 | CTCN_2186 | 7588 | TTCN_333 | 1478 | TTCN_2177 | 7631 |
| TTCN_321 | 1436 | ATCN_1464 | 7589 | ATCN_242 | 1479 | TTCN_2178 | 7632 |
| TTCN_322 | 1437 | TTCN_2162 | 7590 | CTCN_354 | 1480 | ATCN_1474 | 7633 |
| GTCN_167 | 1438 | ATCN_1465 | 7591 | CTCN_355 | 1481 | ATCN_1475 | 7634 |
| ATCN_229 | 1439 | CTCN_2187 | 7592 | TTCN_334 | 1482 | ATCN_1476 | 7635 |
| GTCN_168 | 1440 | TTCN_2163 | 7593 | CTCN_356 | 1483 | CTCN_2196 | 7636 |
| TTCN_323 | 1441 | ATCN_1466 | 7594 | ATCN_243 | 1484 | TTCN_2179 | 7637 |
| TTCN_324 | 1442 | CTCN_2188 | 7595 | TTCN_335 | 1485 | TTCN_2180 | 7638 |

FIG. 33 (continued)

| | | | | | | | |
|---|---|---|---|---|---|---|---|
| TTCN_336 | 1486 | CTCN_2197 | 7639 | ATCN_250 | 1529 | TTCN_2193 | 7682 |
| GTCN_178 | 1487 | ATCN_1477 | 7640 | TTCN_353 | 1530 | CTCN_2205 | 7683 |
| TTCN_337 | 1488 | GTCN_1233 | 7641 | TTCN_354 | 1531 | CTCN_2206 | 7684 |
| TTCN_338 | 1489 | TTCN_2181 | 7642 | ATCN_251 | 1532 | TTCN_2194 | 7685 |
| CTCN_357 | 1490 | GTCN_1234 | 7643 | GTCN_186 | 1533 | ATCN_1488 | 7686 |
| TTCN_339 | 1491 | CTCN_2198 | 7644 | GTCN_187 | 1534 | ATCN_1489 | 7687 |
| TTCN_340 | 1492 | TTCN_2182 | 7645 | ATCN_252 | 1535 | TTCN_2195 | 7688 |
| TTCN_341 | 1493 | TTCN_2183 | 7646 | TTCN_355 | 1536 | TTCN_2196 | 7689 |
| TTCN_342 | 1494 | ATCN_1478 | 7647 | ATCN_253 | 1537 | TTCN_2197 | 7690 |
| TTCN_343 | 1495 | GTCN_1235 | 7648 | CTCN_369 | 1538 | CTCN_2207 | 7691 |
| CTCN_358 | 1496 | GTCN_1236 | 7649 | CTCN_370 | 1539 | CTCN_2208 | 7692 |
| TTCN_344 | 1497 | GTCN_1237 | 7650 | CTCN_371 | 1540 | ATCN_1490 | 7693 |
| TTCN_345 | 1498 | ATCN_1479 | 7651 | CTCN_372 | 1541 | CTCN_2209 | 7694 |
| CTCN_359 | 1499 | TTCN_2184 | 7652 | TTCN_356 | 1542 | TTCN_2198 | 7695 |
| GTCN_179 | 1500 | CTCN_2199 | 7653 | TTCN_357 | 1543 | ATCN_1491 | 7696 |
| CTCN_360 | 1501 | TTCN_2185 | 7654 | TTCN_358 | 1544 | ATCN_1492 | 7697 |
| GTCN_180 | 1502 | ATCN_1480 | 7655 | CTCN_373 | 1545 | TTCN_2199 | 7698 |
| GTCN_181 | 1503 | GTCN_1238 | 7656 | GTCN_188 | 1546 | CTCN_2210 | 7699 |
| TTCN_346 | 1504 | TTCN_2186 | 7657 | CTCN_374 | 1547 | CTCN_2211 | 7700 |
| CTCN_361 | 1505 | TTCN_2187 | 7658 | ATCN_254 | 1548 | ATCN_1493 | 7701 |
| ATCN_244 | 1506 | ATCN_1481 | 7659 | ATCN_255 | 1549 | CTCN_2212 | 7702 |
| ATCN_245 | 1507 | TTCN_2188 | 7660 | CTCN_375 | 1550 | CTCN_2213 | 7703 |
| CTCN_362 | 1508 | ATCN_1482 | 7661 | GTCN_189 | 1551 | ATCN_1494 | 7704 |
| CTCN_363 | 1509 | GTCN_1239 | 7662 | TTCN_359 | 1552 | TTCN_2200 | 7705 |
| CTCN_364 | 1510 | TTCN_2189 | 7663 | TTCN_360 | 1553 | ATCN_1495 | 7706 |
| CTCN_365 | 1511 | GTCN_1240 | 7664 | ATCN_256 | 1554 | ATCN_1496 | 7707 |
| TTCN_347 | 1512 | TTCN_2190 | 7665 | GTCN_190 | 1555 | TTCN_2201 | 7708 |
| GTCN_182 | 1513 | ATCN_1483 | 7666 | GTCN_191 | 1556 | ATCN_1497 | 7709 |
| TTCN_348 | 1514 | ATCN_1484 | 7667 | CTCN_376 | 1557 | CTCN_2214 | 7710 |
| ATCN_246 | 1515 | TTCN_2191 | 7668 | GTCN_192 | 1558 | GTCN_1245 | 7711 |
| TTCN_349 | 1516 | ATCN_1485 | 7669 | TTCN_361 | 1559 | CTCN_2215 | 7712 |
| TTCN_350 | 1517 | CTCN_2200 | 7670 | TTCN_362 | 1560 | CTCN_2216 | 7713 |
| GTCN_183 | 1518 | GTCN_1241 | 7671 | CTCN_377 | 1561 | TTCN_2202 | 7714 |
| ATCN_247 | 1519 | GTCN_1242 | 7672 | TTCN_363 | 1562 | CTCN_2217 | 7715 |
| CTCN_366 | 1520 | GTCN_1243 | 7673 | ATCN_257 | 1563 | ATCN_1498 | 7716 |
| GTCN_184 | 1521 | CTCN_2201 | 7674 | CTCN_378 | 1564 | ATCN_1499 | 7717 |
| TTCN_351 | 1522 | ATCN_1486 | 7675 | GTCN_193 | 1565 | TTCN_2203 | 7718 |
| ATCN_248 | 1523 | ATCN_1487 | 7676 | CTCN_379 | 1566 | TTCN_2204 | 7719 |
| GTCN_185 | 1524 | GTCN_1244 | 7677 | TTCN_364 | 1567 | CTCN_2218 | 7720 |
| TTCN_352 | 1525 | CTCN_2202 | 7678 | GTCN_194 | 1568 | GTCN_1246 | 7721 |
| CTCN_367 | 1526 | CTCN_2203 | 7679 | TTCN_365 | 1569 | CTCN_2219 | 7722 |
| CTCN_368 | 1527 | CTCN_2204 | 7680 | TTCN_366 | 1570 | TTCN_2205 | 7723 |
| ATCN_249 | 1528 | TTCN_2192 | 7681 | TTCN_367 | 1571 | ATCN_1500 | 7724 |

FIG. 33 (continued)

| | | | | | | | |
|---|---|---|---|---|---|---|---|
| TTCN_368 | 1572 | GTCN_1247 | 7725 | TTCN_379 | 1615 | TTCN_2217 | 7768 |
| ATCN_258 | 1573 | CTCN_2220 | 7726 | ATCN_264 | 1616 | ATCN_1513 | 7769 |
| ATCN_259 | 1574 | TTCN_2206 | 7727 | ATCN_265 | 1617 | CTCN_2235 | 7770 |
| GTCN_195 | 1575 | ATCN_1501 | 7728 | CTCN_396 | 1618 | ATCN_1514 | 7771 |
| CTCN_380 | 1576 | ATCN_1502 | 7729 | TTCN_380 | 1619 | CTCN_2236 | 7772 |
| GTCN_196 | 1577 | ATCN_1503 | 7730 | CTCN_397 | 1620 | TTCN_2218 | 7773 |
| CTCN_381 | 1578 | GTCN_1248 | 7731 | CTCN_398 | 1621 | TTCN_2219 | 7774 |
| CTCN_382 | 1579 | ATCN_1504 | 7732 | CTCN_399 | 1622 | GTCN_1252 | 7775 |
| ATCN_260 | 1580 | ATCN_1505 | 7733 | TTCN_381 | 1623 | GTCN_1253 | 7776 |
| TTCN_369 | 1581 | TTCN_2207 | 7734 | TTCN_382 | 1624 | CTCN_2237 | 7777 |
| CTCN_383 | 1582 | CTCN_2221 | 7735 | TTCN_383 | 1625 | ATCN_1515 | 7778 |
| CTCN_384 | 1583 | CTCN_2222 | 7736 | GTCN_205 | 1626 | TTCN_2220 | 7779 |
| CTCN_385 | 1584 | CTCN_2223 | 7737 | CTCN_400 | 1627 | TTCN_2221 | 7780 |
| TTCN_370 | 1585 | CTCN_2224 | 7738 | CTCN_401 | 1628 | TTCN_2222 | 7781 |
| TTCN_371 | 1586 | TTCN_2208 | 7739 | CTCN_402 | 1629 | GTCN_1254 | 7782 |
| CTCN_386 | 1587 | TTCN_2209 | 7740 | CTCN_403 | 1630 | CTCN_2238 | 7783 |
| GTCN_197 | 1588 | CTCN_2225 | 7741 | ATCN_266 | 1631 | GTCN_1255 | 7784 |
| CTCN_387 | 1589 | TTCN_2210 | 7742 | CTCN_404 | 1632 | CTCN_2239 | 7785 |
| GTCN_198 | 1590 | ATCN_1506 | 7743 | CTCN_405 | 1633 | CTCN_2240 | 7786 |
| CTCN_388 | 1591 | ATCN_1507 | 7744 | CTCN_406 | 1634 | TTCN_2223 | 7787 |
| GTCN_199 | 1592 | CTCN_2226 | 7745 | ATCN_267 | 1635 | CTCN_2241 | 7788 |
| GTCN_200 | 1593 | CTCN_2227 | 7746 | ATCN_268 | 1636 | TTCN_2224 | 7789 |
| ATCN_261 | 1594 | ATCN_1508 | 7747 | CTCN_407 | 1637 | CTCN_2242 | 7790 |
| CTCN_389 | 1595 | TTCN_2211 | 7748 | CTCN_408 | 1638 | ATCN_1516 | 7791 |
| TTCN_372 | 1596 | CTCN_2228 | 7749 | TTCN_384 | 1639 | CTCN_2243 | 7792 |
| TTCN_373 | 1597 | ATCN_1509 | 7750 | CTCN_409 | 1640 | CTCN_2244 | 7793 |
| TTCN_374 | 1598 | CTCN_2229 | 7751 | GTCN_206 | 1641 | ATCN_1517 | 7794 |
| CTCN_390 | 1599 | CTCN_2230 | 7752 | TTCN_385 | 1642 | ATCN_1518 | 7795 |
| CTCN_391 | 1600 | ATCN_1510 | 7753 | GTCN_207 | 1643 | TTCN_2225 | 7796 |
| CTCN_392 | 1601 | GTCN_1249 | 7754 | CTCN_410 | 1644 | ATCN_1519 | 7797 |
| GTCN_201 | 1602 | CTCN_2231 | 7755 | GTCN_208 | 1645 | TTCN_2226 | 7798 |
| GTCN_202 | 1603 | CTCN_2232 | 7756 | CTCN_411 | 1646 | CTCN_2245 | 7799 |
| CTCN_393 | 1604 | TTCN_2212 | 7757 | CTCN_412 | 1647 | ATCN_1520 | 7800 |
| TTCN_375 | 1605 | TTCN_2213 | 7758 | TTCN_386 | 1648 | GTCN_1256 | 7801 |
| GTCN_203 | 1606 | GTCN_1250 | 7759 | CTCN_413 | 1649 | ATCN_1521 | 7802 |
| GTCN_204 | 1607 | TTCN_2214 | 7760 | GTCN_209 | 1650 | ATCN_1522 | 7803 |
| TTCN_376 | 1608 | TTCN_2215 | 7761 | ATCN_269 | 1651 | TTCN_2227 | 7804 |
| CTCN_394 | 1609 | ATCN_1511 | 7762 | ATCN_270 | 1652 | ATCN_1523 | 7805 |
| TTCN_377 | 1610 | CTCN_2233 | 7763 | TTCN_387 | 1653 | ATCN_1524 | 7806 |
| ATCN_262 | 1611 | TTCN_2216 | 7764 | ATCN_271 | 1654 | CTCN_2246 | 7807 |
| ATCN_263 | 1612 | GTCN_1251 | 7765 | GTCN_210 | 1655 | CTCN_2247 | 7808 |
| CTCN_395 | 1613 | CTCN_2234 | 7766 | TTCN_388 | 1656 | CTCN_2248 | 7809 |
| TTCN_378 | 1614 | ATCN_1512 | 7767 | TTCN_389 | 1657 | ATCN_1525 | 7810 |

FIG. 33 (continued)

| | | | | | | | |
|---|---|---|---|---|---|---|---|
| TTCN_390 | 1658 | ATCN_1526 | 7811 | TTCN_399 | 1701 | TTCN_2240 | 7854 |
| ATCN_272 | 1659 | TTCN_2228 | 7812 | TTCN_400 | 1702 | CTCN_2262 | 7855 |
| ATCN_273 | 1660 | ATCN_1527 | 7813 | GTCN_221 | 1703 | CTCN_2263 | 7856 |
| ATCN_274 | 1661 | CTCN_2249 | 7814 | CTCN_427 | 1704 | TTCN_2241 | 7857 |
| CTCN_414 | 1662 | CTCN_2250 | 7815 | GTCN_222 | 1705 | CTCN_2264 | 7858 |
| ATCN_275 | 1663 | GTCN_1257 | 7816 | CTCN_428 | 1706 | CTCN_2265 | 7859 |
| TTCN_391 | 1664 | TTCN_2229 | 7817 | GTCN_223 | 1707 | ATCN_1538 | 7860 |
| TTCN_392 | 1665 | GTCN_1258 | 7818 | CTCN_429 | 1708 | CTCN_2266 | 7861 |
| GTCN_211 | 1666 | CTCN_2251 | 7819 | GTCN_224 | 1709 | TTCN_2242 | 7862 |
| GTCN_212 | 1667 | TTCN_2230 | 7820 | CTCN_430 | 1710 | TTCN_2243 | 7863 |
| GTCN_213 | 1668 | TTCN_2231 | 7821 | ATCN_283 | 1711 | CTCN_2267 | 7864 |
| ATCN_276 | 1669 | TTCN_2232 | 7822 | ATCN_284 | 1712 | CTCN_2268 | 7865 |
| TTCN_393 | 1670 | TTCN_2233 | 7823 | CTCN_431 | 1713 | TTCN_2244 | 7866 |
| CTCN_415 | 1671 | CTCN_2252 | 7824 | CTCN_432 | 1714 | GTCN_1263 | 7867 |
| ATCN_277 | 1672 | ATCN_1528 | 7825 | CTCN_433 | 1715 | TTCN_2245 | 7868 |
| CTCN_416 | 1673 | TTCN_2234 | 7826 | TTCN_401 | 1716 | ATCN_1539 | 7869 |
| GTCN_214 | 1674 | ATCN_1529 | 7827 | ATCN_285 | 1717 | ATCN_1540 | 7870 |
| CTCN_417 | 1675 | TTCN_2235 | 7828 | TTCN_402 | 1718 | CTCN_2269 | 7871 |
| CTCN_418 | 1676 | GTCN_1259 | 7829 | TTCN_403 | 1719 | TTCN_2246 | 7872 |
| GTCN_215 | 1677 | CTCN_2253 | 7830 | GTCN_225 | 1720 | TTCN_2247 | 7873 |
| CTCN_419 | 1678 | ATCN_1530 | 7831 | TTCN_404 | 1721 | GTCN_1264 | 7874 |
| TTCN_394 | 1679 | CTCN_2254 | 7832 | CTCN_434 | 1722 | CTCN_2270 | 7875 |
| GTCN_216 | 1680 | CTCN_2255 | 7833 | TTCN_405 | 1723 | CTCN_2271 | 7876 |
| GTCN_217 | 1681 | ATCN_1531 | 7834 | CTCN_435 | 1724 | TTCN_2248 | 7877 |
| CTCN_420 | 1682 | CTCN_2256 | 7835 | GTCN_226 | 1725 | TTCN_2249 | 7878 |
| TTCN_395 | 1683 | ATCN_1532 | 7836 | GTCN_227 | 1726 | CTCN_2272 | 7879 |
| CTCN_421 | 1684 | ATCN_1533 | 7837 | TTCN_406 | 1727 | ATCN_1541 | 7880 |
| GTCN_218 | 1685 | TTCN_2236 | 7838 | CTCN_436 | 1728 | TTCN_2250 | 7881 |
| CTCN_422 | 1686 | GTCN_1260 | 7839 | CTCN_437 | 1729 | CTCN_2273 | 7882 |
| ATCN_278 | 1687 | CTCN_2257 | 7840 | CTCN_438 | 1730 | TTCN_2251 | 7883 |
| ATCN_279 | 1688 | TTCN_2237 | 7841 | ATCN_286 | 1731 | TTCN_2252 | 7884 |
| CTCN_423 | 1689 | CTCN_2258 | 7842 | TTCN_407 | 1732 | ATCN_1542 | 7885 |
| ATCN_280 | 1690 | TTCN_2238 | 7843 | TTCN_408 | 1733 | TTCN_2253 | 7886 |
| ATCN_281 | 1691 | CTCN_2259 | 7844 | TTCN_409 | 1734 | ATCN_1543 | 7887 |
| TTCN_396 | 1692 | GTCN_1261 | 7845 | CTCN_439 | 1735 | ATCN_1544 | 7888 |
| CTCN_424 | 1693 | TTCN_2239 | 7846 | ATCN_287 | 1736 | GTCN_1265 | 7889 |
| TTCN_397 | 1694 | CTCN_2260 | 7847 | TTCN_410 | 1737 | CTCN_2274 | 7890 |
| GTCN_219 | 1695 | ATCN_1534 | 7848 | TTCN_411 | 1738 | CTCN_2275 | 7891 |
| ATCN_282 | 1696 | ATCN_1535 | 7849 | CTCN_440 | 1739 | GTCN_1266 | 7892 |
| GTCN_220 | 1697 | ATCN_1536 | 7850 | GTCN_228 | 1740 | TTCN_2254 | 7893 |
| TTCN_398 | 1698 | ATCN_1537 | 7851 | TTCN_412 | 1741 | CTCN_2276 | 7894 |
| CTCN_425 | 1699 | GTCN_1262 | 7852 | CTCN_441 | 1742 | TTCN_2255 | 7895 |
| CTCN_426 | 1700 | CTCN_2261 | 7853 | GTCN_229 | 1743 | GTCN_1267 | 7896 |

FIG. 33 (continued)

| | | | | | | | |
|---|---|---|---|---|---|---|---|
| ATCN_288 | 1744 | TTCN_2256 | 7897 | TTCN_423 | 1787 | CTCN_2288 | 7940 |
| TTCN_413 | 1745 | TTCN_2257 | 7898 | TTCN_424 | 1788 | TTCN_2275 | 7941 |
| TTCN_414 | 1746 | TTCN_2258 | 7899 | TTCN_425 | 1789 | CTCN_2289 | 7942 |
| GTCN_230 | 1747 | TTCN_2259 | 7900 | ATCN_295 | 1790 | GTCN_1271 | 7943 |
| CTCN_442 | 1748 | ATCN_1545 | 7901 | ATCN_296 | 1791 | TTCN_2276 | 7944 |
| GTCN_231 | 1749 | ATCN_1546 | 7902 | TTCN_426 | 1792 | TTCN_2277 | 7945 |
| CTCN_443 | 1750 | TTCN_2260 | 7903 | CTCN_458 | 1793 | TTCN_2278 | 7946 |
| TTCN_415 | 1751 | CTCN_2277 | 7904 | GTCN_240 | 1794 | TTCN_2279 | 7947 |
| CTCN_444 | 1752 | TTCN_2261 | 7905 | ATCN_297 | 1795 | TTCN_2280 | 7948 |
| CTCN_445 | 1753 | CTCN_2278 | 7906 | CTCN_459 | 1796 | ATCN_1555 | 7949 |
| GTCN_232 | 1754 | ATCN_1547 | 7907 | ATCN_298 | 1797 | ATCN_1556 | 7950 |
| TTCN_416 | 1755 | GTCN_1268 | 7908 | CTCN_460 | 1798 | CTCN_2290 | 7951 |
| GTCN_233 | 1756 | CTCN_2279 | 7909 | ATCN_299 | 1799 | ATCN_1557 | 7952 |
| CTCN_446 | 1757 | ATCN_1548 | 7910 | GTCN_241 | 1800 | CTCN_2291 | 7953 |
| CTCN_447 | 1758 | CTCN_2280 | 7911 | CTCN_461 | 1801 | TTCN_2281 | 7954 |
| CTCN_448 | 1759 | TTCN_2262 | 7912 | GTCN_242 | 1802 | ATCN_1558 | 7955 |
| TTCN_417 | 1760 | ATCN_1549 | 7913 | ATCN_300 | 1803 | TTCN_2282 | 7956 |
| TTCN_418 | 1761 | CTCN_2281 | 7914 | CTCN_462 | 1804 | ATCN_1559 | 7957 |
| CTCN_449 | 1762 | CTCN_2282 | 7915 | TTCN_427 | 1805 | ATCN_1560 | 7958 |
| CTCN_450 | 1763 | TTCN_2263 | 7916 | CTCN_463 | 1806 | ATCN_1561 | 7959 |
| CTCN_451 | 1764 | TTCN_2264 | 7917 | ATCN_301 | 1807 | ATCN_1562 | 7960 |
| CTCN_452 | 1765 | CTCN_2283 | 7918 | GTCN_243 | 1808 | ATCN_1563 | 7961 |
| ATCN_289 | 1766 | CTCN_2284 | 7919 | ATCN_302 | 1809 | TTCN_2283 | 7962 |
| ATCN_290 | 1767 | GTCN_1269 | 7920 | CTCN_464 | 1810 | TTCN_2284 | 7963 |
| CTCN_453 | 1768 | TTCN_2265 | 7921 | TTCN_428 | 1811 | GTCN_1272 | 7964 |
| ATCN_291 | 1769 | TTCN_2266 | 7922 | CTCN_465 | 1812 | TTCN_2285 | 7965 |
| TTCN_419 | 1770 | ATCN_1550 | 7923 | CTCN_466 | 1813 | TTCN_2286 | 7966 |
| GTCN_234 | 1771 | TTCN_2267 | 7924 | ATCN_303 | 1814 | TTCN_2287 | 7967 |
| GTCN_235 | 1772 | CTCN_2285 | 7925 | ATCN_304 | 1815 | ATCN_1564 | 7968 |
| TTCN_420 | 1773 | GTCN_1270 | 7926 | ATCN_305 | 1816 | TTCN_2288 | 7969 |
| CTCN_454 | 1774 | TTCN_2268 | 7927 | TTCN_429 | 1817 | TTCN_2289 | 7970 |
| GTCN_236 | 1775 | CTCN_2286 | 7928 | TTCN_430 | 1818 | TTCN_2290 | 7971 |
| GTCN_237 | 1776 | TTCN_2269 | 7929 | CTCN_467 | 1819 | CTCN_2292 | 7972 |
| ATCN_292 | 1777 | ATCN_1551 | 7930 | TTCN_431 | 1820 | TTCN_2291 | 7973 |
| CTCN_455 | 1778 | TTCN_2270 | 7931 | TTCN_432 | 1821 | TTCN_2292 | 7974 |
| ATCN_293 | 1779 | TTCN_2271 | 7932 | CTCN_468 | 1822 | TTCN_2293 | 7975 |
| ATCN_294 | 1780 | CTCN_2287 | 7933 | TTCN_433 | 1823 | CTCN_2293 | 7976 |
| CTCN_456 | 1781 | TTCN_2272 | 7934 | TTCN_434 | 1824 | CTCN_2294 | 7977 |
| TTCN_421 | 1782 | TTCN_2273 | 7935 | TTCN_435 | 1825 | TTCN_2294 | 7978 |
| CTCN_457 | 1783 | TTCN_2274 | 7936 | TTCN_436 | 1826 | TTCN_2295 | 7979 |
| GTCN_238 | 1784 | ATCN_1552 | 7937 | CTCN_469 | 1827 | TTCN_2296 | 7980 |
| GTCN_239 | 1785 | ATCN_1553 | 7938 | TTCN_437 | 1828 | CTCN_2295 | 7981 |
| TTCN_422 | 1786 | ATCN_1554 | 7939 | TTCN_438 | 1829 | TTCN_2297 | 7982 |

FIG. 33 (continued)

| | | | | | | | | |
|---|---|---|---|---|---|---|---|---|
| CTCN_470 | 1830 | TTCN_2298 | 7983 | ATCN_312 | 1873 | ATCN_1577 | 8026 |
| CTCN_471 | 1831 | CTCN_2296 | 7984 | TTCN_448 | 1874 | TTCN_2315 | 8027 |
| CTCN_472 | 1832 | TTCN_2299 | 7985 | CTCN_489 | 1875 | ATCN_1578 | 8028 |
| TTCN_439 | 1833 | ATCN_1565 | 7986 | ATCN_313 | 1876 | TTCN_2316 | 8029 |
| GTCN_244 | 1834 | TTCN_2300 | 7987 | TTCN_449 | 1877 | CTCN_2306 | 8030 |
| CTCN_473 | 1835 | ATCN_1566 | 7988 | ATCN_314 | 1878 | ATCN_1579 | 8031 |
| TTCN_440 | 1836 | ATCN_1567 | 7989 | ATCN_315 | 1879 | ATCN_1580 | 8032 |
| TTCN_441 | 1837 | ATCN_1568 | 7990 | TTCN_450 | 1880 | TTCN_2317 | 8033 |
| GTCN_245 | 1838 | TTCN_2301 | 7991 | TTCN_451 | 1881 | TTCN_2318 | 8034 |
| GTCN_246 | 1839 | CTCN_2297 | 7992 | TTCN_452 | 1882 | ATCN_1581 | 8035 |
| TTCN_442 | 1840 | ATCN_1569 | 7993 | TTCN_453 | 1883 | TTCN_2319 | 8036 |
| GTCN_247 | 1841 | TTCN_2302 | 7994 | GTCN_253 | 1884 | TTCN_2320 | 8037 |
| ATCN_306 | 1842 | CTCN_2298 | 7995 | CTCN_490 | 1885 | GTCN_1277 | 8038 |
| GTCN_248 | 1843 | TTCN_2303 | 7996 | ATCN_316 | 1886 | ATCN_1582 | 8039 |
| TTCN_443 | 1844 | CTCN_2299 | 7997 | TTCN_454 | 1887 | ATCN_1583 | 8040 |
| GTCN_249 | 1845 | TTCN_2304 | 7998 | ATCN_317 | 1888 | CTCN_2307 | 8041 |
| CTCN_474 | 1846 | ATCN_1570 | 7999 | TTCN_455 | 1889 | CTCN_2308 | 8042 |
| CTCN_475 | 1847 | CTCN_2300 | 8000 | ATCN_318 | 1890 | CTCN_2309 | 8043 |
| ATCN_307 | 1848 | ATCN_1571 | 8001 | TTCN_456 | 1891 | TTCN_2321 | 8044 |
| CTCN_476 | 1849 | GTCN_1273 | 8002 | ATCN_319 | 1892 | CTCN_2310 | 8045 |
| TTCN_444 | 1850 | CTCN_2301 | 8003 | ATCN_320 | 1893 | ATCN_1584 | 8046 |
| CTCN_477 | 1851 | ATCN_1572 | 8004 | CTCN_491 | 1894 | GTCN_1278 | 8047 |
| TTCN_445 | 1852 | ATCN_1573 | 8005 | GTCN_254 | 1895 | CTCN_2311 | 8048 |
| CTCN_478 | 1853 | ATCN_1574 | 8006 | TTCN_457 | 1896 | CTCN_2312 | 8049 |
| TTCN_446 | 1854 | TTCN_2305 | 8007 | CTCN_492 | 1897 | CTCN_2313 | 8050 |
| CTCN_479 | 1855 | TTCN_2306 | 8008 | ATCN_321 | 1898 | ATCN_1585 | 8051 |
| CTCN_480 | 1856 | TTCN_2307 | 8009 | ATCN_322 | 1899 | TTCN_2322 | 8052 |
| CTCN_481 | 1857 | CTCN_2302 | 8010 | TTCN_458 | 1900 | TTCN_2323 | 8053 |
| CTCN_482 | 1858 | TTCN_2308 | 8011 | GTCN_255 | 1901 | GTCN_1279 | 8054 |
| CTCN_483 | 1859 | ATCN_1575 | 8012 | TTCN_459 | 1902 | CTCN_2314 | 8055 |
| GTCN_250 | 1860 | TTCN_2309 | 8013 | GTCN_256 | 1903 | CTCN_2315 | 8056 |
| CTCN_484 | 1861 | CTCN_2303 | 8014 | TTCN_460 | 1904 | GTCN_1280 | 8057 |
| CTCN_485 | 1862 | GTCN_1274 | 8015 | TTCN_461 | 1905 | CTCN_2316 | 8058 |
| ATCN_308 | 1863 | TTCN_2310 | 8016 | GTCN_257 | 1906 | TTCN_2324 | 8059 |
| CTCN_486 | 1864 | ATCN_1576 | 8017 | CTCN_493 | 1907 | CTCN_2317 | 8060 |
| CTCN_487 | 1865 | TTCN_2311 | 8018 | TTCN_462 | 1908 | GTCN_1281 | 8061 |
| CTCN_488 | 1866 | TTCN_2312 | 8019 | TTCN_463 | 1909 | TTCN_2325 | 8062 |
| GTCN_251 | 1867 | GTCN_1275 | 8020 | ATCN_323 | 1910 | TTCN_2326 | 8063 |
| ATCN_309 | 1868 | CTCN_2304 | 8021 | TTCN_464 | 1911 | GTCN_1282 | 8064 |
| TTCN_447 | 1869 | TTCN_2313 | 8022 | CTCN_494 | 1912 | TTCN_2327 | 8065 |
| ATCN_310 | 1870 | CTCN_2305 | 8023 | TTCN_465 | 1913 | CTCN_2318 | 8066 |
| GTCN_252 | 1871 | GTCN_1276 | 8024 | CTCN_495 | 1914 | TTCN_2328 | 8067 |
| ATCN_311 | 1872 | TTCN_2314 | 8025 | TTCN_466 | 1915 | TTCN_2329 | 8068 |

FIG. 33 (continued)

| | | | | | | | |
|---|---|---|---|---|---|---|---|
| GTCN_258 | 1916 | CTCN_2319 | 8069 | TTCN_487 | 1959 | ATCN_1596 | 8112 |
| CTCN_496 | 1917 | TTCN_2330 | 8070 | TTCN_488 | 1960 | TTCN_2355 | 8113 |
| TTCN_467 | 1918 | TTCN_2331 | 8071 | TTCN_489 | 1961 | ATCN_1597 | 8114 |
| TTCN_468 | 1919 | TTCN_2332 | 8072 | TTCN_490 | 1962 | ATCN_1598 | 8115 |
| CTCN_497 | 1920 | ATCN_1586 | 8073 | TTCN_491 | 1963 | ATCN_1599 | 8116 |
| CTCN_498 | 1921 | TTCN_2333 | 8074 | TTCN_492 | 1964 | TTCN_2356 | 8117 |
| GTCN_259 | 1922 | ATCN_1587 | 8075 | TTCN_493 | 1965 | ATCN_1600 | 8118 |
| TTCN_469 | 1923 | ATCN_1588 | 8076 | TTCN_494 | 1966 | TTCN_2357 | 8119 |
| TTCN_470 | 1924 | ATCN_1589 | 8077 | CTCN_508 | 1967 | ATCN_1601 | 8120 |
| GTCN_260 | 1925 | ATCN_1590 | 8078 | TTCN_495 | 1968 | TTCN_2358 | 8121 |
| CTCN_499 | 1926 | TTCN_2334 | 8079 | TTCN_496 | 1969 | ATCN_1602 | 8122 |
| TTCN_471 | 1927 | TTCN_2335 | 8080 | TTCN_497 | 1970 | ATCN_1603 | 8123 |
| CTCN_500 | 1928 | TTCN_2336 | 8081 | TTCN_498 | 1971 | ATCN_1604 | 8124 |
| GTCN_261 | 1929 | TTCN_2337 | 8082 | TTCN_499 | 1972 | TTCN_2359 | 8125 |
| TTCN_472 | 1930 | TTCN_2338 | 8083 | CTCN_509 | 1973 | TTCN_2360 | 8126 |
| TTCN_473 | 1931 | TTCN_2339 | 8084 | TTCN_500 | 1974 | GTCN_1286 | 8127 |
| ATCN_324 | 1932 | CTCN_2320 | 8085 | TTCN_501 | 1975 | TTCN_2361 | 8128 |
| CTCN_501 | 1933 | TTCN_2340 | 8086 | CTCN_510 | 1976 | CTCN_2324 | 8129 |
| TTCN_474 | 1934 | TTCN_2341 | 8087 | TTCN_502 | 1977 | GTCN_1287 | 8130 |
| ATCN_325 | 1935 | TTCN_2342 | 8088 | TTCN_503 | 1978 | ATCN_1605 | 8131 |
| ATCN_326 | 1936 | TTCN_2343 | 8089 | CTCN_511 | 1979 | TTCN_2362 | 8132 |
| CTCN_502 | 1937 | ATCN_1591 | 8090 | CTCN_512 | 1980 | ATCN_1606 | 8133 |
| CTCN_503 | 1938 | ATCN_1592 | 8091 | TTCN_504 | 1981 | ATCN_1607 | 8134 |
| CTCN_504 | 1939 | ATCN_1593 | 8092 | TTCN_505 | 1982 | CTCN_2325 | 8135 |
| TTCN_475 | 1940 | CTCN_2321 | 8093 | TTCN_506 | 1983 | GTCN_1288 | 8136 |
| CTCN_505 | 1941 | ATCN_1594 | 8094 | CTCN_513 | 1984 | TTCN_2363 | 8137 |
| TTCN_476 | 1942 | TTCN_2344 | 8095 | ATCN_329 | 1985 | GTCN_1289 | 8138 |
| TTCN_477 | 1943 | TTCN_2345 | 8096 | ATCN_330 | 1986 | CTCN_2326 | 8139 |
| TTCN_478 | 1944 | CTCN_2322 | 8097 | CTCN_514 | 1987 | TTCN_2364 | 8140 |
| CTCN_506 | 1945 | TTCN_2346 | 8098 | ATCN_331 | 1988 | ATCN_1608 | 8141 |
| TTCN_479 | 1946 | TTCN_2347 | 8099 | TTCN_507 | 1989 | ATCN_1609 | 8142 |
| ATCN_327 | 1947 | TTCN_2348 | 8100 | GTCN_264 | 1990 | CTCN_2327 | 8143 |
| GTCN_262 | 1948 | TTCN_2349 | 8101 | TTCN_508 | 1991 | CTCN_2328 | 8144 |
| CTCN_507 | 1949 | TTCN_2350 | 8102 | CTCN_515 | 1992 | ATCN_1610 | 8145 |
| GTCN_263 | 1950 | GTCN_1283 | 8103 | GTCN_265 | 1993 | GTCN_1290 | 8146 |
| ATCN_328 | 1951 | GTCN_1284 | 8104 | TTCN_509 | 1994 | ATCN_1611 | 8147 |
| TTCN_480 | 1952 | TTCN_2351 | 8105 | CTCN_516 | 1995 | CTCN_2329 | 8148 |
| TTCN_481 | 1953 | CTCN_2323 | 8106 | ATCN_332 | 1996 | TTCN_2365 | 8149 |
| TTCN_482 | 1954 | ATCN_1595 | 8107 | GTCN_266 | 1997 | ATCN_1612 | 8150 |
| TTCN_483 | 1955 | TTCN_2352 | 8108 | TTCN_510 | 1998 | TTCN_2366 | 8151 |
| TTCN_484 | 1956 | GTCN_1285 | 8109 | TTCN_511 | 1999 | GTCN_1291 | 8152 |
| TTCN_485 | 1957 | TTCN_2353 | 8110 | ATCN_333 | 2000 | CTCN_2330 | 8153 |
| TTCN_486 | 1958 | TTCN_2354 | 8111 | GTCN_267 | 2001 | TTCN_2367 | 8154 |

FIG. 33 (continued)

| | | | | | | | |
|---|---|---|---|---|---|---|---|
| CTCN_517 | 2002 | TTCN_2368 | 8155 | TTCN_520 | 2045 | CTCN_2340 | 8198 |
| TTCN_512 | 2003 | CTCN_2331 | 8156 | TTCN_521 | 2046 | GTCN_1294 | 8199 |
| TTCN_513 | 2004 | TTCN_2369 | 8157 | CTCN_532 | 2047 | ATCN_1625 | 8200 |
| ATCN_334 | 2005 | GTCN_1292 | 8158 | CTCN_533 | 2048 | ATCN_1626 | 8201 |
| GTCN_268 | 2006 | TTCN_2370 | 8159 | CTCN_534 | 2049 | ATCN_1627 | 8202 |
| ATCN_335 | 2007 | TTCN_2371 | 8160 | CTCN_535 | 2050 | CTCN_2341 | 8203 |
| ATCN_336 | 2008 | ATCN_1613 | 8161 | TTCN_522 | 2051 | TTCN_2388 | 8204 |
| TTCN_514 | 2009 | ATCN_1614 | 8162 | CTCN_536 | 2052 | ATCN_1628 | 8205 |
| GTCN_269 | 2010 | ATCN_1615 | 8163 | CTCN_537 | 2053 | TTCN_2389 | 8206 |
| GTCN_270 | 2011 | TTCN_2372 | 8164 | CTCN_538 | 2054 | TTCN_2390 | 8207 |
| CTCN_518 | 2012 | TTCN_2373 | 8165 | TTCN_523 | 2055 | CTCN_2342 | 8208 |
| CTCN_519 | 2013 | TTCN_2374 | 8166 | ATCN_345 | 2056 | GTCN_1295 | 8209 |
| TTCN_515 | 2014 | CTCN_2332 | 8167 | ATCN_346 | 2057 | TTCN_2391 | 8210 |
| GTCN_271 | 2015 | ATCN_1616 | 8168 | GTCN_277 | 2058 | TTCN_2392 | 8211 |
| CTCN_520 | 2016 | TTCN_2375 | 8169 | TTCN_524 | 2059 | ATCN_1629 | 8212 |
| CTCN_521 | 2017 | CTCN_2333 | 8170 | GTCN_278 | 2060 | ATCN_1630 | 8213 |
| CTCN_522 | 2018 | TTCN_2376 | 8171 | TTCN_525 | 2061 | TTCN_2393 | 8214 |
| GTCN_272 | 2019 | TTCN_2377 | 8172 | TTCN_526 | 2062 | CTCN_2343 | 8215 |
| CTCN_523 | 2020 | TTCN_2378 | 8173 | TTCN_527 | 2063 | GTCN_1296 | 8216 |
| TTCN_516 | 2021 | ATCN_1617 | 8174 | TTCN_528 | 2064 | CTCN_2344 | 8217 |
| TTCN_517 | 2022 | TTCN_2379 | 8175 | TTCN_529 | 2065 | CTCN_2345 | 8218 |
| GTCN_273 | 2023 | TTCN_2380 | 8176 | CTCN_539 | 2066 | TTCN_2394 | 8219 |
| CTCN_524 | 2024 | CTCN_2334 | 8177 | CTCN_540 | 2067 | ATCN_1631 | 8220 |
| TTCN_518 | 2025 | CTCN_2335 | 8178 | CTCN_541 | 2068 | ATCN_1632 | 8221 |
| CTCN_525 | 2026 | GTCN_1293 | 8179 | ATCN_347 | 2069 | ATCN_1633 | 8222 |
| ATCN_337 | 2027 | TTCN_2381 | 8180 | ATCN_348 | 2070 | GTCN_1297 | 8223 |
| CTCN_526 | 2028 | TTCN_2382 | 8181 | GTCN_279 | 2071 | TTCN_2395 | 8224 |
| ATCN_338 | 2029 | CTCN_2336 | 8182 | TTCN_530 | 2072 | CTCN_2346 | 8225 |
| GTCN_274 | 2030 | ATCN_1618 | 8183 | ATCN_349 | 2073 | ATCN_1634 | 8226 |
| GTCN_275 | 2031 | TTCN_2383 | 8184 | ATCN_350 | 2074 | TTCN_2396 | 8227 |
| CTCN_527 | 2032 | ATCN_1619 | 8185 | TTCN_531 | 2075 | ATCN_1635 | 8228 |
| ATCN_339 | 2033 | ATCN_1620 | 8186 | TTCN_532 | 2076 | ATCN_1636 | 8229 |
| GTCN_276 | 2034 | TTCN_2384 | 8187 | TTCN_533 | 2077 | ATCN_1637 | 8230 |
| ATCN_340 | 2035 | ATCN_1621 | 8188 | TTCN_534 | 2078 | ATCN_1638 | 8231 |
| CTCN_528 | 2036 | ATCN_1622 | 8189 | CTCN_542 | 2079 | CTCN_2347 | 8232 |
| ATCN_341 | 2037 | TTCN_2385 | 8190 | CTCN_543 | 2080 | TTCN_2397 | 8233 |
| ATCN_342 | 2038 | ATCN_1623 | 8191 | ATCN_351 | 2081 | ATCN_1639 | 8234 |
| CTCN_529 | 2039 | ATCN_1624 | 8192 | TTCN_535 | 2082 | CTCN_2348 | 8235 |
| CTCN_530 | 2040 | CTCN_2337 | 8193 | TTCN_536 | 2083 | GTCN_1298 | 8236 |
| ATCN_343 | 2041 | TTCN_2386 | 8194 | CTCN_544 | 2084 | ATCN_1640 | 8237 |
| ATCN_344 | 2042 | CTCN_2338 | 8195 | CTCN_545 | 2085 | TTCN_2398 | 8238 |
| CTCN_531 | 2043 | TTCN_2387 | 8196 | CTCN_546 | 2086 | CTCN_2349 | 8239 |
| TTCN_519 | 2044 | CTCN_2339 | 8197 | CTCN_547 | 2087 | CTCN_2350 | 8240 |

FIG. 33 (continued)

| | | | | | | | |
|---|---|---|---|---|---|---|---|
| ATCN_352 | 2088 | GTCN_1299 | 8241 | ATCN_362 | 2311 | GTCN_1306 | 8284 |
| GTCN_280 | 2089 | CTCN_2351 | 8242 | CTCN_552 | 2312 | ATCN_1652 | 8285 |
| TTCN_537 | 2090 | ATCN_1641 | 8243 | TTCN_558 | 2313 | GTCN_1307 | 8286 |
| CTCN_548 | 2091 | ATCN_1642 | 8244 | GTCN_288 | 2314 | TTCN_2410 | 8287 |
| ATCN_353 | 2092 | GTCN_1300 | 8245 | TTCN_559 | 2315 | CTCN_2365 | 8288 |
| ATCN_354 | 2093 | ATCN_1643 | 8246 | ATCN_363 | 2316 | ATCN_1653 | 8289 |
| GTCN_281 | 2094 | TTCN_2399 | 8247 | TTCN_560 | 2317 | ATCN_1654 | 8290 |
| ATCN_355 | 2095 | GTCN_1301 | 8248 | TTCN_561 | 2318 | ATCN_1655 | 8291 |
| TTCN_538 | 2096 | CTCN_2352 | 8249 | TTCN_562 | 2319 | GTCN_1308 | 8292 |
| TTCN_539 | 2097 | TTCN_2400 | 8250 | TTCN_563 | 2320 | GTCN_1309 | 8293 |
| ATCN_356 | 2098 | ATCN_1644 | 8251 | GTCN_289 | 2321 | TTCN_2411 | 8294 |
| TTCN_540 | 2099 | GTCN_1302 | 8252 | CTCN_553 | 2322 | CTCN_2366 | 8295 |
| TTCN_541 | 2100 | TTCN_2401 | 8253 | CTCN_554 | 2323 | CTCN_2367 | 8296 |
| CTCN_549 | 2281 | CTCN_2353 | 8254 | CTCN_555 | 2324 | ATCN_1656 | 8297 |
| TTCN_542 | 2282 | CTCN_2354 | 8255 | TTCN_564 | 2325 | CTCN_2368 | 8298 |
| TTCN_543 | 2283 | TTCN_2402 | 8256 | TTCN_565 | 2326 | TTCN_2412 | 8299 |
| ATCN_357 | 2284 | ATCN_1645 | 8257 | CTCN_556 | 2327 | TTCN_2413 | 8300 |
| TTCN_544 | 2285 | TTCN_2403 | 8258 | ATCN_364 | 2328 | ATCN_1657 | 8301 |
| GTCN_282 | 2286 | CTCN_2355 | 8259 | TTCN_566 | 2329 | TTCN_2414 | 8302 |
| TTCN_545 | 2287 | CTCN_2356 | 8260 | GTCN_290 | 2330 | GTCN_1310 | 8303 |
| ATCN_358 | 2288 | CTCN_2357 | 8261 | TTCN_567 | 2331 | TTCN_2415 | 8304 |
| TTCN_546 | 2289 | ATCN_1646 | 8262 | CTCN_557 | 2332 | CTCN_2369 | 8305 |
| TTCN_547 | 2290 | CTCN_2358 | 8263 | GTCN_291 | 2333 | TTCN_2416 | 8306 |
| TTCN_548 | 2291 | ATCN_1647 | 8264 | ATCN_365 | 2334 | ATCN_1658 | 8307 |
| GTCN_283 | 2292 | CTCN_2359 | 8265 | TTCN_568 | 2335 | TTCN_2417 | 8308 |
| TTCN_549 | 2293 | GTCN_1303 | 8266 | ATCN_366 | 2336 | CTCN_2370 | 8309 |
| TTCN_550 | 2294 | CTCN_2360 | 8267 | ATCN_367 | 2337 | CTCN_2371 | 8310 |
| GTCN_284 | 2295 | CTCN_2361 | 8268 | TTCN_569 | 2338 | TTCN_2418 | 8311 |
| ATCN_359 | 2296 | GTCN_1304 | 8269 | CTCN_558 | 2339 | ATCN_1659 | 8312 |
| CTCN_550 | 2297 | ATCN_1648 | 8270 | CTCN_559 | 2340 | TTCN_2419 | 8313 |
| GTCN_285 | 2298 | CTCN_2362 | 8271 | GTCN_292 | 2341 | ATCN_1660 | 8314 |
| CTCN_551 | 2299 | TTCN_2404 | 8272 | CTCN_560 | 2342 | TTCN_2420 | 8315 |
| TTCN_551 | 2300 | CTCN_2363 | 8273 | TTCN_570 | 2343 | ATCN_1661 | 8316 |
| ATCN_360 | 2301 | GTCN_1305 | 8274 | CTCN_561 | 2344 | ATCN_1662 | 8317 |
| TTCN_552 | 2302 | TTCN_2405 | 8275 | TTCN_571 | 2345 | ATCN_1663 | 8318 |
| GTCN_286 | 2303 | ATCN_1649 | 8276 | TTCN_572 | 2346 | ATCN_1664 | 8319 |
| TTCN_553 | 2304 | ATCN_1650 | 8277 | ATCN_368 | 2347 | GTCN_1311 | 8320 |
| TTCN_554 | 2305 | TTCN_2406 | 8278 | TTCN_573 | 2348 | TTCN_2421 | 8321 |
| GTCN_287 | 2306 | TTCN_2407 | 8279 | CTCN_562 | 2349 | ATCN_1665 | 8322 |
| TTCN_555 | 2307 | ATCN_1651 | 8280 | ATCN_369 | 2350 | ATCN_1666 | 8323 |
| TTCN_556 | 2308 | TTCN_2408 | 8281 | ATCN_370 | 2351 | GTCN_1312 | 8324 |
| TTCN_557 | 2309 | TTCN_2409 | 8282 | ATCN_371 | 2352 | ATCN_1667 | 8325 |
| ATCN_361 | 2310 | CTCN_2364 | 8283 | ATCN_372 | 2353 | TTCN_2422 | 8326 |

FIG. 33 (continued)

| TTCN_574 | 2354 | TTCN_2423 | 8327 | ATCN_381 | 2397 | CTCN_2378 | 8370 |
|---|---|---|---|---|---|---|---|
| CTCN_563 | 2355 | CTCN_2372 | 8328 | CTCN_581 | 2398 | TTCN_2447 | 8371 |
| GTCN_293 | 2356 | TTCN_2424 | 8329 | CTCN_582 | 2399 | ATCN_1674 | 8372 |
| ATCN_373 | 2357 | CTCN_2373 | 8330 | GTCN_301 | 2400 | GTCN_1320 | 8373 |
| CTCN_564 | 2358 | GTCN_1313 | 8331 | CTCN_583 | 2401 | GTCN_1321 | 8374 |
| GTCN_294 | 2359 | TTCN_2425 | 8332 | GTCN_302 | 2402 | ATCN_1675 | 8375 |
| TTCN_575 | 2360 | ATCN_1668 | 8333 | CTCN_584 | 2403 | ATCN_1676 | 8376 |
| CTCN_565 | 2361 | TTCN_2426 | 8334 | GTCN_303 | 2404 | GTCN_1322 | 8377 |
| TTCN_576 | 2362 | TTCN_2427 | 8335 | TTCN_583 | 2405 | ATCN_1677 | 8378 |
| TTCN_577 | 2363 | GTCN_1314 | 8336 | ATCN_382 | 2406 | TTCN_2448 | 8379 |
| CTCN_566 | 2364 | GTCN_1315 | 8337 | ATCN_383 | 2407 | TTCN_2449 | 8380 |
| CTCN_567 | 2365 | TTCN_2428 | 8338 | TTCN_584 | 2408 | TTCN_2450 | 8381 |
| GTCN_295 | 2366 | TTCN_2429 | 8339 | ATCN_384 | 2409 | TTCN_2451 | 8382 |
| ATCN_374 | 2367 | TTCN_2430 | 8340 | TTCN_585 | 2410 | CTCN_2379 | 8383 |
| CTCN_568 | 2368 | TTCN_2431 | 8341 | CTCN_585 | 2411 | GTCN_1323 | 8384 |
| ATCN_375 | 2369 | CTCN_2374 | 8342 | TTCN_586 | 2412 | TTCN_2452 | 8385 |
| CTCN_569 | 2370 | GTCN_1316 | 8343 | CTCN_586 | 2413 | CTCN_2380 | 8386 |
| CTCN_570 | 2371 | TTCN_2432 | 8344 | ATCN_385 | 2414 | ATCN_1678 | 8387 |
| ATCN_376 | 2372 | TTCN_2433 | 8345 | GTCN_304 | 2415 | ATCN_1679 | 8388 |
| ATCN_377 | 2373 | TTCN_2434 | 8346 | TTCN_587 | 2416 | CTCN_2381 | 8389 |
| GTCN_296 | 2374 | TTCN_2435 | 8347 | GTCN_305 | 2417 | TTCN_2453 | 8390 |
| CTCN_571 | 2375 | GTCN_1317 | 8348 | ATCN_386 | 2418 | ATCN_1680 | 8391 |
| TTCN_578 | 2376 | TTCN_2436 | 8349 | ATCN_387 | 2419 | TTCN_2454 | 8392 |
| CTCN_572 | 2377 | TTCN_2437 | 8350 | GTCN_306 | 2420 | GTCN_1324 | 8393 |
| GTCN_297 | 2378 | ATCN_1669 | 8351 | TTCN_588 | 2421 | TTCN_2455 | 8394 |
| TTCN_579 | 2379 | TTCN_2438 | 8352 | ATCN_388 | 2422 | GTCN_1325 | 8395 |
| GTCN_298 | 2380 | TTCN_2439 | 8353 | CTCN_587 | 2423 | ATCN_1681 | 8396 |
| TTCN_580 | 2381 | TTCN_2440 | 8354 | GTCN_307 | 2424 | TTCN_2456 | 8397 |
| GTCN_299 | 2382 | TTCN_2441 | 8355 | CTCN_588 | 2425 | TTCN_2457 | 8398 |
| CTCN_573 | 2383 | TTCN_2442 | 8356 | CTCN_589 | 2426 | CTCN_2382 | 8399 |
| GTCN_300 | 2384 | ATCN_1670 | 8357 | CTCN_590 | 2427 | CTCN_2383 | 8400 |
| CTCN_574 | 2385 | ATCN_1671 | 8358 | CTCN_591 | 2428 | TTCN_2458 | 8401 |
| CTCN_575 | 2386 | ATCN_1672 | 8359 | CTCN_592 | 2429 | CTCN_2384 | 8402 |
| CTCN_576 | 2387 | TTCN_2443 | 8360 | TTCN_589 | 2430 | ATCN_1682 | 8403 |
| TTCN_581 | 2388 | TTCN_2444 | 8361 | CTCN_593 | 2431 | ATCN_1683 | 8404 |
| ATCN_378 | 2389 | GTCN_1318 | 8362 | GTCN_308 | 2432 | TTCN_2459 | 8405 |
| TTCN_582 | 2390 | TTCN_2445 | 8363 | CTCN_594 | 2433 | CTCN_2385 | 8406 |
| CTCN_577 | 2391 | CTCN_2375 | 8364 | ATCN_389 | 2434 | TTCN_2460 | 8407 |
| CTCN_578 | 2392 | TTCN_2446 | 8365 | GTCN_309 | 2435 | TTCN_2461 | 8408 |
| CTCN_579 | 2393 | CTCN_2376 | 8366 | ATCN_390 | 2436 | GTCN_1326 | 8409 |
| ATCN_379 | 2394 | CTCN_2377 | 8367 | TTCN_590 | 2437 | ATCN_1684 | 8410 |
| ATCN_380 | 2395 | GTCN_1319 | 8368 | GTCN_310 | 2438 | GTCN_1327 | 8411 |
| CTCN_580 | 2396 | ATCN_1673 | 8369 | CTCN_595 | 2439 | ATCN_1685 | 8412 |

FIG. 33 (continued)

| | | | | | | | |
|---|---|---|---|---|---|---|---|
| CTCN_596 | 2440 | ATCN_1686 | 8413 | TTCN_610 | 2483 | TTCN_2477 | 8456 |
| CTCN_597 | 2441 | TTCN_2462 | 8414 | ATCN_394 | 2484 | TTCN_2478 | 8457 |
| CTCN_598 | 2442 | ATCN_1687 | 8415 | ATCN_395 | 2485 | TTCN_2479 | 8458 |
| GTCN_311 | 2443 | ATCN_1688 | 8416 | ATCN_396 | 2486 | TTCN_2480 | 8459 |
| CTCN_599 | 2444 | TTCN_2463 | 8417 | TTCN_611 | 2487 | GTCN_1332 | 8460 |
| TTCN_591 | 2445 | TTCN_2464 | 8418 | CTCN_608 | 2488 | CTCN_2392 | 8461 |
| GTCN_312 | 2446 | ATCN_1689 | 8419 | GTCN_320 | 2489 | GTCN_1333 | 8462 |
| GTCN_313 | 2447 | ATCN_1690 | 8420 | GTCN_321 | 2490 | CTCN_2393 | 8463 |
| CTCN_600 | 2448 | TTCN_2465 | 8421 | TTCN_612 | 2491 | GTCN_1334 | 8464 |
| TTCN_592 | 2449 | ATCN_1691 | 8422 | CTCN_609 | 2492 | ATCN_1704 | 8465 |
| GTCN_314 | 2450 | TTCN_2466 | 8423 | GTCN_322 | 2493 | CTCN_2394 | 8466 |
| ATCN_391 | 2451 | ATCN_1692 | 8424 | CTCN_610 | 2494 | CTCN_2395 | 8467 |
| TTCN_593 | 2452 | TTCN_2467 | 8425 | GTCN_323 | 2495 | ATCN_1705 | 8468 |
| TTCN_594 | 2453 | ATCN_1693 | 8426 | TTCN_613 | 2496 | TTCN_2481 | 8469 |
| CTCN_601 | 2454 | ATCN_1694 | 8427 | ATCN_397 | 2497 | TTCN_2482 | 8470 |
| GTCN_315 | 2455 | TTCN_2468 | 8428 | TTCN_614 | 2498 | CTCN_2396 | 8471 |
| GTCN_316 | 2456 | TTCN_2469 | 8429 | CTCN_611 | 2499 | ATCN_1706 | 8472 |
| TTCN_595 | 2457 | GTCN_1328 | 8430 | CTCN_612 | 2500 | TTCN_2483 | 8473 |
| TTCN_596 | 2458 | TTCN_2470 | 8431 | ATCN_398 | 2501 | TTCN_2484 | 8474 |
| TTCN_597 | 2459 | TTCN_2471 | 8432 | CTCN_613 | 2502 | CTCN_2397 | 8475 |
| ATCN_392 | 2460 | ATCN_1695 | 8433 | ATCN_399 | 2503 | GTCN_1335 | 8476 |
| GTCN_317 | 2461 | GTCN_1329 | 8434 | TTCN_615 | 2504 | TTCN_2485 | 8477 |
| TTCN_598 | 2462 | TTCN_2472 | 8435 | CTCN_614 | 2505 | CTCN_2398 | 8478 |
| TTCN_599 | 2463 | TTCN_2473 | 8436 | TTCN_616 | 2506 | CTCN_2399 | 8479 |
| TTCN_600 | 2464 | GTCN_1330 | 8437 | TTCN_617 | 2507 | ATCN_1707 | 8480 |
| GTCN_318 | 2465 | CTCN_2386 | 8438 | TTCN_618 | 2508 | TTCN_2486 | 8481 |
| CTCN_602 | 2466 | TTCN_2474 | 8439 | TTCN_619 | 2509 | ATCN_1708 | 8482 |
| CTCN_603 | 2467 | CTCN_2387 | 8440 | CTCN_615 | 2510 | TTCN_2487 | 8483 |
| CTCN_604 | 2468 | ATCN_1696 | 8441 | CTCN_616 | 2511 | TTCN_2488 | 8484 |
| TTCN_601 | 2469 | TTCN_2475 | 8442 | ATCN_400 | 2512 | ATCN_1709 | 8485 |
| TTCN_602 | 2470 | ATCN_1697 | 8443 | GTCN_324 | 2513 | GTCN_1336 | 8486 |
| TTCN_603 | 2471 | CTCN_2388 | 8444 | TTCN_620 | 2514 | ATCN_1710 | 8487 |
| CTCN_605 | 2472 | ATCN_1698 | 8445 | CTCN_617 | 2515 | TTCN_2489 | 8488 |
| CTCN_606 | 2473 | ATCN_1699 | 8446 | GTCN_325 | 2516 | CTCN_2400 | 8489 |
| TTCN_604 | 2474 | ATCN_1700 | 8447 | CTCN_618 | 2517 | ATCN_1711 | 8490 |
| TTCN_605 | 2475 | ATCN_1701 | 8448 | GTCN_326 | 2518 | ATCN_1712 | 8491 |
| TTCN_606 | 2476 | CTCN_2389 | 8449 | CTCN_619 | 2519 | ATCN_1713 | 8492 |
| ATCN_393 | 2477 | ATCN_1702 | 8450 | CTCN_620 | 2520 | GTCN_1337 | 8493 |
| TTCN_607 | 2478 | TTCN_2476 | 8451 | GTCN_327 | 2521 | ATCN_1714 | 8494 |
| CTCN_607 | 2479 | CTCN_2390 | 8452 | CTCN_621 | 2522 | ATCN_1715 | 8495 |
| GTCN_319 | 2480 | ATCN_1703 | 8453 | ATCN_401 | 2523 | ATCN_1716 | 8496 |
| TTCN_608 | 2481 | GTCN_1331 | 8454 | GTCN_328 | 2524 | TTCN_2490 | 8497 |
| TTCN_609 | 2482 | CTCN_2391 | 8455 | CTCN_622 | 2525 | ATCN_1717 | 8498 |

FIG. 33 (continued)

| | | | | | | | |
|---|---|---|---|---|---|---|---|
| CTCN_623 | 2526 | CTCN_2401 | 8499 | CTCN_637 | 2569 | GTCN_1344 | 8542 |
| CTCN_624 | 2527 | CTCN_2402 | 8500 | TTCN_632 | 2570 | CTCN_2411 | 8543 |
| TTCN_621 | 2528 | CTCN_2403 | 8501 | TTCN_633 | 2571 | ATCN_1730 | 8544 |
| TTCN_622 | 2529 | CTCN_2404 | 8502 | TTCN_634 | 2572 | TTCN_2506 | 8545 |
| CTCN_625 | 2530 | TTCN_2491 | 8503 | GTCN_340 | 2573 | CTCN_2412 | 8546 |
| CTCN_626 | 2531 | CTCN_2405 | 8504 | TTCN_635 | 2574 | CTCN_2413 | 8547 |
| CTCN_627 | 2532 | TTCN_2492 | 8505 | CTCN_638 | 2575 | ATCN_1731 | 8548 |
| GTCN_329 | 2533 | TTCN_2493 | 8506 | TTCN_636 | 2576 | ATCN_1732 | 8549 |
| CTCN_628 | 2534 | ATCN_1718 | 8507 | TTCN_637 | 2577 | GTCN_1345 | 8550 |
| CTCN_629 | 2535 | ATCN_1719 | 8508 | TTCN_638 | 2578 | CTCN_2414 | 8551 |
| GTCN_330 | 2536 | ATCN_1720 | 8509 | TTCN_639 | 2579 | TTCN_2507 | 8552 |
| TTCN_623 | 2537 | TTCN_2494 | 8510 | TTCN_640 | 2580 | ATCN_1733 | 8553 |
| ATCN_402 | 2538 | TTCN_2495 | 8511 | ATCN_409 | 2581 | ATCN_1734 | 8554 |
| GTCN_331 | 2539 | GTCN_1338 | 8512 | CTCN_639 | 2582 | TTCN_2508 | 8555 |
| CTCN_630 | 2540 | TTCN_2496 | 8513 | GTCN_341 | 2583 | CTCN_2415 | 8556 |
| ATCN_403 | 2541 | ATCN_1721 | 8514 | TTCN_641 | 2584 | GTCN_1346 | 8557 |
| CTCN_631 | 2542 | ATCN_1722 | 8515 | CTCN_640 | 2585 | TTCN_2509 | 8558 |
| GTCN_332 | 2543 | GTCN_1339 | 8516 | GTCN_342 | 2586 | ATCN_1735 | 8559 |
| CTCN_632 | 2544 | GTCN_1340 | 8517 | TTCN_642 | 2587 | ATCN_1736 | 8560 |
| ATCN_404 | 2545 | CTCN_2406 | 8518 | ATCN_410 | 2588 | TTCN_2510 | 8561 |
| ATCN_405 | 2546 | TTCN_2497 | 8519 | TTCN_643 | 2589 | ATCN_1737 | 8562 |
| TTCN_624 | 2547 | TTCN_2498 | 8520 | TTCN_644 | 2590 | TTCN_2511 | 8563 |
| ATCN_406 | 2548 | ATCN_1723 | 8521 | TTCN_645 | 2591 | TTCN_2512 | 8564 |
| CTCN_633 | 2549 | CTCN_2407 | 8522 | ATCN_411 | 2592 | CTCN_2416 | 8565 |
| CTCN_634 | 2550 | TTCN_2499 | 8523 | ATCN_412 | 2593 | ATCN_1738 | 8566 |
| GTCN_333 | 2551 | CTCN_2408 | 8524 | TTCN_646 | 2594 | TTCN_2513 | 8567 |
| TTCN_625 | 2552 | GTCN_1341 | 8525 | ATCN_413 | 2595 | CTCN_2417 | 8568 |
| TTCN_626 | 2553 | TTCN_2500 | 8526 | TTCN_647 | 2596 | TTCN_2514 | 8569 |
| TTCN_627 | 2554 | TTCN_2501 | 8527 | CTCN_641 | 2597 | GTCN_1347 | 8570 |
| TTCN_628 | 2555 | CTCN_2409 | 8528 | TTCN_648 | 2598 | GTCN_1348 | 8571 |
| ATCN_407 | 2556 | TTCN_2502 | 8529 | TTCN_649 | 2599 | CTCN_2418 | 8572 |
| GTCN_334 | 2557 | CTCN_2410 | 8530 | TTCN_650 | 2600 | TTCN_2515 | 8573 |
| CTCN_635 | 2558 | ATCN_1724 | 8531 | TTCN_651 | 2601 | CTCN_2419 | 8574 |
| CTCN_636 | 2559 | ATCN_1725 | 8532 | GTCN_343 | 2602 | GTCN_1349 | 8575 |
| ATCN_408 | 2560 | TTCN_2503 | 8533 | TTCN_652 | 2603 | TTCN_2516 | 8576 |
| TTCN_629 | 2561 | ATCN_1726 | 8534 | GTCN_344 | 2604 | ATCN_1739 | 8577 |
| GTCN_335 | 2562 | TTCN_2504 | 8535 | CTCN_642 | 2605 | TTCN_2517 | 8578 |
| TTCN_630 | 2563 | ATCN_1727 | 8536 | TTCN_653 | 2606 | ATCN_1740 | 8579 |
| GTCN_336 | 2564 | ATCN_1728 | 8537 | CTCN_643 | 2607 | GTCN_1350 | 8580 |
| TTCN_631 | 2565 | TTCN_2505 | 8538 | CTCN_644 | 2608 | GTCN_1351 | 8581 |
| GTCN_337 | 2566 | GTCN_1342 | 8539 | TTCN_654 | 2609 | TTCN_2518 | 8582 |
| GTCN_338 | 2567 | GTCN_1343 | 8540 | ATCN_414 | 2610 | ATCN_1741 | 8583 |
| GTCN_339 | 2568 | ATCN_1729 | 8541 | CTCN_645 | 2611 | TTCN_2519 | 8584 |

FIG. 33 (continued)

| | | | | | | | |
|---|---|---|---|---|---|---|---|
| CTCN_646 | 2612 | ATCN_1742 | 8585 | TTCN_672 | 2655 | CTCN_2438 | 8628 |
| TTCN_655 | 2613 | TTCN_2520 | 8586 | CTCN_656 | 2656 | CTCN_2439 | 8629 |
| GTCN_345 | 2614 | TTCN_2521 | 8587 | CTCN_657 | 2657 | TTCN_2531 | 8630 |
| GTCN_346 | 2615 | ATCN_1743 | 8588 | GTCN_354 | 2658 | GTCN_1356 | 8631 |
| TTCN_656 | 2616 | CTCN_2420 | 8589 | CTCN_658 | 2659 | CTCN_2440 | 8632 |
| CTCN_647 | 2617 | GTCN_1352 | 8590 | GTCN_355 | 2660 | TTCN_2532 | 8633 |
| ATCN_415 | 2618 | TTCN_2522 | 8591 | TTCN_673 | 2661 | CTCN_2441 | 8634 |
| GTCN_347 | 2619 | ATCN_1744 | 8592 | ATCN_422 | 2662 | CTCN_2442 | 8635 |
| TTCN_657 | 2620 | ATCN_1745 | 8593 | GTCN_356 | 2663 | TTCN_2533 | 8636 |
| TTCN_658 | 2621 | TTCN_2523 | 8594 | ATCN_423 | 2664 | CTCN_2443 | 8637 |
| TTCN_659 | 2622 | CTCN_2421 | 8595 | CTCN_659 | 2665 | CTCN_2444 | 8638 |
| CTCN_648 | 2623 | CTCN_2422 | 8596 | ATCN_424 | 2666 | GTCN_1357 | 8639 |
| TTCN_660 | 2624 | CTCN_2423 | 8597 | ATCN_425 | 2667 | ATCN_1752 | 8640 |
| TTCN_661 | 2625 | CTCN_2424 | 8598 | ATCN_426 | 2668 | GTCN_1358 | 8641 |
| CTCN_649 | 2626 | CTCN_2425 | 8599 | GTCN_357 | 2669 | TTCN_2534 | 8642 |
| TTCN_662 | 2627 | ATCN_1746 | 8600 | TTCN_674 | 2670 | TTCN_2535 | 8643 |
| GTCN_348 | 2628 | TTCN_2524 | 8601 | TTCN_675 | 2671 | ATCN_1753 | 8644 |
| TTCN_663 | 2629 | ATCN_1747 | 8602 | GTCN_358 | 2672 | TTCN_2536 | 8645 |
| TTCN_664 | 2630 | CTCN_2426 | 8603 | CTCN_660 | 2673 | ATCN_1754 | 8646 |
| TTCN_665 | 2631 | CTCN_2427 | 8604 | GTCN_359 | 2674 | GTCN_1359 | 8647 |
| GTCN_349 | 2632 | CTCN_2428 | 8605 | CTCN_661 | 2675 | CTCN_2445 | 8648 |
| ATCN_416 | 2633 | CTCN_2429 | 8606 | CTCN_662 | 2676 | ATCN_1755 | 8649 |
| CTCN_650 | 2634 | TTCN_2525 | 8607 | TTCN_676 | 2677 | ATCN_1756 | 8650 |
| ATCN_417 | 2635 | ATCN_1748 | 8608 | ATCN_427 | 2678 | CTCN_2446 | 8651 |
| TTCN_666 | 2636 | CTCN_2430 | 8609 | CTCN_663 | 2679 | TTCN_2537 | 8652 |
| CTCN_651 | 2637 | CTCN_2431 | 8610 | ATCN_428 | 2680 | ATCN_1757 | 8653 |
| TTCN_667 | 2638 | GTCN_1353 | 8611 | ATCN_429 | 2681 | TTCN_2538 | 8654 |
| GTCN_350 | 2639 | CTCN_2432 | 8612 | ATCN_430 | 2682 | GTCN_1360 | 8655 |
| CTCN_652 | 2640 | TTCN_2526 | 8613 | ATCN_431 | 2683 | TTCN_2539 | 8656 |
| TTCN_668 | 2641 | TTCN_2527 | 8614 | ATCN_432 | 2684 | TTCN_2540 | 8657 |
| CTCN_653 | 2642 | TTCN_2528 | 8615 | ATCN_433 | 2685 | ATCN_1758 | 8658 |
| TTCN_669 | 2643 | GTCN_1354 | 8616 | CTCN_664 | 2686 | TTCN_2541 | 8659 |
| ATCN_418 | 2644 | ATCN_1749 | 8617 | GTCN_360 | 2687 | ATCN_1759 | 8660 |
| GTCN_351 | 2645 | CTCN_2433 | 8618 | GTCN_361 | 2688 | CTCN_2447 | 8661 |
| ATCN_419 | 2646 | ATCN_1750 | 8619 | CTCN_665 | 2689 | ATCN_1760 | 8662 |
| CTCN_654 | 2647 | CTCN_2434 | 8620 | CTCN_666 | 2690 | CTCN_2448 | 8663 |
| GTCN_352 | 2648 | TTCN_2529 | 8621 | CTCN_667 | 2691 | CTCN_2449 | 8664 |
| ATCN_420 | 2649 | GTCN_1355 | 8622 | CTCN_668 | 2692 | ATCN_1761 | 8665 |
| TTCN_670 | 2650 | TTCN_2530 | 8623 | TTCN_677 | 2693 | ATCN_1762 | 8666 |
| CTCN_655 | 2651 | ATCN_1751 | 8624 | CTCN_669 | 2694 | GTCN_1361 | 8667 |
| ATCN_421 | 2652 | CTCN_2435 | 8625 | CTCN_670 | 2695 | CTCN_2450 | 8668 |
| GTCN_353 | 2653 | CTCN_2436 | 8626 | GTCN_362 | 2696 | TTCN_2542 | 8669 |
| TTCN_671 | 2654 | CTCN_2437 | 8627 | ATCN_434 | 2697 | GTCN_1362 | 8670 |

FIG. 33 (continued)

| | | | | | | | |
|---|---|---|---|---|---|---|---|
| GTCN_363 | 2698 | GTCN_1363 | 8671 | GTCN_377 | 2741 | CTCN_2463 | 8714 |
| GTCN_364 | 2699 | TTCN_2543 | 8672 | TTCN_688 | 2742 | GTCN_1373 | 8715 |
| CTCN_671 | 2700 | GTCN_1364 | 8673 | TTCN_689 | 2743 | TTCN_2558 | 8716 |
| GTCN_365 | 2701 | ATCN_1763 | 8674 | TTCN_690 | 2744 | CTCN_2464 | 8717 |
| ATCN_435 | 2702 | CTCN_2451 | 8675 | ATCN_444 | 2745 | GTCN_1374 | 8718 |
| TTCN_678 | 2703 | CTCN_2452 | 8676 | ATCN_445 | 2746 | CTCN_2465 | 8719 |
| CTCN_672 | 2704 | CTCN_2453 | 8677 | ATCN_446 | 2747 | TTCN_2559 | 8720 |
| GTCN_366 | 2705 | CTCN_2454 | 8678 | ATCN_447 | 2748 | CTCN_2466 | 8721 |
| GTCN_367 | 2706 | TTCN_2544 | 8679 | TTCN_691 | 2749 | ATCN_1769 | 8722 |
| GTCN_368 | 2707 | TTCN_2545 | 8680 | ATCN_448 | 2750 | CTCN_2467 | 8723 |
| CTCN_673 | 2708 | CTCN_2455 | 8681 | ATCN_449 | 2751 | ATCN_1770 | 8724 |
| GTCN_369 | 2709 | CTCN_2456 | 8682 | GTCN_378 | 2752 | GTCN_1375 | 8725 |
| GTCN_370 | 2710 | CTCN_2457 | 8683 | TTCN_692 | 2753 | GTCN_1376 | 8726 |
| ATCN_436 | 2711 | CTCN_2458 | 8684 | CTCN_681 | 2754 | TTCN_2560 | 8727 |
| ATCN_437 | 2712 | CTCN_2459 | 8685 | TTCN_693 | 2755 | CTCN_2468 | 8728 |
| GTCN_371 | 2713 | ATCN_1764 | 8686 | ATCN_450 | 2756 | CTCN_2469 | 8729 |
| TTCN_679 | 2714 | CTCN_2460 | 8687 | CTCN_682 | 2757 | CTCN_2470 | 8730 |
| GTCN_372 | 2715 | GTCN_1365 | 8688 | GTCN_379 | 2758 | TTCN_2561 | 8731 |
| CTCN_674 | 2716 | CTCN_2461 | 8689 | ATCN_451 | 2759 | GTCN_1377 | 8732 |
| GTCN_373 | 2717 | GTCN_1366 | 8690 | TTCN_694 | 2760 | ATCN_1771 | 8733 |
| TTCN_680 | 2718 | GTCN_1367 | 8691 | GTCN_380 | 2761 | ATCN_1772 | 8734 |
| GTCN_374 | 2719 | TTCN_2546 | 8692 | CTCN_683 | 2762 | ATCN_1773 | 8735 |
| ATCN_438 | 2720 | TTCN_2547 | 8693 | ATCN_452 | 2763 | GTCN_1378 | 8736 |
| GTCN_375 | 2721 | TTCN_2548 | 8694 | ATCN_453 | 2764 | CTCN_2471 | 8737 |
| TTCN_681 | 2722 | TTCN_2549 | 8695 | GTCN_381 | 2765 | TTCN_2562 | 8738 |
| ATCN_439 | 2723 | TTCN_2550 | 8696 | TTCN_695 | 2766 | GTCN_1379 | 8739 |
| CTCN_675 | 2724 | TTCN_2551 | 8697 | CTCN_684 | 2767 | TTCN_2563 | 8740 |
| ATCN_440 | 2725 | ATCN_1765 | 8698 | ATCN_454 | 2768 | GTCN_1380 | 8741 |
| TTCN_682 | 2726 | CTCN_2462 | 8699 | GTCN_382 | 2769 | ATCN_1774 | 8742 |
| TTCN_683 | 2727 | TTCN_2552 | 8700 | TTCN_696 | 2770 | ATCN_1775 | 8743 |
| TTCN_684 | 2728 | GTCN_1368 | 8701 | ATCN_455 | 2771 | TTCN_2564 | 8744 |
| TTCN_685 | 2729 | TTCN_2553 | 8702 | ATCN_456 | 2772 | CTCN_2472 | 8745 |
| CTCN_676 | 2730 | TTCN_2554 | 8703 | CTCN_685 | 2773 | TTCN_2565 | 8746 |
| CTCN_677 | 2731 | TTCN_2555 | 8704 | TTCN_697 | 2774 | ATCN_1776 | 8747 |
| TTCN_686 | 2732 | GTCN_1369 | 8705 | TTCN_698 | 2775 | ATCN_1777 | 8748 |
| ATCN_441 | 2733 | ATCN_1766 | 8706 | TTCN_699 | 2776 | ATCN_1778 | 8749 |
| TTCN_687 | 2734 | TTCN_2556 | 8707 | GTCN_383 | 2777 | ATCN_1779 | 8750 |
| CTCN_678 | 2735 | GTCN_1370 | 8708 | TTCN_700 | 2778 | CTCN_2473 | 8751 |
| GTCN_376 | 2736 | TTCN_2557 | 8709 | ATCN_457 | 2779 | CTCN_2474 | 8752 |
| CTCN_679 | 2737 | GTCN_1371 | 8710 | ATCN_458 | 2780 | ATCN_1780 | 8753 |
| ATCN_442 | 2738 | ATCN_1767 | 8711 | TTCN_701 | 2781 | TTCN_2566 | 8754 |
| ATCN_443 | 2739 | ATCN_1768 | 8712 | TTCN_702 | 2782 | ATCN_1781 | 8755 |
| CTCN_680 | 2740 | GTCN_1372 | 8713 | ATCN_459 | 2783 | TTCN_2567 | 8756 |

FIG. 33 (continued)

| | | | | | | | |
|---|---|---|---|---|---|---|---|
| TTCN_703 | 2784 | CTCN_2475 | 8757 | ATCN_473 | 2827 | CTCN_2484 | 8800 |
| TTCN_704 | 2785 | GTCN_1381 | 8758 | ATCN_474 | 2828 | TTCN_2585 | 8801 |
| TTCN_705 | 2786 | TTCN_2568 | 8759 | ATCN_475 | 2829 | CTCN_2485 | 8802 |
| TTCN_706 | 2787 | TTCN_2569 | 8760 | ATCN_476 | 2830 | TTCN_2586 | 8803 |
| CTCN_686 | 2788 | TTCN_2570 | 8761 | TTCN_720 | 2831 | TTCN_2587 | 8804 |
| ATCN_460 | 2789 | GTCN_1382 | 8762 | ATCN_477 | 2832 | GTCN_1388 | 8805 |
| ATCN_461 | 2790 | TTCN_2571 | 8763 | CTCN_693 | 2833 | TTCN_2588 | 8806 |
| ATCN_462 | 2791 | CTCN_2476 | 8764 | TTCN_721 | 2834 | ATCN_1792 | 8807 |
| ATCN_463 | 2792 | GTCN_1383 | 8765 | GTCN_390 | 2835 | ATCN_1793 | 8808 |
| CTCN_687 | 2793 | ATCN_1782 | 8766 | ATCN_478 | 2836 | ATCN_1794 | 8809 |
| CTCN_688 | 2794 | TTCN_2572 | 8767 | TTCN_722 | 2837 | TTCN_2589 | 8810 |
| GTCN_384 | 2795 | ATCN_1783 | 8768 | ATCN_479 | 2838 | GTCN_1389 | 8811 |
| TTCN_707 | 2796 | ATCN_1784 | 8769 | ATCN_480 | 2839 | TTCN_2590 | 8812 |
| TTCN_708 | 2797 | TTCN_2573 | 8770 | ATCN_481 | 2840 | TTCN_2591 | 8813 |
| ATCN_464 | 2798 | CTCN_2477 | 8771 | TTCN_723 | 2841 | TTCN_2592 | 8814 |
| ATCN_465 | 2799 | GTCN_1384 | 8772 | TTCN_724 | 2842 | TTCN_2593 | 8815 |
| CTCN_689 | 2800 | TTCN_2574 | 8773 | TTCN_725 | 2843 | GTCN_1390 | 8816 |
| GTCN_385 | 2801 | TTCN_2575 | 8774 | TTCN_726 | 2844 | GTCN_1391 | 8817 |
| TTCN_709 | 2802 | CTCN_2478 | 8775 | CTCN_694 | 2845 | CTCN_2486 | 8818 |
| CTCN_690 | 2803 | ATCN_1785 | 8776 | CTCN_695 | 2846 | ATCN_1795 | 8819 |
| ATCN_466 | 2804 | TTCN_2576 | 8777 | ATCN_482 | 2847 | CTCN_2487 | 8820 |
| GTCN_386 | 2805 | GTCN_1385 | 8778 | TTCN_727 | 2848 | CTCN_2488 | 8821 |
| ATCN_467 | 2806 | TTCN_2577 | 8779 | CTCN_696 | 2849 | CTCN_2489 | 8822 |
| GTCN_387 | 2807 | CTCN_2479 | 8780 | CTCN_697 | 2850 | CTCN_2490 | 8823 |
| TTCN_710 | 2808 | CTCN_2480 | 8781 | GTCN_391 | 2851 | TTCN_2594 | 8824 |
| TTCN_711 | 2809 | GTCN_1386 | 8782 | ATCN_483 | 2852 | TTCN_2595 | 8825 |
| ATCN_468 | 2810 | ATCN_1786 | 8783 | CTCN_698 | 2853 | TTCN_2596 | 8826 |
| TTCN_712 | 2811 | TTCN_2578 | 8784 | CTCN_699 | 2854 | TTCN_2597 | 8827 |
| TTCN_713 | 2812 | TTCN_2579 | 8785 | CTCN_700 | 2855 | TTCN_2598 | 8828 |
| ATCN_469 | 2813 | CTCN_2481 | 8786 | TTCN_728 | 2856 | TTCN_2599 | 8829 |
| ATCN_470 | 2814 | CTCN_2482 | 8787 | TTCN_729 | 2857 | TTCN_2600 | 8830 |
| ATCN_471 | 2815 | TTCN_2580 | 8788 | CTCN_701 | 2858 | CTCN_2491 | 8831 |
| TTCN_714 | 2816 | TTCN_2581 | 8789 | ATCN_484 | 2859 | CTCN_2492 | 8832 |
| GTCN_388 | 2817 | GTCN_1387 | 8790 | ATCN_485 | 2860 | TTCN_2601 | 8833 |
| TTCN_715 | 2818 | TTCN_2582 | 8791 | ATCN_486 | 2861 | TTCN_2602 | 8834 |
| GTCN_389 | 2819 | TTCN_2583 | 8792 | CTCN_702 | 2862 | TTCN_2603 | 8835 |
| TTCN_716 | 2820 | ATCN_1787 | 8793 | CTCN_703 | 2863 | ATCN_1796 | 8836 |
| TTCN_717 | 2821 | CTCN_2483 | 8794 | ATCN_487 | 2864 | TTCN_2604 | 8837 |
| TTCN_718 | 2822 | ATCN_1788 | 8795 | CTCN_704 | 2865 | GTCN_1392 | 8838 |
| ATCN_472 | 2823 | ATCN_1789 | 8796 | CTCN_705 | 2866 | GTCN_1393 | 8839 |
| CTCN_691 | 2824 | ATCN_1790 | 8797 | ATCN_488 | 2867 | TTCN_2605 | 8840 |
| TTCN_719 | 2825 | TTCN_2584 | 8798 | ATCN_489 | 2868 | ATCN_1797 | 8841 |
| CTCN_692 | 2826 | ATCN_1791 | 8799 | CTCN_706 | 2869 | TTCN_2606 | 8842 |

FIG. 33 (continued)

| | | | | | | | |
|---|---|---|---|---|---|---|---|
| GTCN_392 | 2870 | TTCN_2607 | 8843 | GTCN_397 | 2913 | ATCN_1812 | 8886 |
| CTCN_707 | 2871 | TTCN_2608 | 8844 | CTCN_729 | 2914 | ATCN_1813 | 8887 |
| CTCN_708 | 2872 | ATCN_1798 | 8845 | CTCN_730 | 2915 | TTCN_2621 | 8888 |
| GTCN_393 | 2873 | TTCN_2609 | 8846 | TTCN_738 | 2916 | CTCN_2502 | 8889 |
| GTCN_394 | 2874 | ATCN_1799 | 8847 | TTCN_739 | 2917 | CTCN_2503 | 8890 |
| CTCN_709 | 2875 | ATCN_1800 | 8848 | ATCN_498 | 2918 | GTCN_1400 | 8891 |
| TTCN_730 | 2876 | TTCN_2610 | 8849 | CTCN_731 | 2919 | TTCN_2622 | 8892 |
| ATCN_490 | 2877 | TTCN_2611 | 8850 | TTCN_740 | 2920 | ATCN_1814 | 8893 |
| CTCN_710 | 2878 | ATCN_1801 | 8851 | TTCN_741 | 2921 | CTCN_2504 | 8894 |
| ATCN_491 | 2879 | GTCN_1394 | 8852 | TTCN_742 | 2922 | TTCN_2623 | 8895 |
| CTCN_711 | 2880 | CTCN_2493 | 8853 | TTCN_743 | 2923 | CTCN_2505 | 8896 |
| CTCN_712 | 2881 | ATCN_1802 | 8854 | GTCN_398 | 2924 | ATCN_1815 | 8897 |
| CTCN_713 | 2882 | TTCN_2612 | 8855 | TTCN_744 | 2925 | TTCN_2624 | 8898 |
| TTCN_731 | 2883 | TTCN_2613 | 8856 | CTCN_732 | 2926 | CTCN_2506 | 8899 |
| ATCN_492 | 2884 | GTCN_1395 | 8857 | CTCN_733 | 2927 | CTCN_2507 | 8900 |
| TTCN_732 | 2885 | GTCN_1396 | 8858 | GTCN_399 | 2928 | GTCN_1401 | 8901 |
| CTCN_714 | 2886 | TTCN_2614 | 8859 | TTCN_745 | 2929 | CTCN_2508 | 8902 |
| ATCN_493 | 2887 | TTCN_2615 | 8860 | CTCN_734 | 2930 | GTCN_1402 | 8903 |
| CTCN_715 | 2888 | TTCN_2616 | 8861 | TTCN_746 | 2931 | CTCN_2509 | 8904 |
| CTCN_716 | 2889 | GTCN_1397 | 8862 | CTCN_735 | 2932 | TTCN_2625 | 8905 |
| ATCN_494 | 2890 | CTCN_2494 | 8863 | CTCN_736 | 2933 | TTCN_2626 | 8906 |
| CTCN_717 | 2891 | TTCN_2617 | 8864 | TTCN_747 | 2934 | ATCN_1816 | 8907 |
| GTCN_395 | 2892 | CTCN_2495 | 8865 | ATCN_499 | 2935 | ATCN_1817 | 8908 |
| CTCN_718 | 2893 | TTCN_2618 | 8866 | CTCN_737 | 2936 | TTCN_2627 | 8909 |
| CTCN_719 | 2894 | ATCN_1803 | 8867 | GTCN_400 | 2937 | CTCN_2510 | 8910 |
| GTCN_396 | 2895 | TTCN_2619 | 8868 | TTCN_748 | 2938 | TTCN_2628 | 8911 |
| CTCN_720 | 2896 | ATCN_1804 | 8869 | CTCN_738 | 2939 | ATCN_1818 | 8912 |
| ATCN_495 | 2897 | ATCN_1805 | 8870 | GTCN_401 | 2940 | GTCN_1403 | 8913 |
| CTCN_721 | 2898 | ATCN_1806 | 8871 | ATCN_500 | 2941 | ATCN_1819 | 8914 |
| TTCN_733 | 2899 | ATCN_1807 | 8872 | TTCN_749 | 2942 | ATCN_1820 | 8915 |
| TTCN_734 | 2900 | GTCN_1398 | 8873 | CTCN_739 | 2943 | TTCN_2629 | 8916 |
| TTCN_735 | 2901 | CTCN_2496 | 8874 | TTCN_750 | 2944 | GTCN_1404 | 8917 |
| CTCN_722 | 2902 | ATCN_1808 | 8875 | TTCN_751 | 2945 | TTCN_2630 | 8918 |
| ATCN_496 | 2903 | CTCN_2497 | 8876 | TTCN_752 | 2946 | GTCN_1405 | 8919 |
| ATCN_497 | 2904 | ATCN_1809 | 8877 | CTCN_740 | 2947 | GTCN_1406 | 8920 |
| CTCN_723 | 2905 | ATCN_1810 | 8878 | CTCN_741 | 2948 | TTCN_2631 | 8921 |
| CTCN_724 | 2906 | CTCN_2498 | 8879 | CTCN_742 | 2949 | CTCN_2511 | 8922 |
| TTCN_736 | 2907 | CTCN_2499 | 8880 | TTCN_753 | 2950 | CTCN_2512 | 8923 |
| TTCN_737 | 2908 | ATCN_1811 | 8881 | ATCN_501 | 2951 | TTCN_2632 | 8924 |
| CTCN_725 | 2909 | CTCN_2500 | 8882 | ATCN_502 | 2952 | TTCN_2633 | 8925 |
| CTCN_726 | 2910 | TTCN_2620 | 8883 | TTCN_754 | 2953 | CTCN_2513 | 8926 |
| CTCN_727 | 2911 | GTCN_1399 | 8884 | CTCN_743 | 2954 | GTCN_1407 | 8927 |
| CTCN_728 | 2912 | CTCN_2501 | 8885 | TTCN_755 | 2955 | ATCN_1821 | 8928 |

FIG. 33 (continued)

| | | | | | | | |
|---|---|---|---|---|---|---|---|
| TTCN_756 | 2956 | TTCN_2634 | 8929 | CTCN_755 | 2999 | GTCN_1411 | 8972 |
| ATCN_503 | 2957 | CTCN_2514 | 8930 | TTCN_767 | 3000 | TTCN_2658 | 8973 |
| CTCN_744 | 2958 | TTCN_2635 | 8931 | CTCN_756 | 3001 | CTCN_2523 | 8974 |
| ATCN_504 | 2959 | CTCN_2515 | 8932 | TTCN_768 | 3002 | GTCN_1412 | 8975 |
| ATCN_505 | 2960 | CTCN_2516 | 8933 | GTCN_416 | 3003 | TTCN_2659 | 8976 |
| ATCN_506 | 2961 | TTCN_2636 | 8934 | ATCN_510 | 3004 | TTCN_2660 | 8977 |
| CTCN_745 | 2962 | TTCN_2637 | 8935 | ATCN_511 | 3005 | TTCN_2661 | 8978 |
| TTCN_757 | 2963 | TTCN_2638 | 8936 | GTCN_417 | 3006 | ATCN_1829 | 8979 |
| GTCN_402 | 2964 | TTCN_2639 | 8937 | TTCN_769 | 3007 | TTCN_2662 | 8980 |
| TTCN_758 | 2965 | TTCN_2640 | 8938 | GTCN_418 | 3008 | TTCN_2663 | 8981 |
| TTCN_759 | 2966 | TTCN_2641 | 8939 | TTCN_770 | 3009 | TTCN_2664 | 8982 |
| TTCN_760 | 2967 | ATCN_1822 | 8940 | GTCN_419 | 3010 | TTCN_2665 | 8983 |
| GTCN_403 | 2968 | CTCN_2517 | 8941 | ATCN_512 | 3011 | TTCN_2666 | 8984 |
| CTCN_746 | 2969 | TTCN_2642 | 8942 | CTCN_757 | 3012 | TTCN_2667 | 8985 |
| TTCN_761 | 2970 | TTCN_2643 | 8943 | TTCN_771 | 3013 | TTCN_2668 | 8986 |
| GTCN_404 | 2971 | CTCN_2518 | 8944 | CTCN_758 | 3014 | CTCN_2524 | 8987 |
| CTCN_747 | 2972 | TTCN_2644 | 8945 | TTCN_772 | 3015 | CTCN_2525 | 8988 |
| CTCN_748 | 2973 | ATCN_1823 | 8946 | TTCN_773 | 3016 | ATCN_1830 | 8989 |
| CTCN_749 | 2974 | TTCN_2645 | 8947 | ATCN_513 | 3017 | CTCN_2526 | 8990 |
| TTCN_762 | 2975 | TTCN_2646 | 8948 | GTCN_420 | 3018 | CTCN_2527 | 8991 |
| GTCN_405 | 2976 | ATCN_1824 | 8949 | GTCN_421 | 3019 | ATCN_1831 | 8992 |
| GTCN_406 | 2977 | TTCN_2647 | 8950 | CTCN_759 | 3020 | ATCN_1832 | 8993 |
| GTCN_407 | 2978 | TTCN_2648 | 8951 | ATCN_514 | 3021 | CTCN_2528 | 8994 |
| TTCN_763 | 2979 | TTCN_2649 | 8952 | ATCN_515 | 3022 | GTCN_1413 | 8995 |
| CTCN_750 | 2980 | TTCN_2650 | 8953 | ATCN_516 | 3023 | CTCN_2529 | 8996 |
| CTCN_751 | 2981 | TTCN_2651 | 8954 | CTCN_760 | 3024 | TTCN_2669 | 8997 |
| TTCN_764 | 2982 | GTCN_1408 | 8955 | TTCN_774 | 3025 | CTCN_2530 | 8998 |
| GTCN_408 | 2983 | CTCN_2519 | 8956 | CTCN_761 | 3026 | TTCN_2670 | 8999 |
| ATCN_507 | 2984 | TTCN_2652 | 8957 | ATCN_517 | 3027 | GTCN_1414 | 9000 |
| CTCN_752 | 2985 | CTCN_2520 | 8958 | ATCN_518 | 3028 | ATCN_1833 | 9001 |
| GTCN_409 | 2986 | ATCN_1825 | 8959 | CTCN_762 | 3029 | TTCN_2671 | 9002 |
| CTCN_753 | 2987 | TTCN_2653 | 8960 | TTCN_775 | 3030 | CTCN_2531 | 9003 |
| GTCN_410 | 2988 | TTCN_2654 | 8961 | TTCN_776 | 3031 | GTCN_1415 | 9004 |
| GTCN_411 | 2989 | CTCN_2521 | 8962 | ATCN_519 | 3032 | ATCN_1834 | 9005 |
| TTCN_765 | 2990 | TTCN_2655 | 8963 | TTCN_777 | 3033 | TTCN_2672 | 9006 |
| ATCN_508 | 2991 | GTCN_1409 | 8964 | GTCN_422 | 3034 | ATCN_1835 | 9007 |
| GTCN_412 | 2992 | ATCN_1826 | 8965 | CTCN_763 | 3035 | TTCN_2673 | 9008 |
| ATCN_509 | 2993 | ATCN_1827 | 8966 | ATCN_520 | 3036 | ATCN_1836 | 9009 |
| GTCN_413 | 2994 | TTCN_2656 | 8967 | TTCN_778 | 3037 | CTCN_2532 | 9010 |
| GTCN_414 | 2995 | GTCN_1410 | 8968 | TTCN_779 | 3038 | CTCN_2533 | 9011 |
| GTCN_415 | 2996 | ATCN_1828 | 8969 | TTCN_780 | 3039 | GTCN_1416 | 9012 |
| TTCN_766 | 2997 | TTCN_2657 | 8970 | TTCN_781 | 3040 | TTCN_2674 | 9013 |
| CTCN_754 | 2998 | CTCN_2522 | 8971 | ATCN_521 | 3041 | CTCN_2534 | 9014 |

FIG. 33 (continued)

| | | | | | | | |
|---|---|---|---|---|---|---|---|
| GTCN_423 | 3042 | CTCN_2535 | 9015 | CTCN_782 | 3085 | TTCN_2688 | 9058 |
| TTCN_782 | 3043 | CTCN_2536 | 9016 | GTCN_437 | 3086 | TTCN_2689 | 9059 |
| ATCN_522 | 3044 | TTCN_2675 | 9017 | GTCN_438 | 3087 | TTCN_2690 | 9060 |
| CTCN_764 | 3045 | CTCN_2537 | 9018 | CTCN_783 | 3088 | ATCN_1843 | 9061 |
| GTCN_424 | 3046 | CTCN_2538 | 9019 | GTCN_439 | 3089 | ATCN_1844 | 9062 |
| CTCN_765 | 3047 | GTCN_1417 | 9020 | ATCN_527 | 3090 | ATCN_1845 | 9063 |
| GTCN_425 | 3048 | ATCN_1837 | 9021 | CTCN_784 | 3091 | TTCN_2691 | 9064 |
| CTCN_766 | 3049 | ATCN_1838 | 9022 | TTCN_788 | 3092 | ATCN_1846 | 9065 |
| TTCN_783 | 3050 | CTCN_2539 | 9023 | TTCN_789 | 3093 | TTCN_2692 | 9066 |
| GTCN_426 | 3051 | CTCN_2540 | 9024 | CTCN_785 | 3094 | TTCN_2693 | 9067 |
| GTCN_427 | 3052 | GTCN_1418 | 9025 | TTCN_790 | 3095 | GTCN_1426 | 9068 |
| TTCN_784 | 3053 | CTCN_2541 | 9026 | TTCN_791 | 3096 | ATCN_1847 | 9069 |
| ATCN_523 | 3054 | CTCN_2542 | 9027 | CTCN_786 | 3097 | TTCN_2694 | 9070 |
| GTCN_428 | 3055 | ATCN_1839 | 9028 | TTCN_792 | 3098 | TTCN_2695 | 9071 |
| CTCN_767 | 3056 | CTCN_2543 | 9029 | TTCN_793 | 3099 | TTCN_2696 | 9072 |
| ATCN_524 | 3057 | GTCN_1419 | 9030 | ATCN_528 | 3100 | CTCN_2550 | 9073 |
| CTCN_768 | 3058 | TTCN_2676 | 9031 | GTCN_440 | 3101 | CTCN_2551 | 9074 |
| CTCN_769 | 3059 | CTCN_2544 | 9032 | CTCN_787 | 3102 | TTCN_2697 | 9075 |
| ATCN_525 | 3060 | TTCN_2677 | 9033 | ATCN_529 | 3103 | ATCN_1848 | 9076 |
| ATCN_526 | 3061 | GTCN_1420 | 9034 | TTCN_794 | 3104 | ATCN_1849 | 9077 |
| CTCN_770 | 3062 | GTCN_1421 | 9035 | ATCN_530 | 3105 | TTCN_2698 | 9078 |
| CTCN_771 | 3063 | TTCN_2678 | 9036 | CTCN_788 | 3106 | CTCN_2552 | 9079 |
| CTCN_772 | 3064 | CTCN_2545 | 9037 | ATCN_531 | 3107 | TTCN_2699 | 9080 |
| GTCN_429 | 3065 | TTCN_2679 | 9038 | TTCN_795 | 3108 | ATCN_1850 | 9081 |
| GTCN_430 | 3066 | CTCN_2546 | 9039 | TTCN_796 | 3109 | ATCN_1851 | 9082 |
| CTCN_773 | 3067 | CTCN_2547 | 9040 | CTCN_789 | 3110 | CTCN_2553 | 9083 |
| GTCN_431 | 3068 | TTCN_2680 | 9041 | TTCN_797 | 3111 | ATCN_1852 | 9084 |
| CTCN_774 | 3069 | CTCN_2548 | 9042 | ATCN_532 | 3112 | TTCN_2700 | 9085 |
| GTCN_432 | 3070 | GTCN_1422 | 9043 | CTCN_790 | 3113 | ATCN_1853 | 9086 |
| TTCN_785 | 3071 | GTCN_1423 | 9044 | GTCN_441 | 3114 | GTCN_1427 | 9087 |
| GTCN_433 | 3072 | TTCN_2681 | 9045 | GTCN_442 | 3115 | ATCN_1854 | 9088 |
| CTCN_775 | 3073 | TTCN_2682 | 9046 | ATCN_533 | 3116 | TTCN_2701 | 9089 |
| TTCN_786 | 3074 | ATCN_1840 | 9047 | ATCN_534 | 3117 | CTCN_2554 | 9090 |
| TTCN_787 | 3075 | ATCN_1841 | 9048 | GTCN_443 | 3118 | ATCN_1855 | 9091 |
| GTCN_434 | 3076 | TTCN_2683 | 9049 | ATCN_535 | 3119 | TTCN_2702 | 9092 |
| CTCN_776 | 3077 | ATCN_1842 | 9050 | ATCN_536 | 3120 | GTCN_1428 | 9093 |
| CTCN_777 | 3078 | TTCN_2684 | 9051 | CTCN_791 | 3121 | CTCN_2555 | 9094 |
| CTCN_778 | 3079 | TTCN_2685 | 9052 | ATCN_537 | 3122 | TTCN_2703 | 9095 |
| GTCN_435 | 3080 | TTCN_2686 | 9053 | TTCN_798 | 3123 | CTCN_2556 | 9096 |
| CTCN_779 | 3081 | GTCN_1424 | 9054 | ATCN_538 | 3124 | GTCN_1429 | 9097 |
| CTCN_780 | 3082 | GTCN_1425 | 9055 | GTCN_444 | 3125 | ATCN_1856 | 9098 |
| GTCN_436 | 3083 | TTCN_2687 | 9056 | ATCN_539 | 3126 | CTCN_2557 | 9099 |
| CTCN_781 | 3084 | CTCN_2549 | 9057 | GTCN_445 | 3127 | TTCN_2704 | 9100 |

FIG. 33 (continued)

| | | | | | | | |
|---|---|---|---|---|---|---|---|
| CTCN_792 | 3128 | GTCN_1430 | 9101 | TTCN_807 | 3171 | ATCN_1866 | 9144 |
| ATCN_540 | 3129 | CTCN_2558 | 9102 | GTCN_454 | 3172 | CTCN_2574 | 9145 |
| CTCN_793 | 3130 | ATCN_1857 | 9103 | ATCN_551 | 3173 | ATCN_1867 | 9146 |
| TTCN_799 | 3131 | CTCN_2559 | 9104 | ATCN_552 | 3174 | ATCN_1868 | 9147 |
| ATCN_541 | 3132 | ATCN_1858 | 9105 | GTCN_455 | 3175 | CTCN_2575 | 9148 |
| CTCN_794 | 3133 | TTCN_2705 | 9106 | TTCN_808 | 3176 | TTCN_2718 | 9149 |
| ATCN_542 | 3134 | ATCN_1859 | 9107 | ATCN_553 | 3177 | GTCN_1435 | 9150 |
| TTCN_800 | 3135 | CTCN_2560 | 9108 | TTCN_809 | 3178 | GTCN_1436 | 9151 |
| CTCN_795 | 3136 | TTCN_2706 | 9109 | TTCN_810 | 3179 | ATCN_1869 | 9152 |
| GTCN_446 | 3137 | TTCN_2707 | 9110 | TTCN_811 | 3180 | GTCN_1437 | 9153 |
| CTCN_796 | 3138 | ATCN_1860 | 9111 | CTCN_808 | 3181 | CTCN_2576 | 9154 |
| ATCN_543 | 3139 | CTCN_2561 | 9112 | GTCN_456 | 3182 | ATCN_1870 | 9155 |
| ATCN_544 | 3140 | CTCN_2562 | 9113 | GTCN_457 | 3183 | ATCN_1871 | 9156 |
| CTCN_797 | 3141 | GTCN_1431 | 9114 | ATCN_554 | 3184 | CTCN_2577 | 9157 |
| ATCN_545 | 3142 | CTCN_2563 | 9115 | ATCN_555 | 3185 | TTCN_2719 | 9158 |
| ATCN_546 | 3143 | ATCN_1861 | 9116 | ATCN_556 | 3186 | GTCN_1438 | 9159 |
| CTCN_798 | 3144 | CTCN_2564 | 9117 | ATCN_557 | 3187 | ATCN_1872 | 9160 |
| CTCN_799 | 3145 | TTCN_2708 | 9118 | TTCN_812 | 3188 | CTCN_2578 | 9161 |
| CTCN_800 | 3146 | TTCN_2709 | 9119 | TTCN_813 | 3189 | GTCN_1439 | 9162 |
| CTCN_801 | 3147 | TTCN_2710 | 9120 | ATCN_558 | 3190 | TTCN_2720 | 9163 |
| GTCN_447 | 3148 | ATCN_1862 | 9121 | TTCN_814 | 3191 | CTCN_2579 | 9164 |
| TTCN_801 | 3149 | TTCN_2711 | 9122 | ATCN_559 | 3192 | ATCN_1873 | 9165 |
| CTCN_802 | 3150 | CTCN_2565 | 9123 | TTCN_815 | 3193 | ATCN_1874 | 9166 |
| CTCN_803 | 3151 | TTCN_2712 | 9124 | CTCN_809 | 3194 | TTCN_2721 | 9167 |
| ATCN_547 | 3152 | CTCN_2566 | 9125 | TTCN_816 | 3195 | ATCN_1875 | 9168 |
| ATCN_548 | 3153 | TTCN_2713 | 9126 | TTCN_817 | 3196 | ATCN_1876 | 9169 |
| CTCN_804 | 3154 | TTCN_2714 | 9127 | ATCN_560 | 3197 | ATCN_1877 | 9170 |
| GTCN_448 | 3155 | CTCN_2567 | 9128 | GTCN_458 | 3198 | ATCN_1878 | 9171 |
| CTCN_805 | 3156 | CTCN_2568 | 9129 | CTCN_810 | 3199 | CTCN_2580 | 9172 |
| GTCN_449 | 3157 | GTCN_1432 | 9130 | TTCN_818 | 3200 | GTCN_1440 | 9173 |
| GTCN_450 | 3158 | GTCN_1433 | 9131 | TTCN_819 | 3201 | TTCN_2722 | 9174 |
| ATCN_549 | 3159 | TTCN_2715 | 9132 | ATCN_561 | 3202 | CTCN_2581 | 9175 |
| TTCN_802 | 3160 | CTCN_2569 | 9133 | TTCN_820 | 3203 | TTCN_2723 | 9176 |
| TTCN_803 | 3161 | CTCN_2570 | 9134 | TTCN_821 | 3204 | CTCN_2582 | 9177 |
| GTCN_451 | 3162 | CTCN_2571 | 9135 | ATCN_562 | 3205 | TTCN_2724 | 9178 |
| CTCN_806 | 3163 | TTCN_2716 | 9136 | ATCN_563 | 3206 | GTCN_1441 | 9179 |
| GTCN_452 | 3164 | CTCN_2572 | 9137 | GTCN_459 | 3207 | TTCN_2725 | 9180 |
| TTCN_804 | 3165 | ATCN_1863 | 9138 | GTCN_460 | 3208 | GTCN_1442 | 9181 |
| ATCN_550 | 3166 | ATCN_1864 | 9139 | TTCN_822 | 3209 | ATCN_1879 | 9182 |
| TTCN_805 | 3167 | GTCN_1434 | 9140 | ATCN_564 | 3210 | TTCN_2726 | 9183 |
| CTCN_807 | 3168 | TTCN_2717 | 9141 | GTCN_461 | 3211 | TTCN_2727 | 9184 |
| TTCN_806 | 3169 | CTCN_2573 | 9142 | TTCN_823 | 3212 | ATCN_1880 | 9185 |
| GTCN_453 | 3170 | ATCN_1865 | 9143 | GTCN_462 | 3213 | GTCN_1443 | 9186 |

FIG. 33 (continued)

| | | | | | | | |
|---|---|---|---|---|---|---|---|
| TTCN_824 | 3214 | ATCN_1881 | 9187 | GTCN_469 | 3257 | CTCN_2592 | 9230 |
| ATCN_565 | 3215 | ATCN_1882 | 9188 | CTCN_825 | 3258 | ATCN_1890 | 9231 |
| ATCN_566 | 3216 | GTCN_1444 | 9189 | CTCN_826 | 3259 | TTCN_2748 | 9232 |
| TTCN_825 | 3217 | TTCN_2728 | 9190 | TTCN_839 | 3260 | ATCN_1891 | 9233 |
| TTCN_826 | 3218 | ATCN_1883 | 9191 | CTCN_827 | 3261 | CTCN_2593 | 9234 |
| GTCN_463 | 3219 | GTCN_1445 | 9192 | GTCN_470 | 3262 | ATCN_1892 | 9235 |
| GTCN_464 | 3220 | GTCN_1446 | 9193 | CTCN_828 | 3263 | ATCN_1893 | 9236 |
| TTCN_827 | 3221 | CTCN_2583 | 9194 | CTCN_829 | 3264 | TTCN_2749 | 9237 |
| CTCN_811 | 3222 | TTCN_2729 | 9195 | TTCN_840 | 3265 | GTCN_1449 | 9238 |
| CTCN_812 | 3223 | TTCN_2730 | 9196 | TTCN_841 | 3266 | TTCN_2750 | 9239 |
| CTCN_813 | 3224 | TTCN_2731 | 9197 | TTCN_842 | 3267 | TTCN_2751 | 9240 |
| ATCN_567 | 3225 | TTCN_2732 | 9198 | CTCN_830 | 3268 | TTCN_2752 | 9241 |
| CTCN_814 | 3226 | ATCN_1884 | 9199 | ATCN_573 | 3269 | ATCN_1894 | 9242 |
| CTCN_815 | 3227 | CTCN_2584 | 9200 | CTCN_831 | 3270 | TTCN_2753 | 9243 |
| GTCN_465 | 3228 | TTCN_2733 | 9201 | GTCN_471 | 3271 | GTCN_1450 | 9244 |
| CTCN_816 | 3229 | ATCN_1885 | 9202 | CTCN_832 | 3272 | CTCN_2594 | 9245 |
| CTCN_817 | 3230 | ATCN_1886 | 9203 | GTCN_472 | 3273 | ATCN_1895 | 9246 |
| TTCN_828 | 3231 | CTCN_2585 | 9204 | TTCN_843 | 3274 | ATCN_1896 | 9247 |
| TTCN_829 | 3232 | TTCN_2734 | 9205 | CTCN_833 | 3275 | TTCN_2754 | 9248 |
| TTCN_830 | 3233 | ATCN_1887 | 9206 | CTCN_834 | 3276 | CTCN_2595 | 9249 |
| TTCN_831 | 3234 | TTCN_2735 | 9207 | CTCN_835 | 3277 | TTCN_2755 | 9250 |
| CTCN_818 | 3235 | TTCN_2736 | 9208 | ATCN_574 | 3278 | CTCN_2596 | 9251 |
| ATCN_568 | 3236 | TTCN_2737 | 9209 | ATCN_575 | 3279 | TTCN_2756 | 9252 |
| CTCN_819 | 3237 | TTCN_2738 | 9210 | CTCN_836 | 3280 | ATCN_1897 | 9253 |
| ATCN_569 | 3238 | TTCN_2739 | 9211 | CTCN_837 | 3281 | ATCN_1898 | 9254 |
| TTCN_832 | 3239 | CTCN_2586 | 9212 | CTCN_838 | 3282 | TTCN_2757 | 9255 |
| CTCN_820 | 3240 | CTCN_2587 | 9213 | CTCN_839 | 3283 | TTCN_2758 | 9256 |
| TTCN_833 | 3241 | TTCN_2740 | 9214 | TTCN_844 | 3284 | TTCN_2759 | 9257 |
| TTCN_834 | 3242 | ATCN_1888 | 9215 | TTCN_845 | 3285 | ATCN_1899 | 9258 |
| GTCN_466 | 3243 | CTCN_2588 | 9216 | TTCN_846 | 3286 | ATCN_1900 | 9259 |
| CTCN_821 | 3244 | CTCN_2589 | 9217 | GTCN_473 | 3287 | ATCN_1901 | 9260 |
| ATCN_570 | 3245 | TTCN_2741 | 9218 | TTCN_847 | 3288 | TTCN_2760 | 9261 |
| CTCN_822 | 3246 | CTCN_2590 | 9219 | ATCN_576 | 3289 | ATCN_1902 | 9262 |
| TTCN_835 | 3247 | TTCN_2742 | 9220 | GTCN_474 | 3290 | TTCN_2761 | 9263 |
| TTCN_836 | 3248 | TTCN_2743 | 9221 | TTCN_848 | 3291 | TTCN_2762 | 9264 |
| TTCN_837 | 3249 | GTCN_1447 | 9222 | GTCN_475 | 3292 | ATCN_1903 | 9265 |
| TTCN_838 | 3250 | ATCN_1889 | 9223 | TTCN_849 | 3293 | ATCN_1904 | 9266 |
| ATCN_571 | 3251 | GTCN_1448 | 9224 | GTCN_476 | 3294 | ATCN_1905 | 9267 |
| ATCN_572 | 3252 | CTCN_2591 | 9225 | CTCN_840 | 3295 | ATCN_1906 | 9268 |
| CTCN_823 | 3253 | TTCN_2744 | 9226 | CTCN_841 | 3296 | CTCN_2597 | 9269 |
| GTCN_467 | 3254 | TTCN_2745 | 9227 | TTCN_850 | 3297 | TTCN_2763 | 9270 |
| CTCN_824 | 3255 | TTCN_2746 | 9228 | TTCN_851 | 3298 | ATCN_1907 | 9271 |
| GTCN_468 | 3256 | TTCN_2747 | 9229 | TTCN_852 | 3299 | ATCN_1908 | 9272 |

FIG. 33 (continued)

| | | | | | | | |
|---|---|---|---|---|---|---|---|
| ATCN_577 | 3300 | TTCN_2764 | 9273 | TTCN_867 | 3343 | TTCN_2782 | 9316 |
| ATCN_578 | 3301 | TTCN_2765 | 9274 | ATCN_590 | 3344 | GTCN_1457 | 9317 |
| TTCN_853 | 3302 | CTCN_2598 | 9275 | ATCN_591 | 3345 | GTCN_1458 | 9318 |
| TTCN_854 | 3303 | TTCN_2766 | 9276 | ATCN_592 | 3346 | TTCN_2783 | 9319 |
| TTCN_855 | 3304 | TTCN_2767 | 9277 | TTCN_868 | 3347 | ATCN_1917 | 9320 |
| CTCN_842 | 3305 | CTCN_2599 | 9278 | TTCN_869 | 3348 | TTCN_2784 | 9321 |
| GTCN_477 | 3306 | TTCN_2768 | 9279 | CTCN_847 | 3349 | GTCN_1459 | 9322 |
| GTCN_478 | 3307 | CTCN_2600 | 9280 | GTCN_488 | 3350 | TTCN_2785 | 9323 |
| GTCN_479 | 3308 | TTCN_2769 | 9281 | CTCN_848 | 3351 | CTCN_2609 | 9324 |
| TTCN_856 | 3309 | TTCN_2770 | 9282 | ATCN_593 | 3352 | TTCN_2786 | 9325 |
| ATCN_579 | 3310 | TTCN_2771 | 9283 | ATCN_594 | 3353 | TTCN_2787 | 9326 |
| TTCN_857 | 3311 | GTCN_1451 | 9284 | TTCN_870 | 3354 | TTCN_2788 | 9327 |
| ATCN_580 | 3312 | TTCN_2772 | 9285 | CTCN_849 | 3355 | TTCN_2789 | 9328 |
| GTCN_480 | 3313 | ATCN_1909 | 9286 | ATCN_595 | 3356 | GTCN_1460 | 9329 |
| ATCN_581 | 3314 | CTCN_2601 | 9287 | CTCN_850 | 3357 | TTCN_2790 | 9330 |
| ATCN_582 | 3315 | TTCN_2773 | 9288 | GTCN_489 | 3358 | CTCN_2610 | 9331 |
| TTCN_858 | 3316 | CTCN_2602 | 9289 | TTCN_871 | 3359 | CTCN_2611 | 9332 |
| ATCN_583 | 3317 | CTCN_2603 | 9290 | GTCN_490 | 3360 | TTCN_2791 | 9333 |
| TTCN_859 | 3318 | CTCN_2604 | 9291 | ATCN_596 | 3361 | TTCN_2792 | 9334 |
| TTCN_860 | 3319 | CTCN_2605 | 9292 | TTCN_872 | 3362 | ATCN_1918 | 9335 |
| GTCN_481 | 3320 | CTCN_2606 | 9293 | CTCN_851 | 3363 | TTCN_2793 | 9336 |
| ATCN_584 | 3321 | GTCN_1452 | 9294 | CTCN_852 | 3364 | TTCN_2794 | 9337 |
| TTCN_861 | 3322 | GTCN_1453 | 9295 | GTCN_491 | 3365 | ATCN_1919 | 9338 |
| ATCN_585 | 3323 | ATCN_1910 | 9296 | TTCN_873 | 3366 | GTCN_1461 | 9339 |
| CTCN_843 | 3324 | CTCN_2607 | 9297 | ATCN_597 | 3367 | ATCN_1920 | 9340 |
| TTCN_862 | 3325 | TTCN_2774 | 9298 | TTCN_874 | 3368 | CTCN_2612 | 9341 |
| GTCN_482 | 3326 | ATCN_1911 | 9299 | TTCN_875 | 3369 | ATCN_1921 | 9342 |
| TTCN_863 | 3327 | TTCN_2775 | 9300 | CTCN_853 | 3370 | ATCN_1922 | 9343 |
| TTCN_864 | 3328 | TTCN_2776 | 9301 | TTCN_876 | 3371 | TTCN_2795 | 9344 |
| ATCN_586 | 3329 | TTCN_2777 | 9302 | ATCN_598 | 3372 | ATCN_1923 | 9345 |
| GTCN_483 | 3330 | CTCN_2608 | 9303 | TTCN_877 | 3373 | GTCN_1462 | 9346 |
| TTCN_865 | 3331 | ATCN_1912 | 9304 | GTCN_492 | 3374 | ATCN_1924 | 9347 |
| GTCN_484 | 3332 | ATCN_1913 | 9305 | ATCN_599 | 3375 | TTCN_2796 | 9348 |
| CTCN_844 | 3333 | GTCN_1454 | 9306 | ATCN_600 | 3376 | TTCN_2797 | 9349 |
| GTCN_485 | 3334 | ATCN_1914 | 9307 | ATCN_601 | 3377 | ATCN_1925 | 9350 |
| CTCN_845 | 3335 | ATCN_1915 | 9308 | TTCN_878 | 3378 | ATCN_1926 | 9351 |
| GTCN_486 | 3336 | TTCN_2778 | 9309 | GTCN_493 | 3379 | ATCN_1927 | 9352 |
| ATCN_587 | 3337 | TTCN_2779 | 9310 | ATCN_602 | 3380 | ATCN_1928 | 9353 |
| ATCN_588 | 3338 | GTCN_1455 | 9311 | TTCN_879 | 3381 | TTCN_2798 | 9354 |
| TTCN_866 | 3339 | TTCN_2780 | 9312 | GTCN_494 | 3382 | ATCN_1929 | 9355 |
| GTCN_487 | 3340 | GTCN_1456 | 9313 | ATCN_603 | 3383 | TTCN_2799 | 9356 |
| ATCN_589 | 3341 | ATCN_1916 | 9314 | ATCN_604 | 3384 | ATCN_1930 | 9357 |
| CTCN_846 | 3342 | TTCN_2781 | 9315 | ATCN_605 | 3385 | TTCN_2800 | 9358 |

FIG. 33 (continued)

| | | | | | | | |
|---|---|---|---|---|---|---|---|
| GTCN_495 | 3386 | ATCN_1931 | 9359 | CTCN_861 | 3429 | TTCN_2818 | 9402 |
| TTCN_880 | 3387 | CTCN_2613 | 9360 | CTCN_862 | 3430 | TTCN_2819 | 9403 |
| ATCN_606 | 3388 | CTCN_2614 | 9361 | ATCN_616 | 3431 | TTCN_2820 | 9404 |
| ATCN_607 | 3389 | GTCN_1463 | 9362 | GTCN_499 | 3432 | TTCN_2821 | 9405 |
| TTCN_881 | 3390 | ATCN_1932 | 9363 | GTCN_500 | 3433 | ATCN_1943 | 9406 |
| GTCN_496 | 3391 | ATCN_1933 | 9364 | TTCN_902 | 3434 | CTCN_2625 | 9407 |
| TTCN_882 | 3392 | CTCN_2615 | 9365 | ATCN_617 | 3435 | GTCN_1465 | 9408 |
| ATCN_608 | 3393 | TTCN_2801 | 9366 | TTCN_903 | 3436 | CTCN_2626 | 9409 |
| TTCN_883 | 3394 | ATCN_1934 | 9367 | GTCN_501 | 3437 | ATCN_1944 | 9410 |
| TTCN_884 | 3395 | TTCN_2802 | 9368 | TTCN_904 | 3438 | TTCN_2822 | 9411 |
| TTCN_885 | 3396 | TTCN_2803 | 9369 | TTCN_905 | 3439 | CTCN_2627 | 9412 |
| CTCN_854 | 3397 | CTCN_2616 | 9370 | TTCN_906 | 3440 | ATCN_1945 | 9413 |
| ATCN_609 | 3398 | ATCN_1935 | 9371 | GTCN_502 | 3441 | GTCN_1466 | 9414 |
| TTCN_886 | 3399 | CTCN_2617 | 9372 | CTCN_863 | 3442 | CTCN_2628 | 9415 |
| TTCN_887 | 3400 | TTCN_2804 | 9373 | GTCN_503 | 3443 | GTCN_1467 | 9416 |
| TTCN_888 | 3401 | ATCN_1936 | 9374 | TTCN_907 | 3444 | CTCN_2629 | 9417 |
| TTCN_889 | 3402 | TTCN_2805 | 9375 | GTCN_504 | 3445 | TTCN_2823 | 9418 |
| CTCN_855 | 3403 | TTCN_2806 | 9376 | GTCN_505 | 3446 | GTCN_1468 | 9419 |
| TTCN_890 | 3404 | TTCN_2807 | 9377 | CTCN_864 | 3447 | TTCN_2824 | 9420 |
| TTCN_891 | 3405 | ATCN_1937 | 9378 | CTCN_865 | 3448 | ATCN_1946 | 9421 |
| CTCN_856 | 3406 | TTCN_2808 | 9379 | TTCN_908 | 3449 | ATCN_1947 | 9422 |
| TTCN_892 | 3407 | TTCN_2809 | 9380 | CTCN_866 | 3450 | TTCN_2825 | 9423 |
| GTCN_497 | 3408 | TTCN_2810 | 9381 | CTCN_867 | 3451 | TTCN_2826 | 9424 |
| TTCN_893 | 3409 | TTCN_2811 | 9382 | CTCN_868 | 3452 | TTCN_2827 | 9425 |
| TTCN_894 | 3410 | TTCN_2812 | 9383 | TTCN_909 | 3453 | ATCN_1948 | 9426 |
| ATCN_610 | 3411 | CTCN_2618 | 9384 | CTCN_869 | 3454 | TTCN_2828 | 9427 |
| TTCN_895 | 3412 | ATCN_1938 | 9385 | GTCN_506 | 3455 | ATCN_1949 | 9428 |
| TTCN_896 | 3413 | TTCN_2813 | 9386 | TTCN_910 | 3456 | ATCN_1950 | 9429 |
| TTCN_897 | 3414 | ATCN_1939 | 9387 | GTCN_507 | 3457 | GTCN_1469 | 9430 |
| CTCN_857 | 3415 | ATCN_1940 | 9388 | TTCN_911 | 3458 | ATCN_1951 | 9431 |
| TTCN_898 | 3416 | TTCN_2814 | 9389 | CTCN_870 | 3459 | TTCN_2829 | 9432 |
| ATCN_611 | 3417 | CTCN_2619 | 9390 | GTCN_508 | 3460 | TTCN_2830 | 9433 |
| GTCN_498 | 3418 | TTCN_2815 | 9391 | CTCN_871 | 3461 | TTCN_2831 | 9434 |
| CTCN_858 | 3419 | ATCN_1941 | 9392 | ATCN_618 | 3462 | ATCN_1952 | 9435 |
| ATCN_612 | 3420 | CTCN_2620 | 9393 | ATCN_619 | 3463 | TTCN_2832 | 9436 |
| TTCN_899 | 3421 | TTCN_2816 | 9394 | CTCN_872 | 3464 | GTCN_1470 | 9437 |
| TTCN_900 | 3422 | CTCN_2621 | 9395 | CTCN_873 | 3465 | GTCN_1471 | 9438 |
| CTCN_859 | 3423 | CTCN_2622 | 9396 | GTCN_509 | 3466 | ATCN_1953 | 9439 |
| TTCN_901 | 3424 | ATCN_1942 | 9397 | TTCN_912 | 3467 | ATCN_1954 | 9440 |
| ATCN_613 | 3425 | CTCN_2623 | 9398 | CTCN_874 | 3468 | GTCN_1472 | 9441 |
| ATCN_614 | 3426 | CTCN_2624 | 9399 | TTCN_913 | 3469 | CTCN_2630 | 9442 |
| CTCN_860 | 3427 | TTCN_2817 | 9400 | ATCN_620 | 3470 | TTCN_2833 | 9443 |
| ATCN_615 | 3428 | GTCN_1464 | 9401 | TTCN_914 | 3471 | TTCN_2834 | 9444 |

FIG. 33 (continued)

| | | | | | | | |
|---|---|---|---|---|---|---|---|
| CTCN_875 | 3472 | TTCN_2835 | 9445 | GTCN_515 | 3515 | TTCN_2852 | 9488 |
| ATCN_621 | 3473 | GTCN_1473 | 9446 | TTCN_930 | 3516 | GTCN_1479 | 9489 |
| TTCN_915 | 3474 | TTCN_2836 | 9447 | TTCN_931 | 3517 | TTCN_2853 | 9490 |
| GTCN_510 | 3475 | CTCN_2631 | 9448 | CTCN_886 | 3518 | TTCN_2854 | 9491 |
| CTCN_876 | 3476 | GTCN_1474 | 9449 | TTCN_932 | 3519 | TTCN_2855 | 9492 |
| GTCN_511 | 3477 | CTCN_2632 | 9450 | ATCN_633 | 3520 | CTCN_2647 | 9493 |
| TTCN_916 | 3478 | GTCN_1475 | 9451 | TTCN_933 | 3521 | GTCN_1480 | 9494 |
| TTCN_917 | 3479 | TTCN_2837 | 9452 | CTCN_887 | 3522 | ATCN_1959 | 9495 |
| ATCN_622 | 3480 | CTCN_2633 | 9453 | TTCN_934 | 3523 | TTCN_2856 | 9496 |
| ATCN_623 | 3481 | ATCN_1955 | 9454 | TTCN_935 | 3524 | ATCN_1960 | 9497 |
| TTCN_918 | 3482 | CTCN_2634 | 9455 | CTCN_888 | 3525 | TTCN_2857 | 9498 |
| TTCN_919 | 3483 | GTCN_1476 | 9456 | CTCN_889 | 3526 | ATCN_1961 | 9499 |
| CTCN_877 | 3484 | CTCN_2635 | 9457 | ATCN_634 | 3527 | TTCN_2858 | 9500 |
| CTCN_878 | 3485 | CTCN_2636 | 9458 | CTCN_890 | 3528 | ATCN_1962 | 9501 |
| CTCN_879 | 3486 | CTCN_2637 | 9459 | GTCN_516 | 3529 | GTCN_1481 | 9502 |
| CTCN_880 | 3487 | TTCN_2838 | 9460 | CTCN_891 | 3530 | ATCN_1963 | 9503 |
| CTCN_881 | 3488 | TTCN_2839 | 9461 | TTCN_936 | 3531 | TTCN_2859 | 9504 |
| CTCN_882 | 3489 | TTCN_2840 | 9462 | CTCN_892 | 3532 | CTCN_2648 | 9505 |
| CTCN_883 | 3490 | CTCN_2638 | 9463 | TTCN_937 | 3533 | TTCN_2860 | 9506 |
| TTCN_920 | 3491 | CTCN_2639 | 9464 | TTCN_938 | 3534 | ATCN_1964 | 9507 |
| ATCN_624 | 3492 | CTCN_2640 | 9465 | TTCN_939 | 3535 | ATCN_1965 | 9508 |
| ATCN_625 | 3493 | TTCN_2841 | 9466 | CTCN_893 | 3536 | ATCN_1966 | 9509 |
| ATCN_626 | 3494 | CTCN_2641 | 9467 | GTCN_517 | 3537 | TTCN_2861 | 9510 |
| TTCN_921 | 3495 | CTCN_2642 | 9468 | ATCN_635 | 3538 | ATCN_1967 | 9511 |
| CTCN_884 | 3496 | ATCN_1956 | 9469 | ATCN_636 | 3539 | GTCN_1482 | 9512 |
| ATCN_627 | 3497 | ATCN_1957 | 9470 | CTCN_894 | 3540 | CTCN_2649 | 9513 |
| TTCN_922 | 3498 | GTCN_1477 | 9471 | CTCN_895 | 3541 | GTCN_1483 | 9514 |
| ATCN_628 | 3499 | TTCN_2842 | 9472 | GTCN_518 | 3542 | GTCN_1484 | 9515 |
| ATCN_629 | 3500 | TTCN_2843 | 9473 | CTCN_896 | 3543 | CTCN_2650 | 9516 |
| ATCN_630 | 3501 | TTCN_2844 | 9474 | CTCN_897 | 3544 | GTCN_1485 | 9517 |
| TTCN_923 | 3502 | GTCN_1478 | 9475 | ATCN_637 | 3545 | ATCN_1968 | 9518 |
| TTCN_924 | 3503 | CTCN_2643 | 9476 | ATCN_638 | 3546 | TTCN_2862 | 9519 |
| TTCN_925 | 3504 | TTCN_2845 | 9477 | CTCN_898 | 3547 | TTCN_2863 | 9520 |
| ATCN_631 | 3505 | TTCN_2846 | 9478 | CTCN_899 | 3548 | ATCN_1969 | 9521 |
| GTCN_512 | 3506 | TTCN_2847 | 9479 | CTCN_900 | 3549 | ATCN_1970 | 9522 |
| TTCN_926 | 3507 | CTCN_2644 | 9480 | CTCN_901 | 3550 | ATCN_1971 | 9523 |
| GTCN_513 | 3508 | TTCN_2848 | 9481 | TTCN_940 | 3551 | ATCN_1972 | 9524 |
| ATCN_632 | 3509 | TTCN_2849 | 9482 | GTCN_519 | 3552 | TTCN_2864 | 9525 |
| GTCN_514 | 3510 | CTCN_2645 | 9483 | CTCN_902 | 3553 | TTCN_2865 | 9526 |
| CTCN_885 | 3511 | CTCN_2646 | 9484 | CTCN_903 | 3554 | TTCN_2866 | 9527 |
| TTCN_927 | 3512 | TTCN_2850 | 9485 | CTCN_904 | 3555 | GTCN_1486 | 9528 |
| TTCN_928 | 3513 | ATCN_1958 | 9486 | CTCN_905 | 3556 | GTCN_1487 | 9529 |
| TTCN_929 | 3514 | TTCN_2851 | 9487 | CTCN_906 | 3557 | ATCN_1973 | 9530 |

FIG. 33 (continued)

| | | | | | | | |
|---|---|---|---|---|---|---|---|
| ATCN_639 | 3558 | TTCN_2867 | 9531 | CTCN_913 | 3601 | ATCN_1981 | 9574 |
| CTCN_907 | 3559 | GTCN_1488 | 9532 | TTCN_952 | 3602 | TTCN_2892 | 9575 |
| ATCN_640 | 3560 | TTCN_2868 | 9533 | GTCN_532 | 3603 | CTCN_2659 | 9576 |
| GTCN_520 | 3561 | TTCN_2869 | 9534 | CTCN_914 | 3604 | ATCN_1982 | 9577 |
| TTCN_941 | 3562 | TTCN_2870 | 9535 | CTCN_915 | 3605 | ATCN_1983 | 9578 |
| CTCN_908 | 3563 | ATCN_1974 | 9536 | TTCN_953 | 3606 | CTCN_2660 | 9579 |
| CTCN_909 | 3564 | TTCN_2871 | 9537 | GTCN_533 | 3607 | TTCN_2893 | 9580 |
| ATCN_641 | 3565 | TTCN_2872 | 9538 | GTCN_534 | 3608 | ATCN_1984 | 9581 |
| CTCN_910 | 3566 | TTCN_2873 | 9539 | GTCN_535 | 3609 | ATCN_1985 | 9582 |
| TTCN_942 | 3567 | GTCN_1489 | 9540 | ATCN_653 | 3610 | CTCN_2661 | 9583 |
| TTCN_943 | 3568 | TTCN_2874 | 9541 | GTCN_536 | 3611 | CTCN_2662 | 9584 |
| GTCN_521 | 3569 | CTCN_2651 | 9542 | CTCN_916 | 3612 | ATCN_1986 | 9585 |
| TTCN_944 | 3570 | GTCN_1490 | 9543 | ATCN_654 | 3613 | CTCN_2663 | 9586 |
| GTCN_522 | 3571 | TTCN_2875 | 9544 | CTCN_917 | 3614 | TTCN_2894 | 9587 |
| TTCN_945 | 3572 | TTCN_2876 | 9545 | ATCN_655 | 3615 | ATCN_1987 | 9588 |
| ATCN_642 | 3573 | CTCN_2652 | 9546 | CTCN_918 | 3616 | TTCN_2895 | 9589 |
| TTCN_946 | 3574 | ATCN_1975 | 9547 | ATCN_656 | 3617 | CTCN_2664 | 9590 |
| TTCN_947 | 3575 | CTCN_2653 | 9548 | CTCN_919 | 3618 | GTCN_1491 | 9591 |
| ATCN_643 | 3576 | CTCN_2654 | 9549 | CTCN_920 | 3619 | TTCN_2896 | 9592 |
| GTCN_523 | 3577 | CTCN_2655 | 9550 | TTCN_954 | 3620 | TTCN_2897 | 9593 |
| ATCN_644 | 3578 | ATCN_1976 | 9551 | TTCN_955 | 3621 | TTCN_2898 | 9594 |
| ATCN_645 | 3579 | ATCN_1977 | 9552 | GTCN_537 | 3622 | TTCN_2899 | 9595 |
| TTCN_948 | 3580 | TTCN_2877 | 9553 | CTCN_921 | 3623 | CTCN_2665 | 9596 |
| GTCN_524 | 3581 | TTCN_2878 | 9554 | ATCN_657 | 3624 | CTCN_2666 | 9597 |
| ATCN_646 | 3582 | TTCN_2879 | 9555 | GTCN_538 | 3625 | ATCN_1988 | 9598 |
| GTCN_525 | 3583 | TTCN_2880 | 9556 | CTCN_922 | 3626 | GTCN_1492 | 9599 |
| ATCN_647 | 3584 | TTCN_2881 | 9557 | CTCN_923 | 3627 | CTCN_2667 | 9600 |
| TTCN_949 | 3585 | CTCN_2656 | 9558 | GTCN_539 | 3628 | TTCN_2900 | 9601 |
| GTCN_526 | 3586 | TTCN_2882 | 9559 | CTCN_924 | 3629 | CTCN_2668 | 9602 |
| TTCN_950 | 3587 | TTCN_2883 | 9560 | GTCN_540 | 3630 | TTCN_2901 | 9603 |
| GTCN_527 | 3588 | TTCN_2884 | 9561 | CTCN_925 | 3631 | TTCN_2902 | 9604 |
| ATCN_648 | 3589 | TTCN_2885 | 9562 | GTCN_541 | 3632 | ATCN_1989 | 9605 |
| ATCN_649 | 3590 | CTCN_2657 | 9563 | CTCN_926 | 3633 | GTCN_1493 | 9606 |
| GTCN_528 | 3591 | TTCN_2886 | 9564 | ATCN_658 | 3634 | ATCN_1990 | 9607 |
| GTCN_529 | 3592 | ATCN_1978 | 9565 | CTCN_927 | 3635 | TTCN_2903 | 9608 |
| GTCN_530 | 3593 | ATCN_1979 | 9566 | CTCN_928 | 3636 | CTCN_2669 | 9609 |
| ATCN_650 | 3594 | ATCN_1980 | 9567 | CTCN_929 | 3637 | CTCN_2670 | 9610 |
| CTCN_911 | 3595 | TTCN_2887 | 9568 | TTCN_956 | 3638 | CTCN_2671 | 9611 |
| TTCN_951 | 3596 | TTCN_2888 | 9569 | TTCN_957 | 3639 | TTCN_2904 | 9612 |
| ATCN_651 | 3597 | CTCN_2658 | 9570 | CTCN_930 | 3640 | GTCN_1494 | 9613 |
| ATCN_652 | 3598 | TTCN_2889 | 9571 | CTCN_931 | 3641 | CTCN_2672 | 9614 |
| GTCN_531 | 3599 | TTCN_2890 | 9572 | CTCN_932 | 3642 | GTCN_1495 | 9615 |
| CTCN_912 | 3600 | TTCN_2891 | 9573 | CTCN_933 | 3643 | TTCN_2905 | 9616 |

FIG. 33 (continued)

| | | | | | | | |
|---|---|---|---|---|---|---|---|
| GTCN_542 | 3644 | ATCN_1991 | 9617 | ATCN_665 | 3687 | GTCN_1502 | 9660 |
| CTCN_934 | 3645 | TTCN_2906 | 9618 | CTCN_956 | 3688 | GTCN_1503 | 9661 |
| CTCN_935 | 3646 | CTCN_2673 | 9619 | ATCN_666 | 3689 | GTCN_1504 | 9662 |
| GTCN_543 | 3647 | TTCN_2907 | 9620 | GTCN_549 | 3690 | TTCN_2917 | 9663 |
| TTCN_958 | 3648 | CTCN_2674 | 9621 | GTCN_550 | 3691 | ATCN_2001 | 9664 |
| ATCN_659 | 3649 | CTCN_2675 | 9622 | TTCN_966 | 3692 | ATCN_2002 | 9665 |
| GTCN_544 | 3650 | GTCN_1496 | 9623 | TTCN_967 | 3693 | GTCN_1505 | 9666 |
| CTCN_936 | 3651 | CTCN_2676 | 9624 | GTCN_551 | 3694 | CTCN_2689 | 9667 |
| ATCN_660 | 3652 | ATCN_1992 | 9625 | CTCN_957 | 3695 | GTCN_1506 | 9668 |
| ATCN_661 | 3653 | TTCN_2908 | 9626 | ATCN_667 | 3696 | TTCN_2918 | 9669 |
| CTCN_937 | 3654 | CTCN_2677 | 9627 | TTCN_968 | 3697 | ATCN_2003 | 9670 |
| GTCN_545 | 3655 | TTCN_2909 | 9628 | ATCN_668 | 3698 | TTCN_2919 | 9671 |
| CTCN_938 | 3656 | TTCN_2910 | 9629 | TTCN_969 | 3699 | TTCN_2920 | 9672 |
| ATCN_662 | 3657 | GTCN_1497 | 9630 | TTCN_970 | 3700 | CTCN_2690 | 9673 |
| ATCN_663 | 3658 | CTCN_2678 | 9631 | CTCN_958 | 3701 | ATCN_2004 | 9674 |
| CTCN_939 | 3659 | GTCN_1498 | 9632 | TTCN_971 | 3702 | ATCN_2005 | 9675 |
| CTCN_940 | 3660 | ATCN_1993 | 9633 | GTCN_552 | 3703 | TTCN_2921 | 9676 |
| ATCN_664 | 3661 | GTCN_1499 | 9634 | GTCN_553 | 3704 | CTCN_2691 | 9677 |
| CTCN_941 | 3662 | CTCN_2679 | 9635 | TTCN_972 | 3705 | TTCN_2922 | 9678 |
| CTCN_942 | 3663 | GTCN_1500 | 9636 | ATCN_669 | 3706 | ATCN_2006 | 9679 |
| TTCN_959 | 3664 | CTCN_2680 | 9637 | CTCN_959 | 3707 | TTCN_2923 | 9680 |
| CTCN_943 | 3665 | CTCN_2681 | 9638 | CTCN_960 | 3708 | TTCN_2924 | 9681 |
| TTCN_960 | 3666 | CTCN_2682 | 9639 | GTCN_554 | 3709 | TTCN_2925 | 9682 |
| TTCN_961 | 3667 | TTCN_2911 | 9640 | TTCN_973 | 3710 | ATCN_2007 | 9683 |
| TTCN_962 | 3668 | ATCN_1994 | 9641 | TTCN_974 | 3711 | CTCN_2692 | 9684 |
| TTCN_963 | 3669 | CTCN_2683 | 9642 | TTCN_975 | 3712 | TTCN_2926 | 9685 |
| CTCN_944 | 3670 | CTCN_2684 | 9643 | TTCN_976 | 3713 | CTCN_2693 | 9686 |
| CTCN_945 | 3671 | ATCN_1995 | 9644 | TTCN_977 | 3714 | TTCN_2927 | 9687 |
| CTCN_946 | 3672 | ATCN_1996 | 9645 | GTCN_555 | 3715 | TTCN_2928 | 9688 |
| GTCN_546 | 3673 | GTCN_1501 | 9646 | TTCN_978 | 3716 | TTCN_2929 | 9689 |
| CTCN_947 | 3674 | TTCN_2912 | 9647 | CTCN_961 | 3717 | CTCN_2694 | 9690 |
| CTCN_948 | 3675 | CTCN_2685 | 9648 | CTCN_962 | 3718 | GTCN_1507 | 9691 |
| CTCN_949 | 3676 | TTCN_2913 | 9649 | ATCN_670 | 3719 | CTCN_2695 | 9692 |
| CTCN_950 | 3677 | ATCN_1997 | 9650 | TTCN_979 | 3720 | CTCN_2696 | 9693 |
| TTCN_964 | 3678 | TTCN_2914 | 9651 | CTCN_963 | 3721 | CTCN_2697 | 9694 |
| CTCN_951 | 3679 | ATCN_1998 | 9652 | ATCN_671 | 3722 | TTCN_2930 | 9695 |
| GTCN_547 | 3680 | CTCN_2686 | 9653 | CTCN_964 | 3723 | ATCN_2008 | 9696 |
| CTCN_952 | 3681 | ATCN_1999 | 9654 | ATCN_672 | 3724 | TTCN_2931 | 9697 |
| TTCN_965 | 3682 | TTCN_2915 | 9655 | ATCN_673 | 3725 | CTCN_2698 | 9698 |
| CTCN_953 | 3683 | TTCN_2916 | 9656 | ATCN_674 | 3726 | GTCN_1508 | 9699 |
| CTCN_954 | 3684 | CTCN_2687 | 9657 | GTCN_556 | 3727 | CTCN_2699 | 9700 |
| CTCN_955 | 3685 | ATCN_2000 | 9658 | TTCN_980 | 3728 | TTCN_2932 | 9701 |
| GTCN_548 | 3686 | CTCN_2688 | 9659 | TTCN_981 | 3729 | TTCN_2933 | 9702 |

FIG. 33 (continued)

| | | | | | | | |
|---|---|---|---|---|---|---|---|
| CTCN_965 | 3730 | TTCN_2934 | 9703 | CTCN_984 | 3773 | CTCN_2707 | 9746 |
| CTCN_966 | 3731 | ATCN_2009 | 9704 | TTCN_993 | 3774 | ATCN_2020 | 9747 |
| CTCN_967 | 3732 | ATCN_2010 | 9705 | CTCN_985 | 3775 | CTCN_2708 | 9748 |
| GTCN_557 | 3733 | TTCN_2935 | 9706 | GTCN_564 | 3776 | TTCN_2952 | 9749 |
| TTCN_982 | 3734 | ATCN_2011 | 9707 | TTCN_994 | 3777 | TTCN_2953 | 9750 |
| GTCN_558 | 3735 | GTCN_1509 | 9708 | CTCN_986 | 3778 | ATCN_2021 | 9751 |
| CTCN_968 | 3736 | TTCN_2936 | 9709 | ATCN_681 | 3779 | ATCN_2022 | 9752 |
| CTCN_969 | 3737 | TTCN_2937 | 9710 | CTCN_987 | 3780 | GTCN_1516 | 9753 |
| TTCN_983 | 3738 | TTCN_2938 | 9711 | GTCN_565 | 3781 | TTCN_2954 | 9754 |
| GTCN_559 | 3739 | ATCN_2012 | 9712 | CTCN_988 | 3782 | TTCN_2955 | 9755 |
| GTCN_560 | 3740 | GTCN_1510 | 9713 | CTCN_989 | 3783 | TTCN_2956 | 9756 |
| CTCN_970 | 3741 | TTCN_2939 | 9714 | GTCN_566 | 3784 | GTCN_1517 | 9757 |
| ATCN_675 | 3742 | TTCN_2940 | 9715 | CTCN_990 | 3785 | ATCN_2023 | 9758 |
| ATCN_676 | 3743 | GTCN_1511 | 9716 | CTCN_991 | 3786 | TTCN_2957 | 9759 |
| TTCN_984 | 3744 | CTCN_2700 | 9717 | TTCN_995 | 3787 | CTCN_2709 | 9760 |
| CTCN_971 | 3745 | CTCN_2701 | 9718 | ATCN_682 | 3788 | ATCN_2024 | 9761 |
| TTCN_985 | 3746 | TTCN_2941 | 9719 | TTCN_996 | 3789 | TTCN_2958 | 9762 |
| TTCN_986 | 3747 | ATCN_2013 | 9720 | CTCN_992 | 3790 | GTCN_1518 | 9763 |
| CTCN_972 | 3748 | ATCN_2014 | 9721 | CTCN_993 | 3791 | ATCN_2025 | 9764 |
| CTCN_973 | 3749 | TTCN_2942 | 9722 | ATCN_683 | 3792 | TTCN_2959 | 9765 |
| ATCN_677 | 3750 | TTCN_2943 | 9723 | CTCN_994 | 3793 | ATCN_2026 | 9766 |
| TTCN_987 | 3751 | TTCN_2944 | 9724 | GTCN_567 | 3794 | CTCN_2710 | 9767 |
| TTCN_988 | 3752 | CTCN_2702 | 9725 | GTCN_568 | 3795 | CTCN_2711 | 9768 |
| CTCN_974 | 3753 | TTCN_2945 | 9726 | CTCN_995 | 3796 | TTCN_2960 | 9769 |
| CTCN_975 | 3754 | TTCN_2946 | 9727 | GTCN_569 | 3797 | TTCN_2961 | 9770 |
| CTCN_976 | 3755 | CTCN_2703 | 9728 | CTCN_996 | 3798 | TTCN_2962 | 9771 |
| GTCN_561 | 3756 | CTCN_2704 | 9729 | GTCN_570 | 3799 | GTCN_1519 | 9772 |
| CTCN_977 | 3757 | CTCN_2705 | 9730 | CTCN_997 | 3800 | TTCN_2963 | 9773 |
| GTCN_562 | 3758 | GTCN_1512 | 9731 | GTCN_571 | 3801 | TTCN_2964 | 9774 |
| ATCN_678 | 3759 | GTCN_1513 | 9732 | ATCN_684 | 3802 | ATCN_2027 | 9775 |
| ATCN_679 | 3760 | TTCN_2947 | 9733 | TTCN_997 | 3803 | ATCN_2028 | 9776 |
| CTCN_978 | 3761 | ATCN_2015 | 9734 | TTCN_998 | 3804 | TTCN_2965 | 9777 |
| TTCN_989 | 3762 | ATCN_2016 | 9735 | CTCN_998 | 3805 | CTCN_2712 | 9778 |
| TTCN_990 | 3763 | TTCN_2948 | 9736 | ATCN_685 | 3806 | CTCN_2713 | 9779 |
| TTCN_991 | 3764 | GTCN_1514 | 9737 | TTCN_999 | 3807 | TTCN_2966 | 9780 |
| TTCN_992 | 3765 | ATCN_2017 | 9738 | TTCN_1000 | 3808 | TTCN_2967 | 9781 |
| CTCN_979 | 3766 | ATCN_2018 | 9739 | CTCN_999 | 3809 | CTCN_2714 | 9782 |
| ATCN_680 | 3767 | ATCN_2019 | 9740 | GTCN_572 | 3810 | GTCN_1520 | 9783 |
| CTCN_980 | 3768 | TTCN_2949 | 9741 | GTCN_573 | 3811 | CTCN_2715 | 9784 |
| CTCN_981 | 3769 | TTCN_2950 | 9742 | CTCN_1000 | 3812 | ATCN_2029 | 9785 |
| CTCN_982 | 3770 | TTCN_2951 | 9743 | CTCN_1001 | 3813 | ATCN_2030 | 9786 |
| GTCN_563 | 3771 | GTCN_1515 | 9744 | GTCN_574 | 3814 | CTCN_2716 | 9787 |
| CTCN_983 | 3772 | CTCN_2706 | 9745 | ATCN_686 | 3815 | GTCN_1521 | 9788 |

FIG. 33 (continued)

| | | | | | | | |
|---|---|---|---|---|---|---|---|
| CTCN_1002 | 3816 | ATCN_2031 | 9789 | ATCN_694 | 3859 | ATCN_2042 | 9832 |
| CTCN_1003 | 3817 | ATCN_2032 | 9790 | TTCN_1012 | 3860 | GTCN_1525 | 9833 |
| CTCN_1004 | 3818 | TTCN_2968 | 9791 | ATCN_695 | 3861 | CTCN_2726 | 9834 |
| TTCN_1001 | 3819 | TTCN_2969 | 9792 | CTCN_1023 | 3862 | GTCN_1526 | 9835 |
| TTCN_1002 | 3820 | TTCN_2970 | 9793 | ATCN_696 | 3863 | CTCN_2727 | 9836 |
| CTCN_1005 | 3821 | TTCN_2971 | 9794 | GTCN_579 | 3864 | GTCN_1527 | 9837 |
| ATCN_687 | 3822 | ATCN_2033 | 9795 | CTCN_1024 | 3865 | CTCN_2728 | 9838 |
| TTCN_1003 | 3823 | GTCN_1522 | 9796 | CTCN_1025 | 3866 | TTCN_2988 | 9839 |
| CTCN_1006 | 3824 | CTCN_2717 | 9797 | CTCN_1026 | 3867 | TTCN_2989 | 9840 |
| CTCN_1007 | 3825 | TTCN_2972 | 9798 | TTCN_1013 | 3868 | TTCN_2990 | 9841 |
| GTCN_575 | 3826 | TTCN_2973 | 9799 | ATCN_697 | 3869 | CTCN_2729 | 9842 |
| CTCN_1008 | 3827 | TTCN_2974 | 9800 | CTCN_1027 | 3870 | TTCN_2991 | 9843 |
| TTCN_1004 | 3828 | CTCN_2718 | 9801 | CTCN_1028 | 3871 | CTCN_2730 | 9844 |
| ATCN_688 | 3829 | TTCN_2975 | 9802 | CTCN_1029 | 3872 | GTCN_1528 | 9845 |
| CTCN_1009 | 3830 | TTCN_2976 | 9803 | CTCN_1030 | 3873 | TTCN_2992 | 9846 |
| GTCN_576 | 3831 | TTCN_2977 | 9804 | ATCN_698 | 3874 | ATCN_2043 | 9847 |
| TTCN_1005 | 3832 | TTCN_2978 | 9805 | ATCN_699 | 3875 | TTCN_2993 | 9848 |
| GTCN_577 | 3833 | GTCN_1523 | 9806 | CTCN_1031 | 3876 | CTCN_2731 | 9849 |
| CTCN_1010 | 3834 | TTCN_2979 | 9807 | GTCN_580 | 3877 | GTCN_1529 | 9850 |
| CTCN_1011 | 3835 | TTCN_2980 | 9808 | CTCN_1032 | 3878 | ATCN_2044 | 9851 |
| GTCN_578 | 3836 | TTCN_2981 | 9809 | CTCN_1033 | 3879 | CTCN_2732 | 9852 |
| CTCN_1012 | 3837 | TTCN_2982 | 9810 | GTCN_581 | 3880 | ATCN_2045 | 9853 |
| ATCN_689 | 3838 | CTCN_2719 | 9811 | GTCN_582 | 3881 | ATCN_2046 | 9854 |
| ATCN_690 | 3839 | GTCN_1524 | 9812 | CTCN_1034 | 3882 | ATCN_2047 | 9855 |
| CTCN_1013 | 3840 | CTCN_2720 | 9813 | CTCN_1035 | 3883 | TTCN_2994 | 9856 |
| CTCN_1014 | 3841 | TTCN_2983 | 9814 | ATCN_700 | 3884 | GTCN_1530 | 9857 |
| CTCN_1015 | 3842 | CTCN_2721 | 9815 | TTCN_1014 | 3885 | ATCN_2048 | 9858 |
| ATCN_691 | 3843 | TTCN_2984 | 9816 | CTCN_1036 | 3886 | TTCN_2995 | 9859 |
| CTCN_1016 | 3844 | ATCN_2034 | 9817 | ATCN_701 | 3887 | ATCN_2049 | 9860 |
| TTCN_1006 | 3845 | ATCN_2035 | 9818 | ATCN_702 | 3888 | TTCN_2996 | 9861 |
| CTCN_1017 | 3846 | ATCN_2036 | 9819 | GTCN_583 | 3889 | TTCN_2997 | 9862 |
| TTCN_1007 | 3847 | ATCN_2037 | 9820 | CTCN_1037 | 3890 | TTCN_2998 | 9863 |
| TTCN_1008 | 3848 | ATCN_2038 | 9821 | TTCN_1015 | 3891 | CTCN_2733 | 9864 |
| TTCN_1009 | 3849 | ATCN_2039 | 9822 | GTCN_584 | 3892 | TTCN_2999 | 9865 |
| TTCN_1010 | 3850 | TTCN_2985 | 9823 | TTCN_1016 | 3893 | TTCN_3000 | 9866 |
| TTCN_1011 | 3851 | ATCN_2040 | 9824 | ATCN_703 | 3894 | CTCN_2734 | 9867 |
| CTCN_1018 | 3852 | TTCN_2986 | 9825 | CTCN_1038 | 3895 | TTCN_3001 | 9868 |
| ATCN_692 | 3853 | TTCN_2987 | 9826 | ATCN_704 | 3896 | TTCN_3002 | 9869 |
| CTCN_1019 | 3854 | CTCN_2722 | 9827 | GTCN_585 | 3897 | ATCN_2050 | 9870 |
| CTCN_1020 | 3855 | CTCN_2723 | 9828 | TTCN_1017 | 3898 | CTCN_2735 | 9871 |
| CTCN_1021 | 3856 | CTCN_2724 | 9829 | ATCN_705 | 3899 | CTCN_2736 | 9872 |
| CTCN_1022 | 3857 | ATCN_2041 | 9830 | CTCN_1039 | 3900 | CTCN_2737 | 9873 |
| ATCN_693 | 3858 | CTCN_2725 | 9831 | CTCN_1040 | 3901 | TTCN_3003 | 9874 |

FIG. 33 (continued)

| | | | | | | | |
|---|---|---|---|---|---|---|---|
| TTCN_1018 | 3902 | CTCN_2738 | 9875 | ATCN_713 | 3945 | CTCN_2746 | 9918 |
| TTCN_1019 | 3903 | GTCN_1531 | 9876 | CTCN_1057 | 3946 | GTCN_1538 | 9919 |
| CTCN_1041 | 3904 | GTCN_1532 | 9877 | CTCN_1058 | 3947 | ATCN_2061 | 9920 |
| CTCN_1042 | 3905 | TTCN_3004 | 9878 | CTCN_1059 | 3948 | ATCN_2062 | 9921 |
| CTCN_1043 | 3906 | GTCN_1533 | 9879 | CTCN_1060 | 3949 | ATCN_2063 | 9922 |
| ATCN_706 | 3907 | ATCN_2051 | 9880 | CTCN_1061 | 3950 | ATCN_2064 | 9923 |
| CTCN_1044 | 3908 | TTCN_3005 | 9881 | CTCN_1062 | 3951 | ATCN_2065 | 9924 |
| CTCN_1045 | 3909 | ATCN_2052 | 9882 | CTCN_1063 | 3952 | ATCN_2066 | 9925 |
| TTCN_1020 | 3910 | ATCN_2053 | 9883 | GTCN_590 | 3953 | TTCN_3022 | 9926 |
| CTCN_1046 | 3911 | TTCN_3006 | 9884 | TTCN_1034 | 3954 | TTCN_3023 | 9927 |
| GTCN_586 | 3912 | TTCN_3007 | 9885 | CTCN_1064 | 3955 | CTCN_2747 | 9928 |
| TTCN_1021 | 3913 | CTCN_2739 | 9886 | CTCN_1065 | 3956 | GTCN_1539 | 9929 |
| TTCN_1022 | 3914 | CTCN_2740 | 9887 | TTCN_1035 | 3957 | GTCN_1540 | 9930 |
| ATCN_707 | 3915 | TTCN_3008 | 9888 | ATCN_714 | 3958 | TTCN_3024 | 9931 |
| TTCN_1023 | 3916 | ATCN_2054 | 9889 | TTCN_1036 | 3959 | TTCN_3025 | 9932 |
| CTCN_1047 | 3917 | ATCN_2055 | 9890 | TTCN_1037 | 3960 | TTCN_3026 | 9933 |
| TTCN_1024 | 3918 | CTCN_2741 | 9891 | TTCN_1038 | 3961 | TTCN_3027 | 9934 |
| ATCN_708 | 3919 | ATCN_2056 | 9892 | ATCN_715 | 3962 | TTCN_3028 | 9935 |
| CTCN_1048 | 3920 | CTCN_2742 | 9893 | ATCN_716 | 3963 | GTCN_1541 | 9936 |
| TTCN_1025 | 3921 | TTCN_3009 | 9894 | CTCN_1066 | 3964 | CTCN_2748 | 9937 |
| TTCN_1026 | 3922 | TTCN_3010 | 9895 | CTCN_1067 | 3965 | ATCN_2067 | 9938 |
| CTCN_1049 | 3923 | CTCN_2743 | 9896 | GTCN_591 | 3966 | TTCN_3029 | 9939 |
| TTCN_1027 | 3924 | TTCN_3011 | 9897 | ATCN_717 | 3967 | GTCN_1542 | 9940 |
| CTCN_1050 | 3925 | TTCN_3012 | 9898 | CTCN_1068 | 3968 | CTCN_2749 | 9941 |
| CTCN_1051 | 3926 | ATCN_2057 | 9899 | TTCN_1039 | 3969 | TTCN_3030 | 9942 |
| GTCN_587 | 3927 | GTCN_1534 | 9900 | ATCN_718 | 3970 | CTCN_2750 | 9943 |
| ATCN_709 | 3928 | TTCN_3013 | 9901 | TTCN_1040 | 3971 | ATCN_2068 | 9944 |
| ATCN_710 | 3929 | CTCN_2744 | 9902 | ATCN_719 | 3972 | TTCN_3031 | 9945 |
| TTCN_1028 | 3930 | TTCN_3014 | 9903 | ATCN_720 | 3973 | TTCN_3032 | 9946 |
| TTCN_1029 | 3931 | TTCN_3015 | 9904 | TTCN_1041 | 3974 | ATCN_2069 | 9947 |
| CTCN_1052 | 3932 | ATCN_2058 | 9905 | TTCN_1042 | 3975 | ATCN_2070 | 9948 |
| TTCN_1030 | 3933 | TTCN_3016 | 9906 | ATCN_721 | 3976 | GTCN_1543 | 9949 |
| TTCN_1031 | 3934 | TTCN_3017 | 9907 | CTCN_1069 | 3977 | GTCN_1544 | 9950 |
| TTCN_1032 | 3935 | TTCN_3018 | 9908 | CTCN_1070 | 3978 | CTCN_2751 | 9951 |
| ATCN_711 | 3936 | ATCN_2059 | 9909 | TTCN_1043 | 3979 | CTCN_2752 | 9952 |
| CTCN_1053 | 3937 | TTCN_3019 | 9910 | CTCN_1071 | 3980 | CTCN_2753 | 9953 |
| TTCN_1033 | 3938 | CTCN_2745 | 9911 | TTCN_1044 | 3981 | CTCN_2754 | 9954 |
| GTCN_588 | 3939 | ATCN_2060 | 9912 | CTCN_1072 | 3982 | ATCN_2071 | 9955 |
| GTCN_589 | 3940 | GTCN_1535 | 9913 | TTCN_1045 | 3983 | CTCN_2755 | 9956 |
| CTCN_1054 | 3941 | TTCN_3020 | 9914 | GTCN_592 | 3984 | GTCN_1545 | 9957 |
| CTCN_1055 | 3942 | GTCN_1536 | 9915 | TTCN_1046 | 3985 | GTCN_1546 | 9958 |
| CTCN_1056 | 3943 | TTCN_3021 | 9916 | TTCN_1047 | 3986 | CTCN_2756 | 9959 |
| ATCN_712 | 3944 | GTCN_1537 | 9917 | ATCN_722 | 3987 | TTCN_3033 | 9960 |

FIG. 33 (continued)

| | | | | | | | |
|---|---|---|---|---|---|---|---|
| ATCN_723 | 3988 | ATCN_2072 | 9961 | GTCN_600 | 4031 | TTCN_3049 | 10004 |
| TTCN_1048 | 3989 | CTCN_2757 | 9962 | CTCN_1095 | 4032 | ATCN_2080 | 10005 |
| CTCN_1073 | 3990 | CTCN_2758 | 9963 | ATCN_732 | 4033 | TTCN_3050 | 10006 |
| CTCN_1074 | 3991 | CTCN_2759 | 9964 | ATCN_733 | 4034 | TTCN_3051 | 10007 |
| GTCN_593 | 3992 | TTCN_3034 | 9965 | ATCN_734 | 4035 | GTCN_1555 | 10008 |
| ATCN_724 | 3993 | ATCN_2073 | 9966 | GTCN_601 | 4036 | ATCN_2081 | 10009 |
| CTCN_1075 | 3994 | ATCN_2074 | 9967 | ATCN_735 | 4037 | CTCN_2769 | 10010 |
| CTCN_1076 | 3995 | ATCN_2075 | 9968 | CTCN_1096 | 4038 | CTCN_2770 | 10011 |
| CTCN_1077 | 3996 | GTCN_1547 | 9969 | TTCN_1053 | 4039 | GTCN_1556 | 10012 |
| ATCN_725 | 3997 | CTCN_2760 | 9970 | TTCN_1054 | 4040 | TTCN_3052 | 10013 |
| ATCN_726 | 3998 | GTCN_1548 | 9971 | GTCN_602 | 4041 | GTCN_1557 | 10014 |
| CTCN_1078 | 3999 | TTCN_3035 | 9972 | GTCN_603 | 4042 | TTCN_3053 | 10015 |
| GTCN_594 | 4000 | CTCN_2761 | 9973 | CTCN_1097 | 4043 | GTCN_1558 | 10016 |
| CTCN_1079 | 4001 | TTCN_3036 | 9974 | CTCN_1098 | 4044 | GTCN_1559 | 10017 |
| ATCN_727 | 4002 | TTCN_3037 | 9975 | TTCN_1055 | 4045 | GTCN_1560 | 10018 |
| ATCN_728 | 4003 | GTCN_1549 | 9976 | GTCN_604 | 4046 | TTCN_3054 | 10019 |
| TTCN_1049 | 4004 | TTCN_3038 | 9977 | TTCN_1056 | 4047 | CTCN_2771 | 10020 |
| ATCN_729 | 4005 | TTCN_3039 | 9978 | TTCN_1057 | 4048 | GTCN_1561 | 10021 |
| TTCN_1050 | 4006 | TTCN_3040 | 9979 | TTCN_1058 | 4049 | ATCN_2082 | 10022 |
| GTCN_595 | 4007 | ATCN_2076 | 9980 | CTCN_1099 | 4050 | CTCN_2772 | 10023 |
| CTCN_1080 | 4008 | ATCN_2077 | 9981 | TTCN_1059 | 4051 | TTCN_3055 | 10024 |
| CTCN_1081 | 4009 | TTCN_3041 | 9982 | GTCN_605 | 4052 | TTCN_3056 | 10025 |
| CTCN_1082 | 4010 | GTCN_1550 | 9983 | ATCN_736 | 4053 | ATCN_2083 | 10026 |
| CTCN_1083 | 4011 | CTCN_2762 | 9984 | GTCN_606 | 4054 | TTCN_3057 | 10027 |
| GTCN_596 | 4012 | GTCN_1551 | 9985 | TTCN_1060 | 4055 | ATCN_2084 | 10028 |
| CTCN_1084 | 4013 | CTCN_2763 | 9986 | TTCN_1061 | 4056 | ATCN_2085 | 10029 |
| CTCN_1085 | 4014 | GTCN_1552 | 9987 | TTCN_1062 | 4057 | ATCN_2086 | 10030 |
| CTCN_1086 | 4015 | TTCN_3042 | 9988 | CTCN_1100 | 4058 | CTCN_2773 | 10031 |
| CTCN_1087 | 4016 | CTCN_2764 | 9989 | CTCN_1101 | 4059 | CTCN_2774 | 10032 |
| TTCN_1051 | 4017 | CTCN_2765 | 9990 | GTCN_607 | 4060 | TTCN_3058 | 10033 |
| TTCN_1052 | 4018 | TTCN_3043 | 9991 | TTCN_1063 | 4061 | TTCN_3059 | 10034 |
| CTCN_1088 | 4019 | ATCN_2078 | 9992 | CTCN_1102 | 4062 | ATCN_2087 | 10035 |
| CTCN_1089 | 4020 | TTCN_3044 | 9993 | GTCN_608 | 4063 | TTCN_3060 | 10036 |
| GTCN_597 | 4021 | TTCN_3045 | 9994 | GTCN_609 | 4064 | TTCN_3061 | 10037 |
| CTCN_1090 | 4022 | GTCN_1553 | 9995 | GTCN_610 | 4065 | CTCN_2775 | 10038 |
| ATCN_730 | 4023 | CTCN_2766 | 9996 | GTCN_611 | 4066 | ATCN_2088 | 10039 |
| ATCN_731 | 4024 | TTCN_3046 | 9997 | GTCN_612 | 4067 | ATCN_2089 | 10040 |
| CTCN_1091 | 4025 | TTCN_3047 | 9998 | GTCN_613 | 4068 | TTCN_3062 | 10041 |
| GTCN_598 | 4026 | ATCN_2079 | 9999 | ATCN_737 | 4069 | TTCN_3063 | 10042 |
| CTCN_1092 | 4027 | CTCN_2767 | 10000 | ATCN_738 | 4070 | ATCN_2090 | 10043 |
| CTCN_1093 | 4028 | CTCN_2768 | 10001 | TTCN_1064 | 4071 | GTCN_1562 | 10044 |
| GTCN_599 | 4029 | GTCN_1554 | 10002 | TTCN_1065 | 4072 | CTCN_2776 | 10045 |
| CTCN_1094 | 4030 | TTCN_3048 | 10003 | TTCN_1066 | 4073 | GTCN_1563 | 10046 |

FIG. 33 (continued)

| | | | | | | | |
|---|---|---|---|---|---|---|---|
| CTCN_1103 | 4074 | TTCN_3064 | 10047 | ATCN_750 | 4117 | TTCN_3077 | 10090 |
| TTCN_1067 | 4075 | CTCN_2777 | 10048 | ATCN_751 | 4118 | CTCN_2788 | 10091 |
| ATCN_739 | 4076 | ATCN_2091 | 10049 | TTCN_1080 | 4119 | TTCN_3078 | 10092 |
| TTCN_1068 | 4077 | ATCN_2092 | 10050 | ATCN_752 | 4120 | TTCN_3079 | 10093 |
| ATCN_740 | 4078 | TTCN_3065 | 10051 | CTCN_1117 | 4121 | ATCN_2104 | 10094 |
| ATCN_741 | 4079 | TTCN_3066 | 10052 | GTCN_619 | 4122 | TTCN_3080 | 10095 |
| TTCN_1069 | 4080 | CTCN_2778 | 10053 | CTCN_1118 | 4123 | GTCN_1570 | 10096 |
| CTCN_1104 | 4081 | CTCN_2779 | 10054 | CTCN_1119 | 4124 | ATCN_2105 | 10097 |
| CTCN_1105 | 4082 | ATCN_2093 | 10055 | GTCN_620 | 4125 | TTCN_3081 | 10098 |
| TTCN_1070 | 4083 | ATCN_2094 | 10056 | CTCN_1120 | 4126 | TTCN_3082 | 10099 |
| TTCN_1071 | 4084 | ATCN_2095 | 10057 | ATCN_753 | 4127 | CTCN_2789 | 10100 |
| CTCN_1106 | 4085 | CTCN_2780 | 10058 | ATCN_754 | 4128 | CTCN_2790 | 10101 |
| ATCN_742 | 4086 | CTCN_2781 | 10059 | ATCN_755 | 4129 | TTCN_3083 | 10102 |
| CTCN_1107 | 4087 | CTCN_2782 | 10060 | CTCN_1121 | 4130 | TTCN_3084 | 10103 |
| TTCN_1072 | 4088 | TTCN_3067 | 10061 | CTCN_1122 | 4131 | ATCN_2106 | 10104 |
| CTCN_1108 | 4089 | ATCN_2096 | 10062 | CTCN_1123 | 4132 | TTCN_3085 | 10105 |
| ATCN_743 | 4090 | TTCN_3068 | 10063 | GTCN_621 | 4133 | ATCN_2107 | 10106 |
| CTCN_1109 | 4091 | CTCN_2783 | 10064 | CTCN_1124 | 4134 | TTCN_3086 | 10107 |
| TTCN_1073 | 4092 | CTCN_2784 | 10065 | TTCN_1081 | 4135 | CTCN_2791 | 10108 |
| TTCN_1074 | 4093 | TTCN_3069 | 10066 | TTCN_1082 | 4136 | TTCN_3087 | 10109 |
| TTCN_1075 | 4094 | ATCN_2097 | 10067 | TTCN_1083 | 4137 | ATCN_2108 | 10110 |
| ATCN_744 | 4095 | TTCN_3070 | 10068 | CTCN_1125 | 4138 | CTCN_2792 | 10111 |
| CTCN_1110 | 4096 | ATCN_2098 | 10069 | TTCN_1084 | 4139 | TTCN_3088 | 10112 |
| TTCN_1076 | 4097 | ATCN_2099 | 10070 | CTCN_1126 | 4140 | TTCN_3089 | 10113 |
| TTCN_1077 | 4098 | ATCN_2100 | 10071 | GTCN_622 | 4141 | TTCN_3090 | 10114 |
| GTCN_614 | 4099 | TTCN_3071 | 10072 | CTCN_1127 | 4142 | GTCN_1571 | 10115 |
| TTCN_1078 | 4100 | ATCN_2101 | 10073 | GTCN_623 | 4143 | CTCN_2793 | 10116 |
| ATCN_745 | 4101 | CTCN_2785 | 10074 | TTCN_1085 | 4144 | CTCN_2794 | 10117 |
| ATCN_746 | 4102 | GTCN_1564 | 10075 | GTCN_624 | 4145 | CTCN_2795 | 10118 |
| GTCN_615 | 4103 | GTCN_1565 | 10076 | CTCN_1128 | 4146 | GTCN_1572 | 10119 |
| CTCN_1111 | 4104 | GTCN_1566 | 10077 | TTCN_1086 | 4147 | ATCN_2109 | 10120 |
| GTCN_616 | 4105 | GTCN_1567 | 10078 | CTCN_1129 | 4148 | ATCN_2110 | 10121 |
| CTCN_1112 | 4106 | TTCN_3072 | 10079 | CTCN_1130 | 4149 | ATCN_2111 | 10122 |
| CTCN_1113 | 4107 | TTCN_3073 | 10080 | ATCN_756 | 4150 | ATCN_2112 | 10123 |
| GTCN_617 | 4108 | TTCN_3074 | 10081 | ATCN_757 | 4151 | GTCN_1573 | 10124 |
| ATCN_747 | 4109 | TTCN_3075 | 10082 | CTCN_1131 | 4152 | CTCN_2796 | 10125 |
| ATCN_748 | 4110 | CTCN_2786 | 10083 | GTCN_625 | 4153 | TTCN_3091 | 10126 |
| CTCN_1114 | 4111 | GTCN_1568 | 10084 | TTCN_1087 | 4154 | TTCN_3092 | 10127 |
| ATCN_749 | 4112 | TTCN_3076 | 10085 | ATCN_758 | 4155 | ATCN_2113 | 10128 |
| GTCN_618 | 4113 | ATCN_2102 | 10086 | CTCN_1132 | 4156 | GTCN_1574 | 10129 |
| CTCN_1115 | 4114 | CTCN_2787 | 10087 | GTCN_626 | 4157 | CTCN_2797 | 10130 |
| TTCN_1079 | 4115 | ATCN_2103 | 10088 | ATCN_759 | 4158 | TTCN_3093 | 10131 |
| CTCN_1116 | 4116 | GTCN_1569 | 10089 | CTCN_1133 | 4159 | ATCN_2114 | 10132 |

FIG. 33 (continued)

| | | | | | | | |
|---|---|---|---|---|---|---|---|
| GTCN_627 | 4160 | TTCN_3094 | 10133 | TTCN_1095 | 4203 | ATCN_2127 | 10176 |
| GTCN_628 | 4161 | ATCN_2115 | 10134 | GTCN_635 | 4204 | TTCN_3115 | 10177 |
| CTCN_1134 | 4162 | CTCN_2798 | 10135 | CTCN_1155 | 4205 | TTCN_3116 | 10178 |
| CTCN_1135 | 4163 | TTCN_3095 | 10136 | TTCN_1096 | 4206 | TTCN_3117 | 10179 |
| GTCN_629 | 4164 | TTCN_3096 | 10137 | CTCN_1156 | 4207 | GTCN_1580 | 10180 |
| CTCN_1136 | 4165 | CTCN_2799 | 10138 | CTCN_1157 | 4208 | GTCN_1581 | 10181 |
| ATCN_760 | 4166 | ATCN_2116 | 10139 | ATCN_767 | 4209 | TTCN_3118 | 10182 |
| ATCN_761 | 4167 | ATCN_2117 | 10140 | TTCN_1097 | 4210 | ATCN_2128 | 10183 |
| CTCN_1137 | 4168 | TTCN_3097 | 10141 | TTCN_1098 | 4211 | TTCN_3119 | 10184 |
| CTCN_1138 | 4169 | ATCN_2118 | 10142 | ATCN_768 | 4212 | CTCN_2803 | 10185 |
| CTCN_1139 | 4170 | TTCN_3098 | 10143 | TTCN_1099 | 4213 | GTCN_1582 | 10186 |
| TTCN_1088 | 4171 | TTCN_3099 | 10144 | TTCN_1100 | 4214 | TTCN_3120 | 10187 |
| TTCN_1089 | 4172 | TTCN_3100 | 10145 | CTCN_1158 | 4215 | GTCN_1583 | 10188 |
| TTCN_1090 | 4173 | TTCN_3101 | 10146 | TTCN_1101 | 4216 | TTCN_3121 | 10189 |
| CTCN_1140 | 4174 | ATCN_2119 | 10147 | CTCN_1159 | 4217 | TTCN_3122 | 10190 |
| CTCN_1141 | 4175 | ATCN_2120 | 10148 | GTCN_636 | 4218 | TTCN_3123 | 10191 |
| CTCN_1142 | 4176 | ATCN_2121 | 10149 | TTCN_1102 | 4219 | CTCN_2804 | 10192 |
| ATCN_762 | 4177 | TTCN_3102 | 10150 | GTCN_637 | 4220 | TTCN_3124 | 10193 |
| CTCN_1143 | 4178 | GTCN_1575 | 10151 | TTCN_1103 | 4221 | TTCN_3125 | 10194 |
| GTCN_630 | 4179 | TTCN_3103 | 10152 | CTCN_1160 | 4222 | GTCN_1584 | 10195 |
| CTCN_1144 | 4180 | GTCN_1576 | 10153 | CTCN_1161 | 4223 | CTCN_2805 | 10196 |
| GTCN_631 | 4181 | TTCN_3104 | 10154 | ATCN_769 | 4224 | TTCN_3126 | 10197 |
| CTCN_1145 | 4182 | GTCN_1577 | 10155 | ATCN_770 | 4225 | TTCN_3127 | 10198 |
| CTCN_1146 | 4183 | TTCN_3105 | 10156 | TTCN_1104 | 4226 | TTCN_3128 | 10199 |
| ATCN_763 | 4184 | ATCN_2122 | 10157 | TTCN_1105 | 4227 | TTCN_3129 | 10200 |
| ATCN_764 | 4185 | TTCN_3106 | 10158 | GTCN_638 | 4228 | TTCN_3130 | 10201 |
| CTCN_1147 | 4186 | ATCN_2123 | 10159 | GTCN_639 | 4229 | TTCN_3131 | 10202 |
| TTCN_1091 | 4187 | CTCN_2800 | 10160 | TTCN_1106 | 4230 | GTCN_1585 | 10203 |
| TTCN_1092 | 4188 | TTCN_3107 | 10161 | TTCN_1107 | 4231 | GTCN_1586 | 10204 |
| CTCN_1148 | 4189 | ATCN_2124 | 10162 | TTCN_1108 | 4232 | ATCN_2129 | 10205 |
| CTCN_1149 | 4190 | TTCN_3108 | 10163 | ATCN_771 | 4233 | GTCN_1587 | 10206 |
| ATCN_765 | 4191 | TTCN_3109 | 10164 | GTCN_640 | 4234 | TTCN_3132 | 10207 |
| CTCN_1150 | 4192 | CTCN_2801 | 10165 | TTCN_1109 | 4235 | ATCN_2130 | 10208 |
| CTCN_1151 | 4193 | TTCN_3110 | 10166 | ATCN_772 | 4236 | ATCN_2131 | 10209 |
| GTCN_632 | 4194 | CTCN_2802 | 10167 | GTCN_641 | 4237 | ATCN_2132 | 10210 |
| TTCN_1093 | 4195 | GTCN_1578 | 10168 | ATCN_773 | 4238 | TTCN_3133 | 10211 |
| GTCN_633 | 4196 | TTCN_3111 | 10169 | CTCN_1162 | 4239 | ATCN_2133 | 10212 |
| CTCN_1152 | 4197 | ATCN_2125 | 10170 | TTCN_1110 | 4240 | ATCN_2134 | 10213 |
| TTCN_1094 | 4198 | GTCN_1579 | 10171 | TTCN_1111 | 4241 | ATCN_2135 | 10214 |
| CTCN_1153 | 4199 | ATCN_2126 | 10172 | TTCN_1112 | 4242 | TTCN_3134 | 10215 |
| GTCN_634 | 4200 | TTCN_3112 | 10173 | CTCN_1163 | 4243 | GTCN_1588 | 10216 |
| CTCN_1154 | 4201 | TTCN_3113 | 10174 | CTCN_1164 | 4244 | CTCN_2806 | 10217 |
| ATCN_766 | 4202 | TTCN_3114 | 10175 | TTCN_1113 | 4245 | CTCN_2807 | 10218 |

FIG. 33 (continued)

| | | | | | | | |
|---|---|---|---|---|---|---|---|
| TTCN_1114 | 4246 | ATCN_2136 | 10219 | TTCN_1126 | 4289 | TTCN_3150 | 10262 |
| TTCN_1115 | 4247 | ATCN_2137 | 10220 | TTCN_1127 | 4290 | ATCN_2150 | 10263 |
| ATCN_774 | 4248 | GTCN_1589 | 10221 | ATCN_784 | 4291 | ATCN_2151 | 10264 |
| ATCN_775 | 4249 | CTCN_2808 | 10222 | TTCN_1128 | 4292 | GTCN_1594 | 10265 |
| GTCN_642 | 4250 | TTCN_3135 | 10223 | CTCN_1176 | 4293 | CTCN_2817 | 10266 |
| TTCN_1116 | 4251 | TTCN_3136 | 10224 | CTCN_1177 | 4294 | CTCN_2818 | 10267 |
| TTCN_1117 | 4252 | CTCN_2809 | 10225 | CTCN_1178 | 4295 | CTCN_2819 | 10268 |
| CTCN_1165 | 4253 | TTCN_3137 | 10226 | TTCN_1129 | 4296 | ATCN_2152 | 10269 |
| GTCN_643 | 4254 | TTCN_3138 | 10227 | CTCN_1179 | 4297 | CTCN_2820 | 10270 |
| CTCN_1166 | 4255 | GTCN_1590 | 10228 | CTCN_1180 | 4298 | TTCN_3151 | 10271 |
| GTCN_644 | 4256 | ATCN_2138 | 10229 | TTCN_1130 | 4299 | ATCN_2153 | 10272 |
| ATCN_776 | 4257 | TTCN_3139 | 10230 | ATCN_785 | 4300 | CTCN_2821 | 10273 |
| ATCN_777 | 4258 | CTCN_2810 | 10231 | CTCN_1181 | 4301 | TTCN_3152 | 10274 |
| TTCN_1118 | 4259 | TTCN_3140 | 10232 | TTCN_1131 | 4302 | TTCN_3153 | 10275 |
| ATCN_778 | 4260 | CTCN_2811 | 10233 | GTCN_652 | 4303 | GTCN_1595 | 10276 |
| CTCN_1167 | 4261 | TTCN_3141 | 10234 | CTCN_1182 | 4304 | ATCN_2154 | 10277 |
| ATCN_779 | 4262 | GTCN_1591 | 10235 | ATCN_786 | 4305 | TTCN_3154 | 10278 |
| CTCN_1168 | 4263 | CTCN_2812 | 10236 | TTCN_1132 | 4306 | TTCN_3155 | 10279 |
| GTCN_645 | 4264 | TTCN_3142 | 10237 | CTCN_1183 | 4307 | GTCN_1596 | 10280 |
| ATCN_780 | 4265 | TTCN_3143 | 10238 | TTCN_1133 | 4308 | GTCN_1597 | 10281 |
| TTCN_1119 | 4266 | ATCN_2139 | 10239 | ATCN_787 | 4309 | CTCN_2822 | 10282 |
| GTCN_646 | 4267 | ATCN_2140 | 10240 | GTCN_653 | 4310 | TTCN_3156 | 10283 |
| TTCN_1120 | 4268 | CTCN_2813 | 10241 | TTCN_1134 | 4311 | TTCN_3157 | 10284 |
| GTCN_647 | 4269 | CTCN_2814 | 10242 | TTCN_1135 | 4312 | CTCN_2823 | 10285 |
| TTCN_1121 | 4270 | TTCN_3144 | 10243 | GTCN_654 | 4313 | TTCN_3158 | 10286 |
| TTCN_1122 | 4271 | GTCN_1592 | 10244 | TTCN_1136 | 4314 | TTCN_3159 | 10287 |
| CTCN_1169 | 4272 | TTCN_3145 | 10245 | CTCN_1184 | 4315 | ATCN_2155 | 10288 |
| ATCN_781 | 4273 | CTCN_2815 | 10246 | CTCN_1185 | 4316 | ATCN_2156 | 10289 |
| CTCN_1170 | 4274 | ATCN_2141 | 10247 | TTCN_1137 | 4317 | TTCN_3160 | 10290 |
| CTCN_1171 | 4275 | ATCN_2142 | 10248 | GTCN_655 | 4318 | TTCN_3161 | 10291 |
| CTCN_1172 | 4276 | ATCN_2143 | 10249 | CTCN_1186 | 4319 | ATCN_2157 | 10292 |
| TTCN_1123 | 4277 | TTCN_3146 | 10250 | ATCN_788 | 4320 | TTCN_3162 | 10293 |
| TTCN_1124 | 4278 | ATCN_2144 | 10251 | GTCN_656 | 4321 | CTCN_2824 | 10294 |
| CTCN_1173 | 4279 | TTCN_3147 | 10252 | ATCN_789 | 4322 | CTCN_2825 | 10295 |
| ATCN_782 | 4280 | ATCN_2145 | 10253 | CTCN_1187 | 4323 | TTCN_3163 | 10296 |
| GTCN_648 | 4281 | GTCN_1593 | 10254 | TTCN_1138 | 4324 | TTCN_3164 | 10297 |
| CTCN_1174 | 4282 | CTCN_2816 | 10255 | GTCN_657 | 4325 | TTCN_3165 | 10298 |
| GTCN_649 | 4283 | ATCN_2146 | 10256 | CTCN_1188 | 4326 | TTCN_3166 | 10299 |
| CTCN_1175 | 4284 | ATCN_2147 | 10257 | TTCN_1139 | 4327 | CTCN_2826 | 10300 |
| TTCN_1125 | 4285 | TTCN_3148 | 10258 | ATCN_790 | 4328 | GTCN_1598 | 10301 |
| GTCN_650 | 4286 | ATCN_2148 | 10259 | CTCN_1189 | 4329 | TTCN_3167 | 10302 |
| ATCN_783 | 4287 | ATCN_2149 | 10260 | TTCN_1140 | 4330 | TTCN_3168 | 10303 |
| GTCN_651 | 4288 | TTCN_3149 | 10261 | CTCN_1190 | 4331 | CTCN_2827 | 10304 |

FIG. 33 (continued)

| | | | | | | | |
|---|---|---|---|---|---|---|---|
| GTCN_658 | 4332 | TTCN_3169 | 10305 | CTCN_1207 | 4375 | ATCN_2168 | 10348 |
| TTCN_1141 | 4333 | GTCN_1599 | 10306 | ATCN_802 | 4376 | TTCN_3186 | 10349 |
| TTCN_1142 | 4334 | TTCN_3170 | 10307 | CTCN_1208 | 4377 | GTCN_1604 | 10350 |
| ATCN_791 | 4335 | CTCN_2828 | 10308 | CTCN_1209 | 4378 | GTCN_1605 | 10351 |
| ATCN_792 | 4336 | TTCN_3171 | 10309 | TTCN_1150 | 4379 | TTCN_3187 | 10352 |
| TTCN_1143 | 4337 | TTCN_3172 | 10310 | ATCN_803 | 4380 | ATCN_2169 | 10353 |
| GTCN_659 | 4338 | ATCN_2158 | 10311 | CTCN_1210 | 4381 | TTCN_3188 | 10354 |
| CTCN_1191 | 4339 | ATCN_2159 | 10312 | CTCN_1211 | 4382 | TTCN_3189 | 10355 |
| CTCN_1192 | 4340 | TTCN_3173 | 10313 | ATCN_804 | 4383 | TTCN_3190 | 10356 |
| ATCN_793 | 4341 | TTCN_3174 | 10314 | ATCN_805 | 4384 | GTCN_1606 | 10357 |
| ATCN_794 | 4342 | TTCN_3175 | 10315 | CTCN_1212 | 4385 | CTCN_2839 | 10358 |
| CTCN_1193 | 4343 | TTCN_3176 | 10316 | GTCN_665 | 4386 | TTCN_3191 | 10359 |
| TTCN_1144 | 4344 | GTCN_1600 | 10317 | CTCN_1213 | 4387 | CTCN_2840 | 10360 |
| CTCN_1194 | 4345 | CTCN_2829 | 10318 | ATCN_806 | 4388 | TTCN_3192 | 10361 |
| ATCN_795 | 4346 | ATCN_2160 | 10319 | CTCN_1214 | 4389 | CTCN_2841 | 10362 |
| CTCN_1195 | 4347 | TTCN_3177 | 10320 | GTCN_666 | 4390 | GTCN_1607 | 10363 |
| CTCN_1196 | 4348 | CTCN_2830 | 10321 | ATCN_807 | 4391 | TTCN_3193 | 10364 |
| ATCN_796 | 4349 | ATCN_2161 | 10322 | TTCN_1151 | 4392 | ATCN_2170 | 10365 |
| ATCN_797 | 4350 | CTCN_2831 | 10323 | GTCN_667 | 4393 | TTCN_3194 | 10366 |
| CTCN_1197 | 4351 | TTCN_3178 | 10324 | CTCN_1215 | 4394 | ATCN_2171 | 10367 |
| GTCN_660 | 4352 | TTCN_3179 | 10325 | CTCN_1216 | 4395 | CTCN_2842 | 10368 |
| CTCN_1198 | 4353 | GTCN_1601 | 10326 | GTCN_668 | 4396 | TTCN_3195 | 10369 |
| GTCN_661 | 4354 | CTCN_2832 | 10327 | CTCN_1217 | 4397 | CTCN_2843 | 10370 |
| GTCN_662 | 4355 | CTCN_2833 | 10328 | CTCN_1218 | 4398 | ATCN_2172 | 10371 |
| CTCN_1199 | 4356 | CTCN_2834 | 10329 | CTCN_1219 | 4399 | TTCN_3196 | 10372 |
| TTCN_1145 | 4357 | CTCN_2835 | 10330 | CTCN_1220 | 4400 | ATCN_2173 | 10373 |
| TTCN_1146 | 4358 | ATCN_2162 | 10331 | TTCN_1152 | 4401 | CTCN_2844 | 10374 |
| GTCN_663 | 4359 | TTCN_3180 | 10332 | TTCN_1153 | 4402 | CTCN_2845 | 10375 |
| GTCN_664 | 4360 | TTCN_3181 | 10333 | ATCN_808 | 4403 | CTCN_2846 | 10376 |
| CTCN_1200 | 4361 | GTCN_1602 | 10334 | CTCN_1221 | 4404 | GTCN_1608 | 10377 |
| CTCN_1201 | 4362 | TTCN_3182 | 10335 | CTCN_1222 | 4405 | ATCN_2174 | 10378 |
| TTCN_1147 | 4363 | TTCN_3183 | 10336 | CTCN_1223 | 4406 | ATCN_2175 | 10379 |
| ATCN_798 | 4364 | ATCN_2163 | 10337 | CTCN_1224 | 4407 | ATCN_2176 | 10380 |
| TTCN_1148 | 4365 | CTCN_2836 | 10338 | ATCN_809 | 4408 | TTCN_3197 | 10381 |
| ATCN_799 | 4366 | GTCN_1603 | 10339 | CTCN_1225 | 4409 | TTCN_3198 | 10382 |
| CTCN_1202 | 4367 | ATCN_2164 | 10340 | GTCN_669 | 4410 | ATCN_2177 | 10383 |
| CTCN_1203 | 4368 | TTCN_3184 | 10341 | CTCN_1226 | 4411 | CTCN_2847 | 10384 |
| CTCN_1204 | 4369 | ATCN_2165 | 10342 | CTCN_1227 | 4412 | CTCN_2848 | 10385 |
| ATCN_800 | 4370 | TTCN_3185 | 10343 | GTCN_670 | 4413 | ATCN_2178 | 10386 |
| ATCN_801 | 4371 | ATCN_2166 | 10344 | CTCN_1228 | 4414 | TTCN_3199 | 10387 |
| CTCN_1205 | 4372 | ATCN_2167 | 10345 | ATCN_810 | 4415 | GTCN_1609 | 10388 |
| CTCN_1206 | 4373 | CTCN_2837 | 10346 | CTCN_1229 | 4416 | TTCN_3200 | 10389 |
| TTCN_1149 | 4374 | CTCN_2838 | 10347 | TTCN_1154 | 4417 | CTCN_2849 | 10390 |

FIG. 33 (continued)

| | | | | | | | |
|---|---|---|---|---|---|---|---|
| CTCN_1230 | 4418 | ATCN_2179 | 10391 | CTCN_1245 | 4461 | ATCN_2190 | 10434 |
| GTCN_671 | 4419 | ATCN_2180 | 10392 | TTCN_1175 | 4462 | TTCN_3213 | 10435 |
| TTCN_1155 | 4420 | TTCN_3201 | 10393 | ATCN_814 | 4463 | CTCN_2862 | 10436 |
| TTCN_1156 | 4421 | ATCN_2181 | 10394 | CTCN_1246 | 4464 | TTCN_3214 | 10437 |
| TTCN_1157 | 4422 | TTCN_3202 | 10395 | ATCN_815 | 4465 | ATCN_2191 | 10438 |
| CTCN_1231 | 4423 | GTCN_1610 | 10396 | CTCN_1247 | 4466 | GTCN_1618 | 10439 |
| TTCN_1158 | 4424 | CTCN_2850 | 10397 | TTCN_1176 | 4467 | CTCN_2863 | 10440 |
| ATCN_811 | 4425 | TTCN_3203 | 10398 | ATCN_816 | 4468 | TTCN_3215 | 10441 |
| CTCN_1232 | 4426 | GTCN_1611 | 10399 | TTCN_1177 | 4469 | TTCN_3216 | 10442 |
| TTCN_1159 | 4427 | CTCN_2851 | 10400 | TTCN_1178 | 4470 | ATCN_2192 | 10443 |
| CTCN_1233 | 4428 | GTCN_1612 | 10401 | ATCN_817 | 4471 | TTCN_3217 | 10444 |
| CTCN_1234 | 4429 | CTCN_2852 | 10402 | GTCN_676 | 4472 | CTCN_2864 | 10445 |
| TTCN_1160 | 4430 | ATCN_2182 | 10403 | TTCN_1179 | 4473 | ATCN_2193 | 10446 |
| TTCN_1161 | 4431 | TTCN_3204 | 10404 | TTCN_1180 | 4474 | CTCN_2865 | 10447 |
| CTCN_1235 | 4432 | GTCN_1613 | 10405 | TTCN_1181 | 4475 | ATCN_2194 | 10448 |
| TTCN_1162 | 4433 | ATCN_2183 | 10406 | GTCN_677 | 4476 | TTCN_3218 | 10449 |
| TTCN_1163 | 4434 | ATCN_2184 | 10407 | CTCN_1248 | 4477 | ATCN_2195 | 10450 |
| CTCN_1236 | 4435 | TTCN_3205 | 10408 | ATCN_818 | 4478 | ATCN_2196 | 10451 |
| CTCN_1237 | 4436 | TTCN_3206 | 10409 | CTCN_1249 | 4479 | TTCN_3219 | 10452 |
| CTCN_1238 | 4437 | TTCN_3207 | 10410 | CTCN_1250 | 4480 | CTCN_2866 | 10453 |
| CTCN_1239 | 4438 | TTCN_3208 | 10411 | CTCN_1251 | 4481 | TTCN_3220 | 10454 |
| CTCN_1240 | 4439 | CTCN_2853 | 10412 | CTCN_1252 | 4482 | TTCN_3221 | 10455 |
| CTCN_1241 | 4440 | TTCN_3209 | 10413 | TTCN_1182 | 4483 | ATCN_2197 | 10456 |
| TTCN_1164 | 4441 | ATCN_2185 | 10414 | GTCN_678 | 4484 | ATCN_2198 | 10457 |
| TTCN_1165 | 4442 | TTCN_3210 | 10415 | CTCN_1253 | 4485 | ATCN_2199 | 10458 |
| TTCN_1166 | 4443 | TTCN_3211 | 10416 | GTCN_679 | 4486 | GTCN_1619 | 10459 |
| CTCN_1242 | 4444 | ATCN_2186 | 10417 | CTCN_1254 | 4487 | TTCN_3222 | 10460 |
| GTCN_672 | 4445 | CTCN_2854 | 10418 | ATCN_819 | 4488 | CTCN_2867 | 10461 |
| TTCN_1167 | 4446 | ATCN_2187 | 10419 | ATCN_820 | 4489 | TTCN_3223 | 10462 |
| ATCN_812 | 4447 | GTCN_1614 | 10420 | GTCN_680 | 4490 | TTCN_3224 | 10463 |
| TTCN_1168 | 4448 | CTCN_2855 | 10421 | TTCN_1183 | 4491 | TTCN_3225 | 10464 |
| TTCN_1169 | 4449 | CTCN_2856 | 10422 | GTCN_681 | 4492 | TTCN_3226 | 10465 |
| TTCN_1170 | 4450 | GTCN_1615 | 10423 | TTCN_1184 | 4493 | CTCN_2868 | 10466 |
| TTCN_1171 | 4451 | CTCN_2857 | 10424 | TTCN_1185 | 4494 | ATCN_2200 | 10467 |
| GTCN_673 | 4452 | ATCN_2188 | 10425 | TTCN_1186 | 4495 | TTCN_3227 | 10468 |
| ATCN_813 | 4453 | TTCN_3212 | 10426 | GTCN_682 | 4496 | ATCN_2201 | 10469 |
| CTCN_1243 | 4454 | GTCN_1616 | 10427 | CTCN_1255 | 4497 | ATCN_2202 | 10470 |
| CTCN_1244 | 4455 | GTCN_1617 | 10428 | TTCN_1187 | 4498 | ATCN_2203 | 10471 |
| TTCN_1172 | 4456 | CTCN_2858 | 10429 | TTCN_1188 | 4499 | ATCN_2204 | 10472 |
| GTCN_674 | 4457 | CTCN_2859 | 10430 | ATCN_821 | 4500 | ATCN_2205 | 10473 |
| TTCN_1173 | 4458 | CTCN_2860 | 10431 | CTCN_1256 | 4501 | TTCN_3228 | 10474 |
| GTCN_675 | 4459 | CTCN_2861 | 10432 | CTCN_1257 | 4502 | GTCN_1620 | 10475 |
| TTCN_1174 | 4460 | ATCN_2189 | 10433 | GTCN_683 | 4503 | TTCN_3229 | 10476 |

FIG. 33 (continued)

| CTCN_1258 | 4504 | TTCN_3230 | 10477 | ATCN_833 | 4547 | ATCN_2213 | 10520 |
|---|---|---|---|---|---|---|---|
| ATCN_822 | 4505 | TTCN_3231 | 10478 | TTCN_1197 | 4548 | CTCN_2884 | 10521 |
| CTCN_1259 | 4506 | CTCN_2869 | 10479 | GTCN_691 | 4549 | CTCN_2885 | 10522 |
| CTCN_1260 | 4507 | ATCN_2206 | 10480 | CTCN_1275 | 4550 | CTCN_2886 | 10523 |
| GTCN_684 | 4508 | ATCN_2207 | 10481 | TTCN_1198 | 4551 | CTCN_2887 | 10524 |
| ATCN_823 | 4509 | GTCN_1621 | 10482 | CTCN_1276 | 4552 | CTCN_2888 | 10525 |
| ATCN_824 | 4510 | ATCN_2208 | 10483 | TTCN_1199 | 4553 | ATCN_2214 | 10526 |
| CTCN_1261 | 4511 | GTCN_1622 | 10484 | TTCN_1200 | 4554 | TTCN_3240 | 10527 |
| GTCN_685 | 4512 | CTCN_2870 | 10485 | ATCN_834 | 4555 | TTCN_3241 | 10528 |
| CTCN_1262 | 4513 | TTCN_3232 | 10486 | CTCN_1277 | 4556 | GTCN_1632 | 10529 |
| ATCN_825 | 4514 | TTCN_3233 | 10487 | TTCN_1201 | 4557 | TTCN_3242 | 10530 |
| ATCN_826 | 4515 | CTCN_2871 | 10488 | CTCN_1278 | 4558 | TTCN_3243 | 10531 |
| CTCN_1263 | 4516 | GTCN_1623 | 10489 | TTCN_1202 | 4559 | CTCN_2889 | 10532 |
| GTCN_686 | 4517 | CTCN_2872 | 10490 | CTCN_1279 | 4560 | GTCN_1633 | 10533 |
| ATCN_827 | 4518 | CTCN_2873 | 10491 | TTCN_1203 | 4561 | TTCN_3244 | 10534 |
| TTCN_1189 | 4519 | GTCN_1624 | 10492 | ATCN_835 | 4562 | GTCN_1634 | 10535 |
| ATCN_828 | 4520 | CTCN_2874 | 10493 | TTCN_1204 | 4563 | ATCN_2215 | 10536 |
| ATCN_829 | 4521 | ATCN_2209 | 10494 | ATCN_836 | 4564 | ATCN_2216 | 10537 |
| CTCN_1264 | 4522 | CTCN_2875 | 10495 | TTCN_1205 | 4565 | CTCN_2890 | 10538 |
| CTCN_1265 | 4523 | CTCN_2876 | 10496 | ATCN_837 | 4566 | TTCN_3245 | 10539 |
| GTCN_687 | 4524 | CTCN_2877 | 10497 | ATCN_838 | 4567 | TTCN_3246 | 10540 |
| CTCN_1266 | 4525 | CTCN_2878 | 10498 | ATCN_839 | 4568 | ATCN_2217 | 10541 |
| TTCN_1190 | 4526 | GTCN_1625 | 10499 | ATCN_840 | 4569 | ATCN_2218 | 10542 |
| CTCN_1267 | 4527 | GTCN_1626 | 10500 | GTCN_692 | 4570 | GTCN_1635 | 10543 |
| TTCN_1191 | 4528 | CTCN_2879 | 10501 | CTCN_1280 | 4571 | ATCN_2219 | 10544 |
| TTCN_1192 | 4529 | GTCN_1627 | 10502 | TTCN_1206 | 4572 | ATCN_2220 | 10545 |
| ATCN_830 | 4530 | CTCN_2880 | 10503 | CTCN_1281 | 4573 | CTCN_2891 | 10546 |
| CTCN_1268 | 4531 | TTCN_3234 | 10504 | ATCN_841 | 4574 | ATCN_2221 | 10547 |
| CTCN_1269 | 4532 | GTCN_1628 | 10505 | CTCN_1282 | 4575 | CTCN_2892 | 10548 |
| CTCN_1270 | 4533 | TTCN_3235 | 10506 | ATCN_842 | 4576 | CTCN_2893 | 10549 |
| ATCN_831 | 4534 | TTCN_3236 | 10507 | GTCN_693 | 4577 | ATCN_2222 | 10550 |
| ATCN_832 | 4535 | CTCN_2881 | 10508 | TTCN_1207 | 4578 | ATCN_2223 | 10551 |
| CTCN_1271 | 4536 | GTCN_1629 | 10509 | TTCN_1208 | 4579 | CTCN_2894 | 10552 |
| GTCN_688 | 4537 | TTCN_3237 | 10510 | TTCN_1209 | 4580 | GTCN_1636 | 10553 |
| CTCN_1272 | 4538 | TTCN_3238 | 10511 | ATCN_843 | 4581 | CTCN_2895 | 10554 |
| CTCN_1273 | 4539 | GTCN_1630 | 10512 | TTCN_1210 | 4582 | ATCN_2224 | 10555 |
| GTCN_689 | 4540 | ATCN_2210 | 10513 | CTCN_1283 | 4583 | ATCN_2225 | 10556 |
| CTCN_1274 | 4541 | ATCN_2211 | 10514 | CTCN_1284 | 4584 | GTCN_1637 | 10557 |
| GTCN_690 | 4542 | CTCN_2882 | 10515 | TTCN_1211 | 4585 | TTCN_3247 | 10558 |
| TTCN_1193 | 4543 | TTCN_3239 | 10516 | CTCN_1285 | 4586 | CTCN_2896 | 10559 |
| TTCN_1194 | 4544 | GTCN_1631 | 10517 | GTCN_694 | 4587 | TTCN_3248 | 10560 |
| TTCN_1195 | 4545 | CTCN_2883 | 10518 | TTCN_1212 | 4588 | TTCN_3249 | 10561 |
| TTCN_1196 | 4546 | ATCN_2212 | 10519 | CTCN_1286 | 4589 | TTCN_3250 | 10562 |

FIG. 33 (continued)

| | | | | | | | |
|---|---|---|---|---|---|---|---|
| CTCN_1287 | 4590 | TTCN_3251 | 10563 | ATCN_854 | 4633 | TTCN_3266 | 10606 |
| CTCN_1288 | 4591 | TTCN_3252 | 10564 | ATCN_855 | 4634 | TTCN_3267 | 10607 |
| CTCN_1289 | 4592 | TTCN_3253 | 10565 | GTCN_702 | 4635 | CTCN_2906 | 10608 |
| TTCN_1213 | 4593 | GTCN_1638 | 10566 | CTCN_1301 | 4636 | GTCN_1643 | 10609 |
| ATCN_844 | 4594 | ATCN_2226 | 10567 | TTCN_1225 | 4637 | GTCN_1644 | 10610 |
| CTCN_1290 | 4595 | CTCN_2897 | 10568 | GTCN_703 | 4638 | GTCN_1645 | 10611 |
| CTCN_1291 | 4596 | TTCN_3254 | 10569 | TTCN_1226 | 4639 | CTCN_2907 | 10612 |
| TTCN_1214 | 4597 | TTCN_3255 | 10570 | TTCN_1227 | 4640 | ATCN_2240 | 10613 |
| TTCN_1215 | 4598 | TTCN_3256 | 10571 | ATCN_856 | 4641 | GTCN_1646 | 10614 |
| GTCN_695 | 4599 | CTCN_2898 | 10572 | TTCN_1228 | 4642 | GTCN_1647 | 10615 |
| GTCN_696 | 4600 | ATCN_2227 | 10573 | GTCN_704 | 4643 | TTCN_3268 | 10616 |
| CTCN_1292 | 4601 | TTCN_3257 | 10574 | ATCN_857 | 4644 | ATCN_2241 | 10617 |
| GTCN_697 | 4602 | GTCN_1639 | 10575 | ATCN_858 | 4645 | CTCN_2908 | 10618 |
| ATCN_845 | 4603 | CTCN_2899 | 10576 | CTCN_1302 | 4646 | TTCN_3269 | 10619 |
| CTCN_1293 | 4604 | CTCN_2900 | 10577 | CTCN_1303 | 4647 | GTCN_1648 | 10620 |
| TTCN_1216 | 4605 | ATCN_2228 | 10578 | GTCN_705 | 4648 | CTCN_2909 | 10621 |
| GTCN_698 | 4606 | ATCN_2229 | 10579 | CTCN_1304 | 4649 | CTCN_2910 | 10622 |
| CTCN_1294 | 4607 | TTCN_3258 | 10580 | CTCN_1305 | 4650 | TTCN_3270 | 10623 |
| ATCN_846 | 4608 | ATCN_2230 | 10581 | CTCN_1306 | 4651 | ATCN_2242 | 10624 |
| TTCN_1217 | 4609 | TTCN_3259 | 10582 | ATCN_859 | 4652 | ATCN_2243 | 10625 |
| ATCN_847 | 4610 | CTCN_2901 | 10583 | ATCN_860 | 4653 | ATCN_2244 | 10626 |
| ATCN_848 | 4611 | TTCN_3260 | 10584 | ATCN_861 | 4654 | ATCN_2245 | 10627 |
| CTCN_1295 | 4612 | GTCN_1640 | 10585 | CTCN_1307 | 4655 | CTCN_2911 | 10628 |
| CTCN_1296 | 4613 | TTCN_3261 | 10586 | GTCN_706 | 4656 | CTCN_2912 | 10629 |
| CTCN_1297 | 4614 | ATCN_2231 | 10587 | CTCN_1308 | 4657 | ATCN_2246 | 10630 |
| TTCN_1218 | 4615 | TTCN_3262 | 10588 | CTCN_1309 | 4658 | TTCN_3271 | 10631 |
| CTCN_1298 | 4616 | TTCN_3263 | 10589 | GTCN_707 | 4659 | ATCN_2247 | 10632 |
| CTCN_1299 | 4617 | ATCN_2232 | 10590 | CTCN_1310 | 4660 | TTCN_3272 | 10633 |
| ATCN_849 | 4618 | TTCN_3264 | 10591 | TTCN_1229 | 4661 | TTCN_3273 | 10634 |
| ATCN_850 | 4619 | TTCN_3265 | 10592 | ATCN_862 | 4662 | ATCN_2248 | 10635 |
| GTCN_699 | 4620 | CTCN_2902 | 10593 | ATCN_863 | 4663 | TTCN_3274 | 10636 |
| TTCN_1219 | 4621 | ATCN_2233 | 10594 | CTCN_1311 | 4664 | TTCN_3275 | 10637 |
| CTCN_1300 | 4622 | ATCN_2234 | 10595 | CTCN_1312 | 4665 | TTCN_3276 | 10638 |
| GTCN_700 | 4623 | CTCN_2903 | 10596 | CTCN_1313 | 4666 | CTCN_2913 | 10639 |
| TTCN_1220 | 4624 | CTCN_2904 | 10597 | ATCN_864 | 4667 | TTCN_3277 | 10640 |
| TTCN_1221 | 4625 | CTCN_2905 | 10598 | ATCN_865 | 4668 | CTCN_2914 | 10641 |
| TTCN_1222 | 4626 | ATCN_2235 | 10599 | CTCN_1314 | 4669 | TTCN_3278 | 10642 |
| ATCN_851 | 4627 | GTCN_1641 | 10600 | GTCN_708 | 4670 | ATCN_2249 | 10643 |
| TTCN_1223 | 4628 | ATCN_2236 | 10601 | CTCN_1315 | 4671 | ATCN_2250 | 10644 |
| GTCN_701 | 4629 | ATCN_2237 | 10602 | GTCN_709 | 4672 | TTCN_3279 | 10645 |
| TTCN_1224 | 4630 | GTCN_1642 | 10603 | CTCN_1316 | 4673 | CTCN_2915 | 10646 |
| ATCN_852 | 4631 | ATCN_2238 | 10604 | CTCN_1317 | 4674 | ATCN_2251 | 10647 |
| ATCN_853 | 4632 | ATCN_2239 | 10605 | GTCN_710 | 4675 | TTCN_3280 | 10648 |

FIG. 33 (continued)

| | | | | | | | |
|---|---|---|---|---|---|---|---|
| GTCN_711 | 4676 | CTCN_2916 | 10649 | CTCN_1328 | 4719 | TTCN_3304 | 10692 |
| CTCN_1318 | 4677 | CTCN_2917 | 10650 | GTCN_722 | 4720 | ATCN_2262 | 10693 |
| CTCN_1319 | 4678 | CTCN_2918 | 10651 | CTCN_1329 | 4721 | TTCN_3305 | 10694 |
| CTCN_1320 | 4679 | TTCN_3281 | 10652 | CTCN_1330 | 4722 | TTCN_3306 | 10695 |
| GTCN_712 | 4680 | CTCN_2919 | 10653 | TTCN_1241 | 4723 | TTCN_3307 | 10696 |
| ATCN_866 | 4681 | CTCN_2920 | 10654 | CTCN_1331 | 4724 | ATCN_2263 | 10697 |
| GTCN_713 | 4682 | TTCN_3282 | 10655 | TTCN_1242 | 4725 | TTCN_3308 | 10698 |
| TTCN_1230 | 4683 | TTCN_3283 | 10656 | GTCN_723 | 4726 | TTCN_3309 | 10699 |
| CTCN_1321 | 4684 | GTCN_1649 | 10657 | TTCN_1243 | 4727 | TTCN_3310 | 10700 |
| GTCN_714 | 4685 | TTCN_3284 | 10658 | TTCN_1244 | 4728 | CTCN_2923 | 10701 |
| CTCN_1322 | 4686 | TTCN_3285 | 10659 | ATCN_877 | 4729 | TTCN_3311 | 10702 |
| TTCN_1231 | 4687 | TTCN_3286 | 10660 | TTCN_1245 | 4730 | TTCN_3312 | 10703 |
| ATCN_867 | 4688 | TTCN_3287 | 10661 | ATCN_878 | 4731 | TTCN_3313 | 10704 |
| CTCN_1323 | 4689 | TTCN_3288 | 10662 | CTCN_1332 | 4732 | CTCN_2924 | 10705 |
| GTCN_715 | 4690 | TTCN_3289 | 10663 | TTCN_1246 | 4733 | TTCN_3314 | 10706 |
| GTCN_716 | 4691 | ATCN_2252 | 10664 | ATCN_879 | 4734 | CTCN_2925 | 10707 |
| TTCN_1232 | 4692 | TTCN_3290 | 10665 | TTCN_1247 | 4735 | ATCN_2264 | 10708 |
| GTCN_717 | 4693 | CTCN_2921 | 10666 | TTCN_1248 | 4736 | CTCN_2926 | 10709 |
| ATCN_868 | 4694 | GTCN_1650 | 10667 | GTCN_724 | 4737 | TTCN_3315 | 10710 |
| CTCN_1324 | 4695 | ATCN_2253 | 10668 | TTCN_1249 | 4738 | TTCN_3316 | 10711 |
| TTCN_1233 | 4696 | TTCN_3291 | 10669 | GTCN_725 | 4739 | TTCN_3317 | 10712 |
| TTCN_1234 | 4697 | TTCN_3292 | 10670 | ATCN_880 | 4740 | TTCN_3318 | 10713 |
| CTCN_1325 | 4698 | TTCN_3293 | 10671 | TTCN_1250 | 4741 | TTCN_3319 | 10714 |
| ATCN_869 | 4699 | ATCN_2254 | 10672 | GTCN_726 | 4742 | CTCN_2927 | 10715 |
| TTCN_1235 | 4700 | TTCN_3294 | 10673 | ATCN_881 | 4743 | CTCN_2928 | 10716 |
| ATCN_870 | 4701 | TTCN_3295 | 10674 | ATCN_882 | 4744 | CTCN_2929 | 10717 |
| GTCN_718 | 4702 | ATCN_2255 | 10675 | CTCN_1333 | 4745 | TTCN_3320 | 10718 |
| TTCN_1236 | 4703 | TTCN_3296 | 10676 | CTCN_1334 | 4746 | TTCN_3321 | 10719 |
| CTCN_1326 | 4704 | ATCN_2256 | 10677 | ATCN_883 | 4747 | TTCN_3322 | 10720 |
| ATCN_871 | 4705 | TTCN_3297 | 10678 | TTCN_1251 | 4748 | TTCN_3323 | 10721 |
| ATCN_872 | 4706 | ATCN_2257 | 10679 | TTCN_1252 | 4749 | ATCN_2265 | 10722 |
| TTCN_1237 | 4707 | GTCN_1651 | 10680 | ATCN_884 | 4750 | TTCN_3324 | 10723 |
| TTCN_1238 | 4708 | TTCN_3298 | 10681 | CTCN_1335 | 4751 | TTCN_3325 | 10724 |
| ATCN_873 | 4709 | TTCN_3299 | 10682 | TTCN_1253 | 4752 | CTCN_2930 | 10725 |
| TTCN_1239 | 4710 | ATCN_2258 | 10683 | CTCN_1336 | 4753 | ATCN_2266 | 10726 |
| GTCN_719 | 4711 | TTCN_3300 | 10684 | CTCN_1337 | 4754 | TTCN_3326 | 10727 |
| ATCN_874 | 4712 | TTCN_3301 | 10685 | TTCN_1254 | 4755 | CTCN_2931 | 10728 |
| ATCN_875 | 4713 | ATCN_2259 | 10686 | ATCN_885 | 4756 | ATCN_2267 | 10729 |
| CTCN_1327 | 4714 | ATCN_2260 | 10687 | TTCN_1255 | 4757 | ATCN_2268 | 10730 |
| TTCN_1240 | 4715 | TTCN_3302 | 10688 | TTCN_1256 | 4758 | GTCN_1652 | 10731 |
| GTCN_720 | 4716 | ATCN_2261 | 10689 | CTCN_1338 | 4759 | TTCN_3327 | 10732 |
| ATCN_876 | 4717 | CTCN_2922 | 10690 | ATCN_886 | 4760 | ATCN_2269 | 10733 |
| GTCN_721 | 4718 | TTCN_3303 | 10691 | ATCN_887 | 4761 | ATCN_2270 | 10734 |

FIG. 33 (continued)

| | | | | | | | |
|---|---|---|---|---|---|---|---|
| TTCN_1257 | 4762 | TTCN_3328 | 10735 | TTCN_1277 | 4805 | ATCN_2285 | 10778 |
| ATCN_888 | 4763 | GTCN_1653 | 10736 | CTCN_1342 | 4806 | GTCN_1662 | 10779 |
| GTCN_727 | 4764 | GTCN_1654 | 10737 | TTCN_1278 | 4807 | CTCN_2939 | 10780 |
| TTCN_1258 | 4765 | TTCN_3329 | 10738 | TTCN_1279 | 4808 | CTCN_2940 | 10781 |
| TTCN_1259 | 4766 | ATCN_2271 | 10739 | CTCN_1343 | 4809 | TTCN_3341 | 10782 |
| TTCN_1260 | 4767 | TTCN_3330 | 10740 | TTCN_1280 | 4810 | ATCN_2286 | 10783 |
| GTCN_728 | 4768 | TTCN_3331 | 10741 | TTCN_1281 | 4811 | ATCN_2287 | 10784 |
| TTCN_1261 | 4769 | ATCN_2272 | 10742 | TTCN_1282 | 4812 | CTCN_2941 | 10785 |
| GTCN_729 | 4770 | ATCN_2273 | 10743 | TTCN_1283 | 4813 | TTCN_3342 | 10786 |
| TTCN_1262 | 4771 | GTCN_1655 | 10744 | TTCN_1284 | 4814 | CTCN_2942 | 10787 |
| TTCN_1263 | 4772 | CTCN_2932 | 10745 | CTCN_1344 | 4815 | TTCN_3343 | 10788 |
| TTCN_1264 | 4773 | TTCN_3332 | 10746 | GTCN_736 | 4816 | TTCN_3344 | 10789 |
| GTCN_730 | 4774 | GTCN_1656 | 10747 | ATCN_899 | 4817 | CTCN_2943 | 10790 |
| GTCN_731 | 4775 | ATCN_2274 | 10748 | CTCN_1345 | 4818 | CTCN_2944 | 10791 |
| ATCN_889 | 4776 | TTCN_3333 | 10749 | ATCN_900 | 4819 | TTCN_3345 | 10792 |
| TTCN_1265 | 4777 | ATCN_2275 | 10750 | CTCN_1346 | 4820 | GTCN_1663 | 10793 |
| GTCN_732 | 4778 | CTCN_2933 | 10751 | TTCN_1285 | 4821 | CTCN_2945 | 10794 |
| TTCN_1266 | 4779 | ATCN_2276 | 10752 | CTCN_1347 | 4822 | TTCN_3346 | 10795 |
| GTCN_733 | 4780 | ATCN_2277 | 10753 | CTCN_1348 | 4823 | CTCN_2946 | 10796 |
| TTCN_1267 | 4781 | ATCN_2278 | 10754 | ATCN_901 | 4824 | CTCN_2947 | 10797 |
| TTCN_1268 | 4782 | CTCN_2934 | 10755 | ATCN_902 | 4825 | ATCN_2288 | 10798 |
| ATCN_890 | 4783 | TTCN_3334 | 10756 | CTCN_1349 | 4826 | CTCN_2948 | 10799 |
| ATCN_891 | 4784 | ATCN_2279 | 10757 | GTCN_737 | 4827 | CTCN_2949 | 10800 |
| ATCN_892 | 4785 | TTCN_3335 | 10758 | CTCN_1350 | 4828 | CTCN_2950 | 10801 |
| CTCN_1339 | 4786 | ATCN_2280 | 10759 | ATCN_903 | 4829 | TTCN_3347 | 10802 |
| ATCN_893 | 4787 | TTCN_3336 | 10760 | CTCN_1351 | 4830 | CTCN_2951 | 10803 |
| GTCN_734 | 4788 | TTCN_3337 | 10761 | GTCN_738 | 4831 | GTCN_1664 | 10804 |
| TTCN_1269 | 4789 | GTCN_1657 | 10762 | ATCN_904 | 4832 | TTCN_3348 | 10805 |
| TTCN_1270 | 4790 | CTCN_2935 | 10763 | GTCN_739 | 4833 | GTCN_1665 | 10806 |
| TTCN_1271 | 4791 | GTCN_1658 | 10764 | CTCN_1352 | 4834 | CTCN_2952 | 10807 |
| TTCN_1272 | 4792 | TTCN_3338 | 10765 | TTCN_1286 | 4835 | TTCN_3349 | 10808 |
| ATCN_894 | 4793 | TTCN_3339 | 10766 | CTCN_1353 | 4836 | CTCN_2953 | 10809 |
| TTCN_1273 | 4794 | ATCN_2281 | 10767 | ATCN_905 | 4837 | TTCN_3350 | 10810 |
| CTCN_1340 | 4795 | ATCN_2282 | 10768 | CTCN_1354 | 4838 | CTCN_2954 | 10811 |
| ATCN_895 | 4796 | GTCN_1659 | 10769 | CTCN_1355 | 4839 | CTCN_2955 | 10812 |
| CTCN_1341 | 4797 | GTCN_1660 | 10770 | TTCN_1287 | 4840 | TTCN_3351 | 10813 |
| TTCN_1274 | 4798 | CTCN_2936 | 10771 | TTCN_1288 | 4841 | GTCN_1666 | 10814 |
| TTCN_1275 | 4799 | CTCN_2937 | 10772 | CTCN_1356 | 4842 | CTCN_2956 | 10815 |
| ATCN_896 | 4800 | CTCN_2938 | 10773 | CTCN_1357 | 4843 | CTCN_2957 | 10816 |
| ATCN_897 | 4801 | ATCN_2283 | 10774 | CTCN_1358 | 4844 | TTCN_3352 | 10817 |
| TTCN_1276 | 4802 | ATCN_2284 | 10775 | CTCN_1359 | 4845 | GTCN_1667 | 10818 |
| ATCN_898 | 4803 | TTCN_3340 | 10776 | CTCN_1360 | 4846 | CTCN_2958 | 10819 |
| GTCN_735 | 4804 | GTCN_1661 | 10777 | ATCN_906 | 4847 | CTCN_2959 | 10820 |

FIG. 33 (continued)

| | | | | | | | |
|---|---|---|---|---|---|---|---|
| ATCN_907 | 4848 | CTCN_2960 | 10821 | CTCN_1378 | 4891 | GTCN_1675 | 10864 |
| CTCN_1361 | 4849 | TTCN_3353 | 10822 | GTCN_747 | 4892 | CTCN_2980 | 10865 |
| GTCN_740 | 4850 | TTCN_3354 | 10823 | GTCN_748 | 4893 | CTCN_2981 | 10866 |
| CTCN_1362 | 4851 | ATCN_2289 | 10824 | GTCN_749 | 4894 | CTCN_2982 | 10867 |
| CTCN_1363 | 4852 | CTCN_2961 | 10825 | TTCN_1302 | 4895 | TTCN_3364 | 10868 |
| CTCN_1364 | 4853 | TTCN_3355 | 10826 | ATCN_913 | 4896 | CTCN_2983 | 10869 |
| GTCN_741 | 4854 | ATCN_2290 | 10827 | CTCN_1379 | 4897 | GTCN_1676 | 10870 |
| CTCN_1365 | 4855 | TTCN_3356 | 10828 | GTCN_750 | 4898 | GTCN_1677 | 10871 |
| GTCN_742 | 4856 | CTCN_2962 | 10829 | ATCN_914 | 4899 | CTCN_2984 | 10872 |
| CTCN_1366 | 4857 | TTCN_3357 | 10830 | ATCN_915 | 4900 | GTCN_1678 | 10873 |
| TTCN_1289 | 4858 | CTCN_2963 | 10831 | TTCN_1303 | 4901 | TTCN_3365 | 10874 |
| TTCN_1290 | 4859 | CTCN_2964 | 10832 | GTCN_751 | 4902 | GTCN_1679 | 10875 |
| CTCN_1367 | 4860 | GTCN_1668 | 10833 | TTCN_1304 | 4903 | GTCN_1680 | 10876 |
| GTCN_743 | 4861 | ATCN_2291 | 10834 | TTCN_1305 | 4904 | CTCN_2985 | 10877 |
| GTCN_744 | 4862 | ATCN_2292 | 10835 | CTCN_1380 | 4905 | CTCN_2986 | 10878 |
| CTCN_1368 | 4863 | CTCN_2965 | 10836 | ATCN_916 | 4906 | CTCN_2987 | 10879 |
| TTCN_1291 | 4864 | GTCN_1669 | 10837 | TTCN_1306 | 4907 | TTCN_3366 | 10880 |
| CTCN_1369 | 4865 | GTCN_1670 | 10838 | CTCN_1381 | 4908 | TTCN_3367 | 10881 |
| CTCN_1370 | 4866 | GTCN_1671 | 10839 | ATCN_917 | 4909 | GTCN_1681 | 10882 |
| CTCN_1371 | 4867 | CTCN_2966 | 10840 | ATCN_918 | 4910 | GTCN_1682 | 10883 |
| ATCN_908 | 4868 | CTCN_2967 | 10841 | GTCN_752 | 4911 | CTCN_2988 | 10884 |
| TTCN_1292 | 4869 | CTCN_2968 | 10842 | CTCN_1382 | 4912 | CTCN_2989 | 10885 |
| ATCN_909 | 4870 | TTCN_3358 | 10843 | ATCN_919 | 4913 | TTCN_3368 | 10886 |
| TTCN_1293 | 4871 | CTCN_2969 | 10844 | ATCN_920 | 4914 | CTCN_2990 | 10887 |
| TTCN_1294 | 4872 | CTCN_2970 | 10845 | CTCN_1383 | 4915 | CTCN_2991 | 10888 |
| CTCN_1372 | 4873 | GTCN_1672 | 10846 | GTCN_753 | 4916 | CTCN_2992 | 10889 |
| TTCN_1295 | 4874 | ATCN_2293 | 10847 | ATCN_921 | 4917 | TTCN_3369 | 10890 |
| TTCN_1296 | 4875 | CTCN_2971 | 10848 | TTCN_1307 | 4918 | GTCN_1683 | 10891 |
| ATCN_910 | 4876 | CTCN_2972 | 10849 | GTCN_754 | 4919 | GTCN_1684 | 10892 |
| CTCN_1373 | 4877 | TTCN_3359 | 10850 | CTCN_1384 | 4920 | TTCN_3370 | 10893 |
| CTCN_1374 | 4878 | TTCN_3360 | 10851 | ATCN_922 | 4921 | CTCN_2993 | 10894 |
| CTCN_1375 | 4879 | CTCN_2973 | 10852 | CTCN_1385 | 4922 | GTCN_1685 | 10895 |
| GTCN_745 | 4880 | TTCN_3361 | 10853 | CTCN_1386 | 4923 | GTCN_1686 | 10896 |
| ATCN_911 | 4881 | GTCN_1673 | 10854 | CTCN_1387 | 4924 | CTCN_2994 | 10897 |
| TTCN_1297 | 4882 | CTCN_2974 | 10855 | TTCN_1308 | 4925 | CTCN_2995 | 10898 |
| TTCN_1298 | 4883 | CTCN_2975 | 10856 | TTCN_1309 | 4926 | TTCN_3371 | 10899 |
| ATCN_912 | 4884 | CTCN_2976 | 10857 | CTCN_1388 | 4927 | CTCN_2996 | 10900 |
| CTCN_1376 | 4885 | CTCN_2977 | 10858 | CTCN_1389 | 4928 | GTCN_1687 | 10901 |
| TTCN_1299 | 4886 | CTCN_2978 | 10859 | CTCN_1390 | 4929 | CTCN_2997 | 10902 |
| TTCN_1300 | 4887 | GTCN_1674 | 10860 | CTCN_1391 | 4930 | CTCN_2998 | 10903 |
| CTCN_1377 | 4888 | TTCN_3362 | 10861 | ATCN_923 | 4931 | GTCN_1688 | 10904 |
| GTCN_746 | 4889 | CTCN_2979 | 10862 | ATCN_924 | 4932 | CTCN_2999 | 10905 |
| TTCN_1301 | 4890 | TTCN_3363 | 10863 | CTCN_1392 | 4933 | TTCN_3372 | 10906 |

FIG. 33 (continued)

| | | | | | | | |
|---|---|---|---|---|---|---|---|
| GTCN_755 | 4934 | CTCN_3000 | 10907 | ATCN_937 | 4977 | GTCN_1697 | 10950 |
| CTCN_1393 | 4935 | TTCN_3373 | 10908 | TTCN_1321 | 4978 | GTCN_1698 | 10951 |
| CTCN_1394 | 4936 | CTCN_3001 | 10909 | ATCN_938 | 4979 | GTCN_1699 | 10952 |
| GTCN_756 | 4937 | CTCN_3002 | 10910 | CTCN_1403 | 4980 | TTCN_3379 | 10953 |
| CTCN_1395 | 4938 | CTCN_3003 | 10911 | CTCN_1404 | 4981 | CTCN_3027 | 10954 |
| GTCN_757 | 4939 | CTCN_3004 | 10912 | TTCN_1322 | 4982 | GTCN_1700 | 10955 |
| ATCN_925 | 4940 | CTCN_3005 | 10913 | CTCN_1405 | 4983 | CTCN_3028 | 10956 |
| TTCN_1310 | 4941 | CTCN_3006 | 10914 | GTCN_765 | 4984 | ATCN_2296 | 10957 |
| ATCN_926 | 4942 | CTCN_3007 | 10915 | CTCN_1406 | 4985 | ATCN_2297 | 10958 |
| GTCN_758 | 4943 | GTCN_1689 | 10916 | CTCN_1407 | 4986 | CTCN_3029 | 10959 |
| CTCN_1396 | 4944 | TTCN_3374 | 10917 | CTCN_1408 | 4987 | GTCN_1701 | 10960 |
| CTCN_1397 | 4945 | ATCN_2294 | 10918 | CTCN_1409 | 4988 | CTCN_3030 | 10961 |
| TTCN_1311 | 4946 | CTCN_3008 | 10919 | ATCN_939 | 4989 | CTCN_3031 | 10962 |
| ATCN_927 | 4947 | TTCN_3375 | 10920 | ATCN_940 | 4990 | CTCN_3032 | 10963 |
| ATCN_928 | 4948 | CTCN_3009 | 10921 | CTCN_1410 | 4991 | GTCN_1702 | 10964 |
| CTCN_1398 | 4949 | GTCN_1690 | 10922 | CTCN_1411 | 4992 | CTCN_3033 | 10965 |
| ATCN_929 | 4950 | TTCN_3376 | 10923 | CTCN_1412 | 4993 | GTCN_1703 | 10966 |
| GTCN_759 | 4951 | GTCN_1691 | 10924 | CTCN_1413 | 4994 | CTCN_3034 | 10967 |
| ATCN_930 | 4952 | CTCN_3010 | 10925 | TTCN_1323 | 4995 | TTCN_3380 | 10968 |
| TTCN_1312 | 4953 | GTCN_1692 | 10926 | TTCN_1324 | 4996 | CTCN_3035 | 10969 |
| TTCN_1313 | 4954 | CTCN_3011 | 10927 | CTCN_1414 | 4997 | CTCN_3036 | 10970 |
| TTCN_1314 | 4955 | GTCN_1693 | 10928 | GTCN_766 | 4998 | CTCN_3037 | 10971 |
| ATCN_931 | 4956 | CTCN_3012 | 10929 | CTCN_1415 | 4999 | CTCN_3038 | 10972 |
| TTCN_1315 | 4957 | CTCN_3013 | 10930 | CTCN_1416 | 5000 | TTCN_3381 | 10973 |
| CTCN_1399 | 4958 | CTCN_3014 | 10931 | GTCN_767 | 5001 | ATCN_2298 | 10974 |
| CTCN_1400 | 4959 | CTCN_3015 | 10932 | CTCN_1417 | 5002 | CTCN_3039 | 10975 |
| ATCN_932 | 4960 | CTCN_3016 | 10933 | GTCN_768 | 5003 | CTCN_3040 | 10976 |
| ATCN_933 | 4961 | CTCN_3017 | 10934 | TTCN_1325 | 5004 | CTCN_3041 | 10977 |
| GTCN_760 | 4962 | CTCN_3018 | 10935 | GTCN_769 | 5005 | CTCN_3042 | 10978 |
| ATCN_934 | 4963 | CTCN_3019 | 10936 | CTCN_1418 | 5006 | CTCN_3043 | 10979 |
| TTCN_1316 | 4964 | CTCN_3020 | 10937 | CTCN_1419 | 5007 | TTCN_3382 | 10980 |
| GTCN_761 | 4965 | CTCN_3021 | 10938 | TTCN_1326 | 5008 | TTCN_3383 | 10981 |
| TTCN_1317 | 4966 | ATCN_2295 | 10939 | ATCN_941 | 5009 | TTCN_3384 | 10982 |
| GTCN_762 | 4967 | CTCN_3022 | 10940 | ATCN_942 | 5010 | GTCN_1704 | 10983 |
| TTCN_1318 | 4968 | GTCN_1694 | 10941 | GTCN_770 | 5011 | TTCN_3385 | 10984 |
| GTCN_763 | 4969 | GTCN_1695 | 10942 | CTCN_1420 | 5012 | CTCN_3044 | 10985 |
| CTCN_1401 | 4970 | CTCN_3023 | 10943 | CTCN_1421 | 5013 | TTCN_3386 | 10986 |
| TTCN_1319 | 4971 | CTCN_3024 | 10944 | ATCN_943 | 5014 | CTCN_3045 | 10987 |
| ATCN_935 | 4972 | TTCN_3377 | 10945 | TTCN_1327 | 5015 | TTCN_3387 | 10988 |
| CTCN_1402 | 4973 | TTCN_3378 | 10946 | TTCN_1328 | 5016 | GTCN_1705 | 10989 |
| ATCN_936 | 4974 | GTCN_1696 | 10947 | TTCN_1329 | 5017 | TTCN_3388 | 10990 |
| TTCN_1320 | 4975 | CTCN_3025 | 10948 | TTCN_1330 | 5018 | ATCN_2299 | 10991 |
| GTCN_764 | 4976 | CTCN_3026 | 10949 | TTCN_1331 | 5019 | ATCN_2300 | 10992 |

FIG. 33 (continued)

| | | | | | | | |
|---|---|---|---|---|---|---|---|
| TTCN_1332 | 5020 | TTCN_3389 | 10993 | CTCN_1432 | 5063 | CTCN_3063 | 11036 |
| ATCN_944 | 5021 | CTCN_3046 | 10994 | TTCN_1344 | 5064 | GTCN_1712 | 11037 |
| ATCN_945 | 5022 | CTCN_3047 | 10995 | TTCN_1345 | 5065 | ATCN_2310 | 11038 |
| GTCN_771 | 5023 | CTCN_3048 | 10996 | TTCN_1346 | 5066 | CTCN_3064 | 11039 |
| ATCN_946 | 5024 | ATCN_2301 | 10997 | ATCN_958 | 5067 | TTCN_3400 | 11040 |
| GTCN_772 | 5025 | TTCN_3390 | 10998 | CTCN_1433 | 5068 | CTCN_3065 | 11041 |
| TTCN_1333 | 5026 | TTCN_3391 | 10999 | CTCN_1434 | 5069 | GTCN_1713 | 11042 |
| CTCN_1422 | 5027 | ATCN_2302 | 11000 | ATCN_959 | 5070 | CTCN_3066 | 11043 |
| CTCN_1423 | 5028 | TTCN_3392 | 11001 | CTCN_1435 | 5071 | CTCN_3067 | 11044 |
| TTCN_1334 | 5029 | CTCN_3049 | 11002 | CTCN_1436 | 5072 | CTCN_3068 | 11045 |
| ATCN_947 | 5030 | TTCN_3393 | 11003 | ATCN_960 | 5073 | GTCN_1714 | 11046 |
| ATCN_948 | 5031 | CTCN_3050 | 11004 | CTCN_1437 | 5074 | CTCN_3069 | 11047 |
| CTCN_1424 | 5032 | ATCN_2303 | 11005 | CTCN_1438 | 5075 | CTCN_3070 | 11048 |
| TTCN_1335 | 5033 | ATCN_2304 | 11006 | TTCN_1347 | 5076 | CTCN_3071 | 11049 |
| ATCN_949 | 5034 | TTCN_3394 | 11007 | CTCN_1439 | 5077 | CTCN_3072 | 11050 |
| CTCN_1425 | 5035 | CTCN_3051 | 11008 | CTCN_1440 | 5078 | CTCN_3073 | 11051 |
| ATCN_950 | 5036 | GTCN_1706 | 11009 | GTCN_778 | 5079 | CTCN_3074 | 11052 |
| TTCN_1336 | 5037 | CTCN_3052 | 11010 | ATCN_961 | 5080 | GTCN_1715 | 11053 |
| ATCN_951 | 5038 | GTCN_1707 | 11011 | CTCN_1441 | 5081 | CTCN_3075 | 11054 |
| ATCN_952 | 5039 | TTCN_3395 | 11012 | CTCN_1442 | 5082 | CTCN_3076 | 11055 |
| CTCN_1426 | 5040 | ATCN_2305 | 11013 | GTCN_779 | 5083 | TTCN_3401 | 11056 |
| GTCN_773 | 5041 | TTCN_3396 | 11014 | CTCN_1443 | 5084 | CTCN_3077 | 11057 |
| CTCN_1427 | 5042 | CTCN_3053 | 11015 | CTCN_1444 | 5085 | ATCN_2311 | 11058 |
| GTCN_774 | 5043 | CTCN_3054 | 11016 | GTCN_780 | 5086 | CTCN_3078 | 11059 |
| TTCN_1337 | 5044 | GTCN_1708 | 11017 | GTCN_781 | 5087 | CTCN_3079 | 11060 |
| TTCN_1338 | 5045 | GTCN_1709 | 11018 | CTCN_1445 | 5088 | TTCN_3402 | 11061 |
| TTCN_1339 | 5046 | CTCN_3055 | 11019 | CTCN_1446 | 5089 | TTCN_3403 | 11062 |
| CTCN_1428 | 5047 | ATCN_2306 | 11020 | CTCN_1447 | 5090 | CTCN_3080 | 11063 |
| ATCN_953 | 5048 | TTCN_3397 | 11021 | CTCN_1448 | 5091 | ATCN_2312 | 11064 |
| ATCN_954 | 5049 | CTCN_3056 | 11022 | CTCN_1449 | 5092 | ATCN_2313 | 11065 |
| CTCN_1429 | 5050 | TTCN_3398 | 11023 | CTCN_1450 | 5093 | TTCN_3404 | 11066 |
| ATCN_955 | 5051 | ATCN_2307 | 11024 | CTCN_1451 | 5094 | CTCN_3081 | 11067 |
| GTCN_775 | 5052 | CTCN_3057 | 11025 | CTCN_1452 | 5095 | CTCN_3082 | 11068 |
| TTCN_1340 | 5053 | GTCN_1710 | 11026 | CTCN_1453 | 5096 | TTCN_3405 | 11069 |
| TTCN_1341 | 5054 | TTCN_3399 | 11027 | CTCN_1454 | 5097 | ATCN_2314 | 11070 |
| TTCN_1342 | 5055 | GTCN_1711 | 11028 | CTCN_1455 | 5098 | CTCN_3083 | 11071 |
| ATCN_956 | 5056 | ATCN_2308 | 11029 | TTCN_1348 | 5099 | CTCN_3084 | 11072 |
| GTCN_776 | 5057 | CTCN_3058 | 11030 | CTCN_1456 | 5100 | GTCN_1716 | 11073 |
| ATCN_957 | 5058 | CTCN_3059 | 11031 | TTCN_1349 | 5101 | TTCN_3406 | 11074 |
| TTCN_1343 | 5059 | CTCN_3060 | 11032 | CTCN_1457 | 5102 | TTCN_3407 | 11075 |
| GTCN_777 | 5060 | CTCN_3061 | 11033 | CTCN_1458 | 5103 | GTCN_1717 | 11076 |
| CTCN_1430 | 5061 | CTCN_3062 | 11034 | CTCN_1459 | 5104 | TTCN_3408 | 11077 |
| CTCN_1431 | 5062 | ATCN_2309 | 11035 | CTCN_1460 | 5105 | CTCN_3085 | 11078 |

FIG. 33 (continued)

| | | | | | | | |
|---|---|---|---|---|---|---|---|
| CTCN_1461 | 5106 | TTCN_3409 | 11079 | TTCN_1353 | 5149 | GTCN_1727 | 11122 |
| CTCN_1462 | 5107 | ATCN_2315 | 11080 | GTCN_789 | 5150 | ATCN_2321 | 11123 |
| CTCN_1463 | 5108 | CTCN_3086 | 11081 | ATCN_966 | 5151 | ATCN_2322 | 11124 |
| CTCN_1464 | 5109 | TTCN_3410 | 11082 | ATCN_967 | 5152 | TTCN_3423 | 11125 |
| TTCN_1350 | 5110 | TTCN_3411 | 11083 | GTCN_790 | 5153 | CTCN_3100 | 11126 |
| TTCN_1351 | 5111 | TTCN_3412 | 11084 | CTCN_1490 | 5154 | CTCN_3101 | 11127 |
| CTCN_1465 | 5112 | ATCN_2316 | 11085 | TTCN_1354 | 5155 | GTCN_1728 | 11128 |
| CTCN_1466 | 5113 | TTCN_3413 | 11086 | TTCN_1355 | 5156 | CTCN_3102 | 11129 |
| CTCN_1467 | 5114 | CTCN_3087 | 11087 | ATCN_968 | 5157 | ATCN_2323 | 11130 |
| CTCN_1468 | 5115 | TTCN_3414 | 11088 | GTCN_791 | 5158 | GTCN_1729 | 11131 |
| CTCN_1469 | 5116 | CTCN_3088 | 11089 | CTCN_1491 | 5159 | CTCN_3103 | 11132 |
| CTCN_1470 | 5117 | CTCN_3089 | 11090 | ATCN_969 | 5160 | CTCN_3104 | 11133 |
| CTCN_1471 | 5118 | CTCN_3090 | 11091 | CTCN_1492 | 5161 | GTCN_1730 | 11134 |
| CTCN_1472 | 5119 | GTCN_1718 | 11092 | CTCN_1493 | 5162 | CTCN_3105 | 11135 |
| CTCN_1473 | 5120 | CTCN_3091 | 11093 | CTCN_1494 | 5163 | ATCN_2324 | 11136 |
| ATCN_962 | 5121 | ATCN_2317 | 11094 | TTCN_1356 | 5164 | CTCN_3106 | 11137 |
| TTCN_1352 | 5122 | GTCN_1719 | 11095 | GTCN_792 | 5165 | ATCN_2325 | 11138 |
| CTCN_1474 | 5123 | ATCN_2318 | 11096 | CTCN_1495 | 5166 | ATCN_2326 | 11139 |
| CTCN_1475 | 5124 | TTCN_3415 | 11097 | ATCN_970 | 5167 | TTCN_3424 | 11140 |
| CTCN_1476 | 5125 | GTCN_1720 | 11098 | ATCN_971 | 5168 | ATCN_2327 | 11141 |
| GTCN_782 | 5126 | CTCN_3092 | 11099 | GTCN_793 | 5169 | CTCN_3107 | 11142 |
| CTCN_1477 | 5127 | GTCN_1721 | 11100 | GTCN_794 | 5170 | GTCN_1731 | 11143 |
| CTCN_1478 | 5128 | ATCN_2319 | 11101 | CTCN_1496 | 5171 | TTCN_3425 | 11144 |
| CTCN_1479 | 5129 | TTCN_3416 | 11102 | CTCN_1497 | 5172 | CTCN_3108 | 11145 |
| CTCN_1480 | 5130 | TTCN_3417 | 11103 | ATCN_972 | 5173 | TTCN_3426 | 11146 |
| CTCN_1481 | 5131 | CTCN_3093 | 11104 | ATCN_973 | 5174 | ATCN_2328 | 11147 |
| CTCN_1482 | 5132 | TTCN_3418 | 11105 | ATCN_974 | 5175 | TTCN_3427 | 11148 |
| GTCN_783 | 5133 | GTCN_1722 | 11106 | TTCN_1357 | 5176 | TTCN_3428 | 11149 |
| CTCN_1483 | 5134 | TTCN_3419 | 11107 | CTCN_1498 | 5177 | ATCN_2329 | 11150 |
| GTCN_784 | 5135 | ATCN_2320 | 11108 | GTCN_795 | 5178 | CTCN_3109 | 11151 |
| ATCN_963 | 5136 | GTCN_1723 | 11109 | TTCN_1358 | 5179 | TTCN_3429 | 11152 |
| GTCN_785 | 5137 | GTCN_1724 | 11110 | TTCN_1359 | 5180 | CTCN_3110 | 11153 |
| GTCN_786 | 5138 | GTCN_1725 | 11111 | GTCN_796 | 5181 | TTCN_3430 | 11154 |
| CTCN_1484 | 5139 | TTCN_3420 | 11112 | TTCN_1360 | 5182 | CTCN_3111 | 11155 |
| CTCN_1485 | 5140 | CTCN_3094 | 11113 | ATCN_975 | 5183 | CTCN_3112 | 11156 |
| CTCN_1486 | 5141 | CTCN_3095 | 11114 | CTCN_1499 | 5184 | CTCN_3113 | 11157 |
| CTCN_1487 | 5142 | TTCN_3421 | 11115 | CTCN_1500 | 5185 | CTCN_3114 | 11158 |
| ATCN_964 | 5143 | CTCN_3096 | 11116 | GTCN_797 | 5186 | TTCN_3431 | 11159 |
| ATCN_965 | 5144 | GTCN_1726 | 11117 | CTCN_1501 | 5187 | ATCN_2330 | 11160 |
| GTCN_787 | 5145 | CTCN_3097 | 11118 | CTCN_1502 | 5188 | ATCN_2331 | 11161 |
| CTCN_1488 | 5146 | TTCN_3422 | 11119 | TTCN_1361 | 5189 | CTCN_3115 | 11162 |
| CTCN_1489 | 5147 | CTCN_3098 | 11120 | GTCN_798 | 5190 | GTCN_1732 | 11163 |
| GTCN_788 | 5148 | CTCN_3099 | 11121 | TTCN_1362 | 5191 | CTCN_3116 | 11164 |

FIG. 33 (continued)

| | | | | | | | |
|---|---|---|---|---|---|---|---|
| TTCN_1363 | 5192 | TTCN_3432 | 11165 | CTCN_1516 | 5235 | TTCN_3444 | 11208 |
| CTCN_1503 | 5193 | GTCN_1733 | 11166 | CTCN_1517 | 5236 | CTCN_3133 | 11209 |
| GTCN_799 | 5194 | ATCN_2332 | 11167 | CTCN_1518 | 5237 | ATCN_2339 | 11210 |
| TTCN_1364 | 5195 | TTCN_3433 | 11168 | ATCN_978 | 5238 | ATCN_2340 | 11211 |
| CTCN_1504 | 5196 | TTCN_3434 | 11169 | ATCN_979 | 5239 | GTCN_1741 | 11212 |
| TTCN_1365 | 5197 | GTCN_1734 | 11170 | TTCN_1382 | 5240 | TTCN_3445 | 11213 |
| TTCN_1366 | 5198 | CTCN_3117 | 11171 | ATCN_980 | 5241 | GTCN_1742 | 11214 |
| CTCN_1505 | 5199 | GTCN_1735 | 11172 | TTCN_1383 | 5242 | ATCN_2341 | 11215 |
| GTCN_800 | 5200 | CTCN_3118 | 11173 | GTCN_808 | 5243 | GTCN_1743 | 11216 |
| CTCN_1506 | 5201 | GTCN_1736 | 11174 | CTCN_1519 | 5244 | TTCN_3446 | 11217 |
| CTCN_1507 | 5202 | ATCN_2333 | 11175 | CTCN_1520 | 5245 | ATCN_2342 | 11218 |
| TTCN_1367 | 5203 | ATCN_2334 | 11176 | CTCN_1521 | 5246 | CTCN_3134 | 11219 |
| GTCN_801 | 5204 | CTCN_3119 | 11177 | ATCN_981 | 5247 | ATCN_2343 | 11220 |
| TTCN_1368 | 5205 | TTCN_3435 | 11178 | ATCN_982 | 5248 | TTCN_3447 | 11221 |
| CTCN_1508 | 5206 | CTCN_3120 | 11179 | CTCN_1522 | 5249 | TTCN_3448 | 11222 |
| CTCN_1509 | 5207 | TTCN_3436 | 11180 | CTCN_1523 | 5250 | ATCN_2344 | 11223 |
| CTCN_1510 | 5208 | TTCN_3437 | 11181 | GTCN_809 | 5251 | TTCN_3449 | 11224 |
| GTCN_802 | 5209 | TTCN_3438 | 11182 | CTCN_1524 | 5252 | ATCN_2345 | 11225 |
| TTCN_1369 | 5210 | TTCN_3439 | 11183 | CTCN_1525 | 5253 | ATCN_2346 | 11226 |
| TTCN_1370 | 5211 | GTCN_1737 | 11184 | ATCN_983 | 5254 | GTCN_1744 | 11227 |
| TTCN_1371 | 5212 | TTCN_3440 | 11185 | ATCN_984 | 5255 | CTCN_3135 | 11228 |
| CTCN_1511 | 5213 | CTCN_3121 | 11186 | GTCN_810 | 5256 | GTCN_1745 | 11229 |
| TTCN_1372 | 5214 | TTCN_3441 | 11187 | TTCN_1384 | 5257 | TTCN_3450 | 11230 |
| ATCN_976 | 5215 | CTCN_3122 | 11188 | TTCN_1385 | 5258 | TTCN_3451 | 11231 |
| TTCN_1373 | 5216 | CTCN_3123 | 11189 | TTCN_1386 | 5259 | TTCN_3452 | 11232 |
| ATCN_977 | 5217 | CTCN_3124 | 11190 | TTCN_1387 | 5260 | GTCN_1746 | 11233 |
| TTCN_1374 | 5218 | ATCN_2335 | 11191 | CTCN_1526 | 5261 | CTCN_3136 | 11234 |
| TTCN_1375 | 5219 | CTCN_3125 | 11192 | ATCN_985 | 5262 | GTCN_1747 | 11235 |
| CTCN_1512 | 5220 | CTCN_3126 | 11193 | CTCN_1527 | 5263 | CTCN_3137 | 11236 |
| GTCN_803 | 5221 | CTCN_3127 | 11194 | GTCN_811 | 5264 | GTCN_1748 | 11237 |
| TTCN_1376 | 5222 | GTCN_1738 | 11195 | GTCN_812 | 5265 | CTCN_3138 | 11238 |
| CTCN_1513 | 5223 | ATCN_2336 | 11196 | TTCN_1388 | 5266 | TTCN_3453 | 11239 |
| CTCN_1514 | 5224 | GTCN_1739 | 11197 | ATCN_986 | 5267 | TTCN_3454 | 11240 |
| GTCN_804 | 5225 | TTCN_3442 | 11198 | ATCN_987 | 5268 | GTCN_1749 | 11241 |
| TTCN_1377 | 5226 | GTCN_1740 | 11199 | CTCN_1528 | 5269 | ATCN_2347 | 11242 |
| TTCN_1378 | 5227 | CTCN_3128 | 11200 | GTCN_813 | 5270 | ATCN_2348 | 11243 |
| TTCN_1379 | 5228 | CTCN_3129 | 11201 | ATCN_988 | 5271 | GTCN_1750 | 11244 |
| GTCN_805 | 5229 | CTCN_3130 | 11202 | CTCN_1529 | 5272 | ATCN_2349 | 11245 |
| CTCN_1515 | 5230 | CTCN_3131 | 11203 | ATCN_989 | 5273 | TTCN_3455 | 11246 |
| GTCN_806 | 5231 | ATCN_2337 | 11204 | ATCN_990 | 5274 | TTCN_3456 | 11247 |
| TTCN_1380 | 5232 | ATCN_2338 | 11205 | TTCN_1389 | 5275 | TTCN_3457 | 11248 |
| TTCN_1381 | 5233 | CTCN_3132 | 11206 | TTCN_1390 | 5276 | ATCN_2350 | 11249 |
| GTCN_807 | 5234 | TTCN_3443 | 11207 | TTCN_1391 | 5277 | TTCN_3458 | 11250 |

FIG. 33 (continued)

| | | | | | | | |
|---|---|---|---|---|---|---|---|
| TTCN_1392 | 5278 | TTCN_3459 | 11251 | TTCN_1403 | 5321 | CTCN_3149 | 11294 |
| ATCN_991 | 5279 | TTCN_3460 | 11252 | CTCN_1547 | 5322 | CTCN_3150 | 11295 |
| GTCN_814 | 5280 | TTCN_3461 | 11253 | CTCN_1548 | 5323 | CTCN_3151 | 11296 |
| TTCN_1393 | 5281 | TTCN_3462 | 11254 | CTCN_1549 | 5324 | TTCN_3483 | 11297 |
| GTCN_815 | 5282 | TTCN_3463 | 11255 | GTCN_823 | 5325 | ATCN_2357 | 11298 |
| TTCN_1394 | 5283 | ATCN_2351 | 11256 | TTCN_1404 | 5326 | CTCN_3152 | 11299 |
| TTCN_1395 | 5284 | GTCN_1751 | 11257 | GTCN_824 | 5327 | GTCN_1754 | 11300 |
| TTCN_1396 | 5285 | TTCN_3464 | 11258 | TTCN_1405 | 5328 | GTCN_1755 | 11301 |
| TTCN_1397 | 5286 | TTCN_3465 | 11259 | CTCN_1550 | 5329 | TTCN_3484 | 11302 |
| CTCN_1530 | 5287 | TTCN_3466 | 11260 | ATCN_997 | 5330 | GTCN_1756 | 11303 |
| CTCN_1531 | 5288 | TTCN_3467 | 11261 | TTCN_1406 | 5331 | GTCN_1757 | 11304 |
| CTCN_1532 | 5289 | TTCN_3468 | 11262 | ATCN_998 | 5332 | TTCN_3485 | 11305 |
| CTCN_1533 | 5290 | TTCN_3469 | 11263 | TTCN_1407 | 5333 | CTCN_3153 | 11306 |
| GTCN_816 | 5291 | CTCN_3139 | 11264 | ATCN_999 | 5334 | TTCN_3486 | 11307 |
| TTCN_1398 | 5292 | TTCN_3470 | 11265 | ATCN_1000 | 5335 | ATCN_2358 | 11308 |
| ATCN_992 | 5293 | TTCN_3471 | 11266 | CTCN_1551 | 5336 | CTCN_3154 | 11309 |
| ATCN_993 | 5294 | TTCN_3472 | 11267 | TTCN_1408 | 5337 | CTCN_3155 | 11310 |
| CTCN_1534 | 5295 | ATCN_2352 | 11268 | GTCN_825 | 5338 | CTCN_3156 | 11311 |
| TTCN_1399 | 5296 | CTCN_3140 | 11269 | CTCN_1552 | 5339 | TTCN_3487 | 11312 |
| TTCN_1400 | 5297 | TTCN_3473 | 11270 | TTCN_1409 | 5340 | TTCN_3488 | 11313 |
| ATCN_994 | 5298 | CTCN_3141 | 11271 | ATCN_1001 | 5341 | CTCN_3157 | 11314 |
| CTCN_1535 | 5299 | CTCN_3142 | 11272 | TTCN_1410 | 5342 | TTCN_3489 | 11315 |
| ATCN_995 | 5300 | TTCN_3474 | 11273 | ATCN_1002 | 5343 | CTCN_3158 | 11316 |
| GTCN_817 | 5301 | ATCN_2353 | 11274 | TTCN_1411 | 5344 | TTCN_3490 | 11317 |
| CTCN_1536 | 5302 | CTCN_3143 | 11275 | ATCN_1003 | 5345 | TTCN_3491 | 11318 |
| CTCN_1537 | 5303 | TTCN_3475 | 11276 | ATCN_1004 | 5346 | CTCN_3159 | 11319 |
| CTCN_1538 | 5304 | CTCN_3144 | 11277 | ATCN_1005 | 5347 | CTCN_3160 | 11320 |
| CTCN_1539 | 5305 | GTCN_1752 | 11278 | CTCN_1553 | 5348 | CTCN_3161 | 11321 |
| GTCN_818 | 5306 | ATCN_2354 | 11279 | GTCN_826 | 5349 | GTCN_1758 | 11322 |
| CTCN_1540 | 5307 | TTCN_3476 | 11280 | CTCN_1554 | 5350 | TTCN_3492 | 11323 |
| ATCN_996 | 5308 | CTCN_3145 | 11281 | CTCN_1555 | 5351 | TTCN_3493 | 11324 |
| CTCN_1541 | 5309 | TTCN_3477 | 11282 | TTCN_1412 | 5352 | CTCN_3162 | 11325 |
| CTCN_1542 | 5310 | TTCN_3478 | 11283 | TTCN_1413 | 5353 | GTCN_1759 | 11326 |
| GTCN_819 | 5311 | TTCN_3479 | 11284 | GTCN_827 | 5354 | TTCN_3494 | 11327 |
| CTCN_1543 | 5312 | ATCN_2355 | 11285 | CTCN_1556 | 5355 | TTCN_3495 | 11328 |
| TTCN_1401 | 5313 | CTCN_3146 | 11286 | CTCN_1557 | 5356 | CTCN_3163 | 11329 |
| CTCN_1544 | 5314 | GTCN_1753 | 11287 | CTCN_1558 | 5357 | CTCN_3164 | 11330 |
| GTCN_820 | 5315 | TTCN_3480 | 11288 | TTCN_1414 | 5358 | ATCN_2359 | 11331 |
| TTCN_1402 | 5316 | CTCN_3147 | 11289 | CTCN_1559 | 5359 | TTCN_3496 | 11332 |
| GTCN_821 | 5317 | CTCN_3148 | 11290 | CTCN_1560 | 5360 | CTCN_3165 | 11333 |
| CTCN_1545 | 5318 | TTCN_3481 | 11291 | GTCN_828 | 5361 | CTCN_3166 | 11334 |
| GTCN_822 | 5319 | TTCN_3482 | 11292 | GTCN_829 | 5362 | TTCN_3497 | 11335 |
| CTCN_1546 | 5320 | ATCN_2356 | 11293 | CTCN_1561 | 5363 | TTCN_3498 | 11336 |

FIG. 33 (continued)

| | | | | | | | |
|---|---|---|---|---|---|---|---|
| GTCN_830 | 5364 | TTCN_3499 | 11337 | TTCN_1430 | 5407 | ATCN_2370 | 11380 |
| CTCN_1562 | 5365 | TTCN_3500 | 11338 | TTCN_1431 | 5408 | ATCN_2371 | 11381 |
| CTCN_1563 | 5366 | ATCN_2360 | 11339 | TTCN_1432 | 5409 | TTCN_3520 | 11382 |
| ATCN_1006 | 5367 | ATCN_2361 | 11340 | TTCN_1433 | 5410 | TTCN_3521 | 11383 |
| TTCN_1415 | 5368 | CTCN_3167 | 11341 | CTCN_1578 | 5411 | CTCN_3176 | 11384 |
| GTCN_831 | 5369 | ATCN_2362 | 11342 | TTCN_1434 | 5412 | CTCN_3177 | 11385 |
| CTCN_1564 | 5370 | GTCN_1760 | 11343 | TTCN_1435 | 5413 | TTCN_3522 | 11386 |
| GTCN_832 | 5371 | GTCN_1761 | 11344 | TTCN_1436 | 5414 | TTCN_3523 | 11387 |
| TTCN_1416 | 5372 | CTCN_3168 | 11345 | CTCN_1579 | 5415 | GTCN_1763 | 11388 |
| TTCN_1417 | 5373 | ATCN_2363 | 11346 | CTCN_1580 | 5416 | ATCN_2372 | 11389 |
| CTCN_1565 | 5374 | TTCN_3501 | 11347 | TTCN_1437 | 5417 | TTCN_3524 | 11390 |
| CTCN_1566 | 5375 | GTCN_1762 | 11348 | CTCN_1581 | 5418 | CTCN_3178 | 11391 |
| TTCN_1418 | 5376 | TTCN_3502 | 11349 | TTCN_1438 | 5419 | GTCN_1764 | 11392 |
| TTCN_1419 | 5377 | TTCN_3503 | 11350 | TTCN_1439 | 5420 | TTCN_3525 | 11393 |
| GTCN_833 | 5378 | TTCN_3504 | 11351 | CTCN_1582 | 5421 | TTCN_3526 | 11394 |
| GTCN_834 | 5379 | CTCN_3169 | 11352 | TTCN_1440 | 5422 | TTCN_3527 | 11395 |
| ATCN_1007 | 5380 | TTCN_3505 | 11353 | CTCN_1583 | 5423 | TTCN_3528 | 11396 |
| ATCN_1008 | 5381 | TTCN_3506 | 11354 | CTCN_1584 | 5424 | ATCN_2373 | 11397 |
| ATCN_1009 | 5382 | CTCN_3170 | 11355 | CTCN_1585 | 5425 | ATCN_2374 | 11398 |
| ATCN_1010 | 5383 | CTCN_3171 | 11356 | CTCN_1586 | 5426 | ATCN_2375 | 11399 |
| TTCN_1420 | 5384 | ATCN_2364 | 11357 | CTCN_1587 | 5427 | TTCN_3529 | 11400 |
| CTCN_1567 | 5385 | TTCN_3507 | 11358 | TTCN_1441 | 5428 | TTCN_3530 | 11401 |
| CTCN_1568 | 5386 | TTCN_3508 | 11359 | TTCN_1442 | 5429 | GTCN_1765 | 11402 |
| TTCN_1421 | 5387 | TTCN_3509 | 11360 | TTCN_1443 | 5430 | TTCN_3531 | 11403 |
| GTCN_835 | 5388 | TTCN_3510 | 11361 | GTCN_837 | 5431 | ATCN_2376 | 11404 |
| TTCN_1422 | 5389 | TTCN_3511 | 11362 | TTCN_1444 | 5432 | ATCN_2377 | 11405 |
| GTCN_836 | 5390 | CTCN_3172 | 11363 | TTCN_1445 | 5433 | TTCN_3532 | 11406 |
| TTCN_1423 | 5391 | CTCN_3173 | 11364 | TTCN_1446 | 5434 | TTCN_3533 | 11407 |
| CTCN_1569 | 5392 | TTCN_3512 | 11365 | GTCN_838 | 5435 | CTCN_3179 | 11408 |
| CTCN_1570 | 5393 | CTCN_3174 | 11366 | CTCN_1588 | 5436 | CTCN_3180 | 11409 |
| TTCN_1424 | 5394 | TTCN_3513 | 11367 | CTCN_1589 | 5437 | TTCN_3534 | 11410 |
| CTCN_1571 | 5395 | ATCN_2365 | 11368 | ATCN_1011 | 5438 | TTCN_3535 | 11411 |
| TTCN_1425 | 5396 | TTCN_3514 | 11369 | ATCN_1012 | 5439 | GTCN_1766 | 11412 |
| TTCN_1426 | 5397 | ATCN_2366 | 11370 | TTCN_1447 | 5440 | CTCN_3181 | 11413 |
| CTCN_1572 | 5398 | ATCN_2367 | 11371 | ATCN_1013 | 5441 | GTCN_1767 | 11414 |
| TTCN_1427 | 5399 | TTCN_3515 | 11372 | CTCN_1590 | 5442 | ATCN_2378 | 11415 |
| CTCN_1573 | 5400 | ATCN_2368 | 11373 | ATCN_1014 | 5443 | ATCN_2379 | 11416 |
| CTCN_1574 | 5401 | ATCN_2369 | 11374 | ATCN_1015 | 5444 | TTCN_3536 | 11417 |
| TTCN_1428 | 5402 | TTCN_3516 | 11375 | ATCN_1016 | 5445 | ATCN_2380 | 11418 |
| TTCN_1429 | 5403 | CTCN_3175 | 11376 | ATCN_1017 | 5446 | ATCN_2381 | 11419 |
| CTCN_1575 | 5404 | TTCN_3517 | 11377 | ATCN_1018 | 5447 | TTCN_3537 | 11420 |
| CTCN_1576 | 5405 | TTCN_3518 | 11378 | CTCN_1591 | 5448 | TTCN_3538 | 11421 |
| CTCN_1577 | 5406 | TTCN_3519 | 11379 | GTCN_839 | 5449 | ATCN_2382 | 11422 |

FIG. 33 (continued)

| | | | | | | | |
|---|---|---|---|---|---|---|---|
| ATCN_1019 | 5450 | ATCN_2383 | 11423 | GTCN_845 | 5493 | ATCN_2392 | 11466 |
| TTCN_1448 | 5451 | TTCN_3539 | 11424 | TTCN_1465 | 5494 | TTCN_3560 | 11467 |
| TTCN_1449 | 5452 | ATCN_2384 | 11425 | ATCN_1027 | 5495 | ATCN_2393 | 11468 |
| CTCN_1592 | 5453 | TTCN_3540 | 11426 | ATCN_1028 | 5496 | TTCN_3561 | 11469 |
| ATCN_1020 | 5454 | GTCN_1768 | 11427 | CTCN_1605 | 5497 | GTCN_1773 | 11470 |
| ATCN_1021 | 5455 | GTCN_1769 | 11428 | CTCN_1606 | 5498 | CTCN_3190 | 11471 |
| CTCN_1593 | 5456 | TTCN_3541 | 11429 | TTCN_1466 | 5499 | TTCN_3562 | 11472 |
| CTCN_1594 | 5457 | TTCN_3542 | 11430 | TTCN_1467 | 5500 | TTCN_3563 | 11473 |
| CTCN_1595 | 5458 | TTCN_3543 | 11431 | ATCN_1029 | 5501 | TTCN_3564 | 11474 |
| ATCN_1022 | 5459 | CTCN_3182 | 11432 | ATCN_1030 | 5502 | TTCN_3565 | 11475 |
| ATCN_1023 | 5460 | GTCN_1770 | 11433 | CTCN_1607 | 5503 | GTCN_1774 | 11476 |
| CTCN_1596 | 5461 | CTCN_3183 | 11434 | TTCN_1468 | 5504 | CTCN_3191 | 11477 |
| CTCN_1597 | 5462 | TTCN_3544 | 11435 | TTCN_1469 | 5505 | CTCN_3192 | 11478 |
| CTCN_1598 | 5463 | TTCN_3545 | 11436 | CTCN_1608 | 5506 | CTCN_3193 | 11479 |
| GTCN_840 | 5464 | GTCN_1771 | 11437 | ATCN_1031 | 5507 | ATCN_2394 | 11480 |
| ATCN_1024 | 5465 | CTCN_3184 | 11438 | CTCN_1609 | 5508 | ATCN_2395 | 11481 |
| TTCN_1450 | 5466 | CTCN_3185 | 11439 | CTCN_1610 | 5509 | GTCN_1775 | 11482 |
| TTCN_1451 | 5467 | ATCN_2385 | 11440 | ATCN_1032 | 5510 | CTCN_3194 | 11483 |
| TTCN_1452 | 5468 | CTCN_3186 | 11441 | ATCN_1033 | 5511 | ATCN_2396 | 11484 |
| CTCN_1599 | 5469 | TTCN_3546 | 11442 | CTCN_1611 | 5512 | ATCN_2397 | 11485 |
| ATCN_1025 | 5470 | CTCN_3187 | 11443 | GTCN_846 | 5513 | TTCN_3566 | 11486 |
| ATCN_1026 | 5471 | TTCN_3547 | 11444 | CTCN_1612 | 5514 | CTCN_3195 | 11487 |
| GTCN_841 | 5472 | TTCN_3548 | 11445 | TTCN_1470 | 5515 | TTCN_3567 | 11488 |
| TTCN_1453 | 5473 | ATCN_2386 | 11446 | CTCN_1613 | 5516 | GTCN_1776 | 11489 |
| GTCN_842 | 5474 | TTCN_3549 | 11447 | GTCN_847 | 5517 | GTCN_1777 | 11490 |
| TTCN_1454 | 5475 | TTCN_3550 | 11448 | TTCN_1471 | 5518 | CTCN_3196 | 11491 |
| TTCN_1455 | 5476 | ATCN_2387 | 11449 | ATCN_1034 | 5519 | TTCN_3568 | 11492 |
| TTCN_1456 | 5477 | TTCN_3551 | 11450 | CTCN_1614 | 5520 | TTCN_3569 | 11493 |
| TTCN_1457 | 5478 | TTCN_3552 | 11451 | GTCN_848 | 5521 | CTCN_3197 | 11494 |
| GTCN_843 | 5479 | TTCN_3553 | 11452 | CTCN_1615 | 5522 | ATCN_2398 | 11495 |
| TTCN_1458 | 5480 | TTCN_3554 | 11453 | CTCN_1616 | 5523 | TTCN_3570 | 11496 |
| TTCN_1459 | 5481 | CTCN_3188 | 11454 | CTCN_1617 | 5524 | GTCN_1778 | 11497 |
| TTCN_1460 | 5482 | CTCN_3189 | 11455 | CTCN_1618 | 5525 | CTCN_3198 | 11498 |
| TTCN_1461 | 5483 | TTCN_3555 | 11456 | TTCN_1472 | 5526 | ATCN_2399 | 11499 |
| CTCN_1600 | 5484 | TTCN_3556 | 11457 | ATCN_1035 | 5527 | TTCN_3571 | 11500 |
| CTCN_1601 | 5485 | ATCN_2388 | 11458 | TTCN_1473 | 5528 | TTCN_3572 | 11501 |
| TTCN_1462 | 5486 | TTCN_3557 | 11459 | CTCN_1619 | 5529 | CTCN_3199 | 11502 |
| CTCN_1602 | 5487 | ATCN_2389 | 11460 | CTCN_1620 | 5530 | GTCN_1779 | 11503 |
| TTCN_1463 | 5488 | ATCN_2390 | 11461 | CTCN_1621 | 5531 | TTCN_3573 | 11504 |
| CTCN_1603 | 5489 | ATCN_2391 | 11462 | ATCN_1036 | 5532 | GTCN_1780 | 11505 |
| TTCN_1464 | 5490 | TTCN_3558 | 11463 | CTCN_1622 | 5533 | TTCN_3574 | 11506 |
| CTCN_1604 | 5491 | TTCN_3559 | 11464 | GTCN_849 | 5534 | GTCN_1781 | 11507 |
| GTCN_844 | 5492 | GTCN_1772 | 11465 | CTCN_1623 | 5535 | GTCN_1782 | 11508 |

FIG. 33 (continued)

| | | | | | | | |
|---|---|---|---|---|---|---|---|
| CTCN_1624 | 5536 | GTCN_1783 | 11509 | CTCN_1634 | 5579 | TTCN_3586 | 11552 |
| GTCN_850 | 5537 | TTCN_3575 | 11510 | CTCN_1635 | 5580 | TTCN_3587 | 11553 |
| CTCN_1625 | 5538 | GTCN_1784 | 11511 | ATCN_1050 | 5581 | TTCN_3588 | 11554 |
| ATCN_1037 | 5539 | TTCN_3576 | 11512 | ATCN_1051 | 5582 | ATCN_2406 | 11555 |
| ATCN_1038 | 5540 | GTCN_1785 | 11513 | TTCN_1488 | 5583 | TTCN_3589 | 11556 |
| TTCN_1474 | 5541 | CTCN_3200 | 11514 | CTCN_1636 | 5584 | TTCN_3590 | 11557 |
| CTCN_1626 | 5542 | TTCN_3577 | 11515 | GTCN_856 | 5585 | TTCN_3591 | 11558 |
| ATCN_1039 | 5543 | TTCN_3578 | 11516 | TTCN_1489 | 5586 | TTCN_3592 | 11559 |
| GTCN_851 | 5544 | GTCN_1786 | 11517 | GTCN_857 | 5587 | GTCN_1793 | 11560 |
| TTCN_1475 | 5545 | TTCN_3579 | 11518 | TTCN_1490 | 5588 | TTCN_3593 | 11561 |
| ATCN_1040 | 5546 | GTCN_1787 | 11519 | GTCN_858 | 5589 | TTCN_3594 | 11562 |
| CTCN_1627 | 5547 | GTCN_1788 | 11520 | GTCN_859 | 5590 | TTCN_3595 | 11563 |
| GTCN_852 | 5548 | CTCN_3201 | 11521 | ATCN_1052 | 5591 | GTCN_1794 | 11564 |
| ATCN_1041 | 5549 | TTCN_3580 | 11522 | TTCN_1491 | 5592 | GTCN_1795 | 11565 |
| CTCN_1628 | 5550 | ATCN_2400 | 11523 | ATCN_1053 | 5593 | TTCN_3596 | 11566 |
| ATCN_1042 | 5551 | CTCN_3202 | 11524 | GTCN_860 | 5594 | TTCN_3597 | 11567 |
| TTCN_1476 | 5552 | CTCN_3203 | 11525 | GTCN_861 | 5595 | TTCN_3598 | 11568 |
| TTCN_1477 | 5553 | CTCN_3204 | 11526 | CTCN_1637 | 5596 | TTCN_3599 | 11569 |
| ATCN_1043 | 5554 | CTCN_3205 | 11527 | TTCN_1492 | 5597 | TTCN_3600 | 11570 |
| GTCN_853 | 5555 | TTCN_3581 | 11528 | CTCN_1638 | 5598 | TTCN_3601 | 11571 |
| CTCN_1629 | 5556 | TTCN_3582 | 11529 | TTCN_1493 | 5599 | TTCN_3602 | 11572 |
| TTCN_1478 | 5557 | CTCN_3206 | 11530 | GTCN_862 | 5600 | CTCN_3216 | 11573 |
| GTCN_854 | 5558 | CTCN_3207 | 11531 | CTCN_1639 | 5601 | ATCN_2407 | 11574 |
| GTCN_855 | 5559 | CTCN_3208 | 11532 | CTCN_1640 | 5602 | CTCN_3217 | 11575 |
| TTCN_1479 | 5560 | CTCN_3209 | 11533 | CTCN_1641 | 5603 | CTCN_3218 | 11576 |
| ATCN_1044 | 5561 | ATCN_2401 | 11534 | GTCN_863 | 5604 | GTCN_1796 | 11577 |
| TTCN_1480 | 5562 | ATCN_2402 | 11535 | ATCN_1054 | 5605 | TTCN_3603 | 11578 |
| ATCN_1045 | 5563 | CTCN_3210 | 11536 | ATCN_1055 | 5606 | TTCN_3604 | 11579 |
| CTCN_1630 | 5564 | CTCN_3211 | 11537 | TTCN_1494 | 5607 | CTCN_3219 | 11580 |
| ATCN_1046 | 5565 | GTCN_1789 | 11538 | TTCN_1495 | 5608 | TTCN_3605 | 11581 |
| CTCN_1631 | 5566 | CTCN_3212 | 11539 | ATCN_1056 | 5609 | TTCN_3606 | 11582 |
| TTCN_1481 | 5567 | GTCN_1790 | 11540 | TTCN_1496 | 5610 | TTCN_3607 | 11583 |
| TTCN_1482 | 5568 | CTCN_3213 | 11541 | TTCN_1497 | 5611 | GTCN_1797 | 11584 |
| CTCN_1632 | 5569 | ATCN_2403 | 11542 | TTCN_1498 | 5612 | ATCN_2408 | 11585 |
| ATCN_1047 | 5570 | GTCN_1791 | 11543 | TTCN_1499 | 5613 | ATCN_2409 | 11586 |
| ATCN_1048 | 5571 | TTCN_3583 | 11544 | TTCN_1500 | 5614 | CTCN_3220 | 11587 |
| TTCN_1483 | 5572 | CTCN_3214 | 11545 | TTCN_1501 | 5615 | ATCN_2410 | 11588 |
| CTCN_1633 | 5573 | CTCN_3215 | 11546 | ATCN_1057 | 5616 | ATCN_2411 | 11589 |
| ATCN_1049 | 5574 | TTCN_3584 | 11547 | CTCN_1642 | 5617 | CTCN_3221 | 11590 |
| TTCN_1484 | 5575 | ATCN_2404 | 11548 | GTCN_864 | 5618 | TTCN_3608 | 11591 |
| TTCN_1485 | 5576 | ATCN_2405 | 11549 | TTCN_1502 | 5619 | ATCN_2412 | 11592 |
| TTCN_1486 | 5577 | TTCN_3585 | 11550 | CTCN_1643 | 5620 | GTCN_1798 | 11593 |
| TTCN_1487 | 5578 | GTCN_1792 | 11551 | ATCN_1058 | 5621 | ATCN_2413 | 11594 |

FIG. 33 (continued)

| | | | | | | | |
|---|---|---|---|---|---|---|---|
| ATCN_1059 | 5622 | CTCN_3222 | 11595 | CTCN_1662 | 5665 | CTCN_3231 | 11638 |
| TTCN_1503 | 5623 | CTCN_3223 | 11596 | CTCN_1663 | 5666 | GTCN_1807 | 11639 |
| TTCN_1504 | 5624 | GTCN_1799 | 11597 | ATCN_1069 | 5667 | GTCN_1808 | 11640 |
| CTCN_1644 | 5625 | TTCN_3609 | 11598 | CTCN_1664 | 5668 | TTCN_3629 | 11641 |
| ATCN_1060 | 5626 | TTCN_3610 | 11599 | GTCN_872 | 5669 | TTCN_3630 | 11642 |
| CTCN_1645 | 5627 | TTCN_3611 | 11600 | CTCN_1665 | 5670 | TTCN_3631 | 11643 |
| ATCN_1061 | 5628 | ATCN_2414 | 11601 | CTCN_1666 | 5671 | GTCN_1809 | 11644 |
| CTCN_1646 | 5629 | ATCN_2415 | 11602 | GTCN_873 | 5672 | GTCN_1810 | 11645 |
| GTCN_865 | 5630 | TTCN_3612 | 11603 | GTCN_874 | 5673 | TTCN_3632 | 11646 |
| CTCN_1647 | 5631 | TTCN_3613 | 11604 | CTCN_1667 | 5674 | TTCN_3633 | 11647 |
| GTCN_866 | 5632 | TTCN_3614 | 11605 | ATCN_1070 | 5675 | TTCN_3634 | 11648 |
| ATCN_1062 | 5633 | CTCN_3224 | 11606 | CTCN_1668 | 5676 | ATCN_2420 | 11649 |
| ATCN_1063 | 5634 | TTCN_3615 | 11607 | GTCN_875 | 5677 | CTCN_3232 | 11650 |
| CTCN_1648 | 5635 | TTCN_3616 | 11608 | TTCN_1511 | 5678 | TTCN_3635 | 11651 |
| CTCN_1649 | 5636 | TTCN_3617 | 11609 | CTCN_1669 | 5679 | TTCN_3636 | 11652 |
| TTCN_1505 | 5637 | GTCN_1800 | 11610 | TTCN_1512 | 5680 | CTCN_3233 | 11653 |
| TTCN_1506 | 5638 | TTCN_3618 | 11611 | TTCN_1513 | 5681 | CTCN_3234 | 11654 |
| TTCN_1507 | 5639 | GTCN_1801 | 11612 | TTCN_1514 | 5682 | ATCN_2421 | 11655 |
| GTCN_867 | 5640 | CTCN_3225 | 11613 | TTCN_1515 | 5683 | ATCN_2422 | 11656 |
| TTCN_1508 | 5641 | TTCN_3619 | 11614 | GTCN_876 | 5684 | GTCN_1811 | 11657 |
| GTCN_868 | 5642 | TTCN_3620 | 11615 | ATCN_1071 | 5685 | GTCN_1812 | 11658 |
| CTCN_1650 | 5643 | TTCN_3621 | 11616 | TTCN_1516 | 5686 | CTCN_3235 | 11659 |
| CTCN_1651 | 5644 | ATCN_2416 | 11617 | CTCN_1670 | 5687 | CTCN_3236 | 11660 |
| GTCN_869 | 5645 | GTCN_1802 | 11618 | ATCN_1072 | 5688 | TTCN_3637 | 11661 |
| CTCN_1652 | 5646 | ATCN_2417 | 11619 | TTCN_1517 | 5689 | CTCN_3237 | 11662 |
| GTCN_870 | 5647 | TTCN_3622 | 11620 | TTCN_1518 | 5690 | ATCN_2423 | 11663 |
| ATCN_1064 | 5648 | TTCN_3623 | 11621 | CTCN_1671 | 5691 | ATCN_2424 | 11664 |
| CTCN_1653 | 5649 | GTCN_1803 | 11622 | CTCN_1672 | 5692 | TTCN_3638 | 11665 |
| CTCN_1654 | 5650 | TTCN_3624 | 11623 | GTCN_877 | 5693 | CTCN_3238 | 11666 |
| ATCN_1065 | 5651 | CTCN_3226 | 11624 | ATCN_1073 | 5694 | TTCN_3639 | 11667 |
| CTCN_1655 | 5652 | TTCN_3625 | 11625 | TTCN_1519 | 5695 | GTCN_1813 | 11668 |
| CTCN_1656 | 5653 | CTCN_3227 | 11626 | ATCN_1074 | 5696 | CTCN_3239 | 11669 |
| CTCN_1657 | 5654 | ATCN_2418 | 11627 | TTCN_1520 | 5697 | GTCN_1814 | 11670 |
| TTCN_1509 | 5655 | GTCN_1804 | 11628 | TTCN_1521 | 5698 | CTCN_3240 | 11671 |
| ATCN_1066 | 5656 | GTCN_1805 | 11629 | TTCN_1522 | 5699 | GTCN_1815 | 11672 |
| ATCN_1067 | 5657 | CTCN_3228 | 11630 | TTCN_1523 | 5700 | GTCN_1816 | 11673 |
| GTCN_871 | 5658 | CTCN_3229 | 11631 | TTCN_1524 | 5701 | TTCN_3640 | 11674 |
| CTCN_1658 | 5659 | ATCN_2419 | 11632 | CTCN_1673 | 5702 | GTCN_1817 | 11675 |
| CTCN_1659 | 5660 | TTCN_3626 | 11633 | GTCN_878 | 5703 | TTCN_3641 | 11676 |
| CTCN_1660 | 5661 | TTCN_3627 | 11634 | TTCN_1525 | 5704 | TTCN_3642 | 11677 |
| ATCN_1068 | 5662 | TTCN_3628 | 11635 | TTCN_1526 | 5705 | CTCN_3241 | 11678 |
| TTCN_1510 | 5663 | GTCN_1806 | 11636 | TTCN_1527 | 5706 | TTCN_3643 | 11679 |
| CTCN_1661 | 5664 | CTCN_3230 | 11637 | GTCN_879 | 5707 | GTCN_1818 | 11680 |

FIG. 33 (continued)

| | | | | | | | |
|---|---|---|---|---|---|---|---|
| ATCN_1075 | 5708 | CTCN_3242 | 11681 | ATCN_1080 | 5751 | CTCN_3264 | 11724 |
| CTCN_1674 | 5709 | CTCN_3243 | 11682 | CTCN_1686 | 5752 | ATCN_2434 | 11725 |
| GTCN_880 | 5710 | ATCN_2425 | 11683 | CTCN_1687 | 5753 | ATCN_2435 | 11726 |
| TTCN_1528 | 5711 | CTCN_3244 | 11684 | CTCN_1688 | 5754 | CTCN_3265 | 11727 |
| CTCN_1675 | 5712 | TTCN_3644 | 11685 | GTCN_892 | 5755 | CTCN_3266 | 11728 |
| TTCN_1529 | 5713 | TTCN_3645 | 11686 | GTCN_893 | 5756 | GTCN_1824 | 11729 |
| GTCN_881 | 5714 | TTCN_3646 | 11687 | CTCN_1689 | 5757 | CTCN_3267 | 11730 |
| TTCN_1530 | 5715 | ATCN_2426 | 11688 | GTCN_894 | 5758 | TTCN_3651 | 11731 |
| ATCN_1076 | 5716 | TTCN_3647 | 11689 | GTCN_895 | 5759 | CTCN_3268 | 11732 |
| ATCN_1077 | 5717 | CTCN_3245 | 11690 | GTCN_896 | 5760 | CTCN_3269 | 11733 |
| GTCN_882 | 5718 | CTCN_3246 | 11691 | CTCN_1690 | 5761 | CTCN_3270 | 11734 |
| CTCN_1676 | 5719 | CTCN_3247 | 11692 | GTCN_897 | 5762 | ATCN_2436 | 11735 |
| CTCN_1677 | 5720 | GTCN_1819 | 11693 | TTCN_1542 | 5763 | TTCN_3652 | 11736 |
| GTCN_883 | 5721 | CTCN_3248 | 11694 | GTCN_898 | 5764 | GTCN_1825 | 11737 |
| CTCN_1678 | 5722 | ATCN_2427 | 11695 | CTCN_1691 | 5765 | TTCN_3653 | 11738 |
| GTCN_884 | 5723 | ATCN_2428 | 11696 | TTCN_1543 | 5766 | CTCN_3271 | 11739 |
| GTCN_885 | 5724 | CTCN_3249 | 11697 | GTCN_899 | 5767 | CTCN_3272 | 11740 |
| TTCN_1531 | 5725 | CTCN_3250 | 11698 | CTCN_1692 | 5768 | CTCN_3273 | 11741 |
| GTCN_886 | 5726 | CTCN_3251 | 11699 | CTCN_1693 | 5769 | CTCN_3274 | 11742 |
| GTCN_887 | 5727 | ATCN_2429 | 11700 | GTCN_900 | 5770 | TTCN_3654 | 11743 |
| TTCN_1532 | 5728 | CTCN_3252 | 11701 | TTCN_1544 | 5771 | CTCN_3275 | 11744 |
| ATCN_1078 | 5729 | CTCN_3253 | 11702 | TTCN_1545 | 5772 | GTCN_1826 | 11745 |
| TTCN_1533 | 5730 | ATCN_2430 | 11703 | GTCN_901 | 5773 | CTCN_3276 | 11746 |
| ATCN_1079 | 5731 | ATCN_2431 | 11704 | ATCN_1081 | 5774 | CTCN_3277 | 11747 |
| TTCN_1534 | 5732 | GTCN_1820 | 11705 | ATCN_1082 | 5775 | ATCN_2437 | 11748 |
| TTCN_1535 | 5733 | CTCN_3254 | 11706 | TTCN_1546 | 5776 | TTCN_3655 | 11749 |
| TTCN_1536 | 5734 | ATCN_2432 | 11707 | CTCN_1694 | 5777 | ATCN_2438 | 11750 |
| TTCN_1537 | 5735 | ATCN_2433 | 11708 | TTCN_1547 | 5778 | TTCN_3656 | 11751 |
| CTCN_1679 | 5736 | CTCN_3255 | 11709 | GTCN_902 | 5779 | CTCN_3278 | 11752 |
| TTCN_1538 | 5737 | GTCN_1821 | 11710 | CTCN_1695 | 5780 | GTCN_1827 | 11753 |
| TTCN_1539 | 5738 | TTCN_3648 | 11711 | CTCN_1696 | 5781 | GTCN_1828 | 11754 |
| GTCN_888 | 5739 | GTCN_1822 | 11712 | CTCN_1697 | 5782 | ATCN_2439 | 11755 |
| TTCN_1540 | 5740 | CTCN_3256 | 11713 | CTCN_1698 | 5783 | TTCN_3657 | 11756 |
| CTCN_1680 | 5741 | GTCN_1823 | 11714 | GTCN_903 | 5784 | ATCN_2440 | 11757 |
| GTCN_889 | 5742 | CTCN_3257 | 11715 | CTCN_1699 | 5785 | CTCN_3279 | 11758 |
| CTCN_1681 | 5743 | CTCN_3258 | 11716 | GTCN_904 | 5786 | TTCN_3658 | 11759 |
| GTCN_890 | 5744 | CTCN_3259 | 11717 | CTCN_1700 | 5787 | CTCN_3280 | 11760 |
| TTCN_1541 | 5745 | CTCN_3260 | 11718 | GTCN_905 | 5788 | TTCN_3659 | 11761 |
| CTCN_1682 | 5746 | TTCN_3649 | 11719 | GTCN_906 | 5789 | TTCN_3660 | 11762 |
| GTCN_891 | 5747 | TTCN_3650 | 11720 | GTCN_907 | 5790 | TTCN_3661 | 11763 |
| CTCN_1683 | 5748 | CTCN_3261 | 11721 | TTCN_1548 | 5791 | ATCN_2441 | 11764 |
| CTCN_1684 | 5749 | CTCN_3262 | 11722 | CTCN_1701 | 5792 | TTCN_3662 | 11765 |
| CTCN_1685 | 5750 | CTCN_3263 | 11723 | GTCN_908 | 5793 | TTCN_3663 | 11766 |

FIG. 33 (continued)

| | | | | | | | |
|---|---|---|---|---|---|---|---|
| GTCN_909 | 5794 | CTCN_3281 | 11767 | GTCN_922 | 5837 | TTCN_3676 | 11810 |
| CTCN_1702 | 5795 | ATCN_2442 | 11768 | ATCN_1086 | 5838 | GTCN_1838 | 11811 |
| CTCN_1703 | 5796 | GTCN_1829 | 11769 | CTCN_1719 | 5839 | CTCN_3290 | 11812 |
| CTCN_1704 | 5797 | CTCN_3282 | 11770 | TTCN_1559 | 5840 | ATCN_2455 | 11813 |
| ATCN_1083 | 5798 | GTCN_1830 | 11771 | TTCN_1560 | 5841 | ATCN_2456 | 11814 |
| CTCN_1705 | 5799 | CTCN_3283 | 11772 | GTCN_1720 | 5842 | CTCN_3291 | 11815 |
| CTCN_1706 | 5800 | TTCN_3664 | 11773 | GTCN_923 | 5843 | ATCN_2457 | 11816 |
| GTCN_910 | 5801 | GTCN_1831 | 11774 | TTCN_1561 | 5844 | ATCN_2458 | 11817 |
| GTCN_911 | 5802 | ATCN_2443 | 11775 | CTCN_1721 | 5845 | GTCN_1839 | 11818 |
| GTCN_912 | 5803 | GTCN_1832 | 11776 | CTCN_1722 | 5846 | TTCN_3677 | 11819 |
| CTCN_1707 | 5804 | ATCN_2444 | 11777 | CTCN_1723 | 5847 | ATCN_2459 | 11820 |
| CTCN_1708 | 5805 | TTCN_3665 | 11778 | CTCN_1724 | 5848 | TTCN_3678 | 11821 |
| GTCN_913 | 5806 | ATCN_2445 | 11779 | CTCN_1725 | 5849 | ATCN_2460 | 11822 |
| TTCN_1549 | 5807 | CTCN_3284 | 11780 | GTCN_924 | 5850 | CTCN_3292 | 11823 |
| CTCN_1709 | 5808 | TTCN_3666 | 11781 | ATCN_1087 | 5851 | TTCN_3679 | 11824 |
| TTCN_1550 | 5809 | TTCN_3667 | 11782 | CTCN_1726 | 5852 | CTCN_3293 | 11825 |
| CTCN_1710 | 5810 | GTCN_1833 | 11783 | ATCN_1088 | 5853 | CTCN_3294 | 11826 |
| GTCN_914 | 5811 | TTCN_3668 | 11784 | ATCN_1089 | 5854 | ATCN_2461 | 11827 |
| GTCN_915 | 5812 | ATCN_2446 | 11785 | TTCN_1562 | 5855 | ATCN_2462 | 11828 |
| CTCN_1711 | 5813 | CTCN_3285 | 11786 | ATCN_1090 | 5856 | TTCN_3680 | 11829 |
| ATCN_1084 | 5814 | TTCN_3669 | 11787 | ATCN_1091 | 5857 | TTCN_3681 | 11830 |
| GTCN_916 | 5815 | ATCN_2447 | 11788 | CTCN_1727 | 5858 | ATCN_2463 | 11831 |
| GTCN_917 | 5816 | ATCN_2448 | 11789 | CTCN_1728 | 5859 | CTCN_3295 | 11832 |
| TTCN_1551 | 5817 | TTCN_3670 | 11790 | GTCN_925 | 5860 | CTCN_3296 | 11833 |
| ATCN_1085 | 5818 | GTCN_1834 | 11791 | ATCN_1092 | 5861 | CTCN_3297 | 11834 |
| CTCN_1712 | 5819 | CTCN_3286 | 11792 | GTCN_926 | 5862 | ATCN_2464 | 11835 |
| CTCN_1713 | 5820 | GTCN_1835 | 11793 | CTCN_1729 | 5863 | GTCN_1840 | 11836 |
| TTCN_1552 | 5821 | ATCN_2449 | 11794 | TTCN_1563 | 5864 | CTCN_3298 | 11837 |
| TTCN_1553 | 5822 | CTCN_3287 | 11795 | TTCN_1564 | 5865 | TTCN_3682 | 11838 |
| CTCN_1714 | 5823 | ATCN_2450 | 11796 | ATCN_1093 | 5866 | CTCN_3299 | 11839 |
| GTCN_918 | 5824 | TTCN_3671 | 11797 | ATCN_1094 | 5867 | TTCN_3683 | 11840 |
| CTCN_1715 | 5825 | CTCN_3288 | 11798 | ATCN_1095 | 5868 | ATCN_2465 | 11841 |
| GTCN_919 | 5826 | TTCN_3672 | 11799 | CTCN_1730 | 5869 | ATCN_2466 | 11842 |
| TTCN_1554 | 5827 | TTCN_3673 | 11800 | TTCN_1565 | 5870 | TTCN_3684 | 11843 |
| CTCN_1716 | 5828 | GTCN_1836 | 11801 | GTCN_927 | 5871 | ATCN_2467 | 11844 |
| TTCN_1555 | 5829 | CTCN_3289 | 11802 | CTCN_1731 | 5872 | TTCN_3685 | 11845 |
| TTCN_1556 | 5830 | ATCN_2451 | 11803 | GTCN_928 | 5873 | TTCN_3686 | 11846 |
| CTCN_1717 | 5831 | ATCN_2452 | 11804 | CTCN_1732 | 5874 | CTCN_3300 | 11847 |
| GTCN_920 | 5832 | ATCN_2453 | 11805 | TTCN_1566 | 5875 | TTCN_3687 | 11848 |
| GTCN_921 | 5833 | GTCN_1837 | 11806 | TTCN_1567 | 5876 | TTCN_3688 | 11849 |
| TTCN_1557 | 5834 | TTCN_3674 | 11807 | TTCN_1568 | 5877 | TTCN_3689 | 11850 |
| CTCN_1718 | 5835 | TTCN_3675 | 11808 | GTCN_929 | 5878 | TTCN_3690 | 11851 |
| TTCN_1558 | 5836 | ATCN_2454 | 11809 | CTCN_1733 | 5879 | TTCN_3691 | 11852 |

FIG. 33 (continued)

| | | | | | | | |
|---|---|---|---|---|---|---|---|
| TTCN_1569 | 5880 | ATCN_2468 | 11853 | TTCN_1588 | 5923 | TTCN_3707 | 11896 |
| TTCN_1570 | 5881 | TTCN_3692 | 11854 | CTCN_1744 | 5924 | GTCN_1851 | 11897 |
| GTCN_930 | 5882 | TTCN_3693 | 11855 | CTCN_1745 | 5925 | TTCN_3708 | 11898 |
| CTCN_1734 | 5883 | GTCN_1841 | 11856 | ATCN_1101 | 5926 | TTCN_3709 | 11899 |
| TTCN_1571 | 5884 | TTCN_3694 | 11857 | CTCN_1746 | 5927 | CTCN_3308 | 11900 |
| TTCN_1572 | 5885 | TTCN_3695 | 11858 | TTCN_1589 | 5928 | CTCN_3309 | 11901 |
| CTCN_1735 | 5886 | CTCN_3301 | 11859 | GTCN_939 | 5929 | CTCN_3310 | 11902 |
| ATCN_1096 | 5887 | CTCN_3302 | 11860 | CTCN_1747 | 5930 | CTCN_3311 | 11903 |
| GTCN_931 | 5888 | ATCN_2469 | 11861 | ATCN_1102 | 5931 | CTCN_3312 | 11904 |
| CTCN_1736 | 5889 | GTCN_1842 | 11862 | TTCN_1590 | 5932 | CTCN_3313 | 11905 |
| GTCN_932 | 5890 | GTCN_1843 | 11863 | TTCN_1591 | 5933 | GTCN_1852 | 11906 |
| TTCN_1573 | 5891 | TTCN_3696 | 11864 | TTCN_1592 | 5934 | GTCN_1853 | 11907 |
| TTCN_1574 | 5892 | TTCN_3697 | 11865 | GTCN_940 | 5935 | CTCN_3314 | 11908 |
| GTCN_933 | 5893 | GTCN_1844 | 11866 | CTCN_1748 | 5936 | ATCN_2479 | 11909 |
| CTCN_1737 | 5894 | ATCN_2470 | 11867 | TTCN_1593 | 5937 | CTCN_3315 | 11910 |
| TTCN_1575 | 5895 | TTCN_3698 | 11868 | GTCN_941 | 5938 | TTCN_3710 | 11911 |
| TTCN_1576 | 5896 | GTCN_1845 | 11869 | GTCN_942 | 5939 | CTCN_3316 | 11912 |
| TTCN_1577 | 5897 | TTCN_3699 | 11870 | TTCN_1594 | 5940 | GTCN_1854 | 11913 |
| ATCN_1097 | 5898 | TTCN_3700 | 11871 | GTCN_943 | 5941 | GTCN_1855 | 11914 |
| TTCN_1578 | 5899 | TTCN_3701 | 11872 | CTCN_1749 | 5942 | TTCN_3711 | 11915 |
| ATCN_1098 | 5900 | ATCN_2471 | 11873 | TTCN_1595 | 5943 | GTCN_1856 | 11916 |
| GTCN_934 | 5901 | ATCN_2472 | 11874 | CTCN_1750 | 5944 | GTCN_1857 | 11917 |
| TTCN_1579 | 5902 | GTCN_1846 | 11875 | TTCN_1596 | 5945 | CTCN_3317 | 11918 |
| TTCN_1580 | 5903 | ATCN_2473 | 11876 | TTCN_1597 | 5946 | CTCN_3318 | 11919 |
| TTCN_1581 | 5904 | TTCN_3702 | 11877 | GTCN_944 | 5947 | CTCN_3319 | 11920 |
| TTCN_1582 | 5905 | CTCN_3303 | 11878 | GTCN_945 | 5948 | CTCN_3320 | 11921 |
| CTCN_1738 | 5906 | GTCN_1847 | 11879 | CTCN_1751 | 5949 | ATCN_2480 | 11922 |
| CTCN_1739 | 5907 | ATCN_2474 | 11880 | CTCN_1752 | 5950 | ATCN_2481 | 11923 |
| ATCN_1099 | 5908 | TTCN_3703 | 11881 | GTCN_946 | 5951 | CTCN_3321 | 11924 |
| CTCN_1740 | 5909 | CTCN_3304 | 11882 | CTCN_1753 | 5952 | GTCN_1858 | 11925 |
| TTCN_1583 | 5910 | GTCN_1848 | 11883 | ATCN_1103 | 5953 | GTCN_1859 | 11926 |
| TTCN_1584 | 5911 | TTCN_3704 | 11884 | ATCN_1104 | 5954 | CTCN_3322 | 11927 |
| CTCN_1741 | 5912 | ATCN_2475 | 11885 | CTCN_1754 | 5955 | ATCN_2482 | 11928 |
| ATCN_1100 | 5913 | GTCN_1849 | 11886 | CTCN_1755 | 5956 | TTCN_3712 | 11929 |
| TTCN_1585 | 5914 | TTCN_3705 | 11887 | CTCN_1756 | 5957 | TTCN_3713 | 11930 |
| GTCN_935 | 5915 | TTCN_3706 | 11888 | CTCN_1757 | 5958 | CTCN_3323 | 11931 |
| TTCN_1586 | 5916 | CTCN_3305 | 11889 | TTCN_1598 | 5959 | TTCN_3714 | 11932 |
| CTCN_1742 | 5917 | CTCN_3306 | 11890 | TTCN_1599 | 5960 | GTCN_1860 | 11933 |
| CTCN_1743 | 5918 | ATCN_2476 | 11891 | CTCN_1758 | 5961 | CTCN_3324 | 11934 |
| GTCN_936 | 5919 | CTCN_3307 | 11892 | CTCN_1759 | 5962 | TTCN_3715 | 11935 |
| TTCN_1587 | 5920 | ATCN_2477 | 11893 | CTCN_1760 | 5963 | CTCN_3325 | 11936 |
| GTCN_937 | 5921 | GTCN_1850 | 11894 | GTCN_947 | 5964 | CTCN_3326 | 11937 |
| GTCN_938 | 5922 | ATCN_2478 | 11895 | CTCN_1761 | 5965 | TTCN_3716 | 11938 |

FIG. 33 (continued)

| | | | | | | | |
|---|---|---|---|---|---|---|---|
| GTCN_948 | 5966 | CTCN_3327 | 11939 | ATCN_1115 | 6009 | CTCN_3340 | 11982 |
| TTCN_1600 | 5967 | CTCN_3328 | 11940 | ATCN_1116 | 6010 | TTCN_3734 | 11983 |
| ATCN_1105 | 5968 | CTCN_3329 | 11941 | TTCN_1614 | 6011 | CTCN_3341 | 11984 |
| GTCN_949 | 5969 | CTCN_3330 | 11942 | ATCN_1117 | 6012 | ATCN_2488 | 11985 |
| CTCN_1762 | 5970 | CTCN_3331 | 11943 | GTCN_954 | 6013 | GTCN_1869 | 11986 |
| ATCN_1106 | 5971 | CTCN_3332 | 11944 | CTCN_1775 | 6014 | TTCN_3735 | 11987 |
| ATCN_1107 | 5972 | GTCN_1861 | 11945 | ATCN_1118 | 6015 | TTCN_3736 | 11988 |
| GTCN_950 | 5973 | CTCN_3333 | 11946 | ATCN_1119 | 6016 | TTCN_3737 | 11989 |
| GTCN_951 | 5974 | GTCN_1862 | 11947 | TTCN_1615 | 6017 | TTCN_3738 | 11990 |
| ATCN_1108 | 5975 | CTCN_3334 | 11948 | TTCN_1616 | 6018 | ATCN_2489 | 11991 |
| ATCN_1109 | 5976 | TTCN_3717 | 11949 | ATCN_1120 | 6019 | GTCN_1870 | 11992 |
| CTCN_1763 | 5977 | TTCN_3718 | 11950 | TTCN_1617 | 6020 | GTCN_1871 | 11993 |
| CTCN_1764 | 5978 | TTCN_3719 | 11951 | TTCN_1618 | 6021 | CTCN_3342 | 11994 |
| ATCN_1110 | 5979 | ATCN_2483 | 11952 | CTCN_1776 | 6022 | CTCN_3343 | 11995 |
| CTCN_1765 | 5980 | TTCN_3720 | 11953 | TTCN_1619 | 6023 | CTCN_3344 | 11996 |
| TTCN_1601 | 5981 | ATCN_2484 | 11954 | TTCN_1620 | 6024 | ATCN_2490 | 11997 |
| GTCN_952 | 5982 | CTCN_3335 | 11955 | CTCN_1777 | 6025 | CTCN_3345 | 11998 |
| CTCN_1766 | 5983 | GTCN_1863 | 11956 | ATCN_1121 | 6026 | ATCN_2491 | 11999 |
| CTCN_1767 | 5984 | TTCN_3721 | 11957 | ATCN_1122 | 6027 | TTCN_3739 | 12000 |
| TTCN_1602 | 5985 | GTCN_1864 | 11958 | CTCN_1778 | 6028 | TTCN_3740 | 12001 |
| ATCN_1111 | 5986 | TTCN_3722 | 11959 | TTCN_1621 | 6029 | GTCN_1872 | 12002 |
| TTCN_1603 | 5987 | CTCN_3336 | 11960 | CTCN_1779 | 6030 | CTCN_3346 | 12003 |
| CTCN_1768 | 5988 | ATCN_2485 | 11961 | TTCN_1622 | 6031 | TTCN_3741 | 12004 |
| CTCN_1769 | 5989 | TTCN_3723 | 11962 | GTCN_955 | 6032 | CTCN_3347 | 12005 |
| TTCN_1604 | 5990 | GTCN_1865 | 11963 | TTCN_1623 | 6033 | ATCN_2492 | 12006 |
| ATCN_1112 | 5991 | ATCN_2486 | 11964 | TTCN_1624 | 6034 | GTCN_1873 | 12007 |
| TTCN_1605 | 5992 | TTCN_3724 | 11965 | TTCN_1625 | 6035 | GTCN_1874 | 12008 |
| TTCN_1606 | 5993 | TTCN_3725 | 11966 | TTCN_1626 | 6036 | TTCN_3742 | 12009 |
| TTCN_1607 | 5994 | CTCN_3337 | 11967 | TTCN_1627 | 6037 | TTCN_3743 | 12010 |
| CTCN_1770 | 5995 | TTCN_3726 | 11968 | GTCN_956 | 6038 | CTCN_3348 | 12011 |
| TTCN_1608 | 5996 | TTCN_3727 | 11969 | CTCN_1780 | 6039 | CTCN_3349 | 12012 |
| TTCN_1609 | 5997 | CTCN_3338 | 11970 | ATCN_1123 | 6040 | CTCN_3350 | 12013 |
| GTCN_953 | 5998 | TTCN_3728 | 11971 | GTCN_957 | 6041 | GTCN_1875 | 12014 |
| TTCN_1610 | 5999 | TTCN_3729 | 11972 | TTCN_1628 | 6042 | GTCN_1876 | 12015 |
| CTCN_1771 | 6000 | TTCN_3730 | 11973 | CTCN_1781 | 6043 | TTCN_3744 | 12016 |
| TTCN_1611 | 6001 | ATCN_2487 | 11974 | TTCN_1629 | 6044 | TTCN_3745 | 12017 |
| CTCN_1772 | 6002 | GTCN_1866 | 11975 | TTCN_1630 | 6045 | ATCN_2493 | 12018 |
| ATCN_1113 | 6003 | CTCN_3339 | 11976 | CTCN_1782 | 6046 | GTCN_1877 | 12019 |
| CTCN_1773 | 6004 | TTCN_3731 | 11977 | ATCN_1124 | 6047 | TTCN_3746 | 12020 |
| TTCN_1612 | 6005 | GTCN_1867 | 11978 | CTCN_1783 | 6048 | CTCN_3351 | 12021 |
| TTCN_1613 | 6006 | GTCN_1868 | 11979 | CTCN_1784 | 6049 | GTCN_1878 | 12022 |
| ATCN_1114 | 6007 | TTCN_3732 | 11980 | GTCN_958 | 6050 | CTCN_3352 | 12023 |
| CTCN_1774 | 6008 | TTCN_3733 | 11981 | TTCN_1631 | 6051 | GTCN_1879 | 12024 |

FIG. 33 (continued)

| | | | | | | | |
|---|---|---|---|---|---|---|---|
| CTCN_1785 | 6052 | CTCN_3353 | 12025 | TTCN_1649 | 6095 | ATCN_2502 | 12068 |
| TTCN_1632 | 6053 | ATCN_2494 | 12026 | ATCN_1134 | 6096 | GTCN_1891 | 12069 |
| TTCN_1633 | 6054 | ATCN_2495 | 12027 | GTCN_969 | 6097 | ATCN_2503 | 12070 |
| CTCN_1786 | 6055 | CTCN_3354 | 12028 | CTCN_1792 | 6098 | TTCN_3755 | 12071 |
| GTCN_959 | 6056 | CTCN_3355 | 12029 | CTCN_1793 | 6099 | CTCN_3369 | 12072 |
| ATCN_1125 | 6057 | GTCN_1880 | 12030 | TTCN_1650 | 6100 | ATCN_2504 | 12073 |
| GTCN_960 | 6058 | TTCN_3747 | 12031 | TTCN_1651 | 6101 | TTCN_3756 | 12074 |
| TTCN_1634 | 6059 | GTCN_1881 | 12032 | GTCN_970 | 6102 | CTCN_3370 | 12075 |
| TTCN_1635 | 6060 | CTCN_3356 | 12033 | ATCN_1135 | 6103 | TTCN_3757 | 12076 |
| ATCN_1126 | 6061 | TTCN_3748 | 12034 | ATCN_1136 | 6104 | TTCN_3758 | 12077 |
| TTCN_1636 | 6062 | ATCN_2496 | 12035 | CTCN_1794 | 6105 | ATCN_2505 | 12078 |
| CTCN_1787 | 6063 | GTCN_1882 | 12036 | CTCN_1795 | 6106 | GTCN_1892 | 12079 |
| ATCN_1127 | 6064 | CTCN_3357 | 12037 | GTCN_971 | 6107 | TTCN_3759 | 12080 |
| TTCN_1637 | 6065 | GTCN_1883 | 12038 | ATCN_1137 | 6108 | ATCN_2506 | 12081 |
| TTCN_1638 | 6066 | CTCN_3358 | 12039 | ATCN_1138 | 6109 | TTCN_3760 | 12082 |
| GTCN_961 | 6067 | TTCN_3749 | 12040 | CTCN_1796 | 6110 | TTCN_3761 | 12083 |
| ATCN_1128 | 6068 | TTCN_3750 | 12041 | GTCN_972 | 6111 | GTCN_1893 | 12084 |
| TTCN_1639 | 6069 | CTCN_3359 | 12042 | ATCN_1139 | 6112 | CTCN_3371 | 12085 |
| CTCN_1788 | 6070 | GTCN_1884 | 12043 | CTCN_1797 | 6113 | CTCN_3372 | 12086 |
| GTCN_962 | 6071 | CTCN_3360 | 12044 | GTCN_973 | 6114 | TTCN_3762 | 12087 |
| GTCN_963 | 6072 | GTCN_1885 | 12045 | ATCN_1140 | 6115 | ATCN_2507 | 12088 |
| GTCN_964 | 6073 | CTCN_3361 | 12046 | TTCN_1652 | 6116 | ATCN_2508 | 12089 |
| ATCN_1129 | 6074 | GTCN_1886 | 12047 | GTCN_974 | 6117 | ATCN_2509 | 12090 |
| GTCN_965 | 6075 | CTCN_3362 | 12048 | CTCN_1798 | 6118 | CTCN_3373 | 12091 |
| CTCN_1789 | 6076 | GTCN_1887 | 12049 | GTCN_975 | 6119 | ATCN_2510 | 12092 |
| ATCN_1130 | 6077 | ATCN_2497 | 12050 | CTCN_1799 | 6120 | TTCN_3763 | 12093 |
| ATCN_1131 | 6078 | CTCN_3363 | 12051 | CTCN_1800 | 6121 | CTCN_3374 | 12094 |
| TTCN_1640 | 6079 | GTCN_1888 | 12052 | CTCN_1801 | 6122 | ATCN_2511 | 12095 |
| ATCN_1132 | 6080 | ATCN_2498 | 12053 | CTCN_1802 | 6123 | TTCN_3764 | 12096 |
| TTCN_1641 | 6081 | CTCN_3364 | 12054 | TTCN_1653 | 6124 | CTCN_3375 | 12097 |
| CTCN_1790 | 6082 | GTCN_1889 | 12055 | TTCN_1654 | 6125 | GTCN_1894 | 12098 |
| GTCN_966 | 6083 | ATCN_2499 | 12056 | CTCN_1803 | 6126 | TTCN_3765 | 12099 |
| TTCN_1642 | 6084 | TTCN_3751 | 12057 | CTCN_1804 | 6127 | GTCN_1895 | 12100 |
| TTCN_1643 | 6085 | CTCN_3365 | 12058 | CTCN_1805 | 6128 | TTCN_3766 | 12101 |
| CTCN_1791 | 6086 | TTCN_3752 | 12059 | CTCN_1806 | 6129 | ATCN_2512 | 12102 |
| TTCN_1644 | 6087 | CTCN_3366 | 12060 | ATCN_1141 | 6130 | TTCN_3767 | 12103 |
| TTCN_1645 | 6088 | GTCN_1890 | 12061 | ATCN_1142 | 6131 | TTCN_3768 | 12104 |
| TTCN_1646 | 6089 | ATCN_2500 | 12062 | GTCN_976 | 6132 | TTCN_3769 | 12105 |
| ATCN_1133 | 6090 | ATCN_2501 | 12063 | CTCN_1807 | 6133 | GTCN_1896 | 12106 |
| TTCN_1647 | 6091 | TTCN_3753 | 12064 | GTCN_977 | 6134 | CTCN_3376 | 12107 |
| TTCN_1648 | 6092 | TTCN_3754 | 12065 | CTCN_1808 | 6135 | CTCN_3377 | 12108 |
| GTCN_967 | 6093 | CTCN_3367 | 12066 | CTCN_1809 | 6136 | ATCN_2513 | 12109 |
| GTCN_968 | 6094 | CTCN_3368 | 12067 | GTCN_978 | 6137 | ATCN_2514 | 12110 |

FIG. 33 (continued)

| | | | | | | | |
|---|---|---|---|---|---|---|---|
| CTCN_1810 | 6138 | ATCN_2515 | 12111 | CTCN_1832 | 6181 | ATCN_2525 | 12154 |
| GTCN_979 | 6139 | TTCN_3770 | 12112 | TTCN_1662 | 6182 | CTCN_3388 | 12155 |
| CTCN_1811 | 6140 | TTCN_3771 | 12113 | TTCN_1663 | 6183 | ATCN_2526 | 12156 |
| TTCN_1655 | 6141 | ATCN_2516 | 12114 | GTCN_989 | 6184 | TTCN_3785 | 12157 |
| ATCN_1143 | 6142 | TTCN_3772 | 12115 | TTCN_1664 | 6185 | GTCN_1905 | 12158 |
| GTCN_980 | 6143 | GTCN_1897 | 12116 | ATCN_1147 | 6186 | ATCN_2527 | 12159 |
| CTCN_1812 | 6144 | TTCN_3773 | 12117 | ATCN_1148 | 6187 | TTCN_3786 | 12160 |
| CTCN_1813 | 6145 | TTCN_3774 | 12118 | CTCN_1833 | 6188 | CTCN_3389 | 12161 |
| CTCN_1814 | 6146 | CTCN_3378 | 12119 | CTCN_1834 | 6189 | CTCN_3390 | 12162 |
| CTCN_1815 | 6147 | CTCN_3379 | 12120 | ATCN_1149 | 6190 | TTCN_3787 | 12163 |
| CTCN_1816 | 6148 | GTCN_1898 | 12121 | TTCN_1665 | 6191 | ATCN_2528 | 12164 |
| GTCN_981 | 6149 | ATCN_2517 | 12122 | CTCN_1835 | 6192 | TTCN_3788 | 12165 |
| GTCN_982 | 6150 | TTCN_3775 | 12123 | TTCN_1666 | 6193 | TTCN_3789 | 12166 |
| TTCN_1656 | 6151 | GTCN_1899 | 12124 | ATCN_1150 | 6194 | TTCN_3790 | 12167 |
| GTCN_983 | 6152 | TTCN_3776 | 12125 | ATCN_1151 | 6195 | GTCN_1906 | 12168 |
| TTCN_1657 | 6153 | CTCN_3380 | 12126 | CTCN_1836 | 6196 | TTCN_3791 | 12169 |
| GTCN_984 | 6154 | TTCN_3777 | 12127 | CTCN_1837 | 6197 | TTCN_3792 | 12170 |
| CTCN_1817 | 6155 | GTCN_1900 | 12128 | GTCN_990 | 6198 | ATCN_2529 | 12171 |
| TTCN_1658 | 6156 | ATCN_2518 | 12129 | CTCN_1838 | 6199 | TTCN_3793 | 12172 |
| CTCN_1818 | 6157 | CTCN_3381 | 12130 | CTCN_1839 | 6200 | TTCN_3794 | 12173 |
| TTCN_1659 | 6158 | CTCN_3382 | 12131 | TTCN_1667 | 6201 | ATCN_2530 | 12174 |
| CTCN_1819 | 6159 | ATCN_2519 | 12132 | TTCN_1668 | 6202 | TTCN_3795 | 12175 |
| CTCN_1820 | 6160 | ATCN_2520 | 12133 | GTCN_991 | 6203 | TTCN_3796 | 12176 |
| ATCN_1144 | 6161 | CTCN_3383 | 12134 | ATCN_1152 | 6204 | TTCN_3797 | 12177 |
| CTCN_1821 | 6162 | ATCN_2521 | 12135 | GTCN_992 | 6205 | TTCN_3798 | 12178 |
| GTCN_985 | 6163 | GTCN_1901 | 12136 | ATCN_1153 | 6206 | CTCN_3391 | 12179 |
| CTCN_1822 | 6164 | CTCN_3384 | 12137 | TTCN_1669 | 6207 | CTCN_3392 | 12180 |
| CTCN_1823 | 6165 | CTCN_3385 | 12138 | CTCN_1840 | 6208 | ATCN_2531 | 12181 |
| TTCN_1660 | 6166 | CTCN_3386 | 12139 | GTCN_993 | 6209 | GTCN_1907 | 12182 |
| TTCN_1661 | 6167 | GTCN_1902 | 12140 | TTCN_1670 | 6210 | TTCN_3799 | 12183 |
| CTCN_1824 | 6168 | TTCN_3778 | 12141 | CTCN_1841 | 6211 | TTCN_3800 | 12184 |
| CTCN_1825 | 6169 | TTCN_3779 | 12142 | ATCN_1154 | 6212 | ATCN_2532 | 12185 |
| CTCN_1826 | 6170 | GTCN_1903 | 12143 | TTCN_1671 | 6213 | CTCN_3393 | 12186 |
| CTCN_1827 | 6171 | TTCN_3780 | 12144 | TTCN_1672 | 6214 | TTCN_3801 | 12187 |
| ATCN_1145 | 6172 | GTCN_1904 | 12145 | TTCN_1673 | 6215 | TTCN_3802 | 12188 |
| ATCN_1146 | 6173 | CTCN_3387 | 12146 | CTCN_1842 | 6216 | GTCN_1908 | 12189 |
| CTCN_1828 | 6174 | ATCN_2522 | 12147 | CTCN_1843 | 6217 | TTCN_3803 | 12190 |
| GTCN_986 | 6175 | TTCN_3781 | 12148 | CTCN_1844 | 6218 | ATCN_2533 | 12191 |
| CTCN_1829 | 6176 | TTCN_3782 | 12149 | TTCN_1674 | 6219 | ATCN_2534 | 12192 |
| CTCN_1830 | 6177 | TTCN_3783 | 12150 | TTCN_1675 | 6220 | CTCN_3394 | 12193 |
| GTCN_987 | 6178 | ATCN_2523 | 12151 | GTCN_994 | 6221 | TTCN_3804 | 12194 |
| CTCN_1831 | 6179 | TTCN_3784 | 12152 | TTCN_1676 | 6222 | TTCN_3805 | 12195 |
| GTCN_988 | 6180 | ATCN_2524 | 12153 | TTCN_1677 | 6223 | TTCN_3806 | 12196 |

FIG. 33 (continued)

| | | | | | | | |
|---|---|---|---|---|---|---|---|
| GTCN_995 | 6224 | TTCN_3807 | 12197 | CTCN_1860 | 6267 | GTCN_1916 | 12240 |
| GTCN_996 | 6225 | TTCN_3808 | 12198 | ATCN_1164 | 6268 | CTCN_3409 | 12241 |
| TTCN_1678 | 6226 | CTCN_3395 | 12199 | CTCN_1861 | 6269 | CTCN_3410 | 12242 |
| ATCN_1155 | 6227 | GTCN_1909 | 12200 | TTCN_1686 | 6270 | TTCN_3819 | 12243 |
| TTCN_1679 | 6228 | TTCN_3809 | 12201 | CTCN_1862 | 6271 | ATCN_2545 | 12244 |
| TTCN_1680 | 6229 | TTCN_3810 | 12202 | TTCN_1687 | 6272 | CTCN_3411 | 12245 |
| CTCN_1845 | 6230 | ATCN_2535 | 12203 | CTCN_1863 | 6273 | TTCN_3820 | 12246 |
| CTCN_1846 | 6231 | GTCN_1910 | 12204 | GTCN_1006 | 6274 | CTCN_3412 | 12247 |
| ATCN_1156 | 6232 | CTCN_3396 | 12205 | TTCN_1688 | 6275 | ATCN_2546 | 12248 |
| GTCN_997 | 6233 | GTCN_1911 | 12206 | GTCN_1007 | 6276 | ATCN_2547 | 12249 |
| TTCN_1681 | 6234 | CTCN_3397 | 12207 | ATCN_1165 | 6277 | CTCN_3413 | 12250 |
| ATCN_1157 | 6235 | TTCN_3811 | 12208 | ATCN_1166 | 6278 | GTCN_1917 | 12251 |
| CTCN_1847 | 6236 | CTCN_3398 | 12209 | CTCN_1864 | 6279 | GTCN_1918 | 12252 |
| CTCN_1848 | 6237 | CTCN_3399 | 12210 | TTCN_1689 | 6280 | CTCN_3414 | 12253 |
| CTCN_1849 | 6238 | CTCN_3400 | 12211 | ATCN_1167 | 6281 | CTCN_3415 | 12254 |
| TTCN_1682 | 6239 | ATCN_2536 | 12212 | TTCN_1690 | 6282 | CTCN_3416 | 12255 |
| GTCN_998 | 6240 | GTCN_1912 | 12213 | GTCN_1008 | 6283 | CTCN_3417 | 12256 |
| CTCN_1850 | 6241 | GTCN_1913 | 12214 | GTCN_1009 | 6284 | ATCN_2548 | 12257 |
| GTCN_999 | 6242 | CTCN_3401 | 12215 | TTCN_1691 | 6285 | CTCN_3418 | 12258 |
| CTCN_1851 | 6243 | ATCN_2537 | 12216 | TTCN_1692 | 6286 | CTCN_3419 | 12259 |
| CTCN_1852 | 6244 | ATCN_2538 | 12217 | GTCN_1010 | 6287 | CTCN_3420 | 12260 |
| ATCN_1158 | 6245 | GTCN_1914 | 12218 | GTCN_1011 | 6288 | GTCN_1919 | 12261 |
| ATCN_1159 | 6246 | TTCN_3812 | 12219 | ATCN_1168 | 6289 | CTCN_3421 | 12262 |
| GTCN_1000 | 6247 | CTCN_3402 | 12220 | GTCN_1012 | 6290 | CTCN_3422 | 12263 |
| GTCN_1001 | 6248 | ATCN_2539 | 12221 | TTCN_1693 | 6291 | GTCN_1920 | 12264 |
| CTCN_1853 | 6249 | TTCN_3813 | 12222 | CTCN_1865 | 6292 | TTCN_3821 | 12265 |
| CTCN_1854 | 6250 | TTCN_3814 | 12223 | TTCN_1694 | 6293 | CTCN_3423 | 12266 |
| ATCN_1160 | 6251 | TTCN_3815 | 12224 | TTCN_1695 | 6294 | CTCN_3424 | 12267 |
| ATCN_1161 | 6252 | CTCN_3403 | 12225 | ATCN_1169 | 6295 | CTCN_3425 | 12268 |
| CTCN_1855 | 6253 | TTCN_3816 | 12226 | ATCN_1170 | 6296 | TTCN_3822 | 12269 |
| GTCN_1002 | 6254 | CTCN_3404 | 12227 | ATCN_1171 | 6297 | CTCN_3426 | 12270 |
| TTCN_1683 | 6255 | CTCN_3405 | 12228 | ATCN_1172 | 6298 | CTCN_3427 | 12271 |
| CTCN_1856 | 6256 | CTCN_3406 | 12229 | TTCN_1696 | 6299 | ATCN_2549 | 12272 |
| TTCN_1684 | 6257 | TTCN_3817 | 12230 | TTCN_1697 | 6300 | CTCN_3428 | 12273 |
| ATCN_1162 | 6258 | GTCN_1915 | 12231 | TTCN_1698 | 6301 | CTCN_3429 | 12274 |
| GTCN_1003 | 6259 | ATCN_2540 | 12232 | CTCN_1866 | 6302 | TTCN_3823 | 12275 |
| TTCN_1685 | 6260 | TTCN_3818 | 12233 | ATCN_1173 | 6303 | CTCN_3430 | 12276 |
| CTCN_1857 | 6261 | ATCN_2541 | 12234 | GTCN_1013 | 6304 | GTCN_1921 | 12277 |
| GTCN_1004 | 6262 | ATCN_2542 | 12235 | ATCN_1174 | 6305 | CTCN_3431 | 12278 |
| ATCN_1163 | 6263 | ATCN_2543 | 12236 | TTCN_1699 | 6306 | CTCN_3432 | 12279 |
| CTCN_1858 | 6264 | ATCN_2544 | 12237 | CTCN_1867 | 6307 | ATCN_2550 | 12280 |
| CTCN_1859 | 6265 | CTCN_3407 | 12238 | CTCN_1868 | 6308 | CTCN_3433 | 12281 |
| GTCN_1005 | 6266 | CTCN_3408 | 12239 | GTCN_1014 | 6309 | TTCN_3824 | 12282 |

FIG. 33 (continued)

| | | | | | | | |
|---|---|---|---|---|---|---|---|
| CTCN_1869 | 6310 | CTCN_3434 | 12283 | CTCN_1892 | 6353 | TTCN_3839 | 12326 |
| GTCN_1015 | 6311 | ATCN_2551 | 12284 | CTCN_1893 | 6354 | TTCN_3840 | 12327 |
| CTCN_1870 | 6312 | CTCN_3435 | 12285 | CTCN_1894 | 6355 | TTCN_3841 | 12328 |
| CTCN_1871 | 6313 | GTCN_1922 | 12286 | TTCN_1706 | 6356 | TTCN_3842 | 12329 |
| ATCN_1175 | 6314 | ATCN_2552 | 12287 | GTCN_1021 | 6357 | ATCN_2566 | 12330 |
| ATCN_1176 | 6315 | ATCN_2553 | 12288 | ATCN_1183 | 6358 | ATCN_2567 | 12331 |
| CTCN_1872 | 6316 | TTCN_3825 | 12289 | TTCN_1707 | 6359 | ATCN_2568 | 12332 |
| CTCN_1873 | 6317 | TTCN_3826 | 12290 | ATCN_1184 | 6360 | TTCN_3843 | 12333 |
| CTCN_1874 | 6318 | TTCN_3827 | 12291 | TTCN_1708 | 6361 | ATCN_2569 | 12334 |
| CTCN_1875 | 6319 | TTCN_3828 | 12292 | CTCN_1895 | 6362 | ATCN_2570 | 12335 |
| TTCN_1700 | 6320 | GTCN_1923 | 12293 | ATCN_1185 | 6363 | TTCN_3844 | 12336 |
| TTCN_1701 | 6321 | CTCN_3436 | 12294 | TTCN_1709 | 6364 | TTCN_3845 | 12337 |
| CTCN_1876 | 6322 | ATCN_2554 | 12295 | ATCN_1186 | 6365 | ATCN_2571 | 12338 |
| CTCN_1877 | 6323 | TTCN_3829 | 12296 | TTCN_1710 | 6366 | TTCN_3846 | 12339 |
| CTCN_1878 | 6324 | TTCN_3830 | 12297 | CTCN_1896 | 6367 | ATCN_2572 | 12340 |
| GTCN_1016 | 6325 | CTCN_3437 | 12298 | TTCN_1711 | 6368 | CTCN_3444 | 12341 |
| CTCN_1879 | 6326 | CTCN_3438 | 12299 | CTCN_1897 | 6369 | CTCN_3445 | 12342 |
| GTCN_1017 | 6327 | ATCN_2555 | 12300 | TTCN_1712 | 6370 | CTCN_3446 | 12343 |
| TTCN_1702 | 6328 | TTCN_3831 | 12301 | TTCN_1713 | 6371 | TTCN_3847 | 12344 |
| ATCN_1177 | 6329 | ATCN_2556 | 12302 | ATCN_1187 | 6372 | ATCN_2573 | 12345 |
| GTCN_1018 | 6330 | ATCN_2557 | 12303 | TTCN_1714 | 6373 | ATCN_2574 | 12346 |
| CTCN_1880 | 6331 | TTCN_3832 | 12304 | TTCN_1715 | 6374 | CTCN_3447 | 12347 |
| CTCN_1881 | 6332 | ATCN_2558 | 12305 | CTCN_1898 | 6375 | CTCN_3448 | 12348 |
| CTCN_1882 | 6333 | ATCN_2559 | 12306 | ATCN_1188 | 6376 | CTCN_3449 | 12349 |
| GTCN_1019 | 6334 | TTCN_3833 | 12307 | ATCN_1189 | 6377 | CTCN_3450 | 12350 |
| CTCN_1883 | 6335 | ATCN_2560 | 12308 | CTCN_1899 | 6378 | GTCN_1926 | 12351 |
| ATCN_1178 | 6336 | GTCN_1924 | 12309 | ATCN_1190 | 6379 | ATCN_2575 | 12352 |
| ATCN_1179 | 6337 | CTCN_3439 | 12310 | ATCN_1191 | 6380 | ATCN_2576 | 12353 |
| GTCN_1020 | 6338 | ATCN_2561 | 12311 | ATCN_1192 | 6381 | GTCN_1927 | 12354 |
| CTCN_1884 | 6339 | TTCN_3834 | 12312 | TTCN_1716 | 6382 | CTCN_3451 | 12355 |
| CTCN_1885 | 6340 | TTCN_3835 | 12313 | TTCN_1717 | 6383 | CTCN_3452 | 12356 |
| ATCN_1180 | 6341 | TTCN_3836 | 12314 | TTCN_1718 | 6384 | ATCN_2577 | 12357 |
| CTCN_1886 | 6342 | ATCN_2562 | 12315 | ATCN_1193 | 6385 | CTCN_3453 | 12358 |
| TTCN_1703 | 6343 | CTCN_3440 | 12316 | TTCN_1719 | 6386 | TTCN_3848 | 12359 |
| CTCN_1887 | 6344 | ATCN_2563 | 12317 | ATCN_1194 | 6387 | CTCN_3454 | 12360 |
| TTCN_1704 | 6345 | TTCN_3837 | 12318 | ATCN_1195 | 6388 | GTCN_1928 | 12361 |
| TTCN_1705 | 6346 | CTCN_3441 | 12319 | ATCN_1196 | 6389 | CTCN_3455 | 12362 |
| CTCN_1888 | 6347 | TTCN_3838 | 12320 | ATCN_1197 | 6390 | GTCN_1929 | 12363 |
| ATCN_1181 | 6348 | CTCN_3442 | 12321 | ATCN_1198 | 6391 | GTCN_1930 | 12364 |
| ATCN_1182 | 6349 | ATCN_2564 | 12322 | ATCN_1199 | 6392 | ATCN_2578 | 12365 |
| CTCN_1889 | 6350 | ATCN_2565 | 12323 | TTCN_1720 | 6393 | ATCN_2579 | 12366 |
| CTCN_1890 | 6351 | GTCN_1925 | 12324 | TTCN_1721 | 6394 | CTCN_3456 | 12367 |
| CTCN_1891 | 6352 | CTCN_3443 | 12325 | TTCN_1722 | 6395 | ATCN_2580 | 12368 |

FIG. 33 (continued)

| | | | | | | | |
|---|---|---|---|---|---|---|---|
| CTCN_1900 | 6396 | TTCN_3849 | 12369 | ATCN_1209 | 6439 | CTCN_3466 | 12412 |
| CTCN_1901 | 6397 | CTCN_3457 | 12370 | ATCN_1210 | 6440 | GTCN_1939 | 12413 |
| GTCN_1022 | 6398 | ATCN_2581 | 12371 | GTCN_1027 | 6441 | CTCN_3467 | 12414 |
| CTCN_1902 | 6399 | ATCN_2582 | 12372 | GTCN_1028 | 6442 | CTCN_3468 | 12415 |
| ATCN_1200 | 6400 | ATCN_2583 | 12373 | TTCN_1737 | 6443 | GTCN_1940 | 12416 |
| CTCN_1903 | 6401 | ATCN_2584 | 12374 | TTCN_1738 | 6444 | TTCN_3862 | 12417 |
| TTCN_1723 | 6402 | CTCN_3458 | 12375 | CTCN_1915 | 6445 | ATCN_2594 | 12418 |
| TTCN_1724 | 6403 | GTCN_1931 | 12376 | TTCN_1739 | 6446 | ATCN_2595 | 12419 |
| CTCN_1904 | 6404 | GTCN_1932 | 12377 | GTCN_1029 | 6447 | ATCN_2596 | 12420 |
| GTCN_1023 | 6405 | GTCN_1933 | 12378 | GTCN_1030 | 6448 | TTCN_3863 | 12421 |
| CTCN_1905 | 6406 | ATCN_2585 | 12379 | TTCN_1740 | 6449 | ATCN_2597 | 12422 |
| CTCN_1906 | 6407 | GTCN_1934 | 12380 | CTCN_1916 | 6450 | GTCN_1941 | 12423 |
| CTCN_1907 | 6408 | CTCN_3459 | 12381 | ATCN_1211 | 6451 | ATCN_2598 | 12424 |
| TTCN_1725 | 6409 | ATCN_2586 | 12382 | CTCN_1917 | 6452 | GTCN_1942 | 12425 |
| GTCN_1024 | 6410 | CTCN_3460 | 12383 | GTCN_1031 | 6453 | TTCN_3864 | 12426 |
| TTCN_1726 | 6411 | TTCN_3850 | 12384 | CTCN_1918 | 6454 | GTCN_1943 | 12427 |
| CTCN_1908 | 6412 | TTCN_3851 | 12385 | CTCN_1919 | 6455 | TTCN_3865 | 12428 |
| GTCN_1025 | 6413 | CTCN_3461 | 12386 | ATCN_1212 | 6456 | TTCN_3866 | 12429 |
| CTCN_1909 | 6414 | TTCN_3852 | 12387 | ATCN_1213 | 6457 | GTCN_1944 | 12430 |
| CTCN_1910 | 6415 | TTCN_3853 | 12388 | CTCN_1920 | 6458 | ATCN_2599 | 12431 |
| TTCN_1727 | 6416 | ATCN_2587 | 12389 | CTCN_1921 | 6459 | TTCN_3867 | 12432 |
| GTCN_1026 | 6417 | GTCN_1935 | 12390 | CTCN_1922 | 6460 | ATCN_2600 | 12433 |
| ATCN_1201 | 6418 | GTCN_1936 | 12391 | CTCN_1923 | 6461 | ATCN_2601 | 12434 |
| TTCN_1728 | 6419 | ATCN_2588 | 12392 | TTCN_1741 | 6462 | TTCN_3868 | 12435 |
| ATCN_1202 | 6420 | ATCN_2589 | 12393 | ATCN_1214 | 6463 | TTCN_3869 | 12436 |
| TTCN_1729 | 6421 | TTCN_3854 | 12394 | TTCN_1742 | 6464 | CTCN_3469 | 12437 |
| CTCN_1911 | 6422 | TTCN_3855 | 12395 | CTCN_1924 | 6465 | GTCN_1945 | 12438 |
| CTCN_1912 | 6423 | TTCN_3856 | 12396 | CTCN_1925 | 6466 | ATCN_2602 | 12439 |
| ATCN_1203 | 6424 | TTCN_3857 | 12397 | GTCN_1032 | 6467 | CTCN_3470 | 12440 |
| TTCN_1730 | 6425 | CTCN_3462 | 12398 | TTCN_1743 | 6468 | GTCN_1946 | 12441 |
| TTCN_1731 | 6426 | GTCN_1937 | 12399 | CTCN_1926 | 6469 | TTCN_3870 | 12442 |
| ATCN_1204 | 6427 | TTCN_3858 | 12400 | GTCN_1033 | 6470 | TTCN_3871 | 12443 |
| TTCN_1732 | 6428 | CTCN_3463 | 12401 | GTCN_1034 | 6471 | CTCN_3471 | 12444 |
| CTCN_1913 | 6429 | CTCN_3464 | 12402 | CTCN_1927 | 6472 | CTCN_3472 | 12445 |
| ATCN_1205 | 6430 | ATCN_2590 | 12403 | CTCN_1928 | 6473 | TTCN_3872 | 12446 |
| CTCN_1914 | 6431 | ATCN_2591 | 12404 | GTCN_1035 | 6474 | CTCN_3473 | 12447 |
| TTCN_1733 | 6432 | CTCN_3465 | 12405 | CTCN_1929 | 6475 | CTCN_3474 | 12448 |
| TTCN_1734 | 6433 | GTCN_1938 | 12406 | ATCN_1215 | 6476 | TTCN_3873 | 12449 |
| ATCN_1206 | 6434 | TTCN_3859 | 12407 | ATCN_1216 | 6477 | TTCN_3874 | 12450 |
| ATCN_1207 | 6435 | TTCN_3860 | 12408 | ATCN_1217 | 6478 | TTCN_3875 | 12451 |
| ATCN_1208 | 6436 | ATCN_2592 | 12409 | CTCN_1930 | 6479 | ATCN_2603 | 12452 |
| TTCN_1735 | 6437 | ATCN_2593 | 12410 | TTCN_1744 | 6480 | TTCN_3876 | 12453 |
| TTCN_1736 | 6438 | TTCN_3861 | 12411 | TTCN_1745 | 6481 | CTCN_3475 | 12454 |

FIG. 33 (continued)

| | | | | | | | |
|---|---|---|---|---|---|---|---|
| GTCN_1036 | 6482 | ATCN_2604 | 12455 | ATCN_1220 | 6504 | ATCN_2612 | 12477 |
| TTCN_1746 | 6483 | CTCN_3476 | 12456 | CTCN_1934 | 6505 | ATCN_2613 | 12478 |
| TTCN_1747 | 6484 | ATCN_2605 | 12457 | ATCN_1221 | 6506 | ATCN_2614 | 12479 |
| TTCN_1748 | 6485 | GTCN_1947 | 12458 | TTCN_1759 | 6507 | CTCN_3480 | 12480 |
| CTCN_1931 | 6486 | GTCN_1948 | 12459 | ATCN_1222 | 6508 | TTCN_3882 | 12481 |
| ATCN_1218 | 6487 | TTCN_3877 | 12460 | TTCN_1760 | 6509 | TTCN_3883 | 12482 |
| TTCN_1749 | 6488 | GTCN_1949 | 12461 | CTCN_1935 | 6510 | TTCN_3884 | 12483 |
| GTCN_1037 | 6489 | GTCN_1950 | 12462 | CTCN_1936 | 6511 | TTCN_3885 | 12484 |
| ATCN_1219 | 6490 | ATCN_2606 | 12463 | ATCN_1223 | 6512 | CTCN_3481 | 12485 |
| GTCN_1038 | 6491 | ATCN_2607 | 12464 | CTCN_1937 | 6513 | ATCN_2615 | 12486 |
| TTCN_1750 | 6492 | ATCN_2608 | 12465 | ATCN_1224 | 6514 | TTCN_3886 | 12487 |
| CTCN_1932 | 6493 | CTCN_3477 | 12466 | TTCN_1761 | 6515 | GTCN_1952 | 12488 |
| TTCN_1751 | 6494 | ATCN_2609 | 12467 | CTCN_1938 | 6516 | CTCN_3482 | 12489 |
| TTCN_1752 | 6495 | TTCN_3878 | 12468 | TTCN_1762 | 6517 | TTCN_3887 | 12490 |
| TTCN_1753 | 6496 | CTCN_3478 | 12469 | ATCN_1225 | 6518 | GTCN_1953 | 12491 |
| TTCN_1754 | 6497 | TTCN_3879 | 12470 | TTCN_1763 | 6519 | TTCN_3888 | 12492 |
| TTCN_1755 | 6498 | ATCN_2610 | 12471 | TTCN_1764 | 6520 | CTCN_3483 | 12493 |
| TTCN_1756 | 6499 | ATCN_2611 | 12472 | TTCN_1765 | 6521 | ATCN_2616 | 12494 |
| TTCN_1757 | 6500 | CTCN_3479 | 12473 | GTCN_1040 | 6522 | CTCN_3484 | 12495 |
| TTCN_1758 | 6501 | TTCN_3880 | 12474 | CTCN_1939 | 6523 | | |
| GTCN_1039 | 6502 | TTCN_3881 | 12475 | ATCN_1226 | 6524 | | |
| CTCN_1933 | 6503 | GTCN_1951 | 12476 | | | | |

COMPOSITIONS AND METHODS FOR THE TARGETING OF SOD1

CROSS REFERENCE TO RELATED APPLICATIONS

This application is a continuation of International Patent Application No. PCT/US2020/050000, filed on Sep. 9, 2020, which claims priority to U.S. Provisional Patent Application Nos. 62/897,941, filed on Sep. 9, 2019, 62/945,138, filed on Dec. 7, 2019 and 63/074,375, filed on Sep. 3, 2020, the contents of each of which are incorporated herein by reference in their entireties.

INCORPORATION BY REFERENCE OF SEQUENCE LISTING

The contents of the text file submitted electronically herewith are incorporated herein by reference in their entirety: A computer readable format copy of the Sequence Listing (filename: SCRB_009_03US_SeqList_ST25.txt, date recorded: Oct. 11, 2021, file size ~3.4 megabytes).

BACKGROUND

The wild-type SOD1 gene produces the enzyme SOD1 (superoxide dismutase 1; superoxide dismutase [Cu—Zn]), which is abundant in cells throughout the body. SOD1 binds copper and zinc ions and is one of three superoxide dismutases responsible for destroying free superoxide radicals in the body. At least 170 mutations across the SOD1 gene and its regulatory element have been found to cause amyotrophic lateral sclerosis (ALS; Lou Gehrig's disease) (Pochet, R. Genetics and ALS: Cause for Optimism. Cerebrum May 1; 2017. pii: cer-05-17), and with the exception of the recessive D90A mutation (Andersen et al., 1995, Nat Genet 10(1): 61-16), they are inherited in a highly penetrant autosomal dominant manner. Most pathogenic mutations are missense mutations, and nonsense and deletion mutations have only rarely been associated with disease (Fox, F. and Yamamoto A. Autophagy: Cancer, Other Pathologies, Inflammation, Immunity, Infection, and Aging. Volume 7: Role of Autophagy in Therapeutic Applications. 2015, Pages 117-137).

ALS is a neurodegenerative disease characterized by selective loss of motor neurons and is characterized by progressive muscle atrophy the inability to control movements. The pathology of ALS is characterized by abnormal accumulation of insoluble and misfolded proteins in degenerating motor neurons. Neuronal death results in progressive paralysis, which typically is fatal 2-5 years after the onset due to respiratory failure. Only about 5-10% of ALS cases are familial, with a Mendelian pattern of inheritance, and the remainder are of spontaneous, or "sporadic" origin. At least 13 genes and loci of major effect known to contribute to familial pathology. Of these, toxic gain-of-function mutations in the SOD1 gene have been most extensively investigated (Petrov, D. et al. ALS Clinical Trials Review: 20 Years of Failure. Are We Any Closer to Registering a New Treatment? Front Aging Neurosci. 9:68 (2017)). SOD1 mutations account for approximately 20% of cases of familial ALS and around 5% of idiopathic/sporadic forms of the disease (Kiernan, M. et al. Amyotrophic lateral sclerosis. Lancet 377:942 (2011)). The exact mechanisms whereby SOD1 contributes to disease progression are currently unknown. Examples of possible pathogenic mechanisms are the localization of mutant SOD1 to mitochondria resulting in caspase activation, formation of cytotoxic SOD1 aggregates that sequester other cellular proteins, perturbing their functions, and the selective inhibition of anterograde fast axonal transport resulting in depletion of mitochondria in axons (Stevens, J C et al. Modification of Superoxide Dismutase 1 (SOD1) Properties by a GFP Tag—Implications for Research into Amyotrophic Lateral Sclerosis (ALS). PLoS ONE 5(3): e9541 (2010).

With respect to ALS, virtually all known SOD1 mutations to date are dominant; a single mutant copy of the SOD1 gene is sufficient to cause ALS, for example. The mechanisms by which SOD1 mutations cause ALS and other SOD1-related disorders are unknown, but some are related to toxic gain of function (Sharma, A. et al. ALS-associated mutant FUS induces selective motor neuron degeneration through toxic gain of function. Nat Commun. 7:10465 (2016); Bunton-Stasyshyn R K et al. SOD1 Function and Its Implications for Amyotrophic Lateral Sclerosis Pathology: New and Renascent Themes. Neuroscientist. 21(5):519 (2015)). An additional cause of ALS is attributed to misfolded SOD1, in the form of small aggregates in the nuclei of glial cells (mostly astrocytes) of the spinal cord from ALS patients (Forsberg et al. Glial nuclear aggregates of superoxide dismutase-1 are regularly present in patients with amyotrophic lateral sclerosis. Acta Neuropathol. 121:623 (2011)).

Clinical trials with experimental therapeutics are difficult because of the complexity of the disease and its manifestations, making assessment of efficacy problematic. Clinical trial endpoints that have been utilized over the past 20 years include the ALS Functional Rating Scale (ALSFRS-(R)); combined assessment of function and survival; time to death, tracheostomy or persistent assisted ventilation (DTP); forced vital capacity (% FVC); manual muscle test; and maximum voluntary isometric contraction (Petrov, D. 2017).

The advent of CRISPR/Cas systems and the programmable nature of these minimal systems has facilitated their use as a versatile technology for genomic manipulation and engineering. Particular CRISPR proteins are particularly well suited for such manipulation. For example CasX, has compact size and ease of delivery, and the nucleotide sequence encoding the protein is relatively short; an advantage for its incorporation into viral vectors for delivery into a cell.

There remains a critical need for developing treatments for ALS and other SOD1-related disorders using such technologies. Provided herein are compositions and methods for targeting SOD1 to the address the same.

SUMMARY

In some aspects, the present disclosure provides CasX: guide nucleic acid systems (CasX:gNA system) and methods used to modify the superoxide dismutase 1 (SOD1) gene in a cell, the SOD1 gene comprising one or more mutations in the encoded SOD1 protein or in the SOD1 regulatory element. In some embodiments, the CasX:gNA system comprises a CasX protein and a guide nucleic acid (gNA), wherein the gNA comprises a targeting sequence complementary to a target nucleic acid sequence comprising a superoxide dismutase 1 (SOD1) gene.

In some embodiments, the disclosure provides CasX:gNA systems comprising a reference CasX or a CasX variant sequence comprising any one of SEQ ID NOS: 1-3 or a sequence of SEQ ID NOs: 36-131, 208, 210, 212, 214, 216-229, 240, 242, 244, 246, 248, 250, 252, 254, 256 or 258, or a sequence having at least about 50%, at least about 60%, at least about 70%, at least about 80%, or at least about 90%, or at least about 95%, or at least about 96%, or at least about 97%, or at least about 98%, or at least about 99% sequence identity thereto.

In some embodiments, the CasX:gNA systems comprises a guide nucleic acid (gNA), wherein the gNA comprises a targeting sequence complementary to a SOD1 gene target nucleic acid sequence. In some embodiments, the SOD1 gene comprises one or more mutations. In some embodiments, the gNA of the CasX:gNA system has a scaffold comprising a sequence of Tables 2A or 2B or a sequence having at least about 50%, at least about 60%, at least about 70%, at least about 80%, or at least about 90%, or at least about 95%, or at least about 96%, or at least about 97%, or at least about 98%, or at least about 99% sequence identity to a sequence of Tables 2A or 2B. In some embodiments, the CasX:gNA system gNA comprises a targeting sequence of Table 3 (Table 3 provides the gNA targeting sequences for the SOD1 gene; the table is provided in FIG. 33, and is referred to as Table 3 throughout), or a sequence having at least about 50%, at least about 60%, at least about 70%, at least about 80%, or at least about 85%, or at least about 90%, or at least about 95% sequence identity to a sequence of Table 3. In some embodiments, the CasX:gNA system further comprises a second gNA, wherein the second gNA has a targeting sequence complementary to a different or overlapping portion of the target nucleic acid.

In other embodiments of the CasX:gNA system, the CasX molecule and the gNA molecule are associated together in a ribonuclear protein complex (RNP).

In some embodiments, the present disclosure provides gene editing pairs comprising the CasX proteins and gNAs described herein.

In some embodiments, the CasX:gNA system further comprises a donor template comprising a nucleic acid; for example a donor template encoding at least a portion of a SOD1 gene selected from the group consisting of a SOD1 exon, a SOD1 intron, a SOD1 intron-exon junction, and a regulatory element.

In other embodiments, the disclosure provides nucleic acids encoding or comprising the CasX:gNA systems of any of the embodiments described herein. In some embodiments, the disclosure provides vectors comprising the nucleic acids encoding any of the CasX:gNA system embodiments described herein. In other embodiments, the disclosure provides vectors comprising the nucleic acid encoding any of the CasX:gNA embodiments described herein and, optionally, further comprising a donor template nucleic acid wherein the donor template nucleic acid comprises a nucleic acid encoding at least a portion of a SOD1 gene. In other cases, the vector comprises a nucleic acid encoding a CasX fusion protein comprising a heterologous protein, a gNA, and the donor template. In some embodiments, the vector is an Adeno-Associated Viral (AAV) vector or is a lentivirus vector. In other embodiments, the disclosure provides a vector wherein the vector is a virus-like particle comprising an RNP of a CasX and gNA of any of the embodiments described herein and, optionally, a donor template.

In some embodiments, the disclosure provides a method of modifying a target nucleic acid sequence of a SOD1 gene comprising one or more mutations in a population of cells, wherein said method comprises contacting said cells with: a) the CasX:gNA system of any of the embodiments described herein; b) a nucleic acid encoding the CasX:gNA system embodiments of (a); c) a vector comprising the nucleic acid of (b); d) a VLP comprising the CasX:gNA system of (a); or e) combinations of two or more of (a)-(d) wherein the SOD1 target nucleic acid sequence of the cells is modified by the CasX protein. In some cases, the vector is an Adeno-Associated Viral (AAV) vector or is a lentiviral vector. In some embodiments of the method, the CasX and gNA are associated together in an RNP. In other embodiments, the method further comprises contacting the target nucleic acid with a donor template comprising at least a portion of a SOD1 gene coding the SOD1 protein or the SOD1 regulatory element for correcting (by knocking in) or knocking down or knocking out the mutant SOD1 gene. In still other embodiments of the method, the cells are contacted with a second gNA or a nucleic acid encoding the second gNA, wherein the second gNA has a targeting sequence complementary to a different or overlapping portion of the SOD1 target nucleic acid compared to the first gNA, resulting in an additional break in the SOD1 target nucleic acid of the cells of the population. In other embodiments, the method further comprises contacting the target nucleic acid with an additional CRISPR protein, or a nucleic acid encoding the additional CRISPR protein wherein the additional CRISPR protein is a CasX protein having a sequence different from the first CasX. In other cases, the additional CRISPR protein is not a CasX protein, and can be a Cas9, Cas12a, Cas12b, Cas12c, Cas12d (CasY), Cas13a, Cas13b, Cas13c, Cas13d, CasX, CasY, Cas14, Cpf1, C2c1, Csn2, Cas Phi, or sequence variants thereof.

In some cases, the modifying of the target nucleic acid occurs in a cell in vitro or ex vivo. In other cases, the modifying of the target nucleic acid occurs in a cell in vivo. In some embodiments, the cells of the population to be modified is are eukaryotic cells selected from the group consisting of rodent cells, mouse cells, rat cells, primate cells, non-human primate cells, and human cells. In some embodiments, the cells of the population are selected from the group consisting of embryonic stem (ES) cells, induced pluripotent stem cell (iPSC), central nervous system (CNS) cells, and peripheral nervous system (PNS) cells. In other embodiments, the cells of the population comprise neuron cells of the CNS or the PNS. In some embodiments, the neuron cells comprise spinal motor neuron cells or oligodendrocyte cells. In other embodiments, the cells of the population are glial cells or Schwann cells of the PNS. In some embodiments, the modification of the target nucleic acid comprises correction of the mutation to the wild-type sequence.

In some embodiments of the method of modifying a SOD1 target nucleic acid sequence of a cell, the vector is administered to a subject at a therapeutically effective dose. The subject can be a rodent, a mouse, a rat, a non-human primate, or a human. The dose can be administered by a route of administration selected from the group consisting of intraparenchymal, intravenous, intra-arterial, intracerebroventricular, intracisternal, intrathecal, intracranial, lumbar, and intraperitoneal routes.

In other embodiments, the disclosure provides populations of cells modified by the foregoing methods. In some embodiments, the cell is a eukaryotic cell selected from the group consisting of a rodent cell, a mouse cell, a rat cell, a primate cell, a non-human primate cell, and a human cell. The cell can be a cell of the central nervous system (CNS) or peripheral nervous system (PNS). In some embodiments, the cells are autologous with respect to the subject to be administered the cell. In other embodiments, the cells are allogeneic with respect to the subject to be administered the cell. In some embodiments, the cell is a neuron, a spinal motor neuron, a glial cell, an oligodendrocyte, or a Schwann cell. In some embodiments, the disclosure provides a method of treating a SOD1-related disorder in a subject in need thereof, comprising administering to the subject an effective amount of the cells of the foregoing.

In other embodiments, the disclosure provides a method of treating a SOD1-related disorder in a subject in need thereof, comprising modifying a SOD1 gene having one or more mutations in the cells of the subject, the modifying comprising contacted said cells with a therapeutically effective dose of: a) the CasX:gNA system of any of the embodiments described herein; b) a nucleic acid encoding the CasX:gNA system embodiments of (a); c) a vector comprising the nucleic acid of (b); d) a VLP comprising the CasX:gNA system of (a); or e) combinations of two or more of (a)-(d) wherein the SOD1 target nucleic acid sequence of the cells is modified by the CasX protein. In some cases, the vector encodes or comprises the CasX protein and the gNA, and optionally further comprises the donor template. In some embodiments, the vector is selected from the group consisting of an Adeno-Associated Viral (AAV) vector, a retroviral vector, or a virus-like particle. In some embodiments, the subject is selected from the group consisting of mouse, rat, non-human primate, and human. In some embodiments, the vector is administered to the subject by a route of administration selected from the group consisting of intraparenchymal, intravenous, intra-arterial, intracerebroventricular, intracisternal, intrathecal, intracranial, lumbar, and intraperitoneal routes. In other embodiments, the SOD1-related disorder is amyotrophic lateral sclerosis (ALS). In some embodiments, the method results in improvement in at least one clinically-relevant endpoint in the subject selected from the group consisting of ALS Functional Rating Scale (ALSFRS-(R)), combined assessment of function and survival, duration of response, time to death, time to tracheostomy, time to persistent assisted ventilation (DTP), forced vital capacity (% FVC); manual muscle test, maximum voluntary isometric contraction, duration of response, progression-free survival, time to progression of disease, and time-to-treatment failure. In other embodiments, the method results in improvement in at least two clinically-relevant endpoints in the subject.

In some embodiments, the present disclosure provides kits comprising the nucleic acids, vectors, CasX proteins, gNAs and gene editing pairs described herein.

In another aspect, provided herein are compositions comprising gene editing pairs, or compositions of vectors comprising or encoding gene editing pairs for use as a medicament for the treatment of a subject having a SOD1 related disorder.

In another aspect, provided herein are CasX:gNA systems, compositions comprising CasX:gNA systems, vectors comprising or encoding CasX:gNA systems, VLP comprising CasX:gNA systems, or populations of cells edited using the CasX:gNA systems for use as a medicament for the treatment of a SOD1-related disorder.

In another aspect, provided herein are CasX:gNA systems, composition comprising g CasX:gNA systems, or vectors comprising or encoding CasX:gNA systems, VLP comprising CasX:gNA systems, populations of cells edited using the CasX:gNA systems, for use in a method of treatment of a SOD-1 related disorder in a subject in need thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

The contents of PCT/US2020/036505, filed on Jun. 5, 2020, which discloses CasX variants and gNA variants, are hereby incorporated by reference in their entirety.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

FIG. 33 provides Table 3, referred to herein throughout, listing SOD1 spacer sequences (SEQ ID NOs: 372-2100, 2281-12495).

DETAILED DESCRIPTION

Figure 1:
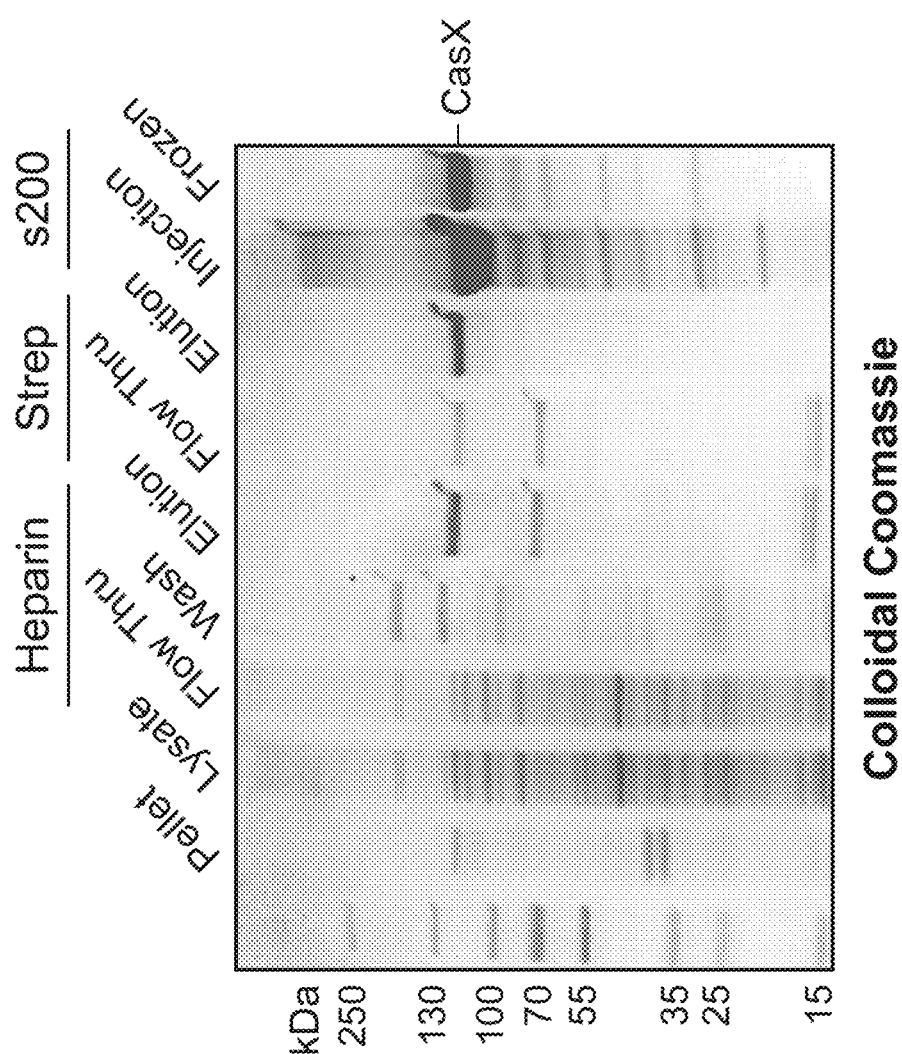
FIG. 1 shows an SDS-PAGE gel of StX2 purification fractions visualized by colloidal Coomassie staining, as described in Example 1.

While exemplary embodiments have been shown and described herein, it will be obvious to those skilled in the art that such embodiments are provided by way of example only. Numerous variations, changes, and substitutions will now occur to those skilled in the art without departing from the inventions claimed herein. It should be understood that various alternatives to the embodiments described herein may be employed in practicing the embodiments of the disclosure. It is intended that the claims define the scope of the invention and that methods and structures within the scope of these claims and their equivalents be covered thereby.

Unless otherwise defined, all technical and scientific terms used herein have the same meaning as commonly understood by one of ordinary skill in the art to which this invention belongs. Although methods and materials similar or equivalent to those described herein can be used in the practice or testing of the present embodiments, suitable methods and materials are described below. In case of conflict, the patent specification, including definitions, will control. In addition, the materials, methods, and examples are illustrative only and not intended to be limiting. Numerous variations, changes, and substitutions will now occur to those skilled in the art without departing from the invention.

Definitions

The terms "polynucleotide" and "nucleic acid," used interchangeably herein, refer to a polymeric form of nucleotides of any length, either ribonucleotides or deoxyribonucleotides. Thus, terms "polynucleotide" and "nucleic acid" encompass single-stranded DNA; double-stranded DNA; multi-stranded DNA; single-stranded RNA; double-stranded RNA; multi-stranded RNA; genomic DNA; cDNA; DNA-RNA hybrids; and a polymer comprising purine and pyrimidine bases or other natural, chemically or biochemically modified, non-natural, or derivatized nucleotide bases.

"Hybridizable" or "complementary" are used interchangeably to mean that a nucleic acid (e.g., RNA, DNA) comprises a sequence of nucleotides that enables it to non-covalently bind, i.e., form Watson-Crick base pairs and/or G/U base pairs, "anneal", or "hybridize," to another nucleic acid in a sequence-specific, antiparallel, manner (i.e., a nucleic acid specifically binds to a complementary nucleic acid) under the appropriate in vitro and/or in vivo conditions of temperature and solution ionic strength. It is understood that the sequence of a polynucleotide need not be 100% complementary to that of its target nucleic acid to be specifically hybridizable; it can have at least about 70%, at least about 80%, or at least about 90%, or at least about 95% sequence identity and still hybridize to the target nucleic acid. Moreover, a polynucleotide may hybridize over one or more segments such that intervening or adjacent segments are not involved in the hybridization event (e.g., a loop structure or hairpin structure, a 'bulge', 'bubble' and the like).

A "gene," for the purposes of the present disclosure, includes a DNA region encoding a gene product (e.g., a protein, RNA), as well as all DNA regions which regulate the production of the gene product, whether or not such regulatory sequences are adjacent to coding and/or transcribed sequences. Accordingly, a gene may include regulatory sequences including, but not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. Coding sequences encode a gene product upon transcription or transcription and translation; the coding sequences of the disclosure may comprise fragments and need not contain a full-length open reading frame. A gene can include both the strand that is transcribed, e.g. the strand containing the coding sequence, as well as the complementary strand.

The term "downstream" refers to a nucleotide sequence that is located 3' to a reference nucleotide sequence. In certain embodiments, downstream nucleotide sequences relate to sequences that follow the starting point of transcription. For example, the translation initiation codon of a gene is located downstream of the start site of transcription.

The term "upstream" refers to a nucleotide sequence that is located 5' to a reference nucleotide sequence. In certain embodiments, upstream nucleotide sequences relate to sequences that are located on the 5' side of a coding region or starting point of transcription. For example, most promoters are located upstream of the start site of transcription.

The term "regulatory element" is used interchangeably herein with the term "regulatory sequence," and is intended to include promoters, enhancers, and other expression regulatory elements (e.g. transcription termination signals, such as polyadenylation signals and poly-U sequences). Exemplary regulatory elements include a transcription promoter such as, but not limited to, CMV, CMV+intron A, SV40, RSV, HIV-Ltr, elongation factor 1 alpha (EF1α), MMLV-ltr, internal ribosome entry site (IRES) or P2A peptide to permit translation of multiple genes from a single transcript, metallothionein, a transcription enhancer element, a transcription termination signal, polyadenylation sequences, sequences for optimization of initiation of translation, and translation termination sequences. It will be understood that the choice of the appropriate regulatory element will depend on the encoded component to be expressed (e.g., protein or RNA) or whether the nucleic acid comprises multiple components that require different polymerases or are not intended to be expressed as a fusion protein.

The term "promoter" refers to a DNA sequence that contains an RNA polymerase binding site, transcription start site, TATA box, and/or B recognition element and assists or promotes the transcription and expression of an associated transcribable polynucleotide sequence and/or gene (or transgene). A promoter can be synthetically produced or can be derived from a known or naturally occurring promoter sequence or another promoter sequence. A promoter can be proximal or distal to the gene to be transcribed. A promoter can also include a chimeric promoter comprising a combination of two or more heterologous sequences to confer certain properties. A promoter of the present disclosure can include variants of promoter sequences that are similar in composition, but not identical to, other promoter sequence(s) known or provided herein. A promoter can be classified according to criteria relating to the pattern of expression of an associated coding or transcribable sequence or gene operably linked to the promoter, such as constitutive.

The term "enhancer" refers to regulatory element DNA sequences that, when bound by specific proteins called transcription factors, regulate the expression of an associated gene. Enhancers may be located in the intron of the gene, or 5' or 3' of the coding sequence of the gene. Enhancers may be proximal to the gene (i.e., within a few tens or hundreds of base pairs (bp) of the promoter), or may be located distal to the gene (i.e., thousands of bp, hundreds of thousands of bp, or even millions of bp away from the promoter). A single gene may be regulated by more than one enhancer, all of which are envisaged as within the scope of the instant disclosure.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "enhancers" and "promoters", above).

The term "recombinant polynucleotide" or "recombinant nucleic acid" refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

Similarly, the term "recombinant polypeptide" or "recombinant protein" refers to a polypeptide or protein which is not naturally occurring, e.g., is made by the artificial combination of two otherwise separated segments of amino sequence through human intervention. Thus, e.g., a protein that comprises a heterologous amino acid sequence is recombinant.

As used herein, the term "contacting" means establishing a physical connection between two or more entities. For example, contacting a target nucleic acid with a guide nucleic acid means that the target nucleic acid and the guide nucleic acid are made to share a physical connection; e.g., can hybridize if the sequences share sequence similarity.

"Dissociation constant", or "$K_d$", are used interchangeably and mean the affinity between a ligand "L" and a protein "P"; i.e., how tightly a ligand binds to a particular protein. It can be calculated using the formula $K_d=[L]$

[P]/[LP], where [P], [L] and [LP] represent molar concentrations of the protein, ligand and complex, respectively.

The disclosure provides compositions and methods useful for editing a target nucleic acid sequence. As used herein "editing" is used interchangeably with "modifying" and includes but is not limited to cleaving, nicking, deleting, knocking in, knocking out, and the like.

The term "knock-out" refers to the elimination of a gene or the expression of a gene. For example, a gene can be knocked out by either a deletion or an addition of a nucleotide sequence that leads to a disruption of the reading frame. As another example, a gene may be knocked out by replacing a part of the gene with an irrelevant sequence. The term "knock-down" as used herein refers to reduction in the expression of a gene or its gene product(s). As a result of a gene knock-down, the protein activity or function may be attenuated or the protein levels may be reduced or eliminated.

As used herein, "homology-directed repair" (HDR) refers to the form of DNA repair that takes place during repair of double-strand breaks in cells. This process requires nucleotide sequence homology, and uses a donor template to repair or knock-out a target DNA, and leads to the transfer of genetic information from the donor (e.g., such as the donor template) to the target. Homology-directed repair can result in an alteration of the sequence of the target nucleic acid sequence by insertion, deletion, or mutation if the donor template differs from the target DNA sequence and part or all of the sequence of the donor template is incorporated into the target DNA.

As used herein, "non-homologous end joining" (NHEJ) refers to the repair of double-strand breaks in DNA by direct ligation of the break ends to one another without the need for a homologous template (in contrast to homology-directed repair, which requires a homologous sequence to guide repair). NHEJ often results in the loss (deletion) of nucleotide sequence near the site of the double-strand break.

As used herein "micro-homology mediated end joining" (MMEJ) refers to a mutagenic DSB repair mechanism, which always associates with deletions flanking the break sites without the need for a homologous template (in contrast to homology-directed repair, which requires a homologous sequence to guide repair). MMEJ often results in the loss (deletion) of nucleotide sequence near the site of the double-strand break.

A polynucleotide or polypeptide (or protein) has a certain percent "sequence similarity" or "sequence identity" to another polynucleotide or polypeptide, meaning that, when aligned, that percentage of bases or amino acids are the same, and in the same relative position, when comparing the two sequences. Sequence similarity (sometimes referred to as percent similarity, percent identity, or homology) can be determined in a number of different manners. To determine sequence similarity, sequences can be aligned using the methods and computer programs that are known in the art, including BLAST, available over the world wide web at ncbi.nlm.nih.gov/BLAST. Percent complementarity between particular stretches of nucleic acid sequences within nucleic acids can be determined using any convenient method. Example methods include BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), e.g., using default settings, which uses the algorithm of Smith and Waterman (Adv. Appl. Math., 1981, 2, 482-489).

The terms "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence.

A "vector" or "expression vector" is a replicon, such as plasmid, phage, virus, or cosmid, to which another DNA segment, i.e., an "insert", may be attached so as to bring about the replication or expression of the attached segment in a cell.

The term "naturally-occurring" or "unmodified" or "wild type" as used herein as applied to a nucleic acid, a polypeptide, a cell, or an organism, refers to a nucleic acid, polypeptide, cell, or organism that is found in nature.

As used herein, a "mutation" refers to an insertion, deletion, substitution, duplication, or inversion of one or more amino acids or nucleotides as compared to a wild-type or reference amino acid sequence or to a wild-type or reference nucleotide sequence.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

A "host cell," as used herein, denotes a eukaryotic cell, a prokaryotic cell, or a cell from a multicellular organism (e.g., a cell line) cultured as a unicellular entity, which eukaryotic or prokaryotic cells are used as recipients for a nucleic acid (e.g., an expression vector), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acid substitution groups are: valine-leucine-isoleucine, phenylalanine-tyrosine, lysine-arginine, alanine-valine, and asparagine-glutamine.

As used herein, "treatment" or "treating," are used interchangeably herein and refer to an approach for obtaining beneficial or desired results, including but not limited to a therapeutic benefit and/or a prophylactic benefit. By therapeutic benefit is meant eradication or amelioration of the underlying disorder or disease being treated. A therapeutic benefit can also be achieved with the eradication or amelioration of one or more of the symptoms or an improvement in one or more clinical parameters associated with the underlying disease such that an improvement is observed in the subject, notwithstanding that the subject may still be afflicted with the underlying disorder.

The terms "therapeutically effective amount" and "therapeutically effective dose", as used herein, refer to an amount of a drug or a biologic, alone or as a part of a composition, that is capable of having any detectable, beneficial effect on any symptom, aspect, measured parameter or characteristics of a disease state or condition when administered in one or repeated doses to a subject such as a human or an experimental animal. Such effect need not be absolute to be beneficial.

As used herein, "administering" is meant a method of giving a dosage of a compound (e.g., a composition of the disclosure) or a composition (e.g., a pharmaceutical composition) to a subject.

A "subject" is a mammal. Mammals include, but are not limited to, domesticated animals, non-human primates, humans, rabbits, mice, rats and other rodents.

All publications, patents, and patent applications mentioned in this specification are herein incorporated by reference to the same extent as if each individual publication, patent, or patent application was specifically and individually indicated to be incorporated by reference.

I. General Methods

The practice of the present invention employs, unless otherwise indicated, conventional techniques of immunology, biochemistry, chemistry, molecular biology, microbiology, cell biology, genomics and recombinant DNA, which can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kdplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

Where a range of values is provided, it is understood that endpoints are included and that each intervening value, to the tenth of the unit of the lower limit unless the context clearly dictates otherwise, between the upper and lower limit of that range and any other stated or intervening value in that stated range, is encompassed. The upper and lower limits of these smaller ranges may independently be included in the smaller ranges, and are also encompassed, subject to any specifically excluded limit in the stated range. Where the stated range includes one or both of the limits, ranges excluding either or both of those included limits are also included.

Unless defined otherwise, all technical and scientific terms used herein have the same meaning as commonly understood by one of ordinary skill in the art to which this invention belongs. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise.

It will be appreciated that certain features of the disclosure, which are, for clarity, described in the context of separate embodiments, may also be provided in combination in a single embodiment. In other cases, various features of the disclosure, which are, for brevity, described in the context of a single embodiment, may also be provided separately or in any suitable sub-combination. It is intended that all combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

II. CasX:gNA Systems for Genetic Editing of SOD1 Genes

In a first aspect, the present disclosure provides systems comprising a CRISPR nuclease and one or more guide nucleic acids (gNA) that have utility in genome editing of eukaryotic cells. In some embodiments, the CRISPR nuclease is selected from the group consisting of Cas9, Cas12a, Cas12b, Cas12c, Cas12d (CasY), CasX, Cas13a, Cas13b, Cas13c, Cas13d, CasX, CasY, Cas14, Cpf1, C2c1, Csn2, and Cas Phi. In some embodiments, the CRISPR nuclease is a is a Type V CRISPR nuclease. In some embodiments, the present disclosure provides CasX:gNA systems comprising a CasX protein and one or more guide nucleic acids (gNA) for use in modifying a SOD1 gene (collectively referred to herein as the "target nucleic acid", inclusive of coding and non-coding regions). The SOD1 gene to be modified may comprise one or more mutations in the sequence region selected from the group consisting of a SOD1 intron, a SOD1 exon, a SOD1 intron-exon junction, a SOD1 regulatory element, and an intergenic region.

In some embodiments, the CasX:gNA systems are specifically designed to modify the SOD1 gene in eukaryotic cells. Generally, any portion of the SOD1 target nucleic acid can be targeted using the programmable compositions and methods provided herein. In some embodiments, the disclosure provides CasX:gNA systems comprising one or more of a CasX protein, one or more guide nucleic acids (gNA) and, optionally, one or more donor template nucleic acids. In other cases, the CasX:gNA system is delivered to a cell to be modified using a vector, which can comprise either nucleic acids encoding the components or deliver the CasX and gNA (and optionally the donor template) in their functional form. Each of these components and their use in the editing of SOD1 target nucleic acid is described herein, below.

In some cases, a gNA and a CasX protein of the disclosure can form a complex and bind via non-covalent interactions, referred to herein as a ribonucleoprotein (RNP) complex. As provided herein, in some embodiments, the use of a pre-complexed CasX:gNA may confer advantages in the delivery of the system components to a cell or target nucleic acid for editing of the target nucleic acid. For example, in the RNP, the gNA can provide target specificity to the complex by including a guide sequence having a nucleotide sequence that is complementary to a sequence of a target nucleic acid while the CasX protein of the pre-complexed CasX:gNA provides the site-specific activity that is guided to a target site (e.g., stabilized at a target site) within a target nucleic acid sequence (e.g., a SOD1 gene to be modified) by virtue of its association with the guide NA. The CasX protein of the complex provides the site-specific activities of the complex such as cleavage or nicking of the target nucleic acid sequence by the CasX protein and/or an activity provided by the fusion partner in the case of a chimeric CasX protein. The CasX proteins and gNA components of the CasX:gNA systems and their features are described more fully, below.

In some embodiments, the CasX:gNA systems utilized in the editing of the SOD1 gene can further comprise a donor template comprising all or at least a portion of a gene encoding a SOD1 protein or encoding a SOD1 regulatory element wherein the donor template comprises one or more mutations for either knocking out or knocking down (described more fully, below) the SOD1 gene. In other cases, the CasX:gNA systems can further comprise a donor template for the introduction (or knocking in) of all or a portion of an open reading frame encoding a protein for the production of a wild-type SOD1 protein in the target cell or a sequence for correcting the one or more mutations of the SOD1 gene. In a particular embodiment of the foregoing, gNAs targeting the upstream sequence Exon 1 and Intron 1 can be used to introduce breaks that permit the insertion of full length cDNA encoding the SOD1 protein, replacing the mutated endogenous SOD1 gene and restoring protein expression. In other embodiments, the CasX:gNA systems can further comprise a donor template for the introduction of a regulatory element to correct the one or more mutations of the SOD1 regulatory element. In some embodiments, the donor polynucleotide comprises at least about 10, at least about 50, at least about 100, or at least about 200, or at least about 300, or at least about 400, or at least about 500, or at least about 600, or at least about 700, or at least about 800, or at least about 900, or at least about 1000, or at least about 10,000, or at least about 15,000 nucleotides of a SOD1 gene, wherein the SOD1 gene portion is selected from the group consisting of a SOD1 exon, a SOD1 intron, a SOD1 intron-exon junction, a SOD1 regulatory element and an intergenic region; either a wild-type sequence or comprising one or more mutations depending on whether the modification is to knock-down/knock-out or knock-in gene function. In other embodiments, the donor polynucleotide comprises at least about 10 to about 10,000 nucleotides, or at least about 100 to about 8000 nucleotides, or at least about 400 to about 6000 nucleotides, or at least about 600 to about 4000 nucleotides, or at least about 1000 to about 2000 nucleotides of a SOD1 gene. In some embodiments, the donor template is a single stranded DNA template or a single stranded RNA template. In other embodiments, the donor template is a double stranded DNA template.

The SOD1 gene encodes superoxide dismutase-1 (EC 1.15.1.1), a cytoplasmic antioxidant enzyme that metabolizes superoxide radicals to molecular oxygen and hydrogen peroxide, thus providing a defense against oxygen toxicity (Niwa et al., JBC 282:28087 (2007)). The SOD1 gene and its regulatory element is defined as the sequence that spans chr21:31659622-31668931 of the human genome (GRCh38/hg38) (the notation refers to the chromosome 21 (chr21), starting at the 31,659,622 bp of that chromosome, and extending to the 31,668,931 bp of that chromosome). The coding region consists of five exons interrupted by four introns.

In some cases, the SOD1 regulatory element is 5' of the SOD1 gene. In other cases, the SOD1 regulatory element is 3' of the SOD1 gene. In some embodiments, a SOD1 regulatory element comprises a 5' untranslated region (UTR) of the SOD1 gene, while in other embodiments, a SOD1 regulatory element comprises a 3'UTR of the SOD1 gene.

The SOD1 regulatory element comprises a promoter, and in some cases further comprises an enhancer.

Soluble cytoplasmic SOD1 is a copper- and zinc-containing enzyme that is highly conserved throughout evolution and makes up 1-2% of the total soluble protein content in the central nervous system (Pardo Calif., et al., Cleveland D W. Superoxide dismutase is an abundant component in cell bodies, dendrites, and axons of motor neurons and in a subset of other neurons (Proc Natl Acad Sci USA. 92:954 (1995); Sherman et al., Nucleotide sequence and expression of human chromosome 21-encoded superoxide dismutase mRNA. Proc. Natl. Acad. Sci. U.S.A. 80:5465 (1983)).

The human SOD1 gene (HGNC:11179; see also GenBank Accession No. CAG46542.1) encodes a protein having the sequence (SEQ ID NO: 100)
MATKAVCVLKGDGPVQGIINFEQKESNGPVKVWGSIKGLTEGLHGFHVHE

FGDNTAGCTSAGPHFNPLSRKHGGPKDEERHVGDLGNVTADKDGVADVSI

EDSVISLSGDHCIIGRTLVVHEKADDLGKGGNEESTKTGNAGSRLACGVI

GIAQ.

Although human SOD1 contains 154 amino acids, the start methionine is cleaved post-translationally, followed by N-acetylation of the first alanine, therefore making the number of actual amino acids in SOD1 153 (Stevens, J C, et al. Modification of Superoxide Dismutase 1 (SOD1) Properties by a GFP Tag—Implications for Research into Amyotrophic Lateral Sclerosis (ALS). PLoS ONE 5(3): e9541 (2010)). At least 170 mutations across the SOD1 gene have been found to cause amyotrophic lateral sclerosis (ALS) (Pochet, R. Genetics and ALS: Cause for Optimism. Cerebrum cer-05-17 (2017)). Table 1 provides representative examples of SOD1 mutations known to contribute to, or that are associated with ALS in a subject.

TABLE 1

| ALS-associated mutations in SOD1 | | |
|---|---|---|
| SOD1 Amino Acid Position* | WT Amino Acid** | Mutant Amino Acid*** |
| 4 | A | S |
| 4 | A | T |
| 4 | A | V |
| 6 | C | F |
| 7 | V | E |
| 8 | L | Q |
| 8 | L | V |
| 12 | G | R |
| 14 | V | G |
| 14 | V | M |
| 16 | G | S |
| 20 | F | C |
| 21 | E | G |
| 21 | E | K |
| 22 | Q | L |
| 37 | G | R |
| 38 | L | R |
| 38 | L | V |
| 41 | G | D |
| 41 | G | S |
| 43 | H | R |
| 45 | F | C |
| 46 | H | R |
| 48 | H | Q |
| 48 | H | R |
| 49 | E | K |

TABLE 1-continued

ALS-associated mutations in SOD1

| SOD1 Amino Acid Position* | WT Amino Acid** | Mutant Amino Acid*** |
|---|---|---|
| 54 | T | R |
| 65 | N | S |
| 67 | L | P |
| 67 | L | R |
| 72 | G | S |
| 76 | D | Y |
| 80 | H | A |
| 84 | L | F |
| 84 | L | V |
| 85 | G | R |
| 86 | N | S |
| 87 | V | A |
| 89 | A | T |
| 89 | A | V |
| 90 | D | A |
| 90 | D | V |
| 93 | G | A |
| 93 | G | C |
| 93 | G | D |
| 93 | G | R |
| 93 | G | V |
| 95 | A | G |
| 97 | V | M |
| 100 | E | G |
| 100 | E | K |
| 101 | D | G |
| 101 | D | N |
| 104 | I | F |
| 105 | S | L |
| 106 | L | V |
| 108 | G | V |
| 111 | C | Y |
| 112 | I | M |
| 112 | I | T |
| 113 | I | T |
| 114 | G | A |
| 115 | R | G |
| 118 | V | L |
| 124 | D | G |
| 124 | D | V |
| 125 | D | H |
| 126 | L | S |
| 134 | S | N |
| 139 | N | K |
| 144 | L | F |
| 144 | L | S |
| 145 | A | T |
| 146 | C | R |
| 147 | G | R |
| 148 | V | G |
| 148 | V | I |
| 149 | I | T |
| 151 | I | T |

*Amino acid position relative to SEQ ID NO: 100 without the N-terminal methionine
**Single letter code for wild-type amino acid
***Single letter code for mutant amino acid In some cases, the mutation of the SOD1 gene in subjects with a SOD1-related disease is an insertion, deletion, substitution, duplication, or inversion of one or more nucleotides as compared to the wild-type sequence. In one case, the mutation is a gain of function mutation. In other embodiments, the mutation is a loss of function mutation. In some embodiments, the mutation is a mutation of the SOD1 protein of SEQ ID NO:100 selected from the group of amino acid substitutions consisting of A4S, A4T, A4V, C6F, V7E, L8Q, L8V, G12R, V14G, V14M, G16S, F20C, E21G, E21K, Q22L, G37R, L38R, L38V, G41D, G41S, H43R, F45C, H46R, H48Q, H48R, E49K, T54R, N65S, L67P, L67R, G72S, D76Y, H80A, L84F, L84V, G85R, N86S, V87A, A89T, A89V, D90A, D90V, G93A, G93C, G93D, G93R, G93V, A95G, V97M, E100G, E100K, D101G, D101N, I104F, S105L, L106V, G108V, C111Y, I112M, I112T, I113T, G114A, R115G, V118L, D124G, D124V, D125H, L126S, S134N, N139K, L144F, L144S, A145T, C146R, G147R, V148G, V148I, I149T, I151T, and one or more amino acid substitutions of SEQ ID NO:100 that disrupt the function or expression of the SOD1 protein, or is selected from a combination thereof. In a particular embodiment, the SOD1 protein comprises a mutation selected from an A4V mutation of SEQ ID NO:100, a D90A mutation of SEQ ID NO:100, and/or a G93A mutation of SEQ ID NO:100. The present disclosure provides compositions and methods for the editing of nucleic acids comprising these mutations.

III. Guide Nucleic Acids of the Systems for Genetic Editing

In another aspect, the disclosure relates to a guide nucleic acid (gNA) comprising a targeting sequence complementary to a target nucleic acid sequence in the target strand of a gene encoding a SOD1 protein, wherein the gNA is capable of forming a complex with a CRISPR protein that is specific to a protospacer adjacent motif (PAM) sequence comprising a TC motif in the complementary non-target strand, and wherein the PAM sequence is located 1 nucleotide 5' of the sequence in the non-target strand that is complementary to the target nucleic acid sequence in the target strand.

In another aspect, the disclosure relates to guide nucleic acids (gNA) utilized in the CasX:gNA systems that have utility in genome editing a SOD1 gene in a cell. In some embodiments, the present disclosure provides guide nucleic acids capable of forming a RNP complex with a CasX protein in which the gNA binds to the CasX protein, and wherein the targeting sequence (or spacer, described more fully, below) of the gNA is complementary to, and therefore is capable of hybridizing with the SOD1 gene sequence. In some embodiments, the gNA is a deoxyribonucleic acid molecule ("gDNA"). In some embodiments, the gNA is a ribonucleic acid molecule ("gRNA"). In some embodiments, the gNA is a chimera, and comprises both DNA and RNA (a "chimera").

The present disclosure provides specifically-designed guide nucleic acids ("gNAs") with targeting sequences that are complementary to, and are therefore able to hybridize with either strand of the SOD1 gene as a component of the gene editing CasX:gNA systems. As described more fully, below, representative, but non-limiting examples of targeting sequences to the SOD1 target nucleic acid are presented in Table 3 (Table 3 is provided in FIG. 33). It is envisioned that in some embodiments, multiple gNAs (e.g., multiple gRNAs) are delivered in the CasX:gNA system for the modification of a gene encoding one or more regions of a SOD1 protein, a non-coding region of the SOD1 gene, or a SOD1 regulatory element. For example, when a deletion or a knock-down/knock-out of a SOD1 intron is desired, a pair of gNAs with targeting sequences to different or overlapping regions of the target nucleic acid sequence can be used in order to bind and the CasX to cleave at two different or overlapping sites within or proximal to the intron of the gene, which is then edited by non-homologous end joining (NHEJ), homology-directed repair (HDR, which can include, for example, insertion of a donor template to replace all or a portion of the SOD1 intron), homology-independent targeted integration (HITI), micro-homology mediated end joining (MMEJ), single strand annealing (SSA) or base excision repair (BER).

a. Reference gNA and gNA Variants

In some embodiments, a gNA of the present disclosure comprises a sequence of a naturally-occurring gNA (a "reference gNA"). In other cases, a reference gNA of the disclosure may be subjected to one or more mutagenesis methods, such as the mutagenesis methods described herein, which may include Deep Mutational Evolution (DME), deep mutational scanning (DMS), error prone PCR, cassette mutagenesis, random mutagenesis, staggered extension PCR, gene shuffling, or domain swapping, in order to generate one or more gNA variants with enhanced or varied properties relative to the reference gNA. gNA variants also include variants comprising one or more exogenous sequences, for example fused to either the 5' or 3' end of the gNA, or inserted internally. The activity of reference gNAs may be used as a benchmark against which the activity of gNA variants are compared, thereby measuring improvements in function or other characteristics of the gNA variants. In other embodiments, a reference gNA may be subjected to one or more deliberate, targeted mutations in order to produce a gNA variant, for example a rationally designed variant. As used herein, the terms gNA, gRNA, and gDNA cover naturally-occurring molecules, as well as sequence variants. Thus, in some embodiments, the gNA is a deoxyribonucleic acid molecule ("gDNA"); in some embodiments, the gNA is a ribonucleic acid molecule ("gRNA"), and in other embodiments, the gNA is a chimera, and comprises both DNA and RNA.

The gNAs of the disclosure comprise two segments: a targeting sequence and a protein-binding segment. The targeting segment of a gNA includes a nucleotide sequence (referred to interchangeably as a guide sequence, a spacer, a targeting sequence, or a targeting region) that is complementary to (and therefore hybridizes with) a specific sequence (a target site) within the target nucleic acid sequence (e.g., a target ssRNA, a target ssDNA, a strand of a double stranded target DNA, etc.), described more fully below. The targeting sequence of a gNA is capable of binding to a target nucleic acid sequence, including a coding sequence, a complement of a coding sequence, a non-coding sequence, and to regulatory elements. The protein-binding segment (or "protein-binding sequence") interacts with (e.g., binds to) a CasX protein. The protein-binding segment is alternatively referred to herein as a "scaffold", which is comprised of several regions, described more fully, below. In some embodiments, the targeting sequence and scaffold each include complementary stretches of nucleotides that hybridize to one another to form a double stranded duplex (dsRNA duplex for a gRNA). Site-specific binding and/or cleavage of a target nucleic acid sequence (e.g., genomic DNA) by the CasX:gNA can occur at one or more locations (e.g., a sequence of a target nucleic acid) determined by base-pairing complementarity between the targeting sequence of the gNA and the target nucleic acid sequence.

The targeting sequence of a gNA is capable of binding to a SOD1 target nucleic acid sequence, including a coding sequence, a complement of a coding sequence, a non-coding sequence, and to regulatory elements. The gNA scaffold (or "protein-binding sequence") interacts with (e.g., binds to) a CasX protein, forming an RNP (described more fully, below). In some embodiments, the targeting sequence and scaffold each include complementary stretches of nucleotides that hybridize to one another to form a double stranded duplex (dsRNA duplex for a dgRNA). Site-specific binding and/or cleavage of a target nucleic acid sequence (e.g., genomic DNA) by the CasX protein can occur at one or more locations (e.g., a sequence of a target nucleic acid) determined by base-pairing complementarity between the targeting sequence of the gNA and the target nucleic acid sequence. Thus, for example, the gNA of the disclosure have sequences complementarity to and therefore can hybridize to a sequence in a eukaryotic cell, e.g., a eukaryotic nucleic acid (e.g., a eukaryotic chromosome, chromosomal sequence, a eukaryotic RNA, etc.) that is adjacent to a sequence complementary to a TC PAM motif or a PAM sequence, such as ATC, CTC, GTC, or TTC.

In the context of nucleic acids, cleavage refers to the breakage of the covalent backbone of a nucleic acid molecule; either DNA or RNA. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends.

In some embodiments, the disclosure provides gene editing pairs of a CasX and a gNA of any of the embodiments described herein that are capable of being bound together prior to their use for gene editing and, thus, are "pre-complexed" as a ribonuclear protein complex (RNP). The use of a pre-complexed RNP confers advantages in the delivery of the system components to a cell or target nucleic acid sequence for editing of the target nucleic acid sequence. The CasX protein of the RNP provides the site-specific activity that is guided to a target site (e.g., stabilized at a target site) within a target nucleic acid sequence by virtue of its association with the guide RNA comprising a targeting sequence capable of hybridizing to the target nucleic acid sequence.

In some embodiments, wherein the gNA is a gRNA, the term "targeter" or "targeter RNA" is used herein to refer to a crRNA-like molecule (crRNA: "CRISPR RNA") of a CasX dual guide RNA (and therefore of a CasX single guide RNA when the "activator" and the "targeter" are linked together, e.g., by intervening nucleotides). Thus, for example, a CasX guide RNA (dgRNA or sgRNA) comprises a guide sequence and a duplex-forming segment of a crRNA, which can also be referred to as a crRNA repeat. Because the sequence of a guide sequence hybridizes with a sequence of a SOD1 target nucleic acid sequence, a targeter can be modified by a user to hybridize with a specific target nucleic acid sequence. Thus, in some cases, the sequence of a targeter may be a non-naturally occurring sequence. In other cases, the sequence of a targeter may be a naturally-occurring sequence, derived from the gene to be edited. In the case of a dual guide RNA, the targeter and the activator each have a duplex-forming segment, where the duplex forming segment of the targeter and the duplex-forming segment of the activator have complementarity with one another and hybridize to one another to form a double stranded duplex (dsRNA duplex for a gRNA). In some embodiments, a targeter comprises both the guide sequence of the guide RNA and a stretch of nucleotides that forms one half of the dsRNA duplex of the protein-binding segment of the gRNA. A corresponding tracrRNA-like molecule (activator) also comprises a duplex-forming stretch of nucleotides that forms the other half of the dsRNA duplex of the protein-binding segment of the CasX guide RNA. Thus, a targeter and an activator, as a corresponding pair, hybridize to form a CasX dual guide NA, referred to herein as a "dual guide NA", a "dual-molecule gNA", a "dgNA", a "double-molecule guide NA", or a "two-molecule guide NA".

In some embodiments, the activator and targeter of the reference gNA are covalently linked to one another and comprise a single molecule, referred to herein as a "single-molecule gNA," "one-molecule guide NA," "single guide NA", "single guide RNA", a "single-molecule guide RNA," a "one-molecule guide RNA", a "single guide DNA", a "single-molecule guide DNA", or a "one-molecule guide DNA", ("sgNA", "sgRNA", or a "sgDNA"). In some embodiments, the sgNA includes an "activator" or a "targeter" and thus can be an "activator-RNA" and a "targeter-RNA," respectively.

Collectively, the gNAs of the disclosure comprise four distinct regions, or domains: the RNA triplex, the scaffold stem, the extended stem, and the targeting sequence that, in the embodiments of the disclosure are specific for a target nucleic acid. The RNA triplex, the scaffold stem, and the extended stem, together, are referred to as the "scaffold" of the gNA. In some embodiments, the targeting sequence is on the 3' end of the gNA.

b. RNA Triplex

In some embodiments of the guide NAs provided herein (including reference sgRNAs), there is a RNA triplex, and the RNA triplex comprises the sequence of a UUU-nX(~4-15)-UUU (SEQ ID NO: 17) stem loop that ends with an AAAG after 2 intervening stem loops (the scaffold stem loop and the extended stem loop), forming a pseudoknot that may also extend past the triplex into a duplex pseudoknot. The UU-UUU-AAA sequence of the triplex forms as a *nexus* between the targeting sequence, scaffold stem, and extended stem. In exemplary CasX sgRNAs, the UUU-loop-UUU region is coded for first, then the scaffold stem loop, and then the extended stem loop, which is linked by the tetraloop, and then an AAAG closes off the triplex before becoming the targeting sequence.

c. Scaffold Stem Loop

In some embodiments of sgNAs of the disclosure, the triplex region is followed by the scaffold stem loop. The scaffold stem loop is a region of the gNA that is bound by CasX protein (such as a reference or CasX variant protein). In some embodiments, the scaffold stem loop is a fairly short and stable stem loop. In some cases, the scaffold stem loop does not tolerate many changes, and requires some form of an RNA bubble. In some embodiments, the scaffold stem is necessary for CasX sgNA function. While it is perhaps analogous to the *nexus* stem of Cas9 as being a critical stem loop, the scaffold stem of a CasX sgNA, in some embodiments, has a necessary bulge (RNA bubble) that is different from many other stem loops found in CRISPR/Cas systems. In some embodiments, the presence of this bulge is conserved across sgNA that interact with different CasX proteins. An exemplary sequence of a scaffold stem loop sequence of a gNA comprises the sequence CCAGCGAC-UAUGUCGUAUGG (SEQ ID NO: 14). In other embodiments, the disclosure provides gNA variants wherein the scaffold stem loop is replaced with an RNA stem loop sequence from a heterologous RNA source with proximal 5' and 3' ends, such as, but not limited to stem loop sequences selected from MS2, Q β, U1 hairpin II, Uvsx, or PP7 stem loops. In some cases, the heterologous RNA stem loop of the gNA is capable of binding a protein, an RNA structure, a DNA sequence, or a small molecule d. Extended Stem Loop In some embodiments of the CasX sgNAs of the disclosure, the scaffold stem loop is followed by the extended stem loop. In some embodiments, the extended stem comprises a synthetic tracr and crRNA fusion that is largely unbound by the CasX protein. In some embodiments, the extended stem loop can be highly malleable. In some embodiments, a single guide gRNA is made with a GAAA tetraloop linker or a GAGAAA linker between the tracr and crRNA in the extended stem loop. In some cases, the targeter and activator of a CasX sgNA are linked to one another by intervening nucleotides and the linker can have a length of from 3 to 20 nucleotides. In some embodiments of the CasX sgNAs of the disclosure, the extended stem is a large 32-bp loop that sits outside of the CasX protein in the ribonucleoprotein complex. An exemplary sequence of an extended stem loop sequence of a sgNA comprises the sequence GCGC-UUAUUUAUCGGAGAGAAAUCCGAUAAAUAA-GAAGC (SEQ ID NO: 15). In some embodiments, the extended stem loop comprises a GAGAAA spacer sequence. In some embodiments, the disclosure provides gNA variants wherein the extended stem loop is replaced with an RNA stem loop sequence from a heterologous RNA source with proximal 5' and 3' ends, such as, but not limited to stem loop sequences selected from MS2, Qβ, U1 hairpin II, Uvsx, or PP7 stem loops. In such cases, the heterologous RNA stem loop increases the stability of the gNA. In other embodiments, the disclosure provides gNA variants having an extended stem loop region comprising at least 10, at least 100, at least 500, at least 1000, or at least 10,000 nucleotides.

e. Targeting Sequence

In some embodiments of the gNAs of the disclosure, the extended stem loop is followed by a region that forms part of the triplex, and then the targeting sequence (or "spacer"). The targeting sequence targets the CasX ribonucleoprotein holo complex to a specific region of the target nucleic acid sequence of the SOD1 gene. Thus, for example, gNA targeting sequences of the disclosure have sequences complementarity to, and therefore can hybridize to, a portion of the SOD1 gene in a nucleic acid in a eukaryotic cell (e.g., a eukaryotic chromosome, chromosomal sequence, a eukaryotic RNA, etc.) as a component of the RNP when any one of the PAM sequences TTC, ATC, GTC, or CTC is located 1 nucleotide 5' to the non-target strand sequence complementary to the target sequence. The targeting sequence of a gNA can be modified so that the gNA can target a desired sequence of any desired target nucleic acid sequence, so long as the PAM sequence location is taken into consideration. In some embodiments, the gNA scaffold is 5' of the targeting sequence, with the targeting sequence on the 3' end of the gNA. In some embodiments, the PAM sequence recognized by the RNP is TC. In other embodiments, the PAM sequence recognized by the RNP is NTC.

In some embodiments, the targeting sequence of the gNA is specific for a portion of a gene encoding a SOD1 protein. In some embodiments, the targeting sequence of a gNA is specific for a SOD1 exon. In one embodiment, the targeting sequence of a gNA is specific for SOD1 exon 1. In another embodiment, the targeting sequence of a gNA is specific for SOD1 exon 2. In another embodiment, the targeting sequence of a gNA is specific for SOD1 exon 3. In another embodiment, the targeting sequence of a gNA is specific for SOD1 exon 4. In another embodiment, the targeting sequence of a gNA is specific for SOD1 exon 5. In some embodiments, the targeting sequence of a gNA is specific for a SOD1 intron. In some embodiments, the targeting sequence of the gNA is specific for a SOD1 intron-exon junction. In some embodiments, the targeting sequence of the gNA has a sequence that hybridizes with a SOD1 regulatory element, a SOD1 coding region, a SOD1 non-coding region, or combinations thereof (e.g., the intersection of two regions). In some embodiments, the targeting sequence of the gNA is complementary to a sequence comprising one or more single nucleotide polymorphisms (SNPs) of the SOD1 gene or its complement. SNPs that are within a SOD1 coding sequence or within a SOD1 non-coding sequence are both within the scope of the instant disclosure. In other embodiments, the targeting sequence of the gNA is complementary to a sequence of an intergenic region of the SOD1 gene.

In some embodiments, the targeting sequence of a gNA is designed to be specific for a regulatory element that regulates expression of the SOD1 gene product. Such regulatory elements include, but are not limited to promoter regions, enhancer regions, intergenic regions, 5' untranslated regions (5' UTR), 3' untranslated regions (3' UTR), conserved elements, and regions comprising cis-regulatory elements. The promoter region is intended to encompass nucleotides within 5 kb of the initiation point of the encoding sequence or, in the case of gene enhancer elements or conserved elements, can be thousands of bp, hundreds of thousands of bp, or even millions of bp away from the encoding sequence of the gene of the target nucleic acid. In the foregoing, the targets are those in which the encoding gene of the target is intended to be knocked out or knocked down such that the SOD1 protein comprising mutations is not expressed or is expressed at a lower level in a cell.

In some embodiments, the targeting sequence of the gNA has between 14 and 35 consecutive nucleotides. In some embodiments, the targeting sequence has 14, 15, 16, 18, 18, 19, 20, 21, 22, 23 24, 25, 26, 27, 28, 29, 30, 31, 32, 33, 34 or 35 consecutive nucleotides. In some embodiments, the targeting sequence consists of 20 consecutive nucleotides. In some embodiments, the targeting sequence consists of 19 consecutive nucleotides. In some embodiments, the targeting sequence consists of 18 consecutive nucleotides. In some embodiments, the targeting sequence consists of 17 consecutive nucleotides. In some embodiments, the targeting sequence consists of 16 consecutive nucleotides. In some embodiments, the targeting sequence consists of 15 consecutive nucleotides. In some embodiments, the targeting sequence has 14, 15, 16, 17, 18, 19, 20, 21, 22, 23, 24, 25, 26, 27, 28, 29, 30, 31, 32, 33, 34 or 35 consecutive nucleotides and the targeting sequence can comprise 0 to 5, 0 to 4, 0 to 3, or 0 to 2 mismatches relative to the target nucleic acid sequence and retain sufficient binding specificity such that the RNP comprising the gNA comprising the targeting sequence can form a complementary bond with respect to the target nucleic acid.

Representative, but non-limiting examples of targeting sequences for inclusion in the gNA of the disclosure are presented in Table 3 (provided as FIG. 33). In Table 3, the first column indicates the PAM sequence, and the second column indicates the SEQ ID of the accompanying spacer sequence (sometimes referred to herein as the targeting sequence). In some embodiments, the disclosure provides targeting sequences for inclusion in the gNA of the disclosure comprising a sequence that is at least 50% identical, at least 55% identical, at least 60% identical, at least 65% identical, at least 70% identical, at least 75% identical, at least 80% identical, at least 85% identical, at least 90% identical, at least 95% identical, or 100% identical to a sequence in Table 3 (FIG. 33). In some embodiments, the targeting sequence of the gNA comprises a sequence a sequence of Table 3 with a single nucleotide removed from the 3' end of the sequence. In other embodiments, the targeting sequence of the gNA comprises a sequence a sequence of Table 3 with two nucleotides removed from the 3' end of the sequence. In other embodiments, the targeting sequence of the gNA comprises a sequence a sequence of Table 3 with three nucleotides removed from the 3' end of the sequence. In other embodiments, the targeting sequence of the gNA comprises a sequence a sequence of Table 3 with four nucleotides removed from the 3' end of the sequence. In other embodiments, the targeting sequence of the gNA comprises a sequence a sequence of Table 3 with five nucleotides removed from the 3' end of the sequence. In the foregoing embodiments of the paragraph, thymine (T) nucleotides can be substituted for one or more or all of the uracil (U) nucleotides in any of the targeting sequences such that the gNA can be a gDNA or a gRNA, or a chimera of RNA and DNA. In some embodiments, a targeting sequence of Table 3 has at least 1, 2, 3, 4, 5, or 6 or more thymine nucleotides substituted for uracil nucleotides. In other embodiments, a gNA, gRNA, or gDNA of the disclosure comprises 1, 2, 3 or more targeting sequences of Table 3, or targeting sequences that are at least 50% identical, at least 55% identical, at least 60% identical, at least 65% identical, at least 70% identical, at least 75% identical, at least 80% identical, at least 85% identical, at least 90% identical, at least 95% identical, or 100% identical to one or more sequences of Table 3.

In some embodiments, the targeting sequence of the gNA encodes or is complementary to a nucleic acid sequence encoding a mutation of the SOD1 protein of SEQ ID NO:100 selected from the group of amino acid substitutions consisting of A4S, A4T, A4V, C6F, V7E, L8Q, L8V, G12R, V14G, V14M, G16S, F20C, E21G, E21K, Q22L, G37R, L38R, L38V, G41D, G41S, H43R, F45C, H46R, H48Q, H48R, E49K, T54R, N65S, L67P, L67R, G72S, D76Y, H80A, L84F, L84V, G85R, N86S, V87A, A89T, A89V, D90A, D90V, G93A, G93C, G93D, G93R, G93V, A95G, V97M, E100G, E100K, D101G, D101N, I104F, S105L, L106V, G108V, C111Y, I112M, I112T, I113T, G114A, R115G, V118L, D124G, D124V, D125H, L126S, S134N, N139K, L144F, L144S, A145T, C146R, G147R, V148G, V148I, I149T, I151T, and one or more amino acid substitutions of SEQ ID NO:100 that disrupt the function or expression of the SOD1 protein, or is selected from a combination thereof. In a particular embodiment, the targeting sequence of the gNA is complementary to a nucleic acid sequence encoding a mutation of the SOD1 protein of SEQ ID NO:100 selected from an A4V mutation of SEQ ID NO:100, a D90A mutation of SEQ ID NO:100, a G93A mutation of SEQ ID NO:100, or a combination thereof.

In some embodiments, the CasX:gNA system comprises a first gNA and further comprises a second (and optionally a third, fourth, fifth, or more) gNA, wherein the second gNA or additional gNA has a targeting sequence complementary to a different or overlapping portion of the target nucleic acid sequence compared to the targeting sequence of the first gNA such that multiple points in the target nucleic acid are targeted, and, for example, multiple breaks are introduced in the target nucleic acid by the CasX. It will be understood that in such cases, the second or additional gNA is complexed with an additional copy of the CasX protein. By selection of the targeting sequences of the gNA, defined regions of the target nucleic acid sequence bracketing a particular location within the target nucleic acid can be modified or edited using the CasX:gNA systems described herein, including facilitating the insertion of a donor template.

f. gNA Scaffolds

With the exception of the targeting sequence domain, the remaining components of the gNA are referred to herein as the scaffold. In some embodiments, the gNA scaffolds are derived from naturally-occurring sequences, described below as reference gNA. In other embodiments, the gNA scaffolds are variants of reference gNA wherein mutations, insertions, deletions or domain substitutions are introduced to confer desirable properties on the gNA.

In some embodiments, a CasX reference gRNA comprises a sequence isolated or derived from *Deltaproteobacter*. In some embodiments, the sequence is a CasX tracrRNA sequence. Exemplary CasX reference tracrRNA sequences isolated or derived from *Deltaproteobacter* may include: ACAUCUGGCGCGUUUAUUCCAUUACUUUGGAGC-CAGUCCCAGCGACUAUGUCG UAUGGACGAAGCG-CUUAUUUAUCGGAGA (SEQ ID NO: 6) and ACAUCUGGCGCGUUUAUUCCAUUACUUUG-GAGCCAGUCCCAGCGACUAUGUCG UAUGGACG-AAGCGCUUAUUUAUCGG (SEQ ID NO: 7). Exemplary crRNA sequences isolated or derived from Deltaproteobacter may comprise a sequence of CCGAUA-AGUAAAACGCAUCAAAG (SEQ ID NO: 18). In some embodiments, a CasX reference gNA comprises a sequence at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence isolated or derived from *Deltaproteobacter*.

In some embodiments, a CasX reference guide RNA comprises a sequence isolated or derived from *Planctomycetes*. In some embodiments, the sequence is a CasX tracrRNA sequence. Exemplary CasX reference tracrRNA sequences isolated or derived from *Planctomycetes* may include: UACUGGCGCUUUUAUCUCAUUACUUUG-AGAGCCAUCACCAGCGACUAUGUCGU AUGG-GUAAAGCGCUUAUUUAUCGGAGA (SEQ ID NO: 8) and UACUGGCGCUUUUAUCUCAUUACUUUGAGA-GCCAUCACCAGCGACUA UGUCGUAUGGGUAA-AGCGCUUAUUUAUCGG (SEQ ID NO: 9). Exemplary crRNA sequences isolated or derived from *Planctomycetes* may comprise a sequence of UCUCCGAUAA-AUAAGAAGCAUCAAAG (SEQ ID NO: 19). In some embodiments, a CasX reference gNA comprises a sequence at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence isolated or derived from *Planctomycetes*.

In some embodiments, a CasX reference gNA comprises a sequence isolated or derived from *Candidatus Sungbacteria*. In some embodiments, the sequence is a CasX tracrRNA sequence. Exemplary CasX reference tracrRNA sequences isolated or derived from *Candidatus Sungbacteria* may comprise sequences of: GUUUACACACUCCCU-CUCAUAGGGU (SEQ ID NO: 10), GUUUACACA-CUCCCUCUCAUGAGGU (SEQ ID NO: 11), UUUUACAUACCCCCUCUCAUGGGAU (SEQ ID NO: 12) and GUUUACACACUCCCUCUCAUGGGGG (SEQ ID NO: 13). In some embodiments, a CasX reference guide RNA comprises a sequence at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence isolated or derived from *Candidatus sungbacteria*.

Table 2A provides the sequences of reference gRNAs tracr and scaffold sequences. In some embodiments, the disclosure provides gNA sequences wherein the gNA has a scaffold comprising a sequence having at least one nucleotide modification relative to a reference gNA sequence having a sequence of any one of SEQ ID NOS: 4-16 of Table 2A. It will be understood that in those embodiments wherein a vector comprises a DNA encoding sequence for a gNA, or where a gNA is a gDNA or a chimera of RNA and DNA, that thymine (T) bases can be substituted for the uracil (U) bases of any of the gNA sequence embodiments described herein.

TABLE 2A

| | Reference gRNA tracr and scaffold sequences |
|---|---|
| SEQ ID NO. | Nucleotide Sequence |
| 4 | ACAUCUGGCGCGUUUAUUCCAUUACUUUGGAGCCAGUCCCAGCGACUAUGUCG UAUGGACGAAGCGCUUAUUUAUCGGAGAGAAACCGAUAAGUAAAACGCAUCAA AG |
| 5 | UACUGGCGCUUUUAUCUCAUUACUUUGAGAGCCAUCACCAGCGACUAUGUCGU AUGGGUAAAGCGCUUAUUUAUCGGAGAGAAAUCCGAUAAAUAAGAAGCAUCAA AG |
| 6 | ACAUCUGGCGCGUUUAUUCCAUUACUUUGGAGCCAGUCCCAGCGACUAUGUCG UAUGGACGAAGCGCUUAUUUAUCGGAGA |
| 7 | ACAUCUGGCGCGUUUAUUCCAUUACUUUGGAGCCAGUCCCAGCGACUAUGUCG UAUGGACGAAGCGCUUAUUUAUCGG |
| 8 | UACUGGCGCUUUUAUCUCAUUACUUUGAGAGCCAUCACCAGCGACUAUGUCGU AUGGGUAAAGCGCUUAUUUAUCGGAGA |

TABLE 2A-continued

Reference gRNA tracr and scaffold sequences

| SEQ ID NO. | Nucleotide Sequence |
|---|---|
| 9 | UACUGGCGCUUUUAUCUCAUUACUUUGAGAGCCAUCACCAGCGACUAUGUCGUAUGGGUAAAGCGCUUAUUUAUCGG |
| 10 | GUUUACACACUCCCUCUCAUAGGGU |
| 11 | GUUUACACACUCCCUCUCAUGAGGU |
| 12 | UUUUACAUACCCCCUCUCAUGGGAU |
| 13 | GUUUACACACUCCCUCUCAUGGGGG |
| 14 | CCAGCGACUAUGUCGUAUGG |
| 15 | GCGCUUAUUUAUCGGAGAGAAAUCCGAUAAAUAAGAAGC |
| 16 | GGCGCUUUUAUCUCAUUACUUUGAGAGCCAUCACCAGCGACUAUGUCGUAUGGGUAAAGCGCUUAUUUAUCGGA | g. gNA Variants

In another aspect, the disclosure relates to guide nucleic acid variants (referred to herein alternatively as "gNA variant" or "gRNA variant"), which comprise one or more modifications relative to a reference gRNA scaffold. As used herein, "scaffold" refers to all parts to the gNA necessary for gNA function with the exception of the spacer sequence.

In some embodiments, a gNA variant comprises one or more nucleotide substitutions, insertions, deletions, or swapped or replaced regions relative to a reference gRNA sequence of the disclosure. In some embodiments, a mutation can occur in any region of a reference gRNA scaffold to produce a gNA variant. In some embodiments, the scaffold of the gNA variant sequence has at least 20%, at least 30%, at least 40%, at least 50%, at least 60%, or at least 70%, at least 80%, at least 85%, at least about 90%, at least about 95%, at least about 96%, at least about 97%, at least about 98%, or at least about 99% identity to the sequence of SEQ ID NO: 4 or SEQ ID NO: 5.

In some embodiments, a gNA variant comprises one or more nucleotide changes within one or more regions of the reference gRNA that improve a characteristic relative to the reference gRNA. Exemplary regions include the RNA triplex, the pseudoknot, the scaffold stem loop, and the extended stem loop. In some cases, the variant scaffold stem further comprises a bubble. In other cases, the variant scaffold further comprises a triplex loop region. In still other cases, the variant scaffold further comprises a 5' unstructured region. In one embodiment, the gNA variant scaffold comprises a scaffold stem loop having at least 60% sequence identity to SEQ ID NO: 14. In another embodiment, the gNA variant comprises a scaffold stem loop having the sequence of CCAGCGACUAUGUCGUAGUGG (SEQ ID NO: 20). In another embodiment, the disclosure provides a gNA scaffold comprising, relative to SEQ ID NO: 5, a C18G substitution, a G55 insertion, a U1 deletion, and a modified extended stem loop in which the original 6 nt loop and 13 most-loop-proximal base pairs (32 nucleotides total) are replaced by a Uvsx hairpin (4 nt loop and 5 loop-proximal base pairs; 14 nucleotides total) and the loop-distal base of the extended stem was converted to a fully base-paired stem contiguous with the new Uvsx hairpin by deletion of the A99 and substitution of G64U. In the foregoing embodiment, the gNA scaffold comprises the sequence (SEQ ID NO: 2238)
ACUGGCGCUUUUAUCUGAUUACUUUGAGAGCCAUCACCAGCGACUAUGUC
GUAGUGGGUAAAGCUCCCUCUUCGGAGGGAGCAUCAAAG.

All gNA variants that have one or more improved functions or characteristics, or add one or more new functions when the variant gNA is compared to a reference gRNA described herein, are envisaged as within the scope of the disclosure. A representative example of such a gNA variant is guide 174 (SEQ ID NO: 2238), the design of which (and the rationale for the design) is described in the Examples. In some embodiments, the gNA variant adds a new function to the RNP comprising the gNA variant. In some embodiments, the gNA variant has an improved characteristic selected from: improved stability; improved solubility; improved transcription of the gNA; improved resistance to nuclease activity; increased folding rate of the gNA; decreased side product formation during folding; increased productive folding; improved binding affinity to a CasX protein; improved binding affinity to a target DNA when complexed with a CasX protein; improved gene editing when complexed with a CasX protein; improved specificity of editing when complexed with a CasX protein; and improved ability to utilize a greater spectrum of one or more PAM sequences, including ATC, CTC, GTC, or TTC, in the editing of target DNA when complexed with a CasX protein, or any combination thereof. In some cases, the one or more of the improved characteristics of the gNA variant is at least about 1.1 to about 100,000-fold improved relative to the reference gNA of SEQ ID NO: 4 or SEQ ID NO: 5. In other cases, the one or more improved characteristics of the gNA variant is at least about 1.1, at least about 10, at least about 100, at least about 1000, at least about 10,000, at least about 100,000-fold or more improved relative to the reference gNA of SEQ ID NO: 4 or SEQ ID NO: 5. In other cases, the one or more of the improved characteristics of the gNA variant is about 1.1 to 100,00-fold, about 1.1 to 10,00-fold, about 1.1 to 1,000-fold, about 1.1 to 500-fold, about 1.1 to 100-fold, about 1.1 to 50-fold, about 1.1 to 20-fold, about 10 to 100,00-fold, about 10 to 10,00-fold, about 10 to 1,000-fold, about 10 to 500-fold, about 10 to 100-fold, about 10 to 50-fold, about 10 to 20-fold, about 2 to 70-fold, about 2 to 50-fold, about 2 to 30-fold, about 2 to 20-fold, about 2 to 10-fold, about 5 to 50-fold, about 5 to 30-fold, about 5 to 10-fold, about 100 to 100,00-fold, about 100 to 10,00-fold, about 100 to 1,000- fold, about 100 to 500-fold, about 500 to 100,00-fold, about 500 to 10,00-fold, about 500 to 1,000-fold, about 500 to 750-fold, about 1,000 to 100,00-fold, about 10,000 to 100,00-fold, about 20 to 500-fold, about 20 to 250-fold, about 20 to 200-fold, about 20 to 100-fold, about 20 to 50-fold, about 50 to 10,000-fold, about 50 to 1,000-fold, about 50 to 500-fold, about 50 to 200-fold, or about 50 to 100-fold, improved relative to the reference gNA of SEQ ID NO: 4 or SEQ ID NO: 5. In other cases, the one or more improved characteristics of the gNA variant is about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 40-fold, 45-fold, 50-fold, 55-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 425-fold, 450-fold, 475-fold, or 500-fold improved relative to the reference gNA of SEQ ID NO: 4 or SEQ ID NO: 5.

In some embodiments, a gNA variant can be created by subjecting a reference gRNA to a one or more mutagenesis methods, such as the mutagenesis methods described herein, below, which may include Deep Mutational Evolution (DME), deep mutational scanning (DMS), error prone PCR, cassette mutagenesis, random mutagenesis, staggered extension PCR, gene shuffling, or domain swapping, in order to generate the gNA variants of the disclosure. The activity of reference gRNAs may be used as a benchmark against which the activity of gNA variants are compared, thereby measuring improvements in function of gNA variants compared to the reference gNA. In other embodiments, a reference gRNA may be subjected to one or more deliberate, targeted mutations, substitutions, or domain swaps in order to produce a gNA variant, for example a rationally designed variant. Exemplary gRNA variants produced by such methods are described in the Examples and representative sequences of gNA scaffolds are presented in Table 2B.

In some embodiments, the gNA variant comprises one or more modifications compared to a reference guide nucleic acid scaffold sequence, wherein the one or more modification is selected from: at least one nucleotide substitution in a region of the gNA variant; at least one nucleotide deletion in a region of the gNA variant; at least one nucleotide insertion in a region of the gNA variant; a substitution of all or a portion of a region of the gNA variant; a deletion of all or a portion of a region of the gNA variant; or any combination of the foregoing. In some cases, the modification is a substitution of 1 to 15 consecutive or non-consecutive nucleotides in the gNA variant in one or more regions. In other cases, the modification is a deletion of 1 to 10 consecutive or non-consecutive nucleotides in the gNA variant in one or more regions. In other cases, the modification is an insertion of 1 to 10 consecutive or non-consecutive nucleotides in the gNA variant in one or more regions. In other cases, the modification is a substitution of the scaffold stem loop or the extended stem loop with an RNA stem loop sequence from a heterologous RNA source with proximal 5' and 3' ends. In some cases, a gNA variant of the disclosure comprises two or more modifications in one region. In other cases, a gNA variant of the disclosure comprises modifications in two or more regions. In other cases, a gNA variant comprises any combination of the foregoing modifications described in this paragraph.

In some embodiments, a 5' G is added to a gNA variant sequence for expression in vivo, as transcription from a U6 promoter is more efficient and more consistent with regard to the start site when the +1 nucleotide is a G. In other embodiments, two 5' Gs are added to a gNA variant sequence for in vitro transcription to increase production efficiency, as T7 polymerase strongly prefers a G in the +1 position and a purine in the +2 position. In some cases, the 5' G bases are added to the reference scaffolds of Table 2A. In other cases, the 5' G bases are added to the variant scaffolds of Table 2B.

Table 2B provides exemplary gNA variant scaffold sequences. In Table 2B, (−) indicates a deletion at the specified position(s) relative to the reference sequence of SEQ ID NO: 5, (+) indicates an insertion of the specified base(s) at the position indicated relative to SEQ ID NO: 5, (:) indicates the range of bases at the specified start:stop coordinates of a deletion or substitution relative to SEQ ID NO: 5, and multiple insertions, deletions or substitutions are separated by commas; e.g., A14C, U17G. In some embodiments, the gNA variant scaffold comprises any one of the sequences listed in Table 2B, SEQ ID NOS: 2101-2280, or a sequence having at least about 50%, at least about 60%, at least about 70%, at least about 80%, at least about 90%, at least about 95%, at least about 95%, at least about 96%, at least about 97%, at least about 98%, at least about 99% sequence identity thereto. It will be understood that in those embodiments wherein a vector comprises a DNA encoding sequence for a gNA, or where a gNA is a gDNA or a chimera of RNA and DNA, that thymine (T) bases can be substituted for the uracil (U) bases of any of the gNA sequence embodiments described herein.

TABLE 2B

Exemplary gNA Scaffold Sequences

| SEQ ID NO: | NAME or Modification | NUCLEOTIDE SEQUENCE |
|---|---|---|
| 2101 | phage replication stable | UACUGGCGCUUUUAUCUCAUUACUUUGAGAGCCAUCACCAGCGACUA UGUCGUAUGGGUAAAGCGCAGGUGGGACGACCUCUCGGUCGUCCUAU CUGAAGCAUCAAAG |
| 2102 | Kissing loop_b1 | UACUGGCGCUUUUAUCUCAUUACUUUGAGAGCCAUCACCAGCGACUA UGUCGUAUGGGUAAAGCGCUGCUCGACGCGUCCUCGAGCAGAAGCAU CAAAG |
| 2103 | Kissing loop_a | UACUGGCGCUUUUAUCUCAUUACUUUGAGAGCCAUCACCAGCGACUA UGUCGUAUGGGUAAAGCGCUGCUCGCUCCGUUCGAGCAGAAGCAUCA AAG |

TABLE 2B-continued

Exemplary gNA Scaffold Sequences

| SEQ ID NO: | NAME or Modification | NUCLEOTIDE SEQUENCE |
|---|---|---|
| 2104 | 32: uvsX hairpin | GUACUGGCGCUUUUAUCUCAUUACUUUGAGAGCCAUCACCAGCGACUAUGUCGUAUGGGUAAAGCGCCCUCUUCGGAGGGAAGCAUCAAAG |
| 2105 | PP7 | UACUGGCGCUUUUAUCUCAUUACUUUGAGAGCCAUCACCAGCGACUAUGUCGUAUGGGUAAAGCGCAGGAGUUUCUAUGGAAACCCUGAAGCAUCAAAG |
| 2106 | 64: trip mut, extended stem truncation | GUACUGGCGCCUUUAUCUCAUUACUUUGAGAGCCAUCACCAGCGACUAUGUCGUAUGGGUAAAGCGCUUACGGACUUCGGUCCGUAAGAAGCAUCAG |
| 2107 | hyperstable tetraloop | UACUGGCGCUUUUAUCUCAUUACUUUGAGAGCCAUCACCAGCGACUAUGUCGUAUGGGUAAAGCGCUGCGCUUGCGCAGAAGCAUCAAAG |
| 2108 | C18G | UACUGGCGCUUUUAUCUGAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2109 | U17G | UACUGGCGCUUUUAUCGCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2110 | CUUCGG loop | UACUGGCGCUUUUAUCUCAUUACUUUGAGAGCCAUCACCAGCGACUAUGUCGUAUGGGUAAAGCGCUUAUUUAUCGGAGACUUCGGUCCGAUAAAUAAGAAGCAUCAAAG |
| 2111 | MS2 | UACUGGCGCUUUUAUCUCAUUACUUUGAGAGCCAUCACCAGCGACUAUGUCGUAUGGGUAAAGCGCACAUGAGGAUUACCCAUGUGAAGCAUCAAAG |
| 2112 | -1, A2G, -78, G77U | GCUGGCGCUUUUAUCUCAUUACUUUGAGAGCCAUCACCAGCGACUAUGUCGUAUGGGUAAAGCGCUUAUUUAUCGUGAGAAAUCCGAUAAAUAAGAAGCAUCAAAG |
| 2113 | QB | UACUGGCGCUUUUAUCUCAUUACUUUGAGAGCCAUCACCAGCGACUAUGUCGUAUGGGUAAAGCGCUGCAUGUCUAAGACAGCAGAAGCAUCAAAG |
| 2114 | 45, 44 hairpin | UACUGGCGCUUUUAUCUCAUUACUUUGAGAGCCAUCACCAGCGACUAUGUCGUAUGGGUAAAGCGCAGGGCUUCGGCCGAAGCAUCAAAG |
| 2115 | U1A | UACUGGCGCUUUUAUCUCAUUACUUUGAGAGCCAUCACCAGCGACUAUGUCGUAUGGGUAAAGCGCAAUCCAUUGCACUCCGGAUUGAAGCAUCAAAG |
| 2116 | A14C, U17G | UACUGGCGCUUUUCUCGCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2117 | CUUCGG loop modified | UACUGGCGCUUUUAUCUCAUUACUUUGAGAGCCAUCACCAGCGACUAUGUCGUAUGGGUAAAGCGCUUAUUUAUCGGACUUCGGUCCGAUAAAUAAGAAGCAUCAAAG |
| 2118 | Kissing loop_b2 | UACUGGCGCUUUUAUCUCAUUACUUUGAGAGCCAUCACCAGCGACUAUGUCGUAUGGGUAAAGCGCUGCUCGUUUGCGGCUACGAGCAGAAGCAUCAAAG |
| 2119 | -76:78, -83:87 | UACUGGCGCUUUUAUCUCAUUACUUUGAGAGCCAUCACCAGCGACUAUGUCGUAUGGGUAAAGCGCUUAUUUAUCGAGAGAUAAAUAAGAAGCAUCAAAG |
| 2120 | -4 | UACGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2121 | extended stem truncation | UACUGGCGCCUUUAUCUCAUUACUUUGAGAGCCAUCACCAGCGACUAUGUCGUAUGGGUAAAGCGCUUACGGACUUCGGUCCGUAAGAAGCAUCAAAG |
| 2122 | C55 | UACUGGCGCUUUUAUCUCAUUACUUUGAGAGCCAUCACCAGCGACUAUGUCGUAUCGGUAAAGCGCUUAUUUAUCGGAGAGAAAUCCGAUAAAUAAGAAGCAUCAAAG |

TABLE 2B-continued

Exemplary gNA Scaffold Sequences

| SEQ ID NO: | NAME or Modification | NUCLEOTIDE SEQUENCE |
|---|---|---|
| 2123 | trip mut | UACUGGCGCCUUUAUCUCAUUACUUUGAGAGCCAUCACCAGCGACUA UGUCGUAUGGGUAAAGCGCUUAUUUAUCGGACUUCGGUCCGAUAAAU AAGAAGCAUCAAAG |
| 2124 | -76:78 | UACUGGCGCUUUUAUCUCAUUACUUUGAGAGCCAUCACCAGCGACUA UGUCGUAUGGGUAAAGCGCUUAUUUAUCGAGAAAUCCGAUAAAUAAG AAGCAUCAAAG |
| 2125 | -1:5 | GCGCUUUUAUCUCAUUACUUUGAGAGCCAUCACCAGCGACUAUGUCG UAUGGGUAAAGCGCUUAUUUAUCGGAGAGAAAUCCGAUAAAUAAGAA GCAUCAAAG |
| 2126 | -83:87 | UACUGGCGCUUUUAUCUCAUUACUUUGAGAGCCAUCACCAGCGACUA UGUCGUAUGGGUAAAGCGCUUAUUUAUCGGAGAGAGAUAAAUAAGAA GCAUCAAAG |
| 2127 | =+G28, A82U, -84, | UACUGGCGCUUUUAUCUCAUUACUUUGGAGAGCCAUCACCAGCGACU AUGUCGUAUGGGUAAAGCGCUUAUUUAUCGGAGAGUAUCCGAUAAAU AAGAAGCAUCAAAG |
| 2128 | =+51U | UACUGGCGCUUUUAUCUCAUUACUUUGAGAGCCAUCACCAGCGACUA UGUUCGUAUGGGUAAAGCGCUUAUUUAUCGGAGAGAAAUCCGAUAAA UAAGAAGCAUCAAAG |
| 2129 | -1:4, +G5A, +G86, | AGCGCUUUUAUCUCAUUACUUUGAGAGCCAUCACCAGCGACUAUGUC GUAUGGGUAAAGCGCUUAUUUAUCGGAGAGAAAUGCCGAUAAAUAAG AAGCAUCAAAG |
| 2130 | =+A94 | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAA UAAGAAGCAUCAAAG |
| 2131 | =+G72 | UACUGGCGCUUUUAUCUCAUUACUUUGAGAGCCAUCACCAGCGACUA UGUCGUAUGGGUAAAGCGCUUAUUGUAUCGGAGAGAAAUCCGAUAAA UAAGAAGCAUCAAAG |
| 2132 | shorten front, CUUCGG loop modified. extend extended | GCGCUUUUAUCUCAUUACUUUGAGAGCCAUCACCAGCGACUAUGUCG UAUGGGUAAAGCGCUUAUUUAUCGGACUUCGGUCCGAUAAAUAAGCG CAUCAAAG |
| 2133 | A14C | UACUGGCGCUUUUCUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAG |
| 2134 | -1:3, +G3 | GUGGCGCUUUUAUCUCAUUACUUUGAGAGCCAUCACCAGCGACUAUG UCGUAUGGGUAAAGCGCUUAUUUAUCGGAGAGAAAUCCGAUAAAUAA GAAGCAUCAAAG |
| 2135 | =+C45, +U46 | UACUGGCGCUUUUAUCUCAUUACUUUGAGAGCCAUCACCAGCGACCU UAUGUCGUAUGGGUAAAGCGCUUAUUUAUCGGAGAGAAAUCCGAUAA AUAAGAAGCAUCAAAG |
| 2136 | CUUCGG loop modified, fun start | GAUGGCGCUUUUAUCUCAUUACUUUGAGAGCCAUCACCAGCGACUAU GUCGUAUGGGUAAAGCGCUUAUUUAUCGGACUUCGGUCCGAUAAAUA AGAAGCAUCAAAG |
| 2137 | -93:94 | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAA GAAGCAUCAAAG |
| 2138 | =+U45 | UACUGGCGCUUUUAUCUCAUUACUUUGAGAGCCAUCACCAGCGAUCU AUGUCGUAUGGGUAAAGCGCUUAUUUAUCGGAGAGAAAUCCGAUAAA UAAGAAGCAUCAAAG |
| 2139 | -69, -94 | UACUGGCGCUUUUAUCUCAUUACUUUGAGAGCCAUCACCAGCGACUA UGUCGUAUGGGUAAAGGCUUAUUUAUCGGAGAGAAAUCCGAUAAAA GAAGCAUCAAAG |
| 2140 | -94 | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAA AGAAGCAUCAAAG |

TABLE 2B-continued

Exemplary gNA Scaffold Sequences

| SEQ ID NO: | NAME or Modification | NUCLEOTIDE SEQUENCE |
|---|---|---|
| 2141 | modified CUUCGG, minus U in 1st triplex | UACUGGCGCUUUUAUCUCAUUACUUUGAGAGCCAUCACCAGCGACUAU GUCGUAUGGGUAAAGCGCUUAUUUAUCGGACUUCGGUCCGAUAAAUA AGAAGCAUCAAAG |
| 2142 | -1:4, +C4, A14C, U17G, +G72, -76:78, -83:87 | CGGCGCUUUUCUCGCAUUACUUUGAGAGCCAUCACCAGCGACUAUGU CGUAUGGGUAAAGCGCUUAUUGUAUCGAGAGAUAAAUAAGAAGCAUC AAAG |
| 2143 | U1C, -73 | CACUGGCGCUUUUAUCUCAUUACUUUGAGAGCCAUCACCAGCGACUA UGUCGUAUGGGUAAAGCGCUUAUUUUCGGAGAGAAAUCCGAUAAAUA AGAAGCAUCAAAG |
| 2144 | Scaffold uuCG, stem uuCG. Stem swap, t shorten | UACUGGCGCUUUUAUCUCAUUACUUUGAGAGCCAUCACCAGCGACUUC GGUCGUAUGGGUAAAGCGCUUAUGUAUCGGCUUCGGCCGAUACAUAA GAAGCAUCAAAG |
| 2145 | Scaffold uuCG, stem uuCG. Stem swap | UACUGGCGCUUUUAUCUCAUUACUUUGAGAGCCAUCACCAGCGACUU CGGUCGUAUGGGUAAAGCGCUUAUGUAUCGGCUUCGGCCGAUACAUA AGAAGCAUCAAAG |
| 2146 | =+G60 | UACUGGCGCUUUUAUCUCAUUACUUUGAGAGCCAUCACCAGCGACUA UGUCGUAUGGGUGAAAGCGCUUAUUUAUCGGAGAGAAAUCCGAUAAA UAAGAAGCAUCAAAG |
| 2147 | no stem Scaffold uuCG | UACUGGCGCUUUUAUCUCAUUACUUUGAGAGCCAUCACCAGCGACUU CGGUCGUAUGGGUAAAG |
| 2148 | no stem Scaffold uuCG, fun start | GAUGGGCUUUUAUCUCAUUACUUUGAGAGCCAUCACCAGCGACUUCG GUCGUAUGGGUAAAG |
| 2149 | Scaffold uuCG, stem uuCG, fun start | GAUGGGCUUUUAUCUCAUUACUUUGAGAGCCAUCACCAGCGACUUCG GUCGUAUGGGUAAAGCGCUUAUUUAUCGGCUUCGGCCGAUAAAUAAG AAGCAUCAAAG |
| 2150 | Pseudoknots | UACUGGCGCUUUUAUCUCAUUACUUUGAGAGCCAUCACCAGCGACUA UGUCGUAUGGGUAAAGCGCUACACUGGGAUCGCUGAAUUAGAGAUCG GCGUCCUUUCAUUCUAUAUACUUUGGAGUUUUAAAAUGUCUCUAAGU ACAGAAGCAUCAAAG |
| 2151 | Scaffold uuCG, stem uuCG | GGCGCUUUUAUCUCAUUACUUUGAGAGCCAUCACCAGCGACUUCGGU CGUAUGGGUAAAGCGCUUAUUUAUCGGCUUCGGCCGAUAAAUAAGAA GCAUCAAAG |
| 2152 | Scaffold uuCG, stem uuCG, no start | GCUGGCGCUUUUAUCUCAUUACUUUGAGAGCCAUCACCAGCGACUUC GGUCGUAUGGGUAAAGCGCUUAUUUAUCGGCUUCGGCCGAUAAAUAA GAAGCAUCAAAG |
| 2153 | Scaffold uuCG | UACUGGCGCUUUUAUCUCAUUACUUUGAGAGCCAUCACCAGCGACUU CGGUCGUAUGGGUAAAGCGCUUAUUUAUCGGAGAGAAAUCCGAUAAA UAAGAAGCAUCAAAG |
| 2154 | =+GCUC36 | UACUGGCGCUUUUAUCUCAUUACUUUGAGAGCCAUGCUCCACCAGCG ACUAUGUCGUAUGGGUAAAGCGCUUAUUUAUCGGAGAGAAAUCCGAU AAAUAAGAAGCAUCAAAG |
| 2155 | G quadriplex telomere basket+ ends | UACUGGCGCUUUUAUCUCAUUACUUUGAGAGCCAUCACCAGCGACUA UGUCGUAUGGGUAAAGCGGGGUUAGGGUUAGGGUUAGGGAAGCAUCA AAG |
| 2156 | G quadriplex M3q | UACUGGCGCUUUUAUCUCAUUACUUUGAGAGCCAUCACCAGCGACUA UGUCGUAUGGGUAAAGCGGAGGGAGGGAGGGAGAGGGAAAGCAUCAA AG |

TABLE 2B-continued

Exemplary gNA Scaffold Sequences

| SEQ ID NO: | NAME or Modification | NUCLEOTIDE SEQUENCE |
|---|---|---|
| 2157 | G quadriplex telomere basket no ends | UACUGGCGCUUUUAUCUCAUUACUUUGAGAGCCAUCACCAGCGACUAUGUCGUAUGGGUAAAGCGUUGGGUUAGGGUUAGGGUUAGGGAAAAGCAUCAAAG |
| 2158 | 45, 44 hairpin (old version) | UACUGGCGCUUUUAUCUCAUUACUUUGAGAGCCAUCACCAGCGACUAUGUCGUAUGGGUAAAGCGC--------AGGGCUUCGGCCG---------GAAGCAUCAAAG |
| 2159 | Sarcin-ricin loop | UACUGGCGCUUUUAUCUCAUUACUUUGAGAGCCAUCACCAGCGACUAUGUCGUAUGGGUAAAGCGCCUGCUCAGUACGAGAGGAACCGCAGGAAGCAUCAAAG |
| 2160 | uvsX, C18G | UACUGGCGCUUUUAUCUGAUUACUUUGAGAGCCAUCACCAGCGACUAUGUCGUAUGGGUAAAGCGCCCUCUUCGGAGGGAAGCAUCAAAG |
| 2161 | truncated stem loop, C18G, trip mut (U10C) | UACUGGCGCCUUUAUCUGAUUACUUUGAGAGCCAUCACCAGCGACUAUGUCGUAUGGGUAAAGCGCUUACGGACUUCGGUCCGUAAGAAGCAUCAAAG |
| 2162 | short phage rep, C18G | UACUGGCGCUUUUAUCUGAUUACUUUGAGAGCCAUCACCAGCGACUAUGUCGUAUGGGUAAAGCGCGGACGACCUCUCGGUCGUCCGAAGCAUCAAAG |
| 2163 | phage rep loop, C18G | UACUGGCGCUUUUAUCUGAUUACUUUGAGAGCCAUCACCAGCGACUAUGUCGUAUGGGUAAAGCGCAGGUGGGACGACCUCUCGGUCGUCCUAUCUGAAGCAUCAAAG |
| 2164 | =+G18, stacked onto 64 | UACUGGCGCCUUUAUCUGCAUUACUUUGAGAGCCAUCACCAGCGACUAUGUCGUAUGGGUAAAGCGCUUACGGACUUCGGUCCGUAAGAAGCAUCAG |
| 2165 | truncated stem loop, C18G, -1 A2G | GCUGGCGCUUUUAUCUGAUUACUUUGAGAGCCAUCACCAGCGACUAUGUCGUAUGGGUAAAGCGCUUACGGACUUCGGUCCGUAAGAAGCAUCAAAG |
| 2166 | phage rep loop, C18G, trip mut (U10C) | UACUGGCGCCUUUAUCUGAUUACUUUGAGAGCCAUCACCAGCGACUAUGUCGUAUGGGUAAAGCGCAGGUGGGACGACCUCUCGGUCGUCCUAUCUGAAGCAUCAAAG |
| 2167 | short phage rep, C18G, trip mut (U10C) | UACUGGCGCCUUUAUCUGAUUACUUUGAGAGCCAUCACCAGCGACUAUGUCGUAUGGGUAAAGCGCGGACGACCUCUCGGUCGUCCGAAGCAUCAAAG |
| 2168 | uvsX, trip mut (U10C) | UACUGGCGCCUUUAUCUCAUUACUUUGAGAGCCAUCACCAGCGACUAUGUCGUAUGGGUAAAGCGCCCUCUUCGGAGGGAAGCAUCAAAG |
| 2169 | truncated stem loop | UACUGGCGCUUUUAUCUCAUUACUUUGAGAGCCAUCACCAGCGACUAUGUCGUAUGGGUAAAGCGCUUACGGACUUCGGUCCGUAAGAAGCAUCAAAG |
| 2170 | =+A17, stacked onto 64 | UACUGGCGCCUUUAUCAUCAUUACUUUGAGAGCCAUCACCAGCGACUAUGUCGUAUGGGUAAAGCGCUUACGGACUUCGGUCCGUAAGAAGCAUCAG |
| 2171 | 3' HDV genomic ribozyme | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGGGCCGGCAUGGUCCCAGCCUCCUCGCUGGCGCCGGCUGGGCAACAUUCCGAGGGGACCGUCCCCUCGGUAAUGGCGAAUGGGACCC |
| 2172 | phage rep loop, trip mut (U10C) | UACUGGCGCCUUUAUCUCAUUACUUUGAGAGCCAUCACCAGCGACUAUGUCGUAUGGGUAAAGCGCAGGUGGGACGACCUCUCGGUCGUCCUAUCUGAAGCAUCAAAG |
| 2173 | -79:80 | UACUGGCGCUUUUAUCUCAUUACUUUGAGAGCCAUCACCAGCGACUAUGUCGUAUGGGUAAAGCGCUUAUUUAUCGGAGAAAUCCGAUAAAUAAGAAGCAUCAAAG |

TABLE 2B-continued

Exemplary gNA Scaffold Sequences

| SEQ ID NO: | NAME or Modification | NUCLEOTIDE SEQUENCE |
|---|---|---|
| 2174 | short phage rep, trip mut (U10C) | UACUGGCGCCUUUUAUCUCAUUACUUUGAGAGCCAUCACCAGCGACUAUGUCGUAUGGGUAAAGCGCGGACGACCUCUCGGUCGUCCGAAGCAUCAAAG |
| 2175 | extra truncated stem loop | UACUGGCGCUUUUAUCUCAUUACUUUGAGAGCCAUCACCAGCGACUAUGUCGUAUGGGUAAAGCGCCGGACUUCGGUCCGGAAGCAUCAAAG |
| 2176 | U17G, C18G | UACUGGCGCUUUUAUCGGAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2177 | short phage rep | UACUGGCGCUUUUAUCUCAUUACUUUGAGAGCCAUCACCAGCGACUAUGUCGUAUGGGUAAAGCGCGGACGACCUCUCGGUCGUCCGAAGCAUCAAAG |
| 2178 | uvsX, C18G, -1 A2G | GCUGGCGCUUUUAUCUGAUUACUUUGAGAGCCAUCACCAGCGACUAUGUCGUAUGGGUAAAGCGCCCUCUUCGGAGGGAAGCAUCAAAG |
| 2179 | uvsX, C18G, trip mut (U10C), -1 A2G, HDV -99 G65U | GCUGGCGCUUUUAUCUGAUUACUUUGAGAGCCAUCACCAGCGACUAUGUCGUAUGGGUAAAGCUCCCUCUUCGGAGGGAGCAUCAAAG |
| 2180 | 3' HDV antigenomic ribozyme | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGGGGUCGGCAUGGCAUCUCCACCUCCUCGCGGUCCGACCUGGGCAUCCGAAGGAGGACGCACGUCCACUCGGAUGGCUAAGGGAGAGCCA |
| 2181 | uvsX, C18G, trip mut (U10C), -1 A2G, HDV AA(98:99)C | GCUGGCGCUUUUAUCUGAUUACUUUGAGAGCCAUCACCAGCGACUAUGUCGUAUGGGUAAAGCGCCCUCUUCGGAGGGCGCAUCAAAG |
| 2182 | 3' HDV ribozyme (Lior Nissim, Timothy Lu) | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGUUUUGGCCGGCAUGGUCCCAGCCUCCUCGCUGGCGCCGGCUGGGCAACAUGCUUCGGCAUGGCGAAUGGGACCCCGGG |
| 2183 | TAC(1:3)GA, stacked onto 64 | GAUGGCGCCUUUAUCUCAUUACUUUGAGAGCCAUCACCAGCGACUAUGUCGUAUGGGUAAAGCGCUUACGGACUUCGGUCCGUAAGAAGCAUCAAAG |
| 2184 | uvsX, -1 A2G | GCUGGCGCUUUUAUCUCAUUACUUUGAGAGCCAUCACCAGCGACUAUGUCGUAUGGGUAAAGCGCCCUCUUCGGAGGGAAGCAUCAAAG |
| 2185 | truncated stem loop, C18G, trip mut (U10C), -1 A2G, HDV-99 G65U | GCUGGCGCCUUUAUCUGAUUACUUUGAGAGCCAUCACCAGCGACUAUGUCGUAUGGGUAAAGCUCUUACGGACUUCGGUCCGUAAGAGCAUCAAAG |
| 2186 | short phage rep, C18G, trip mut (U10C), -1 A2G, HDV -99 G65U | GCUGGCGCCUUUAUCUGAUUACUUUGAGAGCCAUCACCAGCGACUAUGUCGUAUGGGUAAAGCUCGGACGACCUCUCGGUCGUCCGAGCAUCAAAG |
| 2187 | 3' sTRSV WT viral Hammerhead ribozyme | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGCCUGUCACCGGAUGUGCUUUCCGGUCUGAUGAGUCCGUGAGGACGAAACAGG |
| 2188 | short phage rep, C18G, -1 A2G | GCUGGCGCUUUUAUCUGAUUACUUUGAGAGCCAUCACCAGCGACUAUGUCGUAUGGGUAAAGCGCGGACGACCUCUCGGUCGUCCGAGCAUCAAAG |

TABLE 2B-continued

Exemplary gNA Scaffold Sequences

| SEQ ID NO: | NAME or Modification | NUCLEOTIDE SEQUENCE |
|---|---|---|
| 2189 | short phage rep, C18G, trip mut (U10C), -1 A2G, 3' genomic HDV | GCUGGCGCCUUUAUCUGAUUACUUUGAGAGCCAUCACCAGCGACUAU GUCGUAUGGGUAAAGCGCGGACGACCUCUCGGUCGUCCGAAGCAUCA AAG |
| 2190 | phage rep loop, C18G, trip mut (U10C), -1 A2G, HDV -99 G65U | GCUGGCGCCUUUAUCUGAUUACUUUGAGAGCCAUCACCAGCGACUAU GUCGUAUGGGUAAAGCUCAGGUGGGACGACCUCUCGGUCGUCCUAUC UGAGCAUCAAAG |
| 2191 | 3' HDV ribozyme (Owen Ryan, Jamie Cate) | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAGGAUGGCCGGCAUGGUCCCAGCCUCCUCGCUGGC GCCGGCUGGGCAACACCUUCGGGUGGCGAAUGGGAC |
| 2192 | phage rep loop, C18G, -1 A2G | GCUGGCGCUUUUAUCUGAUUACUUUGAGAGCCAUCACCAGCGACUAU GUCGUAUGGGUAAAGCGCAGGUGGGACGACCUCUCGGUCGUCCUAUC UGAAGCAUCAAAG |
| 2193 | 0.14 | UACUGGCGCUUUUAUCUCAUUACUUUGAGAGCCAUCACCAGCGACUA UGUCGUACUGGGUAAAGCGCUUAUUUAUCGGAGAGAAAUCCGAUAAA UAAGAAGCAUCAAAG |
| 2194 | -78, G77U | UACUGGCGCUUUUAUCUCAUUACUUUGAGAGCCAUCACCAGCGACUA UGUCGUAUGGGUAAAGCGCUUAUUUAUCGUGAGAAAUCCGAUAAAUA AGAAGCAUCAAAG |
| 2195 | | GUACUGGCGCUUUUAUCUCAUUACUUUGAGAGCCAUCACCAGCGACU AUGUCGUAUGGGUAAAGCGCUUAUUUAUCGGAGAGAAAUCCGAUAAA UAAGAAGCAUCAAAG |
| 2196 | short phage rep, -1 A2G | GCUGGCGCUUUUAUCUCAUUACUUUGAGAGCCAUCACCAGCGACUAU GUCGUAUGGGUAAAGCGCGGACGACCUCUCGGUCGUCCGAAGCAUCA AAG |
| 2197 | truncated stem loop, C18G, trip mut (U10C), -1 A2G | GCUGGCGCCUUUAUCUGAUUACUUUGAGAGCCAUCACCAGCGACUAU GUCGUAUGGGUAAAGCGCUUACGGACUUCGGUCCGUAAGAAGCAUCA AAG |
| 2198 | -1, A2G | GCUGGCGCUUUUAUCUCAUUACUUUGAGAGCCAUCACCAGCGACUAU GUCGUAUGGGUAAAGCGCUUAUUUAUCGGAGAGAAAUCCGAUAAAUA AGAAGCAUCAAAG |
| 2199 | truncated stem loop, trip mut (U10C), -1 A2G | GCUGGCGCCUUUAUCUCAUUACUUUGAGAGCCAUCACCAGCGACUAU GUCGUAUGGGUAAAGCGCUUACGGACUUCGGUCCGUAAGAAGCAUCA AAG |
| 2200 | uvsX, C18G, trip mut (U10C), -1 A2G | GCUGGCGCCUUUAUCUGAUUACUUUGAGAGCCAUCACCAGCGACUAU GUCGUAUGGGUAAAGCGCCCUCUUCGGAGGGAAGCAUCAAAG |
| 2201 | phage rep loop, -1 A2G | GCUGGCGCUUUUAUCUCAUUACUUUGAGAGCCAUCACCAGCGACUAU GUCGUAUGGGUAAAGCGCAGGUGGGACGACCUCUCGGUCGUCCUAUC UGAAGCAUCAAAG |
| 2202 | phage rep loop, trip mut (U10C), -1 A2G | GCUGGCGCCUUUAUCUCAUUACUUUGAGAGCCAUCACCAGCGACUAU GUCGUAUGGGUAAAGCGCAGGUGGGACGACCUCUCGGUCGUCCUAUC UGAAGCAUCAAAG |
| 2203 | phage rep loop, C18G, trip mut (U10C), -1 A2G | GCUGGCGCCUUUAUCUGAUUACUUUGAGAGCCAUCACCAGCGACUAU GUCGUAUGGGUAAAGCGCAGGUGGGACGACCUCUCGGUCGUCCUAUC UGAAGCAUCAAAG |

TABLE 2B-continued

Exemplary gNA Scaffold Sequences

| SEQ ID NO: | NAME or Modification | NUCLEOTIDE SEQUENCE |
|---|---|---|
| 2204 | truncated stem loop, C18G | UACUGGCGCUUUUAUCUGAUUACUUUGAGAGCCAUCACCAGCGACUAUGUCGUAUGGGUAAAGCGCUUACGGACUUCGGUCCGUAAGAAGCAUCAAAG |
| 2205 | uvsX, trip mut (U10C), -1 A2G | GCUGGCGCCUUUAUCUCAUUACUUUGAGAGCCAUCACCAGCGACUAUGUCGUAUGGGUAAAGCGCCCUCUUCGGAGGGAAGCAUCAAAG |
| 2206 | truncated stem loop, -1 A2G | GCUGGCGCUUUUAUCUCAUUACUUUGAGAGCCAUCACCAGCGACUAUGUCGUAUGGGUAAAGCGCUUACGGACUUCGGUCCGUAAGAAGCAUCAAAG |
| 2207 | short phage rep, trip mut (U10C), -1 A2G | GCUGGCGCCUUUAUCUCAUUACUUUGAGAGCCAUCACCAGCGACUAUGUCGUAUGGGUAAAGCGCGGACGACCUCUCGGUCGUCCGAAGCAUCAAG |
| 2208 | 5'HDV ribozyme (Owen Ryan, Jamie Cate) | GAUGGCCGGCAUGGUCCCAGCCUCCUCGCUGGCGCCGGCUGGGCAACACCUUCGGGUGGCGAAUGGGACUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2209 | 5'HDV genomic ribozyme | GGCCGGCAUGGUCCCAGCCUCCUCGCUGGCGCCGGCUGGGCAACAUUCCGAGGGGACCGUCCCCUCGGUAAUGGCGAAUGGGACCCUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2210 | truncated stem loop, C18G, trip mut (U10C), -1 A2G, HDV AA(98:99)C | GCUGGCGCUUUAUCUGAUUACUUUGAGAGCCAUCACCAGCGACUAUGUCGUAUGGGUAAAGCGCUUACGGACUUCGGUCCGUAAGCGCAUCAAG |
| 2211 | 5' env25 pistol ribozyme (with an added CUUCGG loop) | CGUGGUUAGGGCCACGUUAAAUAGUUGCUUAAGCCCUAAGCGUUGAUCUUCGGAUCAGGUGCAAUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2212 | 5'HDV antigenomic ribozyme | GGGUCGGCAUGGCAUCUCCACCUCCUCGCGGUCCGACCUGGGCAUCCGAAGGAGGACGCACGUCCACUCGGAUGGCUAAGGGAGAGCCAUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2213 | 3' Hammerhead ribozyme (Lior Nissim, Timothy Lu) guide scaffold scar | UACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAGCCAGUACUGAUGAGUCCGUGAGGAAACGACGAGUAAGCUCGUCUACUGGCGCUUUUAUCUCAU |
| 2214 | =+A27, stacked onto 64 | UACUGGCGCCUUUAUCUCAUUACUUUAGAGAGCCAUCACCAGCGACUAUGUCGUAUGGGUAAAGCGCUUACGGACUUCGGUCCGUAAGAAGCAUCAG |
| 2215 | 5'Hammerhead ribozyme (Li or Nissim, Timothy Lu) smaller scar | CGACUACUGAUGAGUCCGUGAGGACGAAACGAGUAAGCUCGUCUAGUCGUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2216 | phage rep loop, C18G, trip mut (U10C), -1 A2G, HDV AA(98:99)C | GCUGGCGCCUUUAUCUGAUUACUUUGAGAGCCAUCACCAGCGACUAUGUCGUAUGGGUAAAGCGCAGGUGGGACGACCUCUCGGUCGUCCUAUCUGCGCAUCAAAG |

TABLE 2B-continued

Exemplary gNA Scaffold Sequences

| SEQ ID NO: | NAME or Modification | NUCLEOTIDE SEQUENCE |
|---|---|---|
| 2217 | -27, stacked onto 64 | UACUGGCGCCUUUAUCUCAUUACUUUAGAGCCAUCACCAGCGACUAU GUCGUAUGGGUAAAGCGCUUACGGACUUCGGUCCGUAAGAAGCAUCA AAG |
| 2218 | 3' Hatchet | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAGCAUUCCUCAGAAAAUGACAAACCUGUGGGGCGU AAGUAGAUCUUCGGAUCUAUGAUCGUGCAGACGUUAAAAUCAGGU |
| 2219 | 3' Hammerhead ribozyme (Lior Nissim, Timothy Lu) | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAGCGACUACUGAUGAGUCCGUGAGGACGAAACGAG UAAGCUCGUCUAGUCGCGUGUAGCGAAGCA |
| 2220 | 5' Hatchet | CAUUCCUCAGAAAAUGACAAACCUGUGGGGCGUAAGUAGAUCUUCGG AUCUAUGAUCGUGCAGACGUUAAAAUCAGGUUACUGGCGCUUUUAUC UCAUUACUUUGAGAGCCAUCACCAGCGACUAUGUCGUAUGGGUAAAG CGCUUAUUUAUCGGAGAGAAAUCCGAUAAAUAAGAAGCAUCAAAG |
| 2221 | 5' HDV ribozyme (Lior Nissim, Timothy Lu) | UUUUGGCCGGCAUGGUCCCAGCCUCCUCGCUGGCGCCGGCUGGGCAA CAUGCUUCGGCAUGGCGAAUGGGACCCCGGGUACUGGCGCUUUUAUC UCAUUACUUUGAGAGCCAUCACCAGCGACUAUGUCGUAUGGGUAAAG CGCUUAUUUAUCGGAGAGAAAUCCGAUAAAUAAGAAGCAUCAAAG |
| 2222 | 5' Hammerhead ribozyme (Lior Nissim, Timothy Lu) | CGACUACUGAUGAGUCCGUGAGGACGAAACGAGUAAGCUCGUCUAGU CGCGUGUAGCGAAGCAUACUGGCGCUUUUAUCUCAUUACUUUGAGAG CCAUCACCAGCGACUAUGUCGUAUGGGUAAAGCGCUUAUUUAUCGGA GAGAAAUCCGAUAAAUAAGAAGCAUCAAAG |
| 2223 | 3' HH15 Minimal Hammerhead ribozyme | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAGGGGAGCCCCGCUGAUGAGGUCGGGGAGACCGAA AGGGACUUCGGUCCCUACGGGGCUCCC |
| 2224 | 5' RBMX recruiting motif | CCACCCCCACCACCACCCCCACCCCCACCACCACCCUACUGGCGCUU UUAUCUCAUUACUUUGAGAGCCAUCACCAGCGACUAUGUCGUAUGGG UAAAGCGCUUAUUUAUCGGAGAGAAAUCCGAUAAAUAAGAAGCAUCA AAG |
| 2225 | 3' Hammerhead ribozyme (Lior Nissim, Timothy Lu) smaller scar | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAGCGACUACUGAUGAGUCCGUGAGGACGAAACGAG UAAGCUCGUCUAGUCG |
| 2226 | 3' env25 pistol ribozyme (with an added CUUCGG loop) | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAGCGUGGUUAGGGCCACGUUUAAAUAGUUGCUUAAG CCCUAAGCGUUGAUCUUCGGAUCAGGUGCAA |
| 2227 | 3' Env-9 Twister | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAGGGCAAUAAAGCGGUUACAAGCCCGCAAAAAUAG CAGAGUAAUGUCGCGAUAGCGCGGCAUUAAUGCAGCUUUAUUG |
| 2228 | =+AUUAUC UCAUUACU 25 | UACUGGCGCUUUUAUCUCAUUACUAUUAUCUCAUUACUUUGAGAGCC AUCACCAGCGACUAUGUCGUAUGGGUAAAGCGCUUAUUUAUCGGAGA GAAAUCCGAUAAAUAAGAAGCAUCAAAG |
| 2229 | 5' Env-9 Twister | GGCAAUAAAGCGGUUACAAGCCCGCAAAAAUAGCAGAGUAAUGUCGC GAUAGCGCGGCAUUAAUGCAGCUUUAUUGUACUGGCGCUUUUAUCUC AUUACUUUGAGAGCCAUCACCAGCGACUAUGUCGUAUGGGUAAAGCG CUUAUUUAUCGGAGAGAAAUCCGAUAAAUAAGAAGCAUCAAAG |
| 2230 | 3' Twisted Sister 1 | UACUGGCGCUUUUAUCUCAUUACUUUGAGAGCCAUCACCAGCGACUA UGUCGUAUGGGUAAAGCGCUUAUUUAUCGGAGAGAAAUCCGAUAAAU AAGAAGCAUCAAAGACCCGCAAGGCCGACGGCAUCCGCCGCCGCUGG UGCAAGUCCAGCCGCCCCUUCGGGGGCGGGCGCUCAUGGGUAAC |

TABLE 2B-continued

Exemplary gNA Scaffold Sequences

| SEQ ID NO: | NAME or Modification | NUCLEOTIDE SEQUENCE |
|---|---|---|
| 2231 | no stem | UACUGGCGCUUUUAUCUCAUUACUUUGAGAGCCAUCACCAGCGACUAUGUCGUAUGGGUAAAG |
| 2232 | 5' HH15 Minimal Hammerhead ribozyme | GGGAGCCCCGCUGAUGAGGUCGGGGAGACCGAAAGGGACUUCGGUCCCUACGGGGCUCCCUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2233 | 5' Hammerhead ribozyme (Li or Nissim, Timothy Lu) guide scaffold scar | CCAGUACUGAUGAGUCCGUGAGGACGAAACGAGUAAGCUCGUCUACUGGCGCUUUUAUCUCAUUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2234 | 5' Twisted Sister 1 | ACCCGCAAGGCCGACGGCAUCCGCCGCCGCUGGUGCAAGUCCAGCCGCCCCUUCGGGGGCGGGCGCUCAUGGGUAACUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2235 | 5' sTRSV WT viral Hammerhead ribozyme | CCUGUCACCGGAUGUGCUUUCCGGUCUGAUGAGUCCGUGAGGACGAAACAGGUACUGGCGCUUUUAUCUCAUUACUUUGAGAGCCAUCACCAGCGACUAUGUCGUAUGGGUAAAGCGCUUAUUUAUCGGAGAGAAAUCCGAUAAAUAAGAAGCAUCAAAG |
| 2236 | 148: =+G55, stacked onto 64 | GUACUGGCGCCUUUUAUCUCAUUACUUUGAGAGCCAUCACCAGCGACUAUGUCGUAGUGGGUAAAGCGCUUACGGACUUCGGUCCGUAAGAAGCAUCAAAG |
| 2237 | 158: 103+148(+G55) -99, G65U | GUACUGGCGCUUUUAUCUGAUUACUUUGAGAGCCAUCACCAGCGACUAUGUCGUAGUGGGUAAAGCUCCCUCUUCGGAGGGAGCAUCAAAG |
| 2238 | 174: Uvsx Extended stem with [A99] G65U), C18G, ^G55, [GU-1] | ACUGGCGCUUUUAUCUGAUUACUUUGAGAGCCAUCACCAGCGACUAUGUCGUAGUGGGUAAAGCUCCCUCUUCGGAGGGAGCAUCAAAG |
| 2239 | 175: extended stem truncation, U10C, [GU-1] | ACUGGCGCCUUUUAUCUCAUUACUUUGAGAGCCAUCACCAGCGACUAUGUCGUAUGGGUAAAGCGCUUACGGACUUCGGUCCGUAAGAAGCAUCAAAG |
| 2240 | 176: 174 with A1G substitution for T7 transcription | GCUGGCGCUUUUAUCUGAUUACUUUGAGAGCCAUCACCAGCGACUAUGUCGUAGUGGGUAAAGCUCCCUCUUCGGAGGGAGCAUCAAAG |
| 2241 | 177: 174 with bubble (+G55) removed | ACUGGCGCUUUUAUCUGAUUACUUUGAGAGCCAUCACCAGCGACUAUGUCGUAUGGGUAAAGCUCCCUCUUCGGAGGGAGCAUCAAAG |
| 2242 | 181: stem 42 (truncated stem loop); U10C, C18G, [GU-1] (95+[GU-1]) | ACUGGCGCCUUUUAUCUGAUUACUUUGAGAGCCAUCACCAGCGACUAUGUCGUAUGGGUAAAGCGCUUACGGACUUCGGUCCGUAAGAAGCAUCAAAG |
| 2243 | 182: stem 42 (truncated stem loop); C18G, [GU-1] | ACUGGCGCUUUUAUCUGAUUACUUUGAGAGCCAUCACCAGCGACUAUGUCGUAUGGGUAAAGCGCUUACGGACUUCGGUCCGUAAGAAGCAUCAAAG |
| 2244 | 183: stem 42 (truncated stem loop); C18G, ^G55, [GU-1] | ACUGGCGCUUUUAUCUGAUUACUUUGAGAGCCAUCACCAGCGACUAUGUCGUAGUGGGUAAAGCGCUUACGGACUUCGGUCCGUAAGAAGCAUCAAAG |

TABLE 2B-continued

Exemplary gNA Scaffold Sequences

| SEQ ID NO: | NAME or Modification | NUCLEOTIDE SEQUENCE |
|---|---|---|
| 2245 | 184: stem 48 (uvsx, -99 g65t); C18G, ^T55, [GU-1] | ACUGGCGCUUUUAUCUGAUUACUUUGAGAGCCAUCACCAGCGACUAU GUCGUAUUGGGUAAAGCUCCCUCUUCGGAGGGAGCAUCAAAG |
| 2246 | 185: stem 42 (truncated stem loop); C18G, ^U55, [GU-1] | ACUGGCGCUUUUAUCUGAUUACUUUGAGAGCCAUCACCAGCGACUAU GUCGUAUUGGGUAAAGCGCUUACGGACUUCGGUCCGUAAGAAGCAUC AAAG |
| 2247 | 186: stem 42 (truncated stem loop); U10C, ^A17, [GU-1] | ACUGGCGCCUUUAUCAUCAUUACUUUGAGAGCCAUCACCAGCGACUA UGUCGUAUGGGUAAAGCGCUUACGGACUUCGGUCCGUAAGAAGCAUC AAAG |
| 2248 | 187: stem 46 (uvsx); C18G, ^G55, [GU-1] | ACUGGCGCUUUUAUCUGAUUACUUUGAGAGCCAUCACCAGCGACUAU GUCGUAGUGGGUAAAGCGCCCUCUUCGGAGGGAAGCAUCAAAG |
| 2249 | 188: stem 50 (m52 U15C, -99, g65t); C18G, ^G55, [GU-1] | ACUGGCGCUUUUAUCUGAUUACUUUGAGAGCCAUCACCAGCGACUAU GUCGUAGUGGGUAAAGCUCACAUGAGGAUCACCCAUGUGAGCAUCAA AG |
| 2250 | 189: 174 + G8A; U15C; U35A | ACUGGCACUUUUACCUGAUUACUUUGAGAGCCAACACCAGCGACUAU GUCGUAGUGGGUAAAGCUCCCUCUUCGGAGGGAGCAUCAAAG |
| 2251 | 190: 174 + G8A | ACUGGCACUUUUAUCUGAUUACUUUGAGAGCCAUCACCAGCGACUAU GUCGUAGUGGGUAAAGCUCCCUCUUCGGAGGGAGCAUCAAAG |
| 2252 | 191: 174 + G8C | ACUGGCCCUUUUAUCUGAUUACUUUGAGAGCCAUCACCAGCGACUAU GUCGUAGUGGGUAAAGCUCCCUCUUCGGAGGGAGCAUCAAAG |
| 2253 | 192: 174 + U15C | ACUGGCGCUUUUACCUGAUUACUUUGAGAGCCAUCACCAGCGACUAU GUCGUAGUGGGUAAAGCUCCCUCUUCGGAGGGAGCAUCAAAG |
| 2254 | 193, 174 + U35A | ACUGGCGCUUUUAUCUGAUUACUUUGAGAGCCAACACCAGCGACUAU GUCGUAGUGGGUAAAGCUCCCUCUUCGGAGGGAGCAUCAAAG |
| 2255 | 195: 175 + C18G + G8A; U15C; U35A | ACUGGCACCUUUACCUGAUUACUUUGAGAGCCAACACCAGCGACUAU GUCGUAUGGGUAAAGCGCUUACGGACUUCGGUCCGUAAGAAGCAUCA AAG |
| 2256 | 196: 175 + C18G + G8A | ACUGGCACCUUUAUCUGAUUACUUUGAGAGCCAUCACCAGCGACUAU GUCGUAUGGGUAAAGCGCUUACGGACUUCGGUCCGUAAGAAGCAUCA AAG |
| 2257 | 197: 175 + C18G + G8C | ACUGGCCCUUUUAUCUGAUUACUUUGAGAGCCAUCACCAGCGACUAU GUCGUAUGGGUAAAGCGCUUACGGACUUCGGUCCGUAAGAAGCAUCA AAG |
| 2258 | 198: 175 + C18G + U35A | ACUGGCGCCUUUAUCUGAUUACUUUGAGAGCCAACACCAGCGACUAU GUCGUAUGGGUAAAGCGCUUACGGACUUCGGUCCGUAAGAAGCAUCA AAG |
| 2259 | 199: 174 + A2G (test G transcription at start; ccGCT...) | GCUGGCGCUUUUAUCUGAUUACUUUGAGAGCCAUCACCAGCGACUAU GUCGUAGUGGGUAAAGCUCCCUCUUCGGAGGGAGCAUCAAAG |
| 2260 | 200: 174 + ^G1 (ccGACU...) | GACUGGCGCUUUUAUCUGAUUACUUUGAGAGCCAUCACCAGCGACUA UGUCGUAGUGGGUAAAGCUCCCUCUUCGGAGGGAGCAUCAAAG |

TABLE 2B-continued

Exemplary gNA Scaffold Sequences

| SEQ ID NO: | NAME or Modification | NUCLEOTIDE SEQUENCE |
|---|---|---|
| 2261 | 201: 174 + U10C; AG28 | ACUGGCGCCUUUAUCUGAUUACUUUGGAGAGCCAUCACCAGCGACUAUGUCGUAGUGGGUAAAGCUCCCUCUUCGGAGGGAGCAUCAAAG |
| 2262 | 202: 174 + U10A; A28U | ACUGGCGCAUUUAUCUGAUUACUUUGUGAGCCAUCACCAGCGACUAUGUCGUAGUGGGUAAAGCUCCCUCUUCGGAGGGAGCAUCAAAG |
| 2263 | 203: 174 + U10C | ACUGGCGCCUUUAUCUGAUUACUUUGAGAGCCAUCACCAGCGACUAUGUCGUAGUGGGUAAAGCUCCCUCUUCGGAGGGAGCAUCAAAG |
| 2264 | 204: 174 + ^G28 | ACUGGCGCUUUUAUCUGAUUACUUUGGAGAGCCAUCACCAGCGACUAUGUCGUAGUGGGUAAAGCUCCCUCUUCGGAGGGAGCAUCAAAG |
| 2265 | 205: 174 + U10A | ACUGGCGCAUUUAUCUGAUUACUUUGAGAGCCAUCACCAGCGACUAUGUCGUAGUGGGUAAAGCUCCCUCUUCGGAGGGAGCAUCAAAG |
| 2266 | 206, 174 + A28U | ACUGGCGCUUUUAUCUGAUUACUUUGUGAGCCAUCACCAGCGACUAUGUCGUAGUGGGUAAAGCUCCCUCUUCGGAGGGAGCAUCAAAG |
| 2267 | 207: 174 + ^U15 | ACUGGCGCUUUUAUUCUGAUUACUUUGAGAGCCAUCACCAGCGACUAUGUCGUAGUGGGUAAAGCUCCCUCUUCGGAGGGAGCAUCAAAG |
| 2268 | 208: 174 + [U4] | ACGGCGCUUUUAUCUGAUUACUUUGAGAGCCAUCACCAGCGACUAUGUCGUAGUGGGUAAAGCUCCCUCUUCGGAGGGAGCAUCAAAG |
| 2269 | 209: 174 + C16A | ACUGGCGCUUUUAUAUGAUUACUUUGAGAGCCAUCACCAGCGACUAUGUCGUAGUGGGUAAAGCUCCCUCUUCGGAGGGAGCAUCAAAG |
| 2270 | 210: 174 + ^U17 | ACUGGCGCUUUUAUCUUGAUUACUUUGAGAGCCAUCACCAGCGACUAUGUCGUAGUGGGUAAAGCUCCCUCUUCGGAGGGAGCAUCAAAG |
| 2271 | 211: 174 + U35G (compare with 174 + U35A above) | ACUGGCGCUUUUAUCUGAUUACUUUGAGAGCCAGCACCAGCGACUAUGUCGUAGUGGGUAAAGCUCCCUCUUCGGAGGGAGCAUCAAAG |
| 2272 | 212: 174 + U11G, A105G (A86G), U26C | ACUGGCGCUGUUAUCUGAUUACUUCGAGAGCCAUCACCAGCGACUAUGUCGUAGUGGGUAAAGCUCCCUCUUCGGAGGGAGCAUCGAAG |
| 2273 | 213: 174 + U11C, A105G (A86G), U26C | ACUGGCGCUCUUAUCUGAUUACUUCGAGAGCCAUCACCAGCGACUAUGUCGUAGUGGGUAAAGCUCCCUCUUCGGAGGGAGCAUCGAAG |
| 2274 | 214: 174 + U12G; A106G (A87G), U25C | ACUGGCGCUUGUAUCUGAUUACUCUGAGAGCCAUCACCAGCGACUAUGUCGUAGUGGGUAAAGCUCCCUCUUCGGAGGGAGCAUCAGAG |
| 2275 | 215: 174 + U12C; A106G (A87G), U25C | ACUGGCGCUUCUAUCUGAUUACUCUGAGAGCCAUCACCAGCGACUAUGUCGUAGUGGGUAAAGCUCCCUCUUCGGAGGGAGCAUCAGAG |
| 2276 | 216: 174_tx_11.G, 87.G, 22.0 | ACUGGCGCUUUGAUCUGAUUACCUUGAGAGCCAUCACCAGCGACUAUGUCGUAGUGGGUAAAGCUCCCUCUUCGGAGGGAGCAUCAAGG |
| 2277 | 217: 174_tx_11.C, 87.G, 22.0 | ACUGGCGCUUUCAUCUGAUUACCUUGAGAGCCAUCACCAGCGACUAUGUCGUAGUGGGUAAAGCUCCCUCUUCGGAGGGAGCAUCAAGG |
| 2278 | 218: 174 + U11G | ACUGGCGCUGUUAUCUGAUUACUUUGAGAGCCAUCACCAGCGACUAUGUCGUAGUGGGUAAAGCUCCCUCUUCGGAGGGAGCAUCAAAG |
| 2279 | 219: 174 + A105G (A86G) | ACUGGCGCUUUUAUCUGAUUACUUUGAGAGCCAUCACCAGCGACUAUGUCGUAGUGGGUAAAGCUCCCUCUUCGGAGGGAGCAUCGAAG |

TABLE 2B-continued

Exemplary gNA Scaffold Sequences

| SEQ ID NO: | NAME or Modification | NUCLEOTIDE SEQUENCE |
|---|---|---|
| 2280 | 220: 174 + U26C | ACUGGCGCUUUUAUCUGAUUACUUCGAGAGCCAUCACCAGCGACUAU GUCGUAGUGGGUAAAGCUCCCUCUUCGGAGGGAGCAUCAAAG |

In some embodiments, the gNA variant comprises a tracrRNA stem loop comprising the sequence -UUU-N4-25-UUU-(SEQ ID NO: 21). For example, the gNA variant comprises a scaffold stem loop or a replacement thereof, flanked by two triplet U motifs that contribute to the triplex region. In some embodiments, the scaffold stem loop or replacement thereof comprises at least 4 nucleotides, at least 5 nucleotides, at least 6 nucleotides, at least 7 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, or at least 25 nucleotides.

In some embodiments, the gNA variant comprises a crRNA sequence with -AAAG-in a location 5' to the spacer region. In some embodiments, the -AAAG- sequence is immediately 5' to the spacer region.

In some embodiments, the at least one nucleotide modification to a reference gNA to produce a gNA variant comprises at least one nucleotide deletion in the CasX variant gNA relative to the reference gRNA. In some embodiments, a gNA variant comprises a deletion of 1, 2, 3, 4, 5, 6, 7, 8, 9, 10, 11, 12, 13, 14, 15, 16, 17, 18, 19 or 20 consecutive or non-consecutive nucleotides relative to a reference gNA. In some embodiments, the at least one deletion comprises a deletion of 1, 2, 3, 4, 5, 6, 7, 8, 9, 10, 11, 12, 13, 14, 15, 16, 17, 18, 19 or 20 or more consecutive nucleotides relative to a reference gNA. In some embodiments, the gNA variant comprises 2, 3, 4, 5, 6, 7, 8, 9, 10, 11, 12, 13, 14, 15, 16, 17, 18, 19 or 20 or more nucleotide deletions relative to the reference gNA, and the deletions are not in consecutive nucleotides. In those embodiments where there are two or more non-consecutive deletions in the gNA variant relative to the reference gRNA, any length of deletions, and any combination of lengths of deletions, as described herein, are contemplated as within the scope of the disclosure. For example, in some embodiments, a gNA variant may comprise a first deletion of one nucleotide, and a second deletion of two nucleotides and the two deletions are not consecutive. In some embodiments, a gNA variant comprises at least two deletions in different regions of the reference gRNA. In some embodiments, a gNA variant comprises at least two deletions in the same region of the reference gRNA. For example, the regions may be the extended stem loop, scaffold stem loop, scaffold stem bubble, triplex loop, pseudoknot, triplex, or a 5' end of the gNA variant. The deletion of any nucleotide in a reference gRNA is contemplated as within the scope of the disclosure.

In some embodiments, the at least one nucleotide modification of a reference gRNA to generate a gNA variant comprises at least one nucleotide insertion. In some embodiments, a gNA variant comprises an insertion of 1, 2, 3, 4, 5, 6, 7, 8, 9 or 10 consecutive or non-consecutive nucleotides relative to a reference gRNA. In some embodiments, the at least one nucleotide insertion comprises an insertion of 1, 2, 3, 4, 5, 6, 7, 8, 9, 10, 11, 12, 13, 14, 15, 16, 17, 18, 19 or 20 or more consecutive nucleotides relative to a reference gRNA. In some embodiments, the gNA variant comprises 2 or more insertions relative to the reference gRNA, and the insertions are not consecutive. In those embodiments where there are two or more non-consecutive insertions in the gNA variant relative to the reference gRNA, any length of insertions, and any combination of lengths of insertions, as described herein, are contemplated as within the scope of the disclosure. For example, in some embodiments, a gNA variant may comprise a first insertion of one nucleotide, and a second insertion of two nucleotides and the two insertions are not consecutive. In some embodiments, a gNA variant comprises at least two insertions in different regions of the reference gRNA. In some embodiments, a gNA variant comprises at least two insertions in the same region of the reference gRNA. For example, the regions may be the extended stem loop, scaffold stem loop, scaffold stem bubble, triplex loop, pseudoknot, triplex, or a 5' end of the gNA variant. Any insertion of A, G, C, U (or T, in the corresponding DNA) or combinations thereof at any location in the reference gRNA is contemplated as within the scope of the disclosure.

In some embodiments, the at least one nucleotide modification of a reference gRNA to generate a gNA variant comprises at least one nucleic acid substitution. In some embodiments, a gNA variant comprises 1, 2, 3, 4, 5, 6, 7, 8, 9, 10, 11, 12, 13, 14, 15, 16, 17, 18, 19 or 20 or more consecutive or non-consecutive substituted nucleotides relative to a reference gRNA. In some embodiments, a gNA variant comprises 1-4 nucleotide substitutions relative to a reference gRNA. In some embodiments, the at least one substitution comprises a substitution of 1, 2, 3, 4, 5, 6, 7, 8, 9, 10, 11, 12, 13, 14, 15, 16, 17, 18, 19 or 20 or more consecutive nucleotides relative to a reference gRNA. In some embodiments, the gNA variant comprises 2 or more substitutions relative to the reference gRNA, and the substitutions are not consecutive. In those embodiments where there are two or more non-consecutive substitutions in the gNA variant relative to the reference gRNA, any length of substituted nucleotides, and any combination of lengths of substituted nucleotides, as described herein, are contemplated as within the scope of the disclosure. For example, in some embodiments, a gNA variant may comprise a first substitution of one nucleotide, and a second substitution of two nucleotides and the two substitutions are not consecutive. In some embodiments, a gNA variant comprises at least two substitutions in different regions of the reference gRNA. In some embodiments, a gNA variant comprises at least two substitutions in the same region of the reference gRNA. For example, the regions may be the triplex, the extended stem loop, scaffold stem loop, scaffold stem bubble, triplex loop, pseudoknot, triplex, or a 5' end of the gNA variant. Any substitution of A, G, C, U (or T, in the corresponding DNA) or combinations thereof at any location in the reference gRNA is contemplated as within the scope of the disclosure.

Any of the substitutions, insertions and deletions described herein can be combined to generate a gNA variant of the disclosure. For example, a gNA variant can comprise at least one substitution and at least one deletion relative to a reference gRNA, at least one substitution and at least one insertion relative to a reference gRNA, at least one insertion and at least one deletion relative to a reference gRNA, or at least one substitution, one insertion and one deletion relative to a reference gRNA.

In some embodiments, the gNA variant comprises a scaffold region at least 20% identical, at least 30% identical, at least 40% identical, at least 50% identical, at least 60% identical, at least 65% identical, at least 70% identical, at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to any one of SEQ ID NOS: 4-16. In some embodiments, the gNA variant comprises a scaffold region at least 60% homologous (or identical) to any one of SEQ ID NOS: 4-16.

In some embodiments, the gNA variant comprises a tracr stem loop at least 60% identical, at least 65% identical, at least 70% identical, at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to SEQ ID NO: 14. In some embodiments, the gNA variant comprises a tracr stem loop at least 60% homologous (or identical) to SEQ ID NO: 14.

In some embodiments, the gNA variant comprises an extended stem loop at least 60% identical, at least 65% identical, at least 70% identical, at least 75% identical, at least 80% identical, at least 85% identical, at least 90% identical, at least 91% identical, at least 92% identical, at least 93% identical, at least 94% identical, at least 95% identical, at least 96% identical, at least 97% identical, at least 98% identical, or at least 99% identical to SEQ ID NO: 15. In some embodiments, the gNA variant comprises an extended stem loop at least 60% homologous (or identical) to SEQ ID NO: 15.

In some embodiments, the gNA variant comprises an exogenous extended stem loop, with such differences from a reference gNA described as follows. In some embodiments, an exogenous extended stem loop has little or no identity to the reference stem loop regions disclosed herein (e.g., SEQ ID NO: 15). In some embodiments, an exogenous stem loop is at least 10 bp, at least 20 bp, at least 30 bp, at least 40 bp, at least 50 bp, at least 60 bp, at least 70 bp, at least 80 bp, at least 90 bp, at least 100 bp, at least 200 bp, at least 300 bp, at least 400 bp, at least 500 bp, at least 600 bp, at least 700 bp, at least 800 bp, at least 900 bp, at least 1,000 bp, at least 2,000 bp, at least 3,000 bp, at least 4,000 bp, at least 5,000 bp, at least 6,000 bp, at least 7,000 bp, at least 8,000 bp, at least 9,000 bp, at least 10,000 bp, at least 12,000 bp, at least 15,000 bp or at least 20,000 bp. In some embodiments, the gNA variant comprises an extended stem loop region comprising at least 10, at least 100, at least 500, at least 1000, or at least 10,000 nucleotides. In some embodiments, the heterologous stem loop increases the stability of the gNA. In some embodiments, the heterologous RNA stem loop is capable of binding a protein, an RNA structure, a DNA sequence, or a small molecule. In some embodiments, an exogenous stem loop region comprises an RNA stem loop or hairpin, for example a thermostable RNA such as MS2 (ACAUGAGGAUUACCCAUGU; SEQ ID NO: 22), Qβ (UGCAUGUCUAAGACAGCA; SEQ ID NO: 23), U1 hairpin II (AAUCCAUUGCACUCCGGAUU; SEQ ID NO: 24), Uvsx (CCUCUUCGGAGG; SEQ ID NO: 25), PP7 (AGGAGUUUCUAUGGAAACCCU; SEQ ID NO: 26), Phage replication loop (AGGUGGGACGACCU-CUCGGUCGUCCUAUCU; SEQ ID NO: 27), Kissing loop_a (UGCUCGCUCCGUUCGAGCA; SEQ ID NO: 28), Kissing loop_b1 (UGCUCGACGCGUCCUCGAGCA; SEQ ID NO: 29), Kissing loop_b2 (UG-CUCGUUUGCGGCUACGAGCA; SEQ ID NO: 30), G quadriplex M3q (AGGGAGGGAGGGAGAGG; SEQ ID NO: 31), G quadriplex telomere basket (GGUUAGG-GUUAGGGUUAGG; SEQ ID NO: 32), Sarcin-ricin loop (CUGCUCAGUACGAGAGGAACCGCAG; SEQ ID NO: 33) or Pseudoknots (UACACUGGGAUCGCUGAAUUA-GAGAUCGGCGUCCUUUCAUUCUAUAUACUUU GGAGUUUUAAAAUGUCUCUAAGUACA; SEQ ID NO: 34). In some embodiments, an exogenous stem loop comprises an RNA scaffold. As used herein, an "RNA scaffold" refers to a multi-dimensional RNA structure capable of interacting with and organizing or localizing one or more proteins. In some embodiments, the RNA scaffold is synthetic or non-naturally occurring. In some embodiments, an exogenous stem loop comprises a long non-coding RNA (lncRNA). As used herein, a lncRNA refers to a non-coding RNA that is longer than approximately 200 bp in length. In some embodiments, the 5' and 3' ends of the exogenous stem loop are base paired, i.e., interact to form a region of duplex RNA. In some embodiments, the 5' and 3' ends of the exogenous stem loop are base paired, and one or more regions between the 5' and 3' ends of the exogenous stem loop are not base paired. In some embodiments, the at least one nucleotide modification comprises: (a) substitution of 1 to 15 consecutive or non-consecutive nucleotides in the gNA variant in one or more regions; (b) a deletion of 1 to 10 consecutive or non-consecutive nucleotides in the gNA variant in one or more regions; (c) an insertion of 1 to 10 consecutive or non-consecutive nucleotides in the gNA variant in one or more regions; (d) a substitution of the scaffold stem loop or the extended stem loop with an RNA stem loop sequence from a heterologous RNA source with proximal 5' and 3' ends; or any combination of (a)-(d).

In some embodiments, the gNA variant comprises a scaffold stem loop having at least 60% identity to SEQ ID NO: 14. In some embodiments, the gNA variant comprises a scaffold stem loop having at least 60% identity, at least 70% identity, at least 80% identity, at least 90% identity, at least 95% identity, at least 98% identity or at least 99% identity to SEQ ID NO: 14. In some embodiments, the gNA variant comprises a scaffold stem loop comprising SEQ ID NO: 14.

In some embodiments, the gNA variant comprises a scaffold stem loop sequence of CCAGCGACUAUGU-CGUAGUGG (SEQ ID NO: 20). In some embodiments, the gNA variant comprises a scaffold stem loop sequence of CCAGCGACUAUGUCGUAGUGG (SEQ ID NO: 20) with at least 1, 2, 3, 4, or 5 mismatches thereto.

In some embodiments, the gNA variant comprises an extended stem loop region comprising less than 32 nucleotides, less than 31 nucleotides, less than 30 nucleotides, less than 29 nucleotides, less than 28 nucleotides, less than 27 nucleotides, less than 26 nucleotides, less than 25 nucleotides, less than 24 nucleotides, less than 23 nucleotides, less than 22 nucleotides, less than 21 nucleotides, or less than 20 nucleotides. In some embodiments, the gNA variant comprises an extended stem loop region comprising less than 32 nucleotides. In some embodiments, the gNA variant further comprises a thermostable stem loop.

In some embodiments, a sgRNA variant comprises a sequence of SEQ ID NO: 2104, SEQ ID NO: 2106, SEQ ID NO: 2163, SEQ ID NO: 2107, SEQ ID NO: 2164, SEQ ID NO: 2165, SEQ ID NO: 2166, SEQ ID NO: 2103, SEQ ID NO: 2167, SEQ ID NO: 2105, SEQ ID NO: 2108, SEQ ID NO: 2112, SEQ ID NO: 2160, SEQ ID NO: 2170, SEQ ID NO: 2114, SEQ ID NO: 2171, SEQ ID NO: 2112, SEQ ID NO: 2173, SEQ ID NO: 2102, SEQ ID NO: 2174, SEQ ID NO: 2175, SEQ ID NO: 2109, SEQ ID NO: 2176, SEQ ID NO: 2238, SEQ ID NO: 2239, SEQ ID NO: 2240, SEQ ID NO: 2241, SEQ ID NO: 2274, or SEQ ID NO: 2275.

In some embodiments, the gNA variant comprises the sequence of any one of SEQ ID NOS: 2236, 2237, 2238, 2241, 2244, 2248, 2249, or 2259-2280, or having at least about 80%, at least about 90%, at least about 95%, at least about 96%, at least about 97%, at least about 98%, at least about 99% identity thereto. In some embodiments, the gNA variant comprises one or more additional changes to a sequence of any one of SEQ ID NOs: 2201-2280. In some embodiments, the gNA variant comprises the sequence of any one of SEQ ID NOS: 2236, 2237, 2238, 2241, 2244, 2248, 2249, or 2259-2280.

In some embodiments, a sgRNA variant comprises one or more additional changes to a sequence of SEQ ID NO: 2104, SEQ ID NO: 2163, SEQ ID NO: 2107, SEQ ID NO: 2164, SEQ ID NO: 2165, SEQ ID NO: 2166, SEQ ID NO: 2103, SEQ ID NO: 2167, SEQ ID NO: 2105, SEQ ID NO: 2108, SEQ ID NO: 2112, SEQ ID NO: 2160, SEQ ID NO: 2170, SEQ ID NO: 2114, SEQ ID NO: 2171, SEQ ID NO: 2112, SEQ ID NO: 2173, SEQ ID NO: 2102, SEQ ID NO: 2174, SEQ ID NO: 2175, SEQ ID NO: 2109, SEQ ID NO: 2176, SEQ ID NO: 2238, SEQ ID NO: 2239, SEQ ID NO: 2240, SEQ ID NO: 2241, SEQ ID NO: 2274, or SEQ ID NO: 2275.

In some embodiments of the gNA variants of the disclosure, the gNA variant comprises at least one modification, wherein the at least one modification compared to the reference guide scaffold of SEQ ID NO: 5 is selected from one or more of: (a) a C18G substitution in the triplex loop; (b) a G55 insertion in the stem bubble; (c) a U1 deletion; (d) a modification of the extended stem loop wherein (i) a 6 nt loop and 13 loop-proximal base pairs are replaced by a Uvsx hairpin; and (ii) a deletion of A99 and a substitution of G65U that results in a loop-distal base that is fully base-paired. In such embodiments, the gNA variant comprises the sequence of any one of SEQ ID NOS: 2236, 2237, 2238, 2241, 2244, 2248, 2249, or 2259-2280.

In some embodiments, the scaffold of the gNA variant comprises the sequence of any one of SEQ ID NOS: 2201-2280 of Table 2B. In some embodiments, the scaffold of the gNA consists or consists essentially of the sequence of any one of SEQ ID NOS: 2201-2280. In some embodiments, the scaffold of the gNA variant sequence is at least about 60% identical, at least about 65% identical, at least about 70% identical, at least about 75% identical, at least about 80% identical, at least about 85% identical, at least about 90% identical, at least about 91% identical, at least about 92% identical, at least about 93% identical, at least about 94% identical, at least about 95% identical, at least about 96% identical, at least about 97% identical, at least about 98% identical or at least about 99% identical to any one of SEQ ID NOS: 2201 to 2280.

In the embodiments of the gNA variants, the gNA further comprises a spacer (or targeting sequence) region, described more fully, supra, which comprises at least 14 to about 35 nucleotides wherein the spacer is designed with a sequence that is complementary to a target DNA. In some embodiments, the gNA variant comprises a targeting sequence of at least 10 to 30 nucleotides complementary to a target DNA. In some embodiments, the targeting sequence has 14, 15, 16, 17, 18, 19, 20, 21, 22, 23, 24, 25, 26, 27, 28, 29, 30, 31, 32, 33, 34 or 35 nucleotides. In some embodiments, the gNA variant comprises a targeting sequence having 20 nucleotides. In some embodiments, the targeting sequence has 25 nucleotides. In some embodiments, the targeting sequence has 24 nucleotides. In some embodiments, the targeting sequence has 23 nucleotides. In some embodiments, the targeting sequence has 22 nucleotides. In some embodiments, the targeting sequence has 21 nucleotides. In some embodiments, the targeting sequence has 20 nucleotides. In some embodiments, the targeting sequence has 19 nucleotides. In some embodiments, the targeting sequence has 18 nucleotides. In some embodiments, the targeting sequence has 17 nucleotides. In some embodiments, the targeting sequence has 16 nucleotides. In some embodiments, the targeting sequence has 15 nucleotides. In some embodiments, the targeting sequence has 14 nucleotides. In some embodiments, the disclosure provides targeting sequences for inclusion in the gNA variants of the disclosure comprising a sequence that is at least 50% identical, at least 55% identical, at least 60% identical, at least 65% identical, at least 70% identical, at least 75% identical, at least 80% identical, at least 85% identical, at least 90% identical, at least 95% identical, or 100% identical to a sequence in Table 3. In some embodiments, the targeting sequence of the gNA variant comprises a sequence a sequence of Table 3 with a single nucleotide removed from the 3' end of the sequence. In other embodiments, the targeting sequence of the gNA variant comprises a sequence a sequence of Table 3 with two nucleotides removed from the 3' end of the sequence. In other embodiments, the targeting sequence of the gNA variant comprises a sequence a sequence of Table 3 with three nucleotides removed from the 3' end of the sequence. In other embodiments, the targeting sequence of the gNA variant comprises a sequence a sequence of Table 3 with four nucleotides removed from the 3' end of the sequence. In other embodiments, the targeting sequence of the gNA variant comprises a sequence a sequence of Table 3 with five nucleotides removed from the 3' end of the sequence.

In some embodiments, the scaffold of the gNA variant is part of an RNP with a reference CasX protein comprising SEQ ID NO: 1, SEQ ID NO: 2, or SEQ ID NO: 3. In other embodiments, the scaffold of the gNA variant is part of an RNP with a CasX variant protein comprising any one of the sequences of Tables 4, 6, 7, 8, or 10, or a sequence having at least about 50%, at least about 60%, at least about 70%, at least about 80%, at least about 85%, at least about 90%, at least about 91%, at least about 92%, at least about 93%, at least about 94%, at least about 95%, at least about 96%, at least about 97%, at least about 98%, or at least about 99% identity thereto. In the foregoing embodiments, the gNA further comprises a spacer sequence.

In some embodiments, the scaffold of the gNA variant is a variant comprising one or more additional changes to a sequence of a reference gRNA that comprises SEQ ID NO: 4 or SEQ ID NO: 5. In those embodiments where the scaffold of the reference gRNA is derived from SEQ ID NO:

4 or SEQ ID NO: 5, the one or more improved or added characteristics of the gNA variant are improved compared to the same characteristic in SEQ ID NO: 4 or SEQ ID NO: 5.

h. Complex Formation with CasX Protein

In some embodiments, a gNA variant has an improved ability to form a complex with a CasX protein (such as a reference CasX or a CasX variant protein) when compared to a reference gRNA. In some embodiments, a gNA variant has an improved affinity for a CasX protein (such as a reference or variant protein) when compared to a reference gRNA, thereby improving its ability to form a ribonucleoprotein (RNP) complex with the CasX protein, as described in the Examples. Improving ribonucleoprotein complex formation may, in some embodiments, improve the efficiency with which functional RNPs are assembled. In some embodiments, greater than 90%, greater than 93%, greater than 95%, greater than 96%, greater than 97%, greater than 98% or greater than 99% of RNPs comprising a gNA variant and its spacer are competent for gene editing of a target nucleic acid.

Exemplary nucleotide changes that can improve the ability of gNA variants to form a complex with CasX protein may, in some embodiments, include replacing the scaffold stem with a thermostable stem loop. Without wishing to be bound by any theory, replacing the scaffold stem with a thermostable stem loop could increase the overall binding stability of the gNA variant with the CasX protein. Alternatively, or in addition, removing a large section of the stem loop could change the gNA variant folding kinetics and make a functional folded gNA easier and quicker to structurally-assemble, for example by lessening the degree to which the gNA variant can get "tangled" in itself. In some embodiments, choice of scaffold stem loop sequence could change with different spacers that are utilized for the gNA. In some embodiments, scaffold sequence can be tailored to the spacer and therefore the target sequence. Biochemical assays can be used to evaluate the binding affinity of CasX protein for the gNA variant to form the RNP, including the assays of the Examples. For example, a person of ordinary skill can measure changes in the amount of a fluorescently tagged gNA that is bound to an immobilized CasX protein, as a response to increasing concentrations of an additional unlabeled "cold competitor" gNA. Alternatively, or in addition, fluorescence signal can be monitored to or seeing how it changes as different amounts of fluorescently labeled gNA are flowed over immobilized CasX protein. Alternatively, the ability to form an RNP can be assessed using in vitro cleavage assays against a defined target nucleic acid sequence.

i. gNA Stability

In some embodiments, a gNA variant has improved stability when compared to a reference gRNA. Increased stability and efficient folding may, in some embodiments, increase the extent to which a gNA variant persists inside a target cell, which may thereby increase the chance of forming a functional RNP capable of carrying out CasX functions such as gene editing. Increased stability of gNA variants may also, in some embodiments, allow for a similar outcome with a lower amount of gNA delivered to a cell, which may in turn reduce the chance of off-target effects during gene editing.

In another aspect, the disclosure provides gNA in which the scaffold stem loop and/or the extended stem loop is replaced with a hairpin loop or a thermostable RNA stem loop in which the resulting gNA has increased stability and, depending on the choice of loop, can interact with certain cellular proteins or RNA. In some embodiments, the replacement RNA loop is selected from MS2, Qβ, U1 hairpin II, Uvsx, PP7, Phage replication loop, Kissing loop_a, Kissing loop_b1, Kissing loop_b2, G quadriplex M3q, G quadriplex telomere basket, Sarcin-ricin loop and Pseudoknots. Sequences of gNA variants including such components are provided in Table 2B.

Guide RNA stability can be assessed in a variety of ways, including for example in vitro by assembling the guide, incubating for varying periods of time in a solution that mimics the intracellular environment, and then measuring functional activity via the in vitro cleavage assays described herein. Alternatively, or in addition, gNAs can be harvested from cells at varying time points after initial transfection/transduction of the gNA to determine how long gNA variants persist relative to reference gRNAs.

j. Solubility

In some embodiments, a gNA variant has improved solubility when compared to a reference gRNA. In some embodiments, a gNA variant has improved solubility of the CasX protein:gNA RNP when compared to a reference gRNA. In some embodiments, solubility of the CasX protein:gNA RNP is improved by the addition of a ribozyme sequence to a 5' or 3' end of the gNA variant, for example the 5' or 3' of a reference sgRNA. Some ribozymes, such as the M1 ribozyme, can increase solubility of proteins through RNA mediated protein folding.

Increased solubility of CasX RNPs comprising a gNA variant as described herein can be evaluated through a variety of means known to one of skill in the art, such as by taking densitometry readings on a gel of the soluble fraction of lysed E. coli in which the CasX and gNA variants are expressed.

k. Resistance to Nuclease Activity

In some embodiments, a gNA variant has improved resistance to nuclease activity compared to a reference gRNA. Without wishing to be bound by any theory, increased resistance to nucleases, such as nucleases found in cells, may for example increase the persistence of a variant gNA in an intracellular environment, thereby improving gene editing.

Many nucleases are processive, and degrade RNA in a 3' to 5' fashion. Therefore, in some embodiments the addition of a nuclease resistant secondary structure to one or both termini of the gNA, or nucleotide changes that change the secondary structure of a sgNA, can produce gNA variants with increased resistance to nuclease activity. Resistance to nuclease activity may be evaluated through a variety of methods known to one of skill in the art. For example, in vitro methods of measuring resistance to nuclease activity may include for example contacting reference gNA and variants with one or more exemplary RNA nucleases and measuring degradation. Alternatively, or in addition, measuring persistence of a gNA variant in a cellular environment using the methods described herein can indicate the degree to which the gNA variant is nuclease resistant.

l. Binding Affinity to a Target DNA

In some embodiments, a gNA variant has improved affinity for the target DNA relative to a reference gRNA. In certain embodiments, a ribonucleoprotein complex comprising a gNA variant has improved affinity for the target DNA, relative to the affinity of an RNP comprising a reference gRNA. In some embodiments, the improved affinity of the RNP for the target DNA comprises improved affinity for the target sequence, improved affinity for the PAM sequence, improved ability of the RNP to search DNA for the target sequence, or any combinations thereof. In some embodiments, the improved affinity for the target DNA is the result of increased overall DNA binding affinity.

Without wishing to be bound by theory, it is possible that nucleotide changes in the gNA variant that affect the function of the OBD in the CasX protein may increase the affinity of CasX variant protein binding to the protospacer adjacent motif (PAM), as well as the ability to bind or utilize an increased spectrum of PAM sequences other than the canonical TTC PAM recognized by the reference CasX protein of SEQ ID NO: 2, including PAM sequences selected from the group consisting of TTC, ATC, GTC, and CTC, thereby increasing the affinity and diversity of the CasX variant protein for target DNA sequences resulting in a substantial increase in the target nucleic acid sequences that can be edited and/or bound, compared to a reference CasX.

As described more fully, below, increasing the sequences of the target nucleic acid that can be edited, compared to a reference CasX, refers to both the PAM and the protospacer sequence and their directionality according to the orientation of the non-target strand. This does not imply that the PAM sequence of the non-target strand, rather than the target strand, is determinative of cleavage or mechanistically involved in target recognition. For example, when reference is to a TTC PAM, it may in fact be the complementary GAA sequence that is required for target cleavage, or it may be some combination of nucleotides from both strands. In the case of the CasX proteins disclosed herein, the PAM is located 5' of the protospacer with at least a single nucleotide separating the PAM from the first nucleotide of the protospacer. Alternatively, or in addition, changes in the gNA that affect function of the helical I and/or helical II domains that increase the affinity of the CasX variant protein for the target DNA strand can increase the affinity of the CasX RNP comprising the variant gNA for target DNA.

m. Adding or Changing gNA Function

In some embodiments, gNA variants can comprise larger structural changes that change the topology of the gNA variant with respect to the reference gRNA, thereby allowing for different gNA functionality. For example, in some embodiments a gNA variant has swapped an endogenous stem loop of the reference gRNA scaffold with a previously identified stable RNA structure or a stem loop that can interact with a protein or RNA binding partner to recruit additional moieties to the CasX or to recruit CasX to a specific location, such as the inside of a viral capsid, that has the binding partner to the said RNA structure. In other scenarios the RNAs may be recruited to each other, as in Kissing loops, such that two CasX proteins can be co-localized for more effective gene editing at the target DNA sequence. Such RNA structures may include MS2, Qβ, U1 hairpin II, Uvsx, PP7, Phage replication loop, Kissing loop_a, Kissing loop_b1, Kissing loop_b2, G quadriplex M3q, G quadriplex telomere basket, Sarcin-ricin loop, or a Pseudoknot.

In some embodiments, a gNA variant comprises a terminal fusion partner. Exemplary terminal fusions may include fusion of the gRNA to a self-cleaving ribozyme or protein binding motif. As used herein, a "ribozyme" refers to an RNA or segment thereof with one or more catalytic activities similar to a protein enzyme. Exemplary ribozyme catalytic activities may include, for example, cleavage and/or ligation of RNA, cleavage and/or ligation of DNA, or peptide bond formation. In some embodiments, such fusions could either improve scaffold folding or recruit DNA repair machinery. For example, a gRNA may in some embodiments be fused to a hepatitis delta virus (HDV) antigenomic ribozyme, HDV genomic ribozyme, hatchet ribozyme (from metagenomic data), env25 pistol ribozyme (representative from Aliistipes putredinis), HH15 Minimal Hammerhead ribozyme, tobacco ringspot virus (TRSV) ribozyme, WT viral Hammerhead ribozyme (and rational variants), or Twisted Sister 1 or RBMX recruiting motif. Hammerhead ribozymes are RNA motifs that catalyze reversible cleavage and ligation reactions at a specific site within an RNA molecule. Hammerhead ribozymes include type I, type II and type III hammerhead ribozymes. The HDV, pistol, and hatchet ribozymes have self-cleaving activities. gNA variants comprising one or more ribozymes may allow for expanded gNA function as compared to a gRNA reference. For example, gNAs comprising self-cleaving ribozymes can, in some embodiments, be transcribed and processed into mature gNAs as part of polycistronic transcripts. Such fusions may occur at either the 5' or the 3' end of the gNA. In some embodiments, a gNA variant comprises a fusion at both the 5' and the 3' end, wherein each fusion is independently as described herein. In some embodiments, a gNA variant comprises a phage replication loop or a tetraloop. In some embodiments, a gNA comprises a hairpin loop that is capable of binding a protein. For example, in some embodiments the hairpin loop is an MS2, Qβ, U1 hairpin II, Uvsx, or PP7 hairpin loop.

In some embodiments, a gNA variant comprises one or more RNA aptamers. As used herein, an "RNA aptamer" refers to an RNA molecule that binds a target with high affinity and high specificity.

In some embodiments, a gNA variant comprises one or more riboswitches. As used herein, a "riboswitch" refers to an RNA molecule that changes state upon binding a small molecule.

In some embodiments, the gNA variant further comprises one or more protein binding motifs. Adding protein binding motifs to a reference gRNA or gNA variant of the disclosure may, in some embodiments, allow a CasX RNP to associate with additional proteins, which can, for example, add the functionality of those proteins to the CasX RNP.

n. Chemically Modified gNA

In some embodiments, the disclosure relates to chemically-modified gNA. In some embodiments, the present disclosure provides a chemically-modified gNA that has guide RNA functionality and has reduced susceptibility to cleavage by a nuclease. A gNA that comprises any nucleotide other than the four canonical ribonucleotides A, C, G, and U, or a deoxynucleotide, is a chemically modified gNA. In some cases, a chemically-modified gNA comprises any backbone or internucleotide linkage other than a natural phosphodiester internucleotide linkage. In certain embodiments, the retained functionality includes the ability of the modified gNA to bind to a CasX of any of the embodiments described herein. In certain embodiments, the retained functionality includes the ability of the modified gNA to bind to a SOD1 target nucleic acid sequence. In certain embodiments, the retained functionality includes targeting a CasX protein or the ability of a pre-complexed CasX protein-gNA to bind to a target nucleic acid sequence. In certain embodiments, the retained functionality includes the ability to nick a target polynucleotide by a CasX-gNA. In certain embodiments, the retained functionality includes the ability to cleave a target nucleic acid sequence by a CasX-gNA. In certain embodiments, the retained functionality is any other known function of a gNA in a CasX system with a CasX protein of the embodiments of the disclosure.

In some embodiments, the disclosure provides a chemically-modified gNA in which a nucleotide sugar modification is incorporated into the gNA selected from the group consisting of 2'-O—C$_{1-4}$alkyl such as 2'-O-methyl (2'-OMe), 2'-deoxy (2'-H), 2'-O—C$_{1-3}$alkyl-O—C$_{1-3}$alkyl such as 2'-methoxyethyl ("2'-MOE"), 2'-fluoro ("2'-F"), 2'-amino ("2'-NH$_2$"), 2'-arabinosyl ("2'-arabino") nucleotide, 2'-F-arabinosyl ("2'-F-arabino") nucleotide, 2'-locked nucleic acid ("LNA") nucleotide, 2'-unlocked nucleic acid ("ULNA") nucleotide, a sugar in L form ("L-sugar"), and 4'-thioribosyl nucleotide. In other embodiments, an internucleotide linkage modification incorporated into the guide RNA is selected from the group consisting of: phosphorothioate "P(S)" (P(S)), phosphonocarboxylate (P(CH$_2$)$_n$COOR) such as phosphonoacetate "PACE" (P(CH$_2$COO$^-$)), thiophosphonocarboxylate ((S)P(CH$_2$)$_n$COOR) such as thiophosphonoacetate "thioPACE" ((S)P(CH$_2$)$_n$COO$^-$)), alkylphosphonate (P(C$_{1-3}$alkyl) such as methylphosphonate—P(CH$_3$), boranophosphonate (P(BH$_3$)), and phosphorodithioate (P(S)$_2$).

In certain embodiments, the disclosure provides a chemically-modified gNA in which a nucleobase ("base") modification is incorporated into the gNA selected from the group consisting of: 2-thiouracil ("2-thioU"), 2-thiocytosine ("2-thioC"), 4-thiouracil ("4-thioU"), 6-thioguanine ("6-thioG"), 2-aminoadenine ("2-aminoA"), 2-aminopurine, pseudouracil, hypoxanthine, 7-deazaguanine, 7-deaza-8-azaguanine, 7-deazaadenine, 7-deaza-8-azaadenine, 5-methylcytosine ("5-methylC"), 5-methyluracil ("5-methylU"), 5-hydroxymethylcytosine, 5-hydroxymethyluracil, 5,6-dehydrouracil, 5-propynylcytosine, 5-propynyluracil, 5-ethynylcytosine, 5-ethynyluracil, 5-allyluracil ("5-allylU"), 5-allylcytosine ("5-allylC"), 5-aminoallyluracil ("5-aminoallylU"), 5-aminoallyl-cytosine ("5-aminoallylC"), an abasic nucleotide, Z base, P base, Unstructured Nucleic Acid ("UNA"), isoguanine ("isoG"), isocytosine ("isoC"), 5-methyl-2-pyrimidine, x(A,G,C,T) and y(A,G,C,T).

In other embodiments, the disclosure provides a chemically-modified gNA in which one or more isotopic modifications are introduced on the nucleotide sugar, the nucleobase, the phosphodiester linkage and/or the nucleotide phosphates, including nucleotides comprising one or more $^{15}$N, $^{13}$C, $^{14}$C, deuterium, $^{3}$H, $^{32}$P, $^{125}$I, $^{131}$I atoms or other atoms or elements used as tracers.

In some embodiments, an "end" modification incorporated into the gNA is selected from the group consisting of: PEG (polyethyleneglycol), hydrocarbon linkers (including: heteroatom (O,S,N)—substituted hydrocarbon spacers; halo-substituted hydrocarbon spacers; keto-, carboxyl-, amido-, thionyl-, carbamoyl-, thionocarbamaoyl-containing hydrocarbon spacers), spermine linkers, dyes including fluorescent dyes (for example fluoresceins, rhodamines, cyanines) attached to linkers such as for example 6-fluorescein-hexyl, quenchers (for example dabcyl, BHQ) and other labels (for example biotin, digoxigenin, acridine, streptavidin, avidin, peptides and/or proteins). In some embodiments, an "end" modification comprises a conjugation (or ligation) of the gNA to another molecule comprising an oligonucleotide of deoxynucleotides and/or ribonucleotides, a peptide, a protein, a sugar, an oligosaccharide, a steroid, a lipid, a folic acid, a vitamin and/or other molecule. In certain embodiments, the disclosure provides a chemically-modified gNA in which an "end" modification (described above) is located internally in the gNA sequence via a linker such as, for example, a 2-(4-butylamidofluorescein)propane-1,3-diol bis(phosphodiester) linker, which is incorporated as a phosphodiester linkage and can be incorporated anywhere between two nucleotides in the gNA.

In some embodiments, the disclosure provides a chemically-modified gNA having an end modification comprising a terminal functional group such as an amine, a thiol (or sulfhydryl), a hydroxyl, a carboxyl, carbonyl, thionyl, thiocarbonyl, a carbamoyl, a thiocarbamoyl, a phoshoryl, an alkene, an alkyne, an halogen or a functional group-terminated linker that can be subsequently conjugated to a desired moiety selected from the group consisting of a fluorescent dye, a non-fluorescent label, a tag (for $^{14}$C, example biotin, avidin, streptavidin, or moiety containing an isotopic label such as $^{15}$N, $^{13}$C, deuterium, $^{3}$H, $^{32}$P, $^{125}$I and the like), an oligonucleotide (comprising deoxynucleotides and/or ribonucleotides, including an aptamer), an amino acid, a peptide, a protein, a sugar, an oligosaccharide, a steroid, a lipid, a folic acid, and a vitamin. The conjugation employs standard chemistry well-known in the art, including but not limited to coupling via N-hydroxysuccinimide, isothiocyanate, DCC (or DCI), and/or any other standard method as described in "Bioconjugate Techniques" by Greg T. Hermanson, Publisher Eslsevier Science, 3$^{rd}$ ed. (2013), the contents of which are incorporated herein by reference in its entirety.

IV. Proteins for Modifying a Target Nucleic Acid

The present disclosure provides systems comprising a CRISPR nuclease that have utility in genome editing of eukaryotic cells. In some embodiments, the CRISPR nuclease is selected from the group consisting of Cas9, Cas12a, Cas12b, Cas12c, Cas12d (CasY), CasX, Cas13a, Cas13b, Cas13c, Cas13d, CasX, CasY, Cas14, Cpf1, C2c1, Csn2, and Cas Phi. In some embodiments, the CRISPR nuclease is a is a Type V CRISPR nuclease. In some embodiments, the present disclosure provides systems comprising a CasX protein and one or more guide nucleic acids (gNA) that are specifically designed to modify a target nucleic acid sequence in eukaryotic cells.

The term "CasX protein", as used herein, refers to a family of proteins, and encompasses all naturally occurring CasX proteins, proteins that share at least 50% identity to naturally occurring CasX proteins, as well as CasX variants possessing one or more improved characteristics relative to a naturally-occurring reference CasX protein. CasX proteins belong to CRISPR-Cas Type V proteins. Exemplary improved characteristics of the CasX variant embodiments include, but are not limited to improved folding of the variant, improved binding affinity to the gNA, improved binding affinity to the target nucleic acid, improved ability to utilize a greater spectrum of PAM sequences in the editing and/or binding of target DNA, improved unwinding of the target DNA, increased editing activity, improved editing efficiency, improved editing specificity, increased percentage of a eukaryotic genome that can be efficiently edited, increased activity of the nuclease, increased target strand loading for double strand cleavage, decreased target strand loading for single strand nicking, decreased off-target cleavage, improved binding of the non-target strand of DNA, improved protein stability, improved protein: gNA (RNP) complex stability, improved protein solubility, improved protein:gNA (RNP) complex solubility, improved protein yield, improved protein expression, and improved fusion characteristics, as described more fully, below. In the foregoing embodiments, the one or more of the improved characteristics of an RNP of the CasX variant and the gNA variant is at least about 1.1 to about 100,000-fold improved relative to an RNP of the reference CasX protein of SEQ ID NO: 1, SEQ ID NO: 2, or SEQ ID NO: 3 and the gNA of Table 2A, when assayed in a comparable fashion. In other cases, the one or more improved characteristics of an RNP of the CasX variant and the gNA variant is at least about 1.1, at least about 10, at least about 100, at least about 1000, at least about 10,000, at least about 100,000-fold or more improved relative to an RNP of the reference CasX protein of SEQ ID NO: 1, SEQ ID NO: 2, or SEQ ID NO: 3 and the gNA of Table 2A. In other cases, the one or more of the improved characteristics of an RNP of the CasX variant and the gNA variant is about 1.1 to 100,00-fold, about 1.1 to 10,00-fold, about 1.1 to 1,000-fold, about 1.1 to 500-fold, about 1.1 to 100-fold, about 1.1 to 50-fold, about 1.1 to 20-fold, about 10 to 100,00-fold, about 10 to 10,00-fold, about 10 to 1,000-fold, about 10 to 500-fold, about 10 to 100-fold, about 10 to 50-fold, about 10 to 20-fold, about 2 to 70-fold, about 2 to 50-fold, about 2 to 30-fold, about 2 to 20-fold, about 2 to 10-fold, about 5 to 50-fold, about 5 to 30-fold, about 5 to 10-fold, about 100 to 100,00-fold, about 100 to 10,00-fold, about 100 to 1,000-fold, about 100 to 500-fold, about 500 to 100,00-fold, about 500 to 10,00-fold, about 500 to 1,000-fold, about 500 to 750-fold, about 1,000 to 100,00-fold, about 10,000 to 100,00-fold, about 20 to 500-fold, about 20 to 250-fold, about 20 to 200-fold, about 20 to 100-fold, about 20 to 50-fold, about 50 to 10,000-fold, about 50 to 1,000-fold, about 50 to 500-fold, about 50 to 200-fold, or about 50 to 100-fold, improved relative to an RNP of the reference CasX protein of SEQ ID NO: 1, SEQ ID NO: 2, or SEQ ID NO: 3 and the gNA of Table 2A, when assayed in a comparable fashion. In other cases, the one or more improved characteristics of an RNP of the CasX variant and the gNA variant is about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 40-fold, 45-fold, 50-fold, 55-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 425-fold, 450-fold, 475-fold, or 500-fold improved relative to an RNP of the reference CasX protein of SEQ ID NO: 1, SEQ ID NO: 2, or SEQ ID NO: 3 and the gNA of Table 2A, when assayed in a comparable fashion.

The term "CasX variant" is inclusive of variants that are fusion proteins; i.e., the CasX is "fused to" a heterologous sequence. This includes CasX variants comprising CasX variant sequences and N-terminal, C-terminal, or internal fusions of the CasX to a heterologous protein or domain thereof.

CasX proteins of the disclosure comprise at least one of the following domains: a non-target strand binding (NTSB) domain, a target strand loading (TSL) domain, a helical I domain, a helical II domain, an oligonucleotide binding domain (OBD), and a RuvC DNA cleavage domain (the last of which may be modified or deleted in a catalytically dead CasX variant), described more fully, below. Additionally, the CasX variant proteins of the disclosure have an enhanced ability to efficiently edit and/or bind target DNA, when complexed with a gNA as an RNP, utilizing PAM sequences selected from TTC, ATC, GTC, or CTC, compared to an RNP of a reference CasX protein and reference gNA. In some embodiments, the PAM sequence comprises a TC motif. In the foregoing, the PAM sequence is located at least 1 nucleotide 5' to the non-target strand of the protospacer having identity with the targeting sequence of the gNA in a assay system compared to the editing efficiency and/or binding of an RNP comprising a reference CasX protein and reference gNA in a comparable assay system. In one embodiment, an RNP of a CasX variant and gNA variant exhibits greater editing efficiency and/or binding of a target sequence in the target DNA compared to an RNP comprising a reference CasX protein and a reference gNA in a comparable assay system, wherein the PAM sequence of the target DNA is TTC. In another embodiment, an RNP of a CasX variant and gNA variant exhibits greater editing efficiency and/or binding of a target sequence in the target DNA compared to an RNP comprising a reference CasX protein and a reference gNA in a comparable assay system, wherein the PAM sequence of the target DNA is ATC. In another embodiment, an RNP of a CasX variant and gNA variant exhibits greater editing efficiency and/or binding of a target sequence in the target DNA compared to an RNP comprising a reference CasX protein and a reference gNA in a comparable assay system, wherein the PAM sequence of the target DNA is CTC. In another embodiment, an RNP of a CasX variant and gNA variant exhibits greater editing efficiency and/or binding of a target sequence in the target DNA compared to an RNP comprising a reference CasX protein and a reference gNA in a comparable assay system, wherein the PAM sequence of the target DNA is GTC.

In the foregoing embodiments, the increased editing efficiency and/or binding affinity for the one or more PAM sequences is at least about 1.1-fold to at least about 100-fold, or at least about 1.5-fold to at least about 10-fold greater compared to the editing efficiency and/or binding affinity of an RNP of any one of the CasX proteins of SEQ ID NOS: 1-3 and the gNA of Table 2A for the PAM sequences.

In some cases, the CasX protein is a naturally-occurring protein (e.g., naturally occurs in and is isolated from prokaryotic cells). In other embodiments, the CasX protein is not a naturally-occurring protein (e.g., the CasX protein is a CasX variant protein, a chimeric protein, and the like). A naturally-occurring CasX protein (referred to herein as a "reference CasX protein") functions as an endonuclease that catalyzes a double strand break at a specific sequence in a targeted double-stranded DNA (dsDNA). The sequence specificity is provided by the targeting sequence of the associated gNA to which it is complexed, which hybridizes to a target sequence within the target nucleic acid.

In some embodiments, a CasX protein can bind and/or modify (e.g., cleave, nick, methylate, demethylate, etc.) a target nucleic acid and/or a polypeptide associated with target nucleic acid (e.g., methylation or acetylation of a histone tail). In some embodiments, the CasX protein is catalytically dead (dCasX) but retains the ability to bind a target nucleic acid. An exemplary catalytically dead CasX protein comprises one or more mutations in the active site of the RuvC domain of the CasX protein. In some embodiments, a catalytically dead CasX protein comprises substitutions at residues 672, 769 and/or 935 of SEQ ID NO: 1. In one embodiment, a catalytically dead CasX protein comprises substitutions of D672A, E769A and/or D935A in a reference CasX protein of SEQ ID NO: 1. In other embodiments, a catalytically dead CasX protein comprises substitutions at amino acids 659, 756 and/or 922 in a reference CasX protein of SEQ ID NO: 2. In some embodiments, a catalytically dead CasX protein comprises D659A, E756A and/or D922A substitutions in a reference CasX protein of SEQ ID NO: 2. In further embodiments, a catalytically dead CasX protein comprises deletions of all or part of the RuvC domain of the CasX protein. It will be understood that the same foregoing substitutions can similarly be introduced into the CasX variants of the disclosure, resulting in a dCasX variant. In one embodiment, all or a portion of the RuvC domain is deleted from the CasX variant, resulting in a dCasX variant. Catalytically inactive dCasX variant proteins can, in some embodiments, be used for base editing or epigenetic modifications. With a higher affinity for DNA, in some embodiments, catalytically inactive dCasX variant proteins can, relative to catalytically active CasX, find their target nucleic acid faster, remain bound to target nucleic acid for longer periods of time, bind target nucleic acid in a more stable fashion, or a combination thereof, thereby improving these functions of the catalytically dead CasX variant protein compared to a CasX variant that retains its cleavage capability.

a. Non-Target Strand Binding Domain

The reference CasX proteins of the disclosure comprise a non-target strand binding domain (NTSBD). The NTSBD is a domain not previously found in any Cas proteins; for example this domain is not present in Cas proteins such as Cas9, Cas12a/Cpf1, Cas13, Cas14, CASCADE, CSM, or CSY. Without being bound to theory or mechanism, a NTSBD in a CasX allows for binding to the non-target DNA strand and may aid in unwinding of the non-target and target strands. The NTSBD is presumed to be responsible for the unwinding, or the capture, of a non-target DNA strand in the unwound state. The NTSBD is in direct contact with the non-target strand in CryoEM model structures derived to date and may contain a non-canonical zinc finger domain. The NTSBD may also play a role in stabilizing DNA during unwinding, guide RNA invasion and R-loop formation. In some embodiments, an exemplary NTSBD comprises amino acids 101-191 of SEQ ID NO: 1 or amino acids 103-192 of SEQ ID NO: 2. In some embodiments, the NTSBD of a reference CasX protein comprises a four-stranded beta sheet.

b. Target Strand Loading Domain

The reference CasX proteins of the disclosure comprise a Target Strand Loading (TSL) domain. The TSL domain is a domain not found in certain Cas proteins such as Cas9, CASCADE, CSM, or CSY. Without wishing to be bound by theory or mechanism, it is thought that the TSL domain is responsible for aiding the loading of the target DNA strand into the RuvC active site of a CasX protein. In some embodiments, the TSL acts to place or capture the target-strand in a folded state that places the scissile phosphate of the target strand DNA backbone in the RuvC active site. The TSL comprises a cys4 (CXXC, CXXC zinc finger/ribbon domain (SEQ ID NO: 35) that is separated by the bulk of the TSL. In some embodiments, an exemplary TSL comprises amino acids 825-934 of SEQ ID NO: 1 or amino acids 813-921 of SEQ ID NO: 2.

c. Helical I Domain

The reference CasX proteins of the disclosure comprise a helical I domain. Certain Cas proteins other than CasX have domains that may be named in a similar way. However, in some embodiments, the helical I domain of a CasX protein comprises one or more unique structural features, or comprises a unique sequence, or a combination thereof, compared to non-CasX proteins. For example, in some embodiments, the helical I domain of a CasX protein comprises one or more unique secondary structures compared to domains in other Cas proteins that may have a similar name. For example, in some embodiments the helical I domain in a CasX protein comprises one or more alpha helices of unique structure and sequence in arrangement, number and length compared to other CRISPR proteins. In certain embodiments, the helical I domain is responsible for interacting with the bound DNA and spacer of the guide RNA. Without wishing to be bound by theory, it is thought that in some cases the helical I domain may contribute to binding of the protospacer adjacent motif (PAM). In some embodiments, an exemplary helical I domain comprises amino acids 57-100 and 192-332 of SEQ ID NO: 1, or amino acids 59-102 and 193-333 of SEQ ID NO: 2. In some embodiments, the helical I domain of a reference CasX protein comprises one or more alpha helices.

d. Helical II Domain

The reference CasX proteins of the disclosure comprise a helical II domain. Certain Cas proteins other than CasX have domains that may be named in a similar way. However, in some embodiments, the helical II domain of a CasX protein comprises one or more unique structural features, or a unique sequence, or a combination thereof, compared to domains in other Cas proteins that may have a similar name. For example, in some embodiments, the helical II domain comprises one or more unique structural alpha helical bundles that align along the target DNA:guide RNA channel. In some embodiments, in a CasX comprising a helical II domain, the target strand and guide RNA interact with helical II (and the helical I domain, in some embodiments) to allow RuvC domain access to the target DNA. The helical II domain is responsible for binding to the guide RNA scaffold stem loop as well as the bound DNA. In some embodiments, an exemplary helical II domain comprises amino acids 333-509 of SEQ ID NO: 1, or amino acids 334-501 of SEQ ID NO: 2.

e. Oligonucleotide Binding Domain

The reference CasX proteins of the disclosure comprise an Oligonucleotide Binding Domain (OBD). Certain Cas proteins other than CasX have domains that may be named in a similar way. However, in some embodiments, the OBD comprises one or more unique functional features, or comprises a sequence unique to a CasX protein, or a combination thereof. For example, in some embodiments the bridged helix (BH), helical I domain, helical II domain, and Oligonucleotide Binding Domain (OBD) together are responsible for binding of a CasX protein to the guide RNA. Thus, for example, in some embodiments the OBD is unique to a CasX protein in that it interacts functionally with a helical I domain, or a helical II domain, or both, each of which may be unique to a CasX protein as described herein. Specifically, in CasX the OBD largely binds the RNA triplex of the guide RNA scaffold. The OBD may also be responsible for binding to the protospacer adjacent motif (PAM). An exemplary OBD comprises amino acids 1-56 and 510-660 of SEQ ID NO: 1, or amino acids 1-58 and 502-647 of SEQ ID NO: 2.

f. RuvC DNA Cleavage Domain

The reference CasX proteins of the disclosure comprise a RuvC domain, that includes 2 partial RuvC domains (RuvC-I and RuvC-II). The RuvC domain is the ancestral domain of all type 12 CRISPR proteins. The RuvC domain originates from a TNPB (transposase B) like transposase. Similar to other RuvC domains, the CasX RuvC domain has a DED catalytic triad that is responsible for coordinating a magnesium (Mg) ion and cleaving DNA. In some embodiments, the RuvC has a DED motif active site that is responsible for cleaving both strands of DNA (one by one, most likely the non-target strand first at 11-14 nucleotides (nt) into the targeted sequence and then the target strand next at 2-4 nucleotides after the target sequence). Specifically in CasX, the RuvC domain is unique in that it is also responsible for binding the guide RNA scaffold stem loop that is critical for CasX function. An exemplary RuvC domain comprises amino acids 661-824 and 935-986 of SEQ ID NO: 1, or amino acids 648-812 and 922-978 of SEQ ID NO: 2.

g. Reference CasX Proteins

The disclosure provides reference CasX proteins. In some embodiments, a reference CasX protein is a naturally-occurring protein. For example, reference CasX proteins can be isolated from naturally occurring prokaryotes, such as *Deltaproteobacteria, Planctomycetes*, or *Candidatus Sungbacteria* species. A reference CasX protein (sometimes referred to herein as a reference CasX polypeptide) is a type II CRISPR/Cas endonuclease belonging to the CasX (sometimes referred to as Cas12e) family of proteins that is capable of interacting with a guide NA to form a ribonucleoprotein (RNP) complex. In some embodiments, the RNP complex comprising the reference CasX protein can be targeted to a particular site in a target nucleic acid via base pairing between the targeting sequence (or spacer) of the gNA and a target sequence in the target nucleic acid. In some embodiments, the RNP comprising the reference CasX protein is capable of cleaving target DNA. In some embodiments, the RNP comprising the reference CasX protein is capable of nicking target DNA. In some embodiments, the RNP comprising the reference CasX protein is capable of editing target DNA, for example in those embodiments where the reference CasX protein is capable of cleaving or nicking DNA, followed by non-homologous end joining (NHEJ), homology-directed repair (HDR), homology-independent targeted integration (HITI), micro-homology mediated end joining (MMEJ), single strand annealing (SSA) or base excision repair (BER). In some embodiments, the RNP comprises a catalytically dead (is catalytically inactive or has substantially no cleavage activity) CasX protein (dCasX), but retains the ability to bind the target DNA, described more fully, supra.

In some cases, a reference CasX protein is isolated or derived from *Deltaproteobacteria*. In some embodiments, a CasX protein comprises a sequence at least 50% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence of:

```
                                                       (SEQ ID NO: 1)
  1   MEKRINKIRK KLSADNATKP VSRSGPMKTL LVRVMTDDLK KRLEKRRKKP EVMPQVISNN

61   AANNLRMLLD DYTKMKEAIL QVYWQEFKDD HVGLMCKFAQ PASKKIDQNK LKPEMDEKGN

121   LTTAGFACSQ CGQPLFVYKL EQVSEKGKAY TNYFGRCNVA EHEKLILLAQ LKPEKDSDEA

181   VTYSLGKFGQ RALDFYSIHV TKESTHPVKP LAQIAGNRYA SGPVGKALSD ACMGTIASFL

241   SKYQDIIIEH QKVVKGNQKR LESLRELAGK ENLEYPSVTL PPQPHTKEGV DAYNEVIARV

301   RMWVNLNLWQ KLKLSRDDAK PLLRLKGFPS FPVVERRENE VDWWNTINEV KKLIDAKRDM

361   GRVFWSGVTA EKRNTILEGY NYLPNENDHK KREGSLENPK KPAKRQFGDL LLYLEKKYAG

421   DWGKVFDEAW ERIDKKIAGL TSHIEREEAR NAEDAQSKAV LTDWLRAKAS FVLERLKEMD

481   EKEFYACEIQ LQKWYGDLRG NPFAVEAENR VVDISGFSIG SDGHSIQYRN LLAWKYLENG

541   KREFYLLMNY GKKGRIRFTD GTDIKKSGKW QGLLYGGGKA KVIDLTFDPD DEQLIILPLA

601   FGTRQGREFI WNDLLSLETG LIKLANGRVI EKTIYNKKIG RDEPALFVAL TFERREVVDP

661   SNIKPVNLIG VDRGENIPAV IALTDPEGCP LPEFKDSSGG PTDILRIGEG YKEKQRAIQA

721   AKEVEQRRAG GYSRKFASKS RNLADDMVRN SARDLFYHAV THDAVLVFEN LSRGFGRQGK

781   RTFMTERQYT KMEDWLTAKL AYEGLTSKTY LSKTLAQYTS KTCSNCGFTI TTADYDGMLV

841   RLKKTSDGWA TTLNNKELKA EGQITYYNRY KRQTVEKELS AELDRLSEES GNNDISKWTK

901   GRRDEALFLL KKRFSHRPVQ EQFVCLDCGH EVHADEQAAL NIARSWLFLN SNSTEFKSYK

961   SGKQPFVGAW QAFYKRRLKE VWKPNA.
```

In some cases, a reference CasX protein is isolated or derived from *Planctomycetes*. In some embodiments, a CasX protein comprises a sequence at least 50% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence of:

```
                                                   (SEQ ID NO: 2)
  1    MQEIKRINKI RRRLVKDSNT KKAGKTGPMK TLLVRVMTPD LRERLENLRK KPENIPQPIS

61    NTSRANLNKL LTDYTEMKKA ILHVYWEEFQ KDPVGLMSRV AQPAPKNIDQ RKLIPVKDGN

121    ERLTSSGFAC SQCCQPLYVY KLEQVNDKGK PHTNYFGRCN VSEHERLILL SPHKPEANDE

181    LVTYSLGKFG QRALDFYSIH VTRESNHPVK PLEQIGGNSC ASGPVGKALS DACMGAVASF

241    LTKYQDIILE HQKVIKKNEK RLANLKDIAS ANGLAFPKIT LPPQPHTKEG IEAYNNVVAQ

301    IVIWVNLNLW QKLKIGRDEA KPLQRLKGFP SFPLVERQAN EVDWWDMVCN VKKLINEKKE

361    DGKVFWQNLA GYKRQEALLP YLSSEEDRKK GKKFARYQFG DLLLHLEKKH GEDWGKVYDE

421    AWERIDKKVE GLSKHIKLEE ERRSEDAQSK AALTDWLRAK ASFVIEGLKE ADKDEFCRCE

481    LKLQKWYGDL RGKPFAIEAE NSILDISGFS KQYNCAFIWQ KDGVKKLNLY LIINYFKGGK

541    LRFKKIKPEA FEANRFYTVI NKKSGEIVPM EVNFNFDDPN LIILPLAFGK RQGREFIWND

601    LLSLETGSLK LANGRVIEKT LYNRRTRQDE PALFVALTFE RREVLDSSNI KPMNLIGIDR

661    GENIPAVIAL TDPEGCPLSR FKDSLGNPTH ILRIGESYKE KQRTIQAAKE VEQRRAGGYS

721    RKYASKAKNL ADDMVRNTAR DLLYYAVTQD AMLIFENLSR GFGRQGKRTF MAERQYTRME

781    DWLTAKLAYE GLPSKTYLSK TLAQYTSKTC SNCGFTITSA DYDRVLEKLK KTATGWMTTI

841    NGKELKVEGQ ITYYNRYKRQ NVVKDLSVEL DRLSEESVNN DISSWTKGRS GEALSLLKKR

901    FSHRPVQEKF VCLNCGFETH ADEQAALNIA RSWLFLRSQE YKKYQTNKTT GNTDKRAFVE

961    TWQSFYRKKL KEVWKPAV.
```

In some embodiments, the CasX protein comprises the sequence of SEQ ID NO: 2, or at least 60% similarity thereto. In some embodiments, the CasX protein comprises the sequence of SEQ ID NO: 2, or at least 80% similarity thereto. In some embodiments, the CasX protein comprises the sequence of SEQ ID NO: 2, or at least 90% similarity thereto. In some embodiments, the CasX protein comprises the sequence of SEQ ID NO: 2, or at least 95% similarity thereto. In some embodiments, the CasX protein consists of the sequence of SEQ ID NO: 2. In some embodiments, the CasX protein comprises or consists of a sequence that has at least 1, at least 2, at least 3, at least 4, at least 5, at least 6, at least 7, at least 8, at least 9, at least 10, at least 20, at least 30, at least 40 or at least 50 mutations relative to the sequence of SEQ ID NO: 2. These mutations can be insertions, deletions, amino acid substitutions, or any combinations thereof.

In some cases, a reference CasX protein is isolated or derived from *Candidatus Sungbacteria*. In some embodiments, a CasX protein comprises a sequence at least 50% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical or 100% identical to a sequence of

```
                                                                (SEQ ID NO: 3)
  1    MDNANKPSTK SLVNTTRISD HFGVTPGQVT RVFSFGIIPT KRQYAIIERW FAAVEAARER

61    LYGMLYAHFQ ENPPAYLKEK FSYETFFKGR PVLNGLRDID PTIMTSAVFT ALRHKAEGAM

121    AAFHTNHRRL FEEARKKMRE YAECLKANEA LLRGAADIDW DKIVNALRTR LNTCLAPEYD

181    AVIADFGALC AFRALIAETN ALKGAYNHAL NQMLPALVKV DEPEEAEESP RLRFFNGRIN

241    DLPKFPVAER ETPPDTETII RQLEDMARVI PDTAEILGYI HRIRHKAARR KPGSAVPLPQ

301    RVALYCAIRM ERNPEEDPST VAGHFLGEID RVCEKRRQGL VRTPFDSQIR ARYMDIISFR

361    ATLAHPDRWT EIQFLRSNAA SRRVRAETIS APFEGFSWTS NRTNPAPQYG MALAKDANAP

421    ADAPELCICL SPSSAAFSVR EKGGDLIYMR PTGGRRGKDN PGKEITWVPG SFDEYPASGV

481    ALKLRLYFGR SQARRMLTNK TWGLLSDNPR VFAANAELVG KKRNPQDRWK LFFHMVISGP

541    PPVEYLDFSS DVRSRARTVI GINRGEVNPL AYAVVSVEDG QVLEEGLLGK KEYIDQLIET

601    RRRISEYQSR EQTPPRDLRQ RVRHLQDTVL GSARAKIHSL IAFWKGILAI ERLDDQFHGR
```

```
661    EQKIIPKKTY  LANKTGFMNA  LSFSGAVRVD  KKGNPWGGMI  EIYPGGISRT  CTQCGTVWLA

721    RRPKNPGHRD  AMVVIPDIVD  DAAATGFDNV  DCDAGTVDYG  ELFTLSREWV  RLTPRYSRVM

781    RGTLGDLERA  IRQGDDRKSR  QMLELALEPQ  PQWGQFFCHR  CGFNGQSDVL  AATNLARRAI

841    SLIRRLPDTD  TPPTP.
```

In some embodiments, the CasX protein comprises the sequence of SEQ ID NO: 3, or at least 60% similarity thereto. In some embodiments, the CasX protein comprises the sequence of SEQ ID NO: 3, or at least 80% similarity thereto. In some embodiments, the CasX protein comprises the sequence of SEQ ID NO: 3, or at least 90% similarity thereto. In some embodiments, the CasX protein comprises the sequence of SEQ ID NO: 3, or at least 95% similarity thereto. In some embodiments, the CasX protein consists of the sequence of SEQ ID NO: 3. In some embodiments, the CasX protein comprises or consists of a sequence that has at least 1, at least 2, at least 3, at least 4, at least 5, at least 6, at least 7, at least 8, at least 9, at least 10, at least 20, at least 30, at least 40 or at least 50 mutations relative to the sequence of SEQ ID NO: 3. These mutations can be insertions, deletions, amino acid substitutions, or any combinations thereof.

h. CasX Variant Proteins

The present disclosure provides variants of a reference CasX protein (interchangeably referred to herein as "CasX variant" or "CasX variant protein"), wherein the CasX variants comprise at least one modification in at least one domain of the reference CasX protein, including the sequences of SEQ ID NOS: 1-3. In some embodiments, the CasX variant exhibits at least one improved characteristic compared to the reference CasX protein. All variants that improve one or more functions or characteristics of the CasX variant protein when compared to a reference CasX protein described herein are envisaged as being within the scope of the disclosure. In some embodiments, the modification is a mutation in one or more amino acids of the reference CasX. In other embodiments, the modification is a substitution of one or more domains of the reference CasX with one or more domains from a different CasX. In some embodiments, insertion includes the insertion of a part or all of a domain from a different CasX protein. Mutations can occur in any one or more domains of the reference CasX protein, and may include, for example, deletion of part or all of one or more domains, or one or more amino acid substitutions, deletions, or insertions in any domain of the reference CasX protein. The domains of CasX proteins include the non-target strand binding (NTSB) domain, the target strand loading (TSL) domain, the helical I domain, the helical II domain, the oligonucleotide binding domain (OBD), and the RuvC DNA cleavage domain. Any change in amino acid sequence of a reference CasX protein that leads to an improved characteristic of the CasX protein is considered a CasX variant protein of the disclosure. For example, CasX variants can comprise one or more amino acid substitutions, insertions, deletions, or swapped domains, or any combinations thereof, relative to a reference CasX protein sequence.

In some embodiments, the CasX variant protein comprises at least one modification in at least each of two domains of the reference CasX protein, including the sequences of SEQ ID NOS:1-3. In some embodiments, the CasX variant protein comprises at least one modification in at least 2 domains, in at least 3 domains, at least 4 domains or at least 5 domains of the reference CasX protein. In some embodiments, the CasX variant protein comprises two or more modifications in at least one domain of the reference CasX protein. In some embodiments, the CasX variant protein comprises at least two modifications in at least one domain of the reference CasX protein, at least three modifications in at least one domain of the reference CasX protein or at least four modifications in at least one domain of the reference CasX protein. In some embodiments, wherein the CasX variant comprises two or more modifications compared to a reference CasX protein, each modification is made in a domain independently selected from the group consisting of a NTSBD, TSLD, Helical I domain, Helical II domain, OBD, and RuvC DNA cleavage domain.

In some embodiments, the at least one modification of the CasX variant protein comprises a deletion of at least a portion of one domain of the reference CasX protein, including the sequences of SEQ ID NOS:1-3. In some embodiments, the deletion is in the NTSBD, TSLD, Helical I domain, Helical II domain, OBD, or RuvC DNA cleavage domain.

Suitable mutagenesis methods for generating CasX variant proteins of the disclosure may include, for example, Deep Mutational Evolution (DME; described in the Examples), deep mutational scanning (DMS), error prone PCR, cassette mutagenesis, random mutagenesis, staggered extension PCR, gene shuffling, or domain swapping. In some embodiments, the CasX variants are designed, for example by selecting one or more desired mutations in a reference CasX. In certain embodiments, the activity of a reference CasX protein is used as a benchmark against which the activity of one or more CasX variants are compared, thereby measuring improvements in function of the CasX variants. Exemplary improvements of CasX variants include, but are not limited to, improved folding of the variant, improved binding affinity to the gNA, improved binding affinity to the target DNA, altered binding affinity to one or more PAM sequences, improved unwinding of the target DNA, increased activity, improved editing efficiency, improved editing specificity, increased activity of the nuclease, increased target strand loading for double strand cleavage, decreased target strand loading for single strand nicking, decreased off-target cleavage, improved binding of the non-target strand of DNA, improved protein stability, improved protein:gNA complex stability, improved protein solubility, improved protein:gNA complex solubility, improved protein yield, improved protein expression, and improved fusion characteristics, as described more fully, below.

In some embodiments of the CasX variants described herein, the at least one modification comprises: (a) a substitution of 1 to 100 consecutive or non-consecutive amino acids in the CasX variant compared to a reference CasX of SEQ ID NO: 1, SEQ ID NO: 2, or SEQ ID NO: 3; (b) a deletion of 1 to 100 consecutive or non-consecutive amino acids in the CasX variant compared to a reference CasX; (c) an insertion of 1 to 100 consecutive or non-consecutive amino acids in the CasX compared to a reference CasX; or (d) any combination of (a)-(c). In some embodiments, the at least one modification comprises: (a) a substitution of 5-10 consecutive or non-consecutive amino acids in the CasX variant compared to a reference CasX of SEQ ID NO: 1, SEQ ID NO: 2, or SEQ ID NO: 3; (b) a deletion of 1-5 consecutive or non-consecutive amino acids in the CasX variant compared to a reference CasX; (c) an insertion of 1-5 consecutive or non-consecutive amino acids in the CasX compared to a reference CasX; or (d) any combination of (a)-(c).

In some embodiments, the CasX variant protein comprises or consists of a sequence that has at least 1, at least 2, at least 3, at least 4, at least 5, at least 6, at least 7, at least 8, at least 9, at least 10, at least 20, at least 30, at least 40 or at least 50 mutations relative to the sequence of SEQ ID NO: 1, SEQ ID NO: 2, or SEQ ID NO: 3. These mutations can be insertions, deletions, amino acid substitutions, or any combinations thereof.

In some embodiments, the CasX variant protein comprises at least one amino acid substitution in at least one domain of a reference CasX protein. In some embodiments, the CasX variant protein comprises at least about 1-4 amino acid substitutions, 1-10 amino acid substitutions, 1-20 amino acid substitutions, 1-30 amino acid substitutions, 1-40 amino acid substitutions, 1-50 amino acid substitutions, 1-60 amino acid substitutions, 1-70 amino acid substitutions, 1-80 amino acid substitutions, 1-90 amino acid substitutions, 1-100 amino acid substitutions, 2-10 amino acid substitutions, 2-20 amino acid substitutions, 2-30 amino acid substitutions, 3-10 amino acid substitutions, 3-20 amino acid substitutions, 3-30 amino acid substitutions, 4-10 amino acid substitutions, 4-20 amino acid substitutions, 3-300 amino acid substitutions, 5-10 amino acid substitutions, 5-20 amino acid substitutions, 5-30 amino acid substitutions, 10-50 amino acid substitutions, or 20-50 amino acid substitutions, relative to a reference CasX protein. In some embodiments, the CasX variant protein comprises at least about 100 amino acid substitutions relative to a reference CasX protein. In some embodiments, the CasX variant protein comprises 1, 2, 3, 4, 5, 6, 7, 8, 9 or 10 amino acid substitutions relative to a reference CasX protein. In some embodiments, the CasX variant protein comprises 1, 2, 3, 4, 5, 6, 7, 8, 9 or 10 amino acid substitutions in a single domain relative to the reference CasX protein. In some embodiments, the amino acid substitutions are conservative substitutions. In other embodiments, the substitutions are non-conservative; e.g., a polar amino acid is substituted for a non-polar amino acid, or vice versa.

In some embodiments, a CasX variant protein comprises 1 amino acid substitution, 2-3 consecutive amino acid substitutions, 2-4 consecutive amino acid substitutions, 2-5 consecutive amino acid substitutions, 2-6 consecutive amino acid substitutions, 2-7 consecutive amino acid substitutions, 2-8 consecutive amino acid substitutions, 2-9 consecutive amino acid substitutions, 2-10 consecutive amino acid substitutions, 2-20 consecutive amino acid substitutions, 2-30 consecutive amino acid substitutions, 2-40 consecutive amino acid substitutions, 2-50 consecutive amino acid substitutions, 2-60 consecutive amino acid substitutions, 2-70 consecutive amino acid substitutions, 2-80 consecutive amino acid substitutions, 2-90 consecutive amino acid substitutions, 2-100 consecutive amino acid substitutions, 3-10 consecutive amino acid substitutions, 3-20 consecutive amino acid substitutions, 3-30 consecutive amino acid substitutions, 4-10 consecutive amino acid substitutions, 4-20 consecutive amino acid substitutions, 3-300 consecutive amino acid substitutions, 5-10 consecutive amino acid substitutions, 5-20 consecutive amino acid substitutions, 5-30 consecutive amino acid substitutions, 10-50 consecutive amino acid substitutions or 20-50 consecutive amino acid substitutions relative to a reference CasX protein. In some embodiments, a CasX variant protein comprises 2, 3, 4, 5, 6, 7, 8, 9, 10, 11, 12, 13, 14, 15, 16, 17, 18, 19 or 20 consecutive amino acid substitutions. In some embodiments, a CasX variant protein comprises a substitution of at least about 100 consecutive amino acids. As used herein "consecutive amino acids" refer to amino acids that are contiguous in the primary sequence of a polypeptide.

In some embodiments, a CasX variant protein comprises two or more substitutions relative to a reference CasX protein, and the two or more substitutions are not in consecutive amino acids of the reference CasX sequence. For example, a first substitution may be in a first domain of the reference CasX protein, and a second substitution may be in a second domain of the reference CasX protein. In some embodiments, a CasX variant protein comprises 2, 3, 4, 5, 6, 7, 8, 9, 10, 11, 12, 13, 14, 15, 16, 17, 18, 19 or 20 non-consecutive substitutions relative to a reference CasX protein. In some embodiments, a CasX variant protein comprises at least 20 non-consecutive substitutions relative to a reference CasX protein. Each non-consecutive substitution may be of any length of amino acids described herein, e.g., 1-4 amino acids, 1-10 amino acids, and the like. In some embodiments, the two or more substitutions relative to the reference CasX protein are not the same length, for example one substitution is one amino acid and a second substitution is three amino acids. In some embodiments, the two or more substitutions relative to the reference CasX protein are the same length, for example both substitutions are two consecutive amino acids in length.

Any amino acid can be substituted for any other amino acid in the substitutions described herein. The substitution can be a conservative substitution (e.g., a basic amino acid is substituted for another basic amino acid). The substitution can be a non-conservative substitution (e.g., a basic amino acid is substituted for an acidic amino acid or vice versa). For example, a proline in a reference CasX protein can be substituted for any of arginine, histidine, lysine, aspartic acid, glutamic acid, serine, threonine, asparagine, glutamine, cysteine, glycine, alanine, isoleucine, leucine, methionine, phenylalanine, tryptophan, tyrosine or valine to generate a CasX variant protein of the disclosure.

In some embodiments, a CasX variant protein comprises at least one amino acid deletion relative to a reference CasX protein. In some embodiments, a CasX variant protein comprises a deletion of 1-4 amino acids, 1-10 amino acids, 1-20 amino acids, 1-30 amino acids, 1-40 amino acids, 1-50 amino acids, 1-60 amino acids, 1-70 amino acids, 1-80 amino acids, 1-90 amino acids, 1-100 amino acids, 2-10 amino acids, 2-20 amino acids, 2-30 amino acids, 3-10 amino acids, 3-20 amino acids, 3-30 amino acids, 4-10 amino acids, 4-20 amino acids, 3-300 amino acids, 5-10 amino acids, 5-20 amino acids, 5-30 amino acids, 10-50 amino acids or 20-50 amino acids relative to a reference CasX protein. In some embodiments, a CasX protein comprises a deletion of at least about 100 consecutive amino acids relative to a reference CasX protein. In some embodiments, a CasX variant protein comprises a deletion of at least 1, 2, 3, 4, 5, 6, 7, 8, 9, 10, 20, 30, 40, 50 or 100 consecutive amino acids relative to a reference CasX protein. In some embodiments, a CasX variant protein comprises a deletion of 1, 2, 3, 4, 5, 6, 7, 8, 9 or 10 consecutive amino acids.

In some embodiments, a CasX variant protein comprises two or more deletions relative to a reference CasX protein, and the two or more deletions are not consecutive amino acids. For example, a first deletion may be in a first domain of the reference CasX protein, and a second deletion may be in a second domain of the reference CasX protein. In some embodiments, a CasX variant protein comprises 2, 3, 4, 5, 6, 7, 8, 9, 10, 11, 12, 13, 14, 15, 16, 17, 18, 19 or 20 non-consecutive deletions relative to a reference CasX protein. In some embodiments, a CasX variant protein comprises at least 20 non-consecutive deletions relative to a reference CasX protein. Each non-consecutive deletion may be of any length of amino acids described herein, e.g., 1-4 amino acids, 1-10 amino acids, and the like.

In some embodiments, the CasX variant protein comprises at least one amino acid insertion relative to the sequence of SEQ ID NOS:1, 2, or 3. In some embodiments, a CasX variant protein comprises an insertion of 1 amino acid, an insertion of 2-3 consecutive amino acids, 2-4 consecutive amino acids, 2-5 consecutive amino acids, 2-6 consecutive amino acids, 2-7 consecutive amino acids, 2-8 consecutive amino acids, 2-9 consecutive amino acids, 2-10 consecutive amino acids, 2-20 consecutive amino acids, 2-30 consecutive amino acids, 2-40 consecutive amino acids, 2-50 consecutive amino acids, 2-60 consecutive amino acids, 2-70 consecutive amino acids, 2-80 consecutive amino acids, 2-90 consecutive amino acids, 2-100 consecutive amino acids, 3-10 consecutive amino acids, 3-20 consecutive amino acids, 3-30 consecutive amino acids, 4-10 consecutive amino acids, 4-20 consecutive amino acids, 3-300 consecutive amino acids, 5-10 consecutive amino acids, 5-20 consecutive amino acids, 5-30 consecutive amino acids, 10-50 consecutive amino acids or 20-50 consecutive amino acids relative to a reference CasX protein. In some embodiments, the CasX variant protein comprises an insertion of 2, 3, 4, 5, 6, 7, 8, 9, 10, 11, 12, 13, 14, 15, 16, 17, 18, 19 or 20 consecutive amino acids. In some embodiments, a CasX variant protein comprises an insertion of at least about 100 consecutive amino acids.

In some embodiments, a CasX variant protein comprises two or more insertions relative to a reference CasX protein, and the two or more insertions are not consecutive amino acids of the sequence. For example, a first insertion may be in a first domain of the reference CasX protein, and a second insertion may be in a second domain of the reference CasX protein. In some embodiments, a CasX variant protein comprises 2, 3, 4, 5, 6, 7, 8, 9, 10, 11, 12, 13, 14, 15, 16, 17, 18, 19 or 20 non-consecutive insertions relative to a reference CasX protein. In some embodiments, a CasX variant protein comprises at least 10 to about 20 or more non-consecutive insertions relative to a reference CasX protein. Each non-consecutive insertion may be of any length of amino acids described herein, e.g., 1-4 amino acids, 1-10 amino acids, and the like.

Any amino acid, or combination of amino acids, can be inserted in the insertions described herein. For example, a proline, arginine, histidine, lysine, aspartic acid, glutamic acid, serine, threonine, asparagine, glutamine, cysteine, glycine, alanine, isoleucine, leucine, methionine, phenylalanine, tryptophan, tyrosine or valine or any combination thereof can be inserted into a reference CasX protein of the disclosure to generate a CasX variant protein.

Any permutation of the substitution, insertion and deletion embodiments described herein can be combined to generate a CasX variant protein of the disclosure. For example, a CasX variant protein can comprise at least one substitution and at least one deletion relative to a reference CasX protein sequence, at least one substitution and at least one insertion relative to a reference CasX protein sequence, at least one insertion and at least one deletion relative to a reference CasX protein sequence, or at least one substitution, one insertion and one deletion relative to a reference CasX protein sequence.

In some embodiments, the CasX variant protein has at least about 60% sequence similarity, at least 70% similarity, at least 80% similarity, at least 85% similarity, at least 86% similarity, at least 87% similarity, at least 88% similarity, at least 89% similarity, at least 90% similarity, at least 91% similarity, at least 92% similarity, at least 93% similarity, at least 94% similarity, at least 95% similarity, at least 96% similarity, at least 97% similarity, at least 98% similarity, at least 99% similarity, at least 99.5% similarity, at least 99.6% similarity, at least 99.7% similarity, at least 99.8% similarity or at least 99.9% similarity to one of SEQ ID NO: 1, SEQ ID NO: 2, or SEQ ID NO: 3.

In some embodiments, the CasX variant protein has at least about 60% sequence similarity to SEQ ID NO: 2 or a portion thereof. In some embodiments, the CasX variant protein comprises a substitution of Y789T of SEQ ID NO: 2, a deletion of P793 of SEQ ID NO: 2, a substitution of Y789D of SEQ ID NO: 2, a substitution of T72S of SEQ ID NO: 2, a substitution of I546V of SEQ ID NO: 2, a substitution of E552A of SEQ ID NO: 2, a substitution of A636D of SEQ ID NO: 2, a substitution of F536S of SEQ ID NO:2, a substitution of A708K of SEQ ID NO: 2, a substitution of Y797L of SEQ ID NO: 2, a substitution of L792G SEQ ID NO: 2, a substitution of A739V of SEQ ID NO: 2, a substitution of G791M of SEQ ID NO: 2, an insertion of A at position 661 of SEQ ID NO: 2, a substitution of A788W of SEQ ID NO: 2, a substitution of K390R of SEQ ID NO: 2, a substitution of A751S of SEQ ID NO: 2, a substitution of E385A of SEQ ID NO: 2, an insertion of P at position 696 of SEQ ID NO: 2, an insertion of M at position 773 of SEQ ID NO: 2, a substitution of G695H of SEQ ID NO: 2, an insertion of AS at position 793 of SEQ ID NO: 2, an insertion of AS at position 795 of SEQ ID NO: 2, a substitution of C477R of SEQ ID NO: 2, a substitution of C477K of SEQ ID NO: 2, a substitution of C479A of SEQ ID NO: 2, a substitution of C479L of SEQ ID NO: 2, a substitution of I55F of SEQ ID NO: 2, a substitution of K210R of SEQ ID NO: 2, a substitution of C233S of SEQ ID NO: 2, a substitution of D231N of SEQ ID NO: 2, a substitution of Q338E of SEQ ID NO: 2, a substitution of Q338R of SEQ ID NO: 2, a substitution of L379R of SEQ ID NO: 2, a substitution of K390R of SEQ ID NO: 2, a substitution of L481Q of SEQ ID NO: 2, a substitution of F495S of SEQ ID NO:2, a substitution of D600N of SEQ ID NO: 2, a substitution of T886K of SEQ ID NO: 2, a substitution of A739V of SEQ ID NO: 2, a substitution of K460N of SEQ ID NO: 2, a substitution of I199F of SEQ ID NO: 2, a substitution of G492P of SEQ ID NO: 2, a substitution of T153I of SEQ ID NO: 2, a substitution of R591I of SEQ ID NO: 2, an insertion of AS at position 795 of SEQ ID NO: 2, an insertion of AS at position 796 of SEQ ID NO:2, an insertion of L at position 889 of SEQ ID NO: 2, a substitution of E121D of SEQ ID NO: 2, a substitution of S270W of SEQ ID NO: 2, a substitution of E712Q of SEQ ID NO: 2, a substitution of K942Q of SEQ ID NO: 2, a substitution of E552K of SEQ ID NO:2, a substitution of K25Q of SEQ ID NO: 2, a substitution of N47D of SEQ ID NO: 2, an insertion of T at position 696 of SEQ ID NO: 2, a substitution of L685I of SEQ ID NO: 2, a substitution of N880D of SEQ ID NO: 2, a substitution of Q102R of SEQ ID NO: 2, a substitution of M734K of SEQ ID NO: 2, a substitution of A724S of SEQ ID NO: 2, a substitution of T704K of SEQ ID NO: 2, a substitution of P224K of SEQ ID NO: 2, a substitution of K25R of SEQ ID NO: 2, a substitution of M29E of SEQ ID NO: 2, a substitution of H152D of SEQ ID NO: 2, a substitution of S219R of SEQ ID NO: 2, a substitution of E475K of SEQ ID NO: 2, a substitution of G226R of SEQ ID NO: 2, a substitution of A377K of SEQ ID NO: 2, a substitution of E480K of SEQ ID NO: 2, a substitution of K416E of SEQ ID NO: 2, a substitution of H164R of SEQ ID NO: 2, a substitution of K767R of SEQ ID NO: 2, a substitution of I7F of SEQ ID NO: 2, a substitution of M29R of SEQ ID NO: 2, a substitution of H435R of SEQ ID NO: 2, a substitution of E385Q of SEQ ID NO: 2, a substitution of E385K of SEQ ID NO: 2, a substitution of I279F of SEQ ID NO: 2, a substitution of D489S of SEQ ID NO: 2, a substitution of D732N of SEQ ID NO: 2, a substitution of A739T of SEQ ID NO: 2, a substitution of W885R of SEQ ID NO: 2, a substitution of E53K of SEQ ID NO: 2, a substitution of A238T of SEQ ID NO: 2, a substitution of P283Q of SEQ ID NO: 2, a substitution of E292K of SEQ ID NO: 2, a substitution of Q628E of SEQ ID NO: 2, a substitution of R388Q of SEQ ID NO: 2, a substitution of G791M of SEQ ID NO: 2, a substitution of L792K of SEQ ID NO: 2, a substitution of L792E of SEQ ID NO: 2, a substitution of M779N of SEQ ID NO: 2, a substitution of G27D of SEQ ID NO: 2, a substitution of K955R of SEQ ID NO: 2, a substitution of S867R of SEQ ID NO: 2, a substitution of R693I of SEQ ID NO: 2, a substitution of F189Y of SEQ ID NO: 2, a substitution of V635M of SEQ ID NO: 2, a substitution of F399L of SEQ ID NO: 2, a substitution of E498K of SEQ ID NO: 2, a substitution of E386R of SEQ ID NO: 2, a substitution of V254G of SEQ ID NO: 2, a substitution of P793S of SEQ ID NO: 2, a substitution of K188E of SEQ ID NO: 2, a substitution of QT945KI of SEQ ID NO: 2, a substitution of T620P of SEQ ID NO: 2, a substitution of T946P of SEQ ID NO: 2, a substitution of TT949PP of SEQ ID NO: 2, a substitution of N952T of SEQ ID NO: 2, a substitution of K682E of SEQ ID NO: 2, a substitution of K975R of SEQ ID NO: 2, a substitution of L212P of SEQ ID NO: 2, a substitution of E292R of SEQ ID NO: 2, a substitution of I303K of SEQ ID NO: 2, a substitution of C349E of SEQ ID NO: 2, a substitution of E385P of SEQ ID NO: 2, a substitution of E386N of SEQ ID NO: 2, a substitution of D387K of SEQ ID NO: 2, a substitution of L404K of SEQ ID NO: 2, a substitution of E466H of SEQ ID NO: 2, a substitution of C477Q of SEQ ID NO: 2, a substitution of C477H of SEQ ID NO: 2, a substitution of C479A of SEQ ID NO: 2, a substitution of D659H of SEQ ID NO: 2, a substitution of T806V of SEQ ID NO: 2, a substitution of K808S of SEQ ID NO: 2, an insertion of AS at position 797 of SEQ ID NO: 2, a substitution of V959M of SEQ ID NO: 2, a substitution of K975Q of SEQ ID NO: 2, a substitution of W974G of SEQ ID NO: 2, a substitution of A708Q of SEQ ID NO: 2, a substitution of V711K of SEQ ID NO: 2, a substitution of D733T of SEQ ID NO: 2, a substitution of L742W of SEQ ID NO: 2, a substitution of V747K of SEQ ID NO: 2, a substitution of F755M of SEQ ID NO: 2, a substitution of M771A of SEQ ID NO: 2, a substitution of M771Q of SEQ ID NO: 2, a substitution of W782Q of SEQ ID NO: 2, a substitution of G791F, of SEQ ID NO: 2 a substitution of L792D of SEQ ID NO: 2, a substitution of L792K of SEQ ID NO: 2, a substitution of P793Q of SEQ ID NO: 2, a substitution of P793G of SEQ ID NO: 2, a substitution of Q804A of SEQ ID NO: 2, a substitution of Y966N of SEQ ID NO: 2, a substitution of Y723N of SEQ ID NO: 2, a substitution of Y857R of SEQ ID NO: 2, a substitution of S890R of SEQ ID NO: 2, a substitution of S932M of SEQ ID NO: 2, a substitution of L897M of SEQ ID NO: 2, a substitution of R624G of SEQ ID NO: 2, a substitution of 5603G of SEQ ID NO: 2, a substitution of N737S of SEQ ID NO: 2, a substitution of L307K of SEQ ID NO: 2, a substitution of I658V of SEQ ID NO: 2, an insertion of PT at position 688 of SEQ ID NO: 2, an insertion of SA at position 794 of SEQ ID NO: 2, a substitution of S877R of SEQ ID NO: 2, a substitution of N580T of SEQ ID NO: 2, a substitution of V335G of SEQ ID NO: 2, a substitution of T620S of SEQ ID NO: 2, a substitution of W345G of SEQ ID NO: 2, a substitution of T280S of SEQ ID NO: 2, a substitution of L406P of SEQ ID NO: 2, a substitution of A612D of SEQ ID NO: 2, a substitution of A751S of SEQ ID NO: 2, a substitution of E386R of SEQ ID NO: 2, a substitution of V351M of SEQ ID NO: 2, a substitution of K210N of SEQ ID NO: 2, a substitution of D40A of SEQ ID NO: 2, a substitution of E773G of SEQ ID NO: 2, a substitution of H207L of SEQ ID NO: 2, a substitution of T62A SEQ ID NO: 2, a substitution of T287P of SEQ ID NO: 2, a substitution of T832A of SEQ ID NO: 2, a substitution of A893S of SEQ ID NO: 2, an insertion of V at position 14 of SEQ ID NO: 2, an insertion of AG at position 13 of SEQ ID NO: 2, a substitution of R11V of SEQ ID NO: 2, a substitution of R12N of SEQ ID NO: 2, a substitution of R13H of SEQ ID NO: 2, an insertion of Y at position 13 of SEQ ID NO: 2, a substitution of R12L of SEQ ID NO: 2, an insertion of Q at position 13 of SEQ ID NO: 2, an substitution of V15S of SEQ ID NO: 2, an insertion of D at position 17 of SEQ ID NO: 2 or a combination thereof.

In some embodiments, the CasX variant comprises at least one modification in the NTSB domain.

In some embodiments, the CasX variant comprises at least one modification in the TSL domain. In some embodiments, the at least one modification in the TSL domain comprises an amino acid substitution of one or more of amino acids Y857, 5890, or 5932 of SEQ ID NO: 2.

In some embodiments, the CasX variant comprises at least one modification in the helical I domain. In some embodiments, the at least one modification in the helical I domain comprises an amino acid substitution of one or more of amino acids 5219, L249, E259, Q252, E292, L307, or D318 of SEQ ID NO: 2.

In some embodiments, the CasX variant comprises at least one modification in the helical II domain. In some embodiments, the at least one modification in the helical II domain comprises an amino acid substitution of one or more of amino acids D361, L379, E385, E386, D387, F399, L404, R458, C477, or D489 of SEQ ID NO: 2.

In some embodiments, the CasX variant comprises at least one modification in the OBD domain. In some embodiments, the at least one modification in the OBD comprises an amino acid substitution of one or more of amino acids F536, E552, T620, or 1658 of SEQ ID NO: 2.

In some embodiments, the CasX variant comprises at least one modification in the RuvC DNA cleavage domain. In some embodiments, the at least one modification in the RuvC DNA cleavage domain comprises an amino acid substitution of one or more of amino acids K682, G695, A708, V711, D732, A739, D733, L742, V747, F755, M771, M779, W782, A788, G791, L792, P793, Y797, M799, Q804, 5819, or Y857 or a deletion of amino acid P793 of SEQ ID NO: 2.

In some embodiments, the CasX variant comprises at least one modification compared to the reference CasX sequence of SEQ ID NO: 2 is selected from one or more of:

(a) an amino acid substitution of L379R; (b) an amino acid substitution of A708K; (c) an amino acid substitution of T620P; (d) an amino acid substitution of E385P; (e) an amino acid substitution of Y857R; (0 an amino acid substitution of I658V; (g) an amino acid substitution of F399L; (h) an amino acid substitution of Q252K; (i) an amino acid substitution of L404K; and (j) an amino acid deletion of P793.

In some embodiments, a CasX variant protein comprises at least two amino acid changes to a reference CasX protein amino acid sequence. The at least two amino acid changes can be substitutions, insertions, or deletions of a reference CasX protein amino acid sequence, or any combination thereof. The substitutions, insertions or deletions can be any substitution, insertion or deletion in the sequence of a reference CasX protein described herein. In some embodiments, the changes are contiguous, non-contiguous, or a combination of contiguous and non-contiguous amino acid changes to a reference CasX protein sequence. In some embodiments, the reference CasX protein is SEQ ID NO: 2. In some embodiments, a CasX variant protein comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 30, at least 40, at least 45, at least 50, at least 55, at least 60, at least 65, at least 70, at least 75, at least 80, at least 85, at least 90, at least 95 or at least 100 amino acid changes to a reference CasX protein sequence. In some embodiments, a CasX variant protein comprises 1-50, 3-40, 5-30, 5-20, 5-15, 5-10, 10-50, 10-40, 10-30, 10-20, 15-50, 15-40, 15-30, 2-25, 2-24, 2-22, 2-23, 2-22, 2-21, 2-20, 2-19, 2-18, 2-17, 2-16, 2-15, 2-14, 2-12, 2-11, 2-10, 2-9, 2-8, 2-7, 2-6, 2-5, 2-4, 2-3, 3-25, 3-24, 3-22, 3-23, 3-22, 3-21, 3-20, 3-19, 3-18, 3-17, 3-16, 3-15, 3-14, 3-12, 3-11, 3-10, 3-9, 3-8, 3-7, 3-6, 3-5, 3-4, 4-25, 4-24, 4-22, 4-23, 4-22, 4-21, 4-20, 4-19, 4-18, 4-17, 4-16, 4-15, 4-14, 4-12, 4-11, 4-10, 4-9, 4-8, 4-7, 4-6, 4-5, 5-25, 5-24, 5-22, 5-23, 5-22, 5-21, 5-20, 5-19, 5-18, 5-17, 5-16, 5-15, 5-14, 5-12, 5-11, 5-10, 5-9, 5-8, 5-7 or 5-6 amino acid changes to a reference CasX protein sequence. In some embodiments, a CasX variant protein comprises 15-20 changes to a reference CasX protein sequence. In some embodiments, a CasX variant protein comprises 1, 2, 3, 4, 5, 6, 7, 8, 9, 10, 11, 12, 13, 14, 15, 16, 17, 18, 19, 20, 21, 22, 23, 24, 25, 26, 27, 28, 29 or 30 amino acid changes to a reference CasX protein sequence. In some embodiments, the at least two amino acid changes to the sequence of a reference CasX variant protein are selected from the group consisting of: a substitution of Y789T of SEQ ID NO: 2, a deletion of P793 of SEQ ID NO: 2, a substitution of Y789D of SEQ ID NO: 2, a substitution of T72S of SEQ ID NO: 2, a substitution of I546V of SEQ ID NO: 2, a substitution of E552A of SEQ ID NO: 2, a substitution of A636D of SEQ ID NO: 2, a substitution of F536S of SEQ ID NO:2, a substitution of A708K of SEQ ID NO: 2, a substitution of Y797L of SEQ ID NO: 2, a substitution of L792G SEQ ID NO: 2, a substitution of A739V of SEQ ID NO: 2, a substitution of G791M of SEQ ID NO: 2, an insertion of A at position 661 of SEQ ID NO: 2, a substitution of A788W of SEQ ID NO: 2, a substitution of K390R of SEQ ID NO: 2, a substitution of A751S of SEQ ID NO: 2, a substitution of E385A of SEQ ID NO: 2, an insertion of P at position 696 of SEQ ID NO: 2, an insertion of M at position 773 of SEQ ID NO: 2, a substitution of G695H of SEQ ID NO: 2, an insertion of AS at position 793 of SEQ ID NO: 2, an insertion of AS at position 795 of SEQ ID NO: 2, a substitution of $C_{477}R$ of SEQ ID NO: 2, a substitution of C477K of SEQ ID NO: 2, a substitution of C479A of SEQ ID NO: 2, a substitution of C479L of SEQ ID NO: 2, a substitution of I55F of SEQ ID NO: 2, a substitution of K210R of SEQ ID NO: 2, a substitution of C233S of SEQ ID NO: 2, a substitution of D231N of SEQ ID NO: 2, a substitution of Q338E of SEQ ID NO: 2, a substitution of Q338R of SEQ ID NO: 2, a substitution of L379R of SEQ ID NO: 2, a substitution of K390R of SEQ ID NO: 2, a substitution of L481Q of SEQ ID NO: 2, a substitution of F495S of SEQ ID NO:2, a substitution of D600N of SEQ ID NO: 2, a substitution of T886K of SEQ ID NO: 2, a substitution of A739V of SEQ ID NO: 2, a substitution of K460N of SEQ ID NO: 2, a substitution of I199F of SEQ ID NO: 2, a substitution of G492P of SEQ ID NO: 2, a substitution of T153I of SEQ ID NO: 2, a substitution of R591I of SEQ ID NO: 2, an insertion of AS at position 795 of SEQ ID NO: 2, an insertion of AS at position 796 of SEQ ID NO:2, an insertion of L at position 889 of SEQ ID NO: 2, a substitution of E121D of SEQ ID NO: 2, a substitution of S270W of SEQ ID NO: 2, a substitution of E712Q of SEQ ID NO: 2, a substitution of K942Q of SEQ ID NO: 2, a substitution of E552K of SEQ ID NO:2, a substitution of K25Q of SEQ ID NO: 2, a substitution of N47D of SEQ ID NO: 2, an insertion of T at position 696 of SEQ ID NO: 2, a substitution of L685I of SEQ ID NO: 2, a substitution of N880D of SEQ ID NO: 2, a substitution of Q102R of SEQ ID NO: 2, a substitution of M734K of SEQ ID NO: 2, a substitution of A724S of SEQ ID NO: 2, a substitution of T704K of SEQ ID NO: 2, a substitution of P224K of SEQ ID NO: 2, a substitution of K25R of SEQ ID NO: 2, a substitution of M29E of SEQ ID NO: 2, a substitution of H152D of SEQ ID NO: 2, a substitution of S219R of SEQ ID NO: 2, a substitution of E475K of SEQ ID NO: 2, a substitution of G226R of SEQ ID NO: 2, a substitution of A377K of SEQ ID NO: 2, a substitution of E480K of SEQ ID NO: 2, a substitution of K416E of SEQ ID NO: 2, a substitution of H164R of SEQ ID NO: 2, a substitution of K767R of SEQ ID NO: 2, a substitution of I7F of SEQ ID NO: 2, a substitution of M29R of SEQ ID NO: 2, a substitution of H435R of SEQ ID NO: 2, a substitution of E385Q of SEQ ID NO: 2, a substitution of E385K of SEQ ID NO: 2, a substitution of I279F of SEQ ID NO: 2, a substitution of D489S of SEQ ID NO: 2, a substitution of D732N of SEQ ID NO: 2, a substitution of A739T of SEQ ID NO: 2, a substitution of W885R of SEQ ID NO: 2, a substitution of E53K of SEQ ID NO: 2, a substitution of A238T of SEQ ID NO: 2, a substitution of P283Q of SEQ ID NO: 2, a substitution of E292K of SEQ ID NO: 2, a substitution of Q628E of SEQ ID NO: 2, a substitution of R388Q of SEQ ID NO: 2, a substitution of G791M of SEQ ID NO: 2, a substitution of L792K of SEQ ID NO: 2, a substitution of L792E of SEQ ID NO: 2, a substitution of M779N of SEQ ID NO: 2, a substitution of G27D of SEQ ID NO: 2, a substitution of K955R of SEQ ID NO: 2, a substitution of S867R of SEQ ID NO: 2, a substitution of R693I of SEQ ID NO: 2, a substitution of F189Y of SEQ ID NO: 2, a substitution of V635M of SEQ ID NO: 2, a substitution of F399L of SEQ ID NO: 2, a substitution of E498K of SEQ ID NO: 2, a substitution of E386R of SEQ ID NO: 2, a substitution of V254G of SEQ ID NO: 2, a substitution of P793S of SEQ ID NO: 2, a substitution of K188E of SEQ ID NO: 2, a substitution of QT945KI of SEQ ID NO: 2, a substitution of T620P of SEQ ID NO: 2, a substitution of T946P of SEQ ID NO: 2, a substitution of TT949PP of SEQ ID NO: 2, a substitution of N952T of SEQ ID NO: 2, a substitution of K682E of SEQ ID NO: 2, a substitution of K975R of SEQ ID NO: 2, a substitution of L212P of SEQ ID NO: 2, a substitution of E292R of SEQ ID NO: 2, a substitution of I303K of SEQ ID NO: 2, a substitution of C349E of SEQ ID NO: 2, a substitution of E385P of SEQ ID NO: 2, a substitution of E386N of SEQ ID NO: 2, a substitution of D387K of SEQ ID NO: 2, a substitution of L404K of SEQ ID NO: 2, a substitution of E466H of SEQ ID NO: 2, a substitution of C477Q of SEQ ID NO: 2, a substitution of C477H of SEQ ID NO: 2, a substitution of C479A of SEQ ID NO: 2, a substitution of D659H of SEQ ID NO: 2, a substitution of T806V of SEQ ID NO: 2, a substitution of K808S of SEQ ID NO: 2, an insertion of AS at position 797 of SEQ ID NO: 2, a substitution of V959M of SEQ ID NO: 2, a substitution of K975Q of SEQ ID NO: 2, a substitution of W974G of SEQ ID NO: 2, a substitution of A708Q of SEQ ID NO: 2, a substitution of V711K of SEQ ID NO: 2, a substitution of D733T of SEQ ID NO: 2, a substitution of L742W of SEQ ID NO: 2, a substitution of V747K of SEQ ID NO: 2, a substitution of F755M of SEQ ID NO: 2, a substitution of M771A of SEQ ID NO: 2, a substitution of M771Q of SEQ ID NO: 2, a substitution of W782Q of SEQ ID NO: 2, a substitution of G791F, of SEQ ID NO: 2 a substitution of L792D of SEQ ID NO: 2, a substitution of L792K of SEQ ID NO: 2, a substitution of P793Q of SEQ ID NO: 2, a substitution of P793G of SEQ ID NO: 2, a substitution of Q804A of SEQ ID NO: 2, a substitution of Y966N of SEQ ID NO: 2, a substitution of Y723N of SEQ ID NO: 2, a substitution of Y857R of SEQ ID NO: 2, a substitution of S890R of SEQ ID NO: 2, a substitution of S932M of SEQ ID NO: 2, a substitution of L897M of SEQ ID NO: 2, a substitution of R624G of SEQ ID NO: 2, a substitution of S603G of SEQ ID NO: 2, a substitution of N737S of SEQ ID NO: 2, a substitution of L307K of SEQ ID NO: 2, a substitution of I658V of SEQ ID NO: 2, an insertion of PT at position 688 of SEQ ID NO: 2, an insertion of SA at position 794 of SEQ ID NO: 2, a substitution of S877R of SEQ ID NO: 2, a substitution of N580T of SEQ ID NO: 2, a substitution of V335G of SEQ ID NO: 2, a substitution of T620S of SEQ ID NO: 2, a substitution of W345G of SEQ ID NO: 2, a substitution of T280S of SEQ ID NO: 2, a substitution of L406P of SEQ ID NO: 2, a substitution of A612D of SEQ ID NO: 2, a substitution of A751S of SEQ ID NO: 2, a substitution of E386R of SEQ ID NO: 2, a substitution of V351M of SEQ ID NO: 2, a substitution of K210N of SEQ ID NO: 2, a substitution of D40A of SEQ ID NO: 2, a substitution of E773G of SEQ ID NO: 2, a substitution of H207L of SEQ ID NO: 2, a substitution of T62A SEQ ID NO: 2, a substitution of T287P of SEQ ID NO: 2, a substitution of T832A of SEQ ID NO: 2, a substitution of A893S of SEQ ID NO: 2, an insertion of V at position 14 of SEQ ID NO: 2, an insertion of AG at position 13 of SEQ ID NO: 2, a substitution of R11V of SEQ ID NO: 2, a substitution of R12N of SEQ ID NO: 2, a substitution of R13H of SEQ ID NO: 2, an insertion of Y at position 13 of SEQ ID NO: 2, a substitution of R12L of SEQ ID NO: 2, an insertion of Q at position 13 of SEQ ID NO: 2, an substitution of V15S of SEQ ID NO: 2 and an insertion of D at position 17 of SEQ ID NO: 2. In some embodiments, the at least two amino acid changes to a reference CasX protein are selected from the amino acid changes disclosed in the sequences of Table 4. In some embodiments, a CasX variant comprises any combination of the foregoing embodiments of this paragraph.

In some embodiments, a CasX variant protein comprises more than one substitution, insertion and/or deletion of a reference CasX protein amino acid sequence. In some embodiments, the reference CasX protein comprises or consists essentially of SEQ ID NO: 2. In some embodiments, a CasX variant protein comprises a substitution of S794R and a substitution of Y797L of SEQ ID NO: 2. In some embodiments, a CasX variant protein comprises a substitution of K416E and a substitution of A708K of SEQ ID NO: 2. In some embodiments, a CasX variant protein comprises a substitution of A708K and a deletion of P793 of SEQ ID NO: 2. In some embodiments, a CasX variant protein comprises a deletion of P793 and an insertion of AS at position 795 SEQ ID NO: 2. In some embodiments, a CasX variant protein comprises a substitution of Q367K and a substitution of I425S of SEQ ID NO: 2. In some embodiments, a CasX variant protein comprises a substitution of A708K, a deletion of P position 793 and a substitution A793V of SEQ ID NO: 2. In some embodiments, a CasX variant protein comprises a substitution of Q338R and a substitution of A339E of SEQ ID NO: 2. In some embodiments, a CasX variant protein comprises a substitution of Q338R and a substitution of A339K of SEQ ID NO: 2. In some embodiments, a CasX variant protein comprises a substitution of S507G and a substitution of G508R of SEQ ID NO: 2. In some embodiments, a CasX variant protein comprises a substitution of L379R, a substitution of A708K and a deletion of P at position 793 of SEQ ID NO: 2. In some embodiments, a CasX variant protein comprises a substitution of C477K, a substitution of A708K and a deletion of P at position 793 of SEQ ID NO: 2. In some embodiments, a CasX variant protein comprises a substitution of L379R, a substitution of C477K, a substitution of A708K and a deletion of P at position of 793 of SEQ ID NO: 2. In some embodiments, a CasX variant protein comprises a substitution of L379R, a substitution of A708K, a deletion of P at position 793 and a substitution A739V of SEQ ID NO: 2. In some embodiments, a CasX variant protein comprises a substitution of C477K, a substitution of A708K, a deletion of P at position 793 and a substitution of A739V of SEQ ID NO: 2. In some embodiments, a CasX variant protein comprises a substitution of L379R, a substitution of C477K, a substitution of A708K, a deletion of P at position 793 and a substitution of A739V of SEQ ID NO: 2. In some embodiments, a CasX variant protein comprises a substitution of L379R, a substitution of A708K, a deletion of P at position 793 and a substitution of M779N of SEQ ID NO: 2. In some embodiments, a CasX variant protein comprises a substitution of L379R, a substitution of A708K, a deletion of P at position 793 and a substitution of M771N of SEQ ID NO: 2. In some embodiments, a CasX variant protein comprises a substitution of L379R, a substitution of 708K, a deletion of P at position 793 and a substitution of D489S of SEQ ID NO: 2. In some embodiments, a CasX variant protein comprises a substitution of L379R, a substitution of A708K, a deletion of P at position 793 and a substitution of A739T of SEQ ID NO: 2. In some embodiments, a CasX variant protein comprises a substitution of L379R, a substitution of A708K, a deletion of P at position 793 and a substitution of D732N of SEQ ID NO: 2. In some embodiments, a CasX variant protein comprises a substitution of L379R, a substitution of A708K, a deletion of P at position 793 and a substitution of G791M of SEQ ID NO: 2. In some embodiments, a CasX variant protein comprises a substitution of L379R, a substitution of 708K, a deletion of P at position 793 and a substitution of Y797L of SEQ ID NO: 2. In some embodiments, a CasX variant protein comprises a substitution of L379R, a substitution of C477K, a substitution of A708K, a deletion of P at position 793 and a substitution of M779N of SEQ ID NO: 2. In some embodiments, a CasX variant protein comprises a substitution of L379R, a substitution of C477K, a substitution of A708K, a deletion of P at position 793 and a substitution of M771N of SEQ ID NO: 2. In some embodiments, a CasX variant protein comprises a substitution of L379R, a substitution of C477K, a substitution of A708K, a deletion of P at position 793 and a substitution of D489S of SEQ ID NO: 2. In some embodiments, a CasX variant protein comprises a substitution of L379R, a substitution of C477K, a substitution of A708K, a deletion of P at position 793 and a substitution of A739T of SEQ ID NO: 2. In some embodiments, a CasX variant protein comprises a substitution of L379R, a substitution of C477K, a substitution of A708K, a deletion of P at position 793 and a substitution of D732N of SEQ ID NO: 2. In some embodiments, a CasX variant protein comprises a substitution of L379R, a substitution of C477K, a substitution of A708K, a deletion of P at position 793 and a substitution of G791M of SEQ ID NO: 2. In some embodiments, a CasX variant protein comprises a substitution of L379R, a substitution of C477K, a substitution of A708K, a deletion of P at position 793 and a substitution of Y797L of SEQ ID NO: 2. In some embodiments, a CasX variant protein comprises a substitution of L379R, a substitution of C477K, a substitution of A708K, a deletion of P at position 793 and a substitution of T620P of SEQ ID NO: 2. In some embodiments, a CasX variant protein comprises a substitution of A708K, a deletion of P at position 793 and a substitution of E386S of SEQ ID NO: 2. In some embodiments, a CasX variant protein comprises a substitution of E386R, a substitution of F399L and a deletion of P at position 793 of SEQ ID NO: 2. In some embodiments, a CasX variant protein comprises a substitution of R581I and A739V of SEQ ID NO: 2. In some embodiments, a CasX variant comprises any combination of the foregoing embodiments of this paragraph.

In some embodiments, a CasX variant protein comprises more than one substitution, insertion and/or deletion of a reference CasX protein amino acid sequence. In some embodiments, a CasX variant protein comprises a substitution of A708K, a deletion of P at position 793 and a substitution of A739V of SEQ ID NO: 2. In some embodiments, a CasX variant protein comprises a substitution of L379R, a substitution of A708K and a deletion of P at position 793 of SEQ ID NO: 2. In some embodiments, a CasX variant protein comprises a substitution of C477K, a substitution of A708K and a deletion of P at position 793 of SEQ ID NO: 2. In some embodiments, a CasX variant protein comprises a substitution of L379R, a substitution of C477K, a substitution of A708K and a deletion of P at position 793 of SEQ ID NO: 2. In some embodiments, a CasX variant protein comprises a substitution of L379R, a substitution of A708K, a deletion of P at position 793 and a substitution of A739V of SEQ ID NO: 2. In some embodiments, a CasX variant protein comprises a substitution of C477K, a substitution of A708K, a deletion of P at position 793 and a substitution of A739 of SEQ ID NO: 2. In some embodiments, a CasX variant protein comprises a substitution of L379R, a substitution of C477K, a substitution of A708K, a deletion of P at position 793 and a substitution of A739V of SEQ ID NO: 2. In some embodiments, a CasX variant protein comprises a substitution of L379R, a substitution of C477K, a substitution of A708K, a deletion of P at position 793 and a substitution of T620P of SEQ ID NO: 2. In some embodiments, a CasX variant protein comprises a substitution of M771A of SEQ ID NO: 2. In some embodiments, a CasX variant protein comprises a substitution of L379R, a substitution of A708K, a deletion of P at position 793 and a substitution of D732N of SEQ ID NO: 2. In some embodiments, a CasX variant comprises any combination of the foregoing embodiments of this paragraph.

In some embodiments, a CasX variant protein comprises a substitution of W782Q of SEQ ID NO: 2. In some embodiments, a CasX variant protein comprises a substitution of M771Q of SEQ ID NO: 2. In some embodiments, a CasX variant protein comprises a substitution of R458I and a substitution of A739V of SEQ ID NO: 2. In some embodiments, a CasX variant protein comprises a substitution of L379R, a substitution of A708K, a deletion of P at position 793 and a substitution of M771N of SEQ ID NO: 2. In some embodiments, a CasX variant protein comprises a substitution of L379R, a substitution of A708K, a deletion of P at position 793 and a substitution of A739T of SEQ ID NO: 2. In some embodiments, a CasX variant protein comprises a substitution of L379R, a substitution of C477K, a substitution of A708K, a deletion of P at position 793 and a substitution of D489S of SEQ ID NO: 2. In some embodiments, a CasX variant protein comprises a substitution of L379R, a substitution of C477K, a substitution of A708K, a deletion of P at position 793 and a substitution of D732N of SEQ ID NO: 2. In some embodiments, a CasX variant protein comprises a substitution of V711K of SEQ ID NO: 2. In some embodiments, a CasX variant protein comprises a substitution of L379R, a substitution of C477K, a substitution of A708K, a deletion of P at position 793 and a substitution of Y797L of SEQ ID NO: 2. In some embodiments, a CasX variant protein comprises a substitution of L379R, a substitution of A708K and a deletion of P at position 793 of SEQ ID NO: 2. In some embodiments, a CasX variant protein comprises a substitution of L379R, a substitution of C477K, a substitution of A708K, a deletion of P at position 793 and a substitution of M771N of SEQ ID NO: 2. In some embodiments, a CasX variant protein comprises a substitution of A708K, a substitution of P at position 793 and a substitution of E386S of SEQ ID NO: 2. In some embodiments, a CasX variant protein comprises a substitution of L379R, a substitution of C477K, a substitution of A708K and a deletion of P at position 793 of SEQ ID NO: 2. In some embodiments, a CasX variant protein comprises a substitution of L792D of SEQ ID NO: 2. In some embodiments, a CasX variant protein comprises a substitution of G791F of SEQ ID NO: 2. In some embodiments, a CasX variant protein comprises a substitution of A708K, a deletion of P at position 793 and a substitution of A739V of SEQ ID NO: 2. In some embodiments, a CasX variant protein comprises a substitution of L379R, a substitution of A708K, a deletion of P at position 793 and a substitution of A739V of SEQ ID NO: 2. In some embodiments, a CasX variant protein comprises a substitution of C477K, a substitution of A708K and a substitution of P at position 793 of SEQ ID NO: 2. In some embodiments, a CasX variant protein comprises a substitution of L249I and a substitution of M771N of SEQ ID NO: 2. In some embodiments, a CasX variant protein comprises a substitution of V747K of SEQ ID NO: 2. In some embodiments, a CasX variant protein comprises a substitution of L379R, a substitution of C477, a substitution of A708K, a deletion of P at position 793 and a substitution of M779N of SEQ ID NO: 2. In some embodiments, a CasX variant protein comprises a substitution of F755M. In some embodiments, a CasX variant comprises any combination of the foregoing embodiments of this paragraph.

In some embodiments, a CasX variant protein comprises at least one modification compared to the reference CasX sequence of SEQ ID NO: 2, wherein the at least one modification is selected from one or more of: an amino acid substitution of L379R; an amino acid substitution of A708K; an amino acid substitution of T620P; an amino acid substitution of E385P; an amino acid substitution of Y857R; an amino acid substitution of I658V; an amino acid substitution of F399L; an amino acid substitution of Q252K; and an amino acid deletion of [P793]. In some embodiments, a CasX variant protein comprises at least one modification compared to the reference CasX sequence of SEQ ID NO: 2, wherein the at least one modification is selected from one or more of: an amino acid substitution of L379R; an amino acid substitution of A708K; an amino acid substitution of T620P; an amino acid substitution of E385P; an amino acid substitution of Y857R; an amino acid substitution of I658V; an amino acid substitution of F399L; an amino acid substitution of Q252K; an amino acid substitution of L404K; and an amino acid deletion of [P793]. In other embodiments, a CasX variant protein comprises any combination of the foregoing substitutions or deletions compared to the reference CasX sequence of SEQ ID NO: 2. In other embodiments, the CasX variant protein can, in addition to the foregoing substitutions or deletions, further comprise a substitution of an NTSB and/or a helical 1b domain from the reference CasX of SEQ ID NO: 1.

In some embodiments, the CasX variant protein comprises between 400 and 2000 amino acids, between 500 and 1500 amino acids, between 700 and 1200 amino acids, between 800 and 1100 amino acids, or between 900 and 1000 amino acids.

In some embodiments, the CasX variant protein comprises one or more modifications in a region of non-contiguous residues that form a channel in which gNA:target DNA complexing occurs. In some embodiments, the CasX variant protein comprises one or more modifications comprising a region of non-contiguous residues that form an interface which binds with the gNA. For example, in some embodiments of a reference CasX protein, the helical I, helical II and OBD domains all contact or are in proximity to the gNA:target DNA complex, and one or more modifications to non-contiguous residues within any of these domains may improve function of the CasX variant protein.

In some embodiments, the CasX variant protein comprises one or more modifications in a region of non-contiguous residues that form a channel which binds with the non-target strand DNA. For example, a CasX variant protein can comprise one or more modifications to non-contiguous residues of the NTSBD. In some embodiments, the CasX variant protein comprises one or more modifications in a region of non-contiguous residues that form an interface which binds with the PAM. For example, a CasX variant protein can comprise one or more modifications to non-contiguous residues of the helical I domain or OBD. In some embodiments, the CasX variant protein comprises one or more modifications comprising a region of non-contiguous surface-exposed residues. As used herein, "surface-exposed residues" refers to amino acids on the surface of the CasX protein, or amino acids in which at least a portion of the amino acid, such as the backbone or a part of the side chain is on the surface of the protein. Surface exposed residues of cellular proteins such as CasX, which are exposed to an aqueous intracellular environment, are frequently selected from positively charged hydrophilic amino acids, for example arginine, asparagine, aspartate, glutamine, glutamate, histidine, lysine, serine, and threonine. Thus, for example, in some embodiments of the variants provided herein, a region of surface exposed residues comprises one or more insertions, deletions, or substitutions compared to a reference CasX protein. In some embodiments, one or more positively charged residues are substituted for one or more other positively charged residues, or negatively charged residues, or uncharged residues, or any combinations thereof. In some embodiments, one or more amino acids residues for substitution are near bound nucleic acid, for example residues in the RuvC domain or helical I domain that contact target DNA, or residues in the OBD or helical II domain that bind the gNA, can be substituted for one or more positively charged or polar amino acids.

In some embodiments, the CasX variant protein comprises one or more modifications in a region of non-contiguous residues that form a core through hydrophobic packing in a domain of the reference CasX protein. Without wishing to be bound by any theory, regions that form cores through hydrophobic packing are rich in hydrophobic amino acids such as valine, isoleucine, leucine, methionine, phenylalanine, tryptophan, and cysteine. For example, in some reference CasX proteins, RuvC domains comprise a hydrophobic pocket adjacent to the active site. In some embodiments, between 2 to 15 residues of the region are charged, polar, or base-stacking. Charged amino acids (sometimes referred to herein as residues) may include, for example, arginine, lysine, aspartic acid, and glutamic acid, and the side chains of these amino acids may form salt bridges provided a bridge partner is also present. Polar amino acids may include, for example, glutamine, asparagine, histidine, serine, threonine, tyrosine, and cysteine. Polar amino acids can, in some embodiments, form hydrogen bonds as proton donors or acceptors, depending on the identity of their side chains. As used herein, "base-stacking" includes the interaction of aromatic side chains of an amino acid residue (such as tryptophan, tyrosine, phenylalanine, or histidine) with stacked nucleotide bases in a nucleic acid. Any modification to a region of non-contiguous amino acids that are in close spatial proximity to form a functional part of the CasX variant protein is envisaged as within the scope of the disclosure.

i. CasX Variant Proteins with Domains from Multiple Source Proteins

In certain embodiments, the disclosure provides a chimeric CasX protein comprising protein domains from two or more different CasX proteins, such as two or more reference CasX proteins, or two or more CasX variant protein sequences as described herein. As used herein, a "chimeric CasX protein" refers to a CasX containing at least two domains isolated or derived from different sources, such as two naturally occurring proteins, which may, in some embodiments, be isolated from different species. For example, in some embodiments, a chimeric CasX protein comprises a first domain from a first CasX protein and a second domain from a second, different CasX protein. In some embodiments, the first domain can be selected from the group consisting of the NTSB, TSL, Helical I, Helical II, OBD and RuvC domains. In some embodiments, the second domain is selected from the group consisting of the NTSB, TSL, Helical I, Helical II, OBD and RuvC domains with the second domain being different from the foregoing first domain. For example, a chimeric CasX protein may comprise an NTSB, TSL, Helical I, Helical II, OBD domains from a CasX protein of SEQ ID NO: 2, and a RuvC domain from a CasX protein of SEQ ID NO: 1, or vice versa. As a further example, a chimeric CasX protein may comprise an NTSB, TSL, Helical II, OBD and RuvC domain from CasX protein of SEQ ID NO: 2, and a Helical I domain from a CasX protein of SEQ ID NO: 1, or vice versa. Thus, in certain embodiments, a chimeric CasX protein may comprise an NTSB, TSL, Helical II, OBD and RuvC domain from a first CasX protein, and a Helical I domain from a second CasX protein. In some embodiments of the chimeric CasX proteins, the domains of the first CasX protein are derived from the sequences of SEQ ID NO: 1, SEQ ID NO: 2 or SEQ ID NO: 3, and the domains of the second CasX protein are derived from the sequences of SEQ ID NO: 1, SEQ ID NO: 2 or SEQ ID NO: 3, and the first and second CasX proteins are not the same. In some embodiments, domains of the first CasX protein comprise sequences derived from SEQ ID NO: 1 and domains of the second CasX protein comprise sequences derived from SEQ ID NO: 2. In some embodiments, domains of the first CasX protein comprise sequences derived from SEQ ID NO: 1 and domains of the second CasX protein comprise sequences derived from SEQ ID NO: 3. In some embodiments, domains of the first CasX protein comprise sequences derived from SEQ ID NO: 2 and domains of the second CasX protein comprise sequences derived from SEQ ID NO: 3. In some embodiments, the CasX variant is selected of group consisting of CasX variants 387, 388, 389, 390, 395, 485, 486, 487, 488, 489, 490, and 491, the sequences of which are set forth in Table 4.

In some embodiments, a CasX variant protein comprises at least one chimeric domain comprising a first part from a first CasX protein and a second part from a second, different CasX protein. As used herein, a "chimeric domain" refers to a domain containing at least two parts isolated or derived from different sources, such as two naturally occurring proteins or portions of domains from two reference CasX proteins. The at least one chimeric domain can be any of the NTSB, TSL, helical I, helical II, OBD or RuvC domains as described herein. In some embodiments, the first portion of a CasX domain comprises a sequence of SEQ ID NO: 1 and the second portion of a CasX domain comprises a sequence of SEQ ID NO: 2. In some embodiments, the first portion of the CasX domain comprises a sequence of SEQ ID NO: 1 and the second portion of the CasX domain comprises a sequence of SEQ ID NO: 3. In some embodiments, the first portion of the CasX domain comprises a sequence of SEQ ID NO: 2 and the second portion of the CasX domain comprises a sequence of SEQ ID NO: 3. In some embodiments, the at least one chimeric domain comprises a chimeric RuvC domain. As an example of the foregoing, the chimeric RuvC domain comprises amino acids 661 to 824 of SEQ ID NO: 1 and amino acids 922 to 978 of SEQ ID NO: 2. As an alternative example of the foregoing, a chimeric RuvC domain comprises amino acids 648 to 812 of SEQ ID NO: 2 and amino acids 935 to 986 of SEQ ID NO: 1. In some embodiments, a CasX protein comprises a first domain from a first CasX protein and a second domain from a second CasX protein, and at least one chimeric domain comprising at least two parts isolated from different CasX proteins using the approach of the embodiments described in this paragraph. In the foregoing embodiments, the chimeric CasX proteins having domains or portions of domains derived from SEQ ID NOS: 1, 2 and 3, can further comprise amino acid insertions, deletions, or substitutions of any of the embodiments disclosed herein.

In some embodiments, a CasX variant protein comprises a sequence set forth in Tables 4, 6, 7, 8, or 10. In some embodiments, a CasX variant protein consists of a sequence set forth in Table 4. In other embodiments, a CasX variant protein comprises a sequence at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 86% identical, at least 87% identical, at least 88% identical, at least 89% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical to a sequence set forth in Tables 4, 6, 7, 8, or 10. In other embodiments, a CasX variant protein comprises a sequence set forth in Table 4, and further comprises one or more NLS disclosed herein at or near either the N-terminus, the C-terminus, or both. It will be understood that in some cases, the N-terminal methionine of the CasX variants of the Tables is removed from the expressed CasX variant during post-translational modification.

TABLE 4

CasX Variant Sequences

| Description* | Amino Acid Sequence |
|---|---|
| TSL, Helical I, Helical II, OBD and RuvC domains from SEQ ID NO: 2 and an NTSB domain from SEQ ID NO: 1 | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPASKKI DQNKLKPEMDEKGNLTTAGFACSQCGQPLFVYKLEQVSEKGKAYTNYFGRCNVA EHEKLILLAQLKPEKDSDEAVTYSLGKFGQRALDFYSIHVTRESNHPVKPLEQI GGNSCASGPVGKALSDACMGAVASFLTKYQDIILEHQKVIKKNEKRLANLKDIA SANGLAFPKITLPPQPHTKEGIEAYNNVVAQIVIWVNLNLWQKLKIGRDEAKPL QRLKGFPSFPLVERQANEVDWWDMVCNVKKLINEKKEDGKVFWQNLAGYKRQEA LRPYLSSEEDRKKGKKFARYQFGDLLLHLEKKHGEDWGKVYDEAWERIDKKVEG LSKHIKLEEERRSEDAQSKAALTDWLRAKASFVIEGLKEADKDEFCRCELKLQK WYGDLRGKPFAIEAENSILDISGFSKQYNCAFIWQKDGVKKLNLYLIINYFKGG KLRFKKIKPEAFEANRFYTVINKKSGEIVPMEVNFNFDDPNLIILPLAFGKRQG REFIWNDLLSLETGSLKLANGRVIEKTLYNRRTRQDEPALFVALTFERREVLDS SNIKPMNLIGIDRGENIPAVIALTDPEGCPLSRFKDSLGNPTHILRIGESYKEK QRTIQAKKEVEQRRAGGYSRKYASKAKNLADDMVRNTARDLLYYAVTQDAMLIF ENLSRGFGRQGKRTFMAERQYTRMEDWLTAKLAYEGLSKTYLSKTLAQYTSKTC SNCGFTITSADYDRVLEKLKKTATGWMTTINGKELKVEGQITYYNRYKRQNVVK DLSVELDRLSEESVNNDISSWTKGRSGEALSLLKKRFSHRPVQEKFVCLNCGFE THADEQAALNIARSWLFLRSQEYKKYQTNKTTGNTDKRAFVETWQSFYRKKLKE VWKPAV (SEQ ID NO: 36) |

TABLE 4-continued

CasX Variant Sequences

| Description* | Amino Acid Sequence |
|---|---|
| NTSB, Helical I, Helical II, OBD and RuvC domains from SEQ ID NO: 2 and a TSL domain from SEQ ID NO: 1. | MQEIKRINKIRRRLVKDSNTKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITTADYDGMLVRLKKTSDGWATTLNNKELKAEGQITYYNRYKRQTVEKE LSAELDRLSEESGNNDISKWTKGRRDEALFLLKKRFSHRPVQEQFVCLDCGHEV HADEQAALNIARSWLFLRSQEYKKYQTNKTTGNTDKRAFVETWQSFYRKKLKEV WKPAV (SEQ ID NO: 37) |
| TSL, Helical I, Helical II, OBD and RuvC domains from SEQ ID NO: 1 and an NTSB domain from SEQ ID NO: 2 | MEKRINKIRKKLSADNATKPVSRSGPMKTLLVRVMTDDLKKRLEKRRKKPEVMP QVISNNAANNLRMLLDDYTKMKEAILQVYWQEFKDDHVGLMCKFAQPAPKNIDQ RKLIPVKDGNERLTSSGFACSQCCQPLYVYKLEQVNDKGKPHTNYFGRCNVSEH ERLILLSPHKPEANDELVTYSLGKFGQRALDFYSIHVTKESTHPVKPLAQIAGN RYASGPVGKALSDACMGTIASFLSKYQDIIIEHQKVVKGNQKRLESLRELAGKE NLEYPSVTLPPQPHTKEGVDAYNEVIARVRMWVNLNLWQKLKLSRDDAKPLLRL KGFPSFPVVERRENEVDWWNTINEVKKLIDAKRDMGRVFWSGVTAEKRNTILEG YNYLPNENDHKKREGSLENPKKPAKRQFGDLLLYLEKKYAGDWGKVFDEAWERI DKKIAGLTSHIEREEARNAEDAQSKAVLTDWLRAKASFVLERLKEMDEKEFYAC EIQLQKWYGDLRGNPFAVEAENRVVDISGFSIGSDGHSIQYRNLLAWKYLENGK REFYLLMNYGKKGRIRFTDGTDIKKSGKWQGLLYGGGKAKVIDLTFDPDDEQLI ILPLAFGTRQGREFIWNDLLSLETGLIKLANGRVIEKTIYNKKIGRDEPALFVA LTFERREVVDPSNIKPVNLIGVDRGENIPAVIALTDPEGCPLPEFKDSSGGPTD ILRIGEGYKEKQRAIQAAKEVEQRRAGGYSRKFASKSRNLADDMVRNSARDLFY HAVTHDAVLVFENLSRGFGRQGKRTFMTERQYTKMEDWLTAKLAYEGLTSKTYL SKTLAQYTSKTCSNCGFTITTADYDGMLVRLKKTSDGWATTLNNKELKAEGQIT YYNRYKRQTVEKELSAELDRLSEESGNNDISKWTKGRRDEALFLLKKRFSHRPV QEQFVCLDCGHEVHADEQAALNIARSWLFNSNSTEFKSYKSGKQPFVGAWQAF YKRRLKEVWKPNA (SEQ ID NO: 38) |
| NTSB, Helical I, Helical II, OBD and RitvC domains from SEQ ID NO: 1 and an TSL domain from SEQ ID NO: 2. | MEKRINKIRKKLSADNATKPVSRSGPMKTLLVRVMTDDLKKRLEKRRKKPEVMP QVISNNAANNLRMLLDDYTKMKEAILQVYWQEFKDDHVGLMCKFAQPASKKIDQ NKLKPEMDEKGNLTTAGFACSQCGQPLFVYKLEQVSEKGKAYTNYFGRCNVAEH EKLILLAQLKPEKDSDEAVTYSLGKFGQRALDFYSIHVTKESTHPVKPLAQIAG NRYASGPVGKALSDACMGTIASFLSKYQDIIIEHQKVVKGNQKRLESLRELAGK ENLEYPSVTLPPQPHTKEGVDAYNEVIARVRMWVNLNLWQKLKLSRDDAKPLLR LKGFPSFPVVERRENEVDWWNTINEVKKLIDAKRDMGRVFWSGVTAEKRNTILE GYNYLPNENDHKKREGSLENPKKPAKRQFGDLLLYLEKKYAGDWGKVFDEAWER IDKKIAGLTSHIEREEARNAEDAQSKAVLTDWLRAKASFVLERLKEMDEKEFYA CEIQLQKWYGDLRGNPFAVEAENRVVDISGFSIGSDGHSIQYRNLLAWKYLENG KREFYLLMNYGKKGRIRFTDGTDIKKSGKWQGLLYGGGKAKVIDLTFDPDDEQL IILPLAFGTRQGREFIWNDLLSLETGLIKLANGRVIEKTIYNKKIGRDEPALFV ALTFERREVVDPSNIKPVNLIGVDRGENIPAVIALTDPEGCPLPEFKDSSGGPT DILRIGEGYKEKQRAIQAAKEVEQRRAGGYSRKFASKSRNLADDMVRNSARDLF YHAVTHDAVLVFENLSRGFGRQGKRTFMTERQYTKMEDWLTAKLAYEGLTSKTY LSKTLAQYTSKTCSNCGFTITSADYDRVLEKLKKTATGWMTTINGKELKVEGQI TYYNRYKRQNVVKDLSVELDRLSEESVNNDISSWTKGRSGEALSLLKKRFSHRP VQEKFVCLNCGFETHADEQAALNIARSWLFLNSNSTEFKSYKSGKQPFVGAWQA FYKRRLKEVWKPNA (SEQ ID NO: 39) |
| NTSB, TSL, Helical I, Helical II and OBD domains SEQ IDINO: 2 and an exogenous RitvC domainora portion thereof from | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR |

TABLE 4-continued

CasX Variant Sequences

| Description* | Amino Acid Sequence |
| --- | --- |
| a second CasX protein | EFIWNDLLSLETGSLKLANGRVIEKTLYNRRTRQDEPALFVALTFERREVLDSS NIKPVNLIGVDRGENIPAVIALTDPEGCPLPEFKDSSGGPTDILRIGEGYKEKQ RAIQAAKEVEQRRAGGYSRKFASKSRNLADDMVRNSARDLFYHAVTHDAVLVFE NLSRGFGRQGKRTFMTERQYTKMEDWLTAKLAYEGLTSKTYLSKTLAQYTSKTC SNCGFTITSADYDRVLEKLKKTATGWMTTINGKELKVEGQITYYNRYKRQNVVK DLSVELDRLSEESVNNDISSWTKGRSGEALSLLKKRFSHRPVQEKFVCLNCGFE THA (SEQ ID NO: 40)<br><br>MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HA (SEQ ID NO: 41) |
| NTSB, TSL, Helical II, OBD and RANC domains from SEQ ID NO: 2 and a Helical I domain from SEQ ID NO: 1 | MQEIKRINKIRRRLVKDSNIKKAGKTGPMKTLLVRVMTPDLRERLENLRKKPEN IPQPISNNAANNLRMLLDDYTKMKEAILQVYWQEFKDDHVGLMCKFAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTKESTHPVKPLAQIA GNRYASGPVGKALSDACMGTIASFLSKYQDIIIEHQKVVKGNQKRLESLRELAG KENLEYPSVTLPPQPHTKEGVDAYNEVIARVRMWVNLNLWQKLKLSRDDAKPLL RLKGFPSFPLVERQANEVDWWDMVCNVKKLINEKKEDGKVFWQNLAGYKRQEAL RPYLSSEEDRKKGKKFARYQFGDLLLHLEKKHGEDWGKVVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 42) |
| NTSB, TSL, Helical I, OBD and RANC domains from SEQ ID NO: 2 and a Helical II domain from SEQ ID NO: 1 | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPVVERRENEVDWWNTINEVKKLIDAKRDMGRVFWSGVTAEKRNTIL EGYNYLPNENDHKKREGSLENPKKPAKRQFGDLLLYLEKKYAGDWGKVFDEAWE RIDKKIAGLTSHIEREEARNAEDAQSKAVLTDWLRAKASFVLERLKEMDEKEFY ACEIQLQKWYGDLRGNPFAVEAENSILDISGFSKQYNCAFIWQKDGVKKLNLYL IINYFKGGKLRFKKIKPEAFEANRFYTVINKKSGEIVPMEVNFNFDDPNLIILP LAFGKRQGREFIWNDLLSLETGSLKLANGRVIEKTLYNRRTRQDEPALFVALTF ERREVLDSSNIKPMNLIGIDRGENIPAVIALTDPEGCPLSRFKDSLGNPTHILR IGESYKEKQRTIQAKKEVEQRRAGGYSRKYASKAKNLADDMVRNTARDLLYYAV TQDAMLIFENLSRGFGRQGKRTFMAERQYTRMEDWLTAKLAYEGLSKTYLSKTL AQYTSKTCSNCGFTITSADYDRVLEKLKKTATGWMTTINGKELKVEGQITYYNR YKRQNVVKDLSVELDRLSEESVNNDISSWTKGRSGEALSLLKKRFSHRPVQEKF VCLNCGFETHADEQAALNIARSWLFLRSQEYKKYQTNKTTGNTDKRAFVETWQS FYRKKLKEVWKPAV (SEQ ID NO: 43) |
| NTSB, TSL, Helical I, Helical II and RitvC domains from a first CasX protein and an exogenous | MISNTSRANLNKLLTDYTEMKKAILHVYWEEFQKDPVGLMSRVAQPAPKNIDQR KLIPVKDGNERLTSSGFACSQCCQPLYVYKLEQVNDKGKPHTNYFGRCNVSEHE RLILLSPHKPEANDELVTYSLGKFGQRALDFYSIHVTRESNHPVKPLEQIGGNS CASGPVGKALSDACMGAVASFLTKYQDIILEHQKVIKKNEKRLANLKDIASANG LAFPKITLPPQPHTKEGIEAYNNVVAQIVIWVNLNLWQKLKIGRDEAKPLQRLK GFPSFPLVERQANEVDWWDMVCNVKKLINEKKEDGKVFWQNLAGYKRQEALRPY LSSEEDRKKGKKFARYQFGDLLLHLEKKHGEDWGKVVYDEAWERIDKKVEGLSKH IKLEEERRSEDAQSKAALTDWLRAKASFVIEGLKEADKDEFCRCELKLQKWYGD LRGKPFAIEAENRVVDISGFSIGSDGHSIQYRNLLAWKYLENGKREFYLLMNYG |

95
96

TABLE 4-continued

CasX Variant Sequences

| Description* | Amino Acid Sequence |
|---|---|
| OBD or a part thereof from a second CasX protein | KKGRIRFTDGTDIKKSGKWQGLLYGGGKAKVIDLTFDPDDEQLIILPLAFGTRQ GREFIWNDLLSLETGLIKLANGRVIEKTIYNKKIGRDEPALFVALTFERREVVD PSNIKPMNLIGIDRGENIPAVIALTDPEGCPLSRFKDSLGNPTHILRIGESYKE KQRTIQAKKEVEQRRAGGYSRKYASKAKNLADDMVRNTARDLLYYAVTQDAMLI FENLSRGFGRQGKRTFMAERQYTRMEDWLTAKLAYEGLSKTYLSKTLAQYTSKT CSNCGFTITSADYDRVLEKLKKTATGWMTTINGKELKVEGQITYYNRYKRQNVV KDLSVELDRLSEESVNNDISSWTKGRSGEALSLLKKRFSHRPVQEKFVCLNCGF ETHADEQAALNIARSWLFLRSQEYKKYQTNKTTGNTDKRAFVETWQSFYRKKLK EVVWKPAV (SEQ ID NO: 44)<br><br>MEKRINKIRKKLSADNATKPVSRSGPMKTLLVRVMTDDLKKRLEKRRKKPEVMP QVISNTSRANLNKLLTDYTEMKKAILHVYWEEFQKDPVGLMSRVAQPAPKNIDQ RKLIPVKDGNERLTSSGFACSQCCQPLYVYKLEQVNDKGKPHTNYFGRCNVSEH ERLILLSPHKPEANDELVTYSLGKFGQRALDFYSIHVTRESNHPVKPLEQIGGN SCASGPVGKALSDACMGAVASFLTKYQDIILEHQKVIKKNEKRLANLKDIASAN GLAFPKITLPPQPHTKEGIEAYNNVVAQIVIWVNLNLWQKLKIGRDEAKPLQRL KGFPSFPLVERQANEVDWWDMVCNVKKLINEKKEDGKVFWQNLAGYKRQEALRP YLSSEEDRKKGKKFARYQFGDLLLHLEKKHGEDWGKVYDEAWERIDKKVEGLSK HIKLEEERRSEDAQSKAALTDWLRAKASFVIEGLKEADKDEFCRCELKLQKWYG DLRGKPFAIEAENSILDISGFSKQYNCAFIWQKDGVKKLNLYLIINYFKGGKLR FKKIKPEAFEANRFYTVINKKSGEIVPMEVNFNFDDPNLIILPLAFGKRQGREF IWNDLLSLETGSLKLANGRVIEKTLYNRRTRQDEPALFVALTFERREVLDSSNI KPMNLIGIDRGENIPAVIALTDPEGCPLSRFKDSLGNPTHILRIGESYKEKQRT IQAKKEVEQRRAGGYSRKYASKAKNLADDMVRNTARDLLYYAVTQDAMLIFENL SRGFGRQGKRTFMAERQYTRMEDWLTAKLAYEGLSKTYLSKTLAQYTSKTCSNC GFTITSADYDRVLEKLKKTATGWMTTINGKELKVEGQITYYNRYKRQNVVKDLS VELDRLSEESVNNDISSWTKGRSGEALSLLKKRFSHRPVQEKFVCLNCGFETHA DEQAALNIARSWLFLRSQEYKKYQTNKTTGNTDKRAFVETWQSFYRKKLKEVWK PAV (SEQ ID NO: 45)<br><br>MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENRVVDISGFSIGSDGHSIQYRNLLAWKYLENGKREFYLLM NYGKKGRIRFTDGTDIKKSGKWQGLLYGGGKAKVIDLTFDPPDEQLIILPLAFG TRQGREFIWNDLLSLETGLIKLANGRVIEKTIYNKKIGRDEPALFVALTFERRE VVDPSNIKPMNLIGIDRGENIPAVIALTDPEGCPLSRFKDSLGNPTHILRIGES YKEKQRTIQAKKEVEQRRAGGYSRKYASKAKNLADDMVRNTARDLLYYAVTQDA MLIFENLSRGFGRQGKRTFMAERQYTRMEDWLTAKLAYEGLSKTYLSKTLAQYT SKTCSNCGFTITSADYDRVLEKLKKTATGWMTTINGKELKVEGQITYYNRYKRQ NVVKDLSVELDRLSEESVNNDISSWTKGRSGEALSLLKKRFSHRPVQEKFVCLN CGFETHADEQAALNIARSWLFLRSQEYKKYQTNKTTGNTDKRAFVETWQSFYRK KLKEVWKPAV (SEQ ID NO: 46) |
| substitution of L379R, a substitution of C477K, a substitution of A708K, a deletion of P at position 793 and a substitution of T620P of SEQ ID NO: 2 | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFKRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKPLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 47) |
| substitution of M771A of SEQ ID NO: 2. | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ |

TABLE 4-continued

CasX Variant Sequences

| Description* | Amino Acid Sequence |
|---|---|
| | RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAAKEVEQRRAGGYSRKYASKAKNLADDMVRNTARDLLYYAVTQDAMLIFE<br>NLSRGFGRQGKRTFAAERQYTRMEDWLTAKLAYEGLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPA (SEQ ID NO: 48) |
| substitution<br>of L379R, a<br>substitution<br>of A708K, a<br>deletion of P<br>at position<br>793 and a<br>substitution<br>of D732N of<br>SEQ ID NO:<br>2. | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLANDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 49) |
| substitution<br>of W782Q of<br>SEQ ID NO:<br>2. | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAAKEVEQRRAGGYSRKYASKAKNLADDMVRNTARDLLYYAVTQDAMLIFE<br>NLSRGFGRQGKRTFMAERQYTRMEDQLTAKLAYEGLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 50) |
| substitution<br>of M771Q of<br>SEQ ID NO:<br>2 | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAAKEVEQRRAGGYSRKYASKAKNLADDMVRNTARDLLYYAVTQDAMLIFE<br>NLSRGFGRQGKRTFQAERQYTRMEDWLTAKLAYEGLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 51) |

TABLE 4-continued

CasX Variant Sequences

| Description* | Amino Acid Sequence |
|---|---|
| substitution of R458I and a substitution of A739V of SEQ ID NO: 2. | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL LPYLSSEEDRKKGKKFARYQFGDLLLHLEKKHGEDWGKVYDEAWERIDKKVEGL SKHIKLEEERRSEDAQSKAALTDWLIAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAAKEVEQRRAGGYSRKYASKAKNLADDMVRNTVRDLLYYAVTQDAMLIFE NLSRGFGRQGKRTFMAERQYTRMEDWLTAKLAYEGLPSKTYLSKTLAQYTSKTC SNCGFTITSADYDRVLEKLKKTATGWMTTINGKELKVEGQITYYNRYKRQNVVK DLSVELDRLSEESVNNDISSWTKGRSGEALSLLKKRFSHRPVQEKFVCLNCGFE THADEQAALNIARSWLFLRSQEYKKYQTNKTTGNTDKRAFVETWQSFYRKKLKE VWKPAV (SEQ ID NO: 52) |
| L379R, a substitution of A708K, a deletion of P at position 793 and a substitution of M771N of SEQ ID NO: 2 | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFNAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 53) |
| substitution of L379R, a substitution of A708K, a deletion of P at position 793 and a substitution of A739T of SEQ ID NO: 2 | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTTRDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 54) |
| substitution of L379R, a substitution of C477K, a substitution of A708K, a deletion of P at position 793 and a substitution of D489S of SEQ ID NO: 2. | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGSLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS |

TABLE 4-continued

CasX Variant Sequences

| Description* | Amino Acid Sequence |
|---|---|
| | NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 55) |
| substitution of L379R, a substitution of C477K, a substitution of A708K, a deletion of P at position 793 and a substitution of D732N of SEQ ID NO: 2. | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFKRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLANDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 56) |
| substitution of V711K of SEQ ID NO: 2. | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKEKEQRRAGGYSRKYASKAKNLADDMVRNTARDLLYYAVTQDAMLIFE<br>NLSRGFGRQGKRTFMAERQYTRMEDWLTAKLAYEGLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 57) |
| substitution of L379R, a substitution of C477K, a substitution of A708K, a deletion of P at position 793 and a substitution of Y797L of SEQ ID NO: 2. | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFKRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKILLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 58) |
| 119: substitution of L379R, a substitution of A708K and a deletion of P | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL |

TABLE 4-continued

CasX Variant Sequences

| Description* | Amino Acid Sequence |
|---|---|
| at position 793 of SEQ ID NO: 2. | RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 59) |
| substitution of L379R, a substitution of C477K, a substitution of A708K, a deletion of P at position 793 and a substitution of M771N of SEQ ID NO: 2. | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFNAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 60) |
| substitution of A708K, a deletion of P at position 793 and a substitution of E386S of SEQ ID NO: 2. | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL LPYLSSESDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 61) |
| substitution of L379R, a substitution of C477K, a substitution of A708K and a deletion of P at position 793 of SEQ ID NO: 2. | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 62) |

TABLE 4-continued

CasX Variant Sequences

| Description* | Amino Acid Sequence |
| --- | --- |
| substitution of L792D of SEQ ID NO: 2. | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL LPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAAKEVEQRRAGGYSRKYASKAKNLADDMVRNTARDLLYYAVTQDAMLIFE NLSRGFGRQGKRTFMAERQYTRMEDWLTAKLAYEGDPSKTYLSKTLAQYTSKTC SNCGFTITSADYDRVLEKLKKTATGWMTTINGKELKVEGQITYYNRYKRQNVVK DLSVELDRLSEESVNNDISSWTKGRSGEALSLLKKRFSHRPVQEKFVCLNCGFE THADEQAALNIARSWLFLRSQEYKKYQTNKTTGNTDKRAFVETWQSFYRKKLKE VWKPAV (SEQ ID NO: 63) |
| substitution of G791F of SEQ ID NO: 2. | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL LPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAAKEVEQRRAGGYSRKYASKAKNLADDMVRNTARDLLYYAVTQDAMLIFE NLSRGFGRQGKRTFMAERQYTRMEDWLTAKLAYEFLPSKTYLSKTLAQYTSKTC SNCGFTITSADYDRVLEKLKKTATGWMTTINGKELKVEGQITYYNRYKRQNVVK DLSVELDRLSEESVNNDISSWTKGRSGEALSLLKKRFSHRPVQEKFVCLNCGFE THADEQAALNIARSWLFLRSQEYKKYQTNKTTGNTDKRAFVETWQSFYRKKLKE VWKPAV (SEQ ID NO: 64) |
| substitution of A708K, a deletion of P at position 793 and a substitution of A739V of SEQ ID NO: 2. | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL LPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTVRDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 65) |
| substitution of L379R, a substitution of A708K, a deletion of P at position 793 and a substitution of A739V of SEQ ID NO: 2. | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAAKEVEQRRAGGYSRKYASKAKNLADDMVRNTVRDLLYYAVTQDAMLIFE NLSRGFGRQGKRTFMAERQYTRMEDWLTAKLAYEGLSKTYLSKTLAQYTSKTCS |

TABLE 4-continued

CasX Variant Sequences

| Description* | Amino Acid Sequence |
|---|---|
| | NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGPET<br>HADEQAALNIARSWLFLRSQEYKKYQTNKTTGNTDKRAFVETWQSFYRKKLKEV<br>WKPAV (SEQ ID NO: 66) |
| substitution of C477K, a substitution of A708K and a deletion of P at position 793 of SEQ ID NO: 2. | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGPET<br>HADEQAALNIARSWLFLRSQEYKKYQTNKTTGNTDKRAFVETWQSFYRKKLKEV<br>WKPAV (SEQ ID NO: 67) |
| substitution of L249I and a substitution of M771N of 2. | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAAKEVEQRRAGGYSRKYASKAKNLADDMVRNTARDLLYYAVTQDAMLIFE<br>NLSRGFGRQGKRTFNAERQYTRMEDWLTAKLAYEGLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 68) |
| substitution of V747K of SEQ ID NO: 2. | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAAKEVEQRRAGGYSRKYASKAKNLADDMVRNTARDLLYYAKTQDAMLIFE<br>NLSRGFGRQGKRTFMAERQYTRMEDWLTAKLAYEGLPSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 69) |
| substitution of L379R, a substitution of C477K, a substitution of A708K, a deletion of P at position | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL |

TABLE 4-continued

CasX Variant Sequences

| Description* | Amino Acid Sequence |
|---|---|
| 793 and a substitution of M779N of SEQ ID NO: 2. | SKHIKLEEERRSEDAQSKAALTDWLRAKASFVIEGLKEADKDEFKRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRNEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 70) |
| L379R, F755M | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL LPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAAKEVEQRRAGGYSRKYASKAKNLADDMVRNTARDLLYYAVTQDAMLIME NLSRGFGRQGKRTFMAERQYTRMEDWLTAKLAYEGLPSKTYLSKTLAQYTSKTC SNCGFTITSADYDRVLEKLKKTATGWMTTINGKELKVEGQITYYNRYKRQNVVK DLSVELDRLSEESVNNDISSWTKGRSGEALSLLKKRFSHRPVQEKFVCLNCGFE THADEQAALNIARSWLFLRSQEYKKYQTNKTTGNTDKRAFVETWQSFYRKKLKE VWKPAV (SEQ ID NO: 71) |
| 429: L379R, A708K, P793_, Y857R | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRRKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 72) |
| 430 L379R, A708K, P793_, Y857R, I658V | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGVDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRRKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 73) |
| 431 L379R, A708K, P793_, | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG |

TABLE 4-continued

CasX Variant Sequences

| Description* | Amino Acid Sequence |
|---|---|
| Y857R,<br>I658V,<br>E386N | GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 74) |
| 432<br>L379R,<br>A708K,<br>P793_,<br>Y857R,<br>I658V,<br>L404K | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLKHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 75) |
| 433<br>L379R,<br>A708K,<br>P793_,<br>Y857R,<br>I658V,<br>^V192 | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQVRALDFYSIHVTRESNHPVKPLEQI<br>GGNSCASGPVGKALSDACMGAVASFLTKYQDIILEHQKVIKKNEKRLANLKDIA<br>SANGLAFPKITLPPQPHTKEGIEAYNNVVAQIVIWVNLNLWQKLKIGRDEAKPL<br>QRLKGFPSFPLVERQANEVDWWDMVCNVKKLINEKKEDGKVFWQNLAGYKRQEA<br>LRPYLSSEEDRKKGKKFARYQFGDLLLHLEKKHGEDWGKVYDEAWERIDKKVEG<br>LSKHIKLEEERRSEDAQSKAALTDWLRAKASFVIEGLKEADKDEFCRCELKLQK<br>WYGDLRGKPFAIEAENSILDISGFSKQYNCAFIWQKDGVKKLNLYLIINYFKGG<br>KLRFKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERREVLDS<br>SNIKPMNLIGVDRGENIPAVIALTDPEGCPLSRFKDSLGNPTHILRIGESYKEK<br>QRTIQAKKEVEQRRAGGYSRKYASKAKNLADDMVRNTARDLLYYAVTQDAMLIF<br>ENLSRGFGRQGKRTFMAERQYTRMEDWLTAKLAYEGLSKTYLSKTLAQYTSKTC<br>SNCGFTITSADYDRVLEKLKKTATGWMTTINGKELKVEGQITYYNRRKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 76) |
| 434<br>L379R,<br>A708K,<br>P793_,<br>Y857R,<br>I658V,<br>L404K,<br>E386N | MQEIKRINKIRRRLVKDSNTKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQFGDLLKHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 77) |

TABLE 4-continued

CasX Variant Sequences

| Description* | Amino Acid Sequence |
|---|---|
| 435<br>L379R,<br>A708K,<br>P793_,<br>Y857R,<br>I658V,<br>F399L | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 78) |
| 436<br>L379R,<br>A708K,<br>P793_,<br>Y857R,<br>I658V,<br>F399L,<br>E386N | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 79) |
| 437<br>L379R,<br>A708K,<br>P793_,<br>Y857R,<br>I658V,<br>F399L,<br>C477S | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFSRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 80) |
| 438:<br>L379R,<br>A708K,<br>P793_,<br>Y857R,<br>I658V,<br>F399L,<br>L404K | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQLGDLLKHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD |

TABLE 4-continued

CasX Variant Sequences

| Description* | Amino Acid Sequence |
|---|---|
| | LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 81) |
| 439:<br>L379R,<br>A708K,<br>P793_,<br>Y857R,<br>I658V,<br>F399L,<br>E386N,<br>C477S,<br>L404K | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQLGDLLKHLEKKHGEDWGKVYDEAWERIDKKVEGL<br>SKHIKLEEERRSEDAQSKAALTDWLRAKASFVIEGLKEADKDEFSRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 82) |
| 440<br>L379R,<br>A708K,<br>P793_,<br>N857R,<br>I658V,<br>F399L,<br>Y797L | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKILLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 83) |
| 441<br>L379R,<br>A708K,<br>P793_,<br>Y857R,<br>I658V,<br>F399L,<br>Y797L,<br>E386N | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKILLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 84) |
| 442<br>L379R,<br>A708K,<br>P793_,<br>Y857R,<br>I658V,<br>F399L,<br>Y797L, | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQLGDLLKHLEKKHGEDWGKVYDEAWERIDKKVEGL |

TABLE 4-continued

CasX Variant Sequences

| Description* | Amino Acid Sequence |
|---|---|
| E386N,<br>C477S,<br>L404K | SKHIKLEEERRSEDAQSKAALTDWLRAKASFVIEGLKEADKDEFSRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKILLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 85) |
| 443<br>L379R,<br>A708K,<br>P793_,<br>Y857L<br>I658V,<br>Y797L | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKILLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 86) |
| 444<br>L379R,<br>A708K,<br>P793_,<br>Y857R,<br>I658V,<br>Y797L,<br>L404K | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKILLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 87) |
| 445<br>L379R,<br>A708K,<br>P793_,<br>Y857R,<br>I658V,<br>Y797L,<br>E386N | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKILLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 88) |
| 446<br>L379R,<br>A708K,<br>P793_, | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG |

TABLE 4-continued

CasX Variant Sequences

| Description* | Amino Acid Sequence |
|---|---|
| Y857R,<br>I658V,<br>Y797L,<br>E386N,<br>C477S,<br>L404K | GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQFGDLLKHLEKKHGEDWGKVYDEAWERIDKKVEGL<br>SKHIKLEEERRSEDAQSKAALTDWLRAKASFVIEGLKEADKDEFSRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKILLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 89) |
| 447<br>L379R,<br>A708K,<br>P793_,<br>Y857R,<br>E386N | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 90) |
| 448:<br>L379R,<br>A708K,<br>P793_,<br>Y857R,<br>E386N,<br>L404K | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQFGDLLKHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 91) |
| 449:<br>L379R,<br>A708K,<br>P793_,<br>D732N,<br>E385P,<br>Y857R | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLANDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 92) |

TABLE 4-continued

CasX Variant Sequences

| Description* | Amino Acid Sequence |
| --- | --- |
| 450<br>L379R,<br>A708K,<br>P793_,<br>D732N,<br>E385P,<br>Y857R,<br>I658V | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLANDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 93) |
| 451:<br>L379R,<br>A708K,<br>P793_,<br>D732N,<br>E385P,<br>Y857R,<br>I658V,<br>F399L | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLANDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 94) |
| 452<br>L379R,<br>A708K,<br>P793_,<br>D732N,<br>E385P,<br>Y857R,<br>I658V,<br>E386N | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPNDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLANDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 95) |
| 453<br>L379R,<br>A708K,<br>P793_,<br>D732N,<br>E385P,<br>Y857R,<br>I658V,<br>L404K | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQFGDLLKHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLANDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD |

TABLE 4-continued

CasX Variant Sequences

| Description* | Amino Acid Sequence |
|---|---|
| | LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 96) |
| 454<br>L379R,<br>A708K,<br>P793_,<br>T620P,<br>E385P,<br>Y857R,<br>Q252K | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHKKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 97) |
| 455<br>L379R,<br>A708K,<br>P793_,<br>T620P,<br>E385P,<br>Y857R,<br>I658V,<br>Q252K | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHKKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 98) |
| 456<br>L379R,<br>A708K,<br>P793_,<br>T620P,<br>E385P,<br>Y857R,<br>I658V,<br>E386N,<br>Q252K | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHKKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPNDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 99) |
| 457<br>L379R,<br>A708K,<br>P793_,<br>T620P,<br>E385P,<br>Y857R,<br>I658V,<br>F399L,<br>Q252K | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHKKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS |

TABLE 4-continued

CasX Variant Sequences

| Description* | Amino Acid Sequence |
|---|---|
| | NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 101) |
| 458:<br>L379R,<br>A708K,<br>P793_,<br>T620P,<br>E385P,<br>Y857R,<br>I658V,<br>L404K,<br>Q252K | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHKKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQFGDLLKHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 102) |
| 459:<br>L379R,<br>A708K,<br>P793_,<br>T620P,<br>Y857R,<br>I658V,<br>E386N | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSENDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 103) |
| 460:<br>L379R,<br>A708K,<br>P793_,<br>T620P,<br>E385P,<br>Q252K | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHKKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSPEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKPLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 104) |
| 278 | QEIKRINKIRRRLVKDSNIKKAGKTGPMKTLLVRVMTPDLRERLENLRKKPENI<br>PQPISNTSRANLNKLLTDYTEMKKAILHVYWEEFQKDPVGLMSRVAQPAPKNID<br>QRKLIPVKDGNERLTSSGFACSQCCQPLYVYKLEQVNDKGKPHTNYFGRCNVSE<br>HERLILLSPHKPEANDELVTYSLGKFGQRALDFYSIHVTRESNHPVKPLEQIGG<br>NSCASGPVGKALSDACMGAVASFLTKYQDIILEHQKVIKKNEKRLANLKDIASA<br>NGLAFPKITLPPQPHTKEGIEAYNNVVAQIVIWVNLNLWQKLKIGRDEAKPLQR<br>LKGFPSFPLVERQANEVDWWDMVCNVKKLINEKKEDGKVFWQNLAGYKRQEALR<br>PYLSSEEDRKKGKKFARYQFGDLLLHLEKKHGEDWGKVYDEAWERIDKKVEGLS |

TABLE 4-continued

CasX Variant Sequences

| Description* | Amino Acid Sequence |
|---|---|
| | KHIKLEEERRSEDAQSKAALTDWLRAKASFVIEGLKEADKEFCRCELKLQKWY GDLRGKPFAIEAENSILDISGFSKQYNCAFIWQKDGVKKLNLYLIINYFKGGKL RFKKIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVLDSSN IKPMNLIGIDRGENIPAVIALTDPEGCPLSRFKDSLGNPTHILRIGESYKEKQR TIQAKKEVEQRRAGGYSRKYASKAKNLADDMVRNTARDLLYYAVTQDAMLIFEN LSRGFGRQGKRTFMAERQYTRMEDWLTAKLAYEGLSKTYLSKTLAQYTSKTCSN CGFTITSADYDRVLEKLKKTATGWMTTINGKELKVEGQITYYNRYKRQNVVKDL SVELDRLSEESVNNDISSWTKGRSGEALSLLKKRFSHRPVQEKFVCLNCGFETH ADEQAALNIARSWLFLRSQEYKKYQTNKTTGNTDKRAFVETWQSFYRKKLKEVW KPAV (SEQ ID NO: 105) |
| 279 | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 106) |
| 280 | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 107) |
| 285 | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 108) |
| 286 | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG |

TABLE 4-continued

CasX Variant Sequences

| Description* | Amino Acid Sequence |
| --- | --- |
| | GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 109) |
| 287 | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 110) |
| 288 | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTMSSGFACSQCCQPLYVYKLEQVNDKGKPHTNYFGRCNV<br>SEHERLILLSPHKPEANDELVTYSLGKFGQRALDFYSIHVTRESNHPVKPLEQI<br>GGNSCASGPVGKALSDACMGAVASFLTKYQDIILEHQKVIKKNEKRLANLKDIA<br>SANGLAFPKITLPPQPHTKEGIEAYNNVVAQIVIWVNLNLWQKLKIGRDEAKPL<br>QRLKGFPSFPLVERQANEVDWWDMVCNVKKLINEKKEDGKVFWQNLAGYKRQEA<br>LRPYLSSEEDRKKGKKFARYQFGDLLLHLEKKHGEDWGKVYDEAWERIDKKVEG<br>LSKHIKLEEERRSEDAQSKAALTDWLRAKASFVIEGLKEADKDEFCRCELKLQK<br>WYGDLRGKPFAIEAENSILDISGFSKQYNCAFIWQKDGVKKLNLYLIINYFKGG<br>KLRFKKIKPEAFEANRFYTVINKKSGEIVPMEVNFNFDDPNLIILPLAFGKRQG<br>REFIWNDLLSLETGSLKLANGRVIEKTLYNRRTRQDEPALFVALTFERREVLDS<br>SNIKPMNLIGIDRGENIPAVIALTDPEGCPLSRFKDSLGNPTHILRIGESYKEK<br>QRTIQAKKEVEQRRAGGYSRKYASKAKNLADDMVRNTARDLLYYAVTQDAMLIF<br>ENLSRGFGRQGKRTFMAERQYTRMEDWLTAKLAYEGLSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 111) |
| 290 | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 112) |

TABLE 4-continued

CasX Variant Sequences

| Description* | Amino Acid Sequence |
|---|---|
| 291 | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 113) |
| 293 | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 114) |
| 300 | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 115) |
| 492 | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD |

TABLE 4-continued

CasX Variant Sequences

| Description* | Amino Acid Sequence |
|---|---|
| | LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 116) |
| 493 | MQEIKRINKIRRRLVKDSNIKKAGKTGPMKTLLVRVMTPDLRERLENLRKKPEN IPQPISNTSRANLNKLLTDYTEMKKAILHVYWEEFQKDPVGLMSRVAQPAPKNI DQRKLIPVKDGNERLTSSGFACSQCCQPLYVYKLEQVNDKGKPHTNYFGRCNVS EHERLILLSPHKPEANDELVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 117) |
| 387:<br>NTSB swap<br>from SEQ ID<br>NO: 1 | QEIKRINKIRRRLVKDSNIKKAGKTGPMKTLLVRVMTPDLRERLENLRKKPENI PQPISNTSRANLNKLLTDYTEMKKAILHVYWEEFQKDPVGLMSRVAQPASKKID QNKLKPEMDEKGNLTTAGFACSQCGQPLFVYKLEQVSEKGKAYTNYFGRCNVAE HEKLILLAQLKPEKDSDEAVTYSLGKFGQRALDFYSIHVTRESNHPVKPLEQIG GNSCASGPVGKALSDACMGAVASFLTKYQDIILEHQKVIKKNEKRLANLKDIAS ANGLAFPKITLPPQPHTKEGIEAYNNVVAQIVIWVNLNLWQKLKIGRDEAKPLQ RLKGFPSFPLVERQANEVDWWDMVCNVKKLINEKKEDGKVFWQNLAGYKRQEAL RPYLSSEEDRKKGKKFARYQFGDLLLHLEKKHGEDWGKVYDEAWERIDKKVEGL SKHIKLEEERRSEDAQSKAALTDWLRAKASFVIEGLKEADKDEFCRCELKLQKW YGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSS NIKPMNLIGIDRGENIPAVIALTDPEGCPLSRFKDSLGNPTHILRIGESYKEKQ RTIQAKKEVEQRRAGGYSRKYASKAKNLADDMVRNTARDLLYYAVTQDAMLIFE NLSRGFGRQGKRTFMAERQYTRMEDWLTAKLAYEGLSKTYLSKTLAQYTSKTCS NCGFTITSADYDRVLEKLKKTATGWMTTINGKELKVEGQITYYNRYKRQNVVKD LSVELDRLSEESVNNDISSWTKGRSGEALSLLKKRFSHRPVQEKFVCLNCGFET HADEQAALNIARSWLFLRSQEYKKYQTNKTTGNTDKRAFVETWQSFYRKKLKEV WKPAV (SEQ ID NO: 118) |
| 395:<br>Helical 1B<br>swap from<br>SEQ ID NO:<br>1 | QEIKRINKIRRRLVKDSNIKKAGKTGPMKTLLVRVMTPDLRERLENLRKKPENI PQPISNTSRANLNKLLTDYTEMKKAILHVYWEEFQKDPVGLMSRVAQPAPKNID QRKLIPVKDGNERLTSSGFACSQCCQPLYVYKLEQVNDKGKPHTNYFGRCNVSE HERLILLSPHKPEANDELVTYSLGKFGQRALDFYSIHVTKESTHPVKPLAQIAG NRYASGPVGKALSDACMGTIASFLSKYQDIIIEHQKVVKGNQKRLESLRELAGK ENLEYPSVTLPPQPHTKEGVDAYNEVIARVRMWVNLNLWQKLKLSRDDAKPLLR LKGFPSFPLVERQANEVDWWDMVCNVKKLINEKKEDGKVFWQNLAGYKRQEALR PYLSSEEDRKKGKKFARYQFGDLLLHLEKKHGEDWGKVYDEAWERIDKKVEGLS KHIKLEEERRSEDAQSKAALTDWLRAKASFVIEGLKEADKDEFCRCELKLQKWY GDLRGKPFAIEAENSILDISGFSKQYNCAFIWQKDGVKKLNLYLIINYFKGGKL RFKKIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVLDSSN IKPMNLIGIDRGENIPAVIALTDPEGCPLSRFKDSLGNPTHILRIGESYKEKQR TIQAKKEVEQRRAGGYSRKYASKAKNLADDMVRNTARDLLYYAVTQDAMLIFEN LSRGFGRQGKRTFMAERQYTRMEDWLTAKLAYEGLSKTYLSKTLAQYTSKTCSN CGFTITSADYDRVLEKLKKTATGWMTTINGKELKVEGQITYYNRYKRQNVVKDL SVELDRLSEESVNNDISSWTKGRSGEALSLLKKRFSHRPVQEKFVCLNCGFETH ADEQAALNIARSWLFLRSQEYKKYQTNKTTGNTDKRAFVETWQSFYRKKLKEVW KPAV (SEQ ID NO: 119) |
| 485:<br>Helical 1B<br>swap from<br>SEQ ID NO:<br>1 | QEIKRINKIRRRLVKDSNTKKAGKTGPMKTLLVRVMTPDLRERLENLRKKPENI PQPISNTSRANLNKLLTDYTEMKKAILHVYWEEFQKDPVGLMSRVAQPAPKNID QRKLIPVKDGNERLTSSGFACSQCCQPLYVYKLEQVNDKGKPHTNYFGRCNVSE HERLILLSPHKPEANDELVTYSLGKFGQRALDFYSIHVTKESTHPVKPLAQIAG NRYASGPVGKALSDACMGTIASFLSKYQDIIIEHQKVVKGNQKRLESLRELAGK ENLEYPSVTLPPQPHTKEGVDAYNEVIARVRMWVNLNLWQKLKLSRDDAKPLLR LKGFPSFPLVERQANEVDWWDMVCNVKKLINEKKEDGKVFWQNLAGYKRQEALR PYLSSEEDRKKGKKFARYQLGDLLLHLEKKHGEDWGKVYDEAWERIDKKVEGLS KHIKLEEERRSEDAQSKAALTDWLRAKASFVIEGLKEADKDEFCRCELKLQKWY GDLRGKPFAIEAENSILDISGFSKQYNCAFIWQKDGVKKLNLYLIINYFKGGKL RFKKIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVLDSSN |

TABLE 4-continued

CasX Variant Sequences

| Description* | Amino Acid Sequence |
|---|---|
| | IKPMNLIGVDRGENIPAVIALTDPEGCPLSRFKDSLGNPTHILRIGESYKEKQR
TIQAKKEVEQRRAGGYSRKYASKAKNLADDMVRNTARDLLYYAVTQDAMLIFEN
LSRGFGRQGKRTFMAERQYTRMEDWLTAKLAYEGLSKTYLSKTLAQYTSKTCSN
CGFTITSADYDRVLEKLKKTATGWMTTINGKELKVEGQITYYNRRKQNVVKDL
SVELDRLSEESVNNDISSWTKGRSGEALSLLKKRFSHRPVQEKFVCLNCGFETH
ADEQAALNIARSWLFLRSQEYKKYQTNKTTGNTDKRAFVETWQSFYRKKLKEVW
KPAV (SEQ ID NO: 120) |
| 486:
Helical 1B
swap from
SEQ ID NO:
1 | QEIKRINKIRRRLVKDSNTKKAGKTGPMKTLLVRVMTPDLRERLENLRKKPENI
PQPISNTSRANLNKLLTDYTEMKKAILHVYWEEFQKDPVGLMSRVAQPAPKNID
QRKLIPVKDGNERLTSSGFACSQCCQPLYVYKLEQVNDKGKPHTNYFGRCNVSE
HERLILLSPHKPEANDELVTYSLGKFGQRALDFYSIHVTKESTHPVKPLAQIAG
NRYASGPVGKALSDACMGTIASFLSKYQDIIIEHQKVVKGNQKRLESLRELAGK
ENLEYPSVTLPPQPHTKEGVDAYNEVIARVRMWVNLNLWQKLKLSRDDAKPLLR
LKGFPSFPLVERQANEVDWWDMVCNVKKLINEKKEDGKVFWQNLAGYKRQEALR
PYLSSEEDRKKGKKFARYQLGDLLKHLEKKHGEDWGKVYDEAWERIDKKVEGLS
KHIKLEEERRSEDAQSKAALTDWLRAKASFVIEGLKEADKDEFCRCELKLQKWY
GDLRGKPFAIEAENSILDISGFSKQYNCAFIWQKDGVKKLNLYLIINYFKGGKL
RFKKIKPEAFEANRFYTVINKKSGEIVPMEVNFNFDDPNLIILPLAFGKRQGRE
FIWNDLLSLETGSLKLANGRVIEKTLYNRRTRQDEPALFVALTFERREVLDSSN
IKPMNLIGVDRGENIPAVIALTDPEGCPLSRFKDSLGNPTHILRIGESYKEKQR
TIQAKKEVEQRRAGGYSRKYASKAKNLADDMVRNTARDLLYYAVTQDAMLIFEN
LSRGFGRQGKRTFMAERQYTRMEDWLTAKLAYEGLSKTYLSKTLAQYTSKTCSN
CGFTITSADYDRVLEKLKKTATGWMTTINGKELKVEGQITYYNRRKQNVVKDL
SVELDRLSEESVNNDISSWTKGRSGEALSLLKKRFSHRPVQEKFVCLNCGFETH
ADEQAALNIARSWLFLRSQEYKKYQTNKTTGNTDKRAFVETWQSFYRKKLKEVW
KPAV (SEQ ID NO: 121) |
| 487:
Helical 1B
swap from
SEQ ID
1 | QEIKRINKIRRRLVKDSNTKKAGKTGPMKTLLVRVMTPDLRERLENLRKKPENI
PQPISNTSRANLNKLLTDYTEMKKAILHVYWEEFQKDPVGLMSRVAQPAPKNID
QRKLIPVKDGNERLTSSGFACSQCCQPLYVYKLEQVNDKGKPHTNYFGRCNVSE
HERLILLSPHKPEANDELVTYSLGKFGQRALDFYSIHVTKESTHPVKPLAQIAG
NRYASGPVGKALSDACMGTIASFLSKYQDIIIEHQKVVKGNQKRLESLRELAGK
ENLEYPSVTLPPQPHTKEGVDAYNEVIARVRMWVNLNLWQKLKLSRDDAKPLLR
LKGFPSFPLVERQANEVDWWDMVCNVKKLINEKKEDGKVFWQNLAGYKRQEALR
PYLSSEEDRKKGKKFARYQLGDLLLHLEKKHGEDWGKVYDEAWERIDKKVEGLS
KHIKLEEERRSEDAQSKAALTDWLRAKASFVIEGLKEADKDEFCRCELKLQKWY
GDLRGKPFAIEAENSILDISGFSKQYNCAFIWQKDGVKKLNLYLIINYFKGGKL
RFKKIKPEAFEANRFYTVINKKSGEIVPMEVNFNFDDPNLIILPLAFGKRQGRE
FIWNDLLSLETGSLKLANGRVIEKTLYNRRTRQDEPALFVALTFERREVLDSSN
IKPMNLIGVDRGENIPAVIALTDPEGCPLSRFKDSLGNPTHILRIGESYKEKQR
TIQAKKEVEQRRAGGYSRKYASKAKNLADDMVRNTARDLLYYAVTQDAMLIFEN
LSRGFGRQGKRTFMAERQYTRMEDWLTAKLAYEGLSKTYLSKTLAQYTSKTCSN
CGFTITSADYDRVLEKLKKTATGWMTTINGKELKVEGQITYYNRYKRQNVVKDL
SVELDRLSEESVNNDISSWTKGRSGEALSLLKKRFSHRPVQEKFVCLNCGFETH
ADEQAALNIARSWLFLRSQEYKKYQTNKTTGNTDKRAFVETWQSFYRKKLKEVW
KPAV (SEQ ID NO: 122) |
| 488:
NTSB and
Helical 1B
swap from
SEQ ID NO:
1 | QEIKRINKIRRRLVKDSNTKKAGKTGPMKTLLVRVMTPDLRERLENLRKKPENI
PQPISNTSRANLNKLLTDYTEMKKAILHVYWEEFQKDPVGLMSRVAQPAPKNID
QNKLKPEMDEKGNLTTAGFACSQCGQPLFVYKLEQVSEKGKAYTNYFGRCNVAE
HEKLILLAQLKPEKDSDEAVTYSLGKFGQRALDFYSIHVTKESTHPVKPLAQIA
GNRYASGPVGKALSDACMGTIASFLSKYQDIIIEHQKVVKGNQKRLESLRELAG
KENLEYPSVTLPPQPHTKEGVDAYNEVIARVRMWVNLNLWQKLKLSRDDAKPLL
RLKGFPSFPLVERQANEVDWWDMVCNVKKLINEKKEDGKVFWQNLAGYKRQEAL
RPYLSSEEDRKKGKKFARYQFGDLLLHLEKKHGEDWGKVYDEAWERIDKKVEGL
SKHIKLEEERRSEDAQSKAALTDWLRAKASFVIEGLKEADKDEFCRCELKLQKW
YGDLRGKPFAIEAENSILDISGFSKQYNCAFIWQKDGVKKLNLYLIINYFKGGK
LRFKKIKPEAFEANRFYTVINKKSGEIVPMEVNFNFDDPNLIILPLAFGKRQGR
EFIWNDLLSLETGSLKLANGRVIEKTLYNRRTRQDEPALFVALTFERREVLDSS
NIKPMNLIGIDRGENIPAVIALTDPEGCPLSRFKDSLGNPTHILRIGESYKEKQ
RTIQAKKEVEQRRAGGYSRKYASKAKNLADDMVRNTARDLLYYAVTQDAMLIFE
NLSRGFGRQGKRTFMAERQYTRMEDWLTAKLAYEGLSKTYLSKTLAQYTSKTCS
NCGFTITSADYDRVLEKLKKTATGWMTTINGKELKVEGQITYYNRYKRQNVVKD
LSVELDRLSEESVNNDISSWTKGRSGEALSLLKKRFSHRPVQEKFVCLNCGFET
HADEQAALNIARSWLFLRSQEYKKYQTNKTTGNTDKRAFVETWQSFYRKKLKEV
WKPAV (SEQ ID NO: 123) |
| 489:
NTSB and
Helical 1B
swap from
SEQ ID NO:
1 | QEIKRINKIRRRLVKDSNTKKAGKTGPMKTLLVRVMTPDLRERLENLRKKPENI
PQPISNTSRANLNKLLTDYTEMKKAILHVYWEEFQKDPVGLMSRVAQPASKKID
QNKLKPEMDEKGNLTTAGFACSQCGQPLFVYKLEQVSEKGKAYTNYFGRCNVAE
HEKLILLAQLKPEKDSDEAVTYSLGKFGQRALDFYSIHVTKESTHPVKPLAQIA
GNRYASGPVGKALSDACMGTIASFLSKYQDIIIEHQKVVKGNQKRLESLRELAG
KENLEYPSVTLPPQPHTKEGVDAYNEVIARVRMWVNLNLWQKLKLSRDDAKPLL
RLKGFPSFPLVERQANEVDWWDMVCNVKKLINEKKEDGKVFWQNLAGYKRQEAL
RPYLSSEEDRKKGKKFARYQLGDLLLHLEKKHGEDWGKVYDEAWERIDKKVEGL |

TABLE 4-continued

CasX Variant Sequences

| Description* | Amino Acid Sequence |
|---|---|
| | SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 124) |
| 490:<br>NTSB and<br>Helical 1B<br>swap from<br>SEQ ID NO:<br>1 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNLWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLKHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRRKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 125) |
| 491:<br>NTSB and<br>Helical 1B<br>swap from<br>SEQ ID NO:<br>1 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTKESTHPVKPLAQIA<br>GNRYASGPVGKALSDACMGTIASFLSKYQDIIIEHQKVVKGNQKRLESLRELAG<br>KENLEYPSVTLPPQPHTKEGVDAYNEVIARVRMWVNLNLWQKLKLSRDDAKPLL<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 126) |
| 494:<br>NTSB swap<br>from SEQ ID<br>NO: 1 | QEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPASKKID<br>QNKLKPEMDEKGNLTTAGFACSQCGQPLFVYKLEQVSEKGKAYTNYFGRCNVAE<br>HEKLILLAQLKPEKDSDEAVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQLGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGVDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLRSQEYKKYQTNKTTGNTDKRAFVETWQSFYRKKLKEV<br>WKPAV (SEQ ID NO: 127) |
| 328: S867G | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG |

TABLE 4-continued

CasX Variant Sequences

| Description* | Amino Acid Sequence |
|---|---|
| | GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>LPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAAKEVEQRRAGGYSRKYASKAKNLADDMVRNTARDLLYYAVTQDAMLIFE<br>NLSRGFGRQGKRTFMAERQYTRMEDWLTAKLAYEGLPSKTYLSKTLAQYTSKTC<br>SNCGFTITSADYDRVLEKLKKTATGWMTTINGKELKVEGQITYYNRYKRQNVVK<br>DLGVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 128) |
| 388:<br>L379R + A708K +<br>+ [P793] +<br>X1<br>Helical2<br>swap | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPVVERRENEVDWWNTINEVKKLIDAKRDMGRVFWSGVTAEKRNTIL<br>EGYNYLPNENDHKKREGSLENPKKPAKRQFGDLLLYLEKKYAGDWGKVFDEAWE<br>RIDKKIAGLTSHIEREEARNAEDAQSKAVLTDWLRAKASFVLERLKEMDEKEFY<br>ACEIQLQKWYGDLRGNPPFAVEAENSILDISGFSKQYNCAFIWQKDGVKKLNYL<br>IINYFKGGKLRFKKIKPEAFEANRFYTVINKKSGEIVPMEVNFNFDDPNLIILP<br>LAFGKRQGREFIWNDLLSLETGSLKLANGRVIEKTLYNRRTRQDEPALFVALTF<br>ERREVLDSSNIKPMNLIGIDRGENIPAVIALTDPEGCPLSRFKDSLGNPTHILR<br>IGESYKEKQRTIQAKKEVEQRRAGGYSRKYASKAKNLADDMVRNTARDLLYYAV<br>TQDAMLIFENLSRGFGRQGKRTFMAERQYTRMEDWLTAKLAYEGLSKTYLSKTL<br>AQYTSKTCSNCGFTITSADYDRVLEKLKKTATGWMTTINGKELKVEGQITYYNR<br>YKRQNVVKDLSVELDRLSEESVNNDISSWTKGRSGEALSLLKKRFSHRPVQEKF<br>VCLNCGFETHADEQAALNIARSWLFLRSQEYKKYQTNKTTGNTDKRAFVETWQS<br>FYRKKLKEVWKPAV (SEQ ID NO: 129) |
| 389:<br>L379R + A708K +<br>+ [P793] +<br>X1 RuvC1<br>swap | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPVNLIGVDRGENIPAVIALTDPEGCPLPEFKDSSGGPTDILRIGEGYKEKQ<br>RAIQAAKEVEQRRAGGYSRKFASKSRNLADDMVRNSARDLFYHAVTHDAVLVFE<br>NLSRGFGRQGKRTFMTERQYTKMEDWLTAKLAYEGLTSKTYLSKTLAQYTSKTC<br>SNCGFTITSADYDRVLEKLKKTATGWMTTINGKELKVEGQITYYNRYKRQNVVK<br>DLSVELDRLSEESVNNDISSWTKGRSGEALSLLKKRFSHRPVQEKFVCLNCGFE<br>THADEQAALNIARSWLFLRSQEYKKYQTNKTTGNTDKRAFVETWQSFYRKKLKE<br>VWKPAV (SEQ ID NO: 130) |
| 390:<br>L379R + A708K +<br>[P793] +<br>X1 RuvC2<br>swap | MQEIKRINKIRRRLVKDSNIKKAGKTGPMKTLLVRVMTPDLRERLENLRKKPEN<br>IPQPISNTSRANLNKLLTDYTEMKKAILHVYWEEFQKDPVGLMSRVAQPAPKNI<br>DQRKLIPVKDGNERLTSSGFACSQCCQPLYVYKLEQVNDKGKPHTNYFGRCNVS<br>EHERLILLSPHKPEANDELVTYSLGKFGQRALDFYSIHVTRESNHPVKPLEQIG<br>GNSCASGPVGKALSDACMGAVASFLTKYQDIILEHQKVIKKNEKRLANLKDIAS<br>ANGLAFPKITLPPQPHTKEGIEAYNNVVAQIVIWVNLNLWQKLKIGRDEAKPLQ<br>RLKGFPSFPLVERQANEVDWWDMVCNVKKLINEKKEDGKVFWQNLAGYKRQEAL<br>RPYLSSEEDRKKGKKFARYQFGDLLLHLEKKHGEDWGKVYDEAWERIDKKVEGL<br>SKHIKLEEERRSEDAQSKAALTDWLRAKASFVIEGLKEADKDEFCRCELKLQKW<br>YGDLRGKPFAIEAENSILDISGFSKQYNCAFIWQKDGVKKLNLYLIINYFKGGK<br>LRFKKIKPEAFEANRFYTVINKKSGEIVPMEVNFNFDDPNLIILPLAFGKRQGR<br>EFIWNDLLSLETGSLKLANGRVIEKTLYNRRTRQDEPALFVALTFERREVLDSS<br>NIKPMNLIGIDRGENIPAVIALTDPEGCPLSRFKDSLGNPTHILRIGESYKEKQ<br>RTIQAKKEVEQRRAGGYSRKYASKAKNLADDMVRNTARDLLYYAVTQDAMLIFE<br>NLSRGFGRQGKRTFMAERQYTRMEDWLTAKLAYEGLSKTYLSKTLAQYTSKTCS<br>NCGFTITSADYDRVLEKLKKTATGWMTTINGKELKVEGQITYYNRYKRQNVVKD<br>LSVELDRLSEESVNNDISSWTKGRSGEALSLLKKRFSHRPVQEKFVCLNCGFET<br>HADEQAALNIARSWLFLNSNSTEFKSYKSGKQPFVGAWQAFYKRRLKEVWKPNA<br>(SEQ ID NO: 131) |

In some embodiments, the CasX variant protein comprises a sequence selected from the group consisting of SEQ ID NOs: 36-131, 208, 210, 212, 214, 216-229, 240, 242, 244, 246, 248, 250, 252, 254, 256 and 258, or a sequence having at least about 50%, at least about 60%, at least about 70%, at least about 80%, at least about 90%, or at least about 95%, or at least about 95%, or at least about 96%, or at least about 97%, or at least about 98%, or at least about 99% sequence identity thereto. In some embodiments, the CasX variant protein comprises a sequence selected from the group consisting of SEQ ID NOs: 36-131, 208, 210, 212, 214, 216-229, 240, 242, 244, 246, 248, 250, 252, 254, 256 and 258. In some embodiments, the CasX variant protein comprises a sequence selected from the group consisting of SEQ ID NOs: 36-131, or a sequence having at least about 50%, at least about 60%, at least about 70%, at least about 80%, at least about 90%, or at least about 95%, or at least about 95%, or at least about 96%, or at least about 97%, or at least about 98%, or at least about 99% sequence identity thereto. In some embodiments, the CasX variant protein comprises a sequence selected from the group consisting of SEQ ID NOs: 36-131.

In some embodiments, the CasX variant protein has one or more improved characteristic of the CasX protein when compared to a reference CasX protein, for example a reference protein of SEQ ID NO: 1, SEQ ID NO: 2 or SEQ ID NO: 3. In some embodiments, the at least one improved characteristic of the CasX variant is at least about 1.1 to about 100,000-fold improved relative to the reference protein. In some embodiments, the at least one improved characteristic of the CasX variant is at least about 1.1 to about 10,000-fold improved, at least about 1.1 to about 1,000-fold improved, at least about 1.1 to about 500-fold improved, at least about 1.1 to about 400-fold improved, at least about 1.1 to about 300-fold improved, at least about 1.1 to about 200-fold improved, at least about 1.1 to about 100-fold improved, at least about 1.1 to about 50-fold improved, at least about 1.1 to about 40-fold improved, at least about 1.1 to about 30-fold improved, at least about 1.1 to about 20-fold improved, at least about 1.1 to about 10-fold improved, at least about 1.1 to about 9-fold improved, at least about 1.1 to about 8-fold improved, at least about 1.1 to about 7-fold improved, at least about 1.1 to about 6-fold improved, at least about 1.1 to about 5-fold improved, at least about 1.1 to about 4-fold improved, at least about 1.1 to about 3-fold improved, at least about 1.1 to about 2-fold improved, at least about 1.1 to about 1.5-fold improved, at least about 1.5 to about 3-fold improved, at least about 1.5 to about 4-fold improved, at least about 1.5 to about 5-fold improved, at least about 1.5 to about 10-fold improved, at least about 5 to about 10-fold improved, at least about 10 to about 20-fold improved, at least 10 to about 30-fold improved, at least 10 to about 50-fold improved or at least 10 to about 100-fold improved than the reference CasX protein. In some embodiments, the at least one improved characteristic of the CasX variant is at least about 10 to about 1000-fold improved relative to the reference CasX protein.

In some embodiments, the one or more improved characteristics of the CasX variant protein is at least about 5, at least about 10, at least about 20, at least about 30, at least about 40, at least about 50, at least about 60, at least about 70, at least about 80, at least about 90, at least about 100, at least about 250, at least about 500, or at least about 1000, at least about 5,000, at least about 10,000, or at least about 100,000-fold improved relative to a reference CasX protein. In some embodiments, an improved characteristics of the CasX variant protein is at least about 1.1, at least about 1.2, at least about 1.3, at least about 1.4, at least about 1.5, at least about 1.6, at least about 1.7, at least about 1.8, at least about 1.9, at least about 2, at least about 2.1, at least about 2.2, at least about 2.3, at least about 2.4, at least about 2.5, at least about 2.6, at least about 2.7, at least about 2.8, at least about 2.9, at least about 3, at least about 3.5, at least about 4, at least about 4.5, at least about 5, at least about 5.5, at least about 6, at least about 6.5, at least about 7.0, at least about 7.5, at least about 8, at least about 8.5, at least about 9, at least about 9.5, at least about 10, at least about 11, at least about 12, at least about 13, at least about 14, at least about 15, at least about 20, at least about 30, at least about 40, at least about 50, at least about 60, at least about 70, at least about 80, at least about 90 at least about 100, at least about 500, at least about 1,000, at least about 10,000, or at least about 100,000-fold improved relative to a reference CasX protein. In other cases, the one or more improved characteristics of the CasX variant is about 1.1 to 100,00-fold, about 1.1 to 10,00-fold, about 1.1 to 1,000-fold, about 1.1 to 500-fold, about 1.1 to 100-fold, about 1.1 to 50-fold, about 1.1 to 20-fold, about 10 to 100,00-fold, about 10 to 10,00-fold, about 10 to 1,000-fold, about 10 to 500-fold, about 10 to 100-fold, about 10 to 50-fold, about 10 to 20-fold, about 2 to 70-fold, about 2 to 50-fold, about 2 to 30-fold, about 2 to 20-fold, about 2 to 10-fold, about 5 to 50-fold, about 5 to 30-fold, about 5 to 10-fold, about 100 to 100,00-fold, about 100 to 10,00-fold, about 100 to 1,000-fold, about 100 to 500-fold, about 500 to 100,00-fold, about 500 to 10,00-fold, about 500 to 1,000-fold, about 500 to 750-fold, about 1,000 to 100,00-fold, about 10,000 to 100,00-fold, about 20 to 500-fold, about 20 to 250-fold, about 20 to 200-fold, about 20 to 100-fold, about 20 to 50-fold, about 50 to 10,000-fold, about 50 to 1,000-fold, about 50 to 500-fold, about 50 to 200-fold, or about 50 to 100-fold, improved relative to the reference CasX of SEQ ID NO: 1, SEQ ID NO: 2 or SEQ ID NO: 3. In other cases, the one or more improved characteristics of the CasX variant is about 1.1-fold, 1.2-fold, 1.3-fold, 1.4-fold, 1.5-fold, 1.6-fold, 1.7-fold, 1.8-fold, 1.9-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 25-fold, 30-fold, 40-fold, 45-fold, 50-fold, 55-fold, 60-fold, 70-fold, 80-fold, 90-fold, 100-fold, 110-fold, 120-fold, 130-fold, 140-fold, 150-fold, 160-fold, 170-fold, 180-fold, 190-fold, 200-fold, 210-fold, 220-fold, 230-fold, 240-fold, 250-fold, 260-fold, 270-fold, 280-fold, 290-fold, 300-fold, 310-fold, 320-fold, 330-fold, 340-fold, 350-fold, 360-fold, 370-fold, 380-fold, 390-fold, 400-fold, 425-fold, 450-fold, 475-fold, or 500-fold or more improved relative to the reference CasX of SEQ ID NO: 1, SEQ ID NO: 2 or SEQ ID NO: 3. Exemplary characteristics that can be improved in CasX variant proteins relative to the same characteristics in reference CasX proteins include, but are not limited to, improved folding of the variant, improved binding affinity to the gNA, improved binding affinity to the target DNA, improved ability to utilize a greater spectrum of PAM sequences in the editing and/or binding of target DNA, improved unwinding of the target DNA, increased editing activity, improved editing efficiency, improved editing specificity, increased activity of the nuclease, increased target strand loading for double strand cleavage, decreased target strand loading for single strand nicking, decreased off-target cleavage, improved binding of the non-target strand of DNA, improved protein stability, improved CasX:gNA RNA complex stability, improved protein solubility, improved CasX:gNA RNP complex solubility, improved protein yield, improved protein expression, and improved fusion characteristics. In some embodiments, the variant comprises at least one improved characteristic. In other embodiments, the variant comprises at least two improved characteristics. In further embodiments, the variant comprises at least three improved characteristics. In some embodiments, the variant comprises at least four improved characteristics. In still further embodiments, the variant comprises at least five, at least six, at least seven, at least eight, at least nine, at least ten, at least eleven, at least twelve, at least thirteen, or more improved characteristics.

Exemplary improved characteristic include, as one example, improved editing efficiency. In some embodiments, an RNP comprising the CasX protein and a gNA of the disclosure, at a concentration of 20 pM or less, is capable of cleaving a double stranded DNA target with an efficiency of at least 80%. In some embodiments, the RNP at a concentration of 20 pM or less, is capable of cleaving a double stranded DNA target with an efficiency of at least 40%, at least 50%, at least 60%, at least 70%, at least 80%, at least 85%, at least 90% or at least 95%. In some embodiments, the RNP at a concentration of 50 pM or less, 40 pM or less, 30 pM or less, 20 pM or less, 10 pM or less, or 5 pM or less, is capable of cleaving a double stranded DNA target with an efficiency of at least 40%, at least 50%, at least 60%, at least 70%, at least 80%, at least 85%, at least 90% or at least 95%.

Further improved characteristics are described in more detail below.

j. Protein Stability

In some embodiments, the disclosure provides a CasX variant protein with improved stability relative to a reference CasX protein. In some embodiments, improved stability of the CasX variant protein results in expression of a higher steady state of protein, which improves editing efficiency. In some embodiments, improved stability of the CasX variant protein results in a larger fraction of CasX protein that remains folded in a functional conformation and improves editing efficiency or improves purifiability for manufacturing purposes. As used herein, a "functional conformation" refers to a CasX protein that is in a conformation where the protein is capable of binding a gNA and target DNA. In embodiments wherein the CasX variant does not carry one or more mutations rendering it catalytically dead, the CasX variant is capable of cleaving, nicking, or otherwise modifying the target DNA. For example, a functional CasX variant can, in some embodiments, be used for gene-editing, and a functional conformation refers to an "editing-competent" conformation. In some exemplary embodiments, including those embodiments where the CasX variant protein results in a larger fraction of CasX protein that remains folded in a functional conformation, a lower concentration of CasX variant is needed for applications such as gene editing compared to a reference CasX protein. Thus, in some embodiments, the CasX variant with improved stability has improved efficiency compared to a reference CasX in one or more gene editing contexts.

In some embodiments, the disclosure provides a CasX variant protein having improved thermostability relative to a reference CasX protein. In some embodiments, the CasX variant protein has improved thermostability of the CasX variant protein at a particular temperature range. Without wishing to be bound by any theory, some reference CasX proteins natively function in organisms with niches in groundwater and sediment; thus, some reference CasX proteins may have evolved to exhibit optimal function at lower or higher temperatures that may be desirable for certain applications. For example, one application of CasX variant proteins is gene editing of mammalian cells, which is typically carried out at about 37° C. In some embodiments, a CasX variant protein as described herein has improved thermostability compared to a reference CasX protein at a temperature of at least 16° C., at least 18° C., at least 20° C., at least 22° C., at least 24° C., at least 26° C., at least 28° C., at least 30° C., at least 32° C., at least 34° C., at least 35° C., at least 36° C., at least 37° C., at least 38° C., at least 39° C., at least 40° C., at least 41° C., at least 42° C., at least 44° C., at least 46° C., at least 48° C., at least 50° C., at least 52° C., or greater. In some embodiments, a CasX variant protein has improved thermostability and functionality compared to a reference CasX protein that results in improved gene editing functionality, such as mammalian gene editing applications, which may include human gene editing applications.

In some embodiments, the disclosure provides a CasX variant protein having improved stability of the CasX variant protein:gNA complex relative to the reference CasX protein:gNA complex such that the RNP remains in a functional form. Stability improvements can include increased thermostability, resistance to proteolytic degradation, enhanced pharmacokinetic properties, stability across a range of pH conditions, salt conditions, and tonicity. Improved stability of the complex may, in some embodiments, lead to improved editing efficiency.

In some embodiments, the disclosure provides a CasX variant protein having improved thermostability of the CasX variant protein:gNA complex relative to the reference CasX protein:gNA complex. In some embodiments, a CasX variant protein has improved thermostability relative to a reference CasX protein. In some embodiments, the CasX variant protein:gNA complex has improved thermostability relative to a complex comprising a reference CasX protein at temperatures of at least 16° C., at least 18° C., at least 20° C., at least 22° C., at least 24° C., at least 26° C., at least 28° C., at least 30° C., at least 32° C., at least 34° C., at least 35° C., at least 36° C., at least 37° C., at least 38° C., at least 39° C., at least 40° C., at least 41° C., at least 42° C., at least 44° C., at least 46° C., at least 48° C., at least 50° C., at least 52° C., or greater. In some embodiments, a CasX variant protein has improved thermostability of the CasX variant protein:gNA complex compared to a reference CasX protein:gNA complex, which results in improved function for gene editing applications, such as mammalian gene editing applications, which may include human gene editing applications.

In some embodiments, the improved stability and/or thermostability of the CasX variant protein comprises faster folding kinetics of the CasX variant protein relative to a reference CasX protein, slower unfolding kinetics of the CasX variant protein relative to a reference CasX protein, a larger free energy release upon folding of the CasX variant protein relative to a reference CasX protein, a higher temperature at which 50% of the CasX variant protein is unfolded (Tm) relative to a reference CasX protein, or any combination thereof. These characteristics may be improved by a wide range of values; for example, at least 1.1, at least 1.5, at least 10, at least 50, at least 100, at least 500, at least 1,000, at least 5,000, or at least a 10,000-fold improved, as compared to a reference CasX protein. In some embodiments, improved thermostability of the CasX variant protein comprises a higher Tm of the CasX variant protein relative to a reference CasX protein. In some embodiments, the Tm of the CasX variant protein is between about 20° C. to about 30° C., between about 30° C. to about 40° C., between about 40° C. to about 50° C., between about 50° C. to about 60° C., between about 60° C. to about 70° C., between about 70°

C. to about 80° C., between about 80° C. to about 90° C. or between about 90° C. to about 100° C. Thermal stability is determined by measuring the "melting temperature" (Tm), which is defined as the temperature at which half of the molecules are denatured. Methods of measuring characteristics of protein stability such as Tm and the free energy of unfolding are known to persons of ordinary skill in the art, and can be measured using standard biochemical techniques in vitro. For example, Tm may be measured using Differential Scanning calorimetry, a thermo-analytical technique in which the difference in the amount of heat required to increase the temperature of a sample and a reference is measured as a function of temperature (Chen et al (2003) Pharm Res 20:1952-60; Ghirlando et al (1999) Immunol Lett 68:47-52). Alternatively, or in addition, CasX variant protein Tm may be measured using commercially available methods such as the ThermoFisher Protein Thermal Shift system. Alternatively, or in addition, circular dichroism may be used to measure the kinetics of folding and unfolding, as well as the Tm (Murray et al. (2002) J. Chromatogr Sci 40:343-9). Circular dichroism (CD) relies on the unequal absorption of left-handed and right-handed circularly polarized light by asymmetric molecules such as proteins. Certain structures of proteins, for example alpha-helices and beta-sheets, have characteristic CD spectra. Accordingly, in some embodiments, CD may be used to determine the secondary structure of a CasX variant protein.

In some embodiments, improved stability and/or thermostability of the CasX variant protein comprises improved folding kinetics of the CasX variant protein relative to a reference CasX protein. In some embodiments, folding kinetics of the CasX variant protein are improved relative to a reference CasX protein by at least about 5, at least about 10, at least about 50, at least about 100, at least about 500, at least about 1,000, at least about 2,000, at least about 3,000, at least about 4,000, at least about 5,000, or at least about a 10,000-fold improvement. In some embodiments, folding kinetics of the CasX variant protein are improved relative to a reference CasX protein by at least about 1 kJ/mol, at least about 5 kJ/mol, at least about 10 kJ/mol, at least about 20 kJ/mol, at least about 30 kJ/mol, at least about 40 kJ/mol, at least about 50 kJ/mol, at least about 60 kJ/mol, at least about 70 kJ/mol, at least about 80 kJ/mol, at least about 90 kJ/mol, at least about 100 kJ/mol, at least about 150 kJ/mol, at least about 200 kJ/mol, at least about 250 kJ/mol, at least about 300 kJ/mol, at least about 350 kJ/mol, at least about 400 kJ/mol, at least about 450 kJ/mol, or at least about 500 kJ/mol.

Exemplary amino acid changes that can increase the stability of a CasX variant protein relative to a reference CasX protein may include, but are not limited to, amino acid changes that increase the number of hydrogen bonds within the CasX variant protein, increase the number of disulfide bridges within the CasX variant protein, increase the number of salt bridges within the CasX variant protein, strengthen interactions between parts of the CasX variant protein, increase the buried hydrophobic surface area of the CasX variant protein, or any combinations thereof.

k. Protein Yield

In some embodiments, the disclosure provides a CasX variant protein having improved yield during expression and purification relative to a reference CasX protein. In some embodiments, the yield of CasX variant proteins purified from bacterial or eukaryotic host cells is improved relative to a reference CasX protein. In some embodiments, the bacterial host cells are *Escherichia coli* cells. In some embodiments, the eukaryotic cells are yeast, plant (e.g. tobacco), insect (e.g. *Spodoptera frugiperda* sf9 cells), mouse, rat, hamster, guinea pig, monkey, or human cells. In some embodiments, the eukaryotic host cells are mammalian cells, including, but not limited to HEK293 cells, BHK cells, NS0 cells, SP2/0 cells, YO myeloma cells, P3X63 mouse myeloma cells, PER cells, PER.C6 cells, hybridoma cells, NIH3T3 cells, COS, HeLa, or CHO cells.

In some embodiments, improved yield of the CasX variant protein is achieved through codon optimization. Cells use 64 different codons, 61 of which encode the 20 standard amino acids, while another 3 function as stop codons. In some cases, a single amino acid is encoded by more than one codon. Different organisms exhibit bias towards use of different codons for the same naturally occurring amino acid. Therefore, the choice of codons in a protein, and matching codon choice to the organism in which the protein will be expressed, can, in some cases, significantly affect protein translation and therefore protein expression levels. In some embodiments, the CasX variant protein is encoded by a nucleic acid that has been codon optimized. In some embodiments, the nucleic acid encoding the CasX variant protein has been codon optimized for expression in a bacterial cell, a yeast cell, an insect cell, a plant cell, or a mammalian cell. In some embodiments, the mammal cell is a mouse, a rat, a hamster, a guinea pig, a monkey, or a human. In some embodiments, the CasX variant protein is encoded by a nucleic acid that has been codon optimized for expression in a human cell. In some embodiments, the CasX variant protein is encoded by a nucleic acid from which nucleotide sequences that reduce translation rates in prokaryotes and eukaryotes have been removed. For example, runs of greater than three thymine residues in a row can reduce translation rates in certain organisms or internal polyadenylation signals can reduce translation.

In some embodiments, improvements in solubility and stability, as described herein, result in improved yield of the CasX variant protein relative to a reference CasX protein.

Improved protein yield during expression and purification can be evaluated by methods known in the art. For example, the amount of CasX variant protein can be determined by running the protein on an SDS-page gel, and comparing the CasX variant protein to a either a control whose amount or concentration is known in advance to determine an absolute level of protein. Alternatively, or in addition, a purified CasX variant protein can be run on an SDS-page gel next to a reference CasX protein undergoing the same purification process to determine relative improvements in CasX variant protein yield. Alternatively, or in addition, levels of protein can be measured using immunohistochemical methods such as Western blot or ELISA with an antibody to CasX, or by HPLC. For proteins in solution, concentration can be determined by measuring of the protein's intrinsic UV absorbance, or by methods which use protein-dependent color changes such as the Lowry assay, the Smith copper/bicinchoninic assay or the Bradford dye assay. Such methods can be used to calculate the total protein (such as, for example, total soluble protein) yield obtained by expression under certain conditions. This can be compared, for example, to the protein yield of a reference CasX protein under similar expression conditions.

l. Protein Solubility

In some embodiments, a CasX variant protein has improved solubility relative to a reference CasX protein. In some embodiments, a CasX variant protein has improved solubility of the CasX:gNA ribonucleoprotein complex variant relative to a ribonucleoprotein complex comprising a reference CasX protein.

In some embodiments, an improvement in protein solubility leads to higher yield of protein from protein purification techniques such as purification from *E. coli*. Improved solubility of CasX variant proteins may, in some embodiments, enable more efficient activity in cells, as a more soluble protein may be less likely to aggregate in cells. Protein aggregates can in certain embodiments be toxic or burdensome on cells, and, without wishing to be bound by any theory, increased solubility of a CasX variant protein may ameliorate this result of protein aggregation. Further, improved solubility of CasX variant proteins may allow for enhanced formulations permitting the delivery of a higher effective dose of functional protein, for example in a desired gene editing application. In some embodiments, improved solubility of a CasX variant protein relative to a reference CasX protein results in improved yield of the CasX variant protein during purification of at least about 5, at least about 10, at least about 20, at least about 30, at least about 40, at least about 50, at least about 60, at least about 70, at least about 80, at least about 90, at least about 100, at least about 250, at least about 500, or at least about 1000-fold greater yield. In some embodiments, improved solubility of a CasX variant protein relative to a reference CasX protein improves activity of the CasX variant protein in cells by at least about 1.1, at least about 1.2, at least about 1.3, at least about 1.4, at least about 1.5, at least about 1.6, at least about 1.7, at least about 1.8, at least about 1.9, at least about 2, at least about 2.1, at least about 2.2, at least about 2.3, at least about 2.4, at least about 2.5, at least about 2.6, at least about 2.7, at least about 2.8, at least about 2.9, at least about 3, at least about 3.5, at least about 4, at least about 4.5, at least about 5, at least about 5.5, at least about 6, at least about 6.5, at least about 7.0, at least about 7.5, at least about 8, at least about 8.5, at least about 9, at least about 9.5, at least about 10, at least about 11, at least about 12, at least about 13, at least about 14, or at least about 15-fold greater activity.

Methods of measuring CasX protein solubility, and improvements thereof in CasX variant proteins, will be readily apparent to the person of ordinary skill in the art. For example, CasX variant protein solubility can in some embodiments be measured by taking densitometry readings on a gel of the soluble fraction of lysed *E. coli*. Alternatively, or addition, improvements in CasX variant protein solubility can be measured by measuring the maintenance of soluble protein product through the course of a full protein purification. For example, soluble protein product can be measured at one or more steps of gel affinity purification, tag cleavage, cation exchange purification, running the protein on a size exclusion chromatography (SEC) column. In some embodiments, the densitometry of every band of protein on a gel is read after each step in the purification process. CasX variant proteins with improved solubility may, in some embodiments, maintain a higher concentration at one or more steps in the protein purification process when compared to the reference CasX protein, while an insoluble protein variant may be lost at one or more steps due to buffer exchanges, filtration steps, interactions with a purification column, and the like.

In some embodiments, improving the solubility of CasX variant proteins results in a higher yield in terms of mg/L of protein during protein purification when compared to a reference CasX protein.

In some embodiments, improving the solubility of CasX variant proteins enables a greater amount of editing events compared to a less soluble protein when assessed in editing assays such as the EGFP disruption assays described herein.

m. Protein Affinity for the gNA

In some embodiments, a CasX variant protein has improved affinity for the gNA relative to a reference CasX protein, leading to the formation of the ribonucleoprotein complex. Increased affinity of the CasX variant protein for the gNA may, for example, result in a lower $K_d$ for the generation of a RNP complex, which can, in some cases, result in a more stable ribonucleoprotein complex formation. In some embodiments, increased affinity of the CasX variant protein for the gNA results in increased stability of the ribonucleoprotein complex when delivered to human cells. This increased stability can affect the function and utility of the complex in the cells of a subject, as well as result in improved pharmacokinetic properties in blood, when delivered to a subject. In some embodiments, increased affinity of the CasX variant protein, and the resulting increased stability of the ribonucleoprotein complex, allows for a lower dose of the CasX variant protein to be delivered to the subject or cells while still having the desired activity, for example in vivo or in vitro gene editing.

In some embodiments, a higher affinity (tighter binding) of a CasX variant protein to a gNA allows for a greater amount of editing events when both the CasX variant protein and the gNA remain in an RNP complex. Increased editing events can be assessed using editing assays such as the EGFP disruption assay described herein.

In some embodiments, the $K_d$ of a CasX variant protein for a gNA is increased relative to a reference CasX protein by a factor of at least about 1.1, at least about 1.2, at least about 1.3, at least about 1.4, at least about 1.5, at least about 1.6, at least about 1.7, at least about 1.8, at least about 1.9, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100. In some embodiments, the CasX variant has about 1.1 to about 10-fold increased binding affinity to the gNA compared to the reference CasX protein of SEQ ID NO: 2.

Without wishing to be bound by theory, in some embodiments amino acid changes in the Helical I domain can increase the binding affinity of the CasX variant protein with the gNA targeting sequence, while changes in the Helical II domain can increase the binding affinity of the CasX variant protein with the gNA scaffold stem loop, and changes in the oligonucleotide binding domain (OBD) increase the binding affinity of the CasX variant protein with the gRNA triplex.

Methods of measuring CasX protein binding affinity for a gNA include in vitro methods using purified CasX protein and gNA. The binding affinity for reference CasX and variant proteins can be measured by fluorescence polarization if the gNA or CasX protein is tagged with a fluorophore. Alternatively, or in addition, binding affinity can be measured by biolayer interferometry, electrophoretic mobility shift assays (EMSAs), or filter binding. Additional standard techniques to quantify absolute affinities of RNA binding proteins such as the reference CasX and variant proteins of the disclosure for specific gNAs such as reference gNAs and variants thereof include, but are not limited to, isothermal calorimetry (ITC), and surface plasmon resonance (SPR), as well as the methods of the Examples.

n. Affinity for Target Nucleic Acid

In some embodiments, a CasX variant protein has improved binding affinity for a target nucleic acid relative to the affinity of a reference CasX protein for a target nucleic acid. In some embodiments, the improved affinity for the target nucleic acid comprises improved affinity for the target nucleic acid sequence, improved affinity for the PAM sequence, an improved ability to search DNA for the target nucleic acid sequence, or any combinations thereof. Without wishing to be bound by theory, it is thought that CRISPR/Cas system proteins such as CasX may find their target nucleic acid sequences by one-dimension diffusion along a DNA molecule. The process is thought to include (1) binding of the ribonucleoprotein to the DNA molecule followed by (2) stalling at the target nucleic acid sequence, either of which may be, in some embodiments, affected by improved affinity of CasX proteins for a target nucleic acid sequence, thereby improving function of the CasX variant protein compared to a reference CasX protein.

In some embodiments, a CasX variant protein with improved target nucleic acid affinity has increased overall affinity for DNA. In some embodiments, a CasX variant protein with improved target nucleic acid affinity has increased affinity for specific PAM sequences other than the canonical TTC PAM recognized by the reference CasX protein of SEQ ID NO: 2, including binding affinity for PAM sequences selected from the group consisting of TTC, ATC, GTC, and CTC. Without wishing to be bound by theory, it is possible that these protein variants will interact more strongly with DNA overall and will have an increased ability to access and edit sequences within the target DNA due to the ability to bind additional PAM sequences beyond those of wild-type Cas X, thereby allowing for a more efficient search process of the CasX protein for the target sequence. A higher overall affinity for DNA also, in some embodiments, can increase the frequency at which a CasX protein can effectively start and finish a binding and unwinding step, thereby facilitating target strand invasion and R-loop formation, and ultimately the cleavage of a target nucleic acid sequence.

Without wishing to be bound by theory, it is possible that amino acid changes in the NTSBD that increase the efficiency of unwinding, or capture, of a non-target DNA strand in the unwound state, can increase the affinity of CasX variant proteins for target DNA. Alternatively, or in addition, amino acid changes in the NTSBD that increase the ability of the NTSBD to stabilize DNA during unwinding can increase the affinity of CasX variant proteins for target DNA. Alternatively, or in addition, amino acid changes in the OBD may increase the affinity of CasX variant protein binding to the protospacer adjacent motif (PAM), thereby increasing affinity of the CasX variant protein for target nucleic acid. Alternatively, or in addition, amino acid changes in the Helical I and/or II, RuvC and TSL domains that increase the affinity of the CasX variant protein for the target nucleic acid strand can increase the affinity of the CasX variant protein for target nucleic acid.

In some embodiments, the CasX variant protein has increased binding affinity to the target nucleic acid sequence compared to the reference protein of SEQ ID NO: 1, SEQ ID NO: 2, or SEQ ID NO: 3. In some embodiments, affinity of a CasX variant protein of the disclosure for a target nucleic acid molecule is increased relative to a reference CasX protein by a factor of at least about 1.1, at least about 1.2, at least about 1.3, at least about 1.4, at least about 1.5, at least about 1.6, at least about 1.7, at least about 1.8, at least about 1.9, at least about 2, at least about 3, at least about 4, at least about 5, at least about 6, at least about 7, at least about 8, at least about 9, at least about 10, at least about 15, at least about 20, at least about 25, at least about 30, at least about 35, at least about 40, at least about 45, at least about 50, at least about 60, at least about 70, at least about 80, at least about 90, or at least about 100.

In some embodiments, a CasX variant protein has improved binding affinity for the non-target strand of the target nucleic acid. As used herein, the term "non-target strand" refers to the strand of the DNA target nucleic acid sequence that does not form Watson and Crick base pairs with the targeting sequence in the gNA, and is complementary to the target strand.

Methods of measuring CasX protein (such as reference or variant) affinity for a target nucleic acid molecule may include electrophoretic mobility shift assays (EMSAs), filter binding, isothermal calorimetry (ITC), and surface plasmon resonance (SPR), fluorescence polarization and biolayer interferometry (BLI). Further methods of measuring CasX protein affinity for a target include in vitro biochemical assays that measure DNA cleavage events over time.

CasX variant proteins with higher affinity for their target nucleic acid may, in some embodiments, cleave the target nucleic acid sequence more rapidly than a reference CasX protein that does not have increased affinity for the target nucleic acid.

In some embodiments, the CasX variant protein is catalytically dead (dCasX). In some embodiments, the disclosure provides RNP comprising a catalytically-dead CasX protein that retains the ability to bind target DNA. An exemplary catalytically-dead CasX variant protein comprises one or more mutations in the active site of the RuvC domain of the CasX protein. In some embodiments, a catalytically-dead CasX variant protein comprises substitutions at residues 672, 769 and/or 935 of SEQ ID NO: 1. In some embodiments, a catalytically-dead CasX variant protein comprises substitutions of D672A, E769A and/or D935A in the reference CasX protein of SEQ ID NO: 1. In some embodiments, a catalytically-dead CasX protein comprises substitutions at amino acids 659, 765 and/or 922 of SEQ ID NO: 2. In some embodiments, a catalytically-dead CasX protein comprises D659A, E756A and/or D922A substitutions in a reference CasX protein of SEQ ID NO: 2. In further embodiments, a catalytically-dead CasX variant protein comprises deletions of all or part of the RuvC domain of the reference CasX protein.

In some embodiments, improved affinity for DNA of a CasX variant protein also improves the function of catalytically inactive versions of the CasX variant protein. In some embodiments, the catalytically inactive version of the CasX variant protein comprises one or mutations in the DED motif in the RuvC. Catalytically dead CasX variant proteins can, in some embodiments, be used for base editing or epigenetic modifications. With a higher affinity for DNA, in some embodiments, catalytically dead CasX variant proteins can, relative to catalytically active CasX, find their target DNA faster, remain bound to target DNA for longer periods of time, bind target DNA in a more stable fashion, or a combination thereof, thereby improving the function of the catalytically dead CasX variant protein.

o. Improved Specificity for a Target Site

In some embodiments, a CasX variant protein has improved specificity for a target nucleic acid sequence relative to a reference CasX protein. As used herein, "specificity," sometimes referred to as "target specificity," refers to the degree to which a CRISPR/Cas system ribonucleoprotein complex cleaves off-target sequences that are similar, but not identical to the target nucleic acid sequence; e.g., a CasX variant RNP with a higher degree of specificity would exhibit reduced off-target cleavage of sequences relative to a reference CasX protein. The specificity, and the reduction of potentially deleterious off-target effects, of CRISPR/Cas system proteins can be vitally important in order to achieve an acceptable therapeutic index for use in mammalian subjects.

In some embodiments, a CasX variant protein has improved specificity for a target site within the target nucleic acid sequence that is complementary to the targeting sequence of the gNA.

Without wishing to be bound by theory, it is possible that amino acid changes in the Helical I and II domains that increase the specificity of the CasX variant protein for the target nucleic acid strand can increase the specificity of the CasX variant protein for the target nucleic acid overall. In some embodiments, amino acid changes that increase specificity of CasX variant proteins for target nucleic acid may also result in decreased affinity of CasX variant proteins for DNA.

Methods of testing CasX protein (such as variant or reference) target specificity may include guide and Circularization for In vitro Reporting of Cleavage Effects by Sequencing (CIRCLE-seq), or similar methods. In brief, in CIRCLE-seq techniques, genomic DNA is sheared and circularized by ligation of stem-loop adapters, which are nicked in the stem-loop regions to expose 4 nucleotide palindromic overhangs. This is followed by intramolecular ligation and degradation of remaining linear DNA. Circular DNA molecules containing a CasX cleavage site are subsequently linearized with CasX, and adapter adapters are ligated to the exposed ends followed by high-throughput sequencing to generate paired end reads that contain information about the off-target site. Additional assays that can be used to detect off-target events, and therefore CasX protein specificity include assays used to detect and quantify indels (insertions and deletions) formed at those selected off-target sites such as mismatch-detection nuclease assays and next generation sequencing (NGS). Exemplary mismatch-detection assays include nuclease assays, in which genomic DNA from cells treated with CasX and sgRNA is PCR amplified, denatured and rehybridized to form hetero-duplex DNA, containing one wild type strand and one strand with an indel. Mismatches are recognized and cleaved by mismatch detection nucleases, such as Surveyor nuclease or T7 endonuclease I.

p. Unwinding of DNA

In some embodiments, a CasX variant protein has improved ability of unwinding DNA relative to a reference CasX protein. Poor dsDNA unwinding has been shown previously to impair or prevent the ability of CRISPR/Cas system proteins AnaCas9 or Cas14s to cleave DNA. Therefore, without wishing to be bound by any theory, it is likely that increased DNA cleavage activity by some CasX variant proteins of the disclosure is due, at least in part, to an increased ability to find and unwind the dsDNA at a target site.

Without wishing to be bound by theory, it is thought that amino acid changes in the NTSB domain may produce CasX variant proteins with increased DNA unwinding characteristics. Alternatively, or in addition, amino acid changes in the OBD or the helical domain regions that interact with the PAM may also produce CasX variant proteins with increased DNA unwinding characteristics.

Methods of measuring the ability of CasX proteins (such as variant or reference) to unwind DNA include, but are not limited to, in vitro assays that observe increased on rates of dsDNA targets in fluorescence polarization or biolayer interferometry.

q. Catalytic Activity

The ribonucleoprotein complex of the CasX:gNA systems disclosed herein comprise a reference CasX protein or variant thereof that bind to a target nucleic acid and cleaves the target nucleic acid. In some embodiments, a CasX variant protein has improved catalytic activity relative to a reference CasX protein. Without wishing to be bound by theory, it is thought that in some cases cleavage of the target strand can be a limiting factor for Cas12-like molecules in creating a dsDNA break. In some embodiments, CasX variant proteins improve bending of the target strand of DNA and cleavage of this strand, resulting in an improvement in the overall efficiency of dsDNA cleavage by the CasX ribonucleoprotein complex.

In some embodiments, a CasX variant protein has increased nuclease activity compared to a reference CasX protein. Variants with increased nuclease activity can be generated, for example, through amino acid changes in the RuvC nuclease domain. In some embodiments, the CasX variant comprises a nuclease domain having nickase activity. In the foregoing, the CasX nickase of a CasX:gNA system generates a single-stranded break within 10-18 nucleotides 3' of a PAM site in the non-target strand. In other embodiments, the CasX variant comprises a nuclease domain having double-stranded cleavage activity. In the foregoing, the CasX of the CasX:gNA system generates a double-stranded break within 18-26 nucleotides 5' of a PAM site on the target strand and 10-18 nucleotides 3' on the non-target strand. Nuclease activity can be assayed by a variety of methods, including those of the Examples. In some embodiments, a CasX variant has a $K_{cleave}$ constant that is at least 2-fold, or at least 3-fold, or at least 4-fold, or at least 5-fold, or at least 6-fold, or at least 7-fold, or at least 8-fold, or at least 9-fold, or at least 10-fold greater compared to a reference CasX.

In some embodiments, a CasX variant protein has the improved characteristic of forming RNP with gNA that result in a higher percentage of cleavage-competent RNP compared to an RNP of a reference CasX protein of SEQ ID NO: 1, SEQ ID NO: 2, or SEQ ID NO: 3 and the gNA, as described in the Examples. By cleavage competent, it is meant that the RNP that is formed has the ability to cleave the target nucleic acid. In some embodiments, the RNP of the CasX variant and the gNA exhibit at least a 2% to at least 30%, or at least a 5% to at least a 20%, or at least a 10% to at least a 15% higher percentage of cleavage-competent RNP compared to an RNP of the reference CasX of SEQ ID NO: 1, SEQ ID NO: 2, or SEQ ID NO: 3 and the gNA of Table 2A.

In some embodiments, a CasX variant protein has increased target strand loading for double strand cleavage compared to a reference CasX. Variants with increased target strand loading activity can be generated, for example, through amino acid changes in the TLS domain.

Without wishing to be bound by theory, amino acid changes in the TSL domain may result in CasX variant proteins with improved catalytic activity. Alternatively, or in addition, amino acid changes around the binding channel for the RNA:DNA duplex may also improve catalytic activity of the CasX variant protein.

In some embodiments, a CasX variant protein has increased collateral cleavage activity compared to a reference CasX protein. As used herein, "collateral cleavage activity" refers to additional, non-targeted cleavage of nucleic acids following recognition and cleavage of a target nucleic acid. In some embodiments, a CasX variant protein has decreased collateral cleavage activity compared to a reference CasX protein.

In some embodiments, for example those embodiments encompassing applications where cleavage of the target nucleic acid is not a desired outcome, improving the catalytic activity of a CasX variant protein comprises altering, reducing, or abolishing the catalytic activity of the CasX variant protein. In some embodiments, a ribonucleoprotein complex comprising a dCasX variant protein binds to a target nucleic acid and does not cleave the target nucleic acid.

In some embodiments, the CasX ribonucleoprotein complex comprising a CasX variant protein binds a target DNA but generates a single stranded nick in the target DNA. In some embodiments, particularly those embodiments wherein the CasX protein is a nickase, a CasX variant protein has decreased target strand loading for single strand nicking. Variants with decreased target strand loading may be generated, for example, through amino acid changes in the TSL domain.

Exemplary methods for characterizing the catalytic activity of CasX proteins may include, but are not limited to, in vitro cleavage assays, including those of the Examples, below. In some embodiments, electrophoresis of DNA products on agarose gels can interrogate the kinetics of strand cleavage.

r. Affinity for SOD1 Target RNA

In some embodiments, a ribonucleoprotein complex comprising a reference CasX protein or variant thereof binds to a target SOD1 RNA and cleaves the target nucleic acid. In some embodiments, variants of a reference CasX protein increase the specificity of the CasX variant protein for a target SOD1 RNA, and increase the activity of the CasX variant protein with respect to a target RNA when compared to the reference CasX protein. For example, CasX variant proteins can display increased binding affinity for target RNAs, or increased cleavage of target RNAs, when compared to reference CasX proteins. In some embodiments, a ribonucleoprotein complex comprising a CasX variant protein binds to a target RNA and/or cleaves the target RNA. In some embodiments, a CasX variant has at least about two-fold to about 10-fold increased binding affinity to the SOD1 target nucleic acid compared to the reference protein of SEQ ID NO: 1, SEQ ID NO: 2, or SEQ ID NO: 3.

s. Combinations of Mutations

The present disclosure provides Cas X variants that are a combination of mutations from separate CasX variant proteins. In some embodiments, any variant to any domain described herein can be combined with other variants described herein. In some embodiments, any variant within any domain described herein can be combined with other variants described herein, in the same domain. Combinations of different amino acid changes may in some embodiments produce new optimized variants whose function is further improved by the combination of amino acid changes. In some embodiments, the effect of combining amino acid changes on CasX protein function is linear. As used herein, a combination that is linear refers to a combination whose effect on function is equal to the sum of the effects of each individual amino acid change when assayed in isolation. In some embodiments, the effect of combining amino acid changes on CasX protein function is synergistic. As used herein, a combination of variants that is synergistic refers to a combination whose effect on function is greater than the sum of the effects of each individual amino acid change when assayed in isolation. In some embodiments, combining amino acid changes produces CasX variant proteins in which more than one function of the CasX protein has been improved relative to the reference CasX protein.

t. CasX Fusion Proteins

In some embodiments, the disclosure provides CasX proteins comprising a heterologous protein fused to the CasX. In some cases, the CasX is a reference CasX protein. In other cases, the CasX is a CasX variant of any of the embodiments described herein.

In some embodiments, the CasX variant protein is fused to one or more proteins or domains thereof that has a different activity of interest, resulting in a fusion protein. For example, in some embodiments, the CasX variant protein is fused to a protein (or domain thereof) that inhibits transcription, modifies a target nucleic acid, or modifies a polypeptide associated with a nucleic acid (e.g., histone modification).

In some embodiments, a heterologous polypeptide (or heterologous amino acid such as a cysteine residue or a non-natural amino acid) can be inserted at one or more positions within a CasX protein to generate a CasX fusion protein. In other embodiments, a cysteine residue can be inserted at one or more positions within a CasX protein followed by conjugation of a heterologous polypeptide described below. In some alternative embodiments, a heterologous polypeptide or heterologous amino acid can be added at the N- or C-terminus of the reference or CasX variant protein. In other embodiments, a heterologous polypeptide or heterologous amino acid can be inserted internally within the sequence of the CasX protein.

In some embodiments, the reference CasX or variant fusion protein retains RNA-guided sequence specific target nucleic acid binding and cleavage activity. In some cases, the reference CasX or variant fusion protein has (retains) 50% or more of the activity (e.g., cleavage and/or binding activity) of the corresponding reference CasX or variant protein that does not have the insertion of the heterologous protein. In some cases, the reference CasX or variant fusion protein retains at least about 60%, or at least about 70% or more, at least about 80%, or at least about 90%, or at least about 92%, or at least about 95%, or at least about 98%, or at least about 100% of the activity (e.g., cleavage and/or binding activity) of the corresponding CasX protein that does not have the insertion of the heterologous protein.

In some cases, the reference CasX or variant fusion protein retains (has) target nucleic acid binding activity relative to the activity of the CasX protein without the inserted heterologous amino acid or heterologous polypeptide. In some cases, the reference CasX or variant fusion protein retains at least about 60%, or at least about 70% or more, at least about 80%, or at least about 90%, or at least about 92%, or at least about 95%, or at least about 98%, or at least about 100% of the binding activity of the corresponding CasX protein that does not have the insertion of the heterologous protein.

In some cases, the reference CasX or variant fusion protein retains (has) target nucleic acid binding and/or cleavage activity relative to the activity of the parent CasX protein without the inserted heterologous amino acid or heterologous polypeptide. For example, in some cases, the reference CasX or variant fusion protein has (retains) 50% or more of the binding and/or cleavage activity of the corresponding parent CasX protein (the CasX protein that does not have the insertion). For example, in some cases, the reference CasX or variant fusion protein has (retains) 60% or more (70% or more, 80% or more, 90% or more, 92% or more, 95% or more, 98% or more, or 100%) of the binding and/or cleavage activity of the corresponding CasX parent protein (the CasX protein that does not have the insertion). Methods of measuring cleaving and/or binding activity of a CasX protein and/or a CasX fusion protein will be known to one of ordinary skill in the art and any convenient method can be used.

A variety of heterologous polypeptides are suitable for inclusion in a reference CasX or CasX variant fusion protein of the disclosure. In some cases, the fusion partner can modulate transcription (e.g., inhibit transcription, increase transcription) of a target DNA. For example, in some cases the fusion partner is a protein (or a domain from a protein) that inhibits transcription (e.g., a transcriptional repressor, a protein that functions via recruitment of transcription inhibitor proteins, modification of target DNA such as methylation, recruitment of a DNA modifier, modulation of histones associated with target DNA, recruitment of a histone modifier such as those that modify acetylation and/or methylation of histones, and the like). In some cases the fusion partner is a protein (or a domain from a protein) that increases transcription (e.g., a transcription activator, a protein that acts via recruitment of transcription activator proteins, modification of target DNA such as demethylation, recruitment of a DNA modifier, modulation of histones associated with target DNA, recruitment of a histone modifier such as those that modify acetylation and/or methylation of histones, and the like).

In some cases, a fusion partner has enzymatic activity that modifies a target nucleic acid; e.g., nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity or glycosylase activity.

In some cases, a fusion partner has enzymatic activity that modifies a polypeptide (e.g., a histone) associated with a target nucleic acid (e.g., methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity or demyristoylation activity).

Examples of proteins (or fragments thereof) that can be used as a fusion partner to increase transcription include but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET domain containing 1A, histone lysine methyltransferase (SET1A), SET domain containing 1B, histone lysine methyltransferase (SET1B), lysine methyltransferase (MLL1 to 5), ASCL1 (ASH1) achaete-scute family bHLH transcription factor 1 (ASH1), SET and MYND domain containing 2 (SYMD2), nuclear receptor binding SET domain protein 1 (NSD1), and the like; histone lysine demethylases such as lysine demethylase 3A (JHDM2a)/Lysine-specific demethylase 3B (JHDM2b), lysine demethylase 6A (UTX), lysine demethylase 6B (JMJD3), and the like; histone acetyltransferases such as lysine acetyltransferase 2A (GCN5), lysine acetyltransferase 2B (PCAF), CREB binding protein (CBP), E1A binding protein p300 (p300), TATA-box binding protein associated factor 1 (TAF1), lysine acetyltransferase 5 (TIP60/PLIP), lysine acetyltransferase 6A (MOZ/MYST3), lysine acetyltransferase 6B (MORF/MYST4), SRC proto-oncogene, non-receptor tyrosine kinase (SRC1), nuclear receptor coactivator 3 (ACTR), MYB binding protein 1a (P160), clock circadian regulator (CLOCK), and the like; and DNA demethylases such as Ten-Eleven Translocation (TET) dioxygenase 1 (TET1CD), tet methylcytosine dioxygenase 1 (TET1), demeter (DME), demeter-like 1 (DML1), demeter-like 2 (DML2), protein ROS1 (ROS1), and the like.

Examples of proteins (or fragments thereof) that can be used as a fusion partner to decrease transcription include but are not limited to: transcriptional repressors such as the Kruppel associated box (KRAB or SKD); KOX1 repression domain; the Mad mSIN3 interaction domain (SID); the ERF repressor domain (ERD), the SRDX repression domain (e.g., for repression in plants), and the like; histone lysine methyltransferases such as PR/SET domain containing protein (Pr-SET7/8), lysine methyltransferase 5B (SUV4-20H1), PR/SET domain 2 (RIZ1), and the like; histone lysine demethylases such as lysine demethylase 4A (JMJD2A/JHDM3A), lysine demethylase 4B (JMJD2B), lysine demethylase 4C (JMJD2C/GASC1), lysine demethylase 4D (JMJD2D), lysine demethylase 5A (JARID1A/RBP2), lysine demethylase 5B (JARID1B/PLU-1), lysine demethylase 5C (JARID 1C/SMCX), lysine demethylase 5D (JARID1D/SMCY), and the like; histone lysine deacetylases such as histone deacetylase 1 (HDAC1), HDAC2, HDAC3, HDAC8, HDAC4, HDAC5, HDAC7, HDAC9, sirtuin 1 (SIRT1), SIRT2, HDAC11, and the like; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), methyltransferase 1 (MET1), S-adenosyl-L-methionine-dependent methyltransferases superfamily protein (DRM3) (plants), DNA cytosine methyltransferase MET2a (ZMET2), chromomethylase 1 (CMT1), chromomethylase 2 (CMT2) (plants), and the like; and periphery recruitment elements such as Lamin A, Lamin B, and the like.

In some cases, the fusion partner has enzymatic activity that modifies the target nucleic acid (e.g., ssRNA, dsRNA, ssDNA, dsDNA). Examples of enzymatic activity that can be provided by the fusion partner include but are not limited to: nuclease activity such as that provided by a restriction enzyme (e.g., FokI nuclease), methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), MET1, DRM3 (plants), ZMET2, CMT1, CMT2 (plants), and the like); demethylase activity such as that provided by a demethylase (e.g., Ten-Eleven Translocation (TET) dioxygenase 1 (TET 1 CD), TET1, DME, DML1, DML2, ROS1, and the like), DNA repair activity, DNA damage activity, deamination activity such as that provided by a deaminase (e.g., a cytosine deaminase enzyme, e.g., an APOBEC protein such as rat apolipoprotein B mRNA editing enzyme, catalytic polypeptide 1 {APOBEC1}), dismutase activity, alkylation activity, depurination activity, oxidation activity, pyrimidine dimer forming activity, integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase; and the like), transposase activity, recombinase activity such as that provided by a recombinase (e.g., catalytic domain of Gin recombinase), polymerase activity, ligase activity, helicase activity, photolyase activity, and glycosylase activity).

In some cases, a reference CasX or CasX variant protein of the present disclosure is fused to a polypeptide selected from a domain for increasing transcription (e.g., a VP16 domain, a VP64 domain), a domain for decreasing transcription (e.g., a KRAB domain, e.g., from the Kox1 protein), a core catalytic domain of a histone acetyltransferase (e.g., histone acetyltransferase p300), a protein/domain that provides a detectable signal (e.g., a fluorescent protein such as GFP), a nuclease domain (e.g., a FokI nuclease), or a base editor (e.g., cytidine deaminase such as APOBEC1).

In some cases, the fusion partner has enzymatic activity that modifies a protein associated with the target nucleic acid (e.g., ssRNA, dsRNA, ssDNA, dsDNA) (e.g., a histone, an RNA binding protein, a DNA binding protein, and the like). Examples of enzymatic activity (that modifies a protein associated with a target nucleic acid) that can be provided by the fusion partner include but are not limited to: methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB 1, and the like, SET1A, SET1B, MLL1 to 5, ASH1, SYMD2, NSD1, DOT1L, Pr-SET7/8, SUV4-20H1, EZH2, RIZ1), demethylase activity such as that provided by a histone demethylase (e.g., Lysine Demethylase 1A (KDM1A also known as LSD1), JHDM2a/b, JMJD2A/ JHDM3A, JMJD2B, JMJD2C/GASC1, JMJD2D, JARID1A/RBP2, JARID1B/PLU-1, JARID1C/SMCX, JARID1D/SMCY, UTX, JMJD3, and the like), acetyltransferase activity such as that provided by a histone acetylase transferase (e.g., catalytic core/fragment of the human acetyltransferase p300, GCN5, PCAF, CBP, TAF1, TIP60/ PLIP, MOZ/MYST3, MORF/MYST4, HB01/MYST2, HMOF/MYST1, SRC1, ACTR, P160, CLOCK, and the like), deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11, and the like), kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

Additional examples of suitable fusion partners are (i) a dihydrofolate reductase (DHFR) destabilization domain (e.g., to generate a chemically controllable subject RNA-guided polypeptide or a conditionally active RNA-guided polypeptide), and (ii) a chloroplast transit peptide.

Suitable chloroplast transit peptides include, but are not limited to:

(SEQ ID NO: 132)
MASMISSSAVTTVSRASRGQSAAMAPFGGLKSMTGFPVRKVNTDITSITSN

GGRVKCMQVWPPIGKKKFETLSYLPPLTRDSRA;

(SEQ ID NO: 133)
MASMISSSAVTTVSRASRGQSAAMAPFGGLKSMTGFPVRKVNTDITSITSN

GGRVKS;

(SEQ ID NO: 134)
MASSMLSSATMVASPAQATMVAPFNGLKSSAAFPATRKANNDITSITSNGG

RVNCMQV WPPIEKKKFETLSYLPDLTDSGGRVNC;

(SEQ ID NO: 135)
MAQVSRICNGVQNPSLISNLSKSSQRKSPLSVSLKTQQHPRAYPISSSWGL

KKSGMTLIG SELRPLKVMSSVSTAC;

(SEQ ID NO: 136)
MAQVSRICNGVWNPSLISNLSKSSQRKSPLSVSLKTQQHPRAYPISSSWGL

KKSGMTLIG SELRPLKVMSSVSTAC;

(SEQ ID NO: 137)
MAQINNMAQGIQTLNPNSNFHKPQVPKSSSFLVFGSKKLKNSANSMLVLKK

DSIFMQLF CSFRISASVATAC;

(SEQ ID NO: 138)
MAALVTSQLATSGTVLSVTDRFRRPGFQGLRPRNPADAALGMRTVGASAAP

KQSRKP HRFDRRCLSMVV;

(SEQ ID NO: 139)
MAALTTSQLATSATGFGIADRSAPSSLLRHGFQGLKPRSPAGGDATSLSVT

TSARATPKQ QRSVQRGSRRFPSVVVC;

(SEQ ID NO: 12496)
MASSVLSSAAVATRSNVAQANMVAPFTGLKSAASFPVSRKQNLDITSIASN

GGRVQC;

(SEQ ID NO: 140)
MESLAATSVFAPSRVAVPAARALVRAGTVVPTRRTSSTSGTSGVKCSAAVT

PQASPVIS RSAAAA;
and (SEQ ID NO: 141)
MGAAATSMQSLKFSNRLVPPSRRLSPVPNNVTCNNLPKSAAPVRTVKCCAS

SWNSTINGAAATTNGASAASS.

In some cases, a reference CasX or variant protein of the present disclosure can include an endosomal escape peptide. In some cases, an endosomal escape polypeptide comprises the amino acid sequence GLFXALLXLLXSLWXLLLXA (SEQ ID NO: 142), wherein each X is independently selected from lysine, histidine, and arginine. In some cases, an endosomal escape polypeptide comprises the amino acid sequence GLFHALLHLLHSLWHLLLHA (SEQ ID NO: 143), or HHHHHHHHH (SEQ ID NO: 144).

Non-limiting examples of fusion partners for use when targeting ssRNA target nucleic acids include (but are not limited to): splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; RNA-binding proteins; and the like. It is understood that a heterologous polypeptide can include the entire protein or, in some cases, can include a fragment of the protein (e.g., a functional domain).

A fusion partner for a reference CasX or CasX variant can be any domain capable of interacting with ssRNA (which, for the purposes of this disclosure, includes intramolecular and/or intermolecular secondary structures, e.g., double-stranded RNA duplexes such as hairpins, stem-loops, etc.), whether transiently or irreversibly, directly or indirectly, including but not limited to an effector domain selected from the group comprising; endonucleases (for example RNase III, the CRR22 DYW domain, Dicer, and PIN (PilT N-terminus) domains from proteins such as SMG5 and SMG6); proteins and protein domains responsible for stimulating RNA cleavage (for example cleavage and polyadenylation specific factor {CPSF}, cleavage stimulation factor {CstF}, CFIm and CFIIm); exonucleases (for example chromatin-binding exonuclease XRN1 (XRN-1) or Exonuclease T); deadenylases (for example DNA 5'-adenosine monophosphate hydrolase {HNT3}); proteins and protein domains responsible for nonsense mediated RNA decay (for example UPF1 RNA helicase and ATPase {UPF1}, UPF2, UPF3, UPF3b, RNP SI, RNA binding motif protein 8A {Y14}, DEK proto-oncogene {DEK}, RNA-processing protein REF2 {REF2}, and Serine-arginine repetitive matrix 1 {SRm160}); proteins and protein domains responsible for stabilizing RNA (for example poly(A) binding protein cytoplasmic 1 {PABP}); proteins and protein domains responsible for repressing translation (for example argonaute RISC catalytic component 2 {Ago2} and Ago4); proteins and protein domains responsible for stimulating translation (for example Staufen); proteins and protein domains responsible for (e.g., capable of) modulating translation (e.g., translation factors such as initiation factors, elongation factors, release factors, etc., e.g., eIF4G); proteins and protein domains responsible for polyadenylation of RNA (for example poly (A) polymerase (PAP1), PAP-associated domain-containing protein;Poly(A) RNA polymerase gld-2 {GLD-2}, and Star-PAP); proteins and protein domains responsible for polyuridinylation of RNA (for example Terminal uridylyltransferase {CID1} and terminal uridylate transferase); proteins and protein domains responsible for RNA localization (for example from insulin like growth factor 2 mRNA binding protein 1 {IMP1}, Z-DNA binding protein 1 {ZBP1}, She2p, She3p, and Bicaudal-D); proteins and protein domains responsible for nuclear retention of RNA (for example Rrp6); proteins and protein domains responsible for nuclear export of RNA (for example nuclear RNA export factor 1 {TAP}, nuclear RNA export factor 1 {NXF1}, THO Complex {THO}, TREX, REF, and Aly/REF export factor {Aly}); proteins and protein domains responsible for repression of RNA splicing (for example polypyrimidine tract binding protein 1 {PTB}, KH RNA binding domain containing, signal transduction associated 1 Sam68}, and heterogeneous nuclear ribonucleoprotein A1 {hnRNP A1}); proteins and protein domains responsible for stimulation of RNA splicing (for example serine/arginine-rich (SR) domains); proteins and protein domains responsible for reducing the efficiency of transcription (for example FUS RNA binding protein {FUS (TLS)}); and proteins and protein domains responsible for stimulating transcription (for example cyclin dependent kinase 7 {CDK7} and HIV Tat). Alternatively, the effector domain may be selected from the group comprising endonucleases; proteins and protein domains capable of stimulating RNA cleavage; exonucleases; deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable heterologous polypeptide is a PUF RNA-binding domain, which is described in more detail in WO2012068627, which is hereby incorporated by reference in its entirety.

Some RNA splicing factors that can be used (in whole or as fragments thereof) as a fusion partner have modular organization, with separate sequence-specific RNA binding modules and splicing effector domains. For example, members of the serine/arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP A1 binds to exonic splicing silencers (ESSs) through its RRM domains and inhibits exon inclusion through a C-terminal glycine-rich domain. Some splicing factors can regulate alternative use of splice site (ss) by binding to regulatory sequences between the two alternative sites. For example, ASF/SF2 can recognize ESEs and promote the use of intron proximal sites, whereas hnRNP A1 can bind to ESSs and shift splicing towards the use of intron distal sites. One application for such factors is to generate ESFs that modulate alternative splicing of endogenous genes, particularly disease associated genes. For example, BCL2 like 1 (Bcl-x) pre-mRNA produces two splicing isoforms with two alternative 5' splice sites to encode proteins of opposite functions. The long splicing isoform Bcl-xL is a potent apoptosis inhibitor expressed in long-lived post mitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple cc-elements that are located in either the core exon region or the exon extension region (i.e., between the two alternative 5' splice sites). For more examples, see WO2010075303, which is hereby incorporated by reference in its entirety.

Further suitable fusion partners include, but are not limited to proteins (or fragments thereof) that are boundary elements (e.g., CTCF), proteins and fragments thereof that provide periphery recruitment (e.g., Lamin A, Lamin B, etc.), and protein docking elements (e.g., FKBP/FRB, Pill/Abyl, etc.).

In some cases, a heterologous polypeptide (a fusion partner) provides for subcellular localization, i.e., the heterologous polypeptide contains a subcellular localization sequence (e.g., a nuclear localization signal (NLS) for targeting to the nucleus, a sequence to keep the fusion protein out of the nucleus, e.g., a nuclear export sequence (NES), a sequence to keep the fusion protein retained in the cytoplasm, a mitochondrial localization signal for targeting to the mitochondria, a chloroplast localization signal for targeting to a chloroplast, an ER retention signal, and the like). In some embodiments, a subject RNA-guided polypeptide or a conditionally active RNA-guided polypeptide and/or subject CasX fusion protein does not include a NLS so that the protein is not targeted to the nucleus (which can be advantageous, e.g., when the target nucleic acid is an RNA that is present in the cytosol). In some embodiments, a fusion partner can provide a tag (i.e., the heterologous polypeptide is a detectable label) for ease of tracking and/or purification (e.g., a fluorescent protein, e.g., green fluorescent protein (GFP), yellow fluorescent protein (YFP), red fluorescent protein (RFP), cyan fluorescent protein (CFP), mCherry, tdTomato, and the like; a histidine tag, e.g., a 6XHis tag; a hemagglutinin (HA) tag; a FLAG tag; a Myc tag; and the like).

In some cases, a reference or CasX variant protein includes (is fused to) a nuclear localization signal (NLS). In some cases, a reference or CasX variant protein is fused to 2 or more, 3 or more, 4 or more, or 5 or more 6 or more, 7 or more, 8 or more NLSs. In some cases, one or more NLSs (2 or more, 3 or more, 4 or more, or 5 or more NLSs) are positioned at or near (e.g., within 50 amino acids of) the N-terminus and/or the C-terminus. In some cases, one or more NLSs (2 or more, 3 or more, 4 or more, or 5 or more NLSs) are positioned at or near (e.g., within 50 amino acids of) the N-terminus. In some cases, one or more NLSs (2 or more, 3 or more, 4 or more, or 5 or more NLSs) are positioned at or near (e.g., within 50 amino acids of) the C-terminus. In some cases, one or more NLSs (2 or more, 3 or more, 4 or more, or 5 or more NLSs) are positioned at or near (e.g., within 50 amino acids of) both the N-terminus and the C-terminus. In some cases, an NLS is positioned at the N-terminus and an NLS is positioned at the C-terminus. In some cases, a reference or CasX variant protein includes (is fused to) between 1 and 10 NLSs (e.g., 1-9, 1-8, 1-7, 1-6, 1-5, 2-10, 2-9, 2-8, 2-7, 2-6, or 2-5 NLSs). In some cases, a reference or CasX variant protein includes (is fused to) between 2 and 5 NLSs (e.g., 2-4, or 2-3 NLSs).

Non-limiting examples of NLSs include sequences derived from: the NLS of the SV40 virus large T-antigen, having the amino acid sequence PKKKRKV (SEQ ID NO: 145); the NLS from nucleoplasmin (e.g., the nucleoplasmin bipartite NLS with the sequence KRPAATKKAGQAKKKK (SEQ ID NO: 146); the c-myc NLS having the amino acid sequence PAAKRVKLD (SEQ ID NO: 147) or RQRR-NELKRSP (SEQ ID NO: 148); the hRNPA1 M9 NLS having the sequence NQSSNFGPMKGGNFG-GRSSGPYGGGGQYFAKPRNQGGY (SEQ ID NO: 149); the sequence RMRIZFKNKGKDTAELRRRRVEVS-VELRKAKKDEQILKRRNV (SEQ ID NO: 150) of the IBB domain from importin-alpha; the sequences VSRKRPRP (SEQ ID NO: 151) and PPKKARED (SEQ ID NO: 152) of the myoma T protein; the sequence PQPKKKPL (SEQ ID NO: 153) of human p53; the sequence SALI AP (SEQ ID NO: 154) of mouse c-abl IV; the sequences DRLRR (SEQ ID NO: 155) and PKQKKRK (SEQ ID NO: 156) of the influenza virus NS1; the sequence RKLKKKIKKL (SEQ ID NO: 157) of the Hepatitis virus delta antigen; the sequence REKKKFLKRR (SEQ ID NO: 158) of the mouse Mx1 protein; the sequence KRKGDEVDGVDEVAKKKSKK (SEQ ID NO: 159) of the human poly(ADP-ribose) polymerase; the sequence RKCLQAGMNLEARKTKK (SEQ ID NO: 160) of the steroid hormone receptors (human) glucocorticoid; the sequence PRPRKIPR (SEQ ID NO: 161) of Borna disease virus P protein (BDV-P1); the sequence PPRKKRTVV (SEQ ID NO: 162) of hepatitis C virus nonstructural protein (HCV-NS5A); the sequence NLSKKKKRKREK (SEQ ID NO: 163) of LEF1; the sequence RRPSRPFRKP (SEQ ID NO: 164) of ORF57 simirae; the sequence KRPRSPSS (SEQ ID NO: 165) of EBV LANA; the sequence KRGINDRNFWRGENERKTR (SEQ ID NO: 166) of Influenza A protein; the sequence PRPPKMARYDN (SEQ ID NO: 167) of human RNA helicase A (RHA); the sequence KRSFSKAF (SEQ ID NO: 168) of nucleolar RNA helicase II; the sequence KLKIKRPVK (SEQ ID NO: 169) of TUS-protein; the sequence PKKKRKVPPPPAAKRVKLD (SEQ ID NO: 170) associated with importin-alpha; the sequence PKTRRR-PRRSQRKRPPT (SEQ ID NO: 171) from the Rex protein in HTLV-1; the sequence MSRRR-KANPTKLSENAKKLAKEVEN (SEQ ID NO: 172) from the EGL-13 protein of Caenorhabditis elegans; and the sequences KTRRRPRRSQRKRPPT (SEQ ID NO: 173), RRKKRRPRRKKRR (SEQ ID NO: 174), PKKKSRKPKKKSRK (SEQ ID NO: 175), HKKKHP-DASVNFSEFSK (SEQ ID NO: 176), QRPGPY-DRPQRPGPYDRP (SEQ ID NO: 177), LSPSLSPLLSPSL-SPL (SEQ ID NO: 178), RGKGGKGLGKGGAKRHRK (SEQ ID NO: 179), PKRGRGRPKRGRGR (SEQ ID NO: 180), PKKKRKVPPPPAAKRVKLD (SEQ ID NO: 181) and PKKKRKVPPPPKKKRKV (SEQ ID NO: 182). In general, NLS (or multiple NLSs) are of sufficient strength to drive accumulation of a reference or CasX variant fusion protein in the nucleus of a eukaryotic cell. Detection of accumulation in the nucleus may be performed by any suitable technique. For example, a detectable marker may be fused to a reference or CasX variant fusion protein such that location within a cell may be visualized. Cell nuclei may also be isolated from cells, the contents of which may then be analyzed by any suitable process for detecting protein, such as immunohistochemistry, Western blot, or enzyme activity assay. Accumulation in the nucleus may also be determined.

In some cases, a reference or CasX variant fusion protein includes a "Protein Transduction Domain" or PTD (also known as a CP—cell penetrating peptide), which refers to a protein, polynucleotide, carbohydrate, or organic or inorganic compound that facilitates traversing a lipid bilayer, micelle, cell membrane, organelle membrane, or vesicle membrane. A PTD attached to another molecule, which can range from a small polar molecule to a large macromolecule and/or a nanoparticle, facilitates the molecule traversing a membrane, for example going from an extracellular space to an intracellular space, or from the cytosol to within an organelle. In some embodiments, a PTD is covalently linked to the amino terminus of a reference or CasX variant fusion protein. In some embodiments, a PTD is covalently linked to the carboxyl terminus of a reference or CasX variant fusion protein. In some cases, the PTD is inserted internally in the sequence of a reference or CasX variant fusion protein at a suitable insertion site. In some cases, a reference or CasX variant fusion protein includes (is conjugated to, is fused to) one or more PTDs (e.g., two or more, three or more, four or more PTDs). In some cases, a PTD includes one or more nuclear localization signals (NLS). Examples of PTDs include but are not limited to peptide transduction domain of HIV TAT comprising YGRKKRRQRRR (SEQ ID NO: 183), RKKRRQRR (SEQ ID NO: 184); YARAAARQARA (SEQ ID NO: 185); THRLPRRRRRR (SEQ ID NO: 186); and GGRRARRRRRR (SEQ ID NO: 187); a polyarginine sequence comprising a number of arginines sufficient to direct entry into a cell (e.g., 3, 4, 5, 6, 7, 8, 9, 10, or 10-50 arginines (SEQ ID NO: 188)); a VP22 domain (Zender et al. (2002) Cancer Gene Ther. 9(6):489-96); an Drosophila Antennapedia protein transduction domain (Noguchi et al. (2003) Diabetes 52(7): 1732-1737); a truncated human calcitonin peptide (Trehin et al. (2004) Pharm. Research 21:1248-1256); polylysine (Wender et al. (2000) Proc. Natl. Acad. Sci. USA 97: 13003-13008); RRQRRTSKLMKR (SEQ ID NO: 189); Transportan GWTLNSAGYLLGKINL-KALAALAKKIL (SEQ ID NO: 190); KALAWEAK-LAKALAKALAKHLAKALAKALKCEA (SEQ ID NO: 191); and RQIKIWFQNRRMKWKK (SEQ ID NO: 192). In some embodiments, the PTD is an activatable CPP (ACPP) (Aguilera et al. (2009) Integr Biol (Camb) June; 1(5-6): 371-381). ACPPs comprise a polycationic CPP (e.g., Arg9 or "R9") connected via a cleavable linker to a matching polyanion (e.g., Glu9 or "E9"), which reduces the net charge to nearly zero and thereby inhibits adhesion and uptake into cells. Upon cleavage of the linker, the polyanion is released, locally unmasking the polyarginine and its inherent adhesiveness, thus "activating" the ACPP to traverse the membrane.

In some embodiments, a reference or CasX variant fusion protein can include a CasX protein that is linked to an internally inserted heterologous amino acid or heterologous polypeptide (a heterologous amino acid sequence) via a linker polypeptide (e.g., one or more linker polypeptides). In some embodiments, a reference or CasX variant fusion protein can be linked at the C-terminal and/or N-terminal end to a heterologous polypeptide (fusion partner) via a linker polypeptide (e.g., one or more linker polypeptides) The linker polypeptide may have any of a variety of amino acid sequences. Proteins can be joined by a spacer peptide, generally of a flexible nature, although other chemical linkages are not excluded. Suitable linkers include polypeptides of between 4 amino acids and 40 amino acids in length, or between 4 amino acids and 25 amino acids in length. These linkers are generally produced by using synthetic, linker-encoding oligonucleotides to couple the proteins. Peptide linkers with a degree of flexibility can be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use. Example linker polypeptides include glycine polymers (G)n, glycine-serine polymer (including, for example, (GS)n, GSGGSn (SEQ ID NO: 193), GGSGGSn (SEQ ID NO: 194), and GGGSn (SEQ ID NO: 195), where n is an integer of at least one), glycine-alanine polymers, alanine-serine polymers, glycine-proline polymers, proline polymers and proline-alanine polymers. Example linkers can comprise amino acid sequences including, but not limited to, GGSG (SEQ ID NO: 196), GGSGG (SEQ ID NO: 197), GSGSG (SEQ ID NO: 198), GSGGG (SEQ ID NO: 199), GGGSG (SEQ ID NO: 200), GSSSG (SEQ ID NO: 201), GPGP (SEQ ID NO: 202), GGP, PPP, PPAPPA (SEQ ID NO: 203), PPPGPPP (SEQ ID NO: 204) and the like. The ordinarily skilled artisan will recognize that design of a peptide conjugated to any elements described above can include linkers that are all or partially flexible, such that the linker can include a flexible linker as well as one or more portions that confer less flexible structure.

V. CasX:gNA Systems and Methods for Modification of SOD1 Genes

The CasX proteins, guide nucleic acids, and variants thereof provided herein are useful for various applications, including as therapeutics, diagnostics, and for research. To effect the methods of the disclosure for gene editing, provided herein are programmable CasX:gNA systems. The programmable nature of the CasX:gNA system provided herein allows for the precise targeting to achieve the desired effect (nicking, cleaving, etc.) at one or more regions of predetermined interest in the SOD1 gene target nucleic acid comprising one or more mutations. In some embodiments, the CasX:gNA systems provided herein comprise a CasX variant of Table 4 or a variant having at least 50%, at least 60%, at least 70%, at least 80%, or at least 90%, or at least 95%, or at least 99% sequence identity to a sequence of Table 4, and a gNA (e.g., a gNA variant comprising a sequence of Table 2B, or a variant having at least 50%, at least 60%, at least 70%, at least 80%, or at least 90%, or at least 95%, or at least 99% sequence identity to a sequence of Table 2B) or one or more polynucleotides encoding a CasX variant protein and a gNA, and further comprising a targeting sequence wherein the targeting sequence of the gNA is complementary to, and therefore is capable of hybridizing with, a SOD1 target nucleic acid. In the foregoing embodiment, the targeting sequence can be a sequence of Table 3, or a sequence having at least about 65%, at least about 75%, at least about 85%, or at least about 95% identity thereto. In some cases, the CasX:gNA system further comprises a donor template nucleic acid.

In some embodiments, the disclosure provides methods of modifying a SOD1 target nucleic acid comprising one or more mutations in a population of cells, the method comprising introducing into each cell of the population: a) a CasX:gNA system of any of the embodiments described herein; b) nucleic acid encoding a CasX:gNA system of any of the embodiments described herein; c) a vector comprising the nucleic acid of (b); d) a VLP comprising a CasX:gNA system of (a); or e) combinations of two or more of (a)-(d), wherein the SOD1 target nucleic acid sequence of the cells is modified by the CasX protein. In those cases where the CasX is delivered to the cell in the protein form and the gNA is delivered in the RNA form, the CasX and gNA can be pre-complexed and delivered as an RNP. In some embodiments of the method, the targeting sequence of the gNA is selected from a sequence of Table 3, or a sequence having at least about 65%, at least about 75%, at least about 85%, or at least about 95% identity thereto. Upon hybridization with the target nucleic acid by the CasX and the gNA, the CasX introduces one or more single-strand breaks or double-strand breaks within or near the SOD1 gene that result in a modification of the target nucleic acid such as a permanent indel (deletion or insertion), mutation, or correction in the target nucleic acid, as described herein, with a corresponding modulation of expression or alteration in the function of the SOD1 gene product, thereby creating an edited cell. In other embodiments, the method comprises contacting the target nucleic acid sequence with a plurality of gNAs targeted to different or overlapping portions of the SOD1 gene wherein the CasX protein introduces multiple breaks in the target nucleic acid sequence that result in a permanent indel (deletion or insertion), mutation, or correction in the target nucleic acid, as described herein, with a corresponding modulation of expression or alteration in the function of the SOD1 gene product, thereby creating an edited cell. In some embodiments, the method comprises insertion of a donor template into the break site(s) of the SOD1 target nucleic acid sequence of the cells of the population. Depending on whether the system is used to knock-down/knock-out a mutant form of SOD1 or is used to knock-in a corrective sequence, the donor template can be a short single-stranded or double-stranded oligonucleotide, or can be a long single-stranded or double-stranded oligonucleotide. For knock-down/knock-outs, the donor template sequence is typically not identical to the genomic sequence that it replaces. The donor template may contain one or more single base changes, insertions, deletions, inversions or rearrangements with respect to the genomic sequence, provided that there is sufficient homology with the target nucleic acid sequence to support homology-directed repair, which can result in a frame-shift or other mutation such that the non-functional SOD1 protein is not expressed or is expressed at a lower level. In some embodiments, the donor template sequence comprises a non-homologous sequence flanked by two regions of homology to the break sites of the target nucleic acid, facilitating insertion of the non-homologous sequence at the target region which can be mediated by homology-directed repair (HDR) or homology-independent targeted integration (HITI). In other cases, an exogenous donor template may comprise a corrective sequence, wherein the sequence is flanked by an upstream sequence and a downstream sequence with homology adjacent to the break sites in the target nucleic acid, facilitating insertion of the donor template sequence. In a particular embodiment of the foregoing, gNAs targeting the upstream sequence Exon 1 and Intron 1 can be used to introduce breaks that permit the insertion of full length cDNA encoding the SOD1 protein, replacing the mutated endogenous SOD1 gene and restoring protein expression. The exogenous sequence inserted by HITI can be any length, for example, a relatively short sequence of between 1 and 50 nucleotides in length, or a longer sequence of about 50-1000 nucleotides in length. The lack of homology can be, for example, having no more than 20-50% sequence identity and/or lacking in specific hybridization at low stringency. In other cases, the lack of homology can further include a criterion of having no more than 5, 6, 7, 8, or 9 bp identity.

In some embodiments, the method of the disclosure provides CasX protein and gNA pairs that generate site-specific double strand breaks (DSBs) or single strand breaks (SSBs) (e.g., when the CasX protein is a nickase that can cleave only one strand of a target nucleic acid) within double-stranded DNA (dsDNA) target nucleic acids, which can then be repaired either by non-homologous end joining (NHEJ), homology-directed repair (HDR), homology-independent targeted integration (HITI), micro-homology mediated end joining (MMEJ), single strand annealing (SSA) or base excision repair (BER). In some cases, contacting a SOD1 gene with a gene editing pair occurs under conditions that are permissive for non-homologous end joining or homology-directed repair. Thus, in some cases, the methods provided herein include contacting the SOD1 gene with a donor template by introducing the donor template (either in vitro outside of a cell, in vitro inside a cell, in vivo inside a cell, or ex vivo), wherein the donor template, a portion of the donor template, a copy of the donor template, or a portion of a copy of the donor template integrates into the SOD1 gene to correct the one or more mutations or to replace the defective SOD1 gene. The donor template sequence may comprise certain sequence differences as compared to the genomic sequence, e.g., restriction sites, nucleotide polymorphisms, selectable markers (e.g., drug resistance genes, fluorescent proteins, enzymes etc.), etc., which may be used to assess for successful insertion of the donor nucleic acid at the cleavage site or, in some cases, may be used for other purposes (e.g., to signify expression at the targeted genomic locus). Alternatively, these sequence differences may include flanking recombination sequences such as FLPs, loxP sequences, or the like, that can be activated at a later time for removal of the marker sequence.

In those cases where the modification results in a knockdown or knock-out of the SOD1 gene, expression of the SOD1 protein is reduced by at least about 10%, at least about 20%, at least about 30%, at least about 40%, at least about 50%, at least about 60%, at least about 70%, at least about 80%, or at least about 90% in comparison to cells that have not been modified. In other cases, the SOD1 target nucleic acid of the cells of the population is modified such that expression of the SOD1 protein cannot be detected. In other cases, wherein the modification results in correction of the one or more mutations of the SOD1 gene in the cells of the population (e.g., insertion of a corrective donor template), the modification results in expression of functional SOD1 protein (e.g., the protein of SEQ ID NO: 100) by the modified cells. Expression of a SOD1 protein can be measured by flow cytometry, ELISA, cell-based assays or other methods know in the art (Lee, H., et al. Assay Development for High Content Quantification of SOD1 Mutant Protein Aggregate Formation in Living Cells. J Vis Exp. 128:56425 (2017)), or as described in the Examples.

In other embodiments of the method of modifying a target nucleic acid sequence, modifying the SOD1 gene comprises binding of a CasX to the target nucleic acid sequence without cleavage. In some embodiments, the CasX is a catalytically inactive CasX (dCasX) protein that retains the ability to bind to the gNA and to the SOD1 target nucleic acid sequence comprising the mutation but lacks the ability to cleave the nucleic acid sequence, thereby interfering with transcription of mutant SOD1 allele. In some embodiments, the dCasX comprises a mutation at residues D672, E769, and/or D935 corresponding to the CasX protein of SEQ ID NO:1 or D659, E756 and/or D922 corresponding to the CasX protein of SEQ ID NO: 2. In some embodiments, the mutation is a substitution of alanine or glycine for the residue.

In some embodiments of the method, the cells of the modified population are eukaryotic, which can include rodent cells, mouse cells, rat cells, primate cells, non-human primate cells, human cells, embryonic stem (ES) cells, induced pluripotent stem cell (iPSC), central nervous system (CNS) cells, and peripheral nervous system (PNS) cells. In the case of cells of the CNS, the cells can be neuron cells, which can include spinal motor neuron cells or oligodendrocyte cells. In the case of cells of the PNS, the cells can include glial cells or Schwann cells.

In some embodiments, the disclosure provides methods of modifying a SOD1 target nucleic acid in a population of cells by in vitro or ex vivo methods. In other embodiments, the disclosure provides methods of modifying a SOD1 target nucleic acid in a population of cells in vivo in a subject. In one embodiment of the method of in vivo modification, the method comprises administration of a vector of the embodiments described herein to the subject at a therapeutically effective dose. In one embodiment, the vector is administered to the subject at a dose of at least about $1\times10^8$ vector genomes (vg), at least about $1\times10^9$ vg, at least about $1\times10^{10}$ vg at least about $1\times10^{11}$ vg, or at least about $1\times10^{12}$ vg, or at least about $1\times10^{13}$ vg, or at least about $1\times10^{14}$ vg, or at least about $1\times10^{15}$ vg, or at least about $1\times10^{16}$ vg. In another embodiment of the method of in vivo modification, the method comprises administration of a VLP to the subject at a therapeutically effective dose. In one embodiment, the VLP is administered to the subject at a dose of at least about $1\times10^8$ particles, at least about $1\times10^9$ particles, at least about $1\times10^{10}$ particles at least about $1\times10^{11}$ particles, or at least about $1\times10^{12}$ particles, or at least about $1\times10^{13}$ particles, or at least about $1\times10^{14}$ particles, or at least about $1\times10^{15}$ particles, or at least about $1\times10^{16}$ particles. In the foregoing embodiments of the paragraph, the vector or VLP is administered to the subject by a route of administration selected from intraparenchymal, intravenous, intra-arterial, intracerebroventricular, intracisternal, intrathecal, intracranial, lumbar, intraperitoneal, or combinations thereof.

In some embodiments of the method of modifying a SOD1 target nucleic acid in a population of cells, the method further comprises contacting the target nucleic acid sequence of the population of cells with: a) an additional CRISPR nuclease and a gNA targeting a different or overlapping portion of the SOD1 target nucleic acid compared to the first gNA; b) a polynucleotide encoding the additional CRISPR nuclease and the gNA of (a); c) a vector comprising the polynucleotide of (b); or d) a VLP comprising the additional CRISPR nuclease and the gNA of (a), wherein the contacting results in modification of the SOD1 target nucleic acid at a different location in the sequence compared to the first gNA. In some cases, the additional CRISPR nuclease is a CasX protein having a sequence different from the CasX protein of any of the preceding claims. In other cases, the additional CRISPR nuclease is not a CasX protein. In other cases, the additional CRISPR nuclease is selected from the group consisting of Cas9, Cas12a, Cas12b, Cas12c, Cas12d (CasY), Cas13a, Cas13b, Cas13c, Cas13d, CasX, CasY, Cas14, Cpf1, C2c1, Csn2, Cas Phi, and sequence variants thereof.

Methods of introducing a nucleic acid (e.g., a nucleic acid comprising a donor polynucleotide sequence, one or more nucleic acids encoding a CasX protein and/or gNA, or a vector comprising same) into a cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, nucleofection, electroporation, direct addition by cell penetrating CasX proteins that are fused to or recruit donor DNA, cell squeezing, calcium phosphate precipitation, direct microinjection, nanoparticle-mediated nucleic acid delivery, and the like.

In some embodiments of the method, a CasX can be provided as an RNA sequence. The RNA can be provided by direct chemical synthesis, or may be transcribed in vitro from a DNA (e.g., a DNA encoding an mRNA comprising a sequence encoding the CasX protein variant). Once synthesized, the RNA may, for example, be introduced into a cell by any of the well-known techniques for introducing nucleic acids into cells, including, but not limited to microinjection, electroporation, and transfection, for translation into the CasX protein.

Nucleic acids may be introduced into the cells using well-developed transfection techniques, and the commercially available TransMessenger® reagents from Qiagen, Stemfect™ RNA Transfection Kit from Stemgent, and TransIT®-mRNA Transfection Kit from Mirus Bio LLC, Lonza nucleofection, Maxagen electroporation and the like.

In other embodiments, the disclosure provides a method of altering a SOD1 target nucleic acid sequence of a cell comprising one or more mutations in the target nucleic acid, comprising contacting said cell with a vector comprising a nucleic acid encoding a CasX:gNA system of the embodiments described herein, wherein the gNA comprises a targeting sequence complementary to the target nucleic acid, and therefore is capable of hybridizing with a sequence encoding the SOD1 protein or the SOD1 regulatory element comprising one or more mutations, or the complement of these sequences. In other embodiments of the method, the vector is a VLP comprising a CasX and gNA complexed in an RNP and, optionally, a donor template (described more fully, supra), wherein the VLP has tropism for the neuronal or glial cells and is able to deliver the RNP for the editing of the SOD1 gene, as described herein. The VLP embodiments utilized in the foregoing method of editing are described herein.

Introducing recombinant expression vectors comprising sequences encoding the CasX:gNA systems (and, optionally, the donor sequences) of the disclosure into cells under in vitro conditions can occur in any suitable culture media and under any suitable culture conditions that promote the survival of the cells. Introducing recombinant expression vectors into a target cell can be carried out in vivo, in vitro or ex vivo. In some embodiments of the method, vectors may be provided directly to a target host cell. For example, cells may be contacted with vectors comprising the subject nucleic acids (e.g., recombinant expression vectors having the donor template sequence and nucleic acid encoding the CasX and gNA) such that the vectors are taken up by the cells. Methods for contacting cells with nucleic acid vectors that are plasmids include electroporation, calcium chloride transfection, microinjection, and lipofection are well known in the art.

Vectors used for providing the nucleic acids encoding gNAs and/or CasX proteins to a target host cell can include suitable promoters for driving the expression, that is, transcriptional activation of the nucleic acid of interest. In some cases, the encoding nucleic acid of interest will be operably linked to a promoter. This may include ubiquitously acting promoters, for example, the CMV-beta-actin promoter, or inducible promoters, such as promoters that are active in particular cell populations or that respond to the presence of drugs such as tetracycline or kanamycin. By transcriptional activation, it is intended that transcription will be increased above basal levels in the target host cell comprising the vector by at least about 10-fold, by at least about 100-fold, more usually by at least about 1000-fold. In addition, vectors used for providing a nucleic acid encoding a gNA and/or a CasX protein to a cell may include nucleic acid sequences that encode for selectable markers in the target cells, so as to identify cells that have taken up the CasX protein and/or the gNA.

For viral vector delivery, cells can be contacted with viral particles comprising the subject viral expression vectors and the nucleic acid encoding the CasX and gNA and, optionally, the donor template. In some embodiments, the vector is an Adeno-Associated Viral (AAV) vector, wherein the AAV is selected from AAV1, AAV2, AAV3, AAV4, AAV5, AAV6, AAV7, AAV8, AAV9, AAV10, AAV-Rh74, or AAVRh10. In other embodiments, the vector is a retroviral vector. In other embodiments, the vector is a lentiviral vector. Retroviruses, for example, lentiviruses, may be suitable for use in methods of the present disclosure. Commonly used retroviral vectors are "defective", e.g., are unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, and this envelope protein determines the specificity or tropisms of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Nucleic acids can also be introduced by direct micro-injection (e.g., injection of RNA).

The present disclosure provides populations of cells modified by the foregoing methods. In some embodiments, the disclosure provides populations of modified cells wherein the cells have been modified such that at least 70%, at least 75%, at least 80%, at least 85%, at least 90%, or at least 95% of the modified cells do not express a detectable level of SOD1 protein. In other embodiments, the disclosure provides populations of modified cells wherein the cells have been modified such that the expression of SOD1 protein is reduced by at least 70%, at least 75%, at least 80%, at least 85%, at least 90%, or at least 95% compared to cells that have not been modified. In other embodiments, the disclosure provides populations of modified cells wherein the mutation of the SOD1 gene is corrected in the modified cells of the population, resulting in expression of functional SOD1 protein (e.g., the protein of SEQ ID NO: 100) by the modified cells. In some cases, the population of modified cells can be used in methods of treatment in a subject having a SOD1-related disorder, such as ALS, described more fully below.

VI. Polynucleotides and Vectors

In other embodiments, the present disclosure provides polynucleotides encoding the CasX proteins and the polynucleotides of the gNAs (e.g., the gDNAs and gRNAs) described herein, as well as sequences complementary to polynucleotides encoding the CasX proteins and the gNAs embodiments. In an additional embodiment, the disclosure provides donor template polynucleotides encoding portions or all of an SOD1 gene. In yet further embodiments, the disclosure relates to vectors comprising polynucleotides encoding the CasX proteins and the gNAs described herein. In yet further embodiments, the disclosure provides vectors comprising the donor templates described herein.

In some embodiments, the disclosure provides polynucleotide sequences encoding the reference CasX of SEQ ID NOS: 1-3. In other embodiments, the disclosure provides polynucleotide sequences encoding the CasX variants of any of the embodiments described herein, including the CasX protein variants of Table 4 or sequences having at least about 50%, at least about 60%, at least about 70%, at least about 80%, or at least about 90%, or at least about 95%, or at least about 96%, or at least about 97%, or at least about 98%, or at least about 99% sequence identity to a sequence of Table 4. In some embodiments, the disclosure provides an isolated polynucleotide sequence encoding a gNA sequence of any of the embodiments described herein, including the sequences of Tables 2A and 2B, together with the targeting sequences of Table 3.

In some embodiments, the polynucleotide encodes a gNA scaffold sequence set forth in Table 2A or Table 2B, or a sequence having at least about 50%, at least about 60%, at least about 70%, at least about 80%, at least about 90%, at least about 95%, at least about 96%, at least about 97%, at least about 98%, at least about 99% sequence identity thereto. In other embodiments, the disclosure provides a targeting sequence polynucleotide set forth in Table 3, or a sequence having at least about 65%, at least about 75%, at least about 85%, or at least about 95% identity to a sequence provided in Table 3. In some embodiments, the targeting sequence polynucleotide is, in turn, linked to the gNA scaffold sequence; either as a sgNA or a dgNA. In other embodiments, the disclosure provides a targeting polynucleotide having a sequence having one or more single nucleotide polymorphisms (SNP) relative to a sequence provided in Table 3.

In other embodiments, the disclosure provides an isolated polynucleotide sequence encoding a gNA comprising a targeting sequence that is complementary to, and therefore hybridizes with the SOD1 gene. In other embodiments, the polynucleotide sequence encodes a gNA comprising a targeting sequence that hybridizes with a SOD1 exon. In other embodiments, the polynucleotide sequence encodes a gNA comprising a targeting sequence that hybridizes with a SOD1 intron. In other embodiments, the polynucleotide sequence encodes a gNA comprising a targeting sequence that hybridizes with a SOD1 intron-exon junction. In other embodiments, the polynucleotide sequence encodes a gNA comprising a targeting sequence that hybridizes with an intergenic region of the SOD1 gene. In other embodiments, the polynucleotide sequence encodes a gNA comprising a targeting sequence that hybridizes with a SOD1 regulatory element. In some cases, the SOD1 regulatory element is 5' of the SOD1 gene. In other cases, the SOD1 regulatory element is 3' of the SOD1 gene. In some cases, the SOD1 regulatory element is in an intron of the SOD1 gene. In other cases, the SOD1 regulatory element comprises the 5' UTR of the SOD1 gene. In still other cases, the SOD1 regulatory element comprises the 3'UTR of the SOD1 gene. In some cases of the foregoing embodiment, the SOD1 sequence is a wild-type sequence. In other cases, the SOD1 sequence comprises one or more mutations.

In other embodiments, the disclosure provides donor template nucleic acids, wherein the donor template comprises a nucleotide sequence having homology to a SOD1 target nucleic acid sequence. In some embodiments, the SOD1 donor template is intended for gene editing and comprises at least a portion of a SOD1 gene. In some embodiments, the SOD1 donor template comprises a sequence that hybridizes with the SOD1 gene. In other embodiments, the SOD1 donor sequence comprises a sequence that encodes at least a portion of a SOD1 exon. In other embodiments, the SOD1 donor sequence has a sequence that encodes at least a portion of a SOD1 intron. In other embodiments, the SOD1 donor sequence has a sequence that encodes at least a portion of with a SOD1 intron-exon junction. In other embodiments, the SOD1 donor sequence has a sequence that encodes at least a portion of an intergenic region of the SOD1 gene. In other embodiments, the SOD1 donor sequence has a sequence that encodes at least a portion of a SOD1 regulatory element. In some cases of the foregoing donor template embodiments, the SOD1 sequence is a wild-type sequence that encodes all or a portion the SOD1 protein (e.g., the protein of SEQ ID NO: 100). In other cases, the SOD1 sequence comprises one or more mutations relative to a wild-type SOD1 gene. In the foregoing embodiments, the donor template ranges in size from 10-15,000 nucleotides. In some embodiments, the donor template is a single-stranded DNA template. In other embodiments, the donor template is a single stranded RNA template. In other embodiments, the donor template is a double-stranded DNA template.

In other aspects, the disclosure relates to methods to produce polynucleotide sequences encoding the reference CasX, the CasX variants, or the gNA of any of the embodiments described herein, or sequences complementary to the polynucleotide sequences, including homologous variants thereof, as well as methods to express the proteins expressed or RNA transcribed by the polynucleotide sequences. In general, the methods include producing a polynucleotide sequence coding for the reference CasX, the CasX variants, or the gNA of any of the embodiments described herein and incorporating the encoding gene into an expression vector appropriate for a host cell. For production of the encoded reference CasX, the CasX variants, or the gNA of any of the embodiments described herein, the methods include transforming an appropriate host cell with an expression vector comprising the encoding polynucleotide, and culturing the host cell under conditions causing or permitting the resulting reference CasX, the CasX variants, or the gNA of any of the embodiments described herein to be expressed or transcribed in the transformed host cell, thereby producing the reference CasX, the CasX variants, or the gNA, which are recovered by methods described herein or by standard purification methods known in the art. Standard recombinant techniques in molecular biology are used to make the polynucleotides and expression vectors of the present disclosure.

In accordance with the disclosure, nucleic acid sequences that encode the reference CasX, the CasX variants, or the gNA of any of the embodiments described herein (or their complement) are used to generate recombinant DNA molecules that direct the expression in appropriate host cells. Several cloning strategies are suitable for performing the present disclosure, many of which are used to generate a construct that comprises a gene coding for a composition of the present disclosure. In some embodiments, the cloning strategy is used to create a gene that encodes a construct that comprises nucleotides encoding the reference CasX, the CasX variants, or the gNA that is used to transform a host cell for expression of the composition.

In some approaches, a construct is first prepared containing the DNA sequence encoding a reference CasX, a CasX variant, or a gNA. Exemplary methods for the preparation of such constructs are described in the Examples. The construct is then used to create an expression vector suitable for transforming a host cell, such as a prokaryotic or eukaryotic host cell for the expression and recovery of the protein construct, in the case of the CasX, or the gNA. Where desired, the host cell is an *E. coli*. In other embodiments, the host cell is a eukaryotic cell. The eukaryotic host cell can be selected from Baby Hamster Kidney fibroblast (BHK) cells, human embryonic kidney 293 (HEK293), human embryonic kidney 293T (HEK293T), NS0 cells, SP2/0 cells, YO myeloma cells, P3X63 mouse myeloma cells, PER cells, PER.C6 cells, hybridoma cells, NIH3T3 cells, CV-1 (simian) in Origin with SV40 genetic material (COS), HeLa, Chinese hamster ovary (CHO), or yeast cells, or other eukaryotic cells known in the art suitable for the production of recombinant products. Exemplary methods for the creation of expression vectors, the transformation of host cells and the expression and recovery of reference CasX, the CasX variants, or the gNA are described in the Examples.

The gene encoding the reference CasX, the CasX variants, or the gNA constructs can be made in one or more steps, either fully synthetically or by synthesis combined with enzymatic processes, such as restriction enzyme-mediated cloning, PCR and overlap extension, including methods more fully described in the Examples. The methods disclosed herein can be used, for example, to ligate sequences of polynucleotides encoding the various components (e.g., CasX and gNA) genes of a desired sequence. Genes encoding polypeptide compositions are assembled from oligonucleotides using standard techniques of gene synthesis.

In some embodiments, the nucleotide sequence encoding a CasX protein or a gNA is codon optimized. This type of optimization can entail a mutation of an encoding nucleotide sequence to mimic the codon preferences of the intended host organism or cell while encoding the same CasX protein or gNA. Thus, the codons can be changed, but the encoded protein or gNA remains unchanged. For example, if the intended target cell of the CasX protein was a human cell, a human codon-optimized CasX-encoding nucleotide sequence could be used. As another non-limiting example, if the intended host cell were a mouse cell, then a mouse codon-optimized CasX-encoding nucleotide sequence could be generated. As another non-limiting example, if the intended host cell were a plant cell, then a plant codon-optimized CasX protein variant-encoding nucleotide sequence could be generated. As another non-limiting example, if the intended host cell were an insect cell, then an insect codon-optimized CasX protein-encoding nucleotide sequence could be generated. The gene design can be performed using algorithms that optimize codon usage and amino acid composition appropriate for the host cell utilized in the production of the reference CasX, the CasX variants, or the gNA. In one method of the disclosure, a library of polynucleotides encoding the components of the constructs is created and then assembled, as described above. The resulting genes are then assembled and the resulting genes used to transform a host cell and produce and recover the reference CasX, the CasX variants, or the gNA compositions for evaluation of its properties, as described herein.

In some embodiments, a nucleotide sequence encoding a gNA is operably linked to a control element, e.g., a transcriptional control element, such as a promoter. In some embodiments, a nucleotide sequence encoding a CasX protein is operably linked to a control element, e.g., a transcriptional control element, such as a promoter. In other cases, the nucleotide encoding the CasX and gNA are linked and are operably linked to a single control element. In some cases, the promoter is a constitutively active promoter. In some cases, the promoter is a regulatable promoter. In some cases, the promoter is an inducible promoter. In some cases, the promoter is a tissue-specific promoter. In some cases, the promoter is a cell type-specific promoter. In some cases, the transcriptional control element (e.g., the promoter) is functional in a targeted cell type or targeted cell population. For example, in some cases, the transcriptional control element can be functional in eukaryotic cells, e.g., neurons, spinal motor neurons, oligodendrocytes, or glial cells.

Non-limiting examples of eukaryotic promoters (promoters functional in a eukaryotic cell) include EF1alpha, EF1alpha core promoter, those from cytomegalovirus (CMV) immediate early, herpes simplex virus (HSV) thymidine kinase, early and late SV40, long terminal repeats (LTRs) from retrovirus, and mouse metallothionein-I. Further non-limiting examples of eukaryotic promoters include the CMV promoter full-length promoter, the minimal CMV promoter, the chicken β-actin promoter, the hPGK promoter, the HSV TK promoter, the Mini-TK promoter, the human synapsin I promoter which confers neuron-specific expression, the Mecp2 promoter for selective expression in neurons, the minimal IL-2 promoter, the Rous sarcoma virus enhancer/promoter (single), the spleen focus-forming virus long terminal repeat (LTR) promoter, the SV40 promoter, the SV40 enhancer and early promoter, the TBG promoter: promoter from the human thyroxine-binding globulin gene (Liver specific), the PGK promoter, the human ubiquitin C promoter, the UCOE promoter (Promoter of HNRPA2B1-CBX3), the Histone H2 promoter, the Histone H3 promoter, the U1 al small nuclear RNA promoter (226 nt), the U1b2 small nuclear RNA promoter (246 nt) 26, the TTR minimal enhancer/promoter, the b-kinesin promoter, the human eIF4A1 promoter, the ROSA26 promoter and the glyceraldehyde 3-phosphate dehydrogenase (GAPDH) promoter. In some embodiments, the promoter used in the gNA construct is U6 (Kunkel, G R et al. U6 small nuclear RNA is transcribed by RNA polymerase III. Proc Natl Acad Sci USA. 83(22):8575 (1986)).

Selection of the appropriate vector and promoter is well within the level of ordinary skill in the art, as it related to controlling expression, e.g., for modifying a SOD1 gene. The expression vector may also contain a ribosome binding site for translation initiation and a transcription terminator. The expression vector may also include appropriate sequences for amplifying expression. The expression vector may also include nucleotide sequences encoding protein tags (e.g., 6xHis tag, hemagglutinin tag, fluorescent protein, etc.) that can be fused to the CasX protein, thus resulting in a chimeric CasX protein that are used for purification or detection.

In some embodiments, a nucleotide sequence encoding a gNA variant and/or a CasX protein is operably linked to an inducible promoter, a constitutively active promoter, a spatially restricted promoter (i.e., transcriptional control element, enhancer, tissue specific promoter, cell type specific promoter, etc.), or a temporally restricted promoter.

In certain embodiments, suitable promoters can be derived from viruses and can therefore be referred to as viral promoters, or they can be derived from any organism, including prokaryotic or eukaryotic organisms. Suitable promoters can be used to drive expression by any RNA polymerase (e.g., pol I, pol II, pol III). Exemplary promoters include, but are not limited to the SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, a human HI promoter (HI), a POL1 promoter, a 7SK promoter, tRNA promoters and the like.

In some embodiments, a nucleotide sequence encoding a CasX and gNA and, optionally, a donor template, is operably linked to (under the control of) an inducible promoter operable in a eukaryotic cell. Examples of inducible promoters may include, but are not limited to, T7 RNA polymerase promoter, T3 RNA polymerase promoter, isopropyl-beta-D-thiogalactopyranoside (IPTG)—regulated promoter, lactose induced promoter, heat shock promoter, tetracycline-regulated promoter, kanamycin-regulated promoter, steroid-regulated promoter, metal-regulated promoter, estrogen receptor-regulated promoter, etc. Inducible promoters can therefore, in some embodiments, be regulated by molecules including, but not limited to, doxycycline; estrogen and/or an estrogen analog; IPTG; etc. Additional examples of inducible promoters include, without limitation, chemically/biochemically-regulated and physically-regulated promoters such as alcohol-regulated promoters, kanamycin-regulated promoters, tetracycline-regulated promoters (e.g., anhydrotetracycline (aTc)—responsive promoters and other tetracycline—responsive promoter systems, which include a tetracycline repressor protein (tetR), a tetracycline operator sequence (tetO) and a tetracycline transactivator fusion protein (tTA), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some cases, the promoter is a spatially restricted promoter (i.e., cell type specific promoter, tissue specific promoter, etc.) such that in a multi-cellular organism, the promoter is active (i.e., "ON") in a subset of specific cells. Spatially restricted promoters may also be referred to as enhancers, transcriptional control elements, control sequences, etc. Any convenient spatially restricted promoter may be used as long as the promoter is functional in the targeted host cell (e.g., eukaryotic cell; prokaryotic cell).

In some cases, the promoter is a reversible promoter. Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR, etc.), tetracycline regulated promoters, (e.g., promoter systems including Tet Activators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

Recombinant expression vectors of the disclosure can also comprise elements that facilitate robust expression of CasX proteins and/or transcription of gNAs of the disclosure. For example, recombinant expression vectors can include one or more of a polyadenylation signal (PolyA), an intronic sequence or a post-transcriptional regulatory element such as a woodchuck hepatitis post-transcriptional regulatory element (WPRE). Exemplary polyA sequences include hGH poly(A) signal (short), HSV TK poly(A) signal, synthetic polyadenylation signals, SV40 poly(A) signal, β-globin poly (A) signal and the like. A person of ordinary skill in the art will be able to select suitable elements to include in the recombinant expression vectors described herein.

The polynucleotides encoding the reference CasX, the CasX variants, or the gNA sequences can then be individually cloned into an expression vector. Vectors include bacterial plasmids, viral vectors, and the like. In some embodiments, the vector is a recombinant expression vector that comprises a nucleotide sequence encoding a CasX protein. In other embodiments, the disclosure provides a recombinant expression vector comprising a nucleotide sequence encoding a CasX protein and a nucleotide sequence encoding a gNA. In some cases, the nucleotide sequence encoding the CasX protein variant and/or the nucleotide sequence encoding the gNA are operably linked to a promoter that is operable in a cell type of choice. In other embodiments, the nucleotide sequence encoding the CasX protein variant and the nucleotide sequence encoding the gNA are provided in separate vectors.

In some embodiments, provided herein are one or more recombinant expression vectors comprising: (i) a nucleotide sequence of a donor template nucleic acid where the donor template comprises a nucleotide sequence having homology to a SOD1 sequence of a target nucleic acid (e.g., a target genome); (ii) a nucleotide sequence that encodes a gNA (e.g., gRNA), that hybridizes to a sequence of the target SOD1 locus of the targeted genome (e.g., configured as a single or dual guide RNA) operably linked to a promoter that is operable in a target cell such as a eukaryotic cell; and (iii) a nucleotide sequence encoding a CasX protein operably linked to a promoter that is operable in a target cell such as a eukaryotic cell. In some embodiments, the sequences comprising the donor template and encoding the gNA and the CasX proteins are in different recombinant expression vectors, and in other embodiments one or more or all three polynucleotide sequences (for the donor template, CasX and gNA) are in the same recombinant expression vector.

The nucleic acid sequence is inserted into the vector by a variety of procedures. In general, DNA is inserted into an appropriate restriction endonuclease site(s) using techniques known in the art. Vector components generally include, but are not limited to, one or more of a signal sequence, an origin of replication, one or more marker genes, an enhancer element, a promoter, and a transcription termination sequence. Construction of suitable vectors containing one or more of these components employs standard ligation techniques which are known to the skilled artisan. Such techniques are well known in the art and well described in the scientific and patent literature. Various vectors are publicly available. The vector may, for example, be in the form of a plasmid, cosmid, viral particle, or phage that may conveniently be subjected to recombinant DNA procedures, and the choice of vector will often depend on the host cell into which it is to be introduced. Thus, the vector may be an autonomously replicating vector, i.e., a vector, which exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated. Once introduced into a suitable host cell, expression of the SOD1 can be determined using any nucleic acid or protein assay known in the art. For example, the presence of transcribed mRNA of reference CasX or the CasX variants can be detected and/or quantified by conventional hybridization assays (e.g., Northern blot analysis), amplification procedures (e.g. RT-PCR), SAGE (U.S. Pat. No. 5,695,937), and array-based technologies (see e.g., U.S. Pat. Nos. 5,405,783, 5,412,087 and 5,445,934), using probes complementary to any region of SOD1 polynucleotide.

The disclosure provides for the use of plasmid expression vectors containing replication and control sequences that are compatible with and recognized by the host cell and are operably linked to the gene encoding the polypeptide for controlled expression of the polypeptide or transcription of the RNA. Such vector sequences are well known for a variety of bacteria, yeast, and viruses. Useful expression vectors that can be used include, for example, segments of chromosomal, non-chromosomal and synthetic DNA sequences. "Expression vector" refers to a DNA construct containing a DNA sequence that is operably linked to a suitable control sequence capable of effecting the expression of the DNA encoding the polypeptide in a suitable host. The requirements are that the vectors are replicable and viable in the host cell of choice. Low- or high-copy number vectors may be used as desired. The control sequences of the vector include a promoter to effect transcription, an optional operator sequence to control such transcription, a sequence encoding suitable mRNA ribosome binding sites, and sequences that control termination of transcription and translation. The promoter may be any DNA sequence, which shows transcriptional activity in the host cell of choice and may be derived from genes encoding proteins either homologous or heterologous to the host cell.

The recombinant expression vectors can be delivered to the target host cells by a variety of methods, as described more fully, below. Such methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, nucleofection, electroporation, direct addition by cell penetrating CasX proteins that are fused to or recruit donor DNA, cell squeezing, calcium phosphate precipitation, direct microinjection, nanoparticle-mediated nucleic acid delivery, and the like.

A recombinant expression vector sequence can be packaged into a virus or virus-like particle (also referred to herein as a "particle", or "virion") for subsequent infection and transformation of a cell, ex vivo, in vitro or in vivo. Such particles or virions will typically include proteins that encapsidate or package the vector genome. Suitable expression vectors may include viral expression vectors based on vaccinia virus; poliovirus; adenovirus; a retroviral vector (e.g., Murine Leukemia Virus), spleen necrosis virus, and vectors derived from retroviruses such as Rous Sarcoma Virus, Harvey Sarcoma Virus, avian leukosis virus, a lentivirus, human immunodeficiency virus, myeloproliferative sarcoma virus, and mammary tumor virus; and the like. In some embodiments, a recombinant expression vector of the present disclosure is a recombinant adeno-associated virus (AAV) vector. In some embodiments, a recombinant expression vector of the present disclosure is a recombinant lentivirus vector. In some embodiments, a recombinant expression vector of the present disclosure is a recombinant retroviral vector.

AAV is a small (20 nm), nonpathogenic virus that is useful in treating human diseases in situations that employ a viral vector for delivery to a cell such as a eukaryotic cell, either in vivo or ex vivo for cells to be prepared for administration to a subject. A construct is generated, for example a construct encoding any of the CasX protein and/or gNA embodiments as described herein, and is flanked with AAV inverted terminal repeat (ITR) sequences, thereby enabling packaging of the AAV vector into an AAV viral particle.

An "AAV" vector may refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are many known serotypes of primate AAVs. In some embodiments, the AAV vector is selected from AAV1, AAV2, AAV3, AAV4, AAV5, AAV6, AAV7, AAV8, AAV9, AAV 10, AAV-Rh74 (Rhesus macaque-derived AAV), and AAVRh10, and modified capsids of these serotypes. For example, serotype AAV-2 is used to refer to an AAV which contains capsid proteins encoded from the cap gene of AAV-2 and a genome containing 5' and 3' ITR sequences from the same AAV-2 serotype. Pseudotyped AAV refers to an AAV that contains capsid proteins from one serotype and a viral genome including 5'-3' ITRs of a second serotype. Pseudotyped rAAV would be expected to have cell surface binding properties of the capsid serotype and genetic properties consistent with the ITR serotype. Pseudotyped recombinant AAV (rAAV) are produced using standard techniques described in the art. As used herein, for example, rAAV1 may be used to refer an AAV having both capsid proteins and 5'-3' ITRs from the same serotype or it may refer to an AAV having capsid proteins from serotype 1 and 5'-3' ITRs from a different AAV serotype, e.g., AAV serotype 2. For each example illustrated herein the description of the vector design and production describes the serotype of the capsid and 5'-3' ITR sequences.

An "AAV virus" or "AAV viral particle" refers to a viral particle composed of at least one AAV capsid protein (preferably by all of the capsid proteins of a wild-type AAV) and an encapsidated polynucleotide. If the particle additionally comprises a heterologous polynucleotide (i.e., a polynucleotide other than a wild-type AAV genome to be delivered to a mammalian cell), it is typically referred to as "rAAV". An exemplary heterologous polynucleotide is a polynucleotide comprising a CasX protein and/or sgRNA and, optionally, a donor template of any of the embodiments described herein.

By "adeno-associated virus inverted terminal repeats" or "AAV ITRs" is meant the art recognized regions found at each end of the AAV genome which function together in cis as origins of DNA replication and as packaging signals for the virus. AAV ITRs, together with the AAV rep coding region, provide for the efficient excision and rescue from, and integration of a nucleotide sequence interposed between two flanking ITRs into a mammalian cell genome.

The nucleotide sequences of AAV ITR regions are known. See, for example Kotin, R. M. (1994) Human Gene Therapy 5:793-801; Berns, K. I. "Parvoviridae and their Replication" in Fundamental Virology, $2^{nd}$ Edition, (B. N. Fields and D. M. Knipe, eds.). As used herein, an AAV ITR need not have the wild-type nucleotide sequence depicted, but may be altered, e.g., by the insertion, deletion or substitution of nucleotides. Additionally, the AAV ITR may be derived from any of several AAV serotypes, including without limitation, AAV1, AAV2, AAV3, AAV4, AAV5, AAV6, AAV7, AAV8, AAV9, AAV10, AAV-Rh74, and AAVRh10, and modified capsids of these serotypes. Furthermore, 5' and 3' ITRs which flank a selected nucleotide sequence in an AAV vector need not necessarily be identical or derived from the same AAV serotype or isolate, so long as they function as intended, i.e., to allow for excision and rescue of the sequence of interest from a host cell genome or vector, and to allow integration of the heterologous sequence into the recipient cell genome when AAV Rep gene products are present in the cell. Use of AAV serotypes for integration of heterologous sequences into a host cell is known in the art (see, e.g., WO2018195555A1 and US20180258424A1, incorporated by reference herein.)

By "AAV rep coding region" is meant the region of the AAV genome which encodes the replication proteins Rep 78, Rep 68, Rep 52 and Rep 40. These Rep expression products have been shown to possess many functions, including recognition, binding and nicking of the AAV origin of DNA replication, DNA helicase activity and modulation of transcription from AAV (or other heterologous) promoters. The Rep expression products are collectively required for replicating the AAV genome.

By "AAV cap coding region" is meant the region of the AAV genome which encodes the capsid proteins VP1, VP2, and VP3, or functional homologues thereof. These Cap expression products supply the packaging functions which are collectively required for packaging the viral genome.

In some embodiments, AAV capsids utilized for delivery of the encoding sequences for the CasX and gNA, and, optionally, the SOD1 donor template nucleotides to a host cell can be derived from any of several AAV serotypes, including without limitation, AAV1, AAV2, AAV3, AAV4, AAV5, AAV6, AAV7, AAV8, AAV9, AAV10, AAV-Rh74 (Rhesus macaque-derived AAV), and AAVRh10, and the AAV ITRs are derived from AAV serotype 2.

In order to produce rAAV viral particles, an AAV expression vector is introduced into a suitable host cell using known techniques, such as by transfection. Packaging cells are typically used to form virus particles; such cells include HEK293 cells (and other cells known in the art), which package adenovirus. A number of transfection techniques are generally known in the art; see, e.g., Sambrook et al. (1989) Molecular Cloning, a laboratory manual, Cold Spring Harbor Laboratories, N.Y. Particularly suitable transfection methods include calcium phosphate co-precipitation, direct microinjection into cultured cells, electroporation, liposome mediated gene transfer, lipid-mediated transduction, and nucleic acid delivery using high-velocity microprojectiles.

In some embodiments, host cells transfected with the above-described AAV expression vectors are rendered capable of providing AAV helper functions in order to replicate and encapsidate the nucleotide sequences flanked by the AAV ITRs to produce rAAV viral particles. AAV helper functions are generally AAV-derived coding sequences which can be expressed to provide AAV gene products that, in turn, function in trans for productive AAV replication. AAV helper functions are used herein to complement necessary AAV functions that are missing from the AAV expression vectors. Thus, AAV helper functions include one, or both of the major AAV ORFs (open reading frames), encoding the rep and cap coding regions, or functional homologues thereof. Accessory functions can be introduced into and then expressed in host cells using methods known to those of skill in the art. Commonly, accessory functions are provided by infection of the host cells with an unrelated helper virus. In some embodiments, accessory functions are provided using an accessory function vector. Depending on the host/vector system utilized, any of a number of suitable transcription and translation control elements, including constitutive and inducible promoters, transcription enhancer elements, transcription terminators, etc., may be used in the expression vector.

In other embodiments, suitable vectors may include virus-like particles (VLP). Virus-like particles (VLPs) are particles that closely resemble viruses, but do not contain viral genetic material and are therefore non-infectious. In some embodiments, VLPs comprise a polynucleotide encoding a transgene of interest, for example any of the CasX protein and/or a gNA embodiments, and, optionally, SOD1 donor template polynucleotides, described herein, packaged with one or more viral structural proteins. In other embodiments, the VLP comprise a CasX and gNA complexed as an RNP and, optionally, a donor template comprising all or a portion of the SOD1 gene to either knock-down/knock-out the SOD1 gene or a portion of the gene to correct the one or more mutations of the SOD1 gene by insertion via HDR or HITI mechanisms.

In other embodiments, the disclosure provides VLPs produced in vitro that comprise a CasX:gNA RNP complex of the CasX and gNA of any of the embodiments described herein and, optionally, a donor template. Combinations of structural proteins from different viruses can be used to create VLPs, including components from virus families including Parvoviridae (e.g., adeno-associated virus), Retroviridae (e.g., HIV), Flaviviridae (e.g., Hepatitis C virus), Paramyxoviridae (e.g., Nipah) and bacteriophages (e.g., Qβ, AP205). In some embodiments, the disclosure provides VLP systems designed using components of retrovirus, including lentiviruses such as HIV, in which individual plasmids comprising nucleic acids encoding the various components are introduced into a packaging cell that, in turn, produce the VLP. In some embodiments, the disclosure provides VLP having an HIV capsid that contains a CasX:gNA RNP wherein upon administration and entry into a target cell, the RNP molecule is free to be transported into the nucleus of the cell. The foregoing offers advantages over other vectors in the art in that viral transduction to dividing and non-dividing cells is efficient and that the VLP delivers potent and short-lived RNP that escape a subject's immune surveillance mechanisms that would otherwise detect a foreign protein. In some embodiments, a system to make VLP in a host cell comprises nucleic acids encoding one or more components selected from i) a gag polyprotein or portions thereof; ii) a CasX protein of any of the embodiments described herein; iii) a protease cleavage site; iv) a protease; v) a gNA of any of the embodiments described herein (including the targeting sequence); vi) a pol polyprotein or portions thereof; and vii) a pseudotyping glycoprotein or antibody fragment that provides for binding and fusion of the VLP to a target cell. The envelope protein or glycoprotein can be derived from any enveloped viruses known in the art to confer tropism to VLP, including but not limited to the group consisting of Argentine hemorrhagic fever virus, Australian bat virus, *Autographa californica* multiple nucleopolyhedrovirus, Avian leukosis virus, baboon endogenous virus, Bolivian hemorrhagic fever virus, Borna disease virus, Breda virus, Bunyamwera virus, Chandipura virus, Chikungunya virus, Crimean-Congo hemorrhagic fever virus, Dengue fever virus, Duvenhage virus, Eastern equine encephalitis virus, Ebola hemorrhagic fever virus, Ebola Zaire virus, enteric adenovirus, Ephemerovirus, Epstein-Bar virus (EBV), European bat virus 1, European bat virus 2, Fug Synthetic gP Fusion, Gibbon ape leukemia virus, Hantavirus, Hendra virus, hepatitis A virus, hepatitis B virus, hepatitis C virus, hepatitis D virus, hepatitis E virus, hepatitis G Virus (GB virus C), herpes simplex virus type 1, herpes simplex virus type 2, human cytomegalovirus (HHV5), human foamy virus, human herpesvirus (HHV), human Herpesvirus 7, human herpesvirus type 6, human herpesvirus type 8, human immunodeficiency virus 1 (HIV-1), human metapneumovirus, human T-lymphotro pic virus 1, influenza A, influenza B, influenza C virus, Japanese encephalitis virus, Kdposi's sarcoma-associated herpesvirus (HHV8), Kdysanur Forest disease virus, La Crosse virus, Lagos bat virus, Lassa fever virus, lymphocytic choriomeningitis virus (LCMV), Machupo virus, Marburg hemorrhagic fever virus, measles virus, Middle eastern respiratory syndrome-related coronavirus, Mokola virus, Moloney murine leukemia virus, monkey pox, mouse mammary tumor virus, mumps virus, murine gammaherpesvirus, Newcastle disease virus, Nipah virus, Nipah virus, Norwalk virus, Omsk hemorrhagic fever virus, papilloma virus, parvovirus, pseudorabies virus, Quaranfil virus, rabies virus, RD114 Endogenous Feline Retrovirus, respiratory syncytial virus (RSV), Rift Valley fever virus, Ross River virus, rRotavirus, Rous sarcoma virus, rubella virus, Sabia-associated hemorrhagic fever virus, SARS-associated coronavirus (SARS-CoV), Sendai virus, Tacaribe virus, Thogotovirus, tick-borne encephalitis causing virus, varicella zoster virus (HHV3), varicella zoster virus (HHV3), variola major virus, variola minor virus, Venezuelan equine encephalitis virus, Venezuelan hemorrhagic fever virus, vesicular stomatitis virus (VSV), VSV-G, Vesiculovirus, West Nile virus, western equine encephalitis virus, and Zika Virus. In some embodiments, the packaging cell used for the production of VLP is selected from the group consisting of HEK293 cells, Lenti-X 293T cells, BHK cells, HepG2 cells, Saos-2 cells, HuH7 cells, NS0 cells, SP2/0 cells, YO myeloma cells, A549 cells, P3X63 mouse myeloma cells, PER cells, PER.C$_6$ cells, hybridoma cells, VERO cells, NIH3T3 cells, COS cells, WI38 cells, MRC5 cells, A549 cells, HeLa cells, CHO cells, or HT1080 cells.

VII. Cells

In still another aspect, provided herein are populations of cells comprising a wild-type or a modified SOD1 gene modified by any of the CasX:gNA system or method embodiments described herein. Cells that have been genetically modified in this way may be administered to a subject for purposes such as gene therapy, e.g., to treat a disease associated with a defect in the SOD1 gene.

In some embodiments, the disclosure provides populations of cells modified by introducing into each cell of the population: a) a CasX:gNA system of any of the embodiments described herein; b) nucleic acid encoding a CasX: gNA system of any of the embodiments described herein; c) a vector comprising the nucleic acid of (b); d) a VLP comprising a CasX:gNA system of (a); or e) combinations of two or more of (a)-(d), wherein the SOD1 target nucleic acid sequence of the cells is modified by the CasX protein. In some embodiments, the disclosure provides a population of cells wherein the cells have been modified such that at least 70%, at least 75%, at least 80%, at least 85%, at least 90%, or at least 95% of the modified cells do not express a detectable level of SOD1 protein. In other embodiments, the disclosure provides a population of cells wherein the cells have been modified such that the expression of SOD1 protein is reduced by at least 70%, at least 75%, at least 80%, at least 85%, at least 90%, or at least 95% compared to cells that have not been modified. In still other embodiments, the disclosure provides a population of cells wherein the mutation of the SOD1 gene is corrected in the modified cells of the population, resulting in expression of a functional SOD1 protein by the modified cells. The effects of the modification can be assessed by ELISA assays, the assays of the examples, or conventional assays known in the art.

In those cases where the CasX is delivered to the cells in the protein form and the gNA is delivered in the RNA form, the CasX and gNA can be pre-complexed and delivered as an RNP. In some embodiments, the targeting sequence of the gNA used to target the SOD1 gene of the cells is selected from a sequence of Table 3, or a sequence having at least about 65%, at least about 75%, at least about 85%, or at least about 95% identity thereto. Upon hybridization with the target nucleic acid by the CasX and the gNA, the CasX introduces one or more single-strand breaks or double-strand breaks within or near the SOD1 gene that results in a modification of the target nucleic acid such as a permanent indel (deletion or insertion) or a mutation in the target nucleic acid that, in connection with the repair mechanisms of the host cell, result in a correction or a compensation of the mutation, with a corresponding expression of functional SOD1 protein, thereby creating the modified population of cells. In other embodiments, the target nucleic acid of the cells is modified using a plurality of gNAs (e.g., two, three, four or more) targeted to different or overlapping portions of the SOD1 gene wherein the CasX protein introduces multiple breaks in the target nucleic acid sequence that result in a permanent indel (deletion or insertion) or corrective mutation. In some embodiments, the disclosure provides populations of cells modified by contacting the SOD1 gene with a CasX, one or more gNA, and a donor template comprising a corrective sequence, wherein the donor template sequence is flanked by an upstream sequence and a downstream sequence with homology adjacent to the break sites in the target nucleic acid, facilitating insertion of the donor template sequence in order to correct the mutation(s) in the population of cells. In one embodiment, the disclosure provides populations of cells that have been modified to express the SOD1 protein of SEQ ID NO: 100. The donor template can be a short single-stranded or double-stranded oligonucleotide, or can be a long single-stranded or double-stranded oligonucleotide. The insertion of the donor template at the target region which can be mediated by homology-directed repair (HDR) or homology-independent targeted integration (HITI). The exogenous sequence inserted by HITI can be any length, for example, a relatively short sequence of between 1 and 50 nucleotides in length, or a longer sequence of about 50-1000 nucleotides in length. The donor template sequence may comprise certain sequence differences as compared to the genomic sequence, e.g., restriction sites, nucleotide polymorphisms, barcodes, selectable markers (e.g., drug resistance genes, fluorescent proteins, enzymes etc.), etc., which may be used to assess for successful insertion of the donor nucleic acid at the cleavage site or, in some cases, may be used for other purposes (e.g., to signify expression at the targeted genomic locus). Alternatively, these sequence differences may include flanking recombination sequences such as FLPs, loxP sequences, or the like, that can be activated at a later time for removal of the marker sequence.

A cell that can serve as a recipient for a CasX variant protein and/or gNA of the present disclosure and/or a nucleic acid comprising a nucleotide sequence encoding a CasX variant protein and/or a gNA variant and, optionally, a donor template, can be any of a variety of cells, including, e.g., in vitro cells; in vivo cells; ex vivo cells; primary cells; cancer cells; animal cells; etc. A cell can be a recipient of a CasX RNP of the present disclosure. A cell can be a recipient of a single component of a CasX system of the present disclosure. In certain embodiments, as provided herein, a cell can be an in vitro cell (e.g., established cultured cell line including, but not limited to HEK293 cells, BHK cells, NS0 cells, SP2/0 cells, YO myeloma cells, P3X63 mouse myeloma cells, PER cells, PER.C6 cells, hybridoma cells, NIH3T3 cells, COS, HeLa, or CHO cells). A cell can be an ex vivo cell (cultured cell from an individual). A cell can be an in vivo cell (e.g., a cell in an individual). A cell can be an isolated cell. A cell can be a cell in a cell culture (e.g., in vitro cell culture). A cell can be one of a collection of cells. A cell can be a eukaryotic cell or derived from a eukaryotic cell. A cell can be an animal cell or derived from an animal cell. A cell can be a mammalian cell or derived from a mammalian cell. A cell can be a rodent cell or derived from a rodent cell. A cell can be a non-human primate cell or derived from a non-human primate cell. A cell can be a human cell or derived from a human cell. A cell can be autologous with respect to the subject to be administered the cells. A cell can be allogenic with respect to the subject to be administered the cells.

The populations of modified cells have utility in the treatment of a SOD1-related disorder, including administration of the population of cells to a subject having a SOD1-related disorder such as ALS. In other embodiments, the disclosure provides populations of modified cells for use in methods to provide functional SOD1 in a subject. In some cases, the modified cell is a cell of the central nervous system (CNS) or peripheral nervous system (PNS). In some embodiments, the modified cell is a neuron. In some embodiments, the modified cell is a spinal motor neuron. In other cases, the modified cell is a glial cell, an oligodendrocyte, or a Schwann cell. In some embodiments, the populations of modified cells are eukaryotic, which can include rodent cells, mouse cells, rat cells, primate cells, non-human primate cells, human cells, embryonic stem (ES) cells, or induced pluripotent stem cells (iPSC). In some embodiments, the population of cells are autologous with respect to the subject to be administered the cells. In other embodiments, the population of cells are allogenic with respect to the subject to be administered the cells. Thus, the CasX:gNA systems and methods described herein can be used to modify a variety of cells in which mutations in SOD1 are associated with disease, e.g., stem cells, cells of the central nervous system (CNS) or peripheral nervous system (PNS), to produce a cell in which the SOD1 comprising mutations is corrected. This approach, therefore, could be used for methods of treatment in a subject with a disease such as ALS.

VIII. Applications

The CasX:gNA systems comprising CasX proteins, guides, and variants thereof provided herein are useful in methods for modifying SOD1 target nucleic acid in various applications, including therapeutics, diagnostics, and research.

In the methods of modifying a SOD1 target nucleic acid, the method utilizes any of the embodiments of the CasX:gNA system described herein, and optionally include a donor template described herein. In some embodiments, the method results in reducing or eliminating expression of the mutant allele at the protein level by introduction of a mutation in the mutant allele in the SOD1 gene by an insertion, substitution or deletion resulting from cleavage of the SOD1 gene by the CasX:gNA system followed by non-homologous end joining (NHEJ), micro-homology mediated end joining (MMEJ), single strand annealing (SSA), base excision repair (BER), or other repair mechanisms. In other embodiments, the method results in correction of the mutation in the SOD1 gene by cleavage of the SOD1 gene by the CasX:gNA system followed by insertion of corrective nucleotides by homology-directed repair (HDR), homology-independent targeted integration (HITI), or other repair mechanisms, resulting in the expression of functional SOD1 protein. In other embodiments, the method results in correction of the mutation in the SOD1 gene by cleavage of the SOD1 gene by the CasX:gNA system followed by insertion, or knocking-in, SOD1 cDNA into the SOD1 gene locus using a donor template, resulting in the expression of functional SOD1 protein.

In some embodiments, the method comprises contacting the target nucleic acid with a CasX protein and a guide nucleic acid (gNA) comprising a targeting sequence wherein said contacting results in modification of the target nucleic acid by the CasX protein.

In some embodiments, the method comprises introducing into a cell the CasX protein or a nucleic acid encoding the CasX protein and the gNA or the nucleic acid encoding the gNA, wherein the target nucleic acid sequence comprises a SOD1 gene and wherein the targeting sequence comprises a sequence complementary to a portion of the SOD1 gene at or near the mutation wherein the contacting results in the modification of the SOD1 gene.

In some embodiments, the method comprises introducing into a cell the CasX protein or a nucleic acid encoding the CasX protein and the gNA or the nucleic acid encoding the gNA, wherein the target nucleic acid comprises a superoxide dismutase 1 (SOD1) gene and wherein the targeting sequence comprises a sequence complementary to a portion of the SOD1 gene, wherein the contacting results in the modification of the SOD1 gene. In some embodiments, the targeting sequence of the gNA comprises a sequence of Table 3, or a sequence having at least about 65%, at least about 75%, at least about 85%, or at least about 95% identity to a sequence selected from the group consisting of sequences set forth in Table 3. In some embodiments, the scaffold of the gNA comprises a sequence of SEQ ID NOS: 4, 5 or 2101-2241, or a sequence having at least about 50%, at least about 60%, at least about 70%, at least about 80%, at least about 90%, at least about 95%, at least about 95%, at least about 96%, at least about 97%, at least about 98%, at least about 99% sequence identity thereto. In some embodiments, the CasX protein is a CasX variant protein of any of the embodiments described herein, or a reference CasX protein SEQ ID NO: 1, SEQ ID NO: 2, or SEQ ID NO: 3.

In some embodiments of the method of modifying a SOD1 target nucleic acid, the target nucleic acid comprises a superoxide dismutase 1 (SOD1) gene having one or more mutations, and the targeting sequence of the gNA has a sequence that is complementary to, and therefore can hybridize with the SOD1 gene. In some cases, the SOD1 gene has a wild-type nucleic acid sequence. In other embodiments, the method comprises contacting the target nucleic acid with a plurality (e.g., two or more) of gNAs targeted to different or overlapping regions of the SOD1 gene with one or more mutations. In some embodiments of the method, the target nucleic acid is a DNA. In some embodiments of the method, the target nucleic acid is an RNA. In some embodiments, the gNA is a guide RNA (gRNA). In some embodiments, the gNA is a guide DNA (gDNA). In some embodiments, the gNA is a single-molecule gNA (sgNA). In other embodiments, the gNA is a dual-molecule gNA (dgNA). In some embodiments, the gNA is a chimeric gRNA-gDNA. In some embodiments, the method comprises contacting the target nucleic acid with a pre-complexed CasX protein-gNA (i.e., an RNP). In some embodiments, the SOD1 gene comprise a mutation and the modifying comprises introducing a single-stranded break in the target nucleic acid. In other embodiments, the SOD1 gene comprise a mutation and the modifying comprises introducing a double-stranded break in the target nucleic acid. In the foregoing, the resulting modification can be an insertion, deletion, substitution, duplication, or inversion of one or more nucleotides as compared to the wild-type sequence. In some embodiments, the modification corrects a gain of function mutation. In other embodiments, the modification corrects a loss of function mutation. The mutations to be modified can be one or more mutations that disrupt the function of the SOD1 protein, including the mutations of Table 1 or mutations of the SOD1 regulatory element.

In some embodiments, the method of modifying a target nucleic acid comprises contacting a SOD1 gene with a CasX protein and gNA pair and a donor template comprising a corrective sequence that can be inserted or knocked-in at the break site introduced by the CasX. For example, an exogenous donor template which may comprise a corrective sequence (or a deletion or insertion to knock-out the defective sequence) to be integrated is flanked by an upstream sequence and a downstream sequence with homology to the target nucleic acid to facilitate its introduction into a cell. In some embodiments, the donor template ranges in size from 10-10,000 nucleotides. In other embodiments, the donor template ranges in size from 100-1,000 nucleotides. In some embodiments, the donor template is a single-stranded DNA template or a single stranded RNA template. In other embodiments, the donor template is a double-stranded DNA template.

In some embodiments of the method, the CasX is a catalytically inactive CasX (dCasX) protein that retains the ability to bind to the gNA and the target nucleic acid sequence comprising the mutation, thereby interfering with transcription of mutant SOD1. In some embodiments, the method comprises contacting a SOD1 gene with a CasX protein and gNA and does not comprise contacting the target nucleic acid with a donor template polynucleotide, and the target nucleic acid is cleaved by the CasX nuclease and is modified such that nucleotides within the target nucleic acid are deleted or inserted according to the cells own repair pathways. In some embodiments, the editing occurs in vitro, inside of a cell, for example in a cell culture system. In some embodiments, the editing occurs in vivo inside of a cell, for example in a cell in an organism or subject. In some embodiments, the editing occurs ex vivo inside of a cell. In some embodiments, the cell is a eukaryotic cell. Exemplary eukaryotic cells may include cells selected from the group consisting of a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell. In some embodiments, the cell is a human cell. In some embodiments, the cell is a non-human primate cell. In some embodiments of the method, the cell is a cell of a central nervous system (CNS) or peripheral nervous system (PNS). In some embodiments, the cell is a neuron. In other embodiments, the neuron is a spinal motor neuron. In other embodiments, the cell is a glial cell, an oligodendrocyte, or a Schwann cell.

Methods of introducing a nucleic acid (e.g., a nucleic acid comprising a donor polynucleotide sequence, one or more nucleic acids encoding a CasX protein and/or gNA) into a cell are known in the art, and any convenient method can be used to introduce a nucleic acid (e.g., an expression construct) into a cell. Suitable methods include e.g., viral infection, transfection, lipofection, electroporation, calcium phosphate precipitation, polyethyleneimine (PEI)-mediated transfection, DEAE-dextran mediated transfection, liposome-mediated transfection, particle gun technology, nucleofection, electroporation, direct addition by cell penetrating CasX proteins that are fused to or recruit donor DNA, cell squeezing, calcium phosphate precipitation, direct microinjection, nanoparticle-mediated nucleic acid delivery, and the commercially available TransMessenger® reagents from Qiagen, Stemfect™ RNA Transfection Kit from Stemgent, the TransIT®-mRNA Transfection Kit from Mirus Bio LLC, Lonza nucleofection, or Maxagen electroporation and the like. Introducing recombinant expression vectors into cells under in vitro conditions can occur in any suitable culture media and under any suitable culture conditions that promote the survival of the cells. Introducing recombinant expression vectors into a target cell can be carried out in vivo, or in vitro.

Retroviruses, for example, lentiviruses, may be suitable for use in methods of the present disclosure. Commonly used retroviral vectors are "defective", e.g., are unable to produce viral proteins required for productive infection. Rather, replication of the vector requires growth in a packaging cell line. To generate viral particles comprising nucleic acids of interest, the retroviral nucleic acids comprising the nucleic acid are packaged into viral capsids by a packaging cell line. Different packaging cell lines provide a different envelope protein (ecotropic, amphotropic or xenotropic) to be incorporated into the capsid, and this envelope protein determines the specificity of the viral particle for the cells (ecotropic for murine and rat; amphotropic for most mammalian cell types including human, dog and mouse; and xenotropic for most mammalian cell types except murine cells). The appropriate packaging cell line may be used to ensure that the cells are targeted by the packaged viral particles. Methods of introducing subject vector expression vectors into packaging cell lines and of collecting the viral particles that are generated by the packaging lines are well known in the art, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989). Nucleic acids can also be introduced by direct micro-injection (e.g., injection of RNA).

In other embodiments, the disclosure relates to methods to produce CasX proteins and nucleic acids encoding the CasX compositions of any of the embodiments described herein, or sequences complementary to the polynucleotide sequences, including homologous variants thereof, as well as methods to express the CasX proteins expressed by the polynucleotide sequences. A CasX protein of the present disclosure may be produced in vitro or by eukaryotic cells or by prokaryotic cells. For production by host cells, in general, the methods include producing a polynucleotide sequence coding for the CasX proteins of any of the embodiments described herein and incorporating the encoding gene into an expression vector appropriate for a host cell. For production of the encoded CasX proteins of any of the embodiments described herein, the method includes transforming an appropriate host cell with an expression vector, and culturing the host cell under conditions causing or permitting the resulting CasX protein to be expressed in the transformed host cell, thereby producing the CasX protein, which is recovered by methods described herein or by standard protein purification methods known in the art. Standard recombinant techniques in molecular biology are used to make the polynucleotides and expression vectors of the present disclosure.

In some embodiments of the method of altering a SOD1 target nucleic acid of a cell, to induce cleavage or any desired modification to a target nucleic acid (e.g., genomic DNA), or any desired modification to a polypeptide associated with the target SOD1 gene, the gNA and/or the CasX protein of the present disclosure and/or the donor template sequence, whether they be introduced as nucleic acids or polypeptides, are provided to the cells for about 30 minutes to about 24 hours, or at least about 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The agent(s) may be provided to the subject cells one or more times, e.g., one time, twice, three times, or more than three times, and the cells allowed to incubate with the agent(s) for some amount of time following each contacting event e.g., 30 minutes to about 24 hours. In the case of in vitro-based methods, after the incubation period with the CasX and gNA (and optionally the donor template), the media is replaced with fresh media and the cells are cultured further.

In embodiments in which two or more different targeting complexes are provided to the cell (e.g., two gNAs comprising two or more different targeting sequences that are complementary to different or overlapping sequences within the same or different regions of the SOD1 gene and/or targeting region), the complexes may be provided simultaneously (e.g., as two polypeptides and/or nucleic acids), or delivered simultaneously. Alternatively, they may be provided consecutively, e.g., the targeting complex being provided first, followed by the second targeting complex, etc. or vice versa.

To improve the delivery of a DNA vector into a target cell, the DNA can be protected from damage and its entry into the cell facilitated, for example, by using lipoplexes and polyplexes. Thus, in some cases, a nucleic acid of the present disclosure (e.g., a recombinant expression vector of the present disclosure) can be covered with lipids in an organized structure like a micelle or a liposome. When the organized structure is complexed with DNA it is called a lipoplex. There are three types of lipids, anionic (negatively-charged), neutral, or cationic (positively-charged). Lipoplexes that utilize cationic lipids have proven utility for gene transfer. Cationic lipids, due to their positive charge, naturally complex with the negatively charged DNA. Also, as a result of their charge, they interact with the cell membrane. Endocytosis of the lipoplex then occurs, and the DNA is released into the cytoplasm. The cationic lipids also protect against degradation of the DNA by the cell.

Complexes of polymers with DNA are referred to as polyplexes. Most polyplexes consist of cationic polymers and their production is regulated by ionic interactions. One large difference between the methods of action of polyplexes and lipoplexes is that polyplexes cannot release their DNA load into the cytoplasm, so to this end, co-transfection with endosome-lytic agents (to lyse the endosome that is made during endocytosis) such as inactivated adenovirus must occur. However, this is not always the case; polymers such as polyethylenimine have their own method of endosome disruption as does chitosan and trimethylchitosan.

Dendrimers, a highly branched macromolecule with a spherical shape, may be also be used to genetically modify stem cells. The surface of the dendrimer particle may be functionalized to alter its properties. In particular, it is possible to construct a cationic dendrimer (i.e., one with a positive surface charge). When in the presence of genetic material such as a DNA plasmid, charge complementarity leads to a temporary association of the nucleic acid with the cationic dendrimer. On reaching its destination, the dendrimer-nucleic acid complex can be taken up into a cell by endocytosis.

IX. Therapeutic Methods

In another aspect, the present disclosure relates to methods of treating a SOD1-related disease in a subject in need thereof, including but not limited to ALS or peripheral neuropathy. In some cases, the allele related to the SOD1-related disorder of the subject to be modified comprises one or more mutations, examples of which have been disclosed, supra. A number of therapeutic strategies have been used to design the compositions for use in the methods of treatment of a subject with a SOD1-related disorder. In some embodiments, the disclosure provides methods of treating a SOD1-related disease in a subject in need thereof in which repression or elimination of expression of the mutant SOD1 protein by modifying the SOD1 gene in target cells of the subject ameliorates the signs, symptoms, or effects of the disease. In such embodiments, the method comprises administering to the subject a therapeutically effective dose of any of the embodiments disclosed herein of: i) the CasX:gNA system comprising a first CasX protein and a first gNA with a targeting sequence complementary to the target nucleic acid and, optionally a donor template; ii) a nucleic acid encoding the CasX:gNA system of (i); iii) a vector comprising the nucleic acid of (ii); a VLP comprising the CasX:gNA system of (i); or iv) combinations thereof, wherein said administering results in 1) modification of the SOD1 target nucleic acid sequence by the CasX protein and, optionally, the donor template; and 2) decreased or elimination of expression of the mutant SOD1 protein in the modified cells of the subject. The methods are described more fully, below.

In some embodiments, the disclosure provides methods of treating a SOD1-related disease in a subject in need thereof in which correction of the mutant SOD1 gene in target cells of the subject ameliorates the signs, symptoms, or effects of the disease. In such embodiments, the method comprises administering to the subject a therapeutically effective dose of any of the embodiments disclosed herein of: i) the CasX:gNA system comprising a first CasX protein and a first gNA with a targeting sequence complementary to the target nucleic acid and, optionally a donor template; ii) a nucleic acid encoding the CasX:gNA system of (i); iii) a vector comprising the nucleic acid of (ii); a VLP comprising the CasX:gNA system of (i); or iv) combinations thereof, wherein said administering results in 1) modification of the SOD1 target nucleic acid sequence by the CasX protein and, optionally, the donor template; and 2) expression of functional SOD1 protein in the modified cells of the subject. In still other embodiments, the disclosure provides a method of treating a SOD1-related disease in a subject in need thereof by ex vivo modification of a mutant SOD1 target nucleic acid in a populations of cells to correct the mutation and administration of a therapeutically effective dose of the cells to the subject, resulting in amelioration of the signs, symptoms, or effects of the disease. The methods are described more fully, below.

In some embodiments, the targeting sequence of the gNA used to target the specific sequence of the SOD1 gene of the cells is selected from a sequence of Table 3, or a sequence having at least about 65%, at least about 75%, at least about 85%, or at least about 95% identity thereto. In some embodiments, the targeting sequence of the gNA has a sequence that hybridizes with a SOD1 exon. In some embodiments, the targeting sequence of the gNA has a sequence that hybridizes with a SOD1 intron. In some embodiments, the targeting sequence of the gNA has a sequence that hybridizes with a SOD1 intron-exon junction. In other embodiments, the targeting sequence of the gNA has a sequence that hybridizes with one or more single nucleotide polymorphisms (SNP) of the SOD1 gene. In some embodiments, the targeting sequence of the gNA has a sequence that hybridizes with an intergenic region of the SOD1 gene. In some embodiments, the targeting sequence of the gNA has a sequence that hybridizes with a SOD1 regulatory element. In some embodiments, the targeting sequence of the gNA has a sequence complementary to the SOD1 regulatory element, wherein the SOD1 regulatory element is 5' of the SOD1 gene. In some embodiments, the targeting sequence of the gNA has a sequence complementary to the SOD1 regulatory element, wherein the SOD1 regulatory element comprises the 5' untranslated region (UTR) of the SOD1 gene. In some embodiments, the targeting sequence of the gNA has a sequence complementary to the SOD1 regulatory element, wherein the SOD1 regulatory element is 3' of the SOD1 gene. In some embodiments, the targeting sequence of the gNA has a sequence complementary to the SOD1 regulatory element, wherein the SOD1 regulatory element comprises the 3'UTR of the SOD1 gene. In some embodiments, the targeting sequence of the gNA has a sequence complementary to the SOD1 regulatory element, wherein the SOD1 regulatory element comprises a promoter. In some embodiments, the targeting sequence of the gNA has a sequence complementary to the SOD1 regulatory element, wherein the SOD1 regulatory element comprises an enhancer. In some cases, the gNA used in the method of treatment is chemically modified. The CasX proteins utilized in the methods of treating a SOD-1 related disorder described herein can be selected from the CasX protein sequences of SEQ ID NOS: 1-3 or Table 4, or sequences having at least about 50%, at least about 60%, at least about 70%, at least about 80%, or at least about 90%, or at least about 95%, or at least about 99% sequence identity to the CasX proteins of SEQ ID NOS:1-3 or Table 4. In some cases, the CasX protein and the gNA utilized in the method of treatment are associated together in a ribonuclear protein complex (RNP).

Upon hybridization with the target nucleic acid by the CasX and the gNA, the CasX introduces one or more single-strand breaks or double-strand breaks within or near the SOD1 gene that results in a modification of the target nucleic acid. In those cases where the method of treatment is intended to knock-down or knock-out the mutant SOD1 gene in the cells of the subject, the CasX:gNA system is designed to modify the target nucleic acid by introducing a permanent indel (deletion or insertion) or a mutation in the target nucleic acid that, together with the host cell repair mechanisms, results in reduced expression of the defective SOD1. In some cases, the expression of the SOD1 protein is reduced by at least about 10%, at least about 20%, at least about 30%, at least about 40%, at least about 50%, at least about 60%, at least about 70%, at least about 80%, or at least about 90% in comparison to cells that have not been modified. In other cases, the SOD1 target nucleic acid of the cells of the subject are modified such that expression of the SOD1 protein cannot be detected. In those cases where the method of treatment is intended to correct the mutant SOD1 gene in the cells of the subject, the CasX:gNA system is designed to modify the target nucleic acid by introducing a permanent indel (deletion or insertion) or a mutation in the target nucleic acid that, together with the host cell repair mechanisms, corrects or compensates for the mutation, with a corresponding expression of functional SOD1 protein by the modified cells.

In other embodiments, the target nucleic acid of the cells of the subject is modified using a CasX and a plurality of gNAs (e.g., two, three, four or more) targeted to different or overlapping portions of the SOD1 gene wherein the CasX protein introduces multiple breaks in the target nucleic acid sequence. Similarly, as described supra, in those cases where the method of treatment is intended to knock-down or knock-out the mutant SOD1 gene in the cells of the subject, the CasX:gNA system is designed to modify the target nucleic acid by introducing one or more permanent indels (deletion or insertion) or mutations in the target nucleic acid that, together with the host cell repair mechanisms, results in reduced expression of the defective SOD1. In those cases where the method of treatment is intended to correct the mutant SOD1 gene in the cells of the subject, the CasX:gNA system is designed to modify the target nucleic acid by introducing one or more permanent indels (deletion or insertion) or mutations in the target nucleic acid that, together with the host cell repair mechanisms, results in correction or compensates for the mutation, with a corresponding expression of functional SOD1 protein by the modified cells.

In some embodiments, the disclosure provides methods of treating a SOD1-related disorder in a subject in need thereof comprising modifying the SOD1 gene with a CasX, one or more gNA, and a donor template, wherein the donor template sequence is flanked by an upstream sequence and a downstream sequence with homology adjacent to the break sites in the target nucleic acid introduced by the CasX, facilitating insertion of the donor template sequence. In those cases where the method of treatment is intended to knock-down or knock-out the mutant SOD1 gene in the cells of the subject, the donor template sequence is typically not identical to the genomic sequence that it replaces and may contain one or more single base changes, insertions, deletions, inversions or rearrangements with respect to the genomic sequence, provided that there is sufficient homology with the target nucleic acid sequence to support homology-directed repair or insertion by HITI, which can result in a frame-shift or other mutation such that the non-functional SOD1 protein is not expressed the expression of the mutant SOD1 is reduced by at least about 10%, at least about 20%, at least about 30%, at least about 40%, at least about 50%, at least about 60%, at least about 70%, at least about 80%, at least about 90% in comparison to cells that have not been modified. In those cases where the method of treatment is intended to correct the mutant SOD1 gene in the cells of the subject, the donor template comprises all or a portion of the wild-type SOD1 gene such that its insertion by HDR or HITI results in correction or compensates for the mutation, with a corresponding expression of functional SOD1 protein by the modified cells. In a particular embodiment of the foregoing, gNAs targeting the upstream sequence Exon 1 and Intron 1 can be used to introduce breaks that permit the insertion of full length cDNA encoding the SOD1 protein, replacing the mutated endogenous SOD1 gene and restoring protein expression of functional SOD1; e.g., the protein of SEQ ID NO:100. The donor template inserted by HITI can be any length, for example, a relatively short sequence of between 1 and 50 nucleotides in length, or a longer sequence of about 50-1000 nucleotides in length. The donor template can be a short single-stranded or double-stranded oligonucleotide, or can be a long single-stranded or double-stranded oligonucleotide. The donor template of the embodiments can be designed to encode a SOD1 exon, a SOD1 intron, a SOD1 intron-exon junction, a SOD1 regulatory element, or an intergenic region. The donor template sequence may comprise certain sequence differences as compared to the genomic sequence, e.g., restriction sites, nucleotide polymorphisms, barcodes, selectable markers (e.g., drug resistance genes, fluorescent proteins, enzymes etc.), etc., which may be used to assess for successful insertion of the donor nucleic acid at the cleavage site or, in some cases, may be used for other purposes (e.g., to signify expression at the targeted genomic locus). Alternatively, these sequence differences may include flanking recombination sequences such as FLPs, loxP sequences, or the like, that can be activated at a later time for removal of the marker sequence.

In other embodiments of the method of treatment, the method further comprises administration to the cells of a subject an additional CRISPR protein, or a polynucleotide (or a vector comprising the polynucleotide) encoding the additional CRISPR protein. In the foregoing embodiment, the additional CRISPR protein has a sequence different from the first CasX protein of the method. In some embodiments, the additional CRISPR protein is not a CasX protein; the additional CRISPR nuclease is selected from the group consisting of Cas9, Cas12a, Cas12b, Cas12c, Cas12d (CasY), Cas13a, Cas13b, Cas13c, Cas13d, CasX, CasY, Cas14, Cpf1, C2c1, Csn2, Cas Phi, and sequence variants thereof.

In some embodiments, the method comprises administering to the subject the compositions of the embodiments described herein (i.e., the CasX protein, the one or more gNA, and, optionally the donor template, or the one or more polynucleotides encoding the CasX protein, the gNA and the donor template) at a therapeutically effective dose via an administration route selected from the group consisting of intraparenchymal, intravenous, intra-arterial, intracerebroventricular, intracisternal, intrathecal, intracranial, lumbar, and intraperitoneal routes. In some embodiments of the methods of treating a SOD1-related disorder in a subject, the subject is selected from the group consisting of mouse, rat, non-human primate, and human. In a particular embodiment, the subject is a human. In some embodiments, the cell to be modified by the administration of the compositions is a cell of the central nervous system (CNS) or the peripheral nervous system (PNS). In some embodiments, the cell is a neuron. In some embodiments, the neuron is a spinal motor neuron. In other embodiments, the cell is a glial cell, an oligodendrocyte, or a Schwann cell.

In some embodiments of the method of treatment, the method comprises administration to the subject a therapeutically effective dose of a vector comprising polynucleotides encoding the CasX protein and the gNA, wherein the contacting of the cells of the subject with the vector results in expression of the CasX and gNA and modification of the target nucleic acid of the cells by the CasX:gNA complex. The vectors disclosed herein may be delivered to a subject by several technologies including DNA injection (also referred to as DNA vaccination) with and without in vivo electroporation, liposome mediated, nanoparticle facilitated, or use of recombinant vectors such as recombinant lentivirus, recombinant adenovirus, and recombinant adenovirus associated virus. In some embodiments, the method comprises administration of the vector comprising a polynucleotide encoding a CasX and a plurality of gNAs targeted to the SOD1 gene wherein the administration results in contacting the subject target nucleic acid within cells of the subject with the expression product(s) of the vectors wherein the SOD1 gene is modified in the cell of the subject. In other embodiments of the method of treatment, the method comprises contacting the cell with a vector encoding the CasX protein and the gNA and further comprising a donor template wherein said contacting results in modification of the target nucleic acid of the cell by cleavage by the CasX protein and insertion of the donor template into the target nucleic acid. In other embodiments of the method of treatment, the method comprises contacting the cell with a first vector encoding the CasX protein and the gNA and a second vector comprising the donor template. In other embodiments, the method comprises administration of the vector comprising a polynucleotide encoding a CasX and a plurality of gNAs targeted to the SOD1 gene and a second vector comprising a donor template polynucleotide encoding at least a portion of or the entirety of a SOD1 gene wherein the administration of the vectors results in contacting the subject target nucleic acid within a cell of the subject with the expression product(s) of the CasX and gNA vectors and the donor template wherein the SOD1 gene is modified in the cell of the subject. In some cases, wherein the CasX:gNA system is designed to correct the SOD1 mutation, the donor template is a SOD1 gene or a gene portion selected from a SOD1 exon, a SOD1 intron, a SOD1 intron-exon junction, or a SOD1 regulatory element and wherein the donor template comprises a corrective sequence that is inserted into the target nucleic acid of the subject. In other cases, wherein the CasX:gNA system is designed to knock-down/knock-out the SOD1 gene, the donor template comprises one or more single base changes, insertions, deletions, inversions or rearrangements with respect to the genomic sequence mutations in the SOD1 gene portion, whereupon insertion of the donor template the gene is knocked-down or knocked-out. In some embodiments, the vector is a viral particle. In some embodiments, the vector is an AAV vector (described supra). The vectors of the embodiments are administered to the subject at a therapeutically effective dose. In some embodiments, the vector is administered at a dose of at least about $1\times10^{10}$ vector genomes (vg), or at least about $1\times10^{11}$ vg, or at least about $1\times10^{12}$ vg, or at least about $1\times10^{13}$ vg, or at least about $1\times10^{14}$ vg, or at least about $1\times10^{15}$ vg, or at least about $1\times10^{16}$ vg. In other embodiments, the subject is administered a dose of at least about $1\times10^{10}$ to about $1\times10^{16}$ vg.

In other embodiments of the method of treatment, the method comprises administration to the subject a therapeutically effective dose of a VLP comprising the CasX protein and the gNA and, optionally, the donor template (described, supra), wherein the contacting of the cells of the subject with the VLP results in modification of the target nucleic acid of the cells by the CasX:gNA complex. In some embodiments, the method comprises administration of the VLP comprising a CasX and a plurality of gNAs targeted to different locations in the SOD1 gene, wherein the contacting of the cells of the subject with the VLP results in modification of the target nucleic acid of the cells by the CasX:gNA complexes. As previously described, the components can be designed to knock-down/knock-out the SOD1 gene or to knock-in a corrective sequence. The VLP of the embodiments are administered to the subject at a therapeutically effective dose. In some embodiments, the VLP is administered to the subject at a dose of at least about $1\times10^{8}$ particles, at least about $1\times10^{9}$ particles, at least about $1\times10^{10}$ particles at least about $1\times10^{11}$ particles, or at least about $1\times10^{12}$ particles, or at least about $1\times10^{13}$ particles, or at least about $1\times10^{14}$ particles, or at least about $1\times10^{15}$ particles, or at least about $1\times10^{16}$ particles.

In some embodiments, the vectors or VLP may be administered to a subject by various routes, wherein the route of administration is selected from the group consisting of intraparenchymal, intravenous, intra-arterial, intracerebroventricular, intracisternal, intrathecal, intracranial, lumbar, and intraperitoneal routes. In some embodiments of the method of treatment, the vector or VLP is delivered to the central nervous system of the subject. In some embodiments, the vector or VLP is delivered to a brain region. Areas of the brain contemplated for delivery include, but are not limited to, the motor cortex and the brain stem. In some embodiments, the vector or VLP is delivered to the spinal cord. In certain embodiments, the vector or VLP is delivered to the cerebrospinal fluid. In some embodiments of the method, the vector or VLP is delivered to the peripheral nervous system region. In some embodiments, the vector or VLP is delivered to nerve and glial cells, including those of the central nervous system and the peripheral nervous system. In some embodiments, the glial cell is a microglial cell, an oligodendrocyte or an astrocyte. In some embodiments of the method, the polynucleotide is delivered to a Schwann cell. In the embodiments, the vector or VLP may be administered according to a treatment regimen comprising one or more consecutive doses using a therapeutically effective dose of the vector. In some embodiments of the treatment regimen, the therapeutically effective dose of the vector or VLP is administered as a single dose. In other embodiments of the treatment regimen, the therapeutically effective dose of the vector or VLP is administered to the subject as two or more doses over a period of at least two weeks, or at least one month, or at least two months, or at least three months, or at least four months, or at least five months, or at least six months, or on an annual basis, or every 2 or 3 years.

In some embodiments, the disclosure provides methods of treating a SOD1-related disorder (e.g., ALS) in a subject comprising administering to the subject a therapeutically effective dose of a population of modified eukaryotic cells of the disclosure, the cells comprising a modified SOD1 gene in which the mutations have been corrected or in which a wild-type SOD1 sequence is inserted such that the cells produce functional SOD1. In some embodiments, the population of cells are autologous with respect to the subject to be administered the cells. In other embodiments, the population of cells are allogenic with respect to the subject to be administered the cells. In some embodiments, the population of modified cells is selected from the group consisting of embryonic stem (ES) cells, induced pluripotent stem cell (iPSC), central nervous system (CNS) cells, and peripheral nervous system (PNS) cells. In some embodiments, the population of cells comprise neuron cells of the CNS or the PNS. In some cases, the neuron cells comprise spinal motor neuron cells or oligodendrocyte cells. In other embodiments, the population of cells comprise glial cells or Schwann cells of the PNS. The cells can be derived from a subject selected from the group consisting of rodent, mouse, rat, non-human primate, and human. In the embodiments, the population of cells can be administered according to a treatment regimen comprising one or more consecutive doses using a therapeutically effective dose of the cells. In some embodiments of the treatment regimen, the therapeutically effective dose of the cells is administered as a single dose. In other embodiments of the treatment regimen, the therapeutically effective dose of the cells is administered to the subject as two or more doses over a period of at least two weeks, or at least one month, or at least two months, or at least three months, or at least four months, or at least five months, or at least six months, or on an annual basis, or every 2 or 3 years. In the embodiments, the route of administration is selected from intraparenchymal, intravenous, intra-arterial, intracerebroventricular, intracisternal, intrathecal, intracranial, lumbar, intraperitoneal, or combinations thereof. This approach, therefore, could be used for methods of treatment in a subject with a SOD1-related disease such as ALS.

In some embodiments, the administration of the therapeutically effective amount of a vector, a VLP, a CasX-gNA composition, or a plurality of modified cell embodiments disclosed herein to the subject leads to the prevention or amelioration of the underlying SOD1-related disorder (e.g., ALS) such that an improvement is observed in the subject, notwithstanding that the subject may still be afflicted with the underlying disorder. In some embodiments, the administration of the therapeutically effective amount of the vector, the VLP, the CasX-gNA composition or the modified cells leads to an improvement in at least one clinically-relevant endpoint selected from the group consisting of ALS Functional Rating Scale (ALSFRS-(R)), combined assessment of function and survival, time to death, time to tracheostomy or persistent assisted ventilation (DTP), forced vital capacity (% FVC), manual muscle test, maximum voluntary isometric contraction, duration of response, progression-free survival, time to progression of disease, and time-to-treatment failure. In some embodiments, the administration of the therapeutically effective amount of the vector, the VLP, the CasX-gNA composition or the modified cells leads to an improvement in at least two clinically-relevant endpoints selected from the group consisting of ALS Functional Rating Scale (ALSFRS-(R)), combined assessment of function and survival, time to death, time to tracheostomy or persistent assisted ventilation (DTP), forced vital capacity (% FVC), manual muscle test, maximum voluntary isometric contraction, duration of response, progression-free survival, time to progression of disease, and time-to-treatment failure. In the embodiments of the foregoing, the subject is a mammal selected from mouse, rat, non-human primate, and human. Several mouse models expressing mutant forms of SOD1 exist. Transgenic mouse models expressing the human SOD1 gene harboring a G93A, G37R, or G85R mutation develop a phenotype similar to what is observed in human ALS patients; the transgenic SOD1 mouse is considered the most accurate representation of the disease process (Gurney M E, et al. Motor neuron degeneration in mice that express a human Cu, Zn superoxide dismutase mutation. Science. 264:1772 (1994); Philips, T and Jeffrey D. Rothstein, J. Rodent Models of Amyotrophic Lateral Sclerosis. Curr Protoc Pharmacol. 69: 5.67.1-5.67.21. (2015).

In some embodiments, the disclosure provides compositions comprising CasX and gNA gene editing pairs, for use as a medicament for the treatment of a subject having a SOD1 related disorder, such as ALS. In the foregoing, the CasX can be a CasX variant of Table 4 and the gNA can be a gNA variant of Table 3. In other embodiments, the disclosure provides compositions of vectors comprising or encoding the gene editing pairs of CasX and gNA for use as a medicament for the treatment of a subject having a SOD1 related disorder, such as ALS.

X. Kits and Articles of Manufacture

In another aspect, provided herein are kits comprising the compositions of the embodiments described herein. In some embodiments, the kit comprises a CasX protein and one or a plurality of gNA of any of the embodiments of the disclosure comprising a targeting sequence region specific for a SOD1 gene, optionally a donor template, and a suitable container (for example a tube, vial or plate). In other embodiments, the kit comprises a nucleic acid encoding a CasX protein and one or a plurality of gNA of any of the embodiments of the disclosure comprising a targeting sequence region specific for a SOD1 gene, optionally a donor template, and a suitable container. In other embodiments, the kit comprises a vector comprising a nucleic acid encoding a CasX protein and one or a plurality of gNA of any of the embodiments of the disclosure comprising a targeting sequence region specific for a SOD1 gene, and a suitable container. In still other embodiments, the kit comprises a VLP comprising a CasX protein and one or a plurality of gNA of any of the embodiments of the disclosure comprising a targeting sequence region specific for a SOD1 gene, optionally a donor template, and a suitable container.

In some embodiments, the kit further comprises a buffer, a nuclease inhibitor, a protease inhibitor, a liposome, a therapeutic agent, a label, a label visualization reagent, or any combination of the foregoing. In some embodiments, the kit further comprises a pharmaceutically acceptable carrier, diluent or excipient.

In some embodiments, the kit comprises appropriate control compositions for gene modifying applications, and instructions for use.

The present description sets forth numerous exemplary configurations, methods, parameters, and the like. It should be recognized, however, that such description is not intended as a limitation on the scope of the present disclosure, but is instead provided as a description of exemplary embodiments.

XI. Enumerated Embodiments

Embodiments of the present subject matter described above may be beneficial alone or in combination, with one or more other embodiments. Without limiting the foregoing description, certain non-limiting enumerated embodiments of the disclosure, numbered 1-234 are provided below. As will be apparent to those of skill in the art upon reading this disclosure, each of the individually numbered embodiments may be used or combined with any of the preceding or following individually numbered embodiments. This is intended to provide support for all such combinations of embodiments and is not limited to combinations of embodiment explicitly provided below:
Set 1

Embodiment 1. A method of modifying a target nucleic acid, the method comprising contacting the target nucleic acid with a CasX polypeptide and a guide nucleic acid (gNA) comprising a targeting sequence wherein said contacting results in modification of the target nucleic acid by the CasX protein, and wherein said contacting comprises introducing into a cell:

a) the CasX protein or a nucleic acid encoding the CasX protein; and b) the gNA or a nucleic acid encoding the gNA, wherein the target nucleic acid comprises a superoxide dismutase 1 (SOD1) gene and/or a SOD1 regulatory element, and wherein the targeting sequence comprises i) a sequence complementary to a portion of the SOD1 gene and/or the SOD1 regulatory element; or ii) a sequence complementary to a complement of the portion of the SOD1 gene and/or SOD1 regulatory element.

Embodiment 2. The method of 1, further comprising a second gNA or a nucleic acid encoding the second gNA, wherein the second gNA has a targeting sequence complementary a different portion of the target nucleic acid or its complement.

Embodiment 3. The method of 1, wherein the target nucleic acid is a target DNA.

Embodiment 4. The method of any one of 1-3, wherein the gNA is a guide RNA (gRNA), a guide DNA (gDNA), or a chimera comprising DNA and RNA.

Embodiment 5. The method of any one of 1-4, wherein the gNA comprises at least one modification relative to a reference gRNA sequence having the sequence of SEQ ID NO:2102.

Embodiment 6. The method of 5, wherein the at least one modification of the reference gRNA comprises at least one substitution, deletion, or substitution of a nucleotide of the gRNA sequence.

Embodiment 7. The method of any one of 1-4, wherein the gNA comprises any one of the sequences listed in Tables 2A or 2B.

Embodiment 8. The method of any one of the preceding embodiments, wherein the CasX polypeptide and the gNA are associated together in a ribonuclear protein complex (RNP).

Embodiment 9. The method of any one of the preceding embodiments, wherein the CasX protein comprises at least one modification relative to a reference CasX protein having a sequence selected from SEQ ID NOS: 1-3.

Embodiment 10. The method of 9, wherein the at least one modification of the reference CasX protein comprises at least one amino acid substitution, deletion, or substitution in a domain of the reference CasX protein.

Embodiment 11. The method of 10, wherein the at least one modification of the reference Cas X protein comprises at least one amino acid deletion in a domain of the reference CasX protein.

Embodiment 12. The method of 10, wherein the at least one modification of the reference Cas X protein comprises at least one amino acid insertion in a domain of the reference CasX protein.

Embodiment 13. The method of 10, wherein the at least one modification of the reference Cas X protein comprises at least one amino acid substitution in a domain of the reference CasX protein.

Embodiment 14. The method of any one of 1-13, wherein the CasX protein comprises a sequence selected from the sequences of Table 4 or a sequence having at least about 50%, at least about 60%, at least about 70%, at least about 80%, or at least about 90%, or at least about 95%, or at least about 99% sequence identity to a sequence of Table 4.

Embodiment 15. The method of any one of the preceding embodiments, wherein the one or more nucleic acids encoding the CasX protein and the gNA are capable of being expressed in a cell.

Embodiment 16. The method of any one of the preceding wherein the CasX protein exhibits at least one or more improved characteristics as compared to a reference CasX protein.

Embodiment 17. The method of 16, wherein the improved characteristic is selected from the group consisting of improved folding of the Cas X protein, improved binding affinity to the guide RNA, improved binding affinity to the target nucleic acid, altered binding affinity to one or more PAM sequences, improved unwinding of the target nucleic acid, increased activity, improved editing efficiency, improved editing specificity, increased activity of the nuclease, increased target strand loading for double strand cleavage, decreased target strand loading for single strand nicking, decreased off-target cleavage, improved binding of the non-target strand of DNA, improved protein stability, improved protein:guide RNA complex stability, improved protein solubility, improved protein:guide RNA complex solubility, improved protein yield, improved protein expression, and improved fusion characteristics.

Embodiment 18. The method of 16 or 17, wherein the improved characteristic of the CasX protein is at least about 1.1 to about 100,000 times improved relative to the reference protein of SEQ ID NO: 1, SEQ ID NO: 2, or SEQ ID NO: 3.

Embodiment 19. The method of 16 or 17, wherein the improved characteristics of the CasX protein is at least about 10 to about 100 times improved relative to the reference protein of SEQ ID NO: 1, SEQ ID NO: 2, or SEQ ID NO:3.

Embodiment 20. The method of 16 or 17, wherein the improved characteristic of the CasX protein is at least about 1.1 to about 100 times increased binding affinity of the CasX protein to the gNA compared to the protein of SEQ ID NO: 1, SEQ ID NO: 2, or SEQ ID NO: 3.

Embodiment 21. The method of 16 or 17, wherein the CasX protein has at least about 1.1 to about 2 times increased binding affinity to the target nucleic acid compared to the protein of SEQ ID NO: 1, SEQ ID NO: 2, or SEQ ID NO: 3.

Embodiment 22. The method of any one of the preceding embodiments, wherein the modifying of the target nucleic acid occurs inside of a cell.

Embodiment 23. The method of 22, wherein the modifying of the target nucleic acid occurs in vivo.

Embodiment 24. The method of 22, wherein the modifying of the target nucleic acid occurs in vitro.

Embodiment 25. The method of any one of 22-24, wherein the cell is a eukaryotic cell.

Embodiment 26. The method of 25, wherein the eukaryotic cell is selected from the group consisting of a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Embodiment 27. The method of 25, wherein the eukaryotic cell is a human cell.

Embodiment 28. The method of any one of 22-25 or 27, wherein the cell is a cell of a central nervous system (CNS) or peripheral nervous system (PNS).

Embodiment 29. The method of 28, wherein the cell is a neuron.

Embodiment 30. The method of 29, wherein the neuron is a spinal motor neuron.

Embodiment 31. The method of 28, wherein the cell is a glial cell, an oligodendrocyte, or a Schwann cell.

Embodiment 32. The method of any one of the preceding embodiments, wherein the CasX protein is selected from the CasX proteins provided in SEQ ID NOS: 1-3 or Table 4 or sequences having at least about 50%, at least about 60%, at least about 70%, at least about 80%, or at least about 90%, or at least about 95%, or at least about 99% sequence identity to the CasX proteins of SEQ ID NOS:1-3 or Table 4.

Embodiment 33. The method of any one of the preceding embodiments, wherein the CasX protein has binding affinity for a PAM sequence selected from the group consisting of TTC, ATC, GTC, and CTC.

Embodiment 34. The method of any one of the preceding embodiments, wherein the CasX protein comprises nickase activity.

Embodiment 35. The method any one of the preceding embodiments, wherein the method comprises modifying the SOD1 gene or the SOD1 regulatory element in a cell.

Embodiment 36. The method of 35, wherein the modifying comprises introducing a single-stranded break in the target nucleic acid, and wherein modification of the SOD1 gene or the SOD1 regulatory element comprises a mutation, an insertion, or a deletion in the SOD1 gene or the SOD1 regulatory element.

Embodiment 37. The method of 35, wherein the modifying comprises introducing a double-stranded break in the target nucleic acid, and wherein modification of the SOD1 gene or the SOD1 regulatory element comprises a mutation, an insertion, or a deletion.

Embodiment 38. The method of any one of 1-35, wherein the CasX protein is a catalytically inactive CasX (dCasX) protein, and wherein the dCasX and the gNA retain the ability to bind to the target nucleic acid.

Embodiment 39. The method of 38, wherein the dCasX comprises a mutation at residues:
i) D672, E769, and/or D935 corresponding to the CasX protein of SEQ ID NO:1; or
ii) D659, E756 and/or D922 corresponding to the CasX protein of SEQ ID NO: 2.

Embodiment 40. The method of 39 wherein the mutation is a substitution of alanine for the residue.

Embodiment 41. The method of any one of 1 to 40, wherein the SOD1 gene and/or the SOD1 regulatory element to be modified comprises a polynucleotide encoding all or a portion of the sequence of SEQ ID NO:100, or comprises a polynucleotide sequence that spans bp 31,659,622 to bp 31,668,931 of chromosome 21 of the human genome (GRCh38/hg38).

Embodiment 42. The method of any one of 1 to 40, wherein the SOD1 gene and/or the SOD1 regulatory element to be modified comprises a wild type sequence.

Embodiment 43. The method of any one of 1 to 40, wherein the SOD1 gene and/or the SOD1 regulatory element to be modified comprises a mutation.

Embodiment 44. The method of 43, wherein the mutation is a gain of function mutation.

Embodiment 45. The method of 43, wherein the mutation is a loss of function mutation.

Embodiment 46. The method of 43, wherein the SOD1 gene encodes a polypeptide comprising a mutation selected from mutations set forth in Table 1 or comprises one or more mutations that disrupt the function of the SOD1 polypeptide.

Embodiment 47. The method of 46, wherein the SOD1 gene encodes a polypeptide comprising an A4V mutation of SEQ ID NO:100, a D90A mutation of SEQ ID NO:100, a G93A mutation of SEQ ID NO:100, or a combination thereof.

Embodiment 48. The method of any one of 43-47, wherein the modification comprises correction of the mutation to wild-type sequence.

Embodiment 49. The method of any one of 43-47, wherein the modification comprises altering or suppressing expression of the SOD1 comprising the mutation.

Embodiment 50. The method of any one of 1-49, wherein the targeting sequence of the gNA consists of 14, 15, 16, 17, 18, 19, 20, 21, 22, 23, 24, 25, 26, 27, 28, 29, or 30 consecutive nucleotides.

Embodiment 51. The method of any one of 1-50, wherein the targeting sequence of the gNA consists of 20 nucleotides.

Embodiment 52. The method of any one of 1-51, wherein the targeting sequence of the gNA comprises a sequence having at least about 65%, at least about 75%, at least about 85%, or at least about 95% identity to a sequence provided in Table 3.

Embodiment 53. The method of any one of 1-52, wherein the targeting sequence of the gNA comprises a sequence having one or more single nucleotide polymorphisms (SNP) relative to a sequence provided in Table 3.

Embodiment 54. The method of 52 or 53, wherein the targeting sequence encodes a mutation of the SOD1 polypeptide of SEQ ID NO:100 selected from the group of amino acid substitutions consisting of A4S, A4T, A4V, C6F, V7E, L8Q, L8V, G12R, V14G, V14M, G16S, F20C, E21G, E21K, Q22L, G37R, L38R, L38V, G41D, G41S, H43R, F45C, H46R, H48Q, H48R, E49K, T54R, N65S, L67P, L67R, G72S, D76Y, H80A, L84F, L84V, G85R, N86S, V87A, A89T, A89V, D90A, D90V, G93A, G93C, G93D, G93R, G93V, A95G, V97M, E100G, E100K, D101G, D101N, I104F, S105L, L106V, G108V, C111Y, I112M, I112T, I113T, G114A, R115G, V118L, D124G, D124V, D125H, L126S, S134N, N139K, L144F, L144S, A145T, C146R, G147R, V148G, V148I, I149T, I151T, and one or more mutations that disrupt the function or expression of the SOD1 polypeptide.

Embodiment 55. The method of any one of the preceding embodiments, wherein the gNA is chemically modified.

Embodiment 56. The method of any one of the preceding embodiments, wherein the targeting sequence of the gNA is complementary to the SOD1 gene or its regulatory element, or complementary to the complement of the SOD1 gene or its regulatory element.

Embodiment 57. The method of 56, wherein the targeting sequence of the gNA has a sequence that is a sequence of a SOD1 exon or a sequence complementary to a SOD1 exon.

Embodiment 58. The method of 56, wherein the targeting sequence of the gNA has a sequence that is a sequence of a SOD1 intron or a sequence complementary to a SOD1 intron.

Embodiment 59. The method of 56, wherein the targeting sequence of the gNA has a sequence that is a sequence of a SOD1 intron-exon junction or a sequence complementary to a SOD1 intron-exon junction.

Embodiment 60. The method of any one of 1-59, wherein the targeting sequence of the gNA has a sequence that hybridizes with one or more single nucleotide polymorphisms (SNPs) of the SOD1 gene and/or a SOD1 regulatory element.

Embodiment 61. The method of 56, wherein the targeting sequence of the gNA has a sequence that is a sequence of an intergenic region of the SOD1 gene or a sequence complementary to an intergenic region of the SOD1 gene.

Embodiment 62. The method of any one of 1 to 55, wherein the targeting sequence of the gNA is a sequence of a SOD1 regulatory element or a sequence that is complementary to a SOD1 regulatory element.

Embodiment 63. The method of 62, wherein the SOD1 regulatory element is 5' of the SOD1 gene.

Embodiment 64. The method of 62, wherein the SOD1 regulatory element is 3' of the SOD1 gene.

Embodiment 65. The method of 62, wherein the SOD1 regulatory element comprises the 5' UTR of the SOD1 gene.

Embodiment 66. The method of 62, wherein the SOD1 regulatory element comprises the 3'UTR of the SOD1 gene.

Embodiment 67. The method of 62, wherein the SOD1 regulatory element comprises a promoter.

Embodiment 68. The method of 62, wherein the SOD1 regulatory element comprises an enhancer.

Embodiment 69. The method of any one of 1 to 68, wherein the targeting sequence of the gNA has binding specificity for the SOD1 gene or the SOD1 regulatory element.

Embodiment 70. The method of any one of the preceding embodiments, wherein the method further comprises contacting the target nucleic acid with a donor template complementary to at least a portion of a SOD1 gene and/or a SOD1 regulatory element, wherein the SOD1 gene portion is selected from the group consisting of a SOD1 exon, a SOD1 intron, a SOD1 intron-exon junction, and wherein the SOD1 gene portion and/or a SOD1 regulatory element is inserted into or replaces the target nucleic acid comprising the one or more mutations.

Embodiment 71. The method of 70, wherein the donor template ranges in size from 10-10,000 nucleotides.

Embodiment 72. The method of 70, wherein the donor template ranges in size from 100-1,000 nucleotides.

Embodiment 73. The method of any one of 70-72, wherein the donor template is a single stranded DNA template or a single stranded RNA template.

Embodiment 74. The method of any one of 70-72, wherein the donor template is a double stranded DNA template.

Embodiment 75. The method of any one of 1 to 74, wherein the method comprises contacting the target nucleic acid with a pre-complexed CasX protein-gNA.

Embodiment 76. The method of 75, wherein the gNA comprises at least one nucleotide modification relative to a reference sequence selected from SEQ ID NOS: 1101-1105 of Table 2A, wherein the modification results in one or more improved characteristic in the method.

Embodiment 77. The method of 76, wherein the one or more improved characteristic comprises improved protein:gNA complex stability, improved protein:gNA complex stability, improved binding affinity between the protein and gNA, improved binding affinity to the target DNA, improved unwinding of the target DNA, increased activity, improved editing efficiency, improved editing specificity, increased activity of the nuclease, increased target strand loading for double strand cleavage, decreased target strand loading for single strand nicking, decreased off-target cleavage, improved binding of the non-target strand of DNA, or improved resistance to nuclease activity.

Embodiment 78. The method of any one of 75-77, wherein the method comprises contacting a eukaryotic cell comprising the target nucleic acid with a liposome, a lipid nanoparticle, or a virus-like particle (VLP) comprising the CasX protein and the gNA.

Embodiment 79. The method of any one of 75-77, wherein the method comprises contacting a eukaryotic cell comprising the target nucleic acid with the one or more nucleic acids encoding the CasX protein and the gNA, and optionally the donor template.

Embodiment 80. The method of 79, wherein the nucleic acid encoding the CasX protein further comprises one or more nuclear localization signals (NLS).

Embodiment 81. The method of 80, wherein the one or more NLS are selected from the group of sequences consisting of PKKKRKV (SEQ ID NO: 145), KRPAATKK-AGQAKKKK (SEQ ID NO: 146), PAAKRVKLD (SEQ ID NO: 147), RQRRNELKRSP (SEQ ID NO: 148), NQSSNFGPMKGGNFGGRSSGPYGGGGQYFAK-PRNQGGY (SEQ ID NO: 149), RMRIZFKNKGKDTAEL-RRRRVEVSVELRKAKKDEQILKRRNV (SEQ ID NO: 150), VSRKRPRP (SEQ ID NO: 151), PPKKARED (SEQ ID NO: 152), PQPKKKPL (SEQ ID NO: 153), SALI AP (SEQ ID NO: 154), DRLRR (SEQ ID NO: 155), PKQKKRK (SEQ ID NO: 156), RKLKKKIKKL (SEQ ID NO: 157), REKKKFLKRR (SEQ ID NO: 158), KRKGDEVDGVDEVAKKKSKK (SEQ ID NO: 159), RKCLQAGMNLEARKTKK (SEQ ID NO: 160), PRPRKIPR (SEQ ID NO: 161), PPRKKRTVV (SEQ ID NO: 162), NLSKKKKRKREK (SEQ ID NO: 163), RRPSRPFRKP (SEQ ID NO: 164), KRPRSPSS (SEQ ID NO: 165), KRGINDRNFWRGENERKTR (SEQ ID NO: 166), PRPPKMARYDN (SEQ ID NO: 167), KRSFSKAF (SEQ ID NO: 168), KLKIKRPVK (SEQ ID NO: 169), PKTRRRPRRSQRKRPPT (SEQ ID NO: 171), RRKKRR-PRRKKRR (SEQ ID NO: 174), PKKKSRKPKKKSRK (SEQ ID NO: 175), HKKKHPDASVNFSEFSK (SEQ ID NO: 176), QRPGPYDRPQRPGPYDRP (SEQ ID NO: 177), LSPSLSPLLSPSLSPL (SEQ ID NO: 178), RGKGGKGLGKGGAKRHRK (SEQ ID NO: 179), PKR-GRGRPKRGRGR (SEQ ID NO: 180), and MSRRR-KANPTKLSENAKKLAKEVEN (SEQ ID NO: 205).

Embodiment 82. The method of 80 or 81, wherein the one or more NLS are expressed at the C-terminus of the CasX protein.

Embodiment 83. The method of 80 or 81, wherein the one or more NLS are expressed at the N-terminus of the CasX protein.

Embodiment 84. The method of 80 or 81, wherein the one or more NLS are expressed at the N-terminus and C-terminus of the CasX protein.

Embodiment 85. The method of any one of 79 to 84, wherein the one or more polynucleotides encoding the CasX protein are codon optimized for expression in a eukaryotic cell.

Embodiment 86. The method of any one of 79 to 85, wherein the method comprises contacting the eukaryotic cell with a vector encoding the CasX protein and the gNA, and optionally further encoding the donor template.

Embodiment 87. The method of 86, wherein the vector is an Adeno-Associated Viral (AAV) vector.

Embodiment 88. The method of 87, wherein the AAV is AAV1, AAV2, AAV3, AAV4, AAV5, AAV6, AAV7, AAV8, AAV9, AAV10, AAV-Rh74, or AAVRh10.

Embodiment 89. The method of 86, wherein the vector is a lentiviral vector.

Embodiment 90. The method of any one of 86-89, wherein the vector is administered to a subject at a therapeutically effective dose.

Embodiment 91. The method of 90, wherein the subject is selected from the group consisting of mouse, rat, non-human primate, and human.

Embodiment 92. The method of 91, wherein the subject is a human.

Embodiment 93. The method of any one of 90-92, wherein the vector is administered at a dose of at least about 1×10¹⁰ vector genomes (vg), or at least about 1×10¹¹ vg, or at least about 1×10¹² vg, or at least about 1×10¹³ vg, or at least about 1×10¹⁴ vg, or at least about 1×10¹⁵ vg, or at least about 1×10¹⁶ vg.

Embodiment 94. The method of any one of 90-93, wherein the vector is administered by a route of administration selected from the group consisting of intraparenchymal, intravenous, intra-arterial, intracerebroventricular, intracisternal, intrathecal, intracranial, and intraperitoneal routes.

Embodiment 95. The method of any one of the preceding embodiments, comprising further contacting the target nucleic acid with an additional CRISPR protein, or a polynucleotide encoding the additional CRISPR protein.

Embodiment 96. The method of 95, wherein the additional CRISPR protein is a CasX protein having a sequence different from the CasX of any of the preceding embodiments.

Embodiment 97. The method of 95, wherein the additional CRISPR protein is not a CasX protein.

Embodiment 98. The method of any one of 1 to 97, wherein the gNA is a single-molecule gNA (sgNA).

Embodiment 99. The method of any one of 1 to 97, wherein the gNA is a dual-molecule gNA (dgNA).

Embodiment 100. The method of any one of 1 to 99, comprising contacting the target nucleic acid with a plurality of gNAs targeted to the SOD1 gene and/or the SOD1 regulatory element having an allele with one or more mutations.

Embodiment 101. A cell comprising a modified SOD1 gene and/or a modified SOD1 regulatory element, wherein the modified SOD1 gene and/or the modified SOD1 regulatory element has been modified by either:

a) delivering to the cell a CasX protein and a guide nucleic acid (gNA) comprising a targeting sequence; or b) delivering to the cell one or more nucleic acids encoding a CasX protein and a gNA comprising a targeting sequence, wherein the targeting sequence of the gNA has binding specificity for the SOD1 gene and/or the SOD1 regulatory element.

Embodiment 102. The cell of 101, wherein the gNA is a guide RNA (gRNA).

Embodiment 103. The cell of 102, wherein the targeting sequence of the gNA comprises a sequence having at least about 65%, at least about 75%, at least about 85%, or at least about 95% identity to a sequence provided in Table 3.

Embodiment 104. The cell of 101 or 102, wherein the targeting sequence of the gNA comprises a sequence having one or more single nucleotide polymorphisms (SNP) relative to a sequence provided in Table 3.

Embodiment 105. The cell of 103 or 104, wherein the targeting sequence encodes a mutation of the SOD1 polypeptide of SEQ ID NO:100 selected from the group of amino acid substitutions consisting of A4S, A4T, A4V, C6F, V7E, L8Q, L8V, G12R, V14G, V14M, G16S, F20C, E21G, E21K, Q22L, G37R, L38R, L38V, G41D, G41S, H43R, F45C, H46R, H48Q, H48R, E49K, T54R, N65S, L67P, L67R, G72S, D76Y, H80A, L84F, L84V, G85R, N86S, V87A, A89T, A89V, D90A, D90V, G93A, G93C, G93D, G93R, G93V, A95G, V97M, E100G, E100K, D101G, D101N, I104F, S105L, L106V, G108V, C111Y, I112M, I112T, I113T, G114A, R115G, V118L, D124G, D124V, D125H, L126S, S134N, N139K, L144F, L144S, A145T, C146R, G147R, V148G, V148I, I149T, I151T or mutations that disrupt the function or expression of the SOD1 polypeptide.

Embodiment 106. The method of any one of 101-105, wherein the CasX polypeptide and the gNA are associated together in a ribonuclear protein complex (RNP).

Embodiment 107. The cell of any one of 101-105, wherein the modified SOD1 gene and/or the SOD1 regulatory element comprises a single-stranded break, and wherein the modified SOD1 gene and/or the SOD1 regulatory element comprises a mutation, an insertion, or a deletion.

Embodiment 108. The cell of any one of 101-105, wherein the modified SOD1 gene and/or the SOD1 regulatory element comprises a double-stranded break, and wherein the modified SOD1 gene and/or the SOD1 regulatory element comprises a mutation, an insertion, or a deletion.

Embodiment 109. The cell of 106 or 108, wherein the insertion comprises a donor template comprising at least a portion of a SOD1 gene and/or the SOD1 regulatory element, and wherein the SOD1 gene portion is selected from the group consisting of a SOD1 exon, a SOD1 intron, and a SOD1 intron-exon junction.

Embodiment 110. The cell of 109, wherein the donor template ranges in size from 20-10,000 nucleotides.

Embodiment 111. The cell of 109 or 110, wherein the donor template is a single-stranded DNA template or a single stranded RNA template.

Embodiment 112. The method of 109 or 110, wherein the donor template is a double-stranded DNA template.

Embodiment 113. The cell of any one of 101-112, wherein modification of the SOD1 gene and/or the SOD1 regulatory element occurs in vivo.

Embodiment 114. The cell of any one of 101-112, wherein modification of the SOD1 gene and/or the SOD1 regulatory element occurs in vitro.

Embodiment 115. The cell of 113 or 114, wherein the modification corrects the one or more mutations, or wherein expression of the SOD1 having the one or more mutations is inhibited or suppressed.

Embodiment 116. The cell of any one of 101-115, wherein the cell is a eukaryotic cell.

Embodiment 117. The cell of 116, wherein the eukaryotic cell is selected from the group consisting of a plant cell, a fungal cell, a mammalian cell, a reptile cell, an insect cell, an avian cell, a fish cell, a parasite cell, an arthropod cell, a cell of an invertebrate, a cell of a vertebrate, a rodent cell, a mouse cell, a rat cell, a primate cell, a non-human primate cell, and a human cell.

Embodiment 118. The cell of 117, wherein the eukaryotic cell is a human cell.

Embodiment 119. The cell of 118, wherein the cell is a cell of the central nervous system (CNS) or peripheral nervous system (PNS).

Embodiment 120. The cell of 119, wherein the cell is a neuron.

Embodiment 121. The cell of 120, wherein the neuron is a spinal motor neuron.

Embodiment 122. The cell of 119, wherein the cell is a glial cell, an oligodendrocyte, or a Schwann cell.

Embodiment 123. The cell of any one of 101 to 122, wherein the SOD1 gene to be modified encodes a SOD1 polypeptide comprising one or more mutations selected from Table 1 or mutations that disrupt the function of the SOD1 polypeptide.

Embodiment 124. The cell of any one of 101 to 122, wherein the SOD1 gene or the SOD1 regulatory element comprises a wild type sequence.

Embodiment 125. The cell of any one of 101-122, wherein the one or more mutations is a gain of function mutation.

Embodiment 126. The cell of any one of 101-122, wherein the one or more mutations is a loss of function mutation.

Embodiment 127. The cell of any one of 101-122, wherein the SOD1 gene encodes a SOD1 polypeptide comprising a mutation at residue position 4, position 90, and/or residue position 93, corresponding to the SOD1 polypeptide of SEQ ID NO: 100.

Embodiment 128. The cell of 127, wherein the SOD1 gene encoding the SOD1 polypeptide comprises an A4V mutation, a D90A mutation, a G93A mutation, or a combination thereof.

Embodiment 129. A method of treating a SOD1 or related disorder in a subject in need thereof, comprising administering to the subject a plurality of cells of any one of the of 101-128.

Embodiment 130. The method of 129 wherein the SOD1-related disorder is amyotrophic lateral sclerosis (ALS).

Embodiment 131. The method of 129 wherein the SOD1-related disorder is a neuropathy.

Embodiment 132. The method of any one of 129 to 131, wherein the cells are allogeneic.

Embodiment 133. The method of any one of 129 to 131, wherein the cells are autologous.

Embodiment 134. The method of any one of 129 to 131, wherein the cells are part of a cell line.

Embodiment 135. The method of any one of 129 to 134, wherein the cells are administered by a route selected from the group consisting of intraparenchymal, intravenous, intra-arterial, intracerebroventricular, intracisternal, intrathecal, intracranial, and intraperitoneal routes.

Embodiment 136. A method of treating a SOD1 or related disorder in a subject in need thereof, comprising modifying a SOD1 gene and/or a SOD1 regulatory element having one or more mutations in a cell of the subject, the modifying comprising either;
a) administering to the subject a CasX protein and a guide nucleic acid (gNA) comprising a targeting sequence; or
b) administering to the subject one or more nucleic acids encoding a CasX protein and a gNA comprising a targeting sequence, wherein the targeting sequence of the gNA has a sequence complementary to the SOD1 gene and/or the SOD1 regulatory element having the one or more mutations.

Embodiment 137. The method of 136, wherein the targeting sequence of the gNA comprises a sequence having at least about 65%, at least about 75%, at least about 85%, or at least about 95% identity to a sequence provided in Table 3.

Embodiment 138. The method of 136 or 137, wherein the one or more nucleic acids encoding the CasX protein and the gNA are capable of being expressed in a cell.

Embodiment 139. The method of any one of 136-138, wherein the CasX polypeptide and the gNA are associated together in a ribonuclear protein complex (RNP).

Embodiment 140. The method of any one of 136-139, wherein the subject is selected from the group consisting of mouse, rat, non-human primate, and human.

Embodiment 141. The method of 136-140139, wherein the subject is a human.

Embodiment 142. The method of any one of 136-141, wherein the cell is a cell of the central nervous system (CNS) or peripheral nervous system (PNS).

Embodiment 143. The method of 142, wherein the cell is a neuron.

Embodiment 144. The method of 143, wherein the neuron is a spinal motor neuron.

Embodiment 145. The method of 144, wherein the cell is a glial cell, an oligodendrocyte, or a Schwann cell.

Embodiment 146. The method any one of 136 to 145, wherein the method comprises modifying an allele of the SOD1 gene and/or the SOD1 regulatory element in the cell.

Embodiment 147. The method of any one of 136 to 146, wherein the method comprises administering to the subject the CasX protein and gNA, or the one or more nucleic acids encoding the CasX protein and gNA, via an administration route selected from the group consisting of intraparenchymal, intravenous, intra-arterial, intracerebroventricular, intracisternal, intrathecal, intracranial, and intraperitoneal routes.

Embodiment 148. The method of any one of 136-147, wherein the CasX protein is selected from the CasX proteins provided in SEQ ID Nos: 1-3 or Table 4, or sequence proteins having at least about 50%, at least about 60%, at least about 70%, at least about 80%, or at least about 90%, or at least about 95%, or at least about 99% sequence identity to the CasX proteins of SEQ ID NOS:1-3 or the sequences of Table 4.

Embodiment 149. The method of any one of 136-148, wherein the CasX protein has binding affinity for a PAM sequence selected from the group consisting of TTC, ATC, GTC, and CTC.

Embodiment 150. The method of any one of 136-149, wherein the CasX protein comprises nickase activity.

Embodiment 151. The method of any one of 136-150, wherein the CasX protein introduces a single-stranded break in the target nucleic acid, and wherein modification of the SOD1 gene and/or the SOD1 regulatory element comprises a mutation, an insertion, or a deletion.

Embodiment 152. The method of any one of 136-149, wherein the CasX protein introduces a double-stranded break in the target nucleic acid, and wherein the modified SOD1 gene and/or the SOD1 regulatory element comprises a mutation, an insertion, or a deletion.

Embodiment 153. The method of any one of 136-152, wherein the modified SOD1 gene comprises an insertion.

Embodiment 154. The method of any one of 136-152, wherein the modified SOD1 gene comprises a deletion.

Embodiment 155. The method of any one of 136-149, wherein the CasX protein is a catalytically inactive CasX (dCasX) protein.

Embodiment 156. The method of 155, wherein the dCasX comprises a mutation at residues:
a) D672, E769, and/or D935 corresponding to the CasX protein of SEQ ID NO: 1; or
b) D659, E756 and/or D922 of SEQ ID NO: 2.

Embodiment 157. The method of 156, wherein the mutation is a substitution of alanine for the residue.

Embodiment 158. The method of any one of 136 to 157, wherein the SOD1 gene and/or the SOD1 regulatory element comprises a DNA sequence encoding a sequence having at least about 65%, at least about 75%, at least about 85%, or at least about 95% sequence identity to a sequence selected from Table 3.

Embodiment 159. The method of any one of 136-157, wherein the targeting sequence of the gNA comprises a sequence having one or more single nucleotide polymorphisms (SNP) relative to a sequence provided in Table 3.

Embodiment 160. The method of 158 or 159, wherein the targeting sequence encodes a mutation of the SOD1 polypeptide of SEQ ID NO:100 selected from the group of amino acid substitutions consisting of A4S, A4T, A4V, C6F, V7E, L8Q, L8V, G12R, V14G, V14M, G16S, F20C, E21G, E21K, Q22L, G37R, L38R, L38V, G41D, G41S, H43R, F45C, H46R, H48Q, H48R, E49K, T54R, N65S, L67P, L67R, G72S, D76Y, H80A, L84F, L84V, G85R, N86S, V87A, A89T, A89V, D90A, D90V, G93A, G93C, G93D, G93R, G93V, A95G, V97M, E100G, E100K, D101G, D101N, I104F, S105L, L106V, G108V, C111Y, I112M, I112T, I113T, G114A, R115G, V118L, D124G, D124V, D125H, L126S, S134N, N139K, L144F, L144S, A145T, C146R, G147R, V148G, V148I, I149T, I151T, and mutations that disrupt the function or expression of the SOD1 polypeptide.

Embodiment 161. The method of any one of 136 to 157, wherein the SOD1 gene and/or the SOD1 regulatory element comprises a wild type sequence.

Embodiment 162. The method of any one of 136-160, wherein the mutation of the SOD1 gene and/or the SOD1 regulatory element is a gain of function mutation.

Embodiment 163. The method of any one of 136-160, wherein the mutation of the SOD1 gene and/or the SOD1 regulatory element is a loss of function mutation.

Embodiment 164. The method of any one of 136-160, wherein the SOD1 gene encodes a SOD1 polypeptide comprising a mutation selected from the mutations provided in Table 1 or mutations that disrupt the function of the SOD1 polypeptide.

Embodiment 165. The method of 164, wherein the SOD1 gene encodes a SOD1 polypeptide comprising an A4V mutation, a D90A mutation, and/or a G93A mutation of the sequence of SEQ ID NO:100.

Embodiment 166. The method of any one of 136-165, wherein the gNA is chemically modified.

Embodiment 167. The method of any one of 136-166, wherein the targeting sequence of the gNA has a sequence of a SOD1 exon or a sequence that is complementary to a SOD1 exon.

Embodiment 168. The method any one of 136-166, wherein the targeting sequence of the gNA has a sequence of a SOD1 intron or a sequence that is complementary to a SOD1 intron.

Embodiment 169. The method of any one of 136-166, wherein the targeting sequence of the gNA has a sequence of a SOD1 intron-exon junction or a sequence that is complementary to a SOD1 intron-exon junction.

Embodiment 170. The method any one of 136-166, wherein the targeting sequence of the gNA has a sequence with one or more single nucleotide polymorphisms of the SOD1 gene and/or SOD1 regulatory element, or a sequence that is complementary to one or more single nucleotide polymorphisms (SNP) of the SOD1 gene and/or SOD1 regulatory element.

Embodiment 171. The method of any one of 136-166, wherein the SOD1 gene and/or SOD1 regulatory element is a wild type sequence.

Embodiment 172. The method of any one of 136-171, wherein the targeting sequence of the gNA has a sequence that is complementary to an intergenic region of the SOD1 gene.

Embodiment 173. The method of any one of 136 to 166, wherein the targeting sequence of the gNA has a sequence that is complementary to a SOD1 regulatory element.

Embodiment 174. The method of 173, wherein the SOD1 regulatory element is 5' of the SOD1 gene.

Embodiment 175. The method of 173, wherein the SOD1 regulatory element is 3' of the SOD1 gene.

Embodiment 176. The method of 173, wherein the SOD1 regulatory element comprises the 5' untranslated region (UTR) of the SOD1 gene.

Embodiment 177. The method of 173, wherein the SOD1 regulatory element comprises the 3'UTR of the SOD1 gene.

Embodiment 178. The method of 173, wherein the SOD1 regulatory element comprises a promoter.

Embodiment 179. The method of 173, wherein the SOD1 regulatory element comprises an enhancer.

Embodiment 180. The method of any one of 136 to 179, wherein the targeting sequence of the gNA has a sequence that hybridizes with the SOD1 gene and/or the SOD1 regulatory element.

Embodiment 181. The method of any one of 136 to 180, wherein the modifying comprises introducing a single-stranded break in the target nucleic acid wherein modification of the SOD1 gene and/or the SOD1 regulatory element comprises a mutation, an insertion, or a deletion.

Embodiment 182. The method of any one of 136 to 180, wherein the modifying comprises introducing a double-stranded break in the target nucleic acid, wherein the modified SOD1 gene and/or the SOD1 regulatory element comprises a mutation, an insertion, or a deletion.

Embodiment 183. The method of any one of 136 to 182, wherein the method further comprises administering a donor template comprising at least a portion of a SOD1 gene, wherein the SOD-1 gene portion is selected from a SOD1 exon, a SOD1 intron, a SOD1 intron-exon junction, a SOD1 regulatory element, and wherein the SOD-1 gene portion is inserted into or replaces the target nucleic acid.

Embodiment 184. The method of 183, wherein the donor DNA template ranges in size from 10-10,000 nucleotides.

Embodiment 185. The method of 183 or 184, wherein the donor template is a single-stranded RNA or DNA template.

Embodiment 186. The method of 183 or 184, wherein the donor template is a double-stranded DNA template.

Embodiment 187. The method of any one of 136 to 186, wherein the SOD1 gene is a wild-type gene.

Embodiment 188. The method of any one of 136 to 187, wherein the method comprises contacting the target nucleic acid of the cell with a CasX protein and a gNA.

Embodiment 189. The method of 188, wherein the method comprises contacting the target nucleic acid of the cell with a pre-complexed CasX protein-gNA.

Embodiment 190. The method of 188, wherein the method comprises contacting the cell acid with a liposome or lipid nanoparticle comprising the CasX protein and the gNA.

Embodiment 191. The method of any one of 136 to 190, wherein the method comprises contacting the cell with the one or more nucleic acids encoding the CasX protein and the gNA, and optionally the donor template.

Embodiment 192. The method of 191, wherein the one or more nucleic encoding the CasX protein further comprise one or more nuclear localization signals (NLSs).

Embodiment 193. The method of 192, wherein the one or more NLS are selected from the sequences PKKKRKV (SEQ ID NO: 145), KRPAATKKAGQAKKKK (SEQ ID NO: 146), PAAKRVKLD (SEQ ID NO: 147), RQRR-NELKRSP (SEQ ID NO: 148), NQSSNFGPMKGGNFG-GRSSGPYGGGGQYFAKPRNQGGY (SEQ ID NO: 149), RMRIZFKNKGKDTAELRRRRVEVSVELRKAKKD-EQILKRRNV (SEQ ID NO: 150), VSRKRPRP (SEQ ID NO: 151), PPKKARED (SEQ ID NO: 152), PQPKKKPL (SEQ ID NO: 153), SALI AP (SEQ ID NO: 154), DRLRR (SEQ ID NO: 155), PKQKKRK (SEQ ID NO: 156), RKLKKKIKKL (SEQ ID NO: 157), REKKKFLKRR (SEQ ID NO: 158), KRKGDEVDGVDEVAKKKSKK (SEQ ID NO: 159), RKCLQAGMNLEARKTKK (SEQ ID NO: 160), PRPRKIPR (SEQ ID NO: 161), PPRKKRTVV (SEQ ID NO: 162), NLSKKKKRKREK (SEQ ID NO: 163), RRPSRPFRKP (SEQ ID NO: 164), KRPRSPSS (SEQ ID NO: 165), KRGINDRNFWRGENERKTR (SEQ ID NO: 166), PRPPKMARYDN (SEQ ID NO: 167), KRSFSKAF (SEQ ID NO: 168), KLKIKRPVK (SEQ ID NO: 169), PKTRRRPRRSQRKRPPT (SEQ ID NO: 171), RRKKRR-PRRKKRR (SEQ ID NO: 174), PKKKSRKPKKKSRK (SEQ ID NO: 175), HKKKHPDASVNFSEFSK (SEQ ID NO: 176), QRPGPYDRPQRPGPYDRP (SEQ ID NO: 177), LSPSLSPLLSPSLSPL (SEQ ID NO: 178), RGKGGKGLGKGGAKRHRK (SEQ ID NO: 179), PKR-GRGRPKRGRGR (SEQ ID NO: 180), and MSRRR-KANPTKLSENAKKLAKEVEN (SEQ ID NO: 205).

Embodiment 194. The method of 192, wherein the one or more NLSs are expressed at the C-terminus of the CasX protein.

Embodiment 195. The method of 192, wherein the one or more NLSs are expressed at the N-terminus of the CasX protein.

Embodiment 196. The method of 192, wherein the one or more NLSs are expressed at the N-terminus and C-terminus of the CasX protein.

Embodiment 197. The method of any one of 191 to 196, wherein the one or more nucleic acids encoding the CasX protein are codon optimized for expression in a eukaryotic cell.

Embodiment 198. The method of any one of 136 to 197, wherein the method comprises contacting the cell with a vector encoding the CasX protein and the gNA, the vector optionally further encoding the donor template.

Embodiment 199. The method of 198, wherein the vector is an AAV vector.

Embodiment 200. The vector of 199, wherein the AAV vector is selected from AAV1, AAV2, AAV3, AAV4, AAV5, AAV6, AAV7, AAV8, AAV9, AAV10, AAV-Rh74, or AAVRh10.

Embodiment 201. The method of 198, wherein the vector is a lentiviral vector.

Embodiment 202. The method of any one of 136 to 200, comprising further contacting the cell with an additional CRISPR protein, or a nucleic acid encoding the additional CRISPR protein.

Embodiment 203. The method of 202, wherein the additional CRISPR protein has a sequence different from the CasX protein of any of the preceding embodiments.

Embodiment 204. The method of 202, wherein the additional CRISPR protein is not a CasX protein.

Embodiment 205. The method of any one of 136 to 204, wherein the gNA is a single-molecule gNA (sgNA).

Embodiment 206. The method of any one of 136 to 204, wherein the gNA is a dual-molecule gNA (dgNA).

Embodiment 207. The method of any one of 136 to 206, comprising contacting the target nucleic acid with a plurality of gNAs targeted to the SOD1 gene and/or the SOD1 regulatory element.

Embodiment 208. The method of any one of 136 to 207, wherein the SOD1-related disorder is ALS.

Embodiment 209. The method of any one of 136 to 207, wherein the SOD1-related disorder is a neuropathy.

Embodiment 210. A CasX/gNA system comprising at least one CasX protein selected from those provided in SEQ ID NOs: 1-3 or Table 4 or sequences having at least about 50%, at least about 60%, at least about 70%, at least about 80%, or at least about 90%, or at least about 95%, or at least about 99% sequence identity to the CasX proteins of SEQ ID NOS:1-3 or Table 4 and at least one gRNA with a targeting sequence wherein the targeting sequence has a sequence that is complementary to a SOD1 gene and/or a SOD1 regulatory element, or polynucleotides encoding the same.

Embodiment 211. A CasX/gNA system comprising at least a CasX protein and at least one gNA with a targeting sequence wherein the targeting sequence has a sequence that is complementary to a SOD1 gene and/or a SOD1 regulatory element and wherein the targeting sequence of the gNA comprises a sequence having at least about 65%, at least about 75%, at least about 85%, or at least about 95% identity to a sequence provided in Table 3, or polynucleotides encoding the same.

Embodiment 212. The CasX/gNA system of 211, wherein the targeting sequence of the gNA comprises a sequence having one or more single nucleotide polymorphisms (SNP) relative to a sequence provided in Table 3.

Embodiment 213. The method of 211 or 212, wherein the targeting sequence encodes a mutation of the SOD1 polypeptide of SEQ ID NO:100 selected from the group of amino acid substitutions consisting of A4S, A4T, A4V, C6F, V7E, L8Q, L8V, G12R, V14G, V14M, G16S, F20C, E21G, E21K, Q22L, G37R, L38R, L38V, G41D, G41S, H43R, F45C, H46R, H48Q, H48R, E49K, T54R, N65S, L67P, L67R, G72S, D76Y, H80A, L84F, L84V, G85R, N86S, V87A, A89T, A89V, D90A, D90V, G93A, G93C, G93D, G93R, G93V, A95G, V97M, E100G, E100K, D101G, D101N, I104F, S105L, L106V, G108V, C111Y, I112M, I112T, I113T, G114A, R115G, V118L, D124G, D124V, D125H, L126S, S134N, N139K, L144F, L144S, A145T, C146R, G147R, V148G, V148I, I149T, I151T, and mutations that disrupt the function or expression of the SOD1 polypeptide.

Embodiment 214. A CasX/gNA system comprising:
a) a CasX polypeptide and a gNA;
b) a CasX polypeptide, a gNA, and a donor template;
c) a CasX fusion polypeptide comprising a heterologous polypeptide and a gNA;
d) a CasX fusion polypeptide comprising a heterologous polypeptide, a gNA, and a donor template;
e) a vector comprising: i) a nucleotide sequence encoding a CasX polypeptide; and ii) a nucleotide sequence encoding a gNA;
f) a vector comprising: i) a nucleotide sequence encoding a CasX polypeptide; ii) a nucleotide sequence encoding a gNA; and iii) a donor template;
g) a vector comprising: i) a nucleotide sequence encoding a CasX fusion polypeptide comprising a heterologous polypeptide; and ii) a nucleotide sequence encoding a gNA; or
h) a vector comprising: i) a nucleotide sequence encoding a CasX fusion polypeptide comprising a heterologous polypeptide; ii) a nucleotide sequence encoding a gNA; and a donor template.

Embodiment 215. The system of 214, wherein the CasX protein is selected from those provided in SEQ ID NOS: 1-3 or Table 4 or sequences having at least about 50%, at least about 60%, at least about 70%, at least about 80%, or at least about 90%, or at least about 95%, or at least about 99% sequence identity to the CasX proteins of SEQ ID NOS:1-3 or Table 4 and the gRNA targeting sequence has a sequence that is complementary to a SOD1 gene and/or a SOD1 regulatory element.

Embodiment 216. The system of 214 or 215, wherein the CasX polypeptide and the gNA are associated together in a ribonuclear protein complex (RNP).

Embodiment 217. The system of any one of 214-216, wherein the donor template comprises at least a portion of a SOD1 gene, wherein the SOD1 gene portion is selected from the group consisting of a SOD1 exon, a SOD1 intron, a SOD1 intron-exon junction, and a SOD1 regulatory element.

Embodiment 218. The system of any one of 214-216, wherein the donor template is a single stranded DNA template or a single stranded RNA template.

Embodiment 219. The method of any one of 214-216, wherein the donor template is a double stranded DNA template.

Embodiment 220. The system of any one of 214-219, wherein the heterologous polypeptide inhibits transcription, modifies a target nucleic acid, or modifies a polypeptide associated with a nucleic acid.

Embodiment 221. The system of any one of 214-220, wherein vector is an Adeno-Associated Viral (AAV) vector.

Embodiment 222. The system of 221, wherein the AAV is AV1, AAV2, AAV3, AAV4, AAV5, AAV6, AAV7, AAV8, AAV9, AAV10, AAV-Rh74, or AAVRh10.

Embodiment 223. A polynucleotide encoding a gNA comprising a targeting sequence, wherein the targeting sequence has a sequence that is complementary to a SOD1 gene and/or a SOD1 regulatory element, wherein the gNA is capable of binding to a CasX protein.

Embodiment 224. A polynucleotide encoding a gNA targeting sequence, wherein the targeting sequence of the gNA comprises a sequence having at least about 65%, at least about 75%, at least about 85%, or at least about 95% identity to a sequence provided in Table 3.

Embodiment 225. The polynucleotide of 224, wherein the targeting sequence of the gNA comprises a sequence having one or more single nucleotide polymorphisms (SNP) relative to a sequence provided in Table 3.

Embodiment 226. The polynucleotide of 224 or 225, wherein the targeting sequence encodes a mutation of the SOD1 polypeptide of SEQ ID NO:100 selected from the group consisting of amino acid substitutions consisting of A4S, A4T, A4V, C6F, V7E, L8Q, L8V, G12R, V14G, V14M, G16S, F20C, E21G, E21K, Q22L, G37R, L38R, L38V, G41D, G41S, H43R, F45C, H46R, H48Q, H48R, E49K, T54R, N65S, L67P, L67R, G72S, D76Y, H80A, L84F, L84V, G85R, N86S, V87A, A89T, A89V, D90A, D90V, G93A, G93C, G93D, G93R, G93V, A95G, V97M, E100G, E100K, D101G, D101N, I104F, S105L, L106V, G108V, C111Y, I112M, I112T, I113T, G114A, R115G, V118L, D124G, D124V, D125H, L126S, S134N, N139K, L144F, L144S, A145T, C146R, G147R, V148G, V148I, I149T, I151T and mutations that disrupt the function or expression of the SOD1 polypeptide.

Embodiment 227. The polynucleotide of 223 or 224, wherein the polynucleotide further encodes a CasX protein.

Embodiment 228. The polynucleotide of any one of 223-227, wherein the polynucleotide is a DNA.

Embodiment 229. A vector comprising any of the polynucleotides of 223-228.

Embodiment 230. The vector of 229, wherein the vector is a viral vector.

Embodiment 231. The vector of 229, wherein the vector is a lentiviral vector.

Embodiment 232. The vector of 229, wherein the vector is an AAV vector.

Embodiment 233. The vector of 232, wherein the AAV vector is AV1, AAV2, AAV3, AAV4, AAV5, AAV6, AAV7, AAV8, AAV9, AAV10, AAV-Rh74, or AAVRh10.

Embodiment 234. A cell comprising the polynucleotide or vector of any one of 223-233.

Set 2

Embodiment 1. A CasX:gNA system comprising a CasX protein and a guide nucleic acid (gNA), wherein the gNA comprises a targeting sequence complementary to a target nucleic acid sequence comprising a superoxide dismutase 1 (SOD1) gene.

Embodiment 2. The CasX:gNA system of 1, wherein the SOD1 gene comprises one or more mutations in the sequence of the SOD1 gene encoding the SOD1 protein.

Embodiment 3. The CasX:gNA system of 1 or 2, wherein the SOD1 gene comprises one or more mutations in the sequence of the SOD1 gene encoding the regulatory region.

Embodiment 4. The CasX:gNA system of 1, wherein the SOD1 gene comprises a wild-type sequence in the sequence encoding the SOD1 protein or the regulatory region.

Embodiment 5. The CasX:gNA system of 4, wherein the wild-type sequence comprises a nucleic acid encoding all or a portion of SEQ ID NO:100, or comprises a nucleic acid sequence that spans all or a portion of bp 31,659,622 to bp 31,668,931 of chromosome 21 of human genome GRCh38/hg38.

Embodiment 6. The CasX:gNA system of 2 or 3, wherein the mutation is an insertion, deletion, substitution, duplication, or inversion of one or more nucleotides as compared to the wild-type sequence.

Embodiment 7. The CasX:gNA system of any one of 2, 3, or 6, wherein the mutation is a gain of function mutation.

Embodiment 8. The CasX:gNA system of any one of 2, 3, or 6, wherein the mutation is a loss of function mutation.

Embodiment 9. The CasX:gNA system of any one of 2, 3, or 6-8, wherein the SOD1 gene encodes a protein comprising a mutation selected from mutations set forth in Table 1 or comprises one or more mutations that disrupt the function of the SOD1 protein.

Embodiment 10. The CasX:gNA system any one of 2, 3, or 6-9, wherein the SOD1 gene encodes a protein comprising a mutation selected from the group of amino acid substitutions of SEQ ID NO:100 consisting of A4S, A4T, A4V, C6F, V7E, L8Q, L8V, G12R, V14G, V14M, G16S, F20C, E21G, E21K, Q22L, G37R, L38R, L38V, G41D, G41S, H43R, F45C, H46R, H48Q, H48R, E49K, T54R, N65S, L67P, L67R, G72S, D76Y, H80A, L84F, L84V, G85R, N86S, V87A, A89T, A89V, D90A, D90V, G93A, G93C, G93D, G93R, G93V, A95G, V97M, E100G, E100K, D101G, D101N, I104F, S105L, L106V, G108V, C111Y, I112M, I112T, I113T, G114A, R115G, V118L, D124G, D124V, D125H, L126S, S134N, N139K, L144F, L144S, A145T, C146R, G147R, V148G, V148I, I149T, I151T and one or more amino acid substitutions of SEQ ID NO:100 that disrupt a function or expression of the SOD1 protein, or is selected from a combination thereof.

Embodiment 11. The CasX:gNA system of 10, wherein the SOD1 gene encodes a protein comprising a mutation selected from an A4V mutation of SEQ ID NO:100, a D90A mutation of SEQ ID NO:100, a G93A mutation of SEQ ID NO:100, or a combination thereof.

Embodiment 12. The CasX:gNA system of any one 1-11, wherein the gNA is a guide RNA (gRNA).

Embodiment 13. The CasX:gNA system of any one of 1-11, wherein the gNA is a guide DNA (gDNA).

Embodiment 14. The CasX:gNA system of any one of 1-11, wherein the gNA is a chimera comprising DNA and RNA.

Embodiment 15. The CasX:gNA system of any one 1-14, wherein the gNA is a single-molecule gNA (sgNA).

Embodiment 16. The CasX:gNA system of any one of 1-14, wherein the gNA is a dual-molecule gNA (dgNA).

Embodiment 17. The CasX:gNA system of any one 1-16, wherein the targeting sequence of the gNA comprises a sequence selected from the group consisting of the sequences set forth in Table 3.

Embodiment 18. The CasX:gNA system of any one of 1-16, wherein the targeting sequence of the gNA comprises a sequence a sequence of Table 3 with a single nucleotide removed from the 3' end of the sequence.

Embodiment 19. The CasX:gNA system of any one of 1-16, wherein the targeting sequence of the gNA comprises a sequence a sequence of Table 3 with two nucleotides removed from the 3' end of the sequence.

Embodiment 20. The CasX:gNA system of any one of 1-16, wherein the targeting sequence of the gNA comprises a sequence a sequence of Table 3 with three nucleotides removed from the 3' end of the sequence.

Embodiment 21. The CasX:gNA system of any one of 1-16, wherein the targeting sequence of the gNA comprises a sequence a sequence of Table 3 with four nucleotides removed from the 3' end of the sequence.

Embodiment 22. The CasX:gNA system of any one of 1-16, wherein the targeting sequence of the gNA comprises a sequence a sequence of Table 3 with five nucleotides removed from the 3' end of the sequence.

Embodiment 23. The CasX:gNA system of any one of 1-22, wherein the targeting sequence of the gNA is complementary to a sequence of a SOD1 exon or a sequence complementary to a SOD1 exon.

Embodiment 24. The CasX:gNA system of any one of 1-22, wherein the targeting sequence of the gNA is complementary to a sequence of a SOD1 intron or a sequence complementary to a SOD1 intron.

Embodiment 25. The CasX:gNA system of any one of 1-22, wherein the targeting sequence of the gNA is complementary to a sequence of a SOD1 intron-exon junction or a sequence complementary to a SOD1 intron-exon junction.

Embodiment 26. The CasX:gNA system of any one of 1-22, wherein the targeting sequence of the gNA is complementary to a sequence comprising one or more single nucleotide polymorphisms (SNPs) of the SOD1 gene.

Embodiment 27. The CasX:gNA system of any one of 1-22, wherein the targeting sequence of the gNA is complementary to a sequence of an intergenic region of the SOD1 gene.

Embodiment 28. The CasX:gNA system of any one of 1-22, wherein the targeting sequence of the gNA comprises a DNA sequence having at least about 65%, at least about 75%, at least about 85%, or at least about 95% identity to a sequence selected from the group consisting of sequences set forth in Table 3.

Embodiment 29. The CasX:gNA system of any one of 1-22, wherein the targeting sequence of the gNA comprises a DNA sequence having one or more single nucleotide polymorphisms (SNP) relative to a sequence set forth in Table 3.

Embodiment 30. The CasX:gNA system of any one of 1-17, wherein the targeting sequence of the gNA consists of a sequence selected from the group consisting of sequences set forth in Table 3.

Embodiment 31. The CasX:gNA system of any one of 1-16, wherein the targeting sequence is complementary to a nucleic acid sequence encoding a mutation of the SOD1 protein of SEQ ID NO:100 selected from the group of amino acid substitutions consisting of A4S, A4T, A4V, C6F, V7E, L8Q, L8V, G12R, V14G, V14M, G16S, F20C, E21G, E21K, Q22L, G37R, L38R, L38V, G41D, G41S, H43R, F45C, H46R, H48Q, H48R, E49K, T54R, N65S, L67P, L67R, G72S, D76Y, H80A, L84F, L84V, G85R, N86S, V87A, A89T, A89V, D90A, D90V, G93A, G93C, G93D, G93R, G93V, A95G, V97M, E100G, E100K, D101G, D101N, I104F, S105L, L106V, G108V, C111Y, I112M, I112T, I113T, G114A, R115G, V118L, D124G, D124V, D125H, L126S, S134N, N139K, L144F, L144S, A145T, C146R, G147R, V148G, V148I, I149T, I151T, and one or more amino acid substitutions of SEQ ID NO:100 that disrupt the function or expression of the SOD1 protein.

Embodiment 32. The CasX:gNA system of any one of 1-31, further comprising a second gNA, wherein the second gNA has a targeting sequence complementary a different or overlapping portion of the target nucleic acid compared to the targeting sequence of the gNA of any one of the preceding.

Embodiment 33. The CasX:gNA system of any one of 1-32, wherein the gNA has a scaffold comprising a sequence having at least about 50%, at least about 60%, at least about 70%, at least about 80%, at least about 90%, at least about 95%, at least about 96%, at least about 97%, at least about 98%, at least about 99%, or 100% sequence identity to a sequence selected from the group consisting of sequences set forth in Table 2A or 2B.

Embodiment 34. The CasX:gNA system of 33, wherein the gNA scaffold comprises a sequence having at least one modification relative to a reference gNA sequence selected from the group consisting of SEQ ID NOS: 4-16 of Table 2A.

Embodiment 35. The CasX:gNA system of 34, wherein the at least one modification of the reference gNA comprises at least one substitution, deletion, or substitution of a nucleotide of the gNA sequence.

Embodiment 36. The CasX:gNA system of any one of 1-35, wherein the gNA is chemically modified.

Embodiment 37. The CasX:gNA system of any one of 1-36, wherein the CasX protein comprises a reference CasX protein having a sequence of any one of SEQ ID NOS: 1-3 or a CasX variant protein having a sequence of Table 4, or a sequence having at least about 50%, at least about 60%, at least about 70%, at least about 80%, at least about 90%, or at least about 95%, or at least about 95%, or at least about 96%, or at least about 97%, or at least about 98%, or at least about 99% sequence identity thereto.

Embodiment 38. The CasX:gNA system of 37, wherein the CasX protein has binding affinity for a protospacer adjacent motif (PAM) sequence selected from the group consisting of TTC, ATC, GTC, and CTC.

Embodiment 39. The CasX:gNA system of 37 or 38, wherein the CasX variant protein comprises at least one modification relative to a reference CasX protein having a sequence selected from SEQ ID NOS:1-3.

Embodiment 40. The CasX:gNA system of 39, wherein the at least one modification comprises at least one amino acid substitution, deletion, or substitution in a domain of the CasX variant protein relative to the reference CasX protein.

Embodiment 41. The CasX:gNA system of 40, wherein the domain is selected from the group consisting of a non-target strand binding (NTSB) domain, a target strand loading (TSL) domain, a helical I domain, a helical II domain, an oligonucleotide binding domain (OBD), and a RuvC DNA cleavage domain.

Embodiment 42. The CasX:gNA system of any one of 37-41, wherein the CasX protein further comprises one or more nuclear localization signals (NLS).

Embodiment 43. The CasX:gNA system of 42, wherein the one or more NLS are selected from the sequences PKKKRKV (SEQ ID NO: 145), KRPAATKKAGQAKKKK (SEQ ID NO: 146), PAAKRVKLD (SEQ ID NO: 147), RQRRNELKRSP (SEQ ID NO: 148), NQSSNFGPMKGG-NFGGRSSGPYGGGGQYFAKPRNQGGY (SEQ ID NO: 149), RMRIZFKNKGKDTAELRRRRVEVS-VELRKAKKDEQILKRRNV (SEQ ID NO: 150), VSRKR-PRP (SEQ ID NO: 151), PPKKARED (SEQ ID NO: 152), PQPKKKPL (SEQ ID NO: 153), SALI AP (SEQ ID NO: 154), DRLRR (SEQ ID NO: 155), PKQKKRK (SEQ ID NO: 156), RKLKKKIKKL (SEQ ID NO: 157), REKKKFLKRR (SEQ ID NO: 158), KRKGDEVDGVDE-VAKKKSKK (SEQ ID NO: 159), RKCLQAGMNLEAR-KTKK (SEQ ID NO: 160), PRPRKIPR (SEQ ID NO: 161), PPRKKRTVV (SEQ ID NO: 162), NLSKKKKRKREK (SEQ ID NO: 163), RRPSRPFRKP (SEQ ID NO: 164), KRPRSPSS (SEQ ID NO: 165), KRGINDRNFWR-GENERKTR (SEQ ID NO: 166), PRPPKMARYDN (SEQ ID NO: 167), KRSFSKAF (SEQ ID NO: 168), KLKIKRPVK (SEQ ID NO: 169), PKTRRRPRR-SQRKRPPT (SEQ ID NO: 171), RRKKRRPRRKKRR (SEQ ID NO: 174), PKKKSRKPKKKSRK (SEQ ID NO: 175), HKKKHPDASVNFSEFSK (SEQ ID NO: 176), QRPGPYDRPQRPGPYDRP (SEQ ID NO: 177), LSPSL-SPLLSPSLSPL (SEQ ID NO: 178), RGKGGKGLGKG-GAKRHRK (SEQ ID NO: 179), PKRGRGRPKRGRGR (SEQ ID NO: 180), and MSRRR-KANPTKLSENAKKLAKEVEN (SEQ ID NO: 205).

Embodiment 44. The CasX:gNA system of 42 or 43, wherein the one or more NLS are expressed at the C-terminus of the CasX protein.

Embodiment 45. The CasX:gNA system of 42 or 43, wherein the one or more NLS are expressed at the N-terminus of the CasX protein.

Embodiment 46. The CasX:gNA system of 42 or 43, wherein the one or more NLS are expressed at the N-terminus and C-terminus of the CasX protein.

Embodiment 47. The CasX:gNA system of any one of 37-46, wherein the CasX variant protein exhibits at least one or more improved characteristics as compared to corresponding characteristics of a reference CasX protein.

Embodiment 48. The CasX:gNA system of 47, wherein the improved characteristic is selected from the group consisting of improved folding of the CasX protein, improved binding affinity of the CasX protein to the guide RNA, improved ribonuclear protein complex (RNP) formation, higher percentage of cleavage-competent RNP, improved binding affinity to the target nucleic acid, altered binding affinity to one or more PAM sequences, improved unwinding of the target nucleic acid, increased activity, increased target nucleic acid cleavage rate, improved editing efficiency, improved editing specificity, increased activity of the nuclease, increased target strand loading for double strand cleavage, decreased target strand loading for single strand nicking, decreased off-target cleavage, improved binding of the non-target strand of DNA, improved CasX protein stability, improved protein:guide RNA complex stability, improved protein solubility, improved protein:guide RNA complex solubility, improved protein yield, improved protein expression, and improved fusion characteristics.

Embodiment 49. The CasX:gNA system of 47 or 48, wherein the improved characteristic of the CasX variant protein is at least about 1.1 to about 100,000-fold improved relative to the characteristic of the reference CasX protein of SEQ ID NO: 1, SEQ ID NO: 2, or SEQ ID NO: 3.

Embodiment 50. The CasX:gNA system of 47 or 48, wherein the improved characteristic of the CasX variant protein is at least about 10-fold, at least about 100-fold, at least about 1,000-fold, or at least about 10,000-fold improved relative to the characteristics of the reference CasX protein of SEQ ID NO: 1, SEQ ID NO: 2, or SEQ ID NO: 3.

Embodiment 51. The CasX:gNA system of any one of 48-50, wherein the improved characteristic is improved binding affinity to the target nucleic acid.

Embodiment 52. The CasX:gNA system of any one of 48-50, wherein the improved characteristic is increased target nucleic acid cleavage rate.

Embodiment 53. The CasX:gNA system of any one of 48-50, wherein the improved characteristic is increased binding affinity to one or more PAM sequences wherein the one or more PAM sequences are selected from the group consisting of TTC, ATC, GTC, and CTC.

Embodiment 54. The CasX:gNA system of any one of 1-53, wherein the CasX protein and the gNA are associated together in an RNP.

Embodiment 55. The CasX:gNA system of 54, wherein the RNP comprising a CasX variant has a higher percentage of cleavage-competent RNP compared to an RNP of a reference CasX protein of SEQ ID NO: 1, SEQ ID NO: 2, or SEQ ID NO: 3 and the gNA.

Embodiment 56. The CasX:gNA system of any one of 41-55, wherein the CasX variant protein comprises a RuvC DNA cleavage domain having nickase activity.

Embodiment 57. The CasX:gNA system of any one of 41-55, wherein the CasX variant protein comprises a RuvC DNA cleavage domain having double-stranded cleavage activity.

Embodiment 58. The CasX:gNA system of any one of 1-46, wherein the CasX protein is a catalytically inactive CasX (dCasX) protein, and wherein the dCasX and the gNA retain the ability to bind to the target nucleic acid.

Embodiment 59. The CasX:gNA system of 58, wherein the dCasX comprises a mutation at residues:
 a. D672, E769, and/or D935 corresponding to the CasX protein of SEQ ID NO:1; or
 b. D659, E756 and/or D922 corresponding to the CasX protein of SEQ ID NO: 2.

Embodiment 60. The CasX:gNA system of 59, wherein the mutation is a substitution of alanine for the residue.

Embodiment 61. The CasX:gNA system of any one of 1-60, further comprising a donor template nucleic acid.

Embodiment 62. The CasX:gNA system of 61, wherein the donor template comprises a nucleic acid comprising at least a portion of a SOD1 gene coding the SOD1 protein or the SOD1 regulatory region, selected from the group consisting of a SOD1 exon, a SOD1 intron, and a SOD1 intron-exon junction.

Embodiment 63. The CasX:gNA system of 61 or 62, wherein the donor template ranges in size from 10-10,000 nucleotides.

Embodiment 64. The CasX:gNA system of any one of 61-63, wherein the donor template is a single-stranded DNA template or a single stranded RNA template.

Embodiment 65. The CasX:gNA system of any one of 61-63, wherein the donor template is a double-stranded DNA template.

Embodiment 66. A nucleic acid comprising a sequence that encodes the CasX:gNA system of any one of 1-65.

Embodiment 67. The nucleic acid of 66, wherein the nucleic acids encoding the CasX protein and gNA are codon optimized for expression in a eukaryotic cell.

Embodiment 68. A vector comprising the nucleic acid of 66 or 67.

Embodiment 69. A vector comprising a donor template, wherein the donor template comprises a nucleic acid comprising at least a portion of a SOD1 gene encoding the SOD1 protein or the SOD1 regulatory region Embodiment 70. The vector of 69, further comprising the nucleic acid of 66 or 67.

Embodiment 71. The vector of any one of 68-70, wherein the vector further comprises a promoter.

Embodiment 72. The vector of any one of 68-70, wherein the vector is selected from the group consisting of a retroviral vector, a lentiviral vector, an adenoviral vector, an adeno-associated viral (AAV) vector, a herpes simplex virus (HSV) vector, a virus-like particle (VLP), a plasmid, a minicircle, a nanoplasmid, and an RNA vector.

Embodiment 73. The vector of 72, wherein the vector is an AAV vector.

Embodiment 74. The vector of 73, wherein the AAV vector is selected from AAV1, AAV2, AAV3, AAV4, AAV5, AAV6, AAV7, AAV8, AAV9, AAV10, AAV-Rh74, or AAVRh10.

Embodiment 75. The vector of 72, wherein the vector is a retroviral vector.

Embodiment 76. The vector of 72, wherein the vector encoding the VLP comprises one or more nucleic acids encoding a gag polyprotein, the CasX protein of any one of 37-57, and the gNA of any one of 1-36.

Embodiment 77. A virus-like particle (VLP) comprising the CasX protein of any one of 37-57, and the gNA of any one of 1-36.

Embodiment 78. The VLP of 77, wherein the CasX protein and the gNA are associated together in an RNP.

Embodiment 79. A method of modifying a SOD1 target nucleic acid, optionally comprising one or more mutations, the method comprising contacting the target nucleic acid with a CasX protein and a guide nucleic acid (gNA) comprising a targeting sequence wherein said contacting comprises introducing into a cell:

a. (i) the CasX protein of any one of 37-57 or a nucleic acid encoding the CasX protein; and (ii) the gNA of any one of 1-36, or a nucleic acid encoding the gNA; or b. the CasX:gNA system of any one of 1-65, or a nucleic acid encoding the system, wherein said contacting results in modification of the target nucleic acid by the CasX protein.

Embodiment 80. The method of 79, wherein the CasX protein and the gNA are associated together in a ribonuclear protein complex (RNP).

Embodiment 81. The method of 79 or 80, further comprising a second gNA or a nucleic acid encoding the second gNA, wherein the second gNA has a targeting sequence complementary to a different or overlapping portion of the target nucleic acid.

Embodiment 82. The method of any one of 79-81, wherein the method comprises modifying the target nucleic acid of the SOD1 gene coding the SOD1 protein or the SOD1 regulatory region.

Embodiment 83. The method of any one of 79-82, further comprising contacting the target nucleic acid with a donor template comprising at least a portion of a SOD1 gene coding the SOD1 protein or the SOD1 regulatory region.

Embodiment 84. The method of any one of 79-83, wherein the modifying comprises introducing a single-stranded break in the target nucleic acid.

Embodiment 85. The method of any one of 79-85, wherein the modifying comprises introducing a double-stranded break in the target nucleic acid.

Embodiment 86. The method of 84 or 85, wherein the modifying results in an insertion, deletion, substitution, duplication, or inversion of one or more nucleotides as compared to the wild-type sequence.

Embodiment 87. The method of any one of 79-86, wherein the mutation is a gain of function mutation.

Embodiment 88. The method of any one of 79-86, wherein the mutation is a loss of function mutation.

Embodiment 89. The method of any one of 79-86, wherein the mutation of the SOD1 gene encodes an amino acid substitution selected from the group of mutations set forth in Table 1 or comprises one or more mutations that disrupt the function of the SOD1 protein.

Embodiment 90. The method of any one of 79-86, wherein the mutation of the SOD1 gene encodes an amino acid substitution selected from the group of amino acid substitutions consisting of A4S, A4T, A4V, C6F, V7E, L8Q, L8V, G12R, V14G, V14M, G16S, F20C, E21G, E21K, Q22L, G37R, L38R, L38V, G41D, G41S, H43R, F45C, H46R, H48Q, H48R, E49K, T54R, N65S, L67P, L67R, G72S, D76Y, H80A, L84F, L84V, G85R, N86S, V87A, A89T, A89V, D90A, D90V, G93A, G93C, G93D, G93R, G93V, A95G, V97M, E100G, E100K, D101G, D101N, I104F, S105L, L106V, G108V, C111Y, I112M, I112T, I113T, G114A, R115G, V118L, D124G, D124V, D125H, L126S, S134N, N139K, L144F, L144S, A145T, C146R, G147R, V148G, V148I, I149T, I151T of SEQ ID NO:100 and one or more amino acid substitutions that disrupt a function or expression of the SOD1 protein.

Embodiment 91. The method of 90, wherein the mutation of the SOD1 gene encodes an amino acid substitution selected from an A4V mutation of SEQ ID NO:100, a D90A mutation of SEQ ID NO:100, a G93A mutation of SEQ ID NO:100, or a combination thereof.

Embodiment 92. The method of any one of 76-91, wherein the modifying of the target nucleic acid occurs inside of a cell.

Embodiment 93. The method of 92, wherein the modifying of the target nucleic acid occurs in vivo.

Embodiment 94. The method of 92, wherein the modifying of the target nucleic acid occurs in vitro.

Embodiment 95. The method of any one of 76-94, wherein the cell is a eukaryotic cell.

Embodiment 96. The method of 95, wherein the eukaryotic cell is selected from the group consisting of a rodent cell, a mouse cell, a rat cell, a primate cell, a non-human primate cell, and a human cell.

Embodiment 97. The method of 96, wherein the eukaryotic cell is a human cell.

Embodiment 98. The method of any one of 76-97, wherein the cell is a cell of a central nervous system (CNS) or a peripheral nervous system (PNS).

Embodiment 99. The method of 98, wherein the cell is a neuron.

Embodiment 100. The method of 99, wherein the neuron is a spinal motor neuron.

Embodiment 101. The method of 98, wherein the cell is a glial cell, an oligodendrocyte, or a Schwann cell.

Embodiment 102. The method of any one of 79-101, wherein the method further comprises contacting the target nucleic acid with a donor template complementary to at least a portion of a SOD1 gene, wherein the donor template is inserted into the target nucleic acid to correct the one or more mutations or is inserted to replace the target nucleic acid.

Embodiment 103. The method of 102, wherein the donor template ranges in size from 10-10,000 nucleotides.

Embodiment 104. The method of 102, wherein the donor template ranges in size from 100-1,000 nucleotides.

Embodiment 105. The method of any one of 102-104, wherein the donor template is a single-stranded DNA template or a single stranded RNA template.

Embodiment 106. The method of any one of 102-104, wherein the donor template is a double-stranded DNA template.

Embodiment 107. The method of any one of 102-106, wherein the donor template is inserted by homology directed repair (HDR).

Embodiment 108. The method of any one of 95-107, wherein the method comprises contacting the eukaryotic cell with a vector encoding or comprising the CasX protein and the gNA, and optionally further comprising the donor template.

Embodiment 109. The method of 108, wherein the vector is an Adeno-Associated Viral (AAV) vector.

Embodiment 110. The method of 109, wherein the AAV is AAV1, AAV2, AAV3, AAV4, AAV5, AAV6, AAV7, AAV8, AAV9, AAV10, AAV-Rh74, or AAVRh10.

Embodiment 111. The method of 108, wherein the vector is a retroviral vector.

Embodiment 112. The method of any one of 95-108, wherein the method comprises contacting the eukaryotic cell with a VLP vector, wherein the VLP vector comprises the RNP of 54.

Embodiment 113. The method of any one of 108-112, wherein the vector is administered to a subject at a therapeutically effective dose.

Embodiment 114. The method of 113, wherein the subject is selected from the group consisting of mouse, rat, non-human primate, and human.

Embodiment 115. The method of 114, wherein the subject is a human.

Embodiment 116. The method of any one of 113-115, wherein the vector is administered at a dose of at least about $1\times10^{10}$ vector genomes (vg), or at least about $1\times10^{11}$ vg, or at least about $1\times10^{12}$ vg, or at least about $1\times10^{13}$ vg, or at least about $1\times10^{14}$ vg, or at least about $1\times10^{15}$ vg, or at least about $1\times10^{16}$ vg.

Embodiment 117. The method of any one of 113-116, wherein the vector is administered by a route of administration selected from the group consisting of intraparenchymal, intravenous, intra-arterial, intracerebroventricular, intracisternal, intrathecal, intracranial, lumbar, and intraperitoneal routes.

Embodiment 118. The method of any one of 79-117, comprising further contacting the target nucleic acid with an additional CRISPR protein, or a polynucleotide encoding the additional CRISPR protein.

Embodiment 119. The method of 118, wherein the additional CRISPR protein is a CasX protein having a sequence different from the CasX of any of the preceding.

Embodiment 120. The method of 118, wherein the additional CRISPR protein is not a CasX protein.

Embodiment 121. A method of altering a SOD1 target nucleic acid of a cell, comprising contacting said cell with: a) CasX:gNA system of any one of 1-65; b) the nucleic acid of 66 or 67; c) the vector as in any one of 68-76; d) the VLP of 77 or 78; or e) a combination thereof.

Embodiment 122. The method of 121, wherein the cell has been modified such that expression of the SOD1 protein is reduced by at least about 50%, at least about 60%, at least about 70%, at least about 80%, at least about 90%, or at least about 95% in comparison to a cell that has not been modified.

Embodiment 123. The method of 121 or 122, wherein the cell has been modified such that the cell does not express a detectable level of the SOD1 protein.

Embodiment 124. The method of 121, wherein the cell has been modified such that it expresses SOD1 protein having the sequence of SEQ ID NO:100.

Embodiment 125. A population of cells modified by the method of 121 or 122, wherein the cells have been modified such that at least 70%, at least 75%, at least 80%, at least 85%, at least 90%, or at least 95% of the modified cells do not express a detectable level of SOD1 protein.

Embodiment 126. A population of cells modified by the method of 124, wherein the cells have been modified such that at least 70%, at least 75%, at least 80%, at least 85%, at least 90%, or at least 95% of the modified cells express a detectable level of SOD1 protein having the sequence of SEQ ID NO:100.

Embodiment 127. The population of cells of 125 or 126, wherein the cell is a non-primate mammalian cell, a non-human primate cell, or a human cell.

Embodiment 128. The population of cells of any one of 125-127, wherein the cell is selected from the group consisting of a neuron, a spinal motor neuron, a glial cell, an oligodendrocyte, or a Schwann cell.

Embodiment 129. The population of cells of any one of 125-128, wherein the cells are autologous with respect to a subject to be administered the cell.

Embodiment 130. The population of cells of any one of 125-128, wherein the cells are allogeneic with respect to a subject to be administered the cell.

Embodiment 131. A population of cells, comprising the CasX:gNA system of any one of 1-65.

Embodiment 132. A method of treating a SOD1 or related disorder in a subject in need thereof, the method comprising administering to the subject an effective amount of the cells of any one of 125-131.

Embodiment 133. The method of 132, wherein the method further comprises administering a chemotherapeutic agent.

Embodiment 134. A method of treating a SOD1 disorder in a subject in need thereof, comprising modifying a SOD1 gene having one or more mutations in a cell of the subject, the modifying comprising contacting said cell with:
 a. CasX:gNA system of any one of 1-65;
 b. the nucleic acid of 66 or 67;
 c. the vector as in any one of 68-75;
 d. the VLP of 77 or 78; or
 e. a combination thereof.

Embodiment 135. The method of 134, further comprising a second gNA or a nucleic acid encoding the second gNA, wherein the second gNA has a targeting sequence complementary to a different or overlapping portion of the target nucleic acid.

Embodiment 136. The method of 134 or 135, wherein the modifying corrects the one or more mutations, or wherein expression of the SOD1 having the one or more mutations is inhibited or suppressed.

Embodiment 137. The method of any one of 134-136, wherein the method comprises contacting the cell with a vector encoding the CasX protein and the gNA, and optionally further comprising the donor template.

Embodiment 138. The method of 137, wherein the vector is an Adeno-Associated Viral (AAV) vector.

Embodiment 139. The method of 138, wherein the AAV is AAV1, AAV2, AAV3, AAV4, AAV5, AAV6, AAV7, AAV8, AAV9, AAV10, AAV-Rh74, or AAVRh10.

Embodiment 140. The method of 137, wherein the vector is a retroviral vector.

Embodiment 141. The method of any one of 134-140, wherein the vector is administered to a subject at a therapeutically effective dose.

Embodiment 142. The method of 141, wherein the subject is selected from the group consisting of mouse, rat, non-human primate, and human.

Embodiment 143. The method of 142, wherein the subject is a human.

Embodiment 144. The method of any one of 137-143, wherein the vector is administered to the subject at a dose of at least about $1\times10^{10}$ vector genomes (vg), or at least about $1\times10^{11}$ vg, or at least about $1\times10^{12}$ vg, or at least about $1\times10^{13}$ vg, or at least about $1\times10^{14}$ vg, or at least about $1\times10^{15}$ vg, or at least about $1\times10^{16}$ vg.

Embodiment 145. The method of any one of 137-144, wherein the vector is administered by a route of administration selected from the group consisting of intraparenchymal, intravenous, intra-arterial, intracerebroventricular, intracisternal, intrathecal, intracranial, lumbar, and intraperitoneal routes.

Embodiment 146. The method of any one of 137-145, comprising further contacting the target nucleic acid with an additional CRISPR protein, or a polynucleotide encoding the additional CRISPR protein.

Embodiment 147. The method of 146, wherein the additional CRISPR protein is a CasX protein having a sequence different from the CasX of any of the preceding.

Embodiment 148. The method of 147, wherein the additional CRISPR protein is not a CasX protein.

Embodiment 149. The method of any one of 134-148, wherein the method results in improvement in at least one clinically-relevant endpoint selected from the group consisting of ALS Functional Rating Scale (ALSFRS-(R)), combined assessment of function and survival, duration of response, time to death, time to tracheostomy, time to persistent assisted ventilation (DTP), forced vital capacity (% FVC); manual muscle test, maximum voluntary isometric contraction, duration of response, progression-free survival, time to progression of disease, and time-to-treatment failure.

Embodiment 150. The method of any one of 134-149, wherein the method results in improvement in at least two clinically-relevant endpoints selected from the group consisting of ALS Functional Rating Scale (ALSFRS-(R)), combined assessment of function and survival, duration of response, time to death, time to tracheostomy, time to persistent assisted ventilation (DTP), forced vital capacity (% FVC); manual muscle test, maximum voluntary isometric contraction, duration of response, progression-free survival, time to progression of disease, and time-to-treatment failure.

EXAMPLES

Example 1: Creation, Expression and Purification of CasX Stx2

1. Growth and Expression

An expression construct for CasX Stx2 (also referred to herein as CasX2), derived from *Planctomycetes* (having the amino acid sequence of SEQ ID NO: 2 and encoded by the sequence of the Table 5, below), was constructed from gene fragments (Twist Biosciences) that were codon optimized for *E. coli*. The assembled construct contains a TEV-cleavable, C-terminal, TwinStrep tag and was cloned into a pBR322-derivative plasmid backbone containing an ampicillin resistance gene. The expression construct was transformed into chemically competent BL21* (DE3) *E. coli* and a starter culture was grown overnight in LB broth supplemented with carbenicillin at 3TC, 200 RPM, in UltraYield Flasks (Thomson Instrument Company). The following day, this culture was used to seed expression cultures at a 1:100 ratio (starter culture:expression culture). Expression cultures were Terrific Broth (Novagen) supplemented with carbenicillin and grown in UltraYield flasks at 37° C., 200 RPM. Once the cultures reached an OD of 2, they were chilled to 16° C. and IPTG (isopropyl β-D-1-thiogalactopyranoside) was added to a final concentration of 1 mM, from a 1 M stock. The cultures were induced at 16° C., 200 RPM for 20 hours before being harvested by centrifugation at 4,000×g for 15 minutes, 4° C. The cell paste was weighed and resuspended in lysis buffer (50 mM HEPES-NaOH, 250 mM NaCl, 5 mM MgCl$_2$, 1 mM TCEP, 1 mM benzamidine-HCL, 1 mM PMSF, 0.5% CHAPS, 10% glycerol, pH 8) at a ratio of 5 mL of lysis buffer per gram of cell paste. Once resuspended, the sample was frozen at −80° C. until purification.

TABLE 5

DNA sequence of CasX Stx2 construct

| Construct | DNA Sequence |
| --- | --- |
| SV40 NLS-CasX-SV40 NLS-TEV cleavage site - TwinStrep tag | (SEQ ID NO: 206) |

2. Purification

Frozen samples were thawed overnight at 4° C. with magnetic stirring. The viscosity of the resulting lysate was reduced by sonication and lysis was completed by homogenization in three passes at 17 k PSI using an Emulsiflex C3 (Avestin). Lysate was clarified by centrifugation at 50,000× g, 4° C., for 30 minutes and the supernatant was collected. The clarified supernatant was applied to a Heparin 6 Fast Flow column (GE Life Sciences) by gravity flow. The column was washed with 5 CV of Heparin Buffer A (50 mM HEPES-NaOH, 250 mM NaCl, 5 mM MgCl$_2$, 1 mM TCEP, 10% glycerol, pH 8), then with 5 CV of Heparin Buffer B (Buffer A with the NaCl concentration adjusted to 500 mM). Protein was eluted with 5 CV of Heparin Buffer C (Buffer A with the NaCl concentration adjusted to 1 M), collected in fractions. Fractions were assayed for protein by Bradford Assay and protein-containing fractions were pooled. The pooled heparin eluate was applied to a Strep-Tactin XT Superflow column (IBA Life Sciences) by gravity flow. The column was washed with 5 CV of Strep Buffer (50 mM HEPES-NaOH, 500 mM NaCl, 5 mM MgCl$_2$, 1 mM TCEP, 10% glycerol, pH 8). Protein was eluted from the column using 5 CV of Strep Buffer with 50 mM D-Biotin added and collected in fractions. CasX-containing fractions were pooled, concentrated at 4° C. using a 30 kDa cut-off spin concentrator, and purified by size exclusion chromatography on a Superdex 200 pg column (GE Life Sciences). The column was equilibrated with SEC Buffer (25 mM sodium phosphate, 300 mM NaCl, 1 mM TCEP, 10% glycerol, pH 7.25) operated by an AKTA Pure FPLC system (GE Life Sciences). CasX-containing fractions that eluted at the appropriate molecular weight were pooled, concentrated at 4° C. using a 30 kDa cut-off spin concentrator, aliquoted, and snap-frozen in liquid nitrogen before being stored at −80° C.

Results

Figure 2:
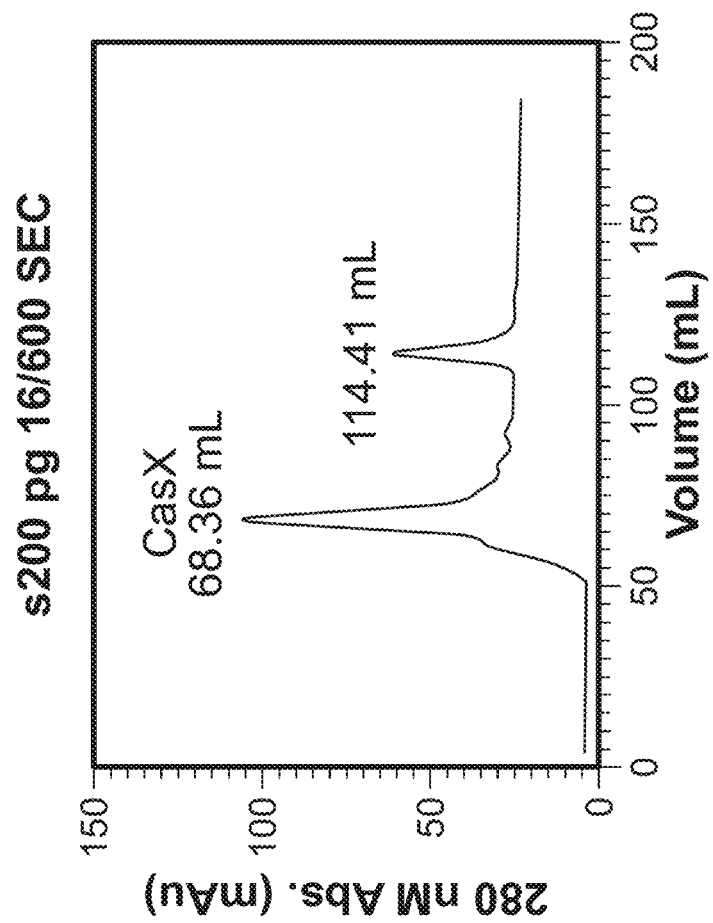
FIG. 2 shows the chromatogram from a size exclusion chromatography assay of the StX2, using of Superdex 200 16/600 pg Gel Filtration, as described in Example 1.
Figure 3:
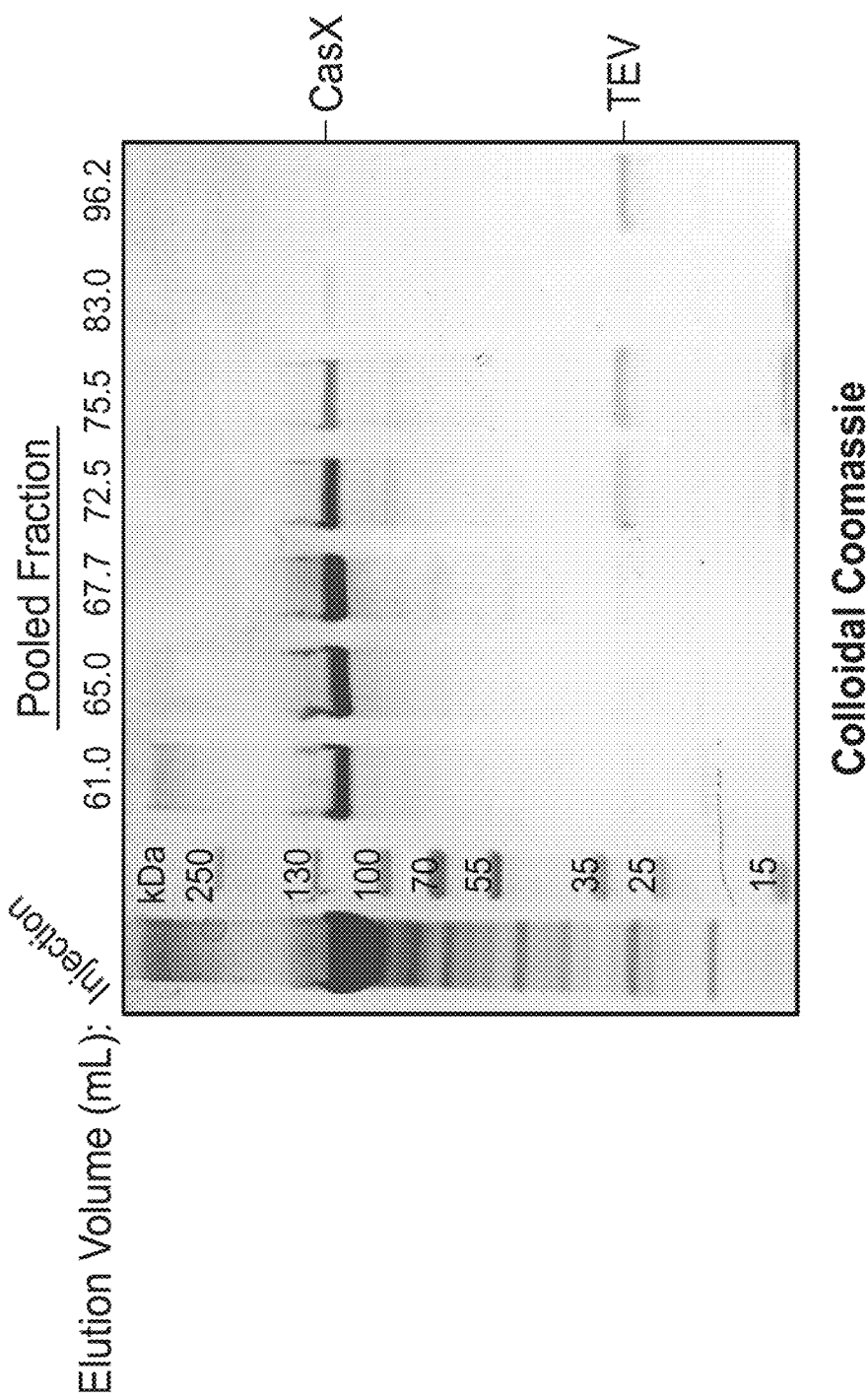
FIG. 3 shows an SDS-PAGE gel of StX2 purification fractions visualized by colloidal Coomassie staining, as described in Example 1.

Samples from throughout the purification were resolved by SDS-PAGE and visualized by colloidal Coomassie staining, as shown in FIG. 1 and FIG. 3. In FIG. 1, the lanes, from left to right, are: molecular weight standards, Pellet: insoluble portion following cell lysis, Lysate: soluble portion following cell lysis, Flow Thru: protein that did not bind the Heparin column, Wash: protein that eluted from the column in wash buffer, Elution: protein eluted from the heparin column with elution buffer, Flow Thru: Protein that did not bind the StrepTactinXT column, Elution: protein eluted from the StrepTactin XT column with elution buffer, Injection: concentrated protein injected onto the s200 gel filtration column, Frozen: pooled fractions from the s200 elution that have been concentrated and frozen. In FIG. 3, the lanes from right to left, are the injection (sample of protein injected onto the gel filtration column,) molecular weight markers, lanes 3-10 are samples from the indicated elution volumes. Results from the gel filtration are shown in FIG. 2. The 68.36 mL peak corresponds to the apparent molecular weight of CasX and contained the majority of CasX protein. The average yield was 0.75 mg of purified CasX protein per liter of culture, with 75% purity, as evaluated by colloidal Coomassie staining.

Example 2: CasX Construct 119, 438 and 457

Figure 4:
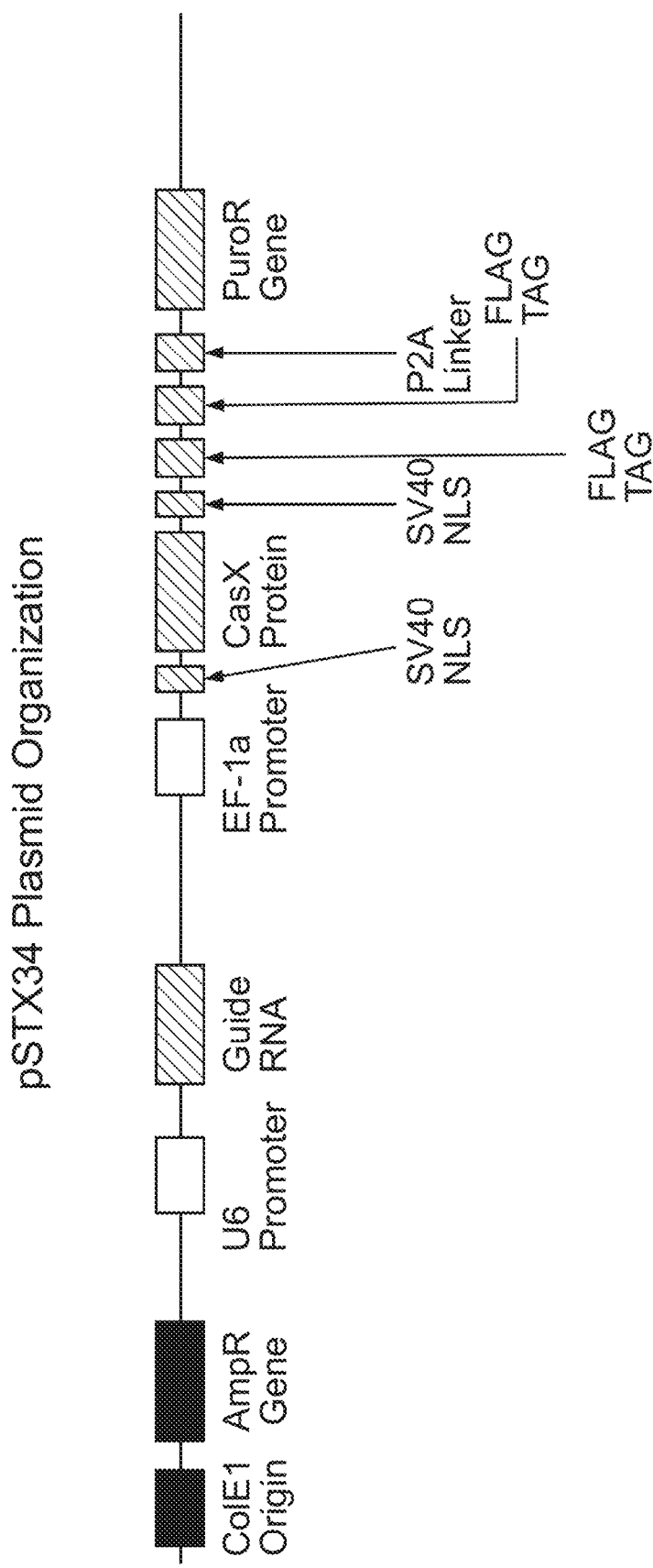
FIG. 4 is a schematic showing the organization of the components in the pSTX34 plasmid used to assemble the CasX constructs, as described in Example 2.
Figure 6:
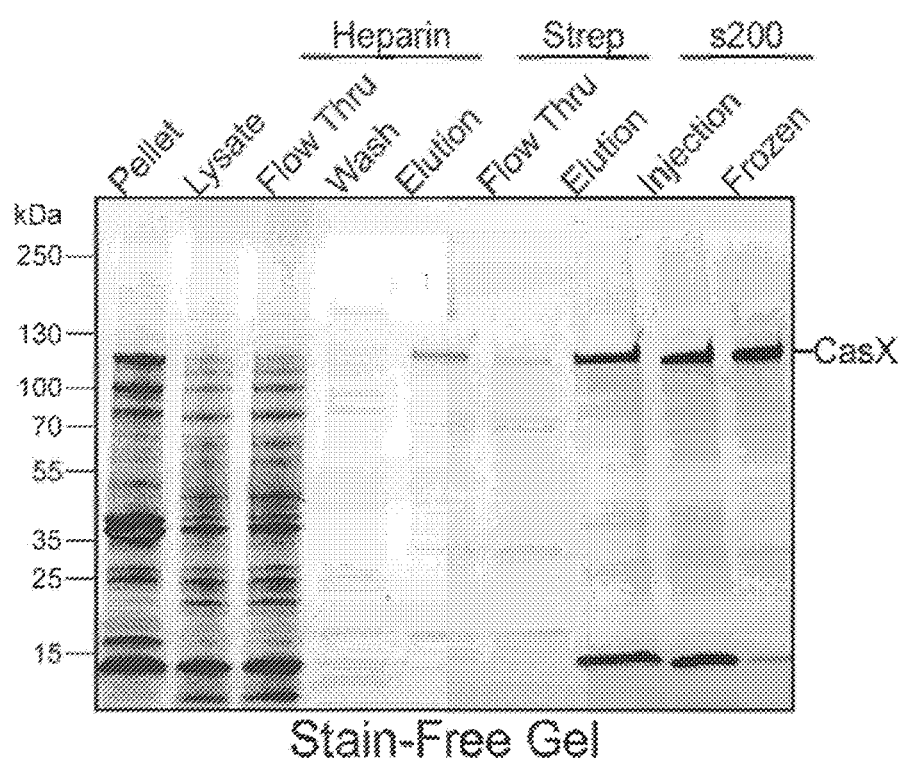
FIG. 6 shows an SDS-PAGE gel of purification samples, visualized on a Bio-Rad Stain-Free™ gel, as described in Example 2.
Figure 7:
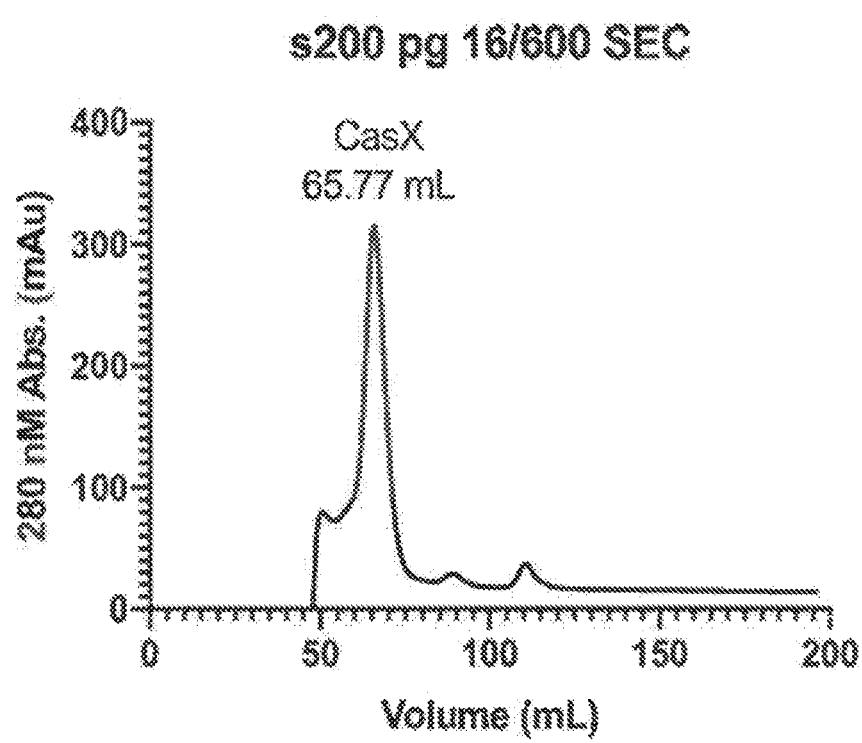
FIG. 7 shows the chromatogram of Superdex 200 16/600 pg Gel Filtration, as described in Example 2.
Figure 8:
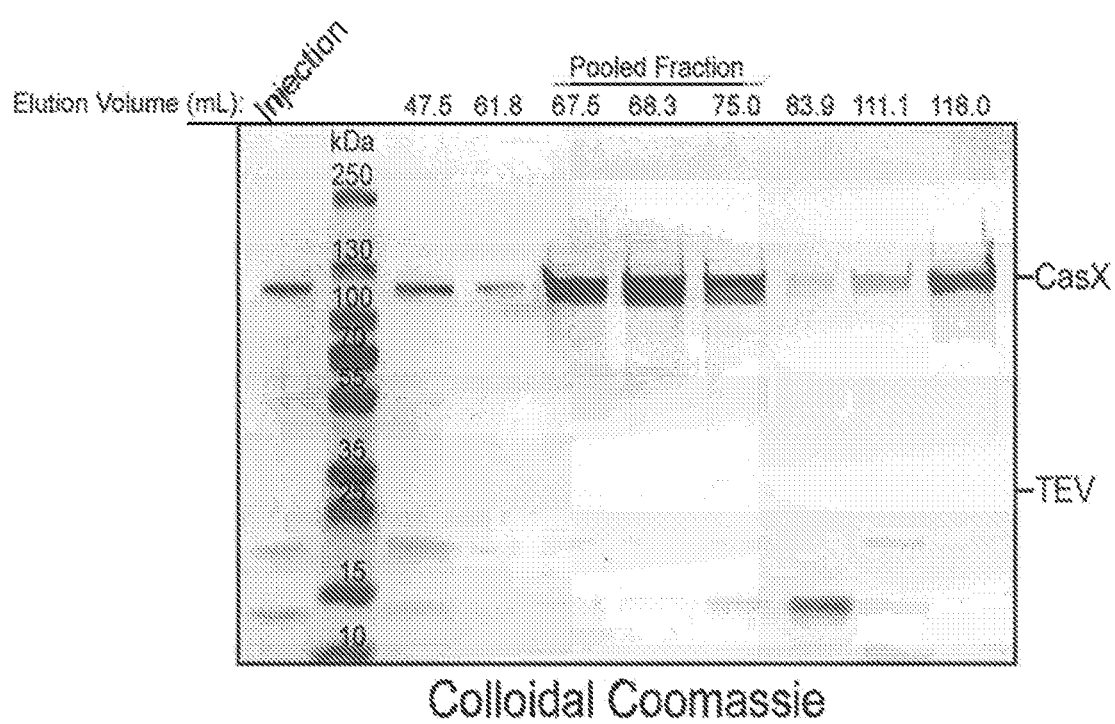
FIG. 8 shows an SDS-PAGE gel of gel filtration samples, stained with colloidal Coomassie, as described in Example 2.

In order to generate the CasX 119, 438, and 457 constructs (sequences in Table 6), the codon-optimized CasX 37 construct (based on the CasX Stx2 construct of Example 1, encoding *Planctomycetes* CasX SEQ ID NO: 2, with a A708K substitution and a [P793] deletion with fused NLS, and linked guide and non-targeting sequences) was cloned into a mammalian expression plasmid (pStX; see FIG. 4) using standard cloning methods. To build CasX 119, the CasX 37 construct DNA was PCR amplified in two reactions using Q5 DNA polymerase (New England BioLabs Cat #M0491L) according to the manufacturer's protocol, using primers oIC539 and oIC88 as well as oIC87 and oIC540 respectively (see FIG. 5). To build CasX 457, the CasX 365 construct DNA was PCR amplified in four reactions using Q5 DNA polymerase (New England BioLabs Cat #M0491L) according to the manufacturer's protocol, using primers oIC539 and oIC212, oIC211 and oIC376, oIC375 and oIC551, and oIC550 and oIC540 respectively. To build CasX 438, the CasX 119 construct DNA was PCR amplified in four reactions using Q5 DNA polymerase (New England BioLabs Cat #M0491L) according to the manufacturer's protocol, using primers oIC539 and oIC689, oIC688 and oIC376, oIC375 and oIC551, and oIC550 and oIC540 respectively. The resulting PCR amplification products were then purified using Zymoclean™ DNA clean and concentrator (Zymo Research Cat #4014) according to the manufacturer's protocol. The pStX backbone was digested using XbaI and SpeI in order to remove the 2931 base pair fragment of DNA between the two sites in plasmid pStx34. The digested backbone fragment was purified by gel extraction from a 1% agarose gel (Gold Bio Cat #A-201-500) using Zymoclean™ Gel DNA Recovery Kit (Zymo Research Cat #D4002) according to the manufacturer's protocol. The three fragments were then pieced together using Gibson assembly® (New England BioLabs Cat #E2621S) following the manufacturer's protocol. Assembled products in the pStx34 were transformed into chemically-competent or electro-competent Turbo Competent *E. coli* bacterial cells, plated on LB-Agar plates (LB: Teknova Cat #L9315, Agar: Quartzy Cat #214510) containing carbenicillin. Individual colonies were picked and miniprepped using Qiagen QIAprep® Spin Miniprep Kit (Qiagen Cat #27104) following the manufacturer's protocol. The resultant plasmids were sequenced using Sanger sequencing to ensure correct assembly. pStX34 includes an EF-1α promoter for the protein as well as a selection marker for both puromycin and carbenicillin. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically or electrocompetent cells such as NEB Turbo competent *E. coli* (NEB Cat #C2984I), plated on LB-Agar plates (LB: Teknova Cat #L9315, Agar: Quartzy Cat #214510) containing carbenicillin. Individual colonies were picked and miniprepped using Qiagen QIAprep® Spin Miniprep Kit (Qiagen Cat #27104) and following the manufacturer's protocol. The resultant plasmids were sequenced using Sanger sequencing to ensure correct ligation. SaCas9 and SpyCas9 control plasmids were prepared similarly to pStX plasmids described above, with the protein and guide regions of pStX exchanged for the respective protein and guide. Targeting sequences for SaCas9 and SpyCas9 were either obtained from the literature or were rationally designed according to established methods. The expression and recovery of the CasX 119 and 457 proteins was performed using the general methodologies of Example 1 (however the DNA sequences were codon optimized for expression in *E. coli*). The results of analytical assays for CasX 119 are shown in FIGS. 6-8. The average yield of the CasX 119 was 1.56 mg of purified CasX protein per liter of culture at 75% purity, as evaluated by colloidal Coomassie staining. FIG. 6 shows an SDS-PAGE gel of purification samples, visualized on a Bio-Rad Stain-Free™ gel, as described. The lanes, from left to right, are: Pellet: insoluble portion following cell lysis, Lysate: soluble portion following cell lysis, Flow Thru: protein that did not bind the Heparin column, Wash: protein that eluted from the column in wash buffer, Elution: protein eluted from the heparin column with elution buffer, Flow Thru: Protein that did not bind the StrepTactinXT column, Elution: protein eluted from the StrepTactin XT column with elution buffer, Injection: concentrated protein injected onto the s200 gel filtration column, Frozen: pooled fractions from the s200 elution that have been concentrated and frozen.

FIG. 7 shows the chromatogram of Superdex 200 16/600 pg Gel Filtration, as described. Gel filtration run of CasX variant 119 protein plotted as 280 nm absorbance against elution volume. The 65.77 mL peak corresponds to the apparent molecular weight of CasX variant 119 and contained the majority of CasX variant 119 protein. FIG. 8 shows an SDS-PAGE gel of gel filtration samples, stained with colloidal Coomassie, as described. Samples from the indicated fractions were resolved by SDS-PAGE and stained with colloidal Coomassie. From right to left, Injection: sample of protein injected onto the gel filtration column, molecular weight markers, lanes 3-10: samples from the indicated elution volumes.

TABLE 6

Sequences of CasX 119, 438 and 457

| Construct | DNA Sequence | Amino Acid Sequence |
|---|---|---|
| CasX 119 | (SEQ ID NO: 207) | QEIKRINKIRRRLVKDSNTKKAGKTGPMKTLLVRVMTPDLRERLE NLRKKPENIPQPISNTSRANLNKLLTDYTEMKKAILHVYWEEFQK DPVGLMSRVAQPAPKNIDQRKLIPVKDGNERLTSSGFACSQCCQP LYVYKLEQVNDKGKPHTNYFGRCNVSEHERLILLSPHKPEANDEL VTYSLGKFGQRALDFYSIHVTRESNHPVKPLEQIGGNSCASGPVG KALSDACMGAVASFLTKYQDIILEHQKVIKKNEKRLANLKDIASA NGLAFPKITLPPQPHTKEGIEAYNNVVAQIVIWVNLNLWQKLKIG |

TABLE 6-continued

Sequences of CasX 119, 438 and 457

| Construct | DNA Sequence | Amino Acid Sequence |
|---|---|---|
| | | RDEAKPLQRLKGFPSFPLVERQANEVDWWDMVCNVKKLINEKKED GKVFWQNLAGYKRQEALRPYLSSEEDRKKGKKFARYQFGDLLLHL EKKHGEDWGKVYDEAWERIDKKVEGLSKHIKLEEERRSEDAQSKA ALTDWLRAKASFVIEGLKEADKDEFCRCELKLQKWYGDLRGKPFA IEAENSILDISGFSKQYNCAFIWQKDGVKKLNLYLIINYFKGGKL RFKKIKPEAFEANRFYTVINKKSGEIVPMEVNFNFDDPNLIILPL AFGKRQGREFIWNDLLSLETGSLKLANGRVIEKTLYNRRTRQDEP ALFVALTFERREVLDSSNIKPMNLIGIDRGENIPAVIALTDPEGC PLSRFKDSLGNPTHILRIGESYKEKQRTIQAKKEVEQRRAGGYSR KYASKAKNLADDMVRNTARDLLYYAVTQDAMLIFENLSRGFGRQG KRTFMAERQYTRMEDWLTAKLAYEGLSKTYLSKTLAQYTSKTCSN CGFTITSADYDRVLEKLKKTATGWMTTINGKELKVEGQITYYNRY KRQNVVKDLSVELDRLSEESVNNDISSWTKGRSGEALSLLKKRFS HRPVQEKFVCLNCGFETHADEQAALNIARSWLFLRSQEYKKYQTN KTTGNTDKRAFVETWQSFYRKKLKEVWKPAV (SEQ ID NO: 208) |
| CasX 457 | (SEQ ID NO: 209) | QEIKRINKIRRRLVKDSNIKKAGKTGPMKTLLVRVMTPDLRERLE NLRKKPENIPQPISNTSRANLNKLLTDYTEMKKAILHVYWEEFQK DPVGLMSRVAQPAPKNIDQRKLIPVKDGNERLTSSGFACSQCCQP LYVYKLEQVNDKGKPHTNYFGRCNVSEHERLILLSPHKPEANDEL VTYSLGKFGQRALDFYSIHVTRESNHPVKPLEQIGGNSCASGPVG KALSDACMGAVASFLTKYQDIILEHKKVIKKNEKRLANLKDIASA NGLAFPKITLPPQPHTKEGIEAYNNVVAQIVIWVNLNLWQKLKIG RDEAKPLQRLKGFPSFPLVERQANEVDWWDMVCNVKKLINEKKED GKVFWQNLAGYKRQEALRPYLSSPEDRKKGKKFARYQLGDLLLHL EKKHGEDWGKVYDEAWERIDKKVEGLSKHIKLEEERRSEDAQSKA ALTDWLRAKASFVIEGLKEADKDEFCRCELKLQKWYGDLRGKPFA IEAENSILDISGFSKQYNCAFIWQKDGVKKLNLYLIINYFKGGKL RFKKIKPEAFEANRFYTVINKKSGEIVPMEVNFNFDDPNLIILPL AFGKRQGREFIWNDLLSLETGSLKLANGRVIEKPLYNRRTRQDEP ALFVALTFERREVLDSSNIKPMNLIGVDRGENIPAVIALTDPEGC PLSRFKDSLGNPTHILRIGESYKEKQRTIQAKKEVEQRRAGGYSR KYASKAKNLADDMVRNTARDLLYYAVTQDAMLIFENLSRGFGRQG KRTFMAERQYTRMEDWLTAKLAYEGLSKTYLSKTLAQYTSKTCSN CGFTITSADYDRVLEKLKKTATGWMTTINGKELKVEGQITYYNRR KRQNVVKDLSVELDRLSEESVNNDISSWTKGRSGEALSLLKKRFS HRPVQEKFVCLNCGFETHADEQAALNIARSWLFLRSQEYKKYQTN KTTGNTDKRAFVETWQSFYRKKLKEVWKPAV (SEQ ID NO: 210) |
| CasX 438 | SEQ ID NO: 211) | QEIKRINKIRRRLVKDSNIKKAGKTGPMKTLLVRVMTPDLRERLE NLRKKPENIPQPISNTSRANLNKLLTDYTEMKKAILHVYWEEFQK DPVGLMSRVAQPAPKNIDQRKLIPVKDGNERLTSSGFACSQCCQP LYVYKLEQVNDKGKPHTNYFGRCNVSEHERLILLSPHKPEANDEL VTYSLGKFGQRALDFYSIHVTRESNHPVKPLEQIGGNSCASGPVG KALSDACMGAVASFLTKYQDIILEHQKVIKKNEKRLANLKDIASA NGLAFPKITLPPQPHTKEGIEAYNNVVAQIVIWVNLNLWQKLKIG RDEAKPLQRLKGFPSFPLVERQANEVDWWDMVCNVKKLINEKKED GKVFWQNLAGYKRQEALRPYLSSEEDRKKGKKFARYQLGDLLKHL EKKHGEDWGKVYDEAWERIDKKVEGLSKHIKLEEERRSEDAQSKA ALTDWLRAKASFVIEGLKEADKDEFCRCELKLQKWYGDLRGKPFA IEAENSILDISGFSKQYNCAFIWQKDGVKKLNLYLIINYFKGGKL RFKKIKPEAFEANRFYTVINKKSGEIVPMEVNFNFDDPNLIILPL AFGKRQGREFIWNDLLSLETGSLKLANGRVIEKTLYNRRTRQDEP ALFVALTFERREVLDSSNIKPMNLIGVDRGENIPAVIALTDPEGC PLSRFKDSLGNPTHILRIGESYKEKQRTIQAKKEVEQRRAGGYSR KYASKAKNLADDMVRNTARDLLYYAVTQDAMLIFENLSRGFGRQG KRTFMAERQYTRMEDWLTAKLAYEGLSKTYLSKTLAQYTSKTCSN CGFTITSADYDRVLEKLKKTATGWMTTINGKELKVEGQITYYNRR KRQNVVKDLSVELDRLSEESVNNDISSWTKGRSGEALSLLKKRFS HRPVQEKFVCLNCGFETHADEQAALNIARSWLFLRSQEYKKYQTN KTTGNTDKRAFVETWQSFYRKKLKEVWKPAV (SEQ ID NO: 212) |

Example 3: CasX Construct 488 and 491

In order to generate the CasX 488 construct (sequences in Table 7), the codon-optimized CasX 119 construct (based on the CasX Stx2 construct of Example 1, encoding *Planctomycetes* CasX SEQ ID NO: 2, with a A708K substitution, a L379R substitution, and a [P793] deletion with fused NLS, and linked guide and non-targeting sequences) was cloned into a mammalian expression plasmid (pStX; see FIG. 4) using standard cloning methods. Construct CasX 1 (based on the CasX Stx1 construct of Example 1, encoding CasX SEQ ID NO: 1) was cloned into a destination vector using standard cloning methods. To build CasX 488, the CasX 119 construct DNA was PCR amplified using Q5 DNA polymerase (New England BioLabs Cat #M0491L) according to the manufacturer's protocol, using primers oIC765 and oIC762 (see FIG. 5). The CasX 1 construct was PCR amplified using Q5 DNA polymerase (New England BioLabs Cat #M0491L) according to the manufacturer's protocol, using primers oIC766 and oIC784. The PCR products were purified by gel extraction from a 1% agarose gel (Gold Bio Cat #A-201-500) using Zymoclean™ Gel DNA Recovery Kit (Zymo Research Cat #D4002) according to the manufacturer's protocol. The two fragments were then pieced together using Gibson assembly® (New England BioLabs Cat #E2621S) following the manufacturer's protocol. Assembled products in pStx1 were transformed into chemically-competent Turbo Competent E. coli bacterial cells, plated on LB-Agar plates (LB: Teknova Cat #L9315, Agar: Quartzy Cat #214510) containing kanamycin. Individual colonies were picked and miniprepped using Qiagen QIAprep® Spin Miniprep Kit (Qiagen Cat #27104) following the manufacturer's protocol. The resultant plasmids were sequenced using Sanger sequencing to ensure correct assembly. The correct clones were then subcloned into the mammalian expression vector pStx34 using restriction enzyme cloning. The pStx34 backbone and the CasX 488 clone in pStx1 were digested with XbaI and BamHI respectively. The digested backbone and insert fragments were purified by gel extraction from a 1% agarose gel (Gold Bio Cat #A-201-500) using Zymoclean™ Gel DNA Recovery Kit (Zymo Research Cat #D4002) according to the manufacturer's protocol. The clean backbone and insert were then ligated together using T4 Ligase (New England Biolabs Cat #M0202L) according to the manufacturer's protocol. The ligated product was transformed into chemically-competent Turbo Competent E. coli bacterial cells, plated on LB-Agar plates (LB: Teknova Cat #L9315, Agar: Quartzy Cat #214510) containing carbenicillin. Individual colonies were picked and miniprepped using Qiagen QIAprep® Spin Miniprep Kit (Qiagen Cat #27104) following the manufacturer's protocol. The resultant plasmids were sequenced using Sanger sequencing to ensure correct assembly.

Figure 5:
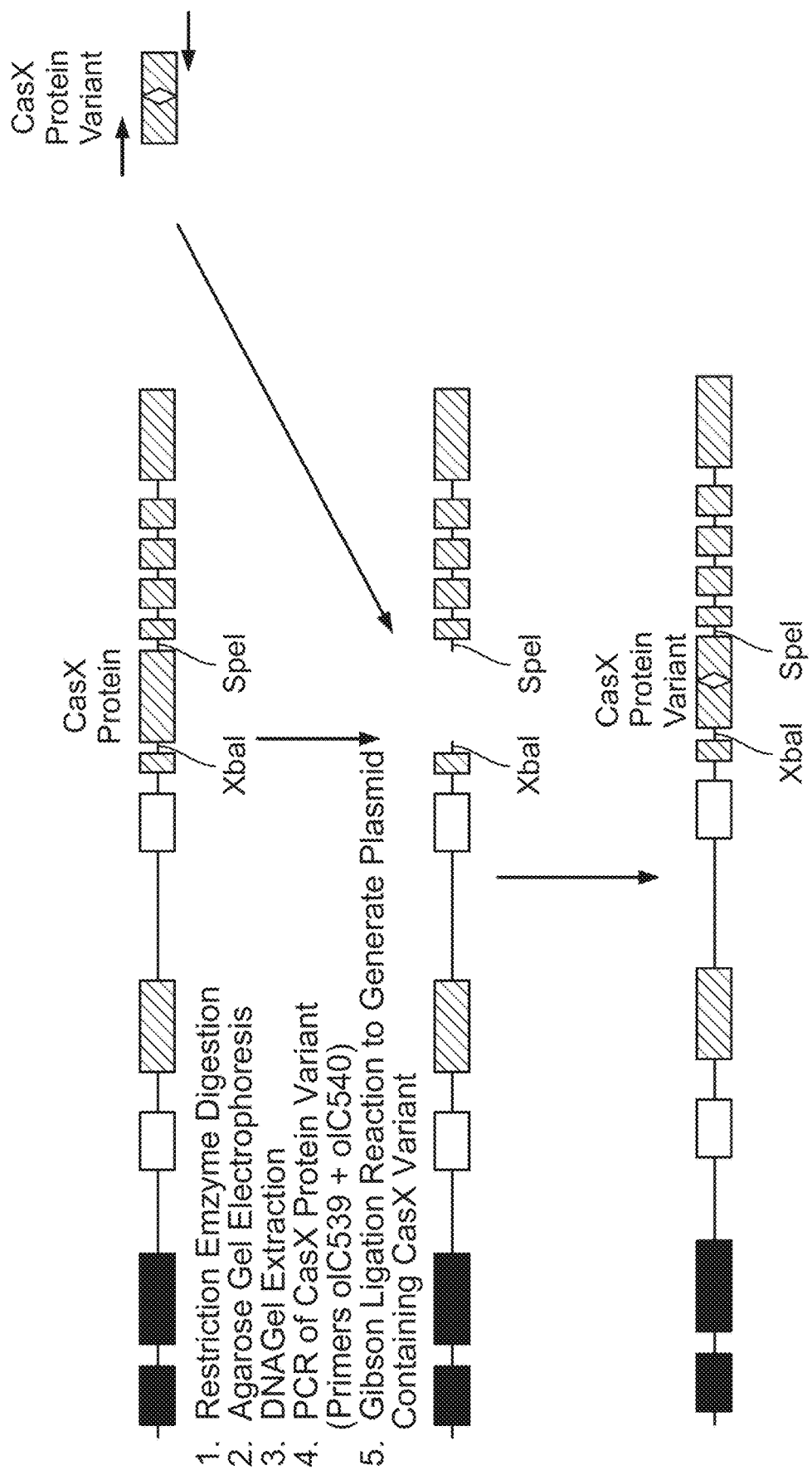
FIG. 5 is a schematic showing the steps of generating the CasX 119 variant, as described in Example 2.

In order to generate CasX 491 (sequences in Table 7), the CasX 484 construct DNA was PCR amplified using Q5 DNA polymerase (New England BioLabs Cat #M0491L) according to the manufacturer's protocol, using primers oIC765 and oIC762 (see FIG. 5). The CasX 1 construct was PCR amplified using Q5 DNA polymerase (New England BioLabs Cat #M0491L) according to the manufacturer's protocol, using primers oIC766 and oIC784. The PCR products were purified by gel extraction from a 1% agarose gel (Gold Bio Cat #A-201-500) using Zymoclean™ Gel DNA Recovery Kit (Zymo Research Cat #D4002) according to the manufacturer's protocol. The two fragments were then pieced together using Gibson assembly® (New England BioLabs Cat #E2621S) following the manufacturer's protocol. Assembled products in pStx1 were transformed into chemically-competent Turbo Competent E. coli bacterial cells, plated on LB-Agar plates (LB: Teknova Cat #L9315, Agar: Quartzy Cat #214510) containing kanamycin. Individual colonies were picked and miniprepped using Qiagen QIAprep® Spin Miniprep Kit (Qiagen Cat #27104) following the manufacturer's protocol. The resultant plasmids were sequenced using Sanger sequencing to ensure correct assembly. The correct clones were then subcloned into the mammalian expression vector pStx34 using restriction enzyme cloning. The pStx34 backbone and the CasX 491 clone in pStx1 were digested with XbaI and BamHI respectively. The digested backbone and insert fragments were purified by gel extraction from a 1% agarose gel (Gold Bio Cat #A-201-500) using Zymoclean™ Gel DNA Recovery Kit (Zymo Research Cat #D4002) according to the manufacturer's protocol. The clean backbone and insert were then ligated together using T4 Ligase (New England Biolabs Cat #M0202L) according to the manufacturer's protocol. The ligated product was transformed into chemically-competent Turbo Competent E. coli bacterial cells, plated on LB-Agar plates (LB: Teknova Cat #L9315, Agar: Quartzy Cat #214510) containing carbenicillin. Individual colonies were picked and miniprepped using Qiagen QIAprep® Spin Miniprep Kit (Qiagen Cat #27104) following the manufacturer's protocol. The resultant plasmids were sequenced using Sanger sequencing to ensure correct assembly. pStX34 includes an EF-1α promoter for the protein as well as a selection marker for both puromycin and carbenicillin. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England Biolabs Cat #M0202L) and an appropriate restriction enzyme for the plasmid. Golden Gate products were transformed into chemically or electro-competent cells such as NEB Turbo competent E. coli (NEB Cat #C2984I), plated on LB-Agar plates (LB: Teknova Cat #L9315, Agar: Quartzy Cat #214510) containing carbenicillin. Individual colonies were picked and miniprepped using Qiagen QIAprep® Spin Miniprep Kit (Qiagen Cat #27104) and following the manufacturer's protocol. The resultant plasmids were sequenced using Sanger sequencing to ensure correct ligation. SaCas9 and SpyCas9 control plasmids were prepared similarly to pStX plasmids described above, with the protein and guide regions of pStX exchanged for the respective protein and guide. Targeting sequences for SaCas9 and SpyCas9 were either obtained from the literature or were rationally designed according to established methods. The expression and recovery of the CasX constructs was performed using the general methodologies of Example 1 and Example 2, with similar results obtained.

TABLE 7

Sequences of CasX 488 and 491

| Construct | DNA Sequence | Amino Acid Sequence |
|---|---|---|
| CasX 488 | (SEQ ID NO: 213) | QEIKRINKIRRRLVKDSNTKKAGKTGPMKTLLVRVMTPDLRERLE NLRKKPENIPQPISNTSRANLNKLLTDYTEMKKAILHVYWEEFQK DPVGLMSRVAQPASKKIDQNKLKPEMDEKGNLTTAGFACSQCGQP LFVYKLEQVSEKGKAYTNYFGRCNVAEHEKLILLAQLKPEKDSDE AVTYSLGKFGQRALDFYSIHVTKESTHPVKPLAQIAGNRYASGPV GKALSDACMGTIASFLSKYQDIIIEHQKVVKGNQKRLESLRELAG |

TABLE 7-continued

Sequences of CasX 488 and 491

| Construct | DNA Sequence | Amino Acid Sequence |
|---|---|---|
| | | KENLEYPSVTLPPQPHTKEGVDAYNEVIARVRMWVNLNLWQKLKL<br>SRDDAKPLLRLKGFPSFPLVERQANEVDWWDMVCNVKKLINEKKE<br>DGKVFWQNLAGYKRQEALRPYLSSEEDRKKGKKFARYQFGDLLLH<br>LEKKHGEDWGKVYDEAWERIDKKVEGLSKHIKLEEERRSEDAQSK<br>AALTDWLRAKASFVIEGLKEADKDEFCRCELKLQKWYGDLRGKPF<br>AIEAENSILDISGFSKQYNCAFIWQKDGVKKLNLYLIINYFKGGK<br>LRFKKIKPEAFEANRFYTVINKKSGEIVPMEVNFNFDDPNLIILP<br>LAFGKRQGREFIWNDLLSLETGSLKLANGRVIEKTLYNRRTRQDE<br>PALFVALTFERREVLDSSNIKPMNLIGIDRGENIPAVIALTDPEG<br>CPLSRFKDSLGNPTHILRIGESYKEKQRTIQAKKEVEQRRAGGYS<br>RKYASKAKNLADDMVRNTARDLLYYAVTQDAMLIFENLSRGFGRQ<br>GKRTFMAERQYTRMEDWLTAKLAYEGLSKTYLSKTLAQYTSKTCS<br>NCGFTITSADYDRVLEKLKKTATGWMTTINGKELKVEGQITYYNR<br>YKRQNVVKDLSVELDRLSEESVNNDISSWTKGRSGEALSLLKKRF<br>SHRPVQEKFVCLNCGFETHADEQAALNIARSWLFLRSQEYKKYQT<br>NKTTGNTDKRAFVETWQSFYRKKLKEVWKPAV<br>(SEQ ID NO: 214) |
| CasX 491 | (SEQ ID NO: 215) | QEIKRINKIRRRLVKDSNTKKAGKTGPMKTLLVRVMTPDLRERLE<br>NLRKKPENIPQPISNTSRANLNKLLTDYTEMKKAILHVYWEEFQK<br>DPVGLMSRVAQPASKKIDQNKLKPEMDEKGNLTTAGFACSQCGQP<br>LFVYKLEQVSEKGKAYTNYFGRCNVAEHEKLILLAQLKPEKDSDE<br>AVTYSLGKFGQRALDFYSIHVTKESTHPVKPLAQIAGNRYASGPV<br>GKALSDACMGTIASFLSKYQDIIIEHQKVVKGNQKRLESLRELAG<br>KENLEYPSVTLPPQPHTKEGVDAYNEVIARVRMWVNLNLWQKLKL<br>SRDDAKPLLRLKGFPSFPLVERQANEVDWWDMVCNVKKLINEKKE<br>DGKVFWQNLAGYKRQEALRPYLSSEEDRKKGKKFARYQLGDLLLH<br>LEKKHGEDWGKVYDEAWERIDKKVEGLSKHIKLEEERRSEDAQSK<br>AALTDWLRAKASFVIEGLKEADKDEFCRCELKLQKWYGDLRGKPF<br>AIEAENSILDISGFSKQYNCAFIWQKDGVKKLNLYLIINYFKGGK<br>LRFKKIKPEAFEANRFYTVINKKSGEIVPMEVNFNFDDPNLIILP<br>LAFGKRQGREFIWNDLLSLETGSLKLANGRVIEKTLYNRRTRQDE<br>PALFVALTFERREVLDSSNIKPMNLIGVDRGENIPAVIALTDPEG<br>CPLSRFKDSLGNPTHILRIGESYKEKQRTIQAKKEVEQRRAGGYS<br>RKYASKAKNLADDMVRNTARDLLYYAVTQDAMLIFENLSRGFGRQ<br>GKRTFMAERQYTRMEDWLTAKLAYEGLSKTYLSKTLAQYTSKTCS<br>NCGFTITSADYDRVLEKLKKTATGWMTTINGKELKVEGQITYYNR<br>YKRQNVVKDLSVELDRLSEESVNNDISSWTKGRSGEALSLLKKRF<br>SHRPVQEKFVCLNCGFETHADEQAALNIARSWLFLRSQEYKKYQT<br>NKTTGNTDKRAFVETWQSFYRKKLKEVWKPAV<br>(SEQ ID NO: 216) |

Example 4: Design and Generation of CasX Constructs 278-280, 285-288, 290, 291, 293, 300, 492, and 493

In order to generate the CasX 278-280, 285-288, 290, 291, 293, 300, 492, and 493 constructs (sequences in Table 8), the N- and C-termini of the codon-optimized CasX 119 construct (based on the CasX Stx37 construct of Example 2, encoding Planctomycetes CasX SEQ ID NO: 2, with a A708K substitution and a [P793] deletion with fused NLS, and linked guide and non-targeting sequences) in a mammalian expression vector were manipulated to delete or add NLS sequences (sequences in Table 9). Constructs 278, 279, and 280 were manipulations of the N- and C-termini using only an SV40 NLS sequence. Construct 280 had no NLS on the N-terminus and added two SV40 NLS' on the C-terminus with a triple proline linker in between the two SV40 NLS sequences. Constructs 278, 279, and 280 were made by amplifying pStx34.119.174.NT with Q5 DNA polymerase (New England BioLabs Cat #M0491L) according to the manufacturer's protocol, using primers oIC527 and oIC528, oIC730 and oIC522, and oIC730 and oIC530 for the first fragments each and using oIC529 and oIC520, oIC519 and oIC731, and oIC529 and oIC731 to create the second fragments each. These fragments were purified by gel extraction from a 1% agarose gel (Gold Bio Cat #A-201-500) using Zymoclean™ Gel DNA Recovery Kit (Zymo Research Cat #D4002) according to the manufacturer's protocol. The respective fragments were cloned together using Gibson assembly® (New England BioLabs Cat #E2621S) following the manufacturer's protocol. Assembled products in the pStx34 were transformed into chemically-competent Turbo Competent E. coli bacterial cells, plated on LB-Agar plates (LB: Teknova Cat #L9315, Agar: Quartzy Cat #214510) containing carbenicillin and incubated at 37° C. Individual colonies were picked and miniprepped using Qiagen QIAprep® Spin Miniprep Kit (Qiagen Cat #27104) following the manufacturer's protocol. The resultant plasmids were sequenced using Sanger sequencing to ensure correct assembly. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically- or electro-competent cells such as NEB Turbo competent E. coli (NEB Cat #C2984I), plated on LB-Agar plates (LB: Teknova Cat

L9315, Agar: Quartzy Cat #214510) containing carbenicillin and incubated at 37° C. Individual colonies were picked and miniprepped using Qiagen QIAprep® Spin Miniprep Kit (Qiagen Cat #27104) and following the manufacturer's protocol. The resultant plasmids were sequenced using Sanger sequencing to ensure correct ligation.

In order to generate constructs 285-288, 290, 291, 293, and 300, a nested PCR method was used for cloning. The backbone vector and PCR template used was construct pStx34 279.119.174.NT, having the CasX 119, guide 174, and non-targeting spacer (see Examples 8 and 9 and Tables therein for sequences). Construct 278 has the configuration SV40NLS-CasX119. Construct 279 has the configuration CasX119-SV40NLS. Construct 280 has the configuration CasX119-SV40NLS-PPP linker-SV40NLS. Construct 285 has the configuration CasX119-SV40NLS-PPP linker-SynthNLS3. Construct 286 has the configuration CasX119-SV40NLS-PPP linker-SynthNLS4. Construct 287 has the configuration CasX119-SV40NLS-PPP linker-SynthNLS5. Construct 288 has the configuration CasX119-SV40NLS-PPP linker-SynthNLS6. Constrict 290 has the configuration CasX119-SV40NLS-PPPlinker-EGL-13 NLS. Construct 291 has the configuration CasX119-SV40NLS-PPP linker-c-Myc NLS. Construct 293 has the configuration CasX119-SV40NLS-PPP linker-Nucleolar RNA Helicase II NLS. Construct 300 has the configuration CasX119-SV40NLS-PPP linker-Influenza A protein NLS. Construct 492 has the configuration SV40NLS-CasX119-SV40NLS-PPP linker-SV40NLS. Construct 493 has the configuration SV40NLS-CasX119-SV40NLS-PPP linker-c-Myc NLS. Each variant had a set of three PCRs; two of which were nested, were purified by gel extraction, digested, and then ligated into the digested and purified backbone. Assembled products in the pStx34 were transformed into chemically-competent Turbo Competent E. coli bacterial cells, plated on LB-Agar plates (LB: Teknova Cat #L9315, Agar: Quartzy Cat #214510) containing carbenicillin and incubated at 37° C. Individual colonies were picked and miniprepped using Qiagen QIAprep® Spin Miniprep Kit (Qiagen Cat #27104) following the manufacturer's protocol. The resultant plasmids were sequenced using Sanger sequencing to ensure correct assembly. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into the resulting pStX individually or in bulk by Golden Gate assembly using T4 DNA Ligase (New England BioLabs Cat #M0202L) and an appropriate restriction enzyme for the plasmid. Golden Gate products were transformed into chemically- or electro-competent cells such as NEB Turbo competent E. coli (NEB Cat #C2984I), plated on LB-Agar plates (LB: Teknova Cat #L9315, Agar: Quartzy Cat #214510) containing carbenicillin and incubated at 37° C. Individual colonies were picked and miniprepped using Qiagen QIAprep® Spin Miniprep Kit (Qiagen Cat #27104) and following the manufacturer's protocol. The resultant plasmids were sequenced using Sanger sequencing to ensure correct ligation.

In order to generate constructs 492 and 493, constructs 280 and 291 were digested using XbaI and BamHI (NEB #R0145S and NEB #R3136S) according to the manufacturer's protocol. Next, they were purified by gel extraction from a 1% agarose gel (Gold Bio Cat #A-201-500) using Zymoclean™ Gel DNA Recovery Kit (Zymo Research Cat #D4002) according to the manufacturer's protocol. Finally, they were ligated using T4 DNA ligase (NEB #M0202S) according to the manufacturer's protocol into the digested and purified pStx34.119.174.NT using XbaI and BamHI and Zymoclean™ Gel DNA Recovery Kit. Assembled products in the pStx34 were transformed into chemically-competent Turbo Competent E. coli bacterial cells, plated on LB-Agar plates (LB: Teknova Cat #L9315, Agar: Quartzy Cat #214510) containing carbenicillin and incubated at 37° C. Individual colonies were picked and miniprepped using Qiagen QIAprep® Spin Miniprep Kit (Qiagen Cat #27104) following the manufacturer's protocol. The resultant plasmids were sequenced using Sanger sequencing to ensure correct assembly. Sequences encoding the targeting spacer sequences that target the gene of interest were designed based on CasX PAM locations. Targeting sequence DNA was ordered as single-stranded DNA (ssDNA) oligos (Integrated DNA Technologies) consisting of the targeting spacer sequence and the reverse complement of this sequence. These two oligos were annealed together and cloned into each pStX individually or in bulk by Golden Gate assembly using T4 DNA Ligase (New England BioLabs Cat #M0202L) and an appropriate restriction enzyme for the respective plasmids. Golden Gate products were transformed into chemically- or electro-competent cells such as NEB Turbo competent E. coli (NEB Cat #C2984I), plated on LB-Agar plates (LB: Teknova Cat #L9315, Agar: Quartzy Cat #214510) containing carbenicillin and incubated at 37° C. Individual colonies were picked and miniprepped using Qiagen QIAprep® Spin Miniprep Kit (Qiagen Cat #27104) and following the manufacturer's protocol. The resultant plasmids were sequenced using Sanger sequencing to ensure correct ligation. The plasmids would be used to produce and recover CasX protein utilizing the general methodologies of Examples 1 and 2.

TABLE 8

CasX 278-280, 285-288, 290, 291, 293, 300, 492, and 493 sequences

| Construct | Amino Acid Sequence |
|---|---|
| 278 | MAPKKKRKVSRQEIKRINKIRRRLVKDSNTKKAGKTGPMKTLLVRVMTPDLRERL ENLRKKPENIPQPISNTSRANLNKLLTDYTEMKKAILHVYWEEFQKDPVGLMSRV AQPAPKNIDQRKLIPVKDGNERLTSSGFACSQCCQPLYVYKLEQVNDKGKPHTNY FGRCNVSEHERLILLSPHKPEANDELVTYSLGKFGQRALDFYSIHVTRESNHPVK PLEQIGGNSCASGPVGKALSDACMGAVASFLTKYQDIILEHQKVIKKNEKRLANL KDIASANGLAFPKITLPPQPHTKEGIEAYNNVVAQIVIWVNLNLWQKLKIGRDEA KPLQRLKGFPSFPLVERQANEVDWWDMVCNVKKLINEKKEDGKVFWQNLAGYKRQ EALRPYLSSEEDRKKGKKFARYQFGDLLLHLEKKHGEDWGKVYDEAWERIDKKVE GLSKHIKLEEERRSEDAQSKAALTDWLRAKASFVIEGLKEADKDEFCRCELKLQK WYGDLRGKPFAIEAENSILDISGFSKQYNCAFIWQKDGVKKLNLYLIINYFKGGK LRFKKIKPEAFEANRFYTVINKKSGEIVPMEVNFNFDDPNLIILPLAFGKRQGRE FIWNDLLSLETGSLKLANGRVIEKTLYNRRTRQDEPALFVALTFERREVLDSSNI |

TABLE 8-continued

CasX 278-280, 285-288, 290, 291, 293, 300, 492, and 493 sequences

| Construct | Amino Acid Sequence |
|---|---|
| | KPMNLIGIDRGENIPAVIALTDPEGCPLSRFKDSLGNPTHILRIGESYKEKQRTI<br>QAKKEVEQRRAGGYSRKYASKAKNLADDMVRNTARDLLYYAVTQDAMLIFENLSR<br>GFGRQGKRTFMAERQYTRMEDWLTAKLAYEGLSKTYLSKTLAQYTSKTCSNCGFT<br>ITSADYDRVLEKLKKTATGWMTTINGKELKVEGQITYYNRYKRQNVVKDLSVELD<br>RLSEESVNNDISSWTKGRSGEALSLLKKRFSHRPVQEKFVCLNCGFETHADEQAA<br>LNIARSWLFLRSQEYKKYQTNKTTGNTDKRAFVETWQSFYRKKLKEVWKPAV<br>(SEQ ID NO: 217) |
| 279 | MQEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPAPKNIDQ<br>RKLIPVKDGNERLTSSGFACSQCCQPLYVYKLEQVNDKGKPHTNYFGRCNVSEHE<br>RLILLSPHKPEANDELVTYSLGKFGQRALDFYSIHVTRESNHPVKPLEQIGGNSC<br>ASGPVGKALSDACMGAVASFLTKYQDIILEHQKVIKKNEKRLANLKDIASANGLA<br>FPKITLPPQPHTKEGIEAYNNVVAQIVIWVNLNLWQKLKIGRDEAKPLQRLKGFP<br>SFPLVERQANEVDWWDMVCNVKKLINEKKEDGKVFWQNLAGYKRQEALRPYLSSE<br>EDRKKGKKFARYQFGDLLLHLEKKHGEDWGKVYDEAWERIDKKVEGLSKHIKLEE<br>ERRSEDAQSKAALTDWLRAKASFVIEGLKEADKDEFCRCELKLQKWYGDLRGKPF<br>AIEAENSILDISGFSKQYNCAFIWQKDGVKKLNLYLIINYFKGGKLRFKKIKPEA<br>FEANRFYTVINKKSGEIVPMEVNFNFDDPNLIILPLAFGKRQGREFIWNDLLSLE<br>TGSLKLANGRVIEKTLYNRRTRQDEPALFVALTFERREVLDSSNIKPMNLIGIDR<br>GENIPAVIALTDPEGCPLSRFKDSLGNPTHILRIGESYKEKQRTIQAKKEVEQRR<br>AGGYSRKYASKAKNLADDMVRNTARDLLYYAVTQDAMLIFENLSRGFGRQGKRTF<br>MAERQYTRMEDWLTAKLAYEGLSKTYLSKTLAQYTSKTCSNCGFTITSADYDRVL<br>EKLKKTATGWMTTINGKELKVEGQITYYNRYKRQNVVKDLSVELDRLSEESVNND<br>ISSWTKGRSGEALSLLKKRFSHRPVQEKFVCLNCGFETHADEQAALNIARSWLFL<br>RSQEYKKYQTNKTTGNTDKRAFVETWQSFYRKKLKEVWKPAVTSPKKKRKV<br>(SEQ ID NO: 218) |
| 280 | MQEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPAPKNIDQ<br>RKLIPVKDGNERLTSSGFACSQCCQPLYVYKLEQVNDKGKPHTNYFGRCNVSEHE<br>RLILLSPHKPEANDELVTYSLGKFGQRALDFYSIHVTRESNHPVKPLEQIGGNSC<br>ASGPVGKALSDACMGAVASFLTKYQDIILEHQKVIKKNEKRLANLKDIASANGLA<br>FPKITLPPQPHTKEGIEAYNNVVAQIVIWVNLNLWQKLKIGRDEAKPLQRLKGFP<br>SFPLVERQANEVDWWDMVCNVKKLINEKKEDGKVFWQNLAGYKRQEALRPYLSSE<br>EDRKKGKKFARYQFGDLLLHLEKKHGEDWGKVYDEAWERIDKKVEGLSKHIKLEE<br>ERRSEDAQSKAALTDWLRAKASFVIEGLKEADKDEFCRCELKLQKWYGDLRGKPF<br>AIEAENSILDISGFSKQYNCAFIWQKDGVKKLNLYLIINYFKGGKLRFKKIKPEA<br>FEANRFYTVINKKSGEIVPMEVNFNFDDPNLIILPLAFGKRQGREFIWNDLLSLE<br>TGSLKLANGRVIEKTLYNRRTRQDEPALFVALTFERREVLDSSNIKPMNLIGIDR<br>GENIPAVIALTDPEGCPLSRFKDSLGNPTHILRIGESYKEKQRTIQAKKEVEQRR<br>AGGYSRKYASKAKNLADDMVRNTARDLLYYAVTQDAMLIFENLSRGFGRQGKRTF<br>MAERQYTRMEDWLTAKLAYEGLSKTYLSKTLAQYTSKTCSNCGFTITSADYDRVL<br>EKLKKTATGWMTTINGKELKVEGQITYYNRYKRQNVVKDLSVELDRLSEESVNND<br>ISSWTKGRSGEALSLLKKRFSHRPVQEKFVCLNCGFETHADEQAALNIARSWLFL<br>RSQEYKKYQTNKTTGNTDKRAFVETWQSFYRKKLKEVWKPAVTSPKKKRKVPPPP<br>KKKRKV (SEQ ID NO: 219) |
| 285 | MQEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPAPKNIDQ<br>RKLIPVKDGNERLTSSGFACSQCCQPLYVYKLEQVNDKGKPHTNYFGRCNVSEHE<br>RLILLSPHKPEANDELVTYSLGKFGQRALDFYSIHVTRESNHPVKPLEQIGGNSC<br>ASGPVGKALSDACMGAVASFLTKYQDIILEHQKVIKKNEKRLANLKDIASANGLA<br>FPKITLPPQPHTKEGIEAYNNVVAQIVIWVNLNLWQKLKIGRDEAKPLQRLKGFP<br>SFPLVERQANEVDWWDMVCNVKKLINEKKEDGKVFWQNLAGYKRQEALRPYLSSE<br>EDRKKGKKFARYQFGDLLLHLEKKHGEDWGKVYDEAWERIDKKVEGLSKHIKLEE<br>ERRSEDAQSKAALTDWLRAKASFVIEGLKEADKDEFCRCELKLQKWYGDLRGKPF<br>AIEAENSILDISGFSKQYNCAFIWQKDGVKKLNLYLIINYFKGGKLRFKKIKPEA<br>FEANRFYTVINKKSGEIVPMEVNFNFDDPNLIILPLAFGKRQGREFIWNDLLSLE<br>TGSLKLANGRVIEKTLYNRRTRQDEPALFVALTFERREVLDSSNIKPMNLIGIDR<br>GENIPAVIALTDPEGCPLSRFKDSLGNPTHILRIGESYKEKQRTIQAKKEVEQRR<br>AGGYSRKYASKAKNLADDMVRNTARDLLYYAVTQDAMLIFENLSRGFGRQGKRTF<br>MAERQYTRMEDWLTAKLAYEGLSKTYLSKTLAQYTSKTCSNCGFTITSADYDRVL<br>EKLKKTATGWMTTINGKELKVEGQITYYNRYKRQNVVKDLSVELDRLSEESVNND<br>ISSWTKGRSGEALSLLKKRFSHRPVQEKFVCLNCGFETHADEQAALNIARSWLFL<br>RSQEYKKYQTNKTTGNTDKRAFVETWQSFYRKKLKEVWKPAVTSPKKKRKVPPPH<br>KKKHPDASVNFSEFSK (SEQ ID NO: 220) |
| 286 | MQEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPAPKNIDQ<br>RKLIPVKDGNERLTSSGFACSQCCQPLYVYKLEQVNDKGKPHTNYFGRCNVSEHE<br>RLILLSPHKPEANDELVTYSLGKFGQRALDFYSIHVTRESNHPVKPLEQIGGNSC<br>ASGPVGKALSDACMGAVASFLTKYQDIILEHQKVIKKNEKRLANLKDIASANGLA<br>FPKITLPPQPHTKEGIEAYNNVVAQIVIWVNLNLWQKLKIGRDEAKPLQRLKGFP<br>SFPLVERQANEVDWWDMVCNVKKLINEKKEDGKVFWQNLAGYKRQEALRPYLSSE<br>EDRKKGKKFARYQFGDLLLHLEKKHGEDWGKVYDEAWERIDKKVEGLSKHIKLEE |

TABLE 8-continued

CasX 278-280, 285-288, 290, 291, 293, 300, 492, and 493 sequences

| Construct | Amino Acid Sequence |
|---|---|
| | ERRSEDAQSKAALTDWLRAKASFVIEGLKEADKDEFCRCELKLQKWYGDLRGKPF<br>AIEAENSILDISGFSKQYNCAFIWQKDGVKKLNLYLIINYFKGGKLRFKKIKPEA<br>FEANRFYTVINKKSGEIVPMEVNFNFDDPNLIILPLAFGKRQGREFIWNDLLSLE<br>TGSLKLANGRVIEKTLYNRRTRQDEPALFVALTFERREVLDSSNIKPMNLIGIDR<br>GENIPAVIALTDPEGCPLSRFKDSLGNPTHILRIGESYKEKQRTIQAKKEVEQRR<br>AGGYSRKYASKAKNLADDMVRNTARDLLYYAVTQDAMLIFENLSRGFGRQGKRTF<br>MAERQYTRMEDWLTAKLAYEGLSKTYLSKTLAQYTSKTCSNCGFTITSADYDRVL<br>EKLKKTATGWMTTINGKELKVEGQITYYNRYKRQNVVKDLSVELDRLSEESVNND<br>ISSWTKGRSGEALSLLKKRFSHRPVQEKFVCLNCGFETHADEQAALNIARSWLFL<br>RSQEYKKYQTNKTTGNTDKRAFVETWQSFYRKKLKEVWKPAVTSPKKKRKVPPPQ<br>RPGPYDRPQRPGPYDRP (SEQ ID NO: 221) |
| 287 | MQEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPAPKNIDQ<br>RKLIPVKDGNERLTSSGFACSQCCQPLYVYKLEQVNDKGKPHTNYFGRCNVSEHE<br>RLILLSPHKPEANDELVTYSLGKFGQRALDFYSIHVTRESNHPVKPLEQIGGNSC<br>ASGPVGKALSDACMGAVASFLTKYQDIILEHQKVIKKNEKRLANLKDIASANGLA<br>FPKITLPPQPHTKEGIEAYNNVVAQIVIWVNLNLWQKLKIGRDEAKPLQRLKGFP<br>SFPPLVERQANEVDWWDMVCNVKKLINEKKEDGKVFWQNLAGYKRQEALRPYLSSE<br>EDRKKGKKFARYQFGDLLLHLEKKHGEDWGKVYDEAWERIDKKVEGLSKHIKLEE<br>ERRSEDAQSKAALTDWLRAKASFVIEGLKEADKDEFCRCELKLQKWYGDLRGKPF<br>AIEAENSILDISGFSKQYNCAFIWQKDGVKKLNLYLIINYFKGGKLRFKKIKPEA<br>FEANRFYTVINKKSGEIVPMEVNFNFDDPNLIILPLAFGKRQGREFIWNDLLSLE<br>TGSLKLANGRVIEKTLYNRRTRQDEPALFVALTFERREVLDSSNIKPMNLIGIDR<br>GENIPAVIALTDPEGCPLSRFKDSLGNPTHILRIGESYKEKQRTIQAKKEVEQRR<br>AGGYSRKYASKAKNLADDMVRNTARDLLYYAVTQDAMLIFENLSRGFGRQGKRTF<br>MAERQYTRMEDWLTAKLAYEGLSKTYLSKTLAQYTSKTCSNCGFTITSADYDRVL<br>EKLKKTATGWMTTINGKELKVEGQITYYNRYKRQNVVKDLSVELDRLSEESVNND<br>ISSWTKGRSGEALSLLKKRFSHRPVQEKFVCLNCGFETHADEQAALNIARSWLFL<br>RSQEYKKYQTNKTTGNTDKRAFVETWQSFYRKKLKEVWKPAVTSPKKKRKVPPPL<br>SPSLSPLLSPSLSPL (SEQ ID NO: 222) |
| 288 | MQEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPAPKNIDQ<br>RKLIPVKDGNERLTMSSGFACSQCCQPLYVYKLEQVNDKGKPHTNYFGRCNVSEH<br>ERLILLSPHKPEANDELVTYSLGKFGQRALDFYSIHVTRESNHPVKPLEQIGGNS<br>CASGPVGKALSDACMGAVASFLTKYQDIILEHQKVIKKNEKRLANLKDIASANGL<br>AFPKITLPPQPHTKEGIEAYNNVVAQIVIWVNLNLWQKLKIGRDEAKPLQRLKGF<br>PSFPLVERQANEVDWWDMVCNVKKLINEKKEDGKVFWQNLAGYKRQEALRPYLSS<br>EEDRKKGKKFARYQFGDLLLHLEKKHGEDWGKVYDEAWERIDKKVEGLSKHIKLE<br>EERRSEDAQSKAALTDWLRAKASFVIEGLKEADKDEFCRCELKLQKWYGDLRGKP<br>FAIEAENSILDISGFSKQYNCAFIWQKDGVKKLNLYLIINYFKGGKLRFKKIKPE<br>AFEANRFYTVINKKSGEIVPMEVNFNFDDPNLIILPLAFGKRQGREFIWNDLLSL<br>ETGSLKLANGRVIEKTLYNRRTRQDEPALFVALTFERREVLDSSNIKPMNLIGID<br>RGENIPAVIALTDPEGCPLSRFKDSLGNPTHILRIGESYKEKQRTIQAKKEVEQR<br>RAGGYSRKYASKAKNLADDMVRNTARDLLYYAVTQDAMLIFENLSRGFGRQGKRT<br>FMAERQYTRMEDWLTAKLAYEGLSKTYLSKTLAQYTSKTCSNCGFTITSADYDRV<br>LEKLKKTATGWMTTINGKELKVEGQITYYNRYKRQNVVKDLSVELDRLSEESVNN<br>DISSWTKGRSGEALSLLKKRFSHRPVQEKFVCLNCGFETHADEQAALNIARSWLF<br>LRSQEYKKYQTNKTTGNTDKRAFVETWQSFYRKKLKEVWKPAVTSPKKKRKVPPP<br>RGKGGKGLGKGGAKRHRK (SEQ ID NO: 223) |
| 290 | MQEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPAPKNIDQ<br>RKLIPVKDGNERLTSSGFACSQCCQPLYVYKLEQVNDKGKPHTNYFGRCNVSEHE<br>RLILLSPHKPEANDELVTYSLGKFGQRALDFYSIHVTRESNHPVKPLEQIGGNSC<br>ASGPVGKALSDACMGAVASFLTKYQDIILEHQKVIKKNEKRLANLKDIASANGLA<br>FPKITLPPQPHTKEGIEAYNNVVAQIVIWVNLNLWQKLKIGRDEAKPLQRLKGFP<br>SFPPLVERQANEVDWWDMVCNVKKLINEKKEDGKVFWQNLAGYKRQEALRPYLSSE<br>EDRKKGKKFARYQFGDLLLHLEKKHGEDWGKVYDEAWERIDKKVEGLSKHIKLEE<br>ERRSEDAQSKAALTDWLRAKASFVIEGLKEADKDEFCRCELKLQKWYGDLRGKPF<br>AIEAENSILDISGFSKQYNCAFIWQKDGVKKLNLYLIINYFKGGKLRFKKIKPEA<br>FEANRFYTVINKKSGEIVPMEVNFNFDDPNLIILPLAFGKRQGREFIWNDLLSLE<br>TGSLKLANGRVIEKTLYNRRTRQDEPALFVALTFERREVLDSSNIKPMNLIGIDR<br>GENIPAVIALTDPEGCPLSRFKDSLGNPTHILRIGESYKEKQRTIQAKKEVEQRR<br>AGGYSRKYASKAKNLADDMVRNTARDLLYYAVTQDAMLIFENLSRGFGRQGKRTF<br>MAERQYTRMEDWLTAKLAYEGLSKTYLSKTLAQYTSKTCSNCGFTITSADYDRVL<br>EKLKKTATGWMTTINGKELKVEGQITYYNRYKRQNVVKDLSVELDRLSEESVNND<br>ISSWTKGRSGEALSLLKKRFSHRPVQEKFVCLNCGFETHADEQAALNIARSWLFL<br>RSQEYKKYQTNKTTGNTDKRAFVETWQSFYRKKLKEVWKPAVTSPKKKRKVPPPS<br>RRRKANPTKLSENAKKLAKEVEN (SEQ ID NO: 224) |
| 291 | MQEIKRINKIRRRLVKDSNTKKAGKTGPMKTLLVRVMTPDLRERLENLRKKPENI<br>PQPISNTSRANLNKLLTDYTEMKKAILHVYWEEFQKDPVGLMSRVAQPAPKNIDQ<br>RKLIPVKDGNERLTSSGFACSQCCQPLYVYKLEQVNDKGKPHTNYFGRCNVSEHE<br>RLILLSPHKPEANDELVTYSLGKFGQRALDFYSIHVTRESNHPVKPLEQIGGNSC |

TABLE 8-continued

CasX 278-280, 285-288, 290, 291, 293, 300, 492, and 493 sequences

| Construct | Amino Acid Sequence |
|---|---|
| | ASGPVGKALSDACMGAVASFLTKYQDIILEHQKVIKKNEKRLANLKDIASANGLA
FPKITLPPQPHTKEGIEAYNNVVAQIVIWVNLNLWQKLKIGRDEAKPLQRLKGFP
SFPLVERQANEVDWWDMVCNVKKLINEKKEDGKVFWQNLAGYKRQEALRPYLSSE
EDRKKGKKFARYQFGDLLLHLEKKHGEDWGKVYDEAWERIDKKVEGLSKHIKLEE
ERRSEDAQSKAALTDWLRAKASFVIEGLKEADKDEFCRCELKLQKWYGDLRGKPF
AIEAENSILDISGFSKQYNCAFIWQKDGVKKLNLYLIINYFKGGKLRFKKIKPEA
FEANRFYTVINKKSGEIVPMEVNFNFDDPNLIILPLAFGKRQGREFIWNDLLSLE
TGSLKLANGRVIEKTLYNRRTRQDEPALFVALTFERREVLDSSNIKPMNLIGIDR
GENIPAVIALTDPEGCPLSRFKDSLGNPTHILRIGESYKEKQRTIQAKKEVEQRR
AGGYSRKYASKAKNLADDMVRNTARDLLYYAVTQDAMLIFENLSRGFGRQGKRTF
MAERQYTRMEDWLTAKLAYEGLSKTYLSKTLAQYTSKTCSNCGFTITSADYDRVL
EKLKKTATGWMTTINGKELKVEGQITYYNRYKRQNVVKDLSVELDRLSEESVNND
ISSWTKGRSGEALSLLKKRFSHRPVQEKFVCLNCGFETHADEQAALNIARSWLFL
RSQEYKKYQTNKTTGNTDKRAFVETWQSFYRKKLKEVWKPAVTSPKKKRKVPPPP
AAKRVKLD (SEQ ID NO: 225) |
| 293 | MQEIKRINKIRRRLVKDSNTKKAGKTGPMKTLLVRVMTPDLRERLENLRKKPENI
PQPISNTSRANLNKLLTDYTEMKKAILHVYWEEFQKDPVGLMSRVAQPAPKNIDQ
RKLIPVKDGNERLTSSGFACSQCCQPLYVYKLEQVNDKGKPHTNYFGRCNVSEHE
RLILLSPHKPEANDELVTYSLGKFGQRALDFYSIHVTRESNHPVKPLEQIGGNSC
ASGPVGKALSDACMGAVASFLTKYQDIILEHQKVIKKNEKRLANLKDIASANGLA
FPKITLPPQPHTKEGIEAYNNVVAQIVIWVNLNLWQKLKIGRDEAKPLQRLKGFP
SFPLVERQANEVDWWDMVCNVKKLINEKKEDGKVFWQNLAGYKRQEALRPYLSSE
EDRKKGKKFARYQFGDLLLHLEKKHGEDWGKVYDEAWERIDKKVEGLSKHIKLEE
ERRSEDAQSKAALTDWLRAKASFVIEGLKEADKDEFCRCELKLQKWYGDLRGKPF
AIEAENSILDISGFSKQYNCAFIWQKDGVKKLNLYLIINYFKGGKLRFKKIKPEA
FEANRFYTVINKKSGEIVPMEVNFNFDDPNLIILPLAFGKRQGREFIWNDLLSLE
TGSLKLANGRVIEKTLYNRRTRQDEPALFVALTFERREVLDSSNIKPMNLIGIDR
GENIPAVIALTDPEGCPLSRFKDSLGNPTHILRIGESYKEKQRTIQAKKEVEQRR
AGGYSRKYASKAKNLADDMVRNTARDLLYYAVTQDAMLIFENLSRGFGRQGKRTF
MAERQYTRMEDWLTAKLAYEGLSKTYLSKTLAQYTSKTCSNCGFTITSADYDRVL
EKLKKTATGWMTTINGKELKVEGQITYYNRYKRQNVVKDLSVELDRLSEESVNND
ISSWTKGRSGEALSLLKKRFSHRPVQEKFVCLNCGFETHADEQAALNIARSWLFL
RSQEYKKYQTNKTTGNTDKRAFVETWQSFYRKKLKEVWKPAVTSPKKKRKVPPPK
RSFSKAF (SEQ ID NO: 226) |
| 300 | MQEIKRINKIRRRLVKDSNTKKAGKTGPMKTLLVRVMTPDLRERLENLRKKPENI
PQPISNTSRANLNKLLTDYTEMKKAILHVYWEEFQKDPVGLMSRVAQPAPKNIDQ
RKLIPVKDGNERLTSSGFACSQCCQPLYVYKLEQVNDKGKPHTNYFGRCNVSEHE
RLILLSPHKPEANDELVTYSLGKFGQRALDFYSIHVTRESNHPVKPLEQIGGNSC
ASGPVGKALSDACMGAVASFLTKYQDIILEHQKVIKKNEKRLANLKDIASANGLA
FPKITLPPQPHTKEGIEAYNNVVAQIVIWVNLNLWQKLKIGRDEAKPLQRLKGFP
SFPLVERQANEVDWWDMVCNVKKLINEKKEDGKVFWQNLAGYKRQEALRPYLSSE
EDRKKGKKFARYQFGDLLLHLEKKHGEDWGKVYDEAWERIDKKVEGLSKHIKLEE
ERRSEDAQSKAALTDWLRAKASFVIEGLKEADKDEFCRCELKLQKWYGDLRGKPF
AIEAENSILDISGFSKQYNCAFIWQKDGVKKLNLYLIINYFKGGKLRFKKIKPEA
FEANRFYTVINKKSGEIVPMEVNFNFDDPNLIILPLAFGKRQGREFIWNDLLSLE
TGSLKLANGRVIEKTLYNRRTRQDEPALFVALTFERREVLDSSNIKPMNLIGIDR
GENIPAVIALTDPEGCPLSRFKDSLGNPTHILRIGESYKEKQRTIQAKKEVEQRR
AGGYSRKYASKAKNLADDMVRNTARDLLYYAVTQDAMLIFENLSRGFGRQGKRTF
MAERQYTRMEDWLTAKLAYEGLSKTYLSKTLAQYTSKTCSNCGFTITSADYDRVL
EKLKKTATGWMTTINGKELKVEGQITYYNRYKRQNVVKDLSVELDRLSEESVNND
ISSWTKGRSGEALSLLKKRFSHRPVQEKFVCLNCGFETHADEQAALNIARSWLFL
RSQEYKKYQTNKTTGNTDKRAFVETWQSFYRKKLKEVWKPAVTSPKKKRKVPPPK
RGINDRNFWRGENERKTR (SEQ ID NO: 227) |
| 492 | MAPKKKRKVSRMQEIKRINKIRRRLVKDSNTKKAGKTGPMKTLLVRVMTPDLRER
LENLRKKPENIPQPISNTSRANLNKLLTDYTEMKKAILHVYWEEFQKDPVGLMSR
VAQPAPKNIDQRKLIPVKDGNERLTSSGFACSQCCQPLYVYKLEQVNDKGKPHTN
YFGRCNVSEHERLILLSPHKPEANDELVTYSLGKFGQRALDFYSIHVTRESNHPV
KPLEQIGGNSCASGPVGKALSDACMGAVASFLTKYQDIILEHQKVIKKNEKRLAN
LKDIASANGLAFPKITLPPQPHTKEGIEAYNNVVAQIVIWVNLNLWQKLKIGRDE
AKPLQRLKGFPSFPLVERQANEVDWWDMVCNVKKLINEKKEDGKVFWQNLAGYKR
QEALRPYLSSEEDRKKGKKFARYQFGDLLLHLEKKHGEDWGKVYDEAWERIDKKV
EGLSKHIKLEEERRSEDAQSKAALTDWLRAKASFVIEGLKEADKDEFCRCELKLQ
KWYGDLRGKPFAIEAENSILDISGFSKQYNCAFIWQKDGVKKLNLYLIINYFKGG
KLRFKKIKPEAFEANRFYTVINKKSGEIVPMEVNFNFDDPNLIILPLAFGKRQGR
EFIWNDLLSLETGSLKLANGRVIEKTLYNRRTRQDEPALFVALTFERREVLDSSN
IKPMNLIGIDRGENIPAVIALTDPEGCPLSRFKDSLGNPTHILRIGESYKEKQRT
IQAKKEVEQRRAGGYSRKYASKAKNLADDMVRNTARDLLYYAVTQDAMLIFENLS
RGFGRQGKRTFMAERQYTRMEDWLTAKLAYEGLSKTYLSKTLAQYTSKTCSNCGF
TITSADYDRVLEKLKKTATGWMTTINGKELKVEGQITYYNRYKRQNVVKDLSVEL
DRLSEESVNNDISSWTKGRSGEALSLLKKRFSHRPVQEKFVCLNCGFETHADEQA
ALNIARSWLFLRSQEYKKYQTNKTTGNTDKRAFVETWQSFYRKKLKEVWKPAVTS
PKKKRKVPPPPKKKRKV (SEQ ID NO: 228) |

TABLE 8-continued

CasX 278-280, 285-288, 290, 291, 293, 300, 492, and 493 sequences

| Construct | Amino Acid Sequence |
|---|---|
| 493 | MAPKKKRKVSRMQEIKRINKIRRRLVKDSNTKKAGKTGPMKTLLVRVMTPDLRER LENLRKKPENIPQPISNTSRANLNKLLTDYTEMKKAILHVYWEEFQKDPVGLMSR VAQPAPKNIDQRKLIPVKDGNERLTSSGFACSQCCQPLYVYKLEQVNDKGKPHTN YFGRCNVSEHERLILLSPHKPEANDELVTYSLGKFGQRALDFYSIHVTRESNHPV KPLEQIGGNSCASGPVGKALSDACMGAVASFLTKYQDIILEHQKVIKKNEKRLAN LKDIASANGLAFPKITLPPQPHTKEGIEAYNNVVAQIVIWVNLNLWQKLKIGRDE AKPLQRLKGFPSFPLVERQANEVDWWDMVCNVKKLINEKKEDGKVFWQNLAGYKR QEALRPYLSSEEDRKKGKKFARYQFGDLLLHLEKKHGEDWGKVYDEAWERIDKKV EGLSKHIKLEEERRSEDAQSKAALTDWLRAKASFVIEGLKEADKDEFCRCELKLQ KWYGDLRGKPFAIEAENSILDISGFSKQYNCAFIWQKDGVKKLNLYLIINYFKGG KLRFKKIKPEAFEANRFYTVINKKSGEIVPMEVNFNFDDPNLIILPLAFGKRQGR EFIWNDLLSLETGSLKLANGRVIEKTLYNRRTRQDEPALFVALTFERREVLDSSN IKPMNLIGIDRGENIPAVIALTDPEGCPLSRFKDSLGNPTHILRIGESYKEKQRT IQAKKEVEQRRAGGYSRKYASKAKNLADDMVRNTARDLLYYAVTQDAMLIFENLS RGFGRQGKRTFMAERQYTRMEDWLTAKLAYEGLSKTYLSKTLAQYTSKTCSNCGF TITSADYDRVLEKLKKTATGWMTTINGKELKVEGQITYYNRYKRQNVVKDLSVEL DRLSEESVNNDISSWTKGRSGEALSLLKKRFSHRPVQEKFVCLNCGFETHADEQA ALNIARSWLFLRSQEYKKYQTNKTTGNTDKRAFVETWQSFYRKKLKEVWKPAVTS PKKKRKVPPPPAAKRVKLD (SEQ ID NO: 229) |

TABLE 9

Nuclear localization sequence list

| CasX | NLS | DNA Sequence | Amino Acid Sequence |
|---|---|---|---|
| 278, 279, 280, 492, 493 | SV40 | CCAAAGAAGAAGCGGAAGGTC (SEQ ID NO: 230) | PKKKRKV (SEQ ID NO: 145) |
| 285 | SynthNLS3 | CACAAGAAGAAACATCCAGACGC ATCAGTCAACTTTAGCGAGTTCA GTAAA (SEQ ID NO: 231) | HKKKHPDASVNFSEFSK (SEQ ID NO: 176) |
| 286 | SynthNLS4 | CAGCGCCCTGGGCCTTACGATAG GCCGCAAAGACCCGGACCGTATG ATCGCCCT (SEQ ID NO: 232) | QRPGPYDRPQRPGPYDRP (SEQ ID NO: 177) |
| 287 | SynthNLS5 | CTCAGCCCGAGTCTTAGTCCACT GCTTTCCCCGTCCCTGTCTCCAC TG (SEQ ID NO: 233) | LSPSLSPLLSPSLSPL (SEQ ID NO: 178) |
| 288 | SynthNLS6 | CGGGGCAAGGGTGGCAAGGGGCT TGGCAAGGGGGGGCAAAGAGGC ACAGGAAG (SEQ ID NO: 234) | RGKGGKGLGKGGAKRHRK (SEQ ID NO: 179) |
| 290 | EGL-13 | AGCCGCCGCAGAAAAGCCAATCC TACAAAACTGTCAGAAAATGCGA AAAAACTTGCTAAGGAGGTGGAA AAC (SEQ ID NO: 235) | SRRRKANPTKLSENAKKLA KEVEN (SEQ ID NO: 172) |
| 291 | c-Myc | CCTGCCGCAAAGCGAGTGAAATT GGAC (SEQ ID NO: 236) | PAAKRVKLD (SEQ ID NO: 147) |
| 293 | Nucleolar RNA Helicase II | AAGCGGTCCTTCAGTAAGGCCTT T (SEQ ID NO: 237) | KRSFSKAF (SEQ ID NO: 168) |
| 300 | Influenza A protein | AAACGGGGAATAAACGACCGGAA CTTCTGGCGCGGGGAAAACGAGC GCAAAACCCGA (SEQ ID NO: 238) | KRGINDRNFWRGENEPKTR (SEQ ID NO: 166) |

Example 5: Design and Generation of CasX Constructs 387, 395, 485-491, and 494

In order to generate CasX 395, CasX 485, CasX 486, CasX 487, the codon optimized CasX 119 (based on the CasX 37 construct of Example 2, encoding *Planctomycetes* CasX SEQ ID NO: 2, with a A708K substitution and a [P793] deletion with fused NLS, and linked guide and non-targeting sequences), CasX 435, CasX 438, and CasX 484 (each based on CasX 119 construct of Example 2 encoding *Planctomycetes* CasX SEQ ID NO: 2, with a L379R substitution, a A708K substitution, and a [P793]

deletion with fused NLS, and linked guide and non-targeting sequences) were cloned respectively into a 4 kb staging vector comprising a KdnR marker, colE1 ori, and CasX with fused NLS (pStx1) using standard cloning methods. Gibson primers were designed to amplify the CasX SEQ ID NO: 1 Helical I domain from amino acid 192-331 in its own vector to replace this corresponding region (aa 193-332) on CasX 119, CasX 435, CasX 438, and CasX 484 in pStx1 respectively. The Helical I domain from CasX SEQ ID NO: 1 was amplified with primers oIC768 and oIC784 using Q5 DNA polymerase (New England BioLabs Cat #M0491L) according to the manufacturer's protocol. The destination vector containing the desired CasX variant was amplified with primers oIC765 and oIC764 using Q5 DNA polymerase (New England BioLabs Cat #M0491L) according to the manufacturer's protocol. The two fragments were purified by gel extraction from a 1% agarose gel (Gold Bio Cat #A-201-500) using Zymoclean™ Gel DNA Recovery Kit (Zymo Research Cat #D4002) according to the manufacturer's protocol. The insert and backbone fragments were then pieced together using Gibson assembly® (New England BioLabs Cat #E2621S) following the manufacturer's protocol. Assembled products in the pStx1 staging vector were transformed into chemically-competent Turbo Competent E. coli bacterial cells, plated on LB-Agar plates (LB: Teknova Cat #L9315, Agar: Quartzy Cat #214510) containing kanamycin and incubated at 37° C. Individual colonies were picked and miniprepped using Qiagen QIAprep® Spin Miniprep Kit (Qiagen Cat #27104) following the manufacturer's protocol. The resultant plasmids were sequenced using Sanger sequencing to ensure correct assembly. Correct clones were then cut and pasted into a mammalian expression plasmid (see FIG. 5) using standard cloning methods. The resultant plasmids were sequenced using Sanger sequencing to ensure correct assembly.

Sequences encoding the targeting spacer sequences that target the gene of interest were designed based on CasX PAM locations. Targeting spacer sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically or electro-competent cells such as NEB Turbo competent E. coli (NEB Cat #C2984I), plated on LB-Agar plates (LB: Teknova Cat #L9315, Agar: Quartzy Cat #214510) containing carbenicillin and incubated at 37° C. Individual colonies were picked and miniprepped using Qiagen QIAprep® Spin Miniprep Kit (Qiagen Cat #27104) following the manufacturer's protocol. The resultant plasmids were sequenced using Sanger sequencing to ensure correct ligation.

In order to generate CasX 488, CasX 489, CasX 490, and CasX 491 (sequences in Table 10), the codon optimized CasX 119 (based on the CasX 37 construct of Example 2, encoding *Planctomycetes* CasX SEQ ID NO: 2, with a A708K substitution and a [P793] deletion with fused NLS, and linked guide and non-targeting sequences), CasX 435, CasX 438, and CasX 484 (each based on CasX119 construct of Example 2 encoding *Planctomycetes* CasX SEQ ID NO: 2, with a L379R substitution, a A708K substitution, and a [P793] deletion with fused NLS, and linked guide and non-targeting sequences) were cloned respectively into a 4 kb staging vector that was made up of a KdnR marker, colE1 ori, and STX with fused NLS (pStx1) using standard cloning methods. Gibson primers were designed to amplify the CasX Stx1 NTSB domain from amino acid 101-191 and Helical I domain from amino acid 192-331 in its own vector to replace this similar region (aa 103-332) on CasX 119, CasX 435, CasX 438, and CasX 484 in pStx1 respectively. The NTSB and Helical I domain from CasX SEQ ID NO: 1 were amplified with primers oIC766 and oIC784 using Q5 DNA polymerase (New England BioLabs Cat #M0491L) according to the manufacturer's protocol. The destination vector containing the desired CasX variant was amplified with primers oIC762 and oIC765 using Q5 DNA polymerase (New England BioLabs Cat #M0491L) according to the manufacturer's protocol. The two fragments were purified by gel extraction from a 1% agarose gel (Gold Bio Cat #A-201-500) using Zymoclean™ Gel DNA Recovery Kit (Zymo Research Cat #D4002) according to the manufacturer's protocol. The insert and backbone fragments were then pieced together using Gibson assembly® (New England BioLabs Cat #E2621S) following the manufacturer's protocol. Assembled products in the pStx1 staging vector were transformed into chemically-competent Turbo Competent *E. coli* bacterial cells, plated on LB-Agar plates (LB: Teknova Cat #L9315, Agar: Quartzy Cat #214510) containing kanamycin and incubated at 37° C. Individual colonies were picked and miniprepped using Qiagen QIAprep® Spin Miniprep Kit (Qiagen Cat #27104) following the manufacturer's protocol. The resultant plasmids were sequenced using Sanger sequencing to ensure correct assembly. Correct clones were then cut and pasted into a mammalian expression plasmid (see FIG. 5) using standard cloning methods. The resultant plasmids were sequenced using Sanger sequencing to ensure correct assembly. Sequences encoding the targeting spacer sequences that target the gene of interest were designed based on CasX PAM locations. Targeting spacer sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically or electro-competent cells such as NEB Turbo competent *E. coli* (NEB Cat #C2984I), plated on LB-Agar plates (LB: Teknova Cat #L9315, Agar: Quartzy Cat #214510) containing carbenicillin and incubated at 37° C. Individual colonies were picked and miniprepped using Qiagen QIAprep® Spin Miniprep Kit (Qiagen Cat #27104) and following the manufacturer's protocol. The resultant plasmids were sequenced using Sanger sequencing to ensure correct ligation.

In order to generate CasX 387 and CasX 494 (sequences in Table 10), the codon optimized CasX 119 (based on the CasX 37 construct of Example 2, encoding *Planctomycetes* CasX SEQ ID NO: 2, with a A708K substitution and a [P793] deletion with fused NLS, and linked guide and non-targeting sequences) and CasX 484 (based on CasX119 construct of Example 2 encoding *Planctomycetes* CasX SEQ ID NO: 2, with a L379R substitution, a A708K substitution, and a [P793] deletion with fused NLS, and linked guide and non-targeting sequences) were cloned respectively into a 4 kb staging vector that was made up of a KdnR marker, colE1 ori, and STX with fused NLS (pStx1) using standard cloning methods. Gibson primers were designed to amplify the CasX Stx1 NTSB domain from amino acid 101-191 in its own vector to replace this similar region (aa 103-192) on CasX 119 and CasX 484 in pStx1 respectively. The NTSB domain from CasX Stx1 was amplified with primers oIC766 and oIC767 using Q5 DNA polymerase (New England BioLabs Cat #M0491L) according to the manufacturer's protocol. The destination vector containing the desired CasX variant was amplified with primers oIC763 and oIC762 using Q5 DNA polymerase (New England BioLabs Cat #M0491L) according to the manufacturer's protocol. The two fragments were purified by gel extraction from a 1% agarose gel (Gold Bio Cat #A-201-500) using Zymoclean™ Gel DNA Recovery Kit (Zymo Research Cat #D4002) according to the manufacturer's protocol. The insert and backbone fragments were then pieced together using Gibson assembly® (New England BioLabs Cat #E2621S) following the manufacturer's protocol. Assembled products in the pStx1 staging vector were transformed into chemically-competent Turbo Competent E. coli bacterial cells, plated on LB-Agar plates (LB: Teknova Cat #L9315, Agar: Quartzy Cat #214510) containing kanamycin and incubated at 37° C. Individual colonies were picked and miniprepped using Qiagen Qiaprep® spin Miniprep Kit (Qiagen Cat #27104) following the manufacturer's protocol. The resultant plasmids were sequenced using Sanger sequencing to ensure correct assembly. Correct clones were then cut and pasted into a mammalian expression plasmid (see FIG. 5) using standard cloning methods. The resultant plasmids were sequenced using Sanger sequencing to ensure correct assembly. Sequences encoding the targeting sequences that target the gene of interest were designed based on CasX PAM locations. Targeting sequence DNA was ordered as single-stranded DNA (ssDNA) oligos (Integrated DNA Technologies) consisting of the targeting sequence and the reverse complement of this sequence. These two oligos were annealed together and cloned into pStX individually or in bulk by Golden Gate assembly using T4 DNA Ligase (New England BioLabs Cat #M0202L) and an appropriate restriction enzyme for the plasmid. Golden Gate products were transformed into chemically or electro-competent cells such as NEB Turbo competent *E. coli* (NEB Cat #C2984I), plated on LB-Agar plates (LB: Teknova Cat #L9315, Agar: Quartzy Cat #214510) containing carbenicillin and incubated at 37° C. Individual colonies were picked and miniprepped using Qiagen Qiaprep® spin Miniprep Kit (Qiagen Cat #27104) and following the manufacturer's protocol. The resultant plasmids were sequenced using Sanger sequencing to ensure correct ligation. Sequences of the resulting constructs are listed in Table 10.

TABLE 10

Sequences of CasX 395 and 485-491

| Construct | DNA Sequence | Amino Acid Sequence |
|---|---|---|
| CasX 387 | (SEQ ID NO: 239) | MAPKKKRKVSRQEIKRINKIRRRLVKDSNTKKAGKTGPMKTLLVRVM TPDLRERLENLRKKPENIPQPISNTSRANLNKLLTDYTEMKKAILHV YWEEFQKDPVGLMSRVAQPASKKIDQNKLKPEMDEKGNLTTAGFACS QCGQPLFVYKLEQVSEKGKAYTNYFGRCNVAEHEKLILLAQLKPEKD SDEAVTYSLGKFGQRALDFYSIHVTRESNHPVKPLEQIGGNSCASGP VGKALSDACMGAVASFLTKYQDIILEHQKVIKKNEKRLANLKDIASA NGLAFPKITLPPQPHTKEGIEAYNNVVAQIVIWVNLNLWQKLKIGRD EAKPLQRLKGFPSFPLVERQANEVDWWDMVCNVKKLINEKKEDGKVF WQNLAGYKRQEALRPYLSSEEDRKKGKKFARYQFGDLLLHLEKKHGE DWGKVYDEAWERIDKKVEGLSKHIKLEEERRSEDAQSKAALTDWLRA KASFVIEGLKEADKDEFCRCELKLQKWYGDLRGKPFAIEAENSILDI SGFSKQYNCAFIWQKDGVKKLNLYLIINYFKGGKLRFKKIKPEAFEA NRFYTVINKKSGEIVPMEVNFNFDDPNLIILPLAFGKRQGREFIWND LLSLETGSLKLANGRVIEKTLYNRRTRQDEPALFVALTFERREVLDS SNIKPMNLIGIDRGENIPAVIALTDPEGCPLSRFKDSLGNPTHILRI GESYKEKQRTIQAKKEVEQRRAGGYSRKYASKAKNLADDMVRNTARD LLYYAVTQDAMLIFENLSRGFGRQGKRTFMAERQYTRMEDWLTAKLA YEGLSKTYLSKTLAQYTSKTCSNCGFTITSADYDRVLEKLKKTATGW MTTINGKELKVEGQITYYNRYKRQNVVKDLSVELDRLSEESVNNDIS SWTKGRSGEALSLLKKRFSHRPVQEKFVCLNCGFETHADEQAALNIA RSWLFLRSQEYKKYQTNKTTGNTDKRAFVETWQSFYRKKLKEVWKPA VTSPKKKRKV (SEQ ID NO: 240) |
| CasX 395 | (SEQ ID NO: 241) | MAPKKKRKVSRQEIKRINKIRRRLVKDSNTKKAGKTGPMKTLLVRVM TPDLRERLENLRKKPENIPQPISNTSRANLNKLLTDYTEMKKAILHV YWEEFQKDPVGLMSRVAQPAPKNIDQRKLIPVKDGNERLTSSGFACS QCCQPLYVYKLEQVNDKGKPHTNYFGRCNVSEHERLILLSPHKPEAN DELVTYSLGKFGQRALDFYSIHVTKESTHPVKPLAQIAGNRYASGPV GKALSDACMGTIASFLSKYQDIIIEHQKVVKGNQKRLESLRELAGKE NLEYPSVTLPPQPHTKEGVDAYNEVIARVRMWVNLNLWQKLKLSRDD AKPLLRLKGFPSFPLVERQANEVDWWDMVCNVKKLINEKKEDGKVFW QNLAGYKRQEALRPYLSSEEDRKKGKKFARYQFGDLLLHLEKKHGED WGKVYDEAWERIDKKVEGLSKHIKLEEERRSEDAQSKAALTDWLRAK ASFVIEGLKEADKDEFCRCELKLQKWYGDLRGKPFAIEAENSILDIS GFSKQYNCAFIWQKDGVKKLNLYLIINYFKGGKLRFKKIKPEAFEAN RFYTVINKKSGEIVPMEVNFNFDDPNLIILPLAFGKRQGREFIWNDL LSLETGSLKLANGRVIEKTLYNRRTRQDEPALFVALTFERREVLDSS NIKPMNLIGIDRGENIPAVIALTDPEGCPLSRFKDSLGNPTHILRIG ESYKEKQRTIQAKKEVEQRRAGGYSRKYASKAKNLADDMVRNTARDL LYYAVTQDAMLIFENLSRGFGRQGKRTFMAERQYTRMEDWLTAKLAY EGLSKTYLSKTLAQYTSKTCSNCGFTITSADYDRVLEKLKKTATGWM TTINGKELKVEGQITYYNRYKRQNVVKDLSVELDRLSEESVNNDISS WTKGRSGEALSLLKKRFSHRPVQEKFVCLNCGFETHADEQAALNIAR SWLFLRSQEYKKYQTNKTTGNTDKRAFVETWQSFYRKKLKEVWKPAV TSPKKKRKVTSPKKKRKV (SEQ ID NO: 242) |

TABLE 10-continued Sequences of CasX 395 and 485-491

| Construct | DNA Sequence | Amino Acid Sequence |
| --- | --- | --- |
| CasX 485 | (SEQ ID NO: 243) | MAPKKKRKVSRQEIKRINKIRRRLVKDSNTKKAGKTGPMKTLLVRVM TPDLRERLENLRKKPENIPQPISNTSRANLNKLLTDYTEMKKAILHV YWEEFQKDPVGLMSRVAQPAPKNIDQRKLIPVKDGNERLTSSGFACS QCCQPLYVYKLEQVNDKGKPHTNYFGRCNVSEHERLILLSPHKPEAN DELVTYSLGKFGQRALDFYSIHVTKESTHPVKPLAQIAGNRYASGPV GKALSDACMGTIASFLSKYQDIIIEHQKVVKGNQKRLESLRELAGKE NLEYPSVTLPPQPHTKEGVDAYNEVIARVRMWVNLNLWQKLKLSRDD AKPLLRLKGFPSFPLVERQANEVDWWDMVCNVKKLINEKKEDGKVFW QNLAGYKRQEALRPYLSSEEDRKKGKKFARYQLGDLLLHLEKKHGED WGKVYDEAWERIDKKVEGLSKHIKLEEERRSEDAQSKAALTDWLRAK ASFVIEGLKEADKDEFCRCELKLQKWYGDLRGKPFAIEAENSILDIS GFSKQYNCAFIWQKDGVKKLNLYLIINYFKGGKLRFKKIKPEAFEAN RFYTVINKKSGEIVPMEVNFNFDDPNLIILPLAFGKRQGREFIWNDL LSLETGSLKLANGRVIEKTLYNRRTRQDEPALFVALTFERREVLDSS NIKPMNLIGVDRGENIPAVIALTDPEGCPLSRFKDSLGNPTHILRIG ESYKEKQRTIQAKKEVEQRRAGGYSRKYASKAKNLADDMVRNTARDL LYYAVTQDAMLIFENLSRGFGRQGKRTFMAERQYTRMEDWLTAKLAY EGLSKTYLSKTLAQYTSKTCSNCGFTITSADYDRVLEKLKKTATGWM TTINGKELKVEGQITYYNRRKRQNVVKDLSVELDRLSEESVNNDISS WTKGRSGEALSLLKKRFSHRPVQEKFVCLNCGFETHADEQAALNIAR SWLFLRSQEYKKYQTNKTTGNTDKRAFVETWQSFYRKKLKEVWKPAV TSPKKKRKV (SEQ ID NO: 244) |
| CasX 486 | (SEQ ID NO: 245) | MAPKKKRKVSRQEIKRINKIRRRLVKDSNTKKAGKTGPMKTLLVRVM TPDLRERLENLRKKPENIPQPISNTSRANLNKLLTDYTEMKKAILHV YWEEFQKDPVGLMSRVAQPAPKNIDQRKLIPVKDGNERLTSSGFACS QCCQPLYVYKLEQVNDKGKPHTNYFGRCNVSEHERLILLSPHKPEAN DELVTYSLGKFGQRALDFYSIHVTKESTHPVKPLAQIAGNRYASGPV GKALSDACMGTIASFLSKYQDIIIEHQKVVKGNQKRLESLRELAGKE NLEYPSVTLPPQPHTKEGVDAYNEVIARVRMWVNLNLWQKLKLSRDD AKPLLRLKGFPSFPLVERQANEVDWWDMVCNVKKLINEKKEDGKVFW QNLAGYKRQEALRPYLSSEEDRKKGKKFARYQLGDLLHLEKKHGED WGKVYDEAWERIDKKVEGLSKHIKLEEERRSEDAQSKAALTDWLRAK ASFVIEGLKEADKDEFCRCELKLQKWYGDLRGKPFAIEAENSILDIS GFSKQYNCAFIWQKDGVKKLNLYLIINYFKGGKLRFKKIKPEAFEAN RFYTVINKKSGEIVPMEVNFNFDDPNLIILPLAFGKRQGREFIWNDL LSLETGSLKLANGRVIEKTLYNRRTRQDEPALFVALTFERREVLDSS NIKPMNLIGVDRGENIPAVIALTDPEGCPLSRFKDSLGNPTHILRIG ESYKEKQRTIQAKKEVEQRRAGGYSRKYASKAKNLADDMVRNTARDL LYYAVTQDAMLIFENLSRGFGRQGKRTFMAERQYTRMEDWLTAKLAY EGLSKTYLSKTLAQYTSKTCSNCGFTITSADYDRVLEKLKKTATGWM TTINGKELKVEGQITYYNRRKRQNVVKDLSVELDRLSEESVNNDISS WTKGRSGEALSLLKKRFSHRPVQEKFVCLNCGFETHADEQAALNIAR SWLFLRSQEYKKYQTNKTTGNTDKRAFVETWQSFYRKKLKEVWKPAV TSPKKKRKV (SEQ ID NO: 246) |
| CasX 487 | (SEQ ID NO: 247) | MAPKKKRKVSRQEIKRINKIRRRLVKDSNTKKAGKTGPMKTLLVRVM TPDLRERLENLRKKPENIPQPISNTSRANLNKLLTDYTEMKKAILHV YWEEFQKDPVGLMSRVAQPAPKNIDQRKLIPVKDGNERLTSSGFACS QCCQPLYVYKLEQVNDKGKPHTNYFGRCNVSEHERLILLSPHKPEAN DELVTYSLGKFGQRALDFYSIHVTKESTHPVKPLAQIAGNRYASGPV GKALSDACMGTIASFLSKYQDIIIEHQKVVKGNQKRLESLRELAGKE NLEYPSVTLPPQPHTKEGVDAYNEVIARVRMWVNLNLWQKLKLSRDD AKPLLRLKGFPSFPLVERQANEVDWWDMVCNVKKLINEKKEDGKVFW QNLAGYKRQEALRPYLSSEEDRKKGKKFARYQLGDLLLHLEKKHGED WGKVYDEAWERIDKKVEGLSKHIKLEEERRSEDAQSKAALTDWLRAK ASFVIEGLKEADKDEFCRCELKLQKWYGDLRGKPFAIEAENSILDIS GFSKQYNCAFIWQKDGVKKLNLYLIINYFKGGKLRFKKIKPEAFEAN RFYTVINKKSGEIVPMEVNFNFDDPNLIILPLAFGKRQGREFIWNDL LSLETGSLKLANGRVIEKTLYNRRTRQDEPALFVALTFERREVLDSS NIKPMNLIGVDRGENIPAVIALTDPEGCPLSRFKDSLGNPTHILRIG ESYKEKQRTIQAKKEVEQRRAGGYSRKYASKAKNLADDMVRNTARDL LYYAVTQDAMLIFENLSRGFGRQGKRTFMAERQYTRMEDWLTAKLAY EGLSKTYLSKTLAQYTSKTCSNCGFTITSADYDRVLEKLKKTATGWM TTINGKELKVEGQITYYNRYKRQNVVKDLSVELDRLSEESVNNDISS WTKGRSGEALSLLKKRFSHRPVQEKFVCLNCGFETHADEQAALNIAR SWLFLRSQEYKKYQTNKTTGNTDKRAFVETWQSFYRKKLKEVWKPAV TSPKKKRKV (SEQ ID NO: 248) |
| CasX 488 | (SEQ ID NO: 249) | MAPKKKRKVSRQEIKRINKIRRRLVKDSNTKKAGKTGPMKTLLVRVM TPDLRERLENLRKKPENIPQPISNTSRANLNKLLTDYTEMKKAILHV YWEEFQKDPVGLMSRVAQPASKKIDQNKLKPEMDEKGNLTTAGFACS QCGQPLFVYKLEQVSEKGKAYTNYFGRCNVAEHEKLILLAQLKPEKD SDEAVTYSLGKFGQRALDFYSIHVTKESTHPVKPLAQIAGNRYASGP VGKALSDACMGTIASFLSKYQDIIIEHQKVVKGNQKRLESLRELAGK ENLEYPSVTLPPQPHTKEGVDAYNEVIARVRMWVNLNLWQKLKLSRD |

TABLE 10-continued

Sequences of CasX 395 and 485-491

| Construct | DNA Sequence | Amino Acid Sequence |
|---|---|---|
| | | DAKPLLRLKGFPSFPLVERQANEVDWWDMVCNVKKLINEKKEDGKVF<br>WQNLAGYKRQEALRPYLSSEEDRKKGKKFARYQFGDLLLHLEKKHGE<br>DWGKVYDEAWERIDKKVEGLSKHIKLEEERRSEDAQSKAALTDWLRA<br>KASFVIEGLKEADKDEFCRCELKLQKWYGDLRGKPFAIEAENSILDI<br>SGFSKQYNCAFIWQKDGVKKLNLYLIINYFKGGKLRFKKIKPEAFEA<br>NRFYTVINKKSGEIVPMEVNFNFDDPNLIILPLAFGKRQGREFIWND<br>LLSLETGSLKLANGRVIEKTLYNRRTRQDEPALFVALTFERREVLDS<br>SNIKPMNLIGIDRGENIPAVIALTDPEGCPLSRFKDSLGNPTHILRI<br>GESYKEKQRTIQAKKEVEQRRAGGYSRKYASKAKNLADDMVRNTARD<br>LLYYAVTQDAMLIFENLSRGFGRQGKRTFMAERQYTRMEDWLTAKLA<br>YEGLSKTYLSKTLAQYTSKTCSNCGFTITSADYDRVLEKLKKTATGW<br>MTTINGKELKVEGQITYYNRYKRQNVVKDLSVELDRLSEESVNNDIS<br>SWTKGRSGEALSLLKKRFSHRPVQEKFVCLNCGFETHADEQAALNIA<br>RSWLFLRSQEYKKYQTNKTTGNTDKRAFVETWQSFYRKKLKEVWKPA<br>VTSPKKKRKV (SEQ ID NO: 250) |
| CasX 489 | (SEQ ID NO: 251) | MAPKKKRKVSRQEIKRINKIRRRLVKDSNTKKAGKTGPMKTLLVRVM<br>TPDLRERLENLRKKPENIPQPISNTSRANLNKLLTDYTEMKKAILHV<br>YWEEFQKDPVGLMSRVAQPASKKIDQNKLKPEMDEKGNLTTAGFACS<br>QCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASGP<br>VGKALSDACMGTIASFLSKYQDIIIEHQKVVKGNQKRLESLRELAGK<br>ENLEYPSVTLPPQPHTKEGVDAYNEVIARVRMWVNLNLWQKLKLSRD<br>DAKPLLRLKGFPSFPLVERQANEVDWWDMVCNVKKLINEKKEDGKVF<br>WQNLAGYKRQEALRPYLSSEEDRKKGKKFARYQLGDLLLHLEKKHGE<br>DWGKVYDEAWERIDKKVEGLSKHIKLEEERRSEDAQSKAALTDWLRA<br>KASFVIEGLKEADKDEFCRCELKLQKWYGDLRGKPFAIEAENSILDI<br>SGFSKQYNCAFIWQKDGVKKLNLYLIINYFKGGKLRFKKIKPEAFEA<br>NRFYTVINKKSGEIVPMEVNFNFDDPNLIILPLAFGKRQGREFIWND<br>LLSLETGSLKLANGRVIEKTLYNRRTRQDEPALFVALTFERREVLDS<br>SNIKPMNLIGVDRGENIPAVIALTDPEGCPLSRFKDSLGNPTHILRI<br>GESYKEKQRTIQAKKEVEQRRAGGYSRKYASKAKNLADDMVRNTARD<br>LLYYAVTQDAMLIFENLSRGFGRQGKRTFMAERQYTRMEDWLTAKLA<br>YEGLSKTYLSKTLAQYTSKTCSNCGFTITSADYDRVLEKLKKTATGW<br>MTTINGKELKVEGQITYYNRRKRQNVVKDLSVELDRLSEESVNNDIS<br>SWTKGRSGEALSLLKKRFSHRPVQEKFVCLNCGFETHADEQAALNIA<br>RSWLFLRSQEYKKYQTNKTTGNTDKRAFVETWQSFYRKKLKEVWKPA<br>VTSPKKKRKV (SEQ ID NO: 252) |
| CasX 490 | (SEQ ID NO: 253) | MAPKKKRKVSRQEIKRINKIRRRLVKDSNTKKAGKTGPMKTLLVRVM<br>TPDLRERLENLRKKPENIPQPISNTSRANLNKLLTDYTEMKKAILHV<br>YWEEFQKDPVGLMSRVAQPASKKIDQNKLKPEMDEKGNLTTAGFACS<br>QCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASGP<br>VGKALSDACMGTIASFLSKYQDIIIEHQKVVKGNQKRLESLRELAGK<br>ENLEYPSVTLPPQPHTKEGVDAYNEVIARVRMWVNLNLWQKLKLSRD<br>DAKPLLRLKGFPSFPLVERQANEVDWWDMVCNVKKLINEKKEDGKVF<br>WQNLAGYKRQEALRPYLSSEEDRKKGKKFARYQLGDLLKHLEKKHGE<br>DWGKVYDEAWERIDKKVEGLSKHIKLEEERRSEDAQSKAALTDWLRA<br>KASFVIEGLKEADKDEFCRCELKLQKWYGDLRGKPFAIEAENSILDI<br>SGFSKQYNCAFIWQKDGVKKLNLYLIINYFKGGKLRFKKIKPEAFEA<br>NRFYTVINKKSGEIVPMEVNFNFDDPNLIILPLAFGKRQGREFIWND<br>LLSLETGSLKLANGRVIEKTLYNRRTRQDEPALFVALTFERREVLDS<br>SNIKPMNLIGVDRGENIPAVIALTDPEGCPLSRFKDSLGNPTHILRI<br>GESYKEKQRTIQAKKEVEQRRAGGYSRKYASKAKNLADDMVRNTARD<br>LLYYAVTQDAMLIFENLSRGFGRQGKRTFMAERQYTRMEDWLTAKLA<br>YEGLSKTYLSKTLAQYTSKTCSNCGFTITSADYDRVLEKLKKTATGW<br>MTTINGKELKVEGQITYYNRRKRQNVVKDLSVELDRLSEESVNNDIS<br>SWTKGRSGEALSLLKKRFSHRPVQEKFVCLNCGFETHADEQAALNIA<br>RSWLFLRSQEYKKYQTNKTTGNTDKRAFVETWQSFYRKKLKEVWKPA<br>VTSPKKKRKV (SEQ ID NO: 254) |
| CasX 491 | (SEQ ID NO: 255) | MAPKKKRKVSRQEIKRINKIRRRLVKDSNTKKAGKTGPMKTLLVRVM<br>TPDLRERLENLRKKPENIPQPISNTSRANLNKLLTDYTEMKKAILHV<br>YWEEFQKDPVGLMSRVAQPASKKIDQNKLKPEMDEKGNLTTAGFACS<br>QCGQPLFVYKLEQVSEKGKAYTNYFGRCNVAEHEKLILLAQLKPEKD<br>SDEAVTYSLGKFGQRALDFYSIHVTKESTHPVKPLAQIAGNRYASGP<br>VGKALSDACMGTIASFLSKYQDIIIEHQKVVKGNQKRLESLRELAGK<br>ENLEYPSVTLPPQPHTKEGVDAYNEVIARVRMWVNLNLWQKLKLSRD<br>DAKPLLRLKGFPSFPLVERQANEVDWWDMVCNVKKLINEKKEDGKVF<br>WQNLAGYKRQEALRPYLSSEEDRKKGKKFARYQLGDLLLHLEKKHGE<br>DWGKVYDEAWERIDKKVEGLSKHIKLEEERRSEDAQSKAALTDWLRA<br>KASFVIEGLKEADKDEFCRCELKLQKWYGDLRGKPFAIEAENSILDI<br>SGFSKQYNCAFIWQKDGVKKLNLYLIINYFKGGKLRFKKIKPEAFEA<br>NRFYTVINKKSGEIVPMEVNFNFDDPNLIILPLAFGKRQGREFIWND<br>LLSLETGSLKLANGRVIEKTLYNRRTRQDEPALFVALTFERREVLDS |

TABLE 10-continued

Sequences of CasX 395 and 485-491

| Construct | DNA Sequence | Amino Acid Sequence |
|---|---|---|
| | | SNIKPMNLIGVDRGENIPAVIALTDPEGCPLSRFKDSLGNPTHILRI GESYKEKQRTIQAKKEVEQRRAGGYSRKYASKAKNLADDMVRNTARD LLYYAVTQDAMLIFENLSRGFGRQGKRTFMAERQYTRMEDWLTAKLA YEGLSKTYLSKTLAQYTSKTCSNCGFTITSADYDRVLEKLKKTATGW MTTINGKELKVEGQITYYNRYKRQNVVKDLSVELDRLSEESVNNDIS SWTKGRSGEALSLLKKRFSHRPVQEKFVCLNCGFETHADEQAALNIA RSWLFLRSQEYKKYQTNKTTGNTDKRAFVETWQSFYRKKLKEVWKPA VTSPKKKRKV (SEQ ID NO: 256) |
| CasX 494 | (SEQ ID NO: 257) | MAPKKKRKVSRQEIKRINKIRRRLVKDSNTKKAGKTGPMKTLLVRVM TPDLRERLENLRKKPENIPQPISNTSRANLNKLLTDYTEMKKAILHV YWEEFQKDPVGLMSRVAQPASKKIDQNKLKPEMDEKGNLTTAGFACS QCGQPLFVYKLEQVSEKGKAYTNYFGRCNVAEHEKLILLAQLKPEKD SDEAVTYSLGKFGQRALDFYSIHVTRESNHPVKPLEQIGGNSCASGP VGKALSDACMGAVASFLTKYQDIILEHQKVIKKNEKRLANLKDIASA NGLAFPKITLPPQPHTKEGIEAYNNVVAQIVIWVNLNLWQKLKIGRD EAKPLQRLKGFPSFPLVERQANEVDWWDMVCNVKKLINEKKEDGKVF WQNLAGYKRQEALRPYLSSEEDRKKGKKFARYQLGDLLLHLEKKHGE DWGKVYDEAWERIDKKVEGLSKHIKLEEERRSEDAQSKAALTDWLRA KASFVIEGLKEADKDEFCRCELKLQKWYGDLRGKPFAIEAENSILDI SGFSKQYNCAFIWQKDGVKKLNLYLIINYFKGGKLRFKKIKPEAFEA NRFYTVINKKSGEIVPMEVNFNFDDPNLIILPLAFGKRQGREFIWND LLSLETGSLKLANGRVIEKTLYNRRTRQDEPALFVALTFERREVLDS SNIKPMNLIGVDRGENIPAVIALTDPEGCPLSRFKDSLGNPTHILRI GESYKEKQRTIQAKKEVEQRRAGGYSRKYASKAKNLADDMVRNTARD LLYYAVTQDAMLIFENLSRGFGRQGKRTFMAERQYTRMEDWLTAKLA YEGLSKTYLSKTLAQYTSKTCSNCGFTITSADYDRVLEKLKKTATGW MTTINGKELKVEGQITYYNRYKRQNVVKDLSVELDRLSEESVNNDIS SWTKGRSGEALSLLKKRFSHRPVQEKFVCLNCGFETHADEQAALNIA RSWLFLRSQEYKKYQTNKTTGNTDKRAFVETWQSFYRKKLKEVWKPA VTSPKKKRKV (SEQ ID NO: 258) |

Example 6: Generation of RNA Guides

For the generation of RNA single guides and spacers, templates for in vitro transcription were generated by performing PCR with Q5 polymerase (NEB M0491) according to the recommended protocol, with template oligos for each backbone and amplification primers with the T7 promoter and the spacer sequence. The DNA primer sequences for the T7 promoter, guide and spacer for guides and spacers are presented in Table 11, below. The template oligos, labeled "backbone fwd" and "backbone rev" for each scaffold, were included at a final concentration of 20 nM each, and the amplification primers (T7 promoter and the unique spacer primer) were included at a final concentration of 1 uM each. The sg2, sg32, sg64, and sg174 guides correspond to SEQ ID NOS: 5, 2104, 2106, and 2238, respectively, with the exception that sg2, sg32, and sg64 were modified with an additional 5' G to increase transcription efficiency (compare sequences in Table 11 to Table 2). The 7.37 spacer targets beta2-microglobulin (B2M). Following PCR amplification, templates were cleaned and isolated by phenol-chloroform-isoamyl alcohol extraction followed by ethanol precipitation.

In vitro transcriptions were carried out in buffer containing 50 mM Tris pH 8.0, 30 mM $MgCl_2$, 0.01% Triton X-100, 2 mM spermidine, 20 mM DTT, 5 mM NTPs, 0.5 μM template, and 100 μg/mL T7 RNA polymerase. Reactions were incubated at 37° C. overnight. 20 units of DNase I (Promega #M6101)) were added per 1 mL of transcription volume and incubated for one hour. RNA products were purified via denaturing PAGE, ethanol precipitated, and resuspended in 1x phosphate buffered saline. To fold the sgRNAs, samples were heated to 70° C. for 5 min and then cooled to room temperature. The reactions were supplemented to 1 mM final $MgCl_2$ concentration, heated to 50° C. for 5 min and then cooled to room temperature. Final RNA guide products were stored at −80° C.

TABLE 11

Sequences for generation of guide RNA

| Primer | Primer sequence | RNA product |
|---|---|---|
| T7 promoter primer | GAAATTAATACGACTCACTATA (SEQ ID NO: 259) | Used for all |
| sg2 backbone fwd | GAAATTAATACGACTCACTATAGGTACTGGCGCTTT TATCTCATTACTTTGAGAGCCATCACCAGCGACTAT GTCGTATGGGTAAAG (SEQ ID NO: 260) | GGUACUGGCGCUUUUAUCUCAUUACUUUGA GAGCCAUCACCAGCGACUAUGUCGUAUGGG UAAAGCGCUUAUUUAUCGGAGAGAAAUCCG |
| sg2 backbone rev | CTTTGATGCTTCTTATTTATCGGATTTCTCTCCGAT AAATAAGCGCTTTACCCATACGACATAGTCGCTGGT GATGGC (SEQ ID NO: 261) | AUAAAUAAGAAGCAUCAAAGGGCCGAGAUG UCUCGCUCCG (SEQ ID NO: 272) |
| sg2.7.37 spacer primer | CGGAGCGAGACATCTCGGCCCTTTGATGCTTCTTAT TTATCGGATTTCTCTCCG (SEQ ID NO: 262) | |

TABLE 11-continued

Sequences for generation of guide RNA

| Primer | Primer sequence | RNA product |
|---|---|---|
| sg32 backbone fwd | GAAATTAATACGACTCACTATAGGTACTGGCGCTTT TATCTCATTACTTTGAGAGCCATCACCAGCGACTAT GTCGTATGGGTAAAGCGC (SEQ ID NO: 263) | GGUACUGGCGCUUUUAUCUCAUUACUUUGA GAGCCAUCACCAGCGACUAUGUCGUAUGGG UAAAGCGCCCUCUUCGGAGGGAAGCAUCAA |
| sg32 backbone rev | CTTTGATGCTTCCCTCCGAAGAGGGCGCTTTACCCA TACGACATAG (SEQ ID NO: 264) | AGGGCCGAGAUGUCUCG (SEQ ID NO: 273) |
| sg32.7.37 spacer primer | CGGAGCGAGACATCTCGGCCCTTTGATGCTTCCCTC CGAAGAG (SEQ ID NO: 265) | |
| sg64 backbone fwd | GAAATTAATACGACTCACTATAGGTACTGGCGCTT TATCTCATTACTTTGAGAGCCATCACCAGCGACTAT GTCGTATGGGTAAAGCGC (SEQ ID NO: 266) | GGUACUGGCGCCUUUAUCUCAUUACUUUGA GAGCCAUCACCAGCGACUAUGUCGUAUGGG UAAAGCGCUUACGGACUUCGGUCCGUAAGA |
| sg64 backbone rev | CTTTGATGCTTCTTACGGACCGAAGTCCGTAAGCGC TTTACCCATACGACATAG (SEQ ID NO: 267) | AGCAUCAAAGGGCCGAGAUGUCUCGCUCCG (SEQ ID NO: 274) |
| sg64.7.37 spacer primer | CGGAGCGAGACATCTCGGCCCTTTGATGCTTCTTAC GGACCGAAG (SEQ ID NO: 268) | |
| sg174 backbone fwd | GAAATTAATACGACTCACTATAACTGGCGCTTTTAT CTGATTACTTTGAGAGCCATCACCAGCGACTATGTC GTAGTGGGTAAAGCT (SEQ ID NO: 269) | ACUGGCGCUUUUAUCUgAUUACUUUGAGAG CCAUCACCAGCGACUAUGUCGUAgUGGGUA AAGCUCCCUCUUCGGAGGGAGCAUCAAAGG |
| sg174 backbone rev | CTTTGATGCTCCCTCCGAAGAGGGAGCTTTACCCAC TACGACATAGTCGC (SEQ ID NO: 270) | GCCGAGAUGUCUCGCUCCG (SEQ ID NO: 275) |
| sg174.7.37 spacer primer | CGGAGCGAGACATCTCGGCCCTTTGATGCTCCCTCC (SEQ ID NO: 271) | |

Example 7: RNP Assembly

Purified wild-type and RNP of CasX and single guide RNA (sgRNA) were either prepared immediately before experiments or prepared and snap-frozen in liquid nitrogen and stored at −80° C. for later use. To prepare the RNP complexes, the CasX protein was incubated with sgRNA at 1:1.2 molar ratio. Briefly, sgRNA was added to Buffer #1 (25 mM NaPi, 150 mM NaCl, 200 mM trehalose, 1 mM MgCl2), then the CasX was added to the sgRNA solution, slowly with swirling, and incubated at 37° C. for 10 min to form RNP complexes. RNP complexes were filtered before use through a 0.22 µm Costar 8160 filters that were pre-wet with 200 µl Buffer #1. If needed, the RNP sample was concentrated with a 0.5 ml Ultra 100-$K_d$ cutoff filter, (Millipore part #UFC510096), until the desired volume was obtained. Formation of competent RNP was assessed as described in Example 14.

Example 8: Assessing Binding Affinity to the Guide RNA

Purified wild-type and improved CasX will be incubated with synthetic single-guide RNA containing a 3' Cy7.5 moiety in low-salt buffer containing magnesium chloride as well as heparin to prevent non-specific binding and aggregation. The sgRNA will be maintained at a concentration of 10 pM, while the protein will be titrated from 1 pM to 100 µM in separate binding reactions. After allowing the reaction to come to equilibrium, the samples will be run through a vacuum manifold filter-binding assay with a nitrocellulose membrane and a positively charged nylon membrane, which bind protein and nucleic acid, respectively. The membranes will be imaged to identify guide RNA, and the fraction of bound vs unbound RNA will be determined by the amount of fluorescence on the nitrocellulose vs nylon membrane for each protein concentration to calculate the dissociation constant of the protein-sgRNA complex. The experiment will also be carried out with improved variants of the sgRNA to determine if these mutations also affect the affinity of the guide for the wild-type and mutant proteins. We will also perform electromobility shift assays to qualitatively compare to the filter-binding assay and confirm that soluble binding, rather than aggregation, is the primary contributor to protein-RNA association.

Example 9: Assessing Binding Affinity to the Target DNA

Purified wild-type and improved CasX will be complexed with single-guide RNA bearing a targeting sequence complementary to the target nucleic acid. The RNP complex will be incubated with double-stranded target DNA containing a PAM and the appropriate target nucleic acid sequence with a 5' Cy7.5 label on the target strand in low-salt buffer containing magnesium chloride as well as heparin to prevent non-specific binding and aggregation. The target DNA will be maintained at a concentration of 1 nM, while the RNP will be titrated from 1 pM to 100 µM in separate binding reactions. After allowing the reaction to come to equilibrium, the samples will be run on a native 5% polyacrylamide gel to separate bound and unbound target DNA. The gel will be imaged to identify mobility shifts of the target DNA, and the fraction of bound vs unbound DNA will be calculated for each protein concentration to determine the dissociation constant of the RNP-target DNA ternary complex.

Example 10: Editing of Gene Targets PCSK9, PMP22, TRAC, SOD1, B2M and HTT

The purpose of this study was to evaluate the ability of the CasX variant 119 and gNA variant 174 to edit nucleic acid sequences in six gene targets.
Materials and Methods
Spacers for all targets except B2M and SOD1 were designed in an unbiased manner based on PAM requirements (TTC or CTC) to target a desired locus of interest. Spacers targeting B2M and SOD1 had been previously identified within targeted exons via lentiviral spacer screens carried out for these genes. Designed spacers for the other targets were ordered from Integrated DNA Technologies (IDT) as single-stranded DNA (ssDNA) oligo pairs. ssDNA spacer pairs were annealed together and cloned via Golden Gate cloning into a base mammalian-expression plasmid construct that contains the following components: codon optimized Cas X 119 protein+NLS under an EF1A promoter, guide scaffold 174 under a U6 promoter, carbenicillin and puromycin resistance genes. Assembled products were transformed into chemically-competent E. coli, plated on Lb-Agar plates (LB: Teknova Cat #L9315, Agar: Quartzy Cat #214510) containing carbenicillin and incubated at 37° C. Individual colonies were picked and miniprepped using Qiagen Qiaprep® spin Miniprep Kit (Qiagen Cat #27104) following the manufacturer's protocol. The resulting plasmids were sequenced through the guide scaffold region via Sanger sequencing (Quintara Biosciences) to ensure correct ligation.

HEK 293T cells were grown in Dulbecco's Modified Eagle Medium (DMEM; Corning Cellgro, #10-013-CV) supplemented with 10% fetal bovine serum (FBS; Seradigm, #1500-500), 100 Units/ml penicillin and 100 mg/ml streptomycin (100x-Pen-Strep; GIBCO #15140-122), sodium pyruvate (100x, Thermofisher #11360070), non-essential amino acids (100× Thermofisher #11140050), HEPES buffer (100× Thermofisher #15630080), and 2-mercaptoethanol (1000× Thermofisher #21985023). Cells were passed every 3-5 days using Tryp1E and maintained in an incubator at 37° C. and 5% CO2.

On day 0, HEK293T cells were seeded in 96-well, flat-bottom plates at 30 k cells/well. On day 1, cells were transfected with 100 ng plasmid DNA using Lipofectamine™ 3000 according to the manufacturer's protocol. On day 2, cells were switched to FB medium containing puromycin. On day 3, this media was replaced with fresh FB medium containing puromycin. The protocol after this point diverged depending on the gene of interest. Day 4 for PCSK9, PMP22, and TRAC: cells were verified to have completed selection and switched to FB medium without puromycin. Day 4 for B2M, SOD1, and HTT: cells were verified to have completed selection and passed 1:3 using Tryp1E into new plates containing FB medium without puromycin. Day 7 for PCSK9, PMP22, and TRAC: cells were lifted from the plate, washed in dPBS, counted, and resuspended in Quick Extract (Lucigen, QE09050) at 10,000 cells/μl. Genomic DNA was extracted according to the manufacturer's protocol and stored at −20° C. Day 7 for B2M, SOD1, and HTT: cells were lifted from the plate, washed in dPBS, and genomic DNA was extracted with the Quick-DNA Miniprep Plus Kit (Zymo, D4068) according to the manufacturer's protocol and stored at −20° C.

NGS Analysis: Editing in cells from each experimental sample was assayed using next generation sequencing (NGS) analysis. All PCRs were carried out using the KAPA HiFi HotStart ReadyMix PCR Kit (KR0370). The template for genomic DNA sample PCR was 5 μl of genomic DNA in QE at 10 k cells/4 for PCSK9, PMP22, and TRAC. The template for genomic DNA sample PCR was 400 ng of genomic DNA in water for B2M, SOD1, and HTT. Primers were designed specific to the target genomic location of interest to form a target amplicon. These primers contain additional sequence at the 5' ends to introduce Illumina read and 2 sequences. Further, they contain a 7 nt randomer sequence that functions as a unique molecular identifier (UMI). Quality and quantification of the amplicon was assessed using a Fragment Analyzer DNA analyzer kit (Agilent, dsDNA 35-1500 bp). Amplicons were sequenced on the Illumina Miseq™ according to the manufacturer's instructions. Resultant sequencing reads were aligned to a reference sequence and analyzed for indels. Samples with editing that did not align to the estimated cut location or with unexpected alleles in the spacer region were discarded.

Results

Figure 9:
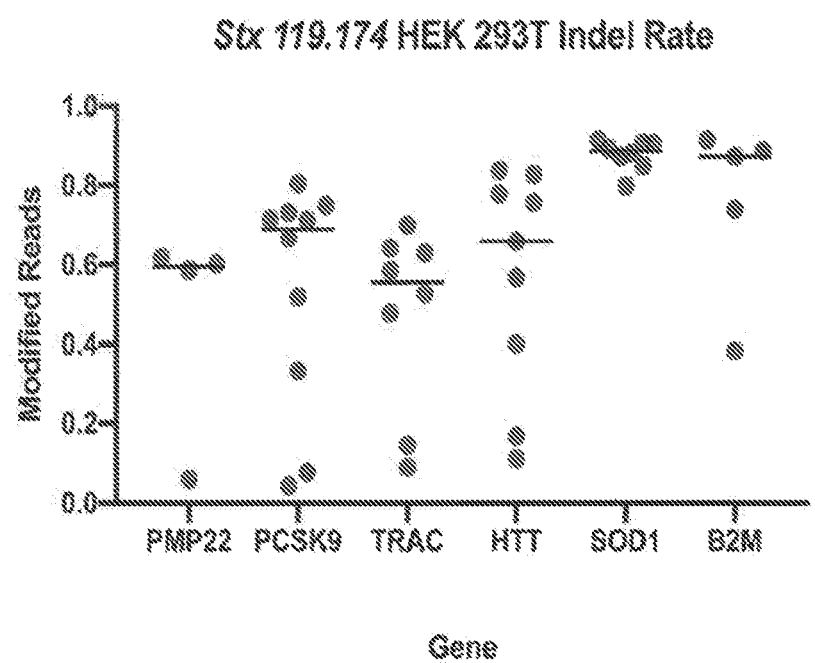
FIG. 9 shows the results of an editing assay of 6 target genes in HEK293T cells, as described in Example 10. Each dot represents results using an individual spacer.
Figure 10:
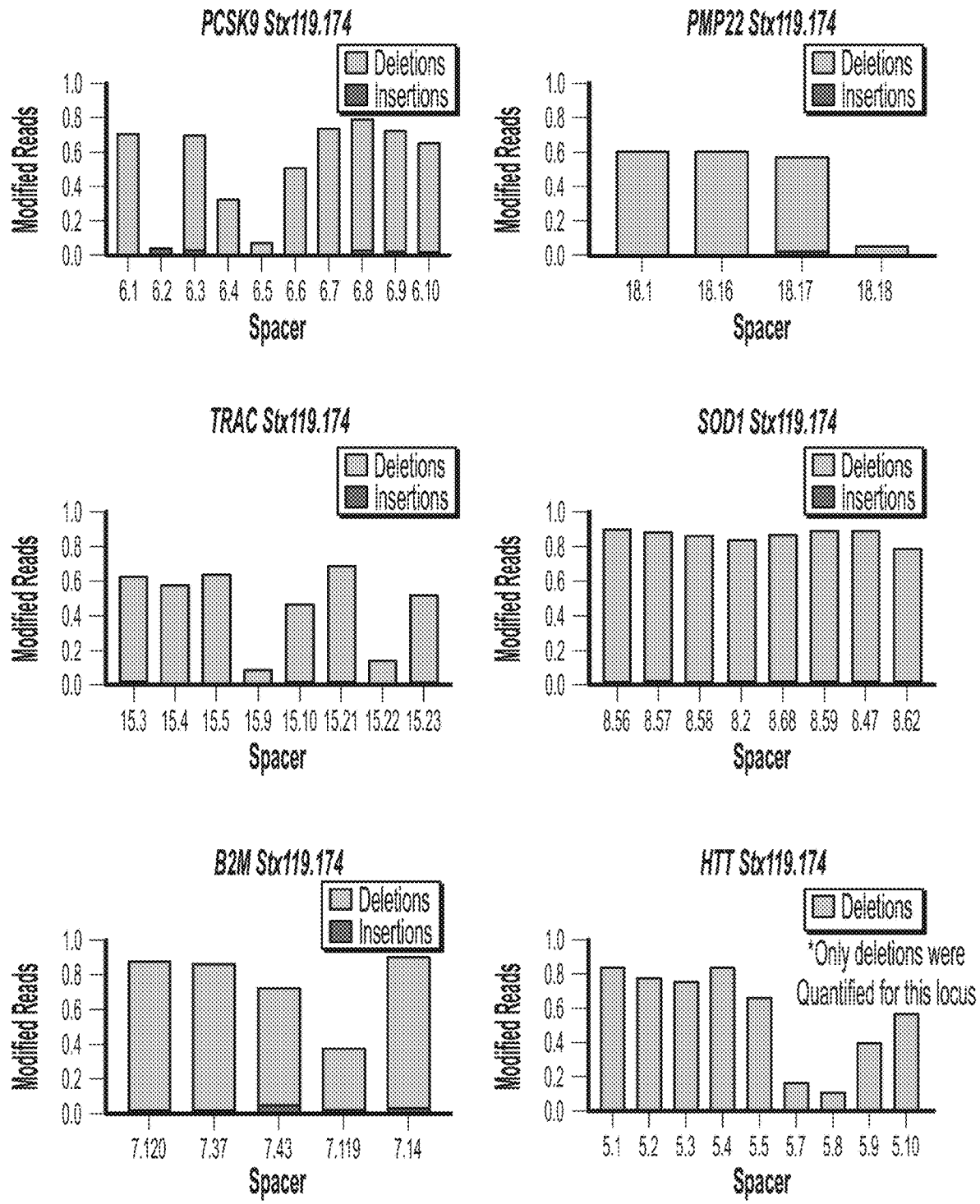
FIG. 10 shows the results of an editing assay of 6 target genes in HEK293T cells, with individual bars representing the results obtained with individual spacers, as described in Example 10.
Figure 11:
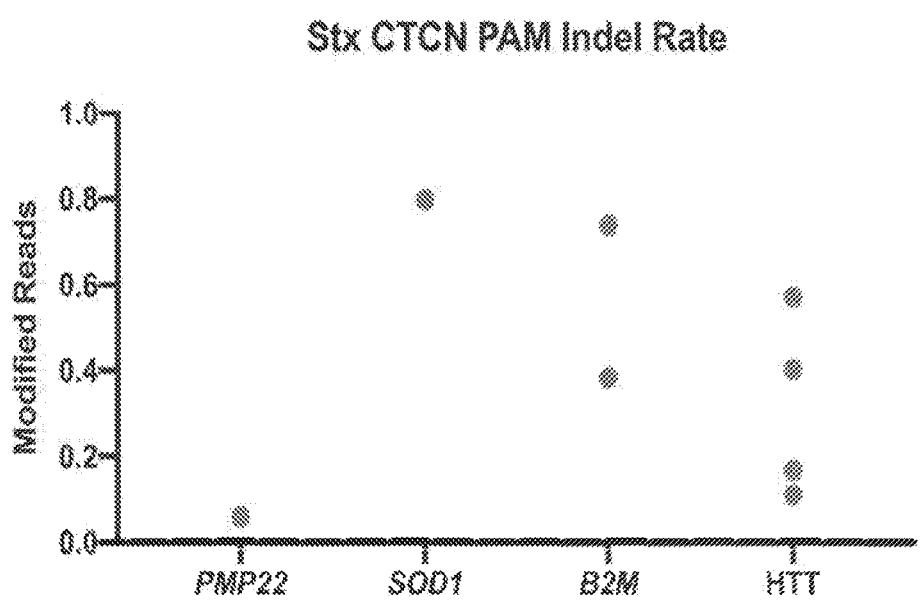
FIG. 11 shows the results of an editing assay of 4 target genes in HEK293T cells, as described in Example 10. Each dot represents results using an individual spacer utilizing a CTC PAM.

In order to validate the editing effected by the CasX:gNA 119.174 at a variety of genetic loci, a clonal plasmid transfection experiment was performed in HEK 293T cells. Multiple spacers (Table 12) were designed and cloned into an expression plasmid encoding the CasX 119 nuclease and guide 174 scaffold. HEK 293T cells were transfected with plasmid DNA, selected with puromycin, and harvested for genomic DNA six days post-transfection. Genomic DNA was analyzed via next generation sequencing (NGS) and aligned to a reference DNA sequence for analysis of insertions or deletions (indels). CasX:gNA 119.174 was able to efficiently generate indels across the 6 target genes, as shown in FIGS. 9 and 10. Indel rates varied between spacers, but median editing rates were consistently at 60% or higher, and in some cases, indel rates as high as 91% were observed. Additionally, spacers with non-canonical CTC PAMs were demonstrated to be able to generate indels with all tested target genes (FIG. 11).

The results demonstrate that the CasX variant 119 and gNA variant 174 can consistently and efficiently generate indels at a wide variety of genetic loci in human cells. The unbiased selection of many of the spacers used in the assays shows the overall effectiveness of the 119.174 RNP molecules to edit genetic loci, while the ability to target to spacers with both a TTC and a CTC PAM demonstrates its increased versatility compared to reference CasX that edit only with the TTC PAM. Table 12 also lists the RNA sequences of the actual spacers; plasmids were created with the corresponding DNA sequences with thymine bases rather than uracil.

TABLE 12

Spacer sequences targeting each genetic locus.

| Gene | Spacer | PAM | Spacer Sequence | Spacer Sequence (RNA) |
|---|---|---|---|---|
| PCSK9 | 6.1 | TTC | GAGGAGGACGGCCTGG CCGA (SEQ ID NO: 276) | GAGGAGGACGGCCUGG CCGA (SEQ ID NO: 320) |
| PCSK9 | 6.2 | TTC | ACCGCTGCGCCAAGGT GCGG (SEQ ID NO: 277) | ACCGCUGCGCCAAGGU GCGG (SEQ ID NO: 321) |
| PCSK9 | 6.4 | TTC | GCCAGGCCGTCCTCCT CGGA (SEQ ID NO: 278) | GCCAGGCCGUCCUCCU CGGA (SEQ ID NO: 322) |
| PCSK9 | 6.5 | TTC | GTGCTCGGGTGCTTCG GCCA (SEQ ID NO: 279) | GUGCUCGGGUGCUUCG GCCA (SEQ ID NO: 323) |
| PCSK9 | 6.3 | TTC | ATGGCCTTCTTCCTGG CTTC (SEQ ID NO: 280) | AUGGCCUUCUUCCUGG CUUC (SEQ ID NO: 324) |
| PCSK9 | 6.6 | TTC | GCACCACCACGTAGGT GCCA (SEQ ID NO: 281) | GCACCACCACGUAGGU GCCA (SEQ ID NO: 325) |
| PCSK9 | 6.7 | TTC | TCCTGGCTTCCTGGTG AAGA (SEQ ID NO: 282) | UCCUGGCUUCCUGGUG AAGA (SEQ ID NO: 326) |
| PCSK9 | 6.8 | TTC | TGGCTTCCTGGTGAAG ATGA (SEQ ID NO: 283) | UGGCUUCCUGGUGAAG AUGA (SEQ ID NO: 327) |

TABLE 12-continued

Spacer sequences targeting each genetic locus.

| Gene | Spacer | PAM | Spacer Sequence | Spacer Sequence (RNA) |
|---|---|---|---|---|
| PCSK9 | 6.9 | TTC | CCAGGAAGCCAGGAAGAAGG (SEQ ID NO: 284) | CCAGGAAGCCAGGAAGAAGG (SEQ ID NO: 328) |
| PCSK9 | 6.10 | TTC | TCCTTGCATGGGGCCAGGAT (SEQ ID NO: 285) | UCCUUGCAUGGGGCCAGGAU (SEQ ID NO: 329) |
| PMP22 | 18.16 | TTC | GGCGGCAAGTTCTGCTCAGC (SEQ ID NO: 286) | GGCGGCAAGUUCUGCUCAGC (SEQ ID NO: 330) |
| PMP22 | 18.17 | TTC | TCTCCACGATCGTCAGCGTG (SEQ ID NO: 287) | UCUCCACGAUCGUCAGCGUG (SEQ ID NO: 331) |
| PMP22 | 18.18 | CTC | ACGATCGTCAGCGTGAGTGC (SEQ ID NO: 288) | ACGAUCGUCAGCGUGAGUGC (SEQ ID NO: 332) |
| PMP22 | 18.1 | TTC | CTCTAGCAATGGATCGTGGG (SEQ ID NO: 289) | CUCUAGCAAUGGAUCGUGGG (SEQ ID NO: 333) |
| TRAC | 15.3 | TTC | CAAACAAATGTGTCACAAAG (SEQ ID NO: 290) | CAAACAAAUGUGUCACAAAG (SEQ ID NO: 334) |
| TRAC | 15.4 | TTC | GATGTGTATATCACAGACAA (SEQ ID NO: 291) | GAUGUGUAUAUCACAGACAA (SEQ ID NO: 335) |
| TRAC | 15.5 | TTC | GGAATAATGCTGTTGTTGAA (SEQ ID NO: 292) | GGAAUAAUGCUGUUGUUGAA (SEQ ID NO: 336) |
| TRAC | 15.9 | TTC | AAATCCAGTGACAAGTCTGT (SEQ ID NO: 293) | AAAUCCAGUGACAAGUCUGU (SEQ ID NO: 337) |
| TRAC | 15.10 | TTC | AGGCCACAGCACTGTTGCTC (SEQ ID NO: 294) | AGGCCACAGCACUGUUGCUC (SEQ ID NO: 338) |
| TRAC | 15.21 | TTC | AGAAGACACCTTCTTCCCCA (SEQ ID NO: 295) | AGAAGACACCUUCUUCCCCA (SEQ ID NO: 339) |
| TRAC | 15.22 | TTC | TCCCCAGCCCAGGTAAGGGC (SEQ ID NO: 296) | UCCCCAGCCCAGGUAAGGGC (SEQ ID NO: 340) |
| TRAC | 15.23 | TTC | CCAGCCCAGGTAAGGGCAGC (SEQ ID NO: 297) | CCAGCCCAGGUAAGGGCAGC (SEQ ID NO: 341) |
| HTT | 5.1 | TTC | AGTCCCTCAAGTCCTTCCAG (SEQ ID NO: 298) | AGUCCCUCAAGUCCUUCCAG (SEQ ID NO: 342) |
| HTT | 5.2 | TTC | AGCAGCAGCAGCAGCAGCAGCA (SEQ ID NO: 299) | AGCAGCAGCAGCAGCAGCA (SEQ ID NO: 343) |
| HTT | 5.3 | TTC | TCAGCCGCCGCCGCAGGCAC (SEQ ID NO: 300) | UCAGCCGCCGCCGCAGGCAC (SEQ ID NO: 344) |
| HTT | 5.4 | TTC | AGGGTCGCCATGGCGGTCTC (SEQ ID NO: 301) | AGGGUCGCCAUGGCGGUCUC (SEQ ID NO: 345) |
| HTT | 5.5 | TTC | TCAGCTTTTCCAGGGTCGCC (SEQ ID NO: 302) | UCAGCUUUUCCAGGGUCGCC (SEQ ID NO: 346) |
| HTT | 5.7 | CTC | GCCGCAGCCGCCCCCGCCGC (SEQ ID NO: 303) | GCCGCAGCCGCCCCCGCCGC (SEQ ID NO: 347) |
| HTT | 5.8 | CTC | GCCACAGCCGGGCCGGTGG (SEQ ID NO: 304) | GCCACAGCCGGGCCGGUGG (SEQ ID NO: 348) |
| HTT | 5.9 | CTC | TCAGCCACAGCCGGGCCGGG (SEQ ID NO: 305) | UCAGCCACAGCCGGGCCGGG (SEQ ID NO: 349) |
| HTT | 5.10 | CTC | CGGTCGGTGCAGCGGCTCCT (SEQ ID NO: 306) | CGGUCGGUGCAGCGGCUCCU (SEQ ID NO: 350) |
| SOD1 | 8.56 | TTC | CCACACCTTCACTGGTCCAT (SEQ ID NO: 307) | CCACACCUUCACUGGUCCAU (SEQ ID NO: 351) |
| SOD1 | 8.57 | TTC | TAAAGGAAAGTAATGGACCA (SEQ ID NO: 308) | UAAAGGAAAGUAAUGGACCA (SEQ ID NO: 352) |
| SOD1 | 8.58 | TTC | CTGGTCCATTACTTTCCTTT (SEQ ID NO: 309) | CUGGUCCAUUACUUUCCUUU (SEQ ID NO: 353) |
| SOD1 | 8.2 | TTC | ATGTTCATGAGTTTGGAGAT (SEQ ID NO: 310) | AUGUUCAUGAGUUUGGAGAU (SEQ ID NO: 354) |
| SOD1 | 8.68 | TTC | TGAGTTTGGAGATAATACAG (SEQ ID NO: 311) | UGAGUUUGGAGAUAAUACAG (SEQ ID NO: 355) |
| SOD1 | 8.59 | TTC | ATAGACACATCGGCCACACC (SEQ ID NO: 312) | AUAGACACAUCGGCCACACC (SEQ ID NO: 356) |
| SOD1 | 8.47 | TTC | TTATTAGGCATGTTGGAGAC (SEQ ID NO: 313) | UUAUUAGGCAUGUUGGAGAC (SEQ ID NO: 357) |
| SOD1 | 8.62 | CTC | CAGGAGACCATTGCATCATT (SEQ ID NO: 314) | CAGGAGACCAUUGCAUCAUU (SEQ ID NO: 358) |
| B2M | 7.120 | TTC | GGCCTGGAGGCTATCCAGCG (SEQ ID NO: 315) | GGCCUGGAGGCUAUCCAGCG (SEQ ID NO: 359) |
| B2M | 7.37 | TTC | GGCCGAGATGTCTCGCTCCG (SEQ ID NO: 316) | GGCCGAGAUGUCUCGCUCCG (SEQ ID NO: 360) |
| B2M | 7.43 | CTC | AGGCCAGAAAGAGAGTAG (SEQ ID NO: 317) | AGGCCAGAAAGAGAGUAG (SEQ ID NO: 361) |
| B2M | 7.119 | CTC | CGCTGGATAGCCTCCAGGCC (SEQ ID NO: 318) | CGCUGGAUAGCCUCCAGGCC (SEQ ID NO: 362) |

Example 11: Assessing Differential PAM Recognition In Vitro

Purified wild-type and engineered CasX variants will be complexed with single-guide RNA bearing a fixed targeting sequence. The RNP complexes will be added to buffer containing MgCl2 at a final concentration of 100 nM and incubated with 5' Cy7.5-labeled double-stranded target DNA at a concentration of 10 nM. Separate reactions will be carried out with different DNA substrates containing different PAMs adjacent to the target nucleic acid sequence. Aliquots of the reactions will be taken at fixed time points and quenched by the addition of an equal volume of 50 mM EDTA and 95% formamide. The samples will be run on a denaturing polyacrylamide gel to separate cleaved and uncleaved DNA substrates. The results will be visualized and the rate of cleavage of the non-canonical PAMs by the CasX variants will be determined.

Example 12: Assessing Nuclease Activity for Double-Strand Cleavage

Purified wild-type and engineered CasX variants will be complexed with single-guide RNA bearing a fixed PM22 targeting sequence. The RNP complexes will be added to buffer containing MgCl2 at a final concentration of 100 nM and incubated with double-stranded target DNA with a 5' Cy7.5 label on either the target or non-target strand at a concentration of 10 nM. Aliquots of the reactions will be taken at fixed time points and quenched by the addition of an equal volume of 50 mM EDTA and 95% formamide. The samples will be run on a denaturing polyacrylamide gel to separate cleaved and uncleaved DNA substrates. The results will be visualized and the cleavage rates of the target and non-target strands by the wild-type and engineered variants will be determined. To more clearly differentiate between changes to target binding vs the rate of catalysis of the nucleolytic reaction itself, the protein concentration will be titrated over a range from 10 nM to 1 uM and cleavage rates will be determined at each concentration to generate a pseudo-Michaelis-Menten fit and determine the kcat* and KM*. Changes to KM* are indicative of altered binding, while changes to kcat* are indicative of altered catalysis.

Example 13: Assessing Target Strand Loading for Cleavage

Purified wild-type and engineered CasX 119 will be complexed with single-guide RNA bearing a fixed PM22 targeting sequence. The RNP complexes will be added to buffer containing MgCl2 at a final concentration of 100 nM and incubated with double-stranded target DNA with a 5' Cy7.5 label on the target strand and a 5' Cy5 label on the non-target strand at a concentration of 10 nM. Aliquots of the reactions will be taken at fixed time points and quenched by the addition of an equal volume of 50 mM EDTA and 95% formamide. The samples will be run on a denaturing polyacrylamide gel to separate cleaved and uncleaved DNA substrates. The results will be visualized and the cleavage rates of both strands by the variants will be determined. Changes to the rate of target strand cleavage but not non-target strand cleavage would be indicative of improvements to the loading of the target strand in the active site for cleavage. This activity could be further isolated by repeating the assay with a dsDNA substrate that has a gap on the non-target strand, mimicking a pre-cleaved substrate. Improved cleavage of the non-target strand in this context would give further evidence that the loading and cleavage of the target strand, rather

Example 14: CasX:gNA In Vitro Cleavage Assays

1. Determining cleavage-competent fractions for protein variants compared to wild-type reference CasX The ability of CasX variants to form active RNP compared to reference CasX was determined using an in vitro cleavage assay. The beta-2 microglobulin (B2M) 7.37 target for the cleavage assay was created as follows. DNA oligos with the sequence TGAAGCTGACAGCAT-TCGGGCCGAGATGTCTCGCTCCGTGGCCT-TAGCTGTGCTC GCGCT (SEQ ID NO: 364; non-target strand, NTS) and TGAAGCTGACAGCAT-TCGGGCCGAGATGTCTCGCTCCGTGGCCT-TAGCTGTGCTC GCGCT (SEQ ID NO: 365; target strand, TS) were purchased with 5' fluorescent labels (LI-COR IRDye 700 and 800, respectively). dsDNA targets were formed by mixing the oligos in a 1:1 ratio in 1× cleavage buffer (20 mM Tris HCl pH 7.5, 150 mM NaCl, 1 mM TCEP, 5% glycerol, 10 mM $MgCl_2$), heating to 95° C. for 10 minutes, and allowing the solution to cool to room temperature.

CasX RNPs were reconstituted with the indicated CasX and guides (see FIGS. 12 and 13) at a final concentration of 1 μM with 1.5-fold excess of the indicated guide unless otherwise specified in 1× cleavage buffer (20 mM Tris HCl pH 7.5, 150 mM NaCl, 1 mM TCEP, 5% glycerol, 10 mM $MgCl_2$) at 37° C. for 10 min before being moved to ice until ready to use. The 7.37 target was used, along with sgRNAs having spacers complementary to the 7.37 target.

Figure 12:
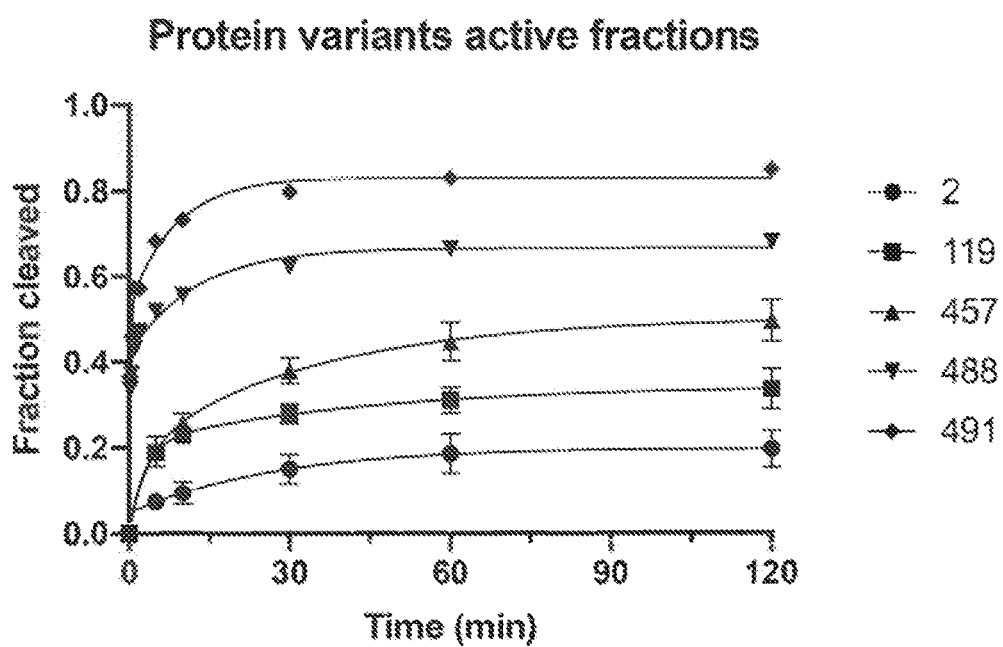
FIG. 12 is a graph of the results of an assay for the quantification of active fractions of RNP formed by sgRNA174 and the CasX variants, as described in Example 14. Equimolar amounts of RNP and target were co-incubated and the amount of cleaved target was determined at the indicated timepoints. Mean and standard deviation of three independent replicates are shown for each timepoint. The biphasic fit of the combined replicates is shown. "2" refers to the reference CasX protein of SEQ ID NO: 2.

Cleavage reactions were prepared with final RNP concentrations of 100 nM and a final target concentration of 100 nM. Reactions were carried out at 37° C. and initiated by the addition of the 7.37 target DNA. Aliquots were taken at 5, 10, 30, 60, and 120 minutes and quenched by adding to 95% formamide, 20 mM EDTA. Samples were denatured by heating at 95° C. for 10 minutes and run on a 10% urea-PAGE gel. The gels were either imaged with a LI-COR Odyssey CLx and quantified using the LI-COR Image Studio software or imaged with a Cytiva Typhoon and quantified using the Cytiva IQTL software. The resulting data were plotted and analyzed using Prism. We assumed that CasX acts essentially as a single-turnover enzyme under the assayed conditions, as indicated by the observation that sub-stoichiometric amounts of enzyme fail to cleave a greater-than-stoichiometric amount of target even under extended time-scales and instead approach a plateau that scales with the amount of enzyme present. Thus, the fraction of target cleaved over long time-scales by an equimolar amount of RNP is indicative of what fraction of the RNP is properly formed and active for cleavage. The cleavage traces were fit with a biphasic rate model, as the cleavage reaction clearly deviates from monophasic under this concentration regime, and the plateau was determined for each of three independent replicates. The mean and standard deviation were calculated to determine the active fraction (Table 13). The results are shown in FIG. 12.

Apparent active (competent) fractions were determined for RNPs formed for CasX2+guide 174+7.37 spacer, CasX119+guide 174+7.37 spacer, CasX457+guide 174+7.37 spacer, CasX488+guide 174+7.37 spacer, and CasX491+guide 174+7.37 spacer. The determined active fractions are shown in Table 13. All CasX variants had higher active fractions than the wild-type CasX2, indicating that the engineered CasX variants form significantly more active and stable RNP with the identical guide under tested conditions compared to wild-type CasX. This may be due to an increased affinity for the sgRNA, increased stability or solubility in the presence of sgRNA, or greater stability of a cleavage-competent conformation of the engineered CasX: sgRNA complex. An increase in solubility of the RNP was indicated by a notable decrease in the observed precipitate formed when CasX457, CasX488, or CasX491 was added to the sgRNA compared to CasX2.

Figure 13:
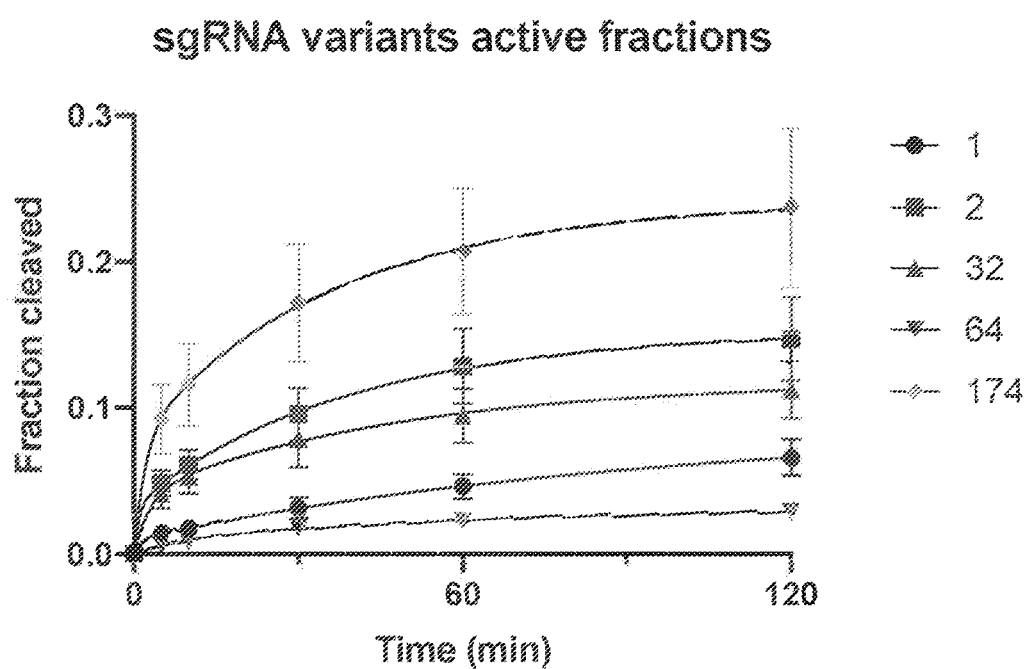
FIG. 13 shows the quantification of active fractions of RNP formed by CasX2 and the modified sgRNAs, as described in Example 14. Equimolar amounts of RNP and target were co-incubated and the amount of cleaved target was determined at the indicated timepoints. Mean and standard deviation of three independent replicates are shown for each timepoint. The biphasic fit of the combined replicates is shown.

2. In vitro Cleavage Assays—Determining $k_{cleave}$ for CasX variants compared to wild-type reference CasX Cleavage-competent fractions were also determined using the same protocol for CasX2.2.7.37, CasX2.32.7.37, CasX2.64.7.37, and CasX2.174.7.37 to be 16±3%, 13±3%, 5±2%, and 22±5%, as shown in FIG. 13 and Table 13.

Figure 14:
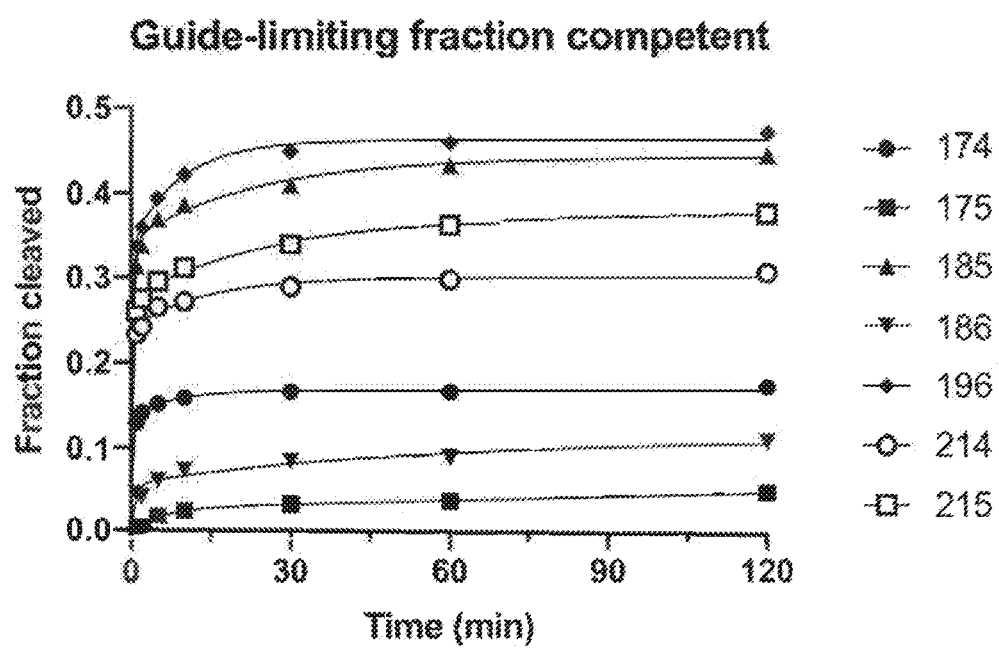
FIG. 14 shows the quantification of active fractions of RNP formed by CasX 491 and the modified sgRNAs under guide-limiting conditions, as described in Example 14. Equimolar amounts of RNP and target were co-incubated and the amount of cleaved target was determined at the indicated timepoints. The biphasic fit of the data is shown.

A second set of guides were tested under different conditions to better isolate the contribution of the guide to RNP formation. 174, 175, 185, 186, 196, 214, and 215 guides with 7.37 spacer were mixed with CasX491 at final concentrations of 1 µM for the guide and 1.5 µM for the protein, rather than with excess guide as before. Results are shown in FIG. 14 and Table 13. Many of these guides exhibited additional improvement over 174, with 185 and 196 achieving 44% and 46% competent fractions, respectively, compared with 17% for 174 under these guide-limiting conditions.

The data indicate that both CasX variants and sgRNA variants are able to form a higher degree of active RNP with guide RNA compare to wild-type CasX and wild-type sgRNA.

The apparent cleavage rates of CasX variants 119, 457, 488, and 491 compared to wild-type reference CasX were determined using an in vitro fluorescent assay for cleavage of the target 7.37.

Figure 18:
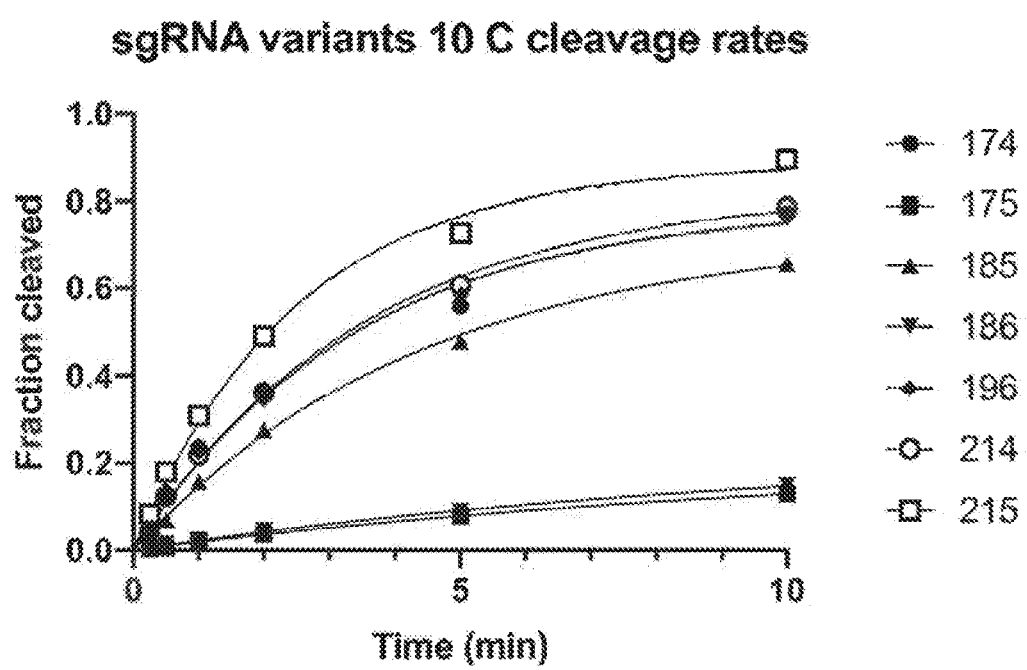
FIG. 18 shows the quantification of cleavage rates of RNP formed by CasX491 and the sgRNA variants, as described in Example 14. Target DNA was incubated with a 20-fold excess of the indicated RNP at 10° C. and the amount of cleaved target was determined at the indicated time points. The monophasic fit of the timepoints is shown.

CasX RNPs were reconstituted with the indicated CasX (see FIG. 14) at a final concentration of 1 µM with 1.5-fold excess of the indicated guide in 1×cleavage buffer (20 mM Tris HCl pH 7.5, 150 mM NaCl, 1 mM TCEP, 5% glycerol, 10 mM $MgCl_2$) at 37° C. for 10 min before being moved to ice until ready to use. Cleavage reactions were set up with a final RNP concentration of 200 nM and a final target concentration of 10 nM. Reactions were carried out at 37° C. except where otherwise noted and initiated by the addition of the target DNA. Aliquots were taken at 0.25, 0.5, 1, 2, 5, and 10 minutes and quenched by adding to 95% formamide, 20 mM EDTA. Samples were denatured by heating at 95° C. for 10 minutes and run on a 10% urea-PAGE gel. The gels were imaged with a LI-COR Odyssey CLx and quantified using the LI-COR Image Studio software or imaged with a Cytiva Typhoon and quantified using the Cytiva IQTL software. The resulting data were plotted and analyzed using Prism, and the apparent first-order rate constant of non-target strand cleavage ($k_{cleave}$) was determined for each CasX:sgRNA combination replicate individually. The mean and standard deviation of three replicates with independent fits are presented in Table 13, and the cleavage traces are shown in FIG. 18.

Figure 15:
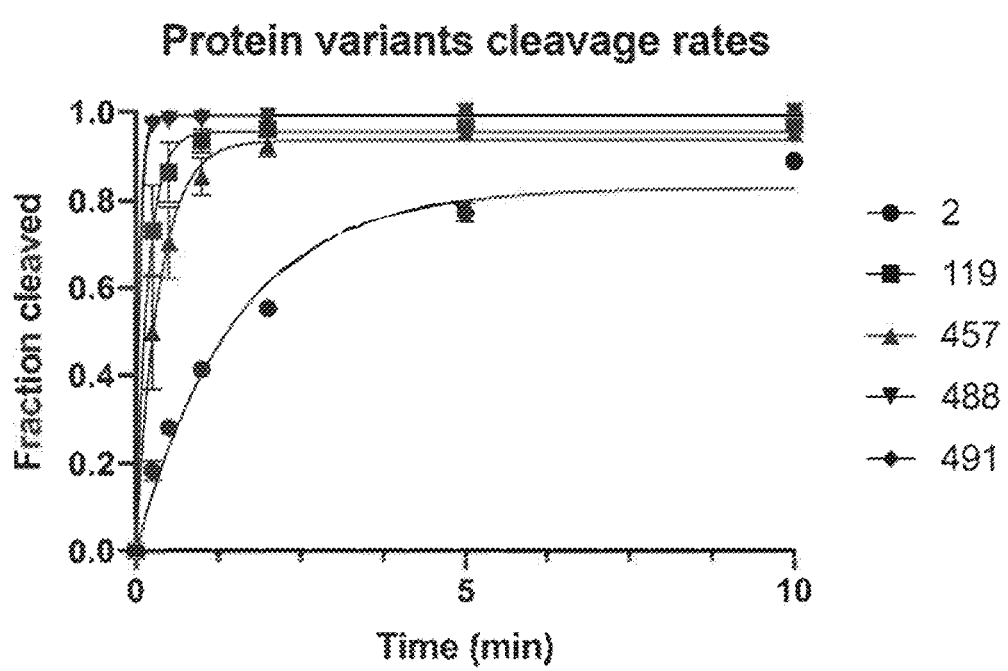
FIG. 15 shows the quantification of cleavage rates of RNP formed by sgRNA174 and the CasX variants, as described in Example 14. Target DNA was incubated with a 20-fold excess of the indicated RNP and the amount of cleaved target was determined at the indicated time points. Mean and standard deviation of three independent replicates are shown for each timepoint, except for 488 and 491 where a single replicate is shown. The monophasic fit of the combined replicates is shown.

Apparent cleavage rate constants were determined for wild-type CasX2, and CasX variants 119, 457, 488, and 491 with guide 174 and spacer 7.37 utilized in each assay (see Table 13 and FIG. 15). All CasX variants had improved cleavage rates relative to the wild-type CasX2. CasX457 cleaved more slowly than 119, despite having a higher competent fraction as determined above. CasX488 and CasX491 had the highest cleavage rates by a large margin; as the target was almost entirely cleaved in the first timepoint, the true cleavage rate exceeds the resolution of this assay, and the reported $k_{cleave}$ should be taken as a lower bound.

The data indicate that the CasX variants have a higher level of activity, with $k_{cleave}$ rates reaching at least 30-fold higher compared to wild-type CasX2.

4. In Vitro Cleavage Assays: Comparison of Guide Variants to Wild-Type Guides

Cleavage assays were also performed with wild-type reference CasX2 and reference guide 2 compared to guide variants 32, 64, and 174 to determine whether the variants improved cleavage. The experiments were performed as described above. As many of the resulting RNPs did not approach full cleavage of the target in the time tested, we determined initial reaction velocities (Vo) rather than first-order rate constants. The first two timepoints (15 and 30 seconds) were fit with a line for each CasX:sgRNA combination and replicate. The mean and standard deviation of the slope for three replicates were determined.

Figure 16:
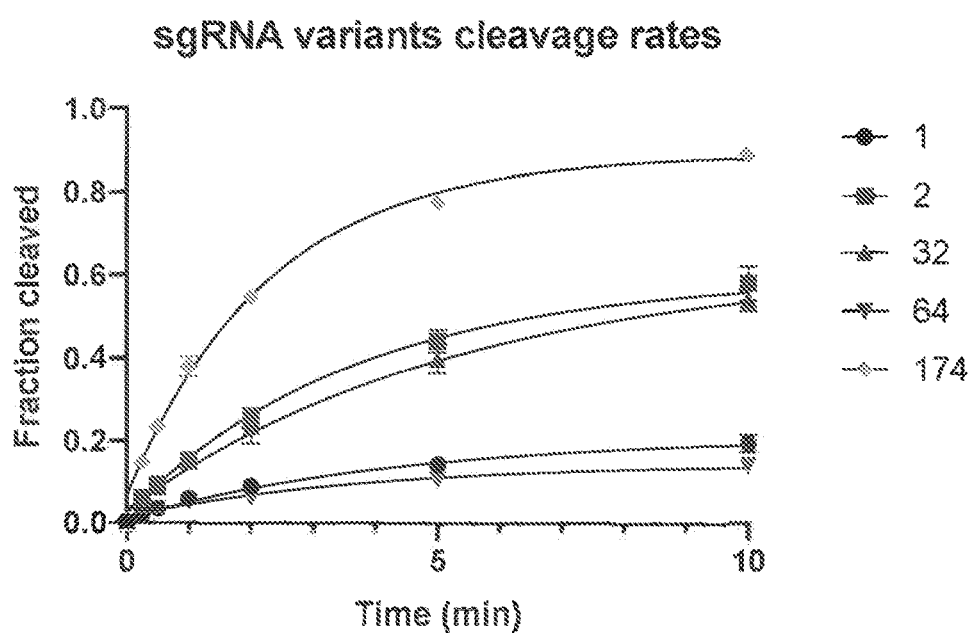
FIG. 16 shows the quantification of cleavage rates of RNP formed by CasX2 and the sgRNA variants, as described in Example 14. Target DNA was incubated with a 20-fold excess of the indicated RNP and the amount of cleaved target was determined at the indicated time points. Mean and standard deviation of three independent replicates are shown for each timepoint. The monophasic fit of the combined replicates is shown.
Figure 17:
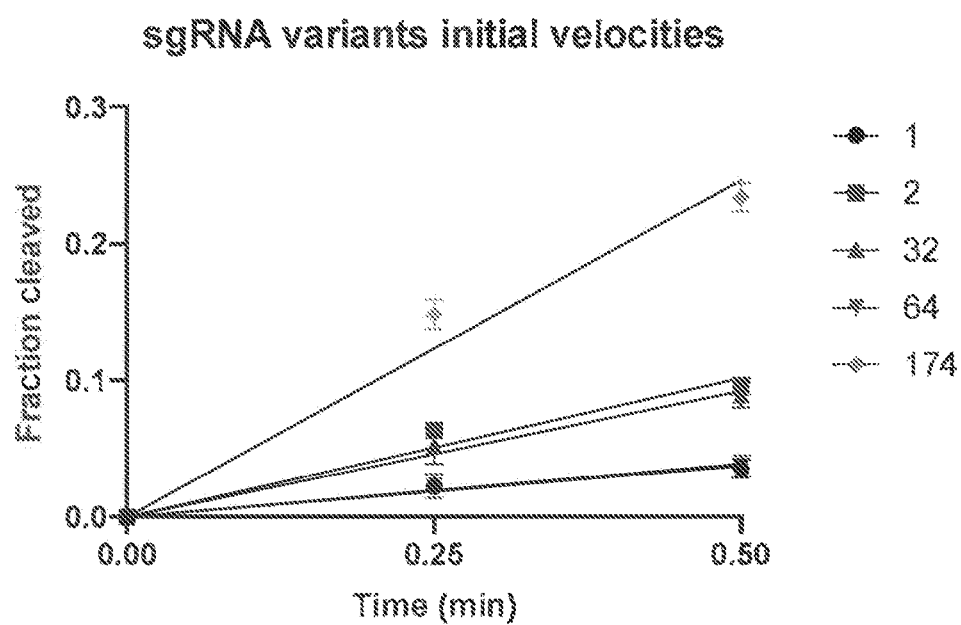
FIG. 17 shows the quantification of initial velocities of RNP formed by CasX2 and the sgRNA variants, as described in Example 14. The first two time-points of the previous cleavage experiment were fit with a linear model to determine the initial cleavage velocity.

Under the assayed conditions, the Vo for CasX2 with guides 2, 32, 64, and 174 were 20.4±1.4 nM/min, 18.4±2.4 nM/min, 7.8±1.8 nM/min, and 49.3±1.4 nM/min (see Table 13, FIG. 16 and FIG. 17). Guide 174 showed substantial improvement in the cleavage rate of the resulting RNP (~2.5-fold relative to 2, see FIG. 17), while guides 32 and 64 performed similar to or worse than guide 2. Notably, guide 64 supports a cleavage rate lower than that of guide 2 but performs much better in vivo (data not shown). Some of the sequence alterations to generate guide 64 likely improve in vivo transcription at the cost of a nucleotide involved in triplex formation. Improved expression of guide 64 likely explains its improved activity in vivo, while its reduced stability may lead to improper folding in vitro.

Additional experiments were carried out with guides 174, 175, 185, 186, 196, 214, and 215 with spacer 7.37 and CasX491 to determine relative cleavage rates. To reduce cleavage kinetics to a range measurable with our assay, the cleavage reactions were incubated at 10° C. Results are in FIG. 18 and Table 13. Under these conditions, 215 was the only guide that supported a faster cleavage rate than 174. 196, which exhibited the highest active fraction of RNP under guide-limiting conditions, had kinetics essentially the same as 174, again highlighting that different variants result in improvements of distinct characteristics. The data support that, under the conditions of the assay, use of the majority of the guide variants with CasX results in RNP with a higher level of activity than one with the wild-type guide, with improvements in initial cleavage velocity ranging from ~2-fold to >6-fold.

TABLE 13

Results of cleavage and RNP formation assays

| RNP Construct | $k_{cleave}$* | Initial velocity* | Competent fraction |
| --- | --- | --- | --- |
| 2.2.7.37 | | 20.4 ± 1.4 nM/min | 16 ± 3% |
| 2.32.7.37 | | 18.4 ± 2.4 nM/min | 13 ± 3% |
| 2.64.7.37 | | 7.8 ± 1.8 nM/min | 5 ± 2% |
| 2.174.7.37 | 0.51 ± 0.01 $min^{-1}$ | 49.3 ± 1.4 nM/min | 22 ± 5% |

TABLE 13-continued

Results of cleavage and RNP formation assays

| RNP Construct | $k_{cleave}$* | Initial velocity* | Competent fraction |
|---|---|---|---|
| 119.174.7.37 | 6.29 ± 2.11 min$^{-1}$ | | 35 ± 6% |
| 457.174.7.37 | 3.01 ± 0.90 min$^{-1}$ | | 53 ± 7% |
| 488.174.7.37 | 15.19 min$^{-1}$ | | 67% |
| 491.174.7.37 | 16.59 min$^{-1}$/0.293 min$^{-1}$ (10° C.) | | 83%/17% (guide-limited) |
| 491.175.7.37 | 0.089 min$^{-1}$ (10° C.) | | 5% (guide-limited) |
| 491.185.7.37 | 0.227 min$^{-1}$ (10° C.) | | 44% (guide-limited) |
| 491.186.7.37 | 0.099 min$^{-1}$ (10° C.) | | 11% (guide-limited) |
| 491.196.7.37 | 0.292 min$^{-1}$ (10° C.) | | 46% (guide-limited) |
| 491.214.7.37 | 0.284 min$^{-1}$ (10° C.) | | 30% (guide-limited) |
| 491.215.7.37 | 0.398 min$^{-1}$ (10° C.) | | 38% (guide-limited) |

*Mean and standard deviation

Example 15: CasX:gNA Editing of SOD1

This example sets forth the parameters to make and test compositions capable of modifying a SOD1 locus.

Experimental Design:

A) SOD1-Modifying Spacer Selection Process:

20 bp XTC PAM spacers were designed to target the following regions in the human genome:

(a) SOD1 cis enhancer elements as described in Fishilevich et al, 2017

(b) SOD1 proximal non-coding genetic elements highly conserved across vertebrates (UCSC genome browser)

(c) SOD1 genomic locus. The SOD1 gene is defined as the sequence that spans chr21:31659622-31668931 of the human genome (GRCh38/hg38) (the notation refers to the chromosome 21 (chr21), starting at the 31,659,622 bp of that chromosome, and extending to the 31,668,931 bp of that chromosome).

SOD1 targeting spacers may be similarly assembled from other genomes.

B) Methods for Generating SOD1 Targeting Constructs:

In order to generate SOD1 targeting constructs, SOD1 targeting spacers were cloned into a base mammalian-expression plasmid construct (pStX) that is comprised of the following components: codon optimized CasX (construct CasX 2 (SEQ ID NO:2) and guide 2 (SEQ ID NO:5) and CasX 119 molecule and rRNA guide 64 (119.64); see Tables 2B and 6 for sequences)+NLS; guide scaffold 64, and a mammalian selection marker, puromycin. Spacer sequence DNA was ordered as single-stranded DNA (ssDNA) oligos from Integrated DNA Technologies (IDT) consisting of the spacer sequence and the reverse complement of this sequence. These two oligos were annealed together and cloned into pStX individually or in bulk by Golden Gate Assembly using T4 DNA Ligase (New England BioLabs Cat #M0202L) and an appropriate restriction enzyme for the plasmid. Assembled products were transformed into chemically- or electro-competent bacterial cells, plated on Lb-Agar plates (LB: Teknova Cat #L9315, Agar: Quartzy Cat #214510) containing carbenicillin and incubated until colonies appeared. Individual colonies were picked and mini-prepped using a Qiagen Qiaprep® spin Miniprep Kit (Qiagen Cat #27104), following the manufacturer's protocol. The resultant plasmids were sequenced using Sanger sequencing to ensure correct ligation. SaCas9 and SpyCas9 control plasmids, with spacers chosen based on Cas protein-specific PAMs, were prepared similarly to pStX plasmids described above.

C) Methods to Generate SOD1 Reporter Line:

A GFP-encoding DNA was knocked in at the 3' end of the last SOD1 exon in a HEK293T cell line. The modified cells were expanded by serial passage every 3-5 days and maintained in Fibroblast (FB) medium, consisting of Dulbecco's Modified Eagle Medium (DMEM; Corning Cellgro, #10-013-CV) supplemented with 10% fetal bovine serum (FBS; Seradigm, #1500-500), and 100 Units/ml penicillin and 100 mg/ml streptomycin (100x-Pen-Strep; GIBCO #15140-122), and can additionally include sodium pyruvate (100x, Thermofisher #11360070), non-essential amino acids (100× Thermofisher #11140050), HEPES buffer (100× Thermofisher #15630080), and 2-mercaptoethanol (1000× Thermofisher #21985023). The cells were incubated at 37° C. and 5% CO2. After 1-2 weeks, single GFP+ cells were sorted into FB medium. The reporter line clones were expanded by serial passage every 3-5 days and maintained in FB medium in an incubator at 37° C. and 5% CO2. The lines were characterized via genomic sequencing, and functional modification of the SOD1 locus using a SOD1 targeting molecule. The optimal reporter lines were identified as ones that i) had a single copy of GFP correctly integrated at the target SOD1 locus, ii) maintained doubling times equivalent to unmodified cells, iii) resulted in reduction in GFP fluorescence upon disruption of the SOD1 gene when assayed using the methods described, below.

D) Methods to Assess SOD1 Modifying Activity in SOD1-GFP Reporter Cell Line:

SOD1-GFP reporter cells were seeded at 20-40 k cells/well in a 96 well plate in 100 µl of FB medium and cultured in a 37C incubator with 5% CO2. The following day, confluence of seeded cells was checked. Ideally, cells should be at ~75% confluence at time of transfection. If cells were at the right confluence, transfection was carried out.

Each CasX construct (CasX 2 (SEQ ID NO:2) and guide 2 (SEQ ID NO:5) and CasX 119 and guide 64, see Tables for sequence) with appropriate spacer targeting SOD1 was transfected at 100-500 ng per well using Lipofectamine™ 3000 following the manufacturer's protocol, using 3 wells per construct as replicates. SaCas9 and SpyCas9 targeting SOD1 were used as benchmarking controls. For each Cas protein type, a non-targeting plasmid was used as a negative control.

After 24-48 hours of puromycin selection at 0.3-3 ug/ml, to select for successfully transfected cells, followed by 24-48 hours of recovery in FB medium, GFP fluorescence in transfected cells was analyzed via flow cytometry. In this process, cells were gated for the appropriate forward and side scatter, selected for single cells and then gated for reporter expression (Attune Nxt Flow Cytometer, Thermo Fisher Scientific) to quantify the expression levels of fluorophores. At least 10,000 events were collected for each sample. The data were then used to calculate the percentage of antibody-label negative (edited) cells.

A subset of cells for each sample from the example was lysed, and genome extracted using a Quick extract solution following the manufacturer's protocol. Editing was analyzed using a T7E1 assay. Briefly, the genomic locus at the targeted edit site was amplified using primers (e.g., a 500 bp region around the intended target) using a PCR program on a thermocycler. The PCR amplicon was then hybridized following a hybridization program on a thermocycler, and then treated with T7 Endonuclease for 30 mins at 37C. The sample was then analyzed on a 2% agarose gel, or on a Fragment Analyzer to visualize DNA bands.

E) Methods to Assess SOD1 Modifying Activity in SY5Y Cells:

SY5Y cells (Cell Culture Facility, UC Berkeley) were seeded at 20-40 k cells/well in a 96 well plate in 100 µl of FB medium and cultured in a 37° C. incubator with 5% CO2. The following day, confluence of seeded cells was checked. Ideally, cells should be at ~75% confluence at time of transfection. If cells were at the right confluence, transfection was carried out.

CasX construct 119 with guide 64 and appropriate spacer targeting SOD1 was transfected at 100-500 ng per well using Lipofectamine™ 3000 following the manufacturer's protocol, and placed into 3 wells per construct as replicates. A non-targeting plasmid was used as a negative control. After 24-48 hours of puromycin selection at 1-3 ug/ml to select for successfully transfected cells, followed by 24-48 hours of recovery in FB medium, cells were analyzed for editing by the T7E1 assay as described above.

F) Methods to Assess SOD1 Modifying Via a Lentiviral Screen

Lentiviral plasmids are cloned as described above and following standard cloning procedures such that each lentiviral plasmid has one spacer-guide scaffold targeting SOD1 and one codon optimized NLS bearing CasX molecule (e.g., construct CasX 119 molecule and rRNA guide 64 (119.64)) with a puromycin selection marker. The cloning is carried out such that the final titer encompasses the full library size by >100× of all possible SOD1 spacers targeting all known PAMs and their corresponding spacer regions in the SOD1 gene. If ~5,000 was the library size; the libraries evaluated would be >5×10$^5$.

Lentiviral particles are produced by transfecting HEK293T at a confluency of 70%-90% using polyethylenimine based transfection of plasmids containing the spacer library, the lentiviral packaging plasmid and the VSV-G envelope plasmids. For particle production, media is changed 12 hr. post-transfection, and virus harvested at 36-48 hr. post-transfection.

Viral supernatants are filtered using 0.45 um membrane filters, diluted in FB media if appropriate, and added to target cells, in this case the SOD1-GFP reporter cell line. Supplement polyberene is added at 5-20 ug/ml to enhance transduction efficiency, if necessary. Transduced cells are selected for 24-48 hr. post-transduction using puromycin at 0.3-3 ug/ml in FB medium, and grown for 7-10 days in FB medium in a 37C incubator with 5% CO2.

Cells are sorted on a SH-100 or MA900 SONY sorter. In this process, cells are gated for the appropriate forward and side scatter, selected for single cells and then gated for reporter expression. Different cell sorting gates are established based on fluorescence level (OFF=full KO, Med=partial disruption or knockdown (KD), High=no edit, Very High=Enhancer) to distinguish between and collect cells editing by i) highly functional SOD1 disrupting molecules, ii) molecules that only lower expression, and iii) molecules that increase expression. This assay can also be run to identify allele specific guides if two colors are used in human patient cells. Genomic DNA are collected from each group of sorted cells using Quick Extract (Lucigen Cat #QE09050) solution following manufacturer's recommended protocol.

Spacer libraries from each collected pool are then amplified via PCR directly from the genome and collected for deep sequencing on a Miseq™. Analysis of the spacers is done according to gate and abundance for a specific activity; see below for detailed methods for NGS analysis of spacer hits.

Selected guides from each sorted group are then re-cloned and individually validated in reporter cell line and in primary human cell lines for activity by flow cytometry and T7E1 assay, and indel spectrum assessed by NGS analysis. Steps followed may be similar to the description provided under Methods to assess SOD1 modifying activity in reporter cell line.

G) Methods for NGS Analysis of Spacer Hits

Provided here are methods on how to analyze the next generation sequencing (NGS) data coming from above described lentiviral screen. Spacers are each assessed for ability to disrupt a SOD1 gene using NGS.

NGS libraries are generated through specific amplification of the lentiviral backbone containing the spacer. A different library is generated for each of the sorted populations (GFP high, med, low, etc., corresponding to low, med, high SOD1 expression), and then assessed with the Illumina Hiseq.

Sequencing reads from the Illumina Hiseq are trimmed for adapter sequences and for regions of low sequencing quality. Paired end reads are merged based on their overlap sequence to form a single consensus sequence per sequenced fragment. Consensus sequences are aligned to the designed spacer sequences using bowtie2. Reads aligning to more than one designed spacer sequence are discarded.

The 'abundance' of each spacer sequence is defined as the number of reads aligning to that sequence. The abundance is tabulated for each sequencing library, forming a count table giving the abundance for each spacer sequence across each of the sequencing libraries (i.e., sorted populations). Finally, the numbers of abundances are then normalized to account for the differing sequencing depth of each library by dividing by the overall read count in that library, multiplied by the mean read count across libraries. The normalized count table is used to determine the activity of each spacer in each gate (high, medium, low, etc.).

Figure 19:
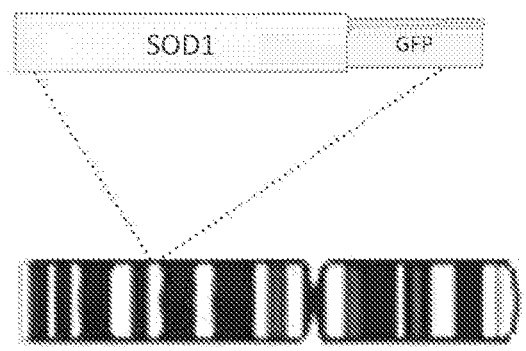
FIG. 19 is a schematic showing construction of the SOD1-GFP reporter line made by knocking in GFP at the endogenous human SOD1 locus, as described in Example 15.
Figure 20:
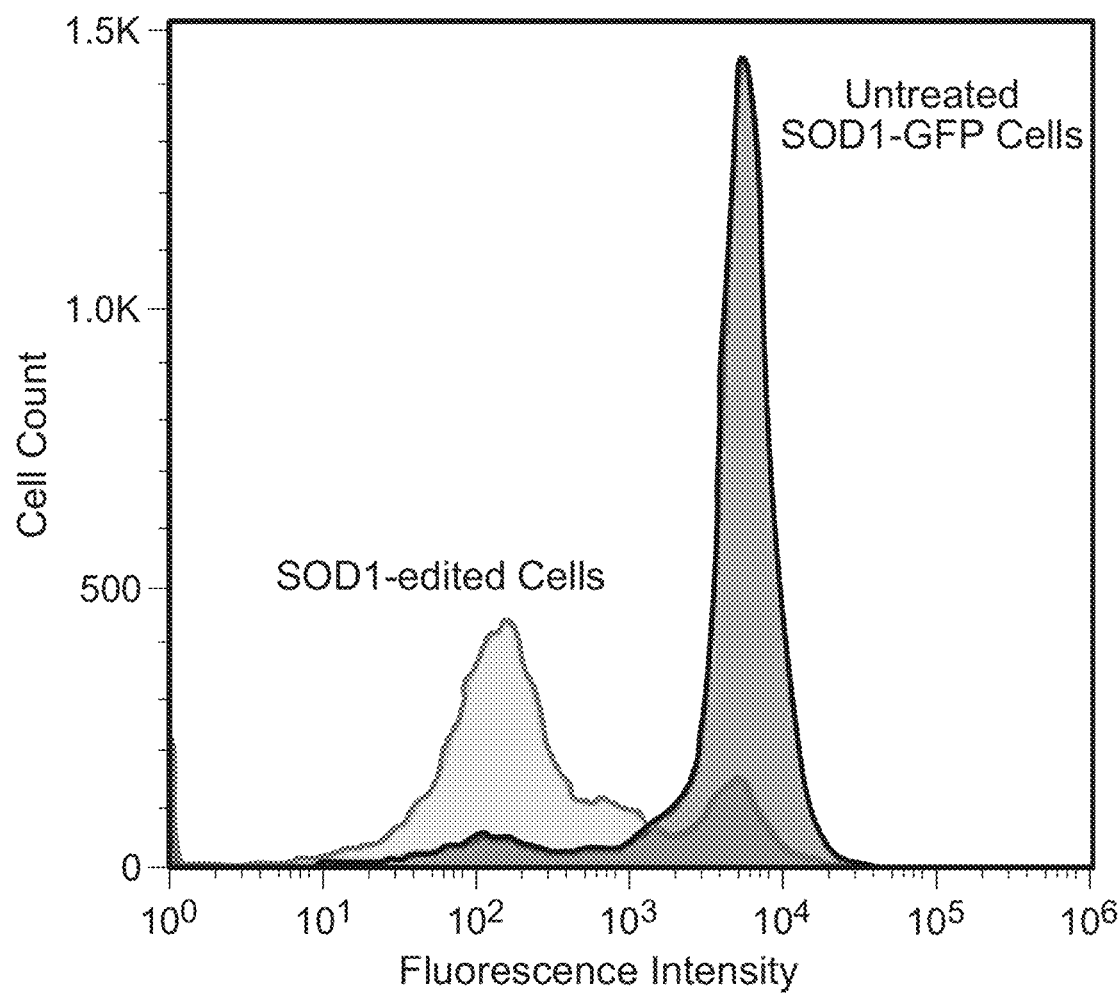
FIG. 20 is an example fluorescence activated cell sorting (FACS) plot illustrating an exemplary method for assaying the effectiveness of a reference CasX protein or single guide RNA (sgRNA), or variants thereof, as described in Example 15.

Results:

A SOD1-GFP reporter line was constructed by knocking in GFP at the endogenous human SOD1 locus, shown schematically in FIG. 19. A reporter (e.g., GFP reporter) coupled to a gRNA targeting sequence, complementary to the gRNA spacer, is integrated into a reporter cell line. Cells are transformed or transfected with a CasX protein and/or sgRNA variant, with the spacer motif of the sgRNA complementary to and targeting the gRNA target sequence of the reporter. The ability of the CasX:sgRNA ribonucleoprotein complex to cleave the target nucleic acid sequence is assayed by FACS. Cells that lose reporter expression indicate occurrence of CasX:sgRNA ribonucleoprotein complex-mediated cleavage and indel formation. The reporting system is based on reduced GFP fluorescence upon successful modifying (editing) of the SOD1 locus, detected by flow cytometry as shown in FIG. 20.

Figure 21:
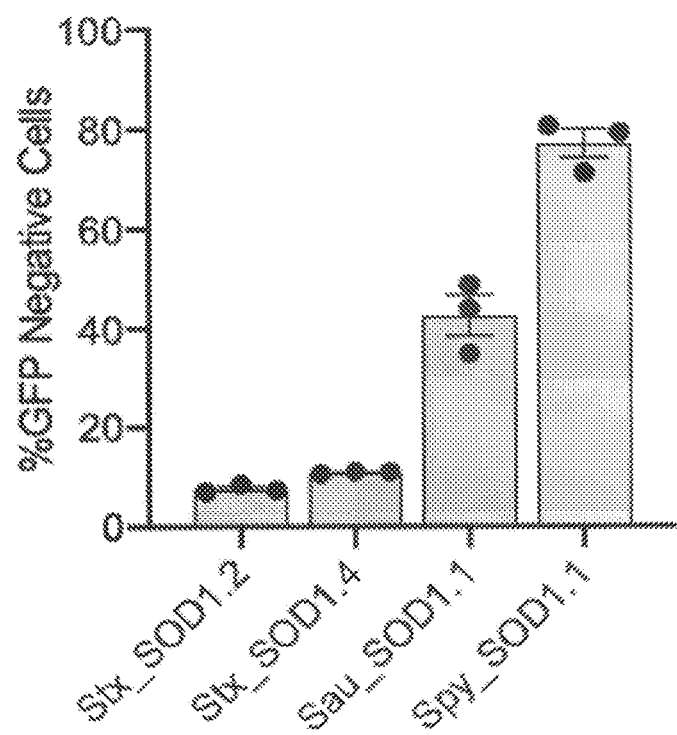
FIG. 21 shows the results of gene editing in the SOD1-GFP reporter cell line, as described in Example 15.
Figure 22:
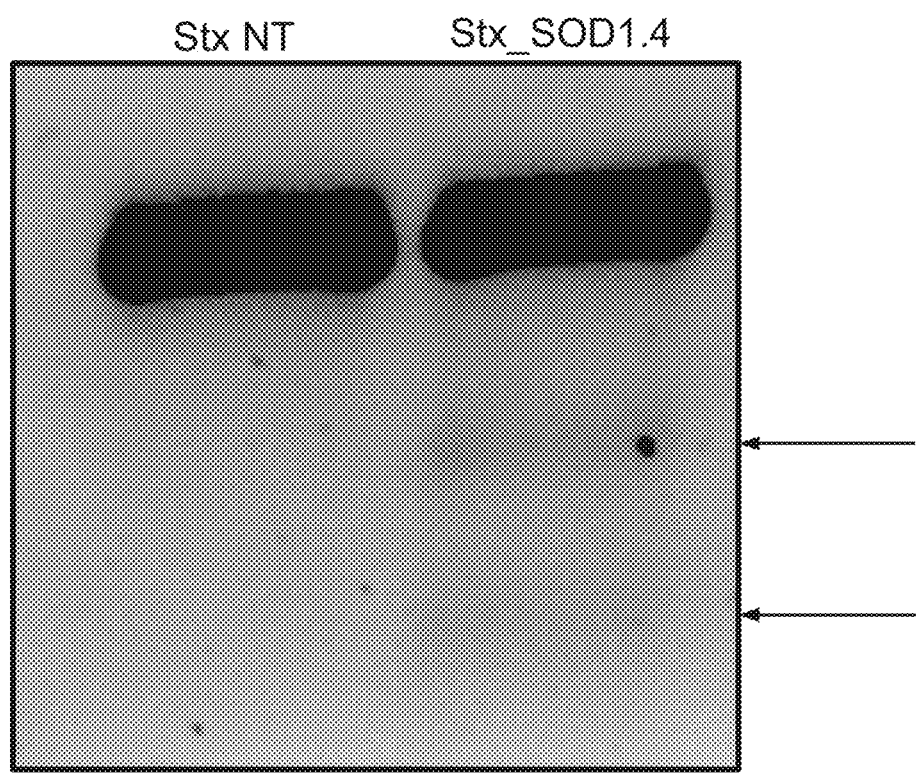
FIG. 22 shows the results of gene editing in the SOD1-GFP reporter cell line, as described in Example 15.

In an initial screen, two SOD1 spacers of the gNA were tested. The spacers 2 (with an encoding sequence ATGTTCATGAGTTTGGAGAT (SEQ ID NO: 310)) and 4 (with an encoding sequence TCGCCATAACTCGCTAGGCC (SEQ ID NO: 366)) were tested with the CasX protein (construct CasX 2 (SEQ ID NO:2) and guide 2 (SEQ ID NO:5)), using SaCas9 and SpyCas9 as controls, in the reporter cell line. The reduction in GFP fluorescence and editing, shown in FIGS. 20 and 21. FIG. 21 shows the edits results of the CasX SOD1 targeting spacers 2 and 4 (first two bars) and benchmarking controls Sa.Cas9 and Spy.Cas9 (second two bars) which were lipofected into SOD1-GFP reporter cells, selected for successful lipofection using puromycin, and later assayed for GFP disruption via FACS. The CasX 2 (SEQ ID NO:2) and guide 2 (SEQ ID NO:5) is shown to edit 5-10% of cells, demonstrating that CasX can modify the endogenous SOD1 locus, and did so more effectively than the SaCas9 and SpyCas9. A T7E1 assay was performed to assay gene editing in the SOD1-GFP reporter cell line. CasX 2 (SEQ ID NO:2) and guide 2 (SEQ ID NO:5) with SOD1 targeting spacer (with an encoding sequence of TCGCCATAACTCGCTAGGCC (SEQ ID NO: 366)) and non-targeting control (NT) were lipofected into SOD1-GFP reporter cells, selected for successful lipofection using puromycin, and later assayed for gene editing in the T7E1 assay. An agarose gel image from the T7E1 assay shown in FIG. 22 demonstrates successful editing of the SOD1 locus, indicated by the double arrows.

Figure 23:
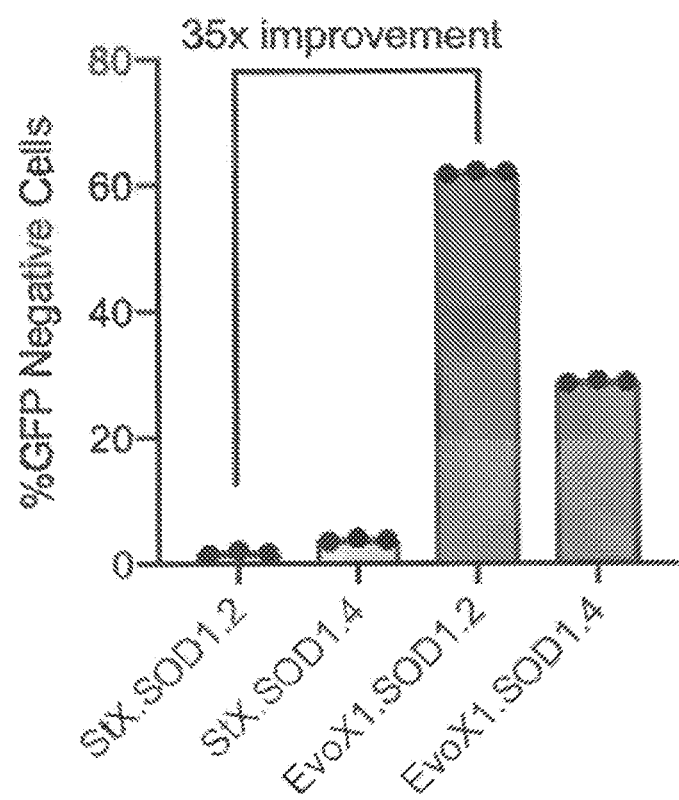
FIG. 23 shows the results of gene editing in the SOD1-GFP reporter cell line, as described in Example 15.

FIG. 23 shows the results of gene editing in the SOD1-GFP reporter cell line. CasX 2 (SEQ ID NO:2) and guide 2 (SEQ ID NO:5) (labeled here as StX) and CasX 119 molecule and rRNA guide 64 (119.64) (labeled here as EvoX1) with SOD1 targeting spacers (2, with an encoding sequence of ATGTTCATGAGTTTGGAGAT (SEQ ID NO: 310), and spacer 4, with an encoding sequence of TCGCCATAACTCGCTAGGCC (SEQ ID NO: 366)), were lipofected into SOD1-GFP reporter cells, selected for successful lipofection using puromycin, and later assayed for GFP disruption via FACS. FIG. 5 shows that CasX 119 with guide 64 edits substantially better than CasX 2 (SEQ ID NO:2) and guide 2 (SEQ ID NO:5); in particular, in the case of spacer 2, CasX 119 with guide 64 shows 35-fold higher editing compared to CasX 2 (SEQ ID NO:2) and guide 2 (SEQ ID NO:5).

Figure 24:
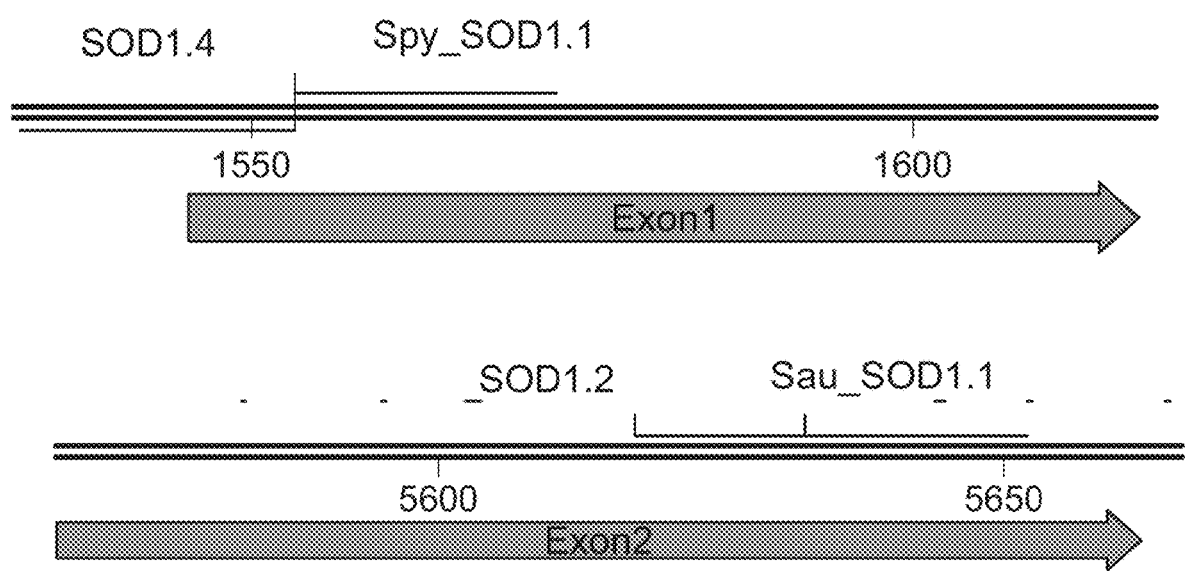
FIG. 24 is a schematic depicting the location of the SOD1 targeting spacers, referred to in Example 15, in the SOD1 gene.

FIG. 23 demonstrates that another CasX variant, construct 119 with guide 64, modifies the SOD1 locus with a 35-fold higher efficiency compared to CasX 2 (SEQ ID NO:2) and guide 2 (SEQ ID NO:5), as measured via flow cytometry of modified SOD1-GFP reporter cells. Rates of about 60% for modifying at the endogenous SOD1 locus were achieved; equal or greater than efficiency demonstrated with SaCas9 (data not shown). The spacers used in these examples are pictorially depicted in FIG. 24, with the CasX SOD1 targeting spacer 4 (SOD1.4) and a SpyCas9 targeting spacer (Spy_SOD1.1) located in Exon 1. The CasX SOD1 targeting spacer 2 (SOD1.2) and a SauCas9 targeting spacer (Sau_SOD1.1) are located in Exon 2.

Figure 25:
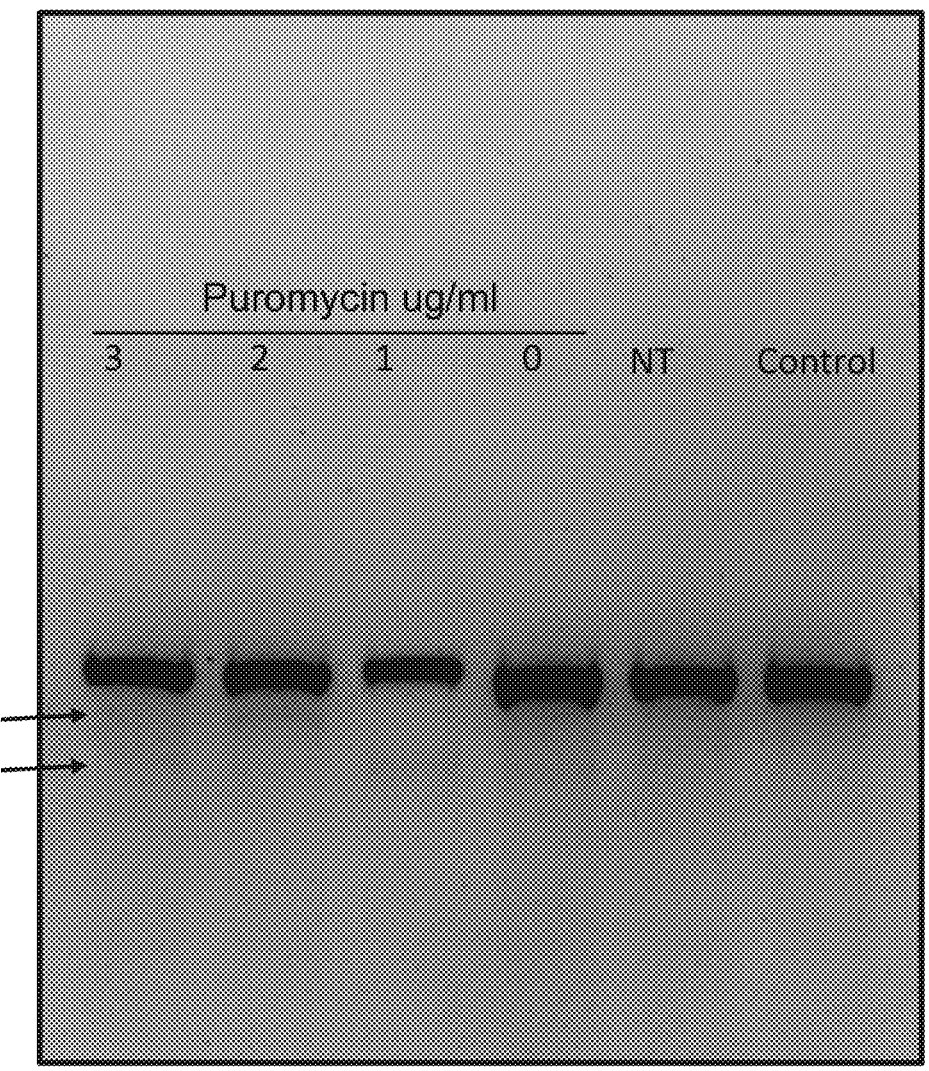
FIG. 25 shows the results of gene editing in the SY5Y cell line, as described in Example 15.

FIG. 25 shows the results of gene editing in the SY5Y cell line. CasX 119 and rRNA guide 64 with a SOD1 targeting spacer (with an encoding sequence of TCGCCATAACTCGCTAGGCC (SEQ ID NO: 366)) and non-targeting control (NT) were lipofected into SY5Y cells, selected for successful lipofection using different concentrations of puromycin (1, 2 or 3 ug/ml), and later assayed for gene editing in the T7E1 assay. The agarose gel image from the T7E1 assay shown in FIG. 25 demonstrates successful editing of the SOD1 locus. The double arrows show the two DNA bands as a result of successful editing in cells selected with 3 µg/ml puromycin.

Figure 26:
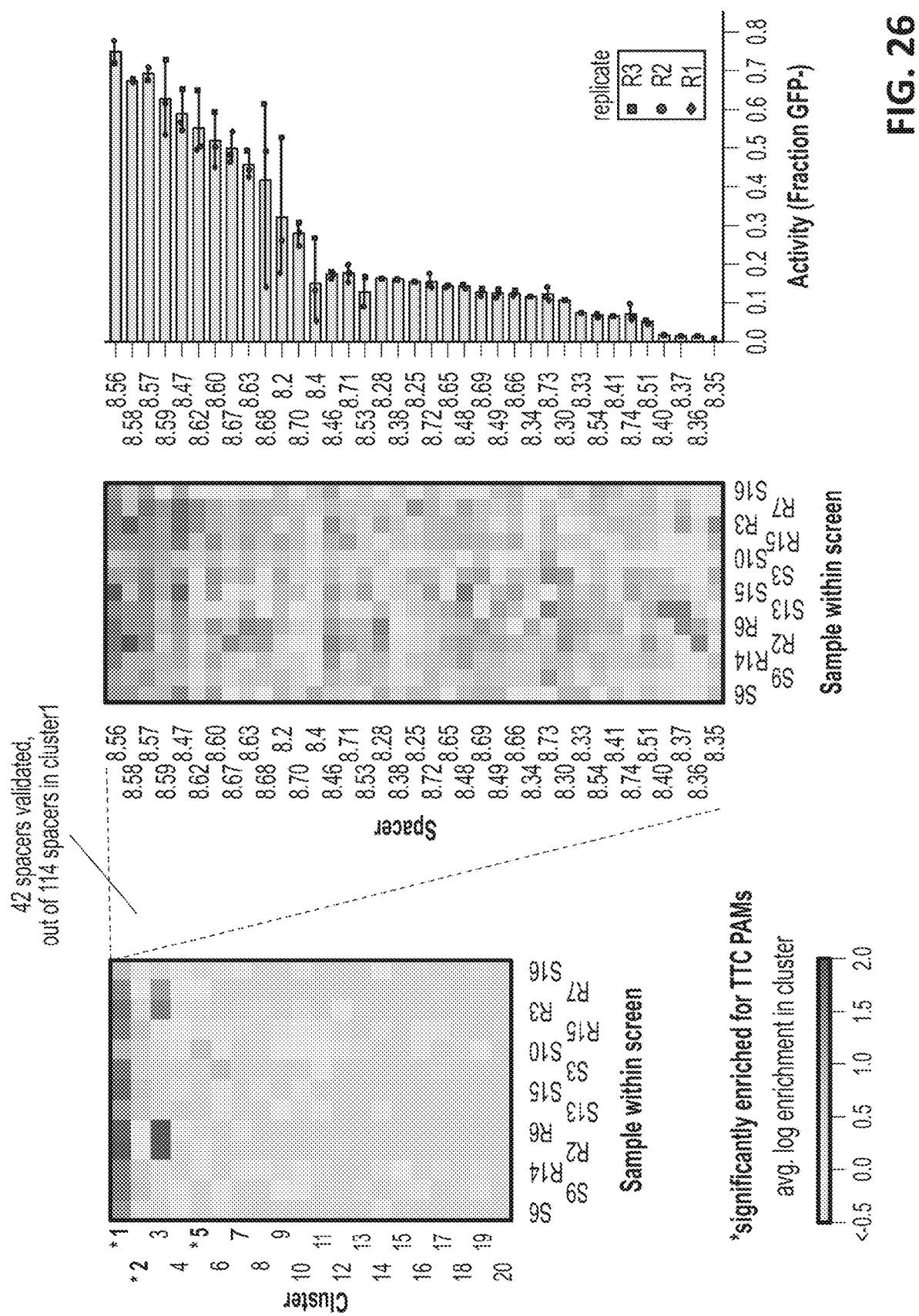
FIG. 26 shows that spacers with improved ability to edit the SOD1 gene can be identified from the screening method described in Example 15.

FIG. 26 shows that spacers with improved ability to edit the SOD1 gene can be identified from the screening method described here. Approximately 5000 different spacers, designed as described in SOD1-modifying spacer selection process were assessed for activity in the SOD1-GFP reporter cell line. The left panel shows that unbiased clustering of the spacers by activity, as described in Methods for NGS analysis of spacer hits across 13 different measurements results in 20 distinct clusters, with cluster 1 containing the most active spacers. 42 of these most active spacers are shown in the middle panel, ranked from top to bottom by activity. The right panel shows that the most active spacers identified in the spacer screen indeed maintain their activity when individually tested via lipofection of CasX construct 119 with scaffold 174 and the respective spacers in the SOD1-GFP cell line.

Conclusions: This example demonstrates that CasX constructs can edit the SOD1 locus in multiple mammalian cell lines. A CasX variant, 119 with guide 64, was found to edit 35-fold better than the previous CasX 2 (SEQ ID NO:2) and guide 2 (SEQ ID NO:5) in some instances, indicating that CasX variants can be designed with improved editing capabilities.

Example 16: Generation and Assay of AAV Vectors Delivering CasX Constructs Targeting SOD1

This example describes a typical protocol followed to produce and characterize AAV2 vectors packaging CasX molecules and guides.

Figure 27:
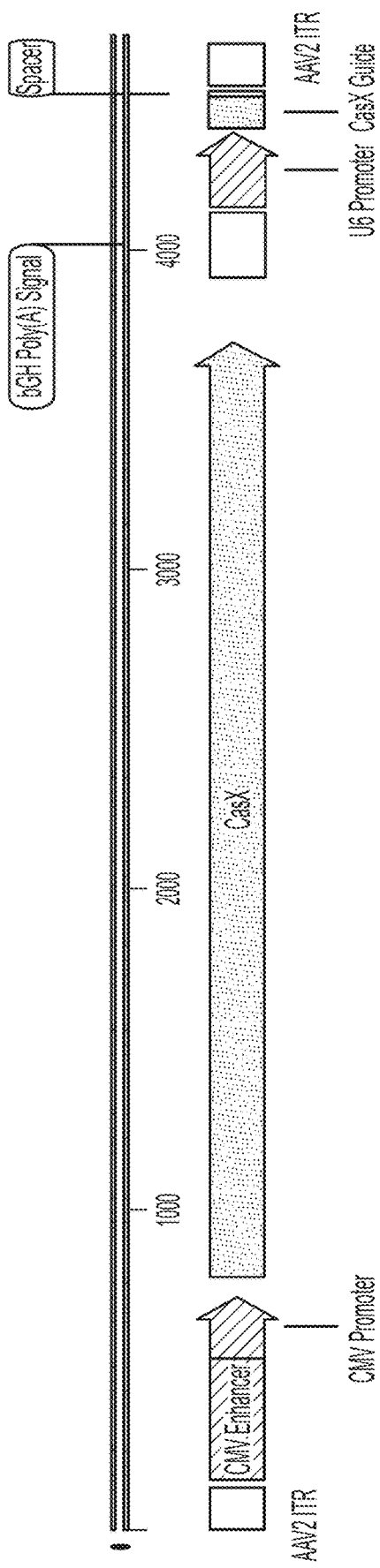
FIG. 27 is a schematic showing an example of CasX protein and scaffold DNA sequence for packaging in adeno-associated virus (AAV), as described in Example 16.

Materials and Methods:

For AAV production, the tri-plasmid transfection method was used, using three essential plasmids—pTransgene carrying the gene of interest to be packaged in AAV, pRC, and pHelper. DNA encoding CasX and guide RNA were cloned into an AAV transgene cassette, between the ITRs (FIG. 27) to generate the pTransgene plasmid. The DNA segment between the AAV inverted terminal repeats (ITRs), comprised of a CasX-encoding DNA and its promoter, and scaffold-encoding DNA and its promoter gets packaged within an AAV capsid during AAV production. The constructed transgene plasmid was verified via full-length plasmid sequencing (see Table 14), restriction digestion, and functional tests including in vitro transfection of mammalian cells. Additional plasmids required for AAV production (pRC plasmid and pHelper plasmid) were purchased from commercial suppliers (Aldevron, Takara).

For AAV production, HEK293/T cells were cultured in FB medium in a 37° C. incubator with 5% CO2. 10-20 15 cm dishes of HEK293T cells were used in a single batch of viral production. For a single 15 cm dish, 15 ug of each plasmid was first mixed together in 4 ml of FB medium, and complexed with 145 ug polyethyleneimine (PEI) i.e., at 3 ug PEI/ug of DNA, for 10 mins at room temperature. The ratio of the three plasmids used may be varied to further optimize virus production as needed.

The PEI-DNA complex was then slowly dripped onto the 15 cm plate of HEK293T cells, and the plate of transfected cells moved back into the incubator. The next day, the medium was changed to FB with 2% FBS (instead of 10% FBS). At 3 days post-transfection, the media from the cells may be collected to increase virus yields. At 5-6 days post-transfection medium and cells were collected. The timing of harvest may be further varied to optimize virus yield.

The cells were pelleted by centrifugation, and the medium collected from the top. Cells were lysed in a buffer with high salt content and high-salt-active nuclease for 1h at 37° C. The cells may also be lysed using additional methods, such as sequential freeze-thaw, or chemical lysis by detergent.

The medium collected at harvest, and any medium collected at earlier time points, were treated with a 1:5 dilution of a solution containing 40% PEG8000 and 2.5M NaCl, and incubated on ice for 2h, in order to precipitate AAV. The incubation may also be carried out overnight at 4° C.

The AAV precipitate from the medium was pelleted by centrifugation, resuspended in high salt content buffer with high-salt-active nuclease and combined with the lysed cell pellet. The combined cell lysate was then clarified by centrifugation and filtration through a 0.45 um filter, and purified on an AAV Poros affinity resin column (Thermofisher Scientific). The virus was eluted from the column into a neutralizing solution. At this stage, the virus may be taken through additional rounds of purification to increase the quality of the virus preparation.

The eluted virus was then titered via qPCR to quantify the virus yield. For titering, a sample of virus was first digested with DNAse to remove any non-packaged viral DNA, the DNAse deactivated, and then viral capsids disrupted with Proteinase K to expose the packaged viral genomes for titering.

Figure 28:
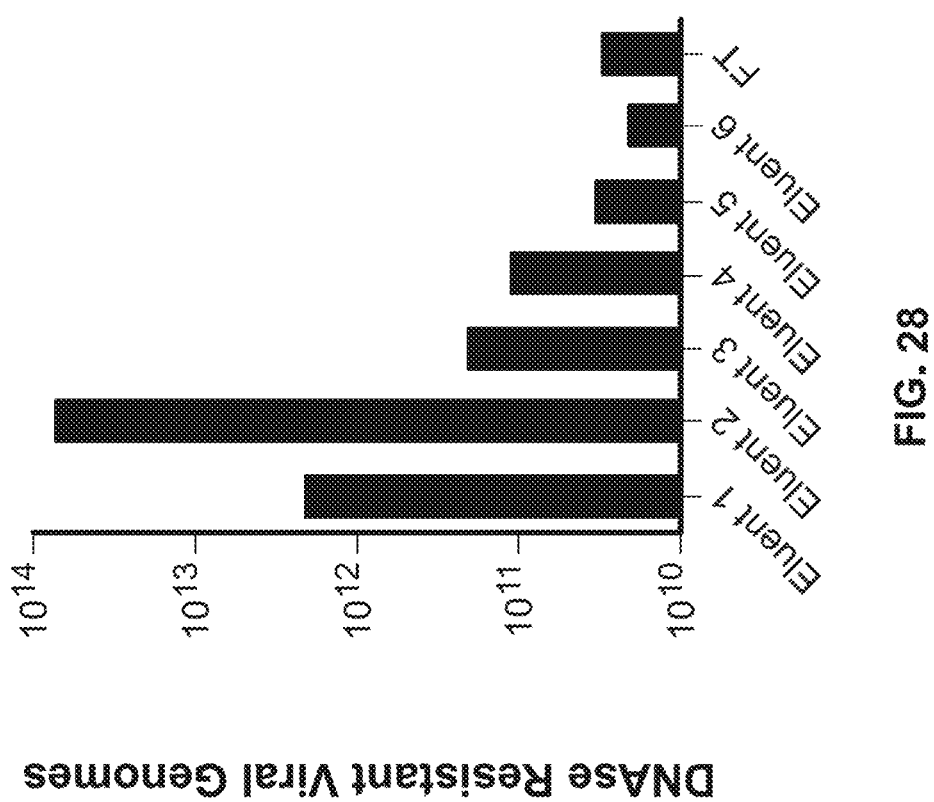
FIG. 28 is a graph showing representative results of AAV titering by qPCR, as described in Example 16.

Results:

Representative titers for AAV packaging DNA encoding a CasX 119 molecule and rRNA guide 64 (119.64) with a spacer having the sequence ATGTTCATGAGTTTGGAGAT (SEQ ID NO: 310) is shown in FIG. 28. During AAV purification, flow through (FT) and consecutive eluent fractions (1-6) are collected and titered by qPCR. Most virus, ~$1\times10^{14}$ viral genomes in this example, is found in the second elution fraction. Typically, ~$1\times10^{12}$ viral genomes were obtained from one batch of virus production as described here.

Conclusion: This example demonstrates that i) CasX and a gNA can be cloned into an AAV transgene construct, and ii) CasX and guide can be packaged in an AAV vector and produced at sufficiently high titers.

TABLE 14

| Plasmid Sequence | |
| --- | --- |
| Construct | DNA sequence |
| pStX17 | (SEQ ID NO: 367) |

Example 17: Administration of AAV Vectors Encoding a CasX System In Vitro and Evidence of SOD1 Gene Editing Materials and Methods:

SOD1-GFP reporter cells were seeded at 30 k cells/well in a 96 well plate in 100u1 of FB medium. Confluence of cells was checked the next day, and cells were transduced at 80% confluence with AAV vectors. CasX 119 molecule and rRNA guide 64 (119.64) with SOD1 targeting spacer (2, with an encoding sequence of ATGTTCATGAGTTTG-GAGAT (SEQ ID NO: 310)) and SauCas9 with SOD1 targeting spacer were packaged in AAV vectors and used to transduce SOD1-GFP reporter cells at a range of different multiplicity of infection (MOIs, no. of viral genomes/cell), for example from 1 to $1\times10^7$ viral genomes per cell. In a separate experiment, neural progenitor cells from the G93A mouse model of ALS (G93A NPCs) were similarly transduced. NPCs are cultured in NPC medium (DMEMF12 with Glutamax, supplemented with 10 mM Hepes (100× Thermofisher #15630080), non-essential amino acids (100× Thermofisher #11140050), penicillin-streptomycin (100x-Pen-Strep; GIBCO #15140-122), 2-mercaptoethanol 1000× (Thermofisher #21985023), B27 without vitamin-A (50x, Thermofisher), N2 (100x, Thermofisher), 20 ng/ml bFGF (Biolegend Cat no #579606), and 20 ng/ml EGF (Thermofisher #PHG0311)) at 37° C. and 5% CO2. The AAV doses were calculated based on viral titers determined by qPCR. Fresh FB medium or NPC medium may be replenished the next day, or as needed. Starting at 5 days post-transduction, and weekly thereafter, a portion of the cells were analyzed via flow cytometry or T7E1 assay.

In a second AAV-mediated gene editing in the SOD1-GFP reporter cell line, CasX 119 molecule and rRNA guide 64 (119.64) with SOD1 targeting spacer (2, with an encoding sequence of ATGTTCATGAGTTTGGAGAT (SEQ ID NO: 310)) and SauCas9 with SOD1 targeting spacer were packaged in AAV vectors and used to transduce SOD1-GFP reporter cells at a range of different multiplicity of infection (MOIs, no. of viral genomes/cell). Twelve days later, cells were assayed for GFP disruption via FACS.

Another AAV-mediated gene editing experiment was conducted in neural progenitor cells (NPCs) from the G93A mouse model of ALS. CasX 119 molecule and rRNA guide 64 (119.64) with SOD1 targeting spacer (2, with an encoding sequence of ATGTTCATGAGTTTGGAGAT (SEQ ID NO: 310)) was packaged in an AAV vector and used to transduce G93A NPCs at a range of different multiplicity of infection (MOIs, no. of viral genomes/cell). Twelve days later, cells were assayed for gene editing via T7E1 assay.

Figure 29:
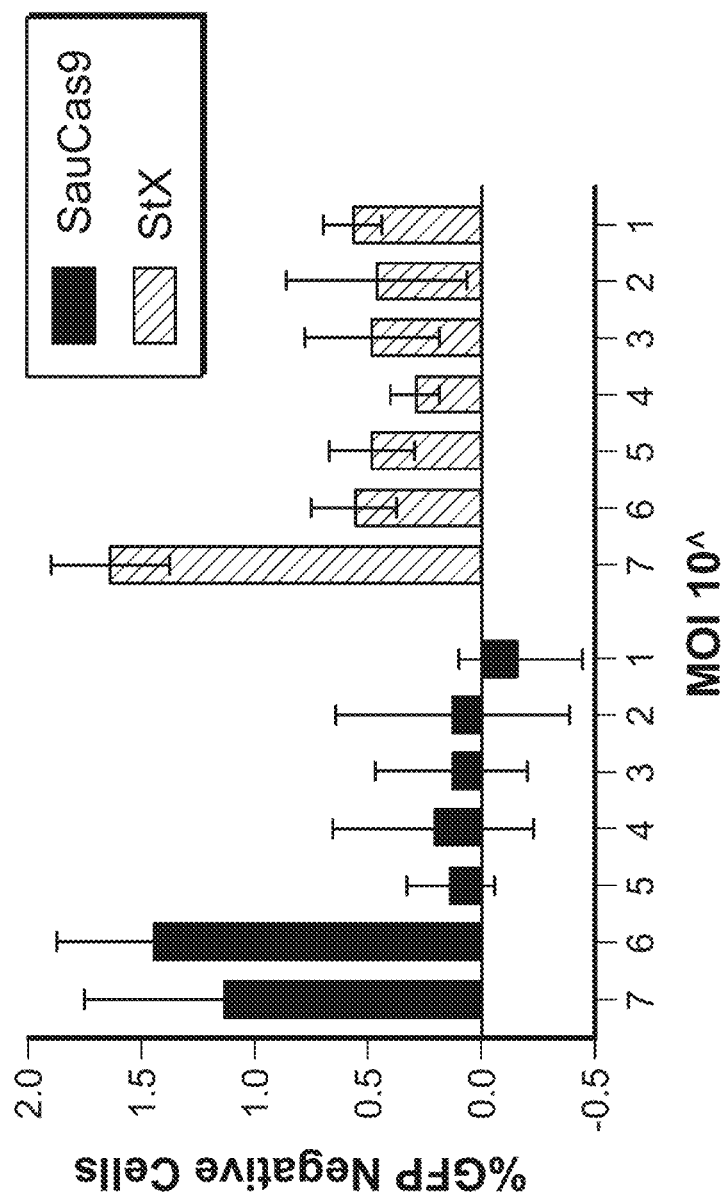
FIG. 29 shows the results of AAV-mediated gene editing in the SOD1-GFP reporter cell line, as described in Example 17.
Figure 30:
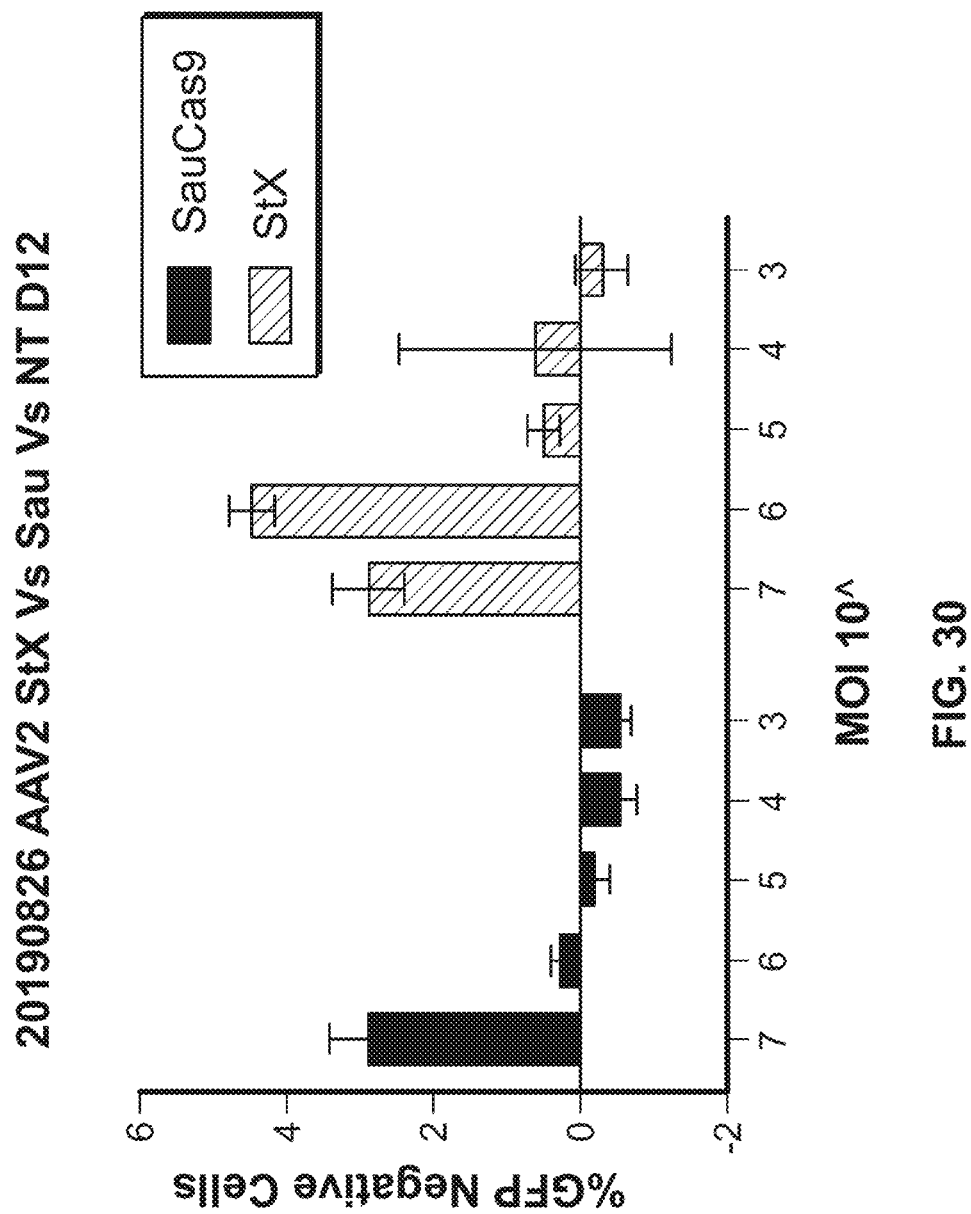
FIG. 30 shows the results of second AAV-mediated gene editing example in the SOD1-GFP reporter cell line, as described in Example 17.

Results:

A representative example of SOD1 editing, as demonstrated by percentage of GFP negative cells, at 12 days post-transduction is shown in FIG. 29 and FIG. 30.

Figure 31:
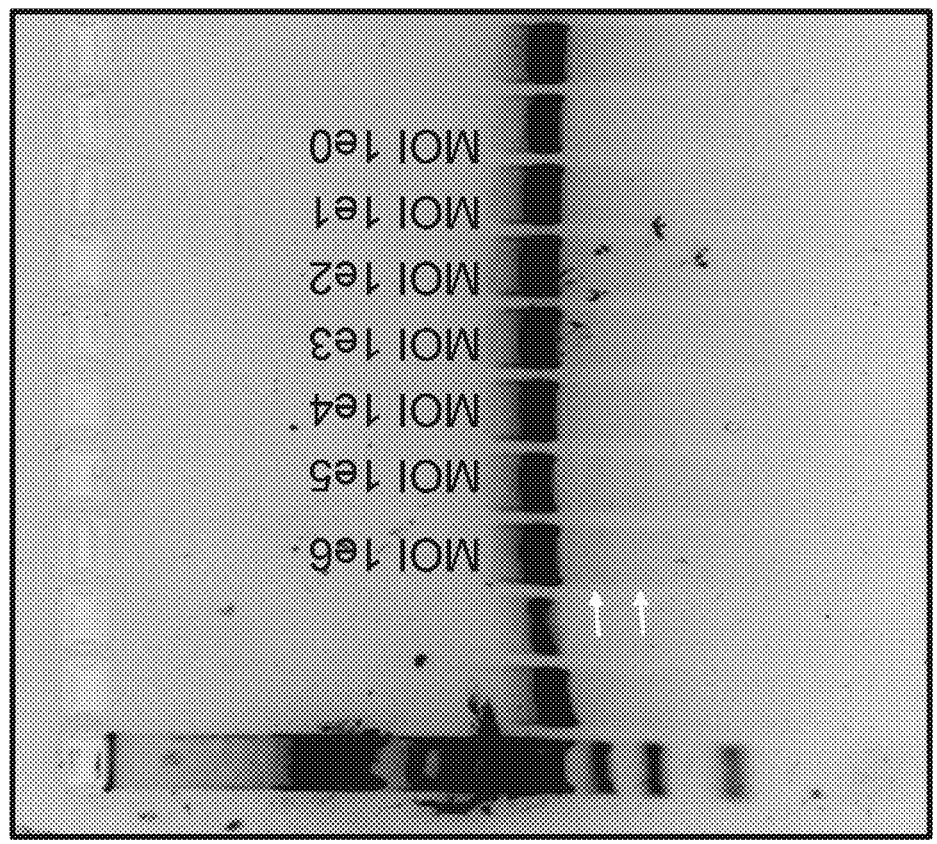
FIG. 31 shows an agarose gel image from the T7E1 assay, demonstrating successful editing of the SOD1 locus by CasX delivered via AAV, as described in Example 17.

Twelve days later, cells were assayed for GFP disruption via FACS. In this example, CasX and SauCas9 shows equivalent levels of editing, where 1-2% of the cells show GFP disruption at the highest MOIs, $1\times10^7$ or $1\times10^6$ (FIG. 29). In FIG. 30, CasX and SauCas9 shows equivalent levels of editing at the highest MOI, where ~2-4% of the cells show GFP disruption. FIG. 31 shows an agarose gel image from the T7E1 assay, demonstrating successful editing of the SOD1 locus by CasX delivered via AAV. Double arrows show the two DNA bands as a result of successful editing of the SOD1 locus in G93A NPCs.

Conclusion: This example demonstrates that CasX constructs targeting SOD1 may be delivered to mammalian cells via AAV, and result in successful editing of the SOD1 locus.

Example 18: Demonstrating Allele-Specific Editing at the A4V SOD1 Locus

The purpose of this example was to demonstrate the proof-of-concept ability of CasX:gNA systems to edit the SOD1 gene at the A4V locus in an allele-specific manner. In order to generate SOD1 targeting constructs, SOD1 targeting spacers were cloned into a base mammalian-expression plasmid construct (pStX34) that is comprised of the following components: codon-optimized CasX (construct 119; see Example 2)+NLS; guide scaffold, and a mammalian selection marker, puromycin. The spacer sequence DNA (WT CasX SOD1 spacer 8.88, having the sequence GCACGCACACGGCCTTCGTC (SEQ ID NO: 368) and CasX A4V spacer 8.89 having the sequence GCACGCACACGACCTTCGTC (SEQ ID NO: 369)) was ordered as single-stranded DNA (ssDNA) oligos from Integrated DNA Technologies (IDT), consisting of the spacer sequence and the reverse complement of this sequence. These two oligos were annealed together and cloned into pStX individually or in bulk by Golden Gate Assembly using T4 DNA Ligase (New England BioLabs Cat #M0202L) and an appropriate restriction enzyme for the plasmid. Assembled products were transformed into chemically- or electro-competent bacterial cells, plated on LBb-Agar plates (LB: Teknova Cat #L9315, Agar: Quartzy Cat #214510) containing carbenicillin. Individual colonies were picked and miniprepped using Qiagen Qiaprep® spin Miniprep Kit (Qiagen Cat #27104) following the manufacturer's protocol. The resultant plasmids were sequenced using Sanger sequencing to ensure correct ligation. One strategy to permanently treat SOD1-related ALS is to specifically disrupt the mutant copy of the gene with the A4V mutation while sparing the WT allele. SOD1-GFP cells with both wild-type alleles should be editable by the WT CasX spacer (8.88, having the RNA sequence GCACGCACACGGCCUUCGUC (SEQ ID NO: 370)), but not by the mutant CasX spacer (8.89 having the RNA sequence GCACGCACACGACCUUCGUC (SEQ ID NO: 371)). This example additionally demonstrates the ability of CasX spacers to distinguish between on-target and off-target alleles that differ by a single nucleotide. SOD1-GFP cells were seeded at 20 -40 k cells/well in a 96 well plate in 100 pl of FB medium and cultured in a 37° C. incubator with 5% CO2. The following day, confluence of seeded cells was checked to ensure that cells were at ~75% confluence at time of transfection. If cells were at the right confluence, transfection was carried out. Each CasX and guide construct (e.g., CasX 119 with guide 174) was transfected into the SOD1-GFP cells at 100-500 ng per well using Lipofectamine™ 3000 following the manufacturer's protocol, using 3 wells per construct as replicates. A non-targeting plasmid was used as a negative control. Cells were selected for successful transfection with puromycin at 0.3-3 µg/ml for 24-48 hours followed by 24-48 hours of recovery in FB medium. Editing was analyzed by measuring the fraction of cells expressing the reporter protein, GFP, via flow cytometry.

Figure 32:
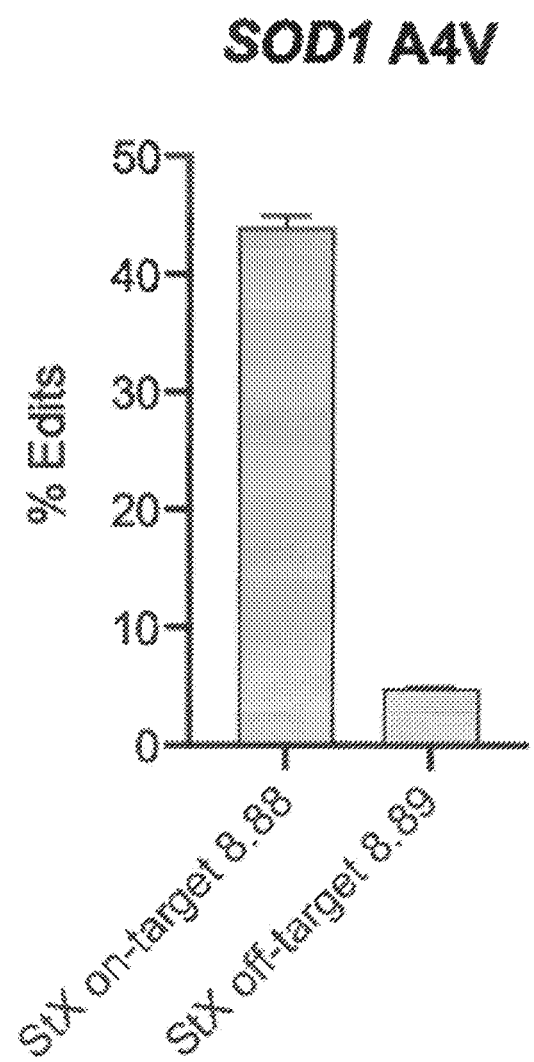
FIG. 32 shows results from a flow cytometry assay, as described in Example 18.

Results: As shown in FIG. 32, flow cytometry demonstrated that the CasX 119, guide 174 and spacer 8.88 construct was able to edit the WT SOD1 locus in SOD1-GFP cells when targeted to the A4 locus using a spacer that targets the WT sequence (on-target). A CasX construct with spacer 8.89 that targets the mutant sequence (off-target), was not able to edit the WT locus with significantly lower efficiency.

Conclusion: This example demonstrates that CasX with an appropriate guide and spacer is able to edit the A4 SOD1 locus in an allele-specific manner.

Example 19: Evaluation of SOD1 Gene Editing in Mouse Model of ALS

The purpose of the examples will be to evaluate the efficacy of CasX:gNA systems used to edit SOD1 mutations in an established mouse model of ALS.

Experimental design: T test article will be evaluated using transgenic overexpressing G93A mutant SOD1 mice. Time pregnant mice (both G93A mutants and wild-type controls) will be purchased from Jackson Labs. Upon receipt, mice will be single housed in OptiMice ventilated racks and acclimated prior to use. On the day of dosing, animals are anesthetized via cryoanesthesia and dosed ICV with a dose volume of 1 µl/g or no more than 2 µl of solution. A micro-liter calibrated sterilized glass micropipette is used that is attached to a 10 uL Hamilton syringe. The needle tip is adjusted to correct length for a 2 mm penetration into the skull. The immobilized mouse is firmly grasped by the skin behind the head. A fiber optic light is used to illuminate relevant anatomical structures used as a guide. The needle will penetrate, perpendicularly, 2 mm into the skull, for ICV at a location approximately 0.25 mm lateral to the sagittal suture and 0.50-0.75 mm rostral to the neonatal coronary suture. Dosing solution will be dispensed slowly (about 1 µl/sec). Body weights will be measured twice a week throughout the study.

Clinical Scoring: Mice will be scored for disease progression twice a week and then daily after 15 weeks of age according to the following scale:

Stage 0: No symptoms;

Stage 1: Body tremor, leg tremor, spiked fur, slowed locomotor behavior. Mouse will look generally un-groomed and slightly weak. Normal righting reflex Stage 2: Hind limb dragging, paw curling, ataxia, slower righting reflex, hind limb splay, stage 1 symptoms.

Stage 3: Hind limb paralysis, hair loss, slightly emaciated, lack of rearing ability, delayed righting reflex, stage 2 symptoms.

Stage 4: Unable to walk and lying on side, hunched back, paralysis of 2 or more limbs, emaciated, delayed righting reflex, prolapsed penis, stage 3 symptoms.

Mice that are unable to right within 30 sec, mouse will be euthanized.

Grip Strength: Grip strength is used to assess muscular strength in limb muscles. Mice are held by the tail and lowered towards the mesh grip piece on the push-pull gauge (San Diego Instruments, San Diego, Calif.) until the animal grabs with both front paws. The animal is lowered toward the platform and gently pulled backwards with consistent force by the experimenter until it releases its grip. The forelimb grip force is recorded on the strain gauge. The experimenter continues to pull the animal backwards along the platform until the animal's hind paws grab the mesh grip piece on the push-pull gauge. The animal is gently pulled backwards with consistent force by the experimenter until it releases its grip. The hind limb grip force is recorded on the strain gauge. After testing animals are placed back into the test or home cage. Grip strength commences when mice are 5 weeks of age and is measured every other week until mice are not able to perform task.

Rotarod: Motor coordination will be assessed by rotarod. Mice will be placed on a constant speed rotating rod (4 rpm) followed by 2 trials on an accelerating rotating rod (4-28 rpm). The time it takes the mice to fall in each of the trials is recorded. The duration of each trial is 3 min. After rotarod testing animals are placed back into the home cage. Rotarod test commences when mice are 5 weeks of age and resumes every other week until animals are not able to perform CMAP: Mice will be anesthetized by isoflurane/02 sufficient anesthesia by testing simple reflexes such as movement reflexes or testing of sensitivity for low-grade pain. Hair will be removed from the hind limb. Skin will be cleaned with alcohol to remove any dirt and body oil. Body temperature will be maintained by a feedback controlled heating plate and rectal thermo probe. Place loop electrodes using contact gel for optimal conductivity/transfer resistance are placed at the position where the gastrocnemius muscle has its maximum diameter. The reference electrode is placed just beneath the effective electrode. Leads will be connected to the EMG machine (Nicolet Viking Quest, Natus Neurology, Middleton, Mich., USA). Five responses evoked by stimulation will be averaged to generate a smooth compound muscle action potential (CMAP). Then the amplitude and the onset latency will be measured based on the averaged CMAPs. Nerve conduction velocity (NCV) can be calculated from the response latency and the distance from stimulating electrode to recording electrode. For MUNE calculation, a maximum CMAP is obtained first by increasing stimulating intensity until the response no longer increases. Then the average single motor unit potential (SMUP) is determined using incremental stimulation technique. Starting from an all-or-none response, 10 increments will be summed and averaged. Then the maximum CMAP will be divided by average SMUP to obtain MUNE number. CMAP and MUNE will be measured at 5 weeks, 9, 13, 17, 20 weeks of age.

Righting Reflex and survival: Righting reflex is used as a surrogate for survival. The animal is simply placed on its back on a flat surface and the time taken to right itself is measured (up to 0.5 min). Only one trial per mouse at each time point is performed. Righting reflex testing will commence when mice are 15 weeks of age and will be performed daily until the mice can no longer right themselves. Mice will be euthanized if no longer able to right themselves.

At the end of each study period, mice are decapitated and trunk blood is collected in microcentrifuge tubes containing EDTA and kept on ice for short term storage. Within 15 minutes the tubes are centrifuged in a refrigerated centrifuge. Plasma is extracted and samples are stored in the −80° C. freezer for future analyses. Brains will be removed and frozen on dry ice. Samples will be stored at −80° C. freezer for future histopathology or other analyses. Spinal Cord: After the removal of the brain, the spinal cord is extracted. A 3 ml syringe attached to a 200 μl pipette tip is filled with saline and used for spinal cord flushing. The pelvic region is cut horizontally so the spinal column could be visible. Once the pelvic area is cut, the pipette tip is inserted through the small opening visible at the base of the spinal column and the spinal cord is flushed out. The whole spinal cord is frozen in pre-chilled Eppendorf tubes on dry ice. Samples are stored in the −80° C. freezer for future histopathology or other analyses.

Results: The data from the example are expected to provide information on the efficacy of the CasX:gNA to prevent or ameliorate ALS conditions in the mouse model.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11613742B2). An electronic copy of the "Sequence Listing" will also be available from the USPTO upon request and payment of the fee set forth in 37 CFR 1.19(b)(3).

What is claimed is:

1. A composition comprising a CasX variant protein comprising the sequence of SEQ ID NO: 126, or a sequence having at least 90% sequence identity thereto, and a first guide ribonucleic acid (gRNA), wherein the CasX variant protein is a chimeric CasX protein comprising protein domains from two or more different CasX proteins, and wherein the gRNA comprises a targeting sequence complementary to a superoxide dismutase 1 (SOD1) gene target nucleic acid sequence comprising one or more mutations.

2. The composition of claim 1, wherein the one or more mutations are in a region selected from the group consisting of:
   a) a SOD1 intron;
   b) a SOD1 exon;
   c) a SOD1 intron-exon junction;
   d) a SOD1 regulatory element; and
   e) an intergenic region.

3. The composition of claim 1, wherein the one or more mutations comprise an insertion, deletion, substitution, duplication, or inversion of one or more nucleotides as compared to a wild-type SOD1 gene sequence.

4. The composition of claim 3, wherein the one or more mutations comprise a gain of function mutation.

5. The composition of claim 1, wherein the one or more mutations in the SOD1 gene target nucleic acid sequence encode a mutation selected from the group consisting of A4S, A4T, A4V, C6F, V7E, L8Q, L8V, G12R, V14G, V14M, G16S, F20C, E21G, E21K, Q22L, G37R, L38R, L38V, G41D, G41S, H43R, F45C, H46R, H48Q, H48R, E49K, T54R, N65S, L67P, L67R, G72S, D76Y, H80A, L84F, L84V, G85R, N86S, V87A, A89T, A89V, D90A, D90V, G93A, G93C, G93D, G93R, G93V, A95G, V97M, E100G, E100K, D101G, D101N, I104F, S105L, L106V, G108V, C111Y, I112M, I112T, I113T, G114A, R115G, V118L, D124G, D124V, D125H, L126S, S134N, N139K, L144F, L144S, A145T, C146R, G147R, V148G, V148 I, I149T, and I151T relative to the wild-type superoxide dismutase 1 protein sequence of SEQ ID NO: 100 without the N-terminal methionine.

6. The composition of claim 1, wherein the SOD1 gene encodes a protein comprising an A4V substitution, a D90A substitution or a G93A substitution compared to the wild-type superoxide dismutase 1 protein sequence of SEQ ID NO: 100 without the N-terminal methionine.

7. The composition of claim 1, wherein the SOD1 gene encodes a non-functional superoxide dismutase 1 protein.

8. The composition of claim 1, wherein the gRNA is a single-molecule gRNA (sgRNA).

9. The composition of claim 1, wherein the targeting sequence of the gRNA comprises a ribonucleic acid (RNA) sequence selected from the group consisting of the sequences of SEQ ID NOS: 351-357, 370, and 371, or a sequence having at least 90% identity thereto.

10. The composition of claim 1, wherein the targeting sequence of the gRNA is complementary to a sequence of a SOD1 exon, to a sequence of a SOD1 intron, to a sequence of a SOD1 intron-exon junction, to a sequence of a SOD1 regulatory element, to a sequence of a sequence of an intergenic region of the SOD1 gene or to a sequence comprising one or more single nucleotide polymorphisms (SNPs) of the SOD1 gene.

11. The composition of claim 1, wherein the targeting sequence of the gRNA is complementary to a sequence of a SOD1 exon 1 or complementary to a target nucleic acid sequence encoding a A4V substitution, a D90A substitution or a G93A substitution compared to the wild-type superoxide dismutase 1 protein sequence of SEQ ID NO: 100 without the N-terminal methionine.

12. The composition of claim 1, further comprising a second gRNA, wherein the second gRNA has a targeting sequence complementary to a different or overlapping portion of the SOD1 target nucleic acid compared to the targeting sequence of the first gRNA.

13. The composition of claim 12, wherein the first or second gRNA has a scaffold comprising the sequence of SEQ ID NO: 2238, or a sequence having at least 70% identity thereto.

14. The composition of claim 1, wherein the CasX variant protein further comprises one or more nuclear localization signals (NLS).

15. The composition of claim 1, further comprising a donor template nucleic acid.

16. The composition of claim 1, wherein the chimeric CasX protein comprising protein domains from two or more different CasX proteins, comprises proteins domains from two or more different reference CasX proteins.

17. The composition of claim 1, wherein the chimeric CasX protein comprising protein domains from two or more different CasX proteins, comprises proteins domains from two or more different CasX variant proteins.

18. A composition comprising a CasX variant protein comprising the sequence of SEQ ID NO: 126, or a sequence having at least 90% sequence identity thereto, and a first guide ribonucleic acid (gRNA), wherein the gRNA has a scaffold comprising a sequence having at least 70% sequence identity to the sequence of SEQ ID NO: 2238, and wherein the gRNA comprises a targeting sequence complementary to a superoxide dismutase 1 (SOD1) gene target nucleic acid sequence comprising one or more mutations.

19. The composition of claim 18, wherein the SOD1 gene comprises one or more mutations in a region selected from the group consisting of:

a) a SOD1 intron;
b) a SOD1 exon;
c) a SOD1 intron-exon junction;
d) a SOD1 regulatory element; and
e) an intergenic region.

20. The composition of claim 18, wherein the SOD1 gene comprising a mutation encodes a protein comprising a A4V substitution, a D90A substitution, or a G93A substitution compared to the wild-type superoxide dismutase 1 protein sequence of SEQ ID NO: 100 without the N-terminal methionine.

21. The composition of claim 18, wherein the targeting sequence of the gRNA comprises a sequence selected from the group consisting of the sequences of SEQ ID NOS: 351-357, 370, and 371, or a sequence having at least 90% identity thereto.

22. A nucleic acid vector:
(a) encoding a CasX variant protein, the CasX variant protein comprising the sequence of SEQ ID NO: 126, or a sequence having at least 90% sequence identity thereto; and
(b) encoding a guide ribonucleic acid (gRNA), wherein the gRNA has a scaffold comprising a sequence having at least 70% sequence identity to the sequence of SEQ ID NO: 2238, and wherein the gRNA comprises a targeting sequence complementary to a superoxide dismutase 1 (SOD1) gene target nucleic acid sequence comprising one or more mutations.

23. The nucleic acid vector of claim 22, wherein the targeting sequence of the gRNA comprises a ribonucleic acid sequence selected from the group consisting of the sequences of SEQ ID NOS: 351-357, 370, and 371, or a sequence having at least 90% identity thereto.

24. The nucleic acid vector of claim 22, wherein the nucleic acid vector is as an adeno-associated viral (AAV) vector.

25. A composition comprising:
(a) a CasX variant protein, or a sequence encoding the CasX variant protein, the CasX variant protein comprising the sequence of SEQ ID NO: 126, or a sequence having at least 90% sequence identity thereto; and
(b) a guide ribonucleic acid (gRNA), wherein the gRNA has a scaffold comprising a sequence having at least 70% sequence identity to the sequence of SEQ ID NO: 2238, and wherein the gRNA comprises a targeting sequence complementary to a superoxide dismutase 1 (SOD1) gene target nucleic acid sequence comprising one or more mutations.

* * * * *